(12) United States Patent
Xiao et al.

(10) Patent No.: US 10,913,712 B2
(45) Date of Patent: Feb. 9, 2021

(54) TETRACYCLINE COMPOUNDS

(71) Applicant: Tetraphase Pharmaceuticals, Inc., Watertown, MA (US)

(72) Inventors: Xiao-Yi Xiao, Lexington, MA (US); Roger B. Clark, Lexington, MA (US); Diana Katharine Hunt, Cambridge, MA (US); Cuixiang Sun, Arlington, MA (US); Magnus P. Ronn, Melrose, MA (US); Wu-Yan Zhang, Lexington, MA (US); Minsheng He, Andover, MA (US)

(73) Assignee: Tetraphase Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/393,725

(22) Filed: Apr. 24, 2019

(65) Prior Publication Data
US 2020/0048193 A1 Feb. 13, 2020

Related U.S. Application Data

(63) Continuation of application No. 15/400,674, filed on Jan. 6, 2017, now Pat. No. 10,315,992, which is a continuation of application No. 14/424,765, filed on Feb. 27, 2015, now Pat. No. 9,573,895, application No. 16/393,725, which is a continuation of application No. 14/424,765, filed as application No. PCT/US2013/057690 on Aug. 30, 2013, now Pat. No. 9,573,895.

(60) Provisional application No. 61/695,947, filed on Aug. 31, 2012.

(51) Int. Cl.
| | | |
|---|---|---|
| C07D 207/09 | (2006.01) | |
| C07D 207/08 | (2006.01) | |
| C07D 221/18 | (2006.01) | |
| C07D 471/04 | (2006.01) | |
| C07C 237/26 | (2006.01) | |
| C07D 295/155 | (2006.01) | |

(52) U.S. Cl.
CPC .......... *C07D 207/09* (2013.01); *C07C 237/26* (2013.01); *C07D 207/08* (2013.01); *C07D 221/18* (2013.01); *C07D 295/155* (2013.01); *C07D 471/04* (2013.01)

(58) Field of Classification Search
CPC combination set(s) only.
See application file for complete search history.

(56) References Cited

U.S. PATENT DOCUMENTS

| | | |
|---|---|---|
| 3,226,436 A | 12/1965 | Petlsi et al. |
| 3,247,226 A | 4/1966 | Esse et al. |
| 3,338,963 A | 8/1967 | Petisi et al. |
| 3,364,123 A | 1/1968 | Neidleman |
| 3,394,178 A | 7/1968 | Dulaney et al. |
| 3,433,709 A | 3/1969 | McCormick et al. |
| 3,824,285 A | 7/1974 | Blackwood et al. |
| 3,849,493 A | 11/1974 | Conover et al. |
| 3,947,517 A | 3/1976 | Muxfeldt et al. |
| 3,988,468 A | 10/1976 | Rogalski et al. |
| 4,024,272 A | 5/1977 | Rogalski et al. |
| 4,160,783 A | 7/1979 | Cakara et al. |
| 5,284,963 A | 2/1994 | Sum et al. |
| 5,328,902 A | 7/1994 | Sum et al. |
| 5,380,888 A | 1/1995 | Sum et al. |
| 5,386,041 A | 1/1995 | Sum et al. |
| 5,401,729 A | 3/1995 | Sum et al. |
| 5,430,162 A | 7/1995 | Sum et al. |
| 5,442,059 A | 8/1995 | Sum et al. |
| 5,466,684 A | 11/1995 | Sum et al. |
| 5,494,903 A | 2/1996 | Hlavka et al. |
| 5,495,031 A | 2/1996 | Sum et al. |
| 5,529,990 A | 6/1996 | Hlavka et al. |
| 5,530,117 A | 6/1996 | Hlavka et al. |
| 5,574,026 A | 11/1996 | Backer et al. |
| 5,668,122 A | 9/1997 | Fife et al. |

(Continued)

FOREIGN PATENT DOCUMENTS

| | | |
|---|---|---|
| BE | 639292 A | 4/1964 |
| CN | 1072172 A | 5/1993 |

(Continued)

OTHER PUBLICATIONS

U.S. Appl. No. 16/328,559, filed Feb. 2019.*

(Continued)

*Primary Examiner* — Amanda L. Aguirre
(74) *Attorney, Agent, or Firm* — Foley Hoag LLP

(57) ABSTRACT

The present invention is directed to a compound represented by Structural Formula (I):

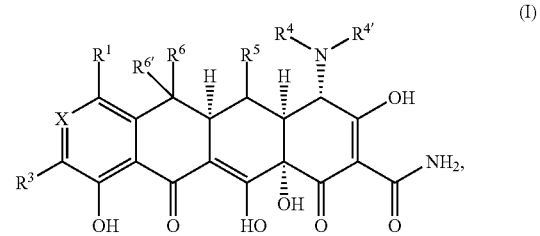

or a pharmaceutically acceptable salt thereof. The variables for Structural Formula (I) are defined herein. Also described is a pharmaceutical composition comprising the compound of Structural Formula (I), or a pharmaceutically acceptable salt thereof, and its therapeutic use.

4 Claims, No Drawings

(56) References Cited

U.S. PATENT DOCUMENTS

| | | | |
|---|---|---|---|
| 5,843,925 | A | 12/1998 | Backer et al. |
| 6,100,248 | A | 8/2000 | Golub et al. |
| 6,277,061 | B1 | 8/2001 | Golub et al. |
| 6,683,068 | B2 | 1/2004 | Nelson et al. |
| 6,841,546 | B2 | 1/2005 | Draper et al. |
| 6,914,057 | B1 | 7/2005 | Ryan et al. |
| 7,045,507 | B2 | 5/2006 | Draper et al. |
| RE40,086 | E | 2/2008 | Hlavka et al. |
| RE40,183 | E | 3/2008 | Hlavka et al. |
| 7,763,735 | B2 | 7/2010 | Myers et al. |
| 7,807,842 | B2 | 10/2010 | Myers et al. |
| 7,820,641 | B2 | 10/2010 | Nelson et al. |
| 7,825,105 | B2 | 11/2010 | Bandarage et al. |
| 7,939,513 | B2 | 5/2011 | Takhi et al. |
| 8,088,820 | B2 | 1/2012 | Draper et al. |
| 8,367,654 | B2 | 2/2013 | Clark et al. |
| 8,501,716 | B2 | 8/2013 | Zhou et al. |
| 8,796,245 | B2 | 8/2014 | Zhou et al. |
| 8,828,988 | B2 | 9/2014 | Clark et al. |
| 8,906,887 | B2 | 12/2014 | Zhou et al. |
| 9,315,451 | B2 | 4/2016 | Chen et al. |
| 9,371,283 | B2 | 6/2016 | Xiao et al. |
| 9,522,872 | B2 | 12/2016 | Seyedi et al. |
| 9,533,943 | B2 | 1/2017 | Bowser et al. |
| 9,562,003 | B2 | 2/2017 | Levy et al. |
| 9,573,895 | B2 * | 2/2017 | Xiao .................. C07D 471/04 |
| 9,624,166 | B2 | 4/2017 | Deng et al. |
| 10,072,007 | B2 | 9/2018 | Clark et al. |
| 10,315,992 | B2 | 6/2019 | Xiao et al. |
| 2004/0063674 | A1 | 4/2004 | Levy et al. |
| 2004/0092490 | A1 | 5/2004 | Draper et al. |
| 2004/0214800 | A1 | 10/2004 | Levy et al. |
| 2004/0224928 | A1 | 11/2004 | Nelson et al. |
| 2004/0242548 | A1 | 12/2004 | Draper et al. |
| 2005/0143352 | A1 | 6/2005 | Nelson et al. |
| 2006/0166944 | A1 | 7/2006 | Berniac et al. |
| 2006/0166945 | A1 | 7/2006 | Abato et al. |
| 2006/0183720 | A1 | 8/2006 | Sum et al. |
| 2006/0194773 | A1 | 8/2006 | Levy et al. |
| 2006/0281717 | A1 | 12/2006 | Berniac et al. |
| 2007/0093455 | A1 | 4/2007 | Abato et al. |
| 2008/0015169 | A1 | 1/2008 | Nelson et al. |
| 2008/0070873 | A1 | 3/2008 | Alekshun et al. |
| 2008/0118979 | A1 | 5/2008 | Draper et al. |
| 2009/0118269 | A1 | 5/2009 | Berniac et al. |
| 2009/0257985 | A1 | 10/2009 | Nelson et al. |
| 2010/0022483 | A1 | 1/2010 | Berniac et al. |
| 2010/0105671 | A1 | 4/2010 | Zhou et al. |
| 2011/0009371 | A1 | 1/2011 | Myers et al. |
| 2011/0269714 | A1 | 11/2011 | Xiao et al. |
| 2012/0108569 | A1 | 5/2012 | Clark et al. |
| 2012/0135968 | A1 | 5/2012 | Chen et al. |
| 2012/0208788 | A1 | 8/2012 | Deng et al. |
| 2012/0302527 | A1 | 11/2012 | Zhou et al. |
| 2012/0329761 | A1 | 12/2012 | Schimmer et al. |
| 2013/0109657 | A1 | 5/2013 | Zhou et al. |
| 2013/0345178 | A1 | 12/2013 | Clark et al. |
| 2015/0274643 | A1 | 10/2015 | Zhou et al. |
| 2016/0107988 | A1 | 4/2016 | Xiao et al. |
| 2017/0044160 | A1 | 2/2017 | Chen et al. |
| 2017/0107179 | A1 | 4/2017 | Xiao et al. |
| 2017/0275244 | A1 | 9/2017 | Zhou et al. |
| 2017/0283368 | A1 | 10/2017 | Seyedi et al. |
| 2017/0305852 | A1 | 10/2017 | Xiao et al. |
| 2017/0334841 | A1 | 11/2017 | Deng et al. |
| 2020/0048193 | A1 | 2/2020 | Xiao et al. |
| 2020/0055813 | A1 | 2/2020 | Zhou et al. |

FOREIGN PATENT DOCUMENTS

| | | | |
|---|---|---|---|
| CN | 1087626 | A | 6/1994 |
| CN | 1090267 | A | 8/1994 |
| CN | 1034216 | C | 3/1997 |
| CN | 1653037 | A | 8/2005 |
| CN | 1845897 | A | 10/2006 |
| CN | 101027279 | A | 8/2007 |
| EP | 0 536 515 | A1 | 4/1993 |
| EP | 0 582 789 | A1 | 2/1994 |
| EP | 0 582 810 | A1 | 2/1994 |
| EP | 0 618 190 | A1 | 10/1994 |
| EP | 230 1916 | A2 | 3/2011 |
| GB | 935 384 | A | 8/1963 |
| GB | 1 034 933 | A | 7/1966 |
| GB | 1065716 | A | 4/1967 |
| GB | 1077598 | A | 8/1967 |
| GB | 1563663 | A | 3/1980 |
| JP | S5141362 | A | 4/1976 |
| JP | H05255219 | A | 10/1993 |
| JP | H07309823 | A | 11/1995 |
| JP | 2004502753 | A | 1/2004 |
| JP | 2005520846 | A | 7/2005 |
| JP | 2008530106 | A | 8/2008 |
| TW | 275616 | B | 5/1996 |
| TW | I299038 | B | 7/2008 |
| TW | I508934 | B | 11/2015 |
| WO | WO-99/37307 | A1 | 7/1999 |
| WO | WO-00/18353 | A2 | 4/2000 |
| WO | WO-01/98260 | A1 | 12/2001 |
| WO | WO-2002/04404 | A2 | 1/2002 |
| WO | WO-2002/04407 | A2 | 1/2002 |
| WO | WO-2002/072022 | A2 | 9/2002 |
| WO | WO-2002/072031 | A2 | 9/2002 |
| WO | WO-2002/085303 | A2 | 10/2002 |
| WO | WO-2003/005971 | A2 | 1/2003 |
| WO | WO-2003/057169 | A2 | 7/2003 |
| WO | WO-2003/079984 | A2 | 10/2003 |
| WO | WO-2004/006850 | A2 | 1/2004 |
| WO | WO-2004/038000 | A2 | 5/2004 |
| WO | WO-2004/038001 | A2 | 5/2004 |
| WO | WO-2005/009943 | A2 | 2/2005 |
| WO | WO-2005/082860 | A1 | 9/2005 |
| WO | WO-2005/112945 | A2 | 12/2005 |
| WO | WO-2006/047671 | A2 | 5/2006 |
| WO | WO-2006/047756 | A2 | 5/2006 |
| WO | WO-2006/084265 | A1 | 8/2006 |
| WO | WO-2006/088720 | A2 | 8/2006 |
| WO | WO-2007/014154 | A2 | 2/2007 |
| WO | WO-2007/087416 | A2 | 8/2007 |
| WO | WO-2007/117639 | A2 | 10/2007 |
| WO | WO-2007/133798 | A2 | 11/2007 |
| WO | WO-2008/045507 | A2 | 4/2008 |
| WO | WO-2008/079339 | A2 | 7/2008 |
| WO | WO-2008/127361 | A2 | 10/2008 |
| WO | WO-2008/127722 | A1 | 10/2008 |
| WO | WO-2009/073056 | A1 | 6/2009 |
| WO | WO-2009/128913 | A1 | 10/2009 |
| WO | WO-2010/006292 | A1 | 1/2010 |
| WO | WO-2010/017470 | A1 | 2/2010 |
| WO | WO-2010/126607 | A2 | 11/2010 |
| WO | WO-2010/129055 | A1 | 11/2010 |
| WO | WO-2010/129057 | A2 | 11/2010 |
| WO | WO-2010/132670 | A2 | 11/2010 |
| WO | WO-2011/025982 | A2 | 3/2011 |
| WO | WO-2011/123536 | A1 | 10/2011 |
| WO | WO-2012/021712 | A1 | 2/2012 |
| WO | WO-2012021712 | A1 * | 2/2012 ............. A01N 43/84 |
| WO | WO-2012/047907 | A1 | 4/2012 |
| WO | WO-2014/036502 | A2 | 3/2014 |
| WO | WO-2016/065290 | A1 | 4/2016 |
| WO | WO-2017/125557 | A1 | 7/2017 |
| WO | WO-2018/045084 | A1 | 3/2018 |
| WO | WO-2018/075767 | A1 | 4/2018 |

OTHER PUBLICATIONS

Final Office Action dated Aug. 25, 2014 for U.S. Appl. No. 13/319,298 "Tetracycline Compounds".
Final Office Action, U.S. Appl. No. 13/391,407, dated Oct. 1, 2014.
Final Rejection for U.S. Appl. No. 13/075,886, "Polycyclic Tetracycline Compounds," dated Feb. 20, 2015.
Final Rejection for U.S. Appl. No. 13/075,886, "Polycyclic Tetracycline Compounds," dated Nov. 7, 2013.

(56) References Cited

OTHER PUBLICATIONS

Final Rejection for U.S. Appl. No. 13/391,401, "Tetracycline Compounds," dated May 18, 2016.
Non-Final Rejection for U.S. Appl. No. 13/075,886, "Polycyclic Tetracycline Compounds," dated Mar. 22, 2013.
Non-Final Rejection for U.S. Appl. No. 13/075,886, "Polycyclic Tetracycline Compounds," dated May 22, 2014.
Non-Final Rejection for U.S. Appl. No. 13/075,886, "Polycyclic Tetracycline Compounds," dated Nov. 24, 2015.
Non-Final Rejection for U.S. Appl. No. 13/391,401, "Tetracycline Compounds," dated Jul. 29, 2015.
Non-Final Rejection for U.S. Appl. No. 14/532,882, "C7-Fluoro Substituted Tetracycline Compounds," dated May 9, 2016.
Non-Final Rejection for U.S. Appl. No. 15/079,926, "Tetracycline Compounds," dated May 10, 2017.
Non-Final Rejection for U.S. Appl. No. 15/164,183 "Polycyclic Tetracycline Compounds," dated Jul. 24, 2017.
Non-Final Rejection for U.S. Appl. No. 15/347,352, "C7-Fluoro Substituted Tetracycline Compounds," dated Jul. 28, 2017.
Non-Final Rejection for U.S. Appl. No. 15/446,831 dated Jun. 28, 2018.
Notice of Allowance dated Dec. 1, 2015 for U.S. Appl. No. 13/319,298 entitled "Tetracycline Compounds".
Notice of Allowance dated Jun. 5, 2014 for U.S. Appl. No. 13/718,909, entitled "C7-Fluro Substituted Tetracycline Compounds".
Notice of Allowance dated Jun. 6, 2013 for U.S. Appl. No. 13/570,837.
Notice of Allowance for U.S. Appl. No. 13/391,401, "Tetracycline Compounds," dated Dec. 1, 2016.
Notice of Allowance for U.S. Appl. No. 13/731,753, dated May 1, 2014.
Notice of Allowance for U.S. Appl. No. 14/424,765, "Tetracycline Compounds," dated Oct. 7, 2016.
Notice of Allowance for U.S. Appl. No. 15/079,926, Titled: "Tetracycline Compounds," dated Jan. 25, 2018.
Notice of Allowance for U.S. Appl. No. 15/400,674 dated Jan. 25, 2019.
Notice of Allowance, U.S. Appl. No. 12/462,795, dated Aug. 4, 2014.
Notice of Allowance, U.S. Appl. No. 13/319,307, dated Sep. 19, 2012.
Notice of Allowance for U.S. Appl. No. 13/075,886, "Polycyclic Tetracycline Compounds," dated Feb. 22, 2016.
Office Action dated Dec. 7, 2011 for U.S. Appl. No. 12/462,795.
Office Action dated Feb. 14, 2014 for U.S. Appl. No. 13/391,407, "Tetracycline Compounds".
Office Action dated Feb. 4, 2013 for U.S. Appl. No. 13/570,837.
Office Action dated Feb. 5, 2013 for U.S. Appl. No. 13/718,909.
Office Action dated Jan. 16, 2014 for U.S. Appl. No. 13/319,298, "Tetracycline Compounds".
Office Action dated Jan. 17, 2014 for U.S. Appl. No. 12/462,795, "C7-Fluoro Substituted Tetracycline Compounds".
Office Action dated Jan. 24, 2012 for U.S. Appl. No. 12/462,795.
Office Action dated Jul. 24, 2012 for U.S. Appl. No. 12/462,795.
Office Action dated Jul. 9, 2013 for U.S. Appl. No. 13/718,909.
Office Action dated Sep. 23, 2013 for U.S. Appl. No. 12/462,795.
Office Action, U.S. Appl. No. 13/319,298; dated Apr. 27, 2015.
Requirement for Restriction/Election for U.S. Appl. No. 13/391,401, "Tetracycline Compounds," dated Jun. 25, 2013.
Requirement for Restriction/Election for U.S. Appl. No. 14/424,765, "Tetracycline Compounds," dated Apr. 8, 2016.
Requirement for Restriction/Election for U.S. Appl. No. 15/446,831, "Tetracycline Compounds," dated Aug. 31, 2017.
Supplemental Notice of Allowability for U.S. Appl. No. 15/079,926, Tetracycline Compounds, dated Feb. 5, 2018.
Abbanat et al., "New agents in development for the treatment of bacterial infections," Curr Opin Pharmacol, 8(5):582-592 (2008).
Bhattacharyya et al., "Studies on Hydrofluorene Derivatives. Part II. Synthesis of 1,1a,1b,2,3,4,4a,5,6,6a-Decahydro-1a-methyl-3-oxochrysofluorene," Journal of the Indian Chemical Society, 41(7): 479-495 (1964).

Blackwood et al., "Some Transformations of Tetracycline at the 4-Position," Can J Chem, 43(5): 1382-1388 (1965).
Bocker, "Analysis and Quantitation of a Metabolite of Doxycycline in Mice, Rats, and Humans by High-Performance Liquid Chromatography," J Chromatogr-Biomed, 274: 255-262 (1983).
Charest et al., "A Convergent Enantioselective Route to Structurally Diverse 6-Deoxytetracycline Antibiotics", Science, 308:395-398 (2005).
Chen et al., "Oxidative Degradation Kinetics and Products of Chlortetracycline by Manganese Dioxide," J Hazard Mater, 193: 128-138 (2011).
Chopra et al., "Tetracycline Antibiotics: Mode of Action, Applications, Molecular Biology, and Epidemiology of Bacterial Resistance," Microbiol Mol Biol Rev, 65(2):232-260 (2001).
Ciara, "Crystalline Polymorphism of Organic Compounds," Topics in Current Chemistry, In: Weber E. et al. (eds) Design of Organic Solids. Topics in Current Chemistry, vol. 198. Springer, Berlin, Heidelberg 163-208 (1998).
Croisy-Delcey et al., "Synthesis of 1-Functionalized-6-hydroxy-4-methyl and 6,11-Dihydroxy-4-methylnaphtho[2,3-g]isoquinoline-5,12-quinoes," J. Heterocyclic Chem., 28:65-71 (1991).
Esse et al., "Tetracycloxides. II. Transformations at the C-4 Position", J Am Chem Soc, 86(18):3875-3877 (1964).
Examination Report for New Zealand Patent Application No. 705849, dated Aug. 7, 2017.
Extended European Search Report for EP Application No. 17183980.6 dated Dec. 8, 2017.
Extended European Search Report for EP Application No. 18192684.1 dated Jan. 21, 2019.
Extended Search Report for European Patent Application No. 13172357.9 dated May 16, 2014 "C7-Fluoro Substituted Tetracycline Compounds".
HCAPLUS, Accession No. 2004:1036703, Document No. 141:420412 (Apr. 24, 2002).
HCAPLUS, Accession No. 2005:99455, Document No. 142:197754 (Jun. 25, 2004).
Hlavka et al., "The 6-Deoxytetracyclines. IV. A Photochemical Displacement of a Diazonium Group," J Org Chem, 27:3674-3675 (1962).
Huenig et al., "Stabiles Radikalkation eines Kohlenwasserstoffs," Angewandte Chemie, 76(19): 818 (1964).
International Preliminary Report on Patentability for International Application No. PCT/US2010/001350; dated Nov. 9, 2011.
International Preliminary Report on Patentability for International Application No. PCT/US2010/047035; dated Feb. 28, 2012.
International Preliminary Report on Patentability for International Application No. PCT/US2011/047428; dated Feb. 12, 2013.
International Preliminary Report on Patentability for International Application No. PCT/US2013/057690, "Tetracycline Compounds", dated Mar. 3, 2015.
International Preliminary Report on Patentability for International Patent Application No. PCT/US2010/034718 dated Nov. 15, 2011.
International Preliminary Report on Patentability for International Patent Application No. PCT/US2011/030532 dated Oct. 2, 2012.
International Search Report and Written Opinion for International Application No. PCT/US2009/053142 dated Oct. 13, 2009.
International Search Report and Written Opinion for International Application No. PCT/US2017/049462 dated Feb. 14, 2018.
International Search Report and Written Opinion for International Application No. PCT/US2017/057385 dated Dec. 6, 2017.
International Search Report and Written Opinion for International Patent Application No. PCT/US2010/034718 dated Nov. 9, 2010.
International Search Report and Written Opinion for International Patent Application No. PCT/US2011/030532 dated Jul. 12, 2011.
International Search Report and Written Opinion of the International Searching Authority for International Application No. PCT/US2010/001348, dated Jul. 19, 2010.
International Search Report and Written Opinion of the International Searching Authority for International Application No. PCT/US2010/001350, dated Nov. 23, 2010.
International Search Report and Written Opinion of the International Searching Authority for International Application No. PCT/US2010/047035; dated Jul. 22, 2011.

(56) References Cited

OTHER PUBLICATIONS

International Search Report and Written Opinion of the International Searching Authority for International Application No. PCT/US2011/047428, dated Jan. 6, 2012.
International Search Report and Written Opinion of the International Searching Authority for International Application No. PCT/US2013/057690; dated Feb. 24, 2014.
International Search Report and Written Opinion of the International Searching Authority for International Application No. PCT/US2009/053142; dated Oct. 13, 2009.
Martin et al., "Totalsynthese von d,1-7-Chlor-6-desoxytetracyclinen und d,1-7-Chlor-6-desmethyl-6-desoxytetracyclinen der naturlichen, der 5a-epi- und der 6-epi-Reihe," Tetrahedron Letts 36:3513-3516 (1973).
Nelis et al., "Metabolism of Minocycline in Humans," Drug Metab Dispos, 10(2): 142-146 (1982).
Plakunov, "Relation Between Chemical Structure of Tetracyclines and Their Analogs and Specific Features of Transport and Mechanism of Antibacterial Effect," Antibiotiki (Moscow), 18(12): 1069-1073 (1973).
Podlogar et al., "Patents on tetracycline and tetracycline derivatives as antimicrobials", Expert Opin. Ther. Patents, 13(4):467-478 (2003).
Pre-appeal Conference Decision dated Feb. 19, 2013 for U.S. Appl. No. 12/462,795.
Remmers et al., "New Alkaline-Stable Species for Selected Members of the Tetracycline Family," J Pharm Sci, 51(1): 86-87 (1962).
Rogalski, "Chemical Modifications of Tetracyclines," in Hlvaka et al., The Tetracyclines. Handbook of Experimental Pharmacology (Continuation of Handbuch der experimentellen Pharmakologie), vol. 78.,Berlin, Spring-Verlag, pp. 179-316 (1985).
Ronn et al., "Process R&D of Eravacycline: The First Fully Synthetic Fluorocycline in Clinical Development," Organic Process Research and Development, 17(5): 838-845 (2013).
Sato et al. "Structure-Activity Relationship Investigation of Some New Tetracyclines by Electronic Index Methodology", arXiv:0708.2931 [q-bio.BM] 1-18 (2007).
Song et al., "Cytotoxic Effects of Tetracycline Analogues (Doxycycline, Minocycline and COL-3) in Acute Myeloid Leukemia HL-60 Cells," PLOS One, 9(12): e114457 (2014).
Sum et al., "Glycylcyclines. 1. A New Generation of Potent Antibacterial Agents Through Modification of 9-Aminotetracyclines," J Med Chem, 37: 184-188 (1994).
Sum et al., "Synthesis and Structure-Activity Relationship of Novel Glycylcycline Derivatives Leading to the Discovery of GAR-936," Bioorg Med Chem Letts 9:1459-1462 (1999).
Sun et al., "A Robust Platform for the Synthesis of New Tetracycline Antibiotics," J. Am. Chem.Soc., 130:17913-17927 (2008).
Sun et al., "Synthesis and Antibacterial Activity of Pentacyclines: A Novel Class of Tetracycline Analogs," J. Med. Chem. 54(11):3704-3731 (2011).
Verma et al., "Antibiotic and non-antibiotic tetracycline patents: 2002-2007", Expert Opin. Ther. Patents, vol. 18, pp. 69-82 (2008).
Zurhelle et al., "Automated Residue Analysis of Tetracyclines and Their Metabolites in Whole Egg, Egg White, Egg Yolk and Hen's Plasma Utilizing a Modified ASTED System," Journal of Chromatography B: Biomedical Sciences and Applications, 739(1): 191-203 (2000).
Van den Bogert et al., "Doxycycline in Combination Chemotherapy of a Rat Leukemia1," Cancer Research, 48: 6686-6690 (1988).

* cited by examiner

TETRACYCLINE COMPOUNDS

RELATED APPLICATIONS

This application is a continuation of U.S. application Ser. No. 15/400,674, filed on Jan. 6, 2017, which is a continuation of U.S. application Ser. No. 14/424,765 (now U.S. Pat. No. 9,573,895), filed on Feb. 27, 2015, which is the U.S. National Stage of International Application No. PCT/US2013/057690, filed Aug. 30, 2013, which claims the benefit of U.S. Provisional Application No. 61/695,947, filed on Aug. 31, 2012. The entire teachings of the above application are incorporated herein by reference.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Therefore, there is need for new tetracycline analogs with improved antibacterial activities and efficacies against other tetracycline responsive diseases or disorders.

SUMMARY OF THE INVENTION

A first embodiment of the present invention is directed to a compound represented by Structural Formula (I):

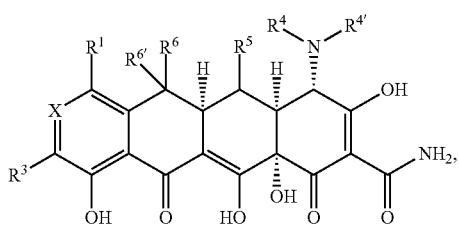

(I)

or a pharmaceutically acceptable salt thereof, wherein the variables are as defined and described herein.

Another embodiment of the present invention is directed to a compound represented by Structural Formula (II):

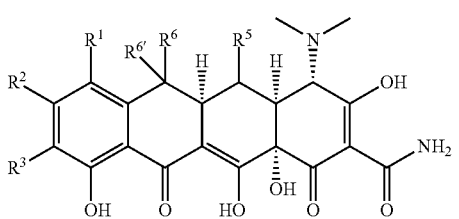

(II)

or a pharmaceutically acceptable salt thereof, wherein the variables are as defined and described herein.

Another embodiment of the present invention is directed to a pharmaceutical composition comprising a pharmaceutically acceptable carrier or diluent and a compound represented by Structural Formula (I) or (II), or a pharmaceutically acceptable salt thereof. The pharmaceutical composition is used in therapy, such as treating an infection (e.g., a bacterial infection) in a subject.

Another embodiment of the present invention is a method of treating an infection (e.g., a bacterial infection) in a subject comprising administering to the subject an effective amount of a compound represented by Structural Formula (I) or (II), or a pharmaceutically acceptable salt thereof.

Another embodiment of the present invention is a method of preventing an infection (e.g., a bacterial infection) in a subject comprising administering to the subject an effective amount of a compound represented by Structural Formula (I) or (II), or a pharmaceutically acceptable salt thereof.

Another embodiment of the present invention is the use of a compound represented by Structural Formula (I) or (II), or a pharmaceutically acceptable salt thereof, for the manufacture of a medicament for treating an infection (e.g., a bacterial infection) in a subject.

Another embodiment of the present invention is the use of a compound represented by Structural Formula (I) or (II), or a pharmaceutically acceptable salt thereof, for the manufacture of a medicament for preventing an infection (e.g., a bacterial infection) in a subject.

Another embodiment of the present invention is the use of a compound represented by Structural Formula (I) or (II), or a pharmaceutically acceptable salt thereof, in therapy, such as treating or preventing an infection (e.g., a bacterial infection) in a subject.

DETAILED DESCRIPTION OF THE INVENTION

The present invention is directed to a compound represented by Structural Formula (I), or a pharmaceutically acceptable salt thereof. The variables in Structural Formula (I) are described herein in the following paragraphs. It is understood that the invention encompasses all combinations of the substituent variables (i.e., $R^1$, $R^2$, $R^3$, etc.) defined herein.

A first embodiment of the invention is a compound having Structural Formula (I):

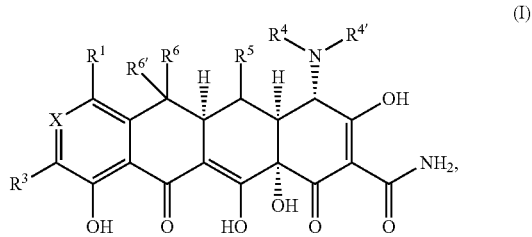

(I)

or a pharmaceutically acceptable salt thereof, wherein:
X is selected from N and $C(R^2)$;
each of $R^1$, $R^2$, $R^3$, $R^5$ and $R^6$ is independently selected from hydrogen, halo, —$(C_1$-$C_6$ alkyl), —$OR^4$, —$C(O)NR^BR^{B'}$, $NR^BR^{B'}$, $S(O)_{0-2}R^C$, —$(C_0$-$C_6$ alkylene)-carbocyclyl, and —$(C_0$-$C_6$ alkylene)-heterocyclyl; or
$R^1$ and $R^2$ are optionally taken together with atoms to which they are bound to form a carbocyclyl or heterocyclyl ring; or
$R^2$ and $R^3$ are optionally taken together with atoms to which they are bound to form a carbocyclyl or heterocyclyl ring;

R⁴ is selected from hydrogen, —(C₁-C₆ alkyl), —(C₀-C₆ alkylene)-carbocyclyl, and —(C₀-C₆ alkylene)-heterocyclyl;

R⁴' is selected from hydrogen, —(C₂-C₆ alkyl), S(O)₁₋₂R^C, —(C₀-C₆ alkylene)-carbocyclyl, —(C₀-C₆ alkylene)-heterocyclyl, —C(O)—(C₁-C₆ alkyl), and —C(O)—(C₁-C₆ alkyl)-NR^D R^E; or R⁴ and R⁴' are optionally taken together with the nitrogen atom to which they are commonly bound to form a 4-8 membered ring optionally comprising 1-2 additional heteroatoms independently selected from N, O and S;

R⁶' is selected from hydrogen, —(C₁-C₆ alkyl) and —(C₃-C₆ cycloalkyl);

each R^A is independently selected from hydrogen, —(C₁-C₆ alkyl), —(C₀-C₆ alkylene)-carbocyclyl, —(C₀-C₆ alkylene)-heterocyclyl, —C(O)—(C₁-C₆ alkyl), —C(O)—(C₀-C₆ alkylene)-carbocyclyl, —C(O)—(C₀-C₆ alkylene)-heterocyclyl, and —C(O)N(R^D)(R^E);

each R^B and each R^B' is independently selected from hydrogen, —(C₁-C₆ alkyl), —(C₁-C₆ haloalkyl), —(C₀-C₆ alkylene)-carbocyclyl, —(C₀-C₆ alkylene)-heterocyclyl, —S(O)₁₋₂—(C₁-C₆ alkyl), —S(O)₁₋₂—(C₀-C₆ alkylene)-carbocyclyl, —S(O)₁₋₂—(C₀-C₆ alkylene)-heterocyclyl, —C(O)—(C₁-C₆ alkyl), —C(O)—(C₀-C₆ alkylene)-carbocyclyl, —C(O)H, —C(O)—(C₀-C₆ alkylene)-heterocyclyl, and —C(O)—(C₀-C₆ alkylene)-N(R^D)(R^E);

each R^C is independently selected from —(C₁-C₆ alkyl), —(C₀-C₆ alkylene)-carbocyclyl and —(C₀-C₆ alkylene)-heterocyclyl; and each R^D and each R^E is independently selected from hydrogen, —(C₁-C₆ alkyl), —(C₀-C₆ alkylene)-carbocyclyl, and —(C₀-C₆ alkylene)-heterocyclyl, wherein any alkyl, alkylene, carbocyclyl or heterocyclyl portion of R¹, R², R³, R⁴, R⁴', R⁵, R⁶, R⁶', R^A, R^B, R^B', R^C, R^D, or R^E or formed by taking R¹ and R², R² and R³, or R⁴ and R⁴' together is optionally and independently substituted.

In a first aspect of the first embodiment:
any alkyl, or alkylene portion of R¹, R², R³, R⁴, R⁴', R⁵, R⁶ is optionally and independently substituted with one or more substituents independently selected from halo, =O, OR^A, NR^B R^B', and S(O)₀₋₂R^C;

any alkyl or alkylene portion of R⁶', R^A, or R^C, is optionally and independently substituted with one or more fluoro;

any carbocyclyl or heterocyclyl portion of any of R¹, R², R³, R⁴, R⁴', R⁵, R⁶, or any ring formed by taking together R¹ and R², R² and R³ or R⁴ and R⁴' is optionally and independently substituted on a carbon atom with one or more substituents independently selected from halo, =O, C₁-C₄ fluoroalkyl, C₁-C₄ alkyl, —(C₀-C₆ alkylene)-(C₃-C₁₀ carbocyclyl), —(C₀-C₆ alkylene)-(4-13 membered heterocyclyl), OR^A, —(C₀-C₆alkylene)-NR^B R^B', and S(O)₀₋₂R^C;

any heterocyclyl portion of any of R¹, R², R³, R⁴, R⁴', R⁵, R⁶, or any ring formed by taking together R¹ and R², R² and R³ or R⁴ and R⁴' is optionally and independently substituted on a substitutable nitrogen atom with R^F;

each R^F is independently selected from —(C₁-C₆ alkyl), —(C₁-C₆ haloalkyl), —(C₁-C₆ hydroxyalkyl), —(C₀-C₆ alkylene)-carbocyclyl, —(C₀-C₆ alkylene)-heterocyclyl, —S(O)₁₋₂—(C₁-C₆ alkyl), —S(O)₁₋₂—(C₀-C₆ alkylene)-carbocyclyl, —S(O)₁₋₂—(C₀-C₆ alkylene)-heterocyclyl, —C(O)—(C₁-C₆ alkyl), —C(O)—(C₀-C₆ alkylene)-carbocyclyl, —C(O)H, —C(O)—(C₀-C₆ alkylene)-heterocyclyl, —(C₀-C₆ alkylene)-C(O)₂—(C₁-C₆ alkyl), —(C₁-C₆ alkylene)-NR^B R^B' and —C(O)N(R^D)(R^E);

any carbocyclyl or heterocyclyl portion of R^A, R^B, R^B', R^C, R^D, R^E, R^F, any cycloalkyl portion of R⁶', or any substituent of R¹, R², R³, R⁴, R⁴', R⁵, R⁶ is optionally and independently substituted on a carbon atom with a one or more substituents independently selected from fluoro, chloro, C₁-C₄ alkyl, C₁-C₄ fluoroalkyl, —O—C₁-C₄ alkyl, —O—C₁-C₄ fluoroalkyl, =O, —OH, —NH₂, —NH(C₁-C₄ alkyl), and —N(C₁-C₄ alkyl)₂;

any heterocyclyl portion of R^A, R^B, R^B', R^C, R^D, R^E, R^F, or any heterocyclyl substituent of R¹, R², R³, R⁴, R⁴', R⁵, or R⁶ is optionally substituted on a substitutable nitrogen atom with —C₁-C₄ alkyl, or —S(O)₁₋₂—(C₁-C₄ alkyl). The remaining variables are as described and defined in the first embodiment.

In a second aspect of the first embodiment, the compound is other than:

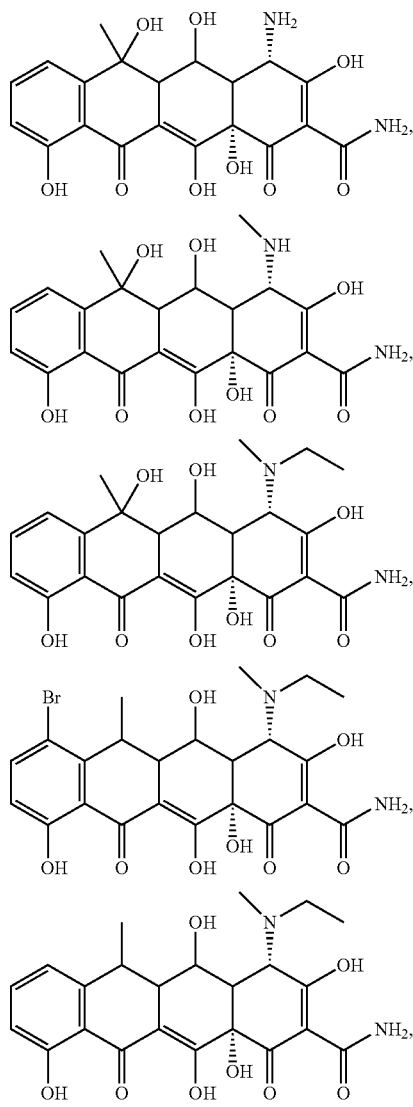

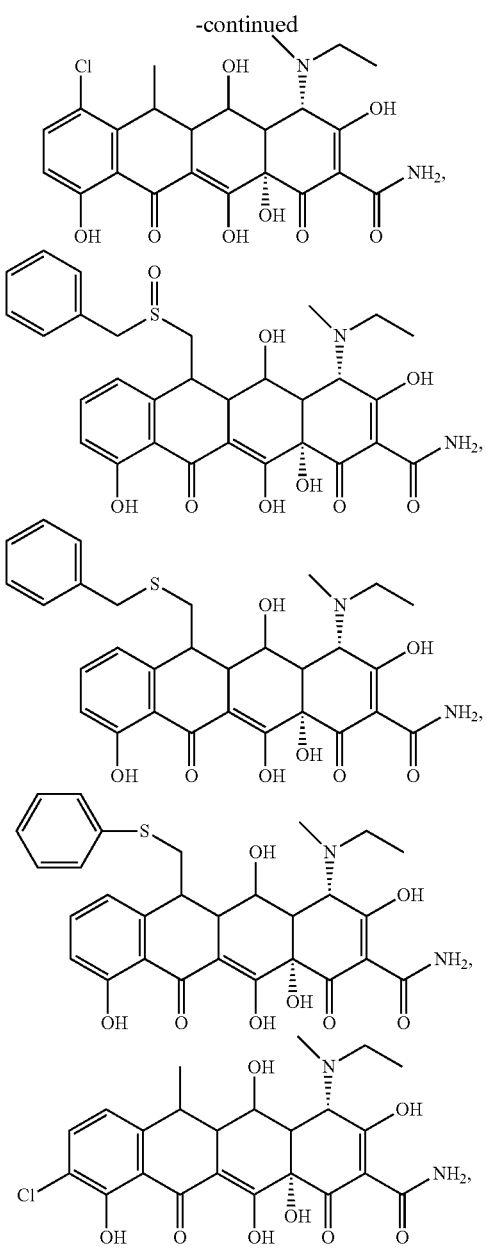

or a salt of any of the foregoing. The remaining variables are as described and defined in the first embodiment, or first aspect thereof.

In a third aspect of the first embodiment, each of $R^5$, $R^6$ and $R^{6'}$ is hydrogen. The remaining variables are as described and defined in the first embodiment, or the first or second aspect thereof.

In a fourth aspect of the first embodiment, X is $C(R^2)$. The remaining variables are as described and defined in the first embodiment, or the first, second or third aspect thereof.

In a fifth aspect of the first embodiment:
X is selected from N and $C(R^2)$;
each of $R^1$, $R^2$, $R^3$, $R^5$ and $R^6$ is independently selected from hydrogen, halo, —($C_1$-$C_6$ alkyl), —$OR^A$, $NR^BR^{B'}$, —$C(O)NR^BR^{B'}$, $S(O)_{0-2}R^C$, —($C_0$-$C_6$ alkylene)-carbocyclyl, and —($C_0$-$C_6$ alkylene)-heterocyclyl; or
$R^1$ and $R^2$ are optionally taken together with atoms to which they are bound to form a carbocyclyl or heterocyclyl ring; or $R^2$ and $R^3$ are optionally taken together with atoms to which they are bound to form a carbocyclyl or heterocyclyl ring;
$R^4$ is selected from hydrogen, —($C_1$-$C_6$ alkyl), —($C_0$-$C_6$ alkylene)-carbocyclyl, and —($C_0$-$C_6$ alkylene)-heterocyclyl;
$R^{4'}$ is selected from hydrogen, —($C_2$-$C_6$ alkyl), $S(O)_{1-2}R^C$, —($C_0$-$C_6$ alkylene)-carbocyclyl, —($C_0$-$C_6$ alkylene)-heterocyclyl, —$C(O)$—($C_1$-$C_6$ alkyl), and —$C(O)$—($C_1$-$C_6$ alkyl)-$NR^DR^E$; or
$R^4$ and $R^{4'}$ are optionally taken together with the nitrogen atom to which they are commonly bound to form a 4-8 membered ring optionally comprising 1-2 additional heteroatoms independently selected from N, O and S;
$R^{6'}$ is selected from hydrogen, —($C_1$-$C_6$ alkyl) and —($C_3$-$C_6$ cycloalkyl);
each $R^A$ is independently selected from hydrogen, —($C_1$-$C_6$ alkyl), —($C_0$-$C_6$ alkylene)-carbocyclyl, —($C_0$-$C_6$ alkylene)-heterocyclyl, —$C(O)$—($C_1$-$C_6$ alkyl), —$C(O)$—($C_0$-$C_6$ alkylene)-carbocyclyl, —$C(O)$—($C_0$-$C_6$ alkylene)-heterocyclyl, and —$C(O)N(R^D)(R^E)$;
each $R^B$ and each $R^{B'}$ is independently selected from hydrogen, —($C_1$-$C_6$ alkyl), —($C_0$-$C_6$ alkylene)-carbocyclyl, —($C_0$-$C_6$ alkylene)-heterocyclyl, —$S(O)_{1-2}$—($C_1$-$C_6$ alkyl), —$S(O)_{1-2}$—($C_0$-$C_6$ alkylene)-carbocyclyl, —$S(O)_{1-2}$—($C_0$-$C_6$ alkylene)-heterocyclyl, —$C(O)$—($C_1$-$C_6$ alkyl), —$C(O)$—($C_0$-$C_6$ alkylene)-carbocyclyl, —$C(O)H$, —$C(O)$—($C_0$-$C_6$ alkylene)-heterocyclyl, and —$C(O)N(R^D)(R^E)$;
each $R^C$ is independently selected from —($C_1$-$C_6$ alkyl), —($C_0$-$C_6$ alkylene)-carbocyclyl and —($C_0$-$C_6$ alkylene)-heterocyclyl; and
each $R^D$ and each $R^E$ is independently selected from hydrogen, —($C_1$-$C_6$ alkyl), —($C_0$-$C_6$ alkylene)-carbocyclyl, and —($C_0$-$C_6$ alkylene)-heterocyclyl;
wherein any alkyl, alkylene, carbocyclyl or heterocyclyl portion of $R^1$, $R^2$, $R^3$, $R^4$, $R^{4'}$, $R^5$, $R^6$, $R^{6'}$, $R^A$, $R^B$, $R^{B'}$, $R^C$, $R^D$, or $R^E$ or formed by taking $R^1$ and $R^2$, $R^2$ and $R^3$, or $R^4$ and $R^{4'}$ together is optionally and independently substituted. The remaining variables are as described and defined in the first embodiment, or the first, second, third or fourth aspect thereof.

In a sixth aspect of the first embodiment:
any alkyl or alkylene portion of $R^1$, $R^2$, $R^3$, $R^4$, $R^{4'}$, $R^5$, or $R^6$ is optionally and independently substituted with one or more substituents independently selected from halo, =O, $OR^A$, $NR^BR^{B'}$, and $S(O)_{0-2}R^C$;
any alkyl or alkylene portion of $R^{6'}$, $R^A$, or $R^C$, is optionally and independently substituted with one or more fluoro;
any carbocyclyl or heterocyclyl portion of any of $R^1$, $R^2$, $R^3$, $R^4$, $R^{4'}$, $R^5$, or $R^6$, or any ring formed by taking together $R^1$ and $R^2$, $R^2$ and $R^3$, or $R^4$ and $R^{4'}$ is optionally and independently substituted on a carbon atom with one or more substituents independently selected from halo, =O, $C_1$-$C_4$ fluoroalkyl, $C_1$-$C_4$ alkyl, $C_3$-$C_{10}$ carbocyclyl, a 4-13 membered heterocyclyl, $OR^A$, $NR^BR^{B'}$, and $S(O)_{0-2}R^C$;
any heterocyclyl portion of any of $R^1$, $R^2$, $R^3$, $R^4$, $R^{4'}$, $R^5$, or $R^6$, or any ring formed by taking together $R^1$ and $R^2$, $R^2$ and $R^3$, or $R^4$ and $R^{4'}$ is optionally and independently substituted on a substitutable nitrogen atom with $R^F$;
each $R^F$ is independently selected from —($C_1$-$C_6$ alkyl), —($C_0$-$C_6$ alkylene)-carbocyclyl, —($C_0$-$C_6$ alkylene)-heterocyclyl, —$S(O)_{1-2}$—($C_1$-$C_6$ alkyl), —$S(O)_{1-2}$—($C_0$-$C_6$ alkylene)-carbocyclyl, —$S(O)_{1-2}$—($C_0$-$C_6$ alkylene)-heterocyclyl, —$C(O)$—($C_1$-$C_6$ alkyl), —$C(O)$—($C_0$-$C_6$ alkylene)- carbocyclyl, —C(O)H, —C(O)—($C_0$-$C_6$ alkylene)-heterocyclyl, and —C(O)N($R^D$)($R^E$);

any carbocyclyl or heterocyclyl portion of $R^A$, $R^B$, $R^{B'}$, $R^C$, $R^D$, $R^E$, $R^F$, any cycloalkyl portion of $R^6$, or any substituent of $R^1$, $R^2$, $R^3$, $R^4$, $R^{4'}$, $R^5$, or $R^{6'}$ is optionally and independently substituted on a carbon atom with a one or more substituents independently selected from halo, $C_1$-$C_4$ alkyl, $C_1$-$C_4$ fluoroalkyl, —O—$C_1$-$C_4$ alkyl, —O—$C_1$-$C_4$ fluoroalkyl, =O, —OH, —$NH_2$, —NH($C_1$-$C_4$ alkyl), and —N($C_1$-$C_4$ alkyl)$_2$; and any heterocyclyl portion of $R^A$, $R^B$, $R^{B'}$, $R^C$, $R^D$, $R^E$, $R^F$, or any heterocyclyl substituent of $R^1$, $R^2$, $R^3$, $R^4$, $R^{4'}$, $R^5$, or $R^6$ is optionally substituted on a substitutable nitrogen atom with —$C_1$-$C_4$ alkyl, or —S(O)$_{1-2}$—($C_1$-$C_4$ alkyl). The remaining variables are as described and defined in the first embodiment, or the first, second, third, fourth or fifth aspect thereof.

In a seventh aspect of the first embodiment, X is N. The remaining variables are as described and defined in the first embodiment, or the first, second, third, fourth, fifth or sixth aspect thereof.

In an eighth aspect of the first embodiment, $R^1$ is selected from hydrogen, halo, —($C_1$-$C_6$ alkyl) optionally substituted with one or more substituents independently selected from halo, —$NR^B R^{B'}$, —C(O)$NR^B R^{B'}$, —$OR^A$, —($C_0$-$C_6$ alkylene)-carbocyclyl, and —($C_0$-$C_6$ alkylene)-heterocyclyl, wherein $R^A$ is $C_1$-$C_6$ alkyl optionally substituted with one or more fluoro. The remaining variables are as described and defined in the first embodiment, or the first, second, third, fourth, fifth, sixth or seventh aspect thereof.

In a ninth aspect of the first embodiment, $R^3$ is selected from hydrogen and —N($R^B$)($R^{B'}$), wherein $R^B$ is hydrogen. The remaining variables are as described and defined in the first embodiment, or the first, second, third, fourth, fifth, sixth, seventh or eighth aspect thereof.

A second embodiment of the invention is a compound of Structural Formula (I), wherein $R^4$ is selected from hydrogen and —($C_1$-$C_6$ alkyl); $R^{4'}$ is selected from hydrogen, —($C_2$-$C_6$ alkyl) optionally substituted with one or more substituents independently selected from hydroxy and halo, —($C_3$-$C_6$ cycloalkyl), —C(O)—($C_1$-$C_6$ alkyl), —C(O)—($C_1$-$C_6$ alkylene)-N($R^D$)($R^E$), and S(O)$_{1-2}R^C$; or $R^4$ and $R^{4'}$ are taken together with the nitrogen atom to which they are commonly bound to form a 4-6 membered ring optionally comprising 1-2 additional heteroatoms independently selected from N, O and S; $R^C$ is —($C_1$-$C_6$ alkyl); and each of $R^D$ and $R^E$ is independently selected from hydrogen and —($C_1$-$C_6$ alkyl). The remaining variables are as described and defined in the first embodiment, or any aspect thereof.

In a first aspect of the second embodiment, $R^4$ is selected from hydrogen, methyl, ethyl and propyl; and $R^{4'}$ is selected from hydrogen, ethyl, propyl, cyclopropyl, —C(O)$CH_3$, —C(O)$CH_2$N($CH_3$)$_2$, and —S(O)$_2$$CH_3$. The remaining variables are as described and defined in the first embodiment, or any aspect thereof, or in the second embodiment.

In a second aspect of the second embodiment, $R^4$ is selected from hydrogen and —($C_1$-$C_6$ alkyl); $R^{4'}$ is selected from hydrogen, —($C_2$-$C_6$ alkyl), —($C_3$-$C_6$ cycloalkyl), —C(O)—($C_1$-$C_6$ alkyl), —C(O)—($C_1$-$C_6$ alkylene)-N($R^D$)($R^E$), and S(O)$_{1-2}R^C$; $R^C$ is —($C_1$-$C_6$ alkyl); and each of $R^D$ and $R^E$ is independently selected from hydrogen and —($C_1$-$C_6$ alkyl). The remaining variables are as described and defined in the first embodiment, or any aspect thereof, or the second embodiment, or first aspect thereof.

A third embodiment of the invention is a compound of Structural Formula (I), wherein $R^1$ is selected from hydrogen, halo, —($C_1$-$C_6$ alkyl) optionally substituted with one or more substituents independently selected from halo, —$NR^B R^{B'}$, —C(O)$NR^B R^{B'}$, —$OR^A$, —($C_0$-$C_6$ alkylene)-carbocyclyl, and —($C_0$-$C_6$ alkylene)-heterocyclyl, wherein $R^A$ is $C_1$-$C_6$ alkyl optionally substituted with one or more fluoro. The remaining variables are as described and defined in the first or second embodiment, or any aspect thereof.

In a first aspect of the third embodiment, X is C($R^2$). The remaining variables are as described and defined in the first or second embodiment, or any aspect thereof, or the third embodiment.

In a second aspect of the third embodiment, $R^1$ is selected from hydrogen, fluoro, chloro, $CF_3$ and $OCF_3$. The remaining variables are as described and defined in the first or second embodiment, or any aspect thereof, or the third embodiment, or first aspect thereof.

In a third aspect of the third embodiment, $R^1$ is selected from hydrogen, halo, —($C_1$-$C_6$ alkyl) optionally substituted with one or more substituents independently selected from halo, and —$OR^A$, wherein $R^A$ is $C_1$-$C_6$ alkyl optionally substituted with one or more fluoro. The remaining variables are as described and defined in the first or second embodiment, or any aspect thereof, or the third embodiment, or first or second aspect thereof.

In a fourth aspect of the third embodiment, $R^1$ is selected from hydrogen, fluoro, chloro, $CF_3$, $OCH_3$, $OCF_3$, N($CH_3$)$_2$ and $NHCH_3$. The remaining variables are as described and defined in the first or second embodiment, or any aspect thereof, or the third embodiment, or first, second or third aspect thereof.

In a fifth aspect of the third embodiment, $R^1$ is selected from hydrogen, halo, —($C_1$-$C_6$ alkyl) optionally substituted with halo, —$NR^B R^{B'}$, —C(O)$NR^B R^{B'}$, —$OR^A$, —($C_0$-$C_6$ alkylene)-carbocyclyl, and —($C_0$-$C_6$ alkylene)-heterocyclyl, wherein $R^A$ is $C_1$-$C_6$ alkyl optionally substituted with one or more fluoro. The remaining variables are as described and defined in the first or second embodiment, or any aspect thereof, or the third embodiment, or first, second, third or fourth aspect thereof.

A fourth embodiment of the invention is a compound of Structural Formula (I), wherein $R^1$ and $R^2$ are taken together with the atoms to which they are bound to form a nitrogen-containing heterocyclyl ring, wherein the ring comprising $R^1$ and $R^2$ is optionally substituted on any substitutable nitrogen atom with $C_1$-$C_4$ alkyl; and optionally substituted on a carbon atom with $NR^B R^{B'}$, wherein each of $R^B$ and $R^{B'}$ is independently selected from hydrogen and $C_1$-$C_6$ alkyl. The remaining variables are as described and defined in the first, second or third embodiment, or any aspect thereof.

In a first aspect of the fourth embodiment, $R^1$ and $R^2$ are taken together with the carbon atoms to which they are bound to form:

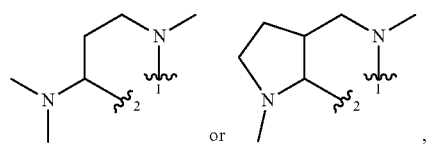

wherein "⁓1" represents a point of attachment to the carbon atom bound to $R^1$ and "⁓2" represents a point of attachment to the carbon atom bound to $R^2$. The remaining variables are as described and defined in the first, second or third embodiment, or any aspect thereof, or the fourth embodiment.

In a second aspect of the fourth embodiment, X is $C(R^2)$. The remaining variables are as described and defined in the first, second or third embodiment, or any aspect thereof, or the fourth embodiment, or the first aspect thereof.

In a third aspect of the fourth embodiment, X is $C(R^2)$; and $R^1$ and $R^2$ are taken together with the carbon atoms to which they are bound to form:

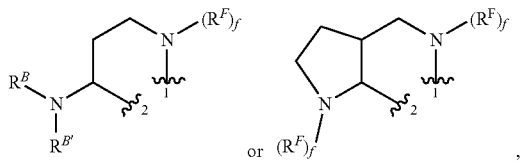

wherein "⌇⌇1" represents a point of attachment to the carbon atom bound to $R^1$; "⌇⌇2" represents a point of attachment to the carbon atom bound to $R^2$; and f is 0 or 1. The remaining variables are as described and defined in the first, second or third embodiment, or any aspect thereof, or the fourth embodiment, or the first or second aspect thereof.

A fifth embodiment of the invention is a compound of Structural Formula (I), wherein $R^2$ is —($C_0$-$C_6$ alkylene)-heterocyclyl optionally substituted on a nitrogen atom with —($C_1$-$C_6$ alkyl); —($C_0$-$C_6$ alkylene)-carbocyclyl; or —($C_1$-$C_6$)alkyl substituted with $NR^BR^{B'}$. The remaining variables are as described and defined in the first, second, third or fourth embodiment, or any aspect thereof.

In a first aspect of the fifth embodiment, $R^2$ is pyrrolidinyl optionally substituted on a nitrogen atom with $C_1$-$C_4$ alkyl or benzyl. The remaining variables are as described and defined in the first, second, third or fourth embodiment, or any aspect thereof, or the fifth embodiment.

In a second aspect of the fifth embodiment, X is $C(R^2)$. The remaining variables are as described and defined in the first, second, third or fourth embodiment, or any aspect thereof, or the fifth embodiment, or first aspect thereof.

In a third aspect of the fifth embodiment, $R^2$ is —($C_0$-$C_6$ alkylene)-heterocyclyl optionally substituted on a nitrogen atom with —($C_1$-$C_6$ alkyl) or —($C_0$-$C_6$ alkylene)-carbocyclyl. The remaining variables are as described and defined in the first, second, third or fourth embodiment, or any aspect thereof, or the fifth embodiment, or first or second aspect thereof.

A sixth embodiment of the invention is a compound of Structural Formula (I), wherein $R^2$ and $R^3$ are taken together with the atoms to which they are bound to form a heterocyclyl, e.g., a nitrogen-containing heterocyclyl ring, wherein the ring comprising $R^2$ and $R^3$ is optionally and independently substituted on any substitutable nitrogen atom with $C_1$-$C_4$ alkyl. The remaining variables are as described and defined in the first, second, third, fourth or fifth embodiment, or any aspect thereof.

In a first aspect of the sixth embodiment, $R^2$ and $R^3$ are taken together with the atoms to which they are bound to form

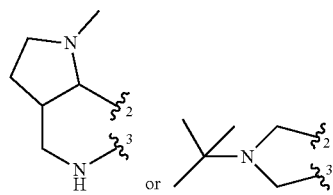

wherein "⌇⌇2" represents a point of attachment to the carbon atom bound to $R^2$, and "⌇⌇3" represents a point of attachment to the carbon atom bound to $R^3$. The remaining variables are as described and defined in the first, second, third, fourth or fifth embodiment, or any aspect thereof, or the sixth embodiment.

In a second aspect of the sixth embodiment, $R^2$ and $R^3$ are taken together with the atoms to which they are bound to form

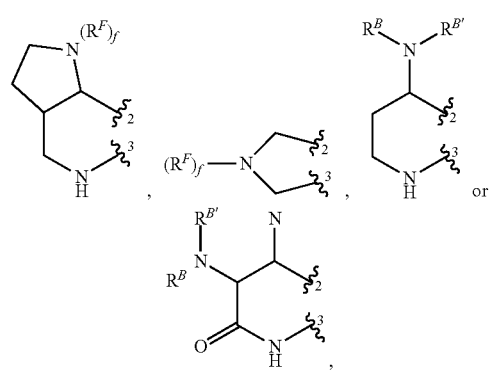

wherein "⌇⌇2" represents a point of attachment to the carbon atom bound to $R^2$; "⌇⌇3" represents a point of attachment to the carbon atom bound to $R^3$; and f is 0 or 1. The remaining variables are as described and defined in the first, second, third, fourth or fifth embodiment, or any aspect thereof, or the sixth embodiment, or first aspect thereof.

A seventh embodiment of the invention is a compound of Structural Formula (I), wherein $R^3$ is selected from hydrogen and —$N(R^B)(R^{B'})$, wherein $R^B$ is hydrogen and $R^{B'}$ is —C(O)—($C_0$-$C_6$ alkylene)-heterocyclyl or —C(O)—($C_0$-$C_6$ alkylene)-$N(R^D)(R^E)$. The remaining variables are as described and defined in the first, second, third, fourth, fifth or sixth embodiment, or any aspect thereof.

In a first aspect of the seventh embodiment, $R^3$ is selected from hydrogen and

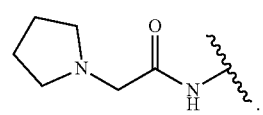 [SMILES: *NC(=O)CN1CCCC1]

The remaining variables are as described and defined in the first, second, third, fourth, fifth or sixth embodiment, or any aspect thereof, or the seventh embodiment.

In a second aspect of the seventh embodiment, X is $C(R^2)$. The remaining variables are as described and defined in the first, second, third, fourth, fifth or sixth embodiment, or any aspect thereof, or the seventh embodiment, or first aspect thereof.

In a third aspect of the seventh embodiment, $R^3$ is selected from hydrogen and —$N(R^B)(R^{B'})$, wherein $R^B$ is hydrogen and $R^{B'}$ is —C(O)—($C_0$-$C_6$ alkylene)-heterocyclyl. The remaining variables are as described and defined in the first, second, third, fourth, fifth or sixth embodiment, or any aspect thereof, or the seventh embodiment, or first or second aspect thereof.

In one embodiment, the compound of the invention is one of the compounds set forth in Table 1, or a pharmaceutically acceptable salt thereof. The compound designations used in Table 1 indicate the scheme used to prepare the compound. For example, Compound S8-4-3 was prepared in accordance with Scheme 8 by selecting the appropriate pathway and reagents.

TABLE 1

| Compound No. | Compound Structure |
|---|---|
| S3-7-1-A (diastereomer A) S3-7-1-B (diastereomer B) | (structure) |
| S3-7-2 | (structure) |
| S3-7-3-A (diastereomer A) S3-7-3-B (diastereomer B) | (structure) |
| S3-7-4-A (diastereomer A) S3-7-4-B (diastereomer B) | (structure) |
| S3-7-5 | (structure) |
| S3-7-6-A (diastereomer A) S3-7-6-B (diastereomer B) | (structure) |

TABLE 1-continued
| Compound No. | Compound Structure |
|---|---|
| S3-7-7-A (diastereomer A) S3-7-7-B (diastereomer B) | 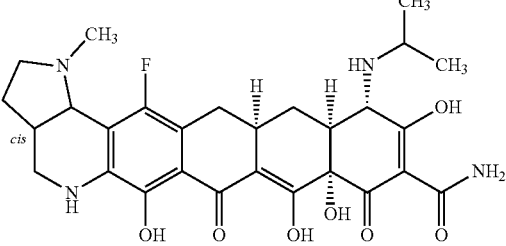 |
| S3-7-8-A (diastereomer A) S3-7-8-B (Diastereomer B) | 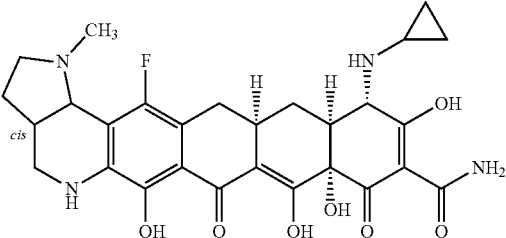 [SMILES: CN1CCC2CNc3c(O)c4c(c(F)c3C21)C[C@H]1C[C@H]2[C@H](NC3CC3)C(O)=C(C(N)=O)C(=O)[C@@]2(O)C(O)=C1C4=O] |
| S3-7-9-A (diastereomer A) S3-7-9-B (diastereomer B) | 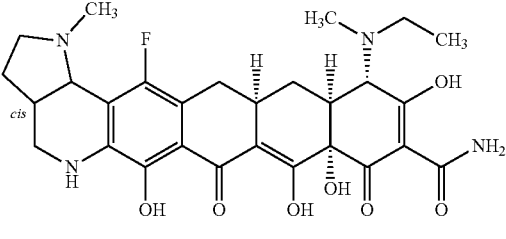 [SMILES: CCN(C)[C@@H]1C(O)=C(C(N)=O)C(=O)[C@@]2(O)C(O)=C3C(=O)c4c(O)c5c(c(F)c4C[C@H]3C[C@@H]12)C1C(CCN1C)CN5] |
| S3-7-10-A (diastereomer A) S3-7-10-B (diastereomer B) | 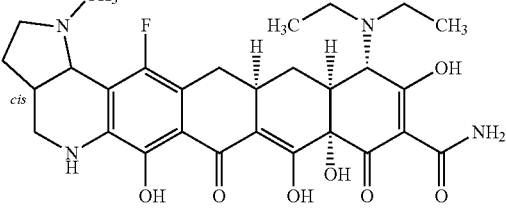 |
| S3-7-11 | 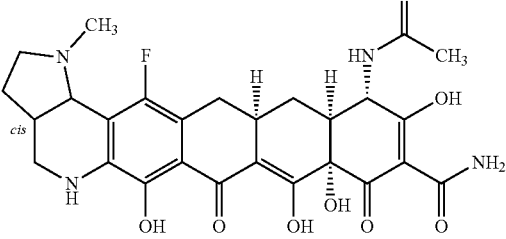 |
| S3-7-12 | 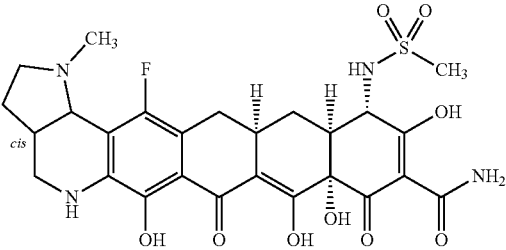 [SMILES: CN1CCC2CNc3c(O)c4c(c(F)c3C21)C[C@H]1C[C@H]2[C@H](NS(C)(=O)=O)C(O)=C(C(N)=O)C(=O)[C@@]2(O)C(O)=C1C4=O] |

TABLE 1-continued

| Compound No. | Compound Structure |
|---|---|
| S3-7-13-A (diastereomer A) S3-7-13-B (diastereomer B) | 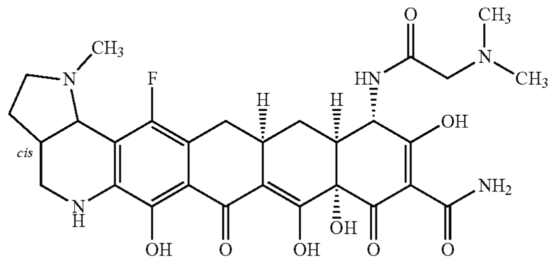 [SMILES: CN(C)CC(=O)N[C@@H]1C(O)=C(C(N)=O)C(=O)[C@@]2(O)C(O)=C3C(=O)c4c(O)c5c(c(F)c4C[C@H]3C[C@@H]12)C1C(CCN1C)CN5] |
| S4-14-1 (diastereomer A) | 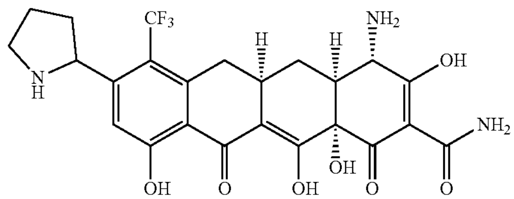 [SMILES: NC(=O)C1=C(O)[C@@H](N)[C@@H]2C[C@@H]3Cc4c(c(O)cc(C5CCCN5)c4C(F)(F)F)C(=O)C3=C(O)[C@]2(O)C1=O] |
| S4-14-2 (diastereomer A) | 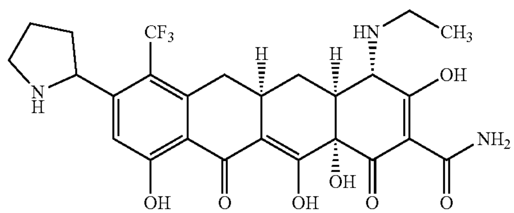 [SMILES: CCN[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-3 (diastereomer A) | 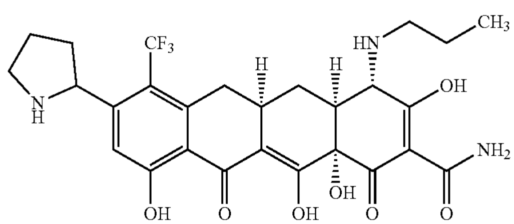 [SMILES: CCCN[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-4 (diastereomer A) | 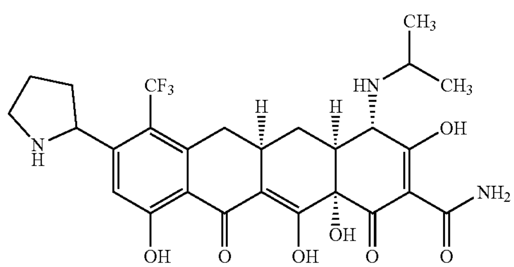 [SMILES: CC(C)N[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-5-A (diastereomer A) S4-14-S-B (diastereomer B) | 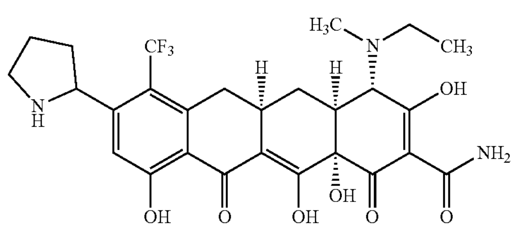 [SMILES: CCN(C)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |

TABLE 1-continued

| Compound No. | Compound Structure |
|---|---|
| S4-14-7 (diastereomer A) | 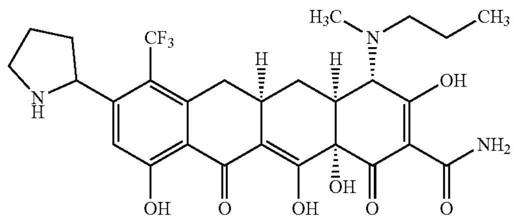 [SMILES: CCCN(C)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-8 (diastereomer A) | 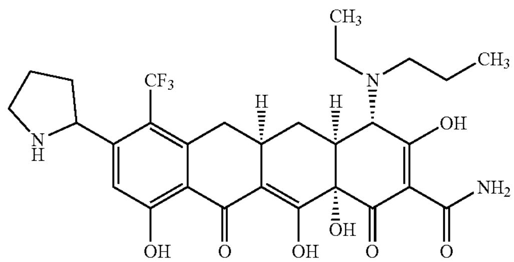 [SMILES: CCCN(CC)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-9 (diastereomer A) | 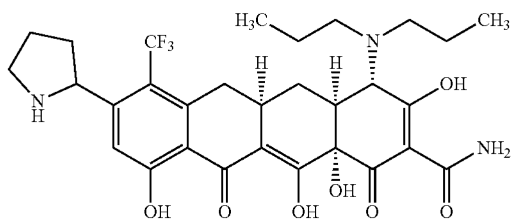 [SMILES: CCCN(CCC)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-10 (diastereomer A) | 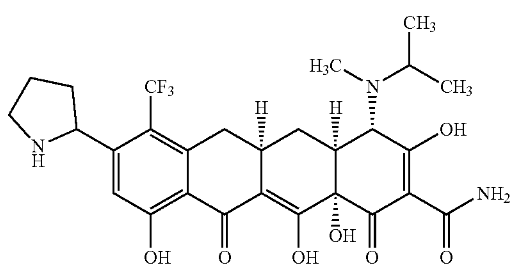 [SMILES: CC(C)N(C)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-11 (diastereomer A) | 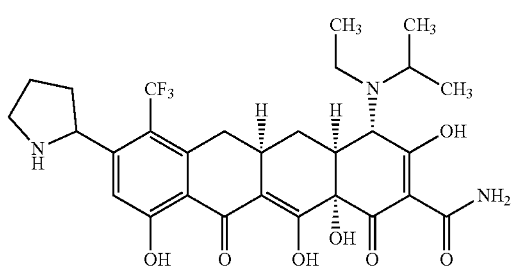 [SMILES: CCN(C(C)C)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-12 (diastereomer A) | 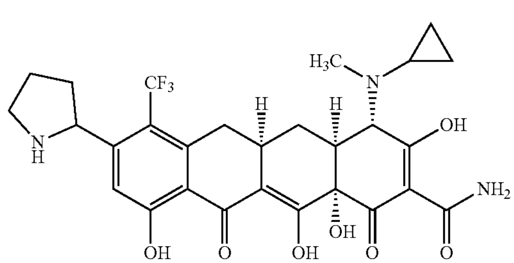 [SMILES: CN(C1CC1)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |

TABLE 1-continued

| Compound No. | Compound Structure |
| --- | --- |
| S4-14-13 (diastereomer A) | 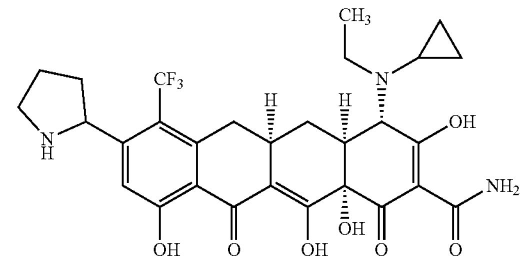 [SMILES: CCN(C1CC1)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-14-A (diastereomer A) S4-14-14-B (diastereomer B) | 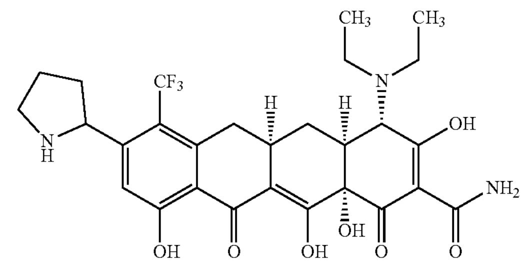 [SMILES: CCN(CC)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12] |
| S4-14-16 (diastereomer A) | 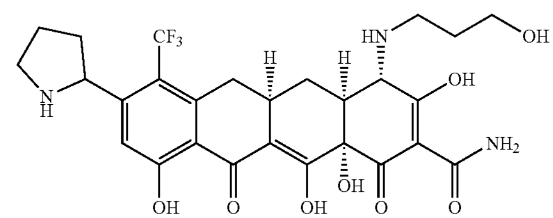 [SMILES: NC(=O)C1=C(O)[C@@H](NCCCO)[C@@H]2C[C@@H]3Cc4c(c(O)cc(C5CCCN5)c4C(F)(F)F)C(=O)C3=C(O)[C@]2(O)C1=O] |
| S4-14-17 (diastereomer A) | 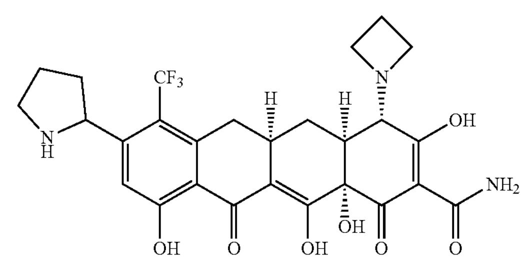 [SMILES: NC(=O)C1=C(O)[C@@H](N2CCC2)[C@@H]2C[C@@H]3Cc4c(c(O)cc(C5CCCN5)c4C(F)(F)F)C(=O)C3=C(O)[C@]2(O)C1=O] |
| S4-14-18 (diastereomer A) | 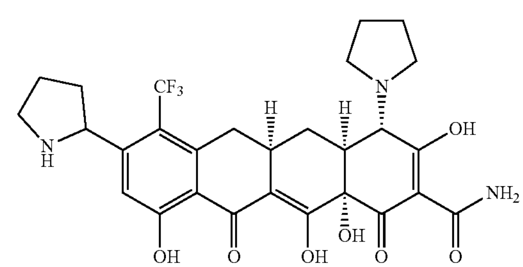 [SMILES: NC(=O)C1=C(O)[C@@H](N2CCCC2)[C@@H]2C[C@@H]3Cc4c(c(O)cc(C5CCCN5)c4C(F)(F)F)C(=O)C3=C(O)[C@]2(O)C1=O] |
| S5-10-1-A (diastereomer A) S5-10-1-B (diastereomer B) | 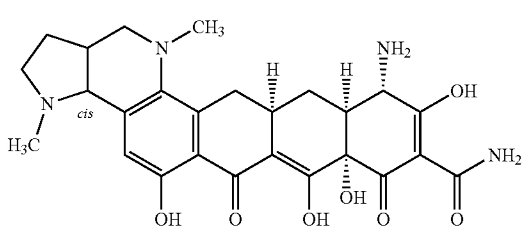 [SMILES: CN1CC2CCN(C)C2c2cc(O)c3c(c21)C[C@H]1C[C@H]2[C@H](N)C(O)=C(C(N)=O)C(=O)[C@@]2(O)C(O)=C1C3=O] |

TABLE 1-continued

| Compound No. | Compound Structure |
|---|---|
| S5-10-2-A (diastereomer A) S5-10-1-2-B (diastereomer B) | 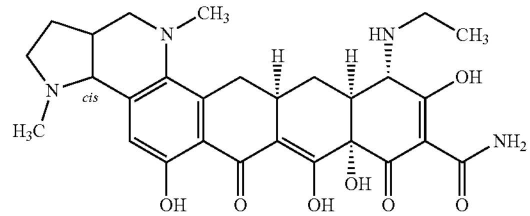 [SMILES: CCN[C@@H]1C(O)=C(C(N)=O)C(=O)[C@@]2(O)C(O)=C3C(=O)c4c(O)cc5c(c4C[C@H]3C[C@@H]12)N(C)CC1CCN(C)C51] |
| S5-10-3-A (diastereomer A) S5-10-3-B (diastereomer B) | 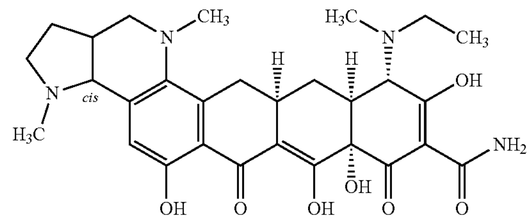 [SMILES: CCN(C)[C@@H]1C(O)=C(C(N)=O)C(=O)[C@@]2(O)C(O)=C3C(=O)c4c(O)cc5c(c4C[C@H]3C[C@@H]12)N(C)CC1CCN(C)C51] |
| S5-10-4-A (diastereomer A) S5-10-4-B (diastereomer B) | 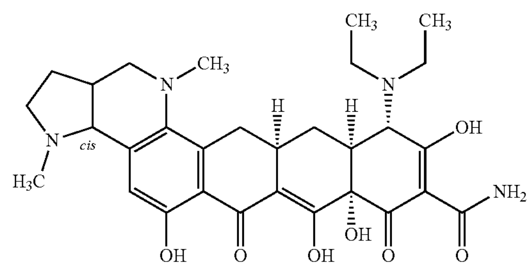 [SMILES: CCN(CC)[C@@H]1C(O)=C(C(N)=O)C(=O)[C@@]2(O)C(O)=C3C(=O)c4c(O)cc5c(c4C[C@H]3C[C@@H]12)N(C)CC1CCN(C)C51] |
| S6-6-1 (single diastereomer) | 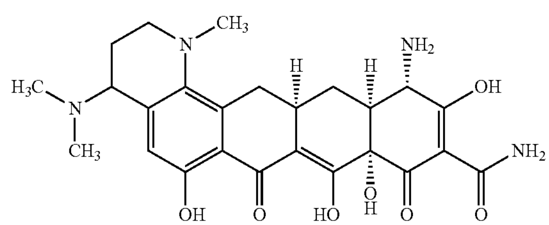 [SMILES: CN1CCC(N(C)C)c2cc(O)c3c(c21)C[C@H]1C[C@H]2[C@H](N)C(O)=C(C(N)=O)C(=O)[C@@]2(O)C(O)=C1C3=O] |
| S6-6-2 (single diastereomer) | 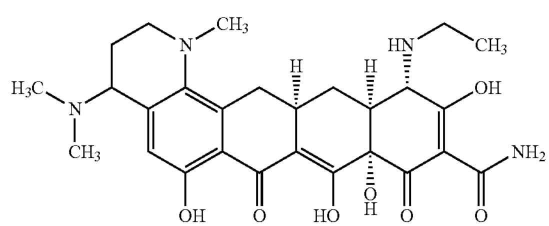 [SMILES: CCN[C@@H]1C(O)=C(C(N)=O)C(=O)[C@@]2(O)C(O)=C3C(=O)c4c(O)cc5c(c4C[C@H]3C[C@@H]12)N(C)CCC5N(C)C] |
| S6-6-3 (single diastereomer) | 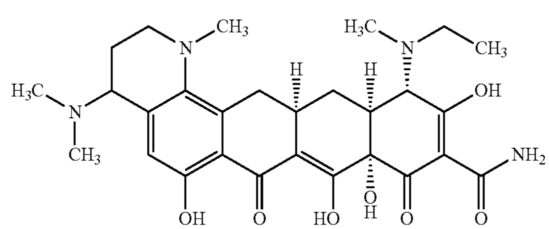 [SMILES: CCN(C)[C@@H]1C(O)=C(C(N)=O)C(=O)[C@@]2(O)C(O)=C3C(=O)c4c(O)cc5c(c4C[C@H]3C[C@@H]12)N(C)CCC5N(C)C] |
| S7-14-1-A (diastereomer A) S7-14-1-B (diastereomer B) | 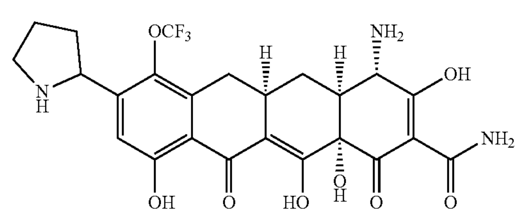 [SMILES: NC(=O)C1=C(O)[C@@H](N)[C@@H]2C[C@@H]3Cc4c(OC(F)(F)F)c(C5CCCN5)cc(O)c4C(=O)C3=C(O)[C@]2(O)C1=O] |

TABLE 1-continued

| Compound No. | Compound Structure |
|---|---|
| S7-14-2-A (diastereomer A) | 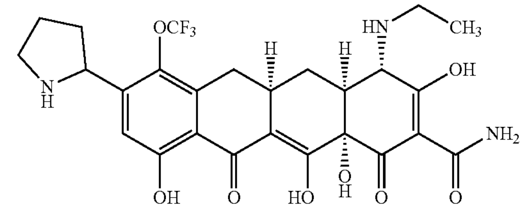 [SMILES: CCN[C@@H]1C(O)=C(C(N)=O)C(=O)[C@@]2(O)C(O)=C3C(=O)c4c(O)cc(C5CCCN5)c(OC(F)(F)F)c4C[C@H]3C[C@@H]12] |
| S7-14-3-A (diastereomer A) | 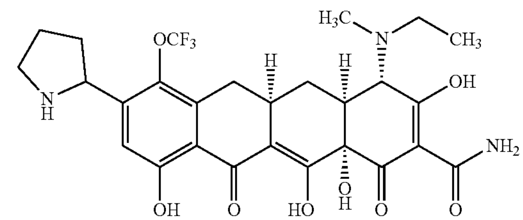 [SMILES: CCN(C)[C@@H]1C(O)=C(C(N)=O)C(=O)[C@@]2(O)C(O)=C3C(=O)c4c(O)cc(C5CCCN5)c(OC(F)(F)F)c4C[C@H]3C[C@@H]12] |
| S8-4-1 | 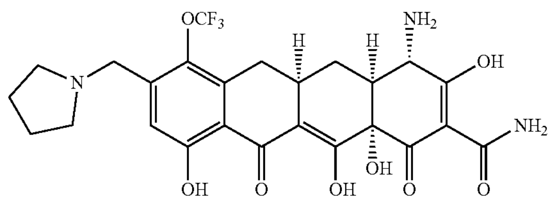 [SMILES: NC(=O)C1=C(O)[C@@H](N)[C@@H]2C[C@@H]3Cc4c(OC(F)(F)F)c(CN5CCCC5)cc(O)c4C(=O)C3=C(O)[C@]2(O)C1=O] |
| S8-4-2 | 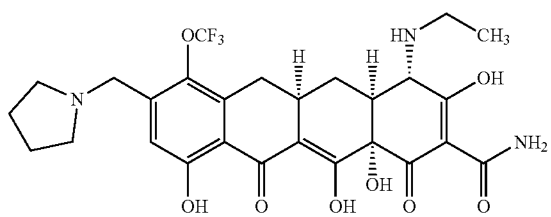 [SMILES: CCN[C@@H]1C(O)=C(C(N)=O)C(=O)[C@@]2(O)C(O)=C3C(=O)c4c(O)cc(CN5CCCC5)c(OC(F)(F)F)c4C[C@H]3C[C@@H]12] |
| S8-4-3 | 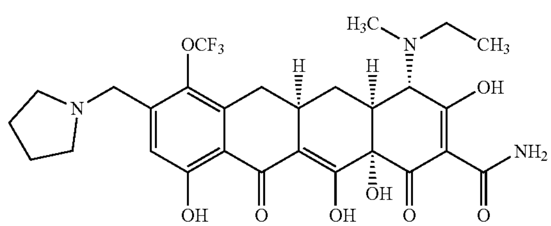 [SMILES: CCN(C)[C@@H]1C(O)=C(C(N)=O)C(=O)[C@@]2(O)C(O)=C3C(=O)c4c(O)cc(CN5CCCC5)c(OC(F)(F)F)c4C[C@H]3C[C@@H]12] |
| S9-4-1 | 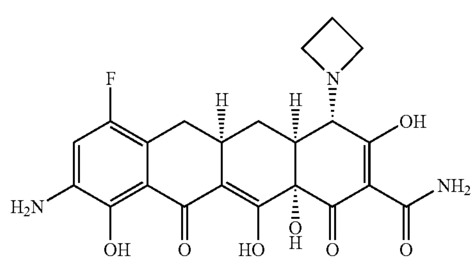 [SMILES: NC(=O)C1=C(O)[C@@H](N2CCC2)[C@@H]2C[C@@H]3Cc4c(F)cc(N)c(O)c4C(=O)C3=C(O)[C@]2(O)C1=O] |
| S9-5-1 | 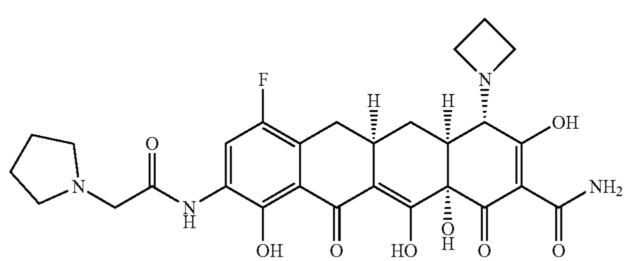 [SMILES: NC(=O)C1=C(O)[C@@H](N2CCC2)[C@@H]2C[C@@H]3Cc4c(F)cc(NC(=O)CN5CCCC5)c(O)c4C(=O)C3=C(O)[C@]2(O)C1=O] |

TABLE 1-continued

| Compound No. | Compound Structure |
| --- | --- |
| S9-5-2 | 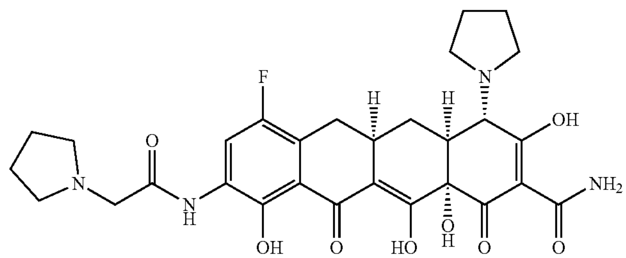 [SMILES: NC(=O)C1=C(O)[C@@H](N2CCCC2)[C@@H]2C[C@@H]3Cc4c(F)cc(NC(=O)CN5CCCC5)c(O)c4C(=O)C3=C(O)[C@]2(O)C1=O] |
| S9-5-3 | 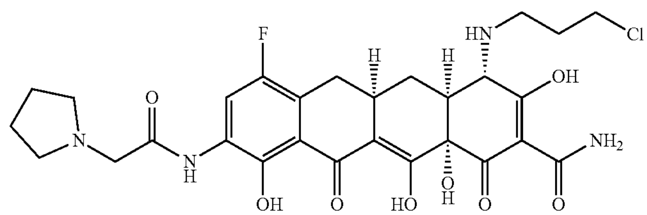 [SMILES: NC(=O)C1=C(O)[C@@H](NCCCCl)[C@@H]2C[C@@H]3Cc4c(F)cc(NC(=O)CN5CCCC5)c(O)c4C(=O)C3=C(O)[C@]2(O)C1=O] |
| S9-5-4 | 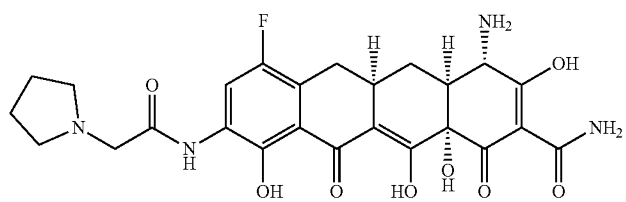 [SMILES: NC(=O)C1=C(O)[C@@H](N)[C@@H]2C[C@@H]3Cc4c(F)cc(NC(=O)CN5CCCC5)c(O)c4C(=O)C3=C(O)[C@]2(O)C1=O] |
| S9-5-5 | 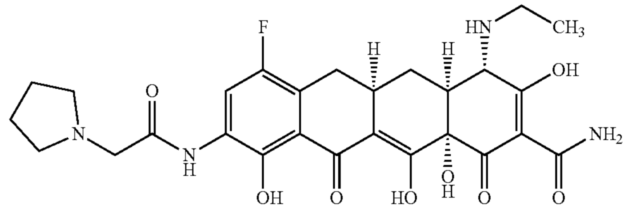 [SMILES: CCN[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12] |
| S9-5-6 | 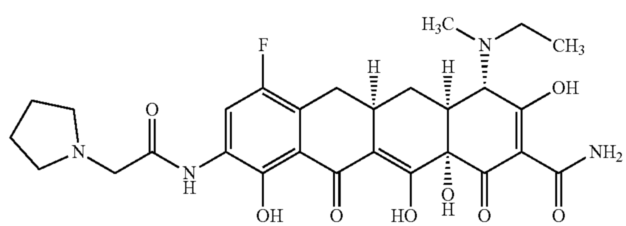 [SMILES: CCN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12] |
| S10-4-1 (single diastereomer) | 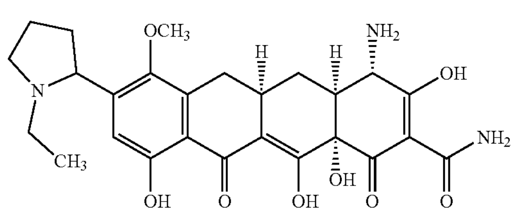 [SMILES: CCN1CCCC1c1cc(O)c2c(c1OC)C[C@H]1C[C@H]3[C@H](N)C(O)=C(C(N)=O)C(=O)[C@@]3(O)C(O)=C1C2=O] |
| S10-4-2 (single diastereomer) | 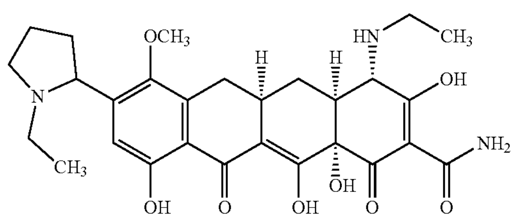 [SMILES: CCN[C@@H]1C(O)=C(C(N)=O)C(=O)[C@@]2(O)C(O)=C3C(=O)c4c(O)cc(C5CCCN5CC)c(OC)c4C[C@H]3C[C@@H]12] |

TABLE 1-continued

| Compound No. | Compound Structure |
|---|---|
| S10-4-3 (single diastereomer) | 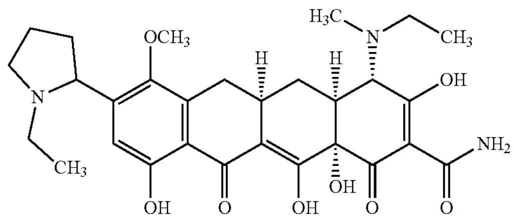 [SMILES: CCN1CCCC1c1cc(O)c2c(c1OC)C[C@H]1C[C@H]3[C@H](N(C)CC)C(O)=C(C(N)=O)C(=O)[C@@]3(O)C(O)=C1C2=O] |
| S11-3-1 | 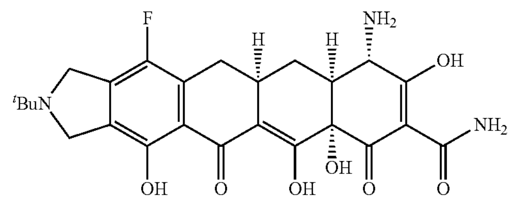 |
| S11-3-2 | 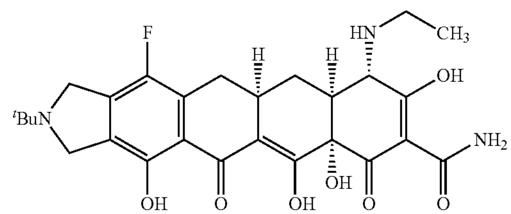 |
| S11-3-3 | 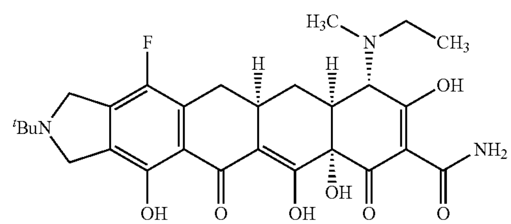 |
| S12-8-1-A (diastereomer A) S12-8-1-B (diastereomer B) | 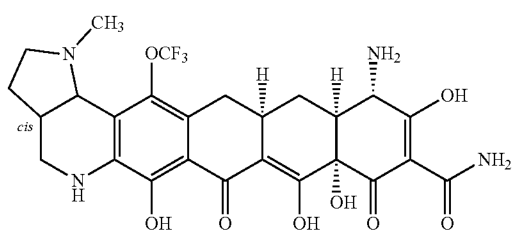 [SMILES: CN1CCC2CNc3c(O)c4c(c(OC(F)(F)F)c3C21)C[C@H]1C[C@H]2[C@H](N)C(O)=C(C(N)=O)C(=O)[C@@]2(O)C(O)=C1C4=O] |
| S12-8-2-A (diastereomer A) | 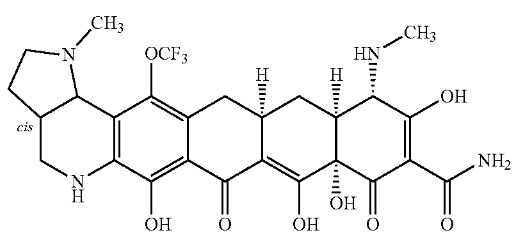 [SMILES: CN[C@@H]1C(O)=C(C(N)=O)C(=O)[C@@]2(O)C(O)=C3C(=O)c4c(O)c5c(c(OC(F)(F)F)c4C[C@H]3C[C@@H]12)C1C(CCN1C)CN5] |
| S12-8-3-A (diastereomer A) S12-8-3-B) (diastereomer B) | 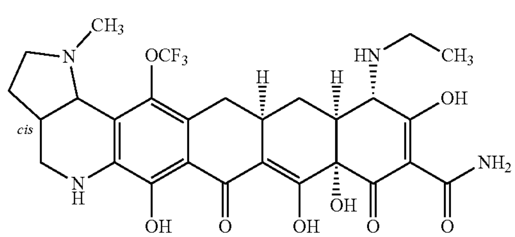 [SMILES: CCN[C@@H]1C(O)=C(C(N)=O)C(=O)[C@@]2(O)C(O)=C3C(=O)c4c(O)c5c(c(OC(F)(F)F)c4C[C@H]3C[C@@H]12)C1C(CCN1C)CN5] |

TABLE 1-continued

| Compound No. | Compound Structure |
|---|---|
| S12-8-4-A (diastereomer A) | 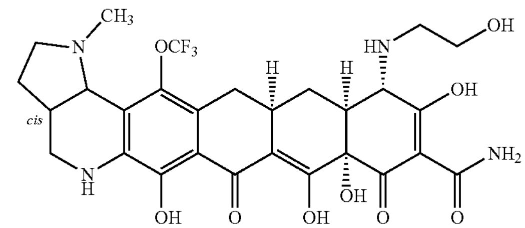 [SMILES: CN1CCC2CNc3c(O)c4c(c(OC(F)(F)F)c3C21)C[C@H]1C[C@H]2[C@H](NCCO)C(O)=C(C(N)=O)C(=O)[C@@]2(O)C(O)=C1C4=O] |
| S12-8-5-A (diastereomer A) | 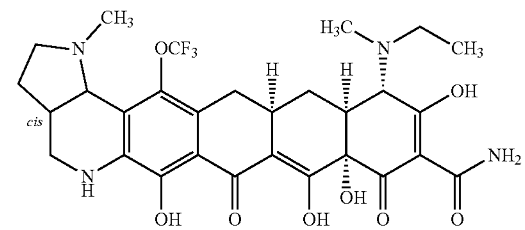 [SMILES: CCN(C)[C@@H]1C(O)=C(C(N)=O)C(=O)[C@@]2(O)C(O)=C3C(=O)c4c(O)c5c(c(OC(F)(F)F)c4C[C@H]3C[C@@H]12)C1C(CCN1C)CN5] |
| S12-8-6-A (diastereomer A) S12-8-6-B (diastereomer B) | 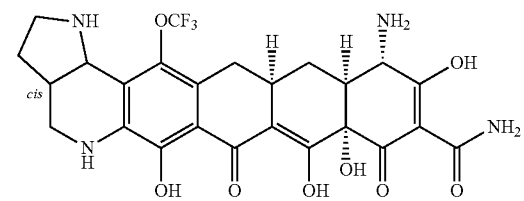 [SMILES: NC(=O)C1=C(O)[C@@H](N)[C@@H]2C[C@@H]3Cc4c(OC(F)(F)F)c5c(c(O)c4C(=O)C3=C(O)[C@]2(O)C1=O)NCC1CCNC51] |
| S12-8-7-A (diastereomer A) | 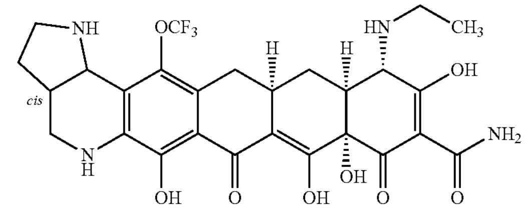 [SMILES: CCN[C@@H]1C(O)=C(C(N)=O)C(=O)[C@@]2(O)C(O)=C3C(=O)c4c(O)c5c(c(OC(F)(F)F)c4C[C@H]3C[C@@H]12)C1NCCC1CN5] |
| S12-8-8-A (diastereomer A) | 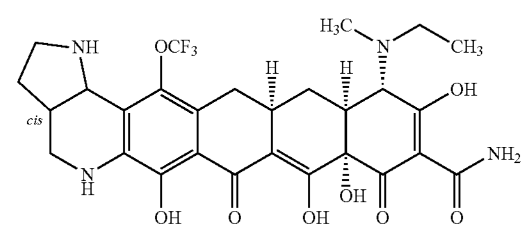 [SMILES: CCN(C)[C@@H]1C(O)=C(C(N)=O)C(=O)[C@@]2(O)C(O)=C3C(=O)c4c(O)c5c(c(OC(F)(F)F)c4C[C@H]3C[C@@H]12)C1NCCC1CN5] |
| S13-5-1 | 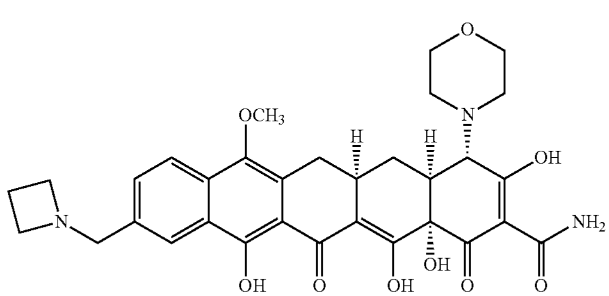 [SMILES: COc1c2c(c(O)c3cc(CN4CCC4)ccc13)C(=O)C1=C(O)[C@]3(O)C(=O)C(C(N)=O)=C(O)[C@@H](N4CCOCC4)[C@@H]3C[C@@H]1C2] |

TABLE 1-continued

| Compound No. | Compound Structure |
|---|---|
| S13-5-2 | 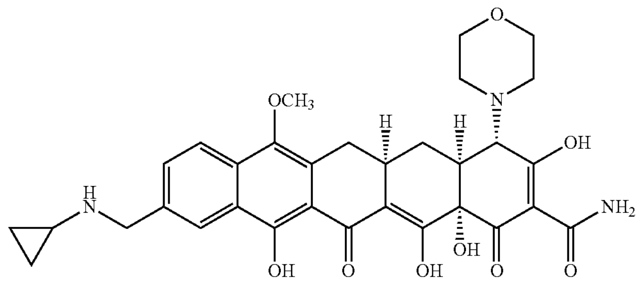 [SMILES: COc1c2c(c(O)c3cc(CNC4CC4)ccc13)C(=O)C1=C(O)[C@]3(O)C(=O)C(C(N)=O)=C(O)[C@@H](N4CCOCC4)[C@@H]3C[C@@H]1C2] |
| S14-8-1 | 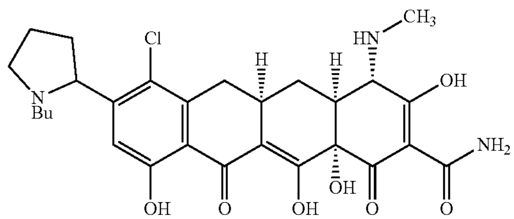 |
| S14-8-2 | 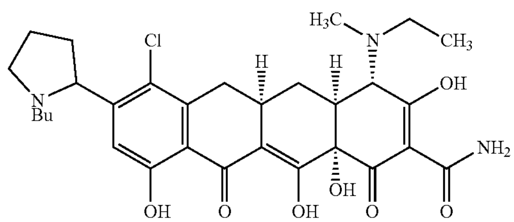 |
| S14-8-3-A (diastereomer A) S14-8-3-B (diastereomer B) | 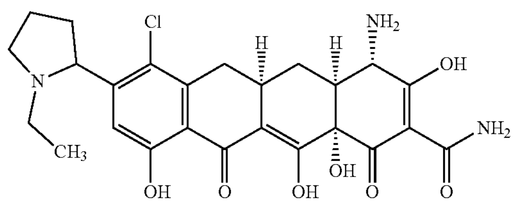 [SMILES: CCN1CCCC1c1cc(O)c2c(c1Cl)C[C@H]1C[C@H]3[C@H](N)C(O)=C(C(N)=O)C(=O)[C@@]3(O)C(O)=C1C2=O] |
| S15-10-1 | 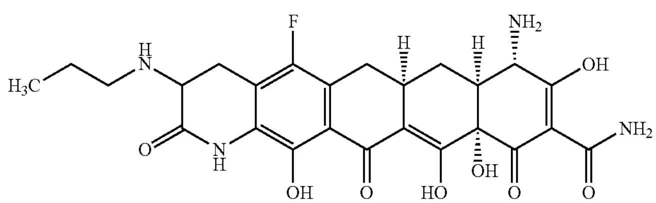 [SMILES: CCCNC1Cc2c(F)c3c(c(O)c2NC1=O)C(=O)C1=C(O)[C@]2(O)C(=O)C(C(N)=O)=C(O)[C@@H](N)[C@@H]2C[C@@H]1C3] |
| S15-10-2 | 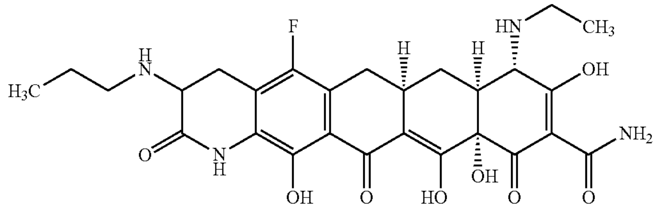 [SMILES: CCCNC1Cc2c(F)c3c(c(O)c2NC1=O)C(=O)C1=C(O)[C@]2(O)C(=O)C(C(N)=O)=C(O)[C@@H](NCC)[C@@H]2C[C@@H]1C3] |
| S15-10-3-A (diastereomer A) S15-10-3-B (diastereomer B) | 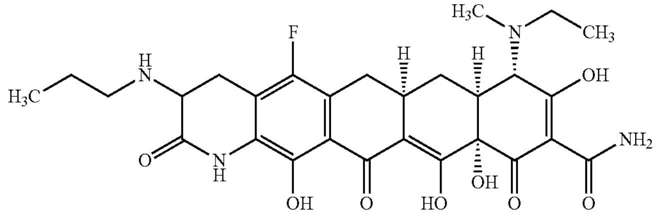 [SMILES: CCCNC1Cc2c(F)c3c(c(O)c2NC1=O)C(=O)C1=C(O)[C@]2(O)C(=O)C(C(N)=O)=C(O)[C@@H](N(C)CC)[C@@H]2C[C@@H]1C3] |

TABLE 1-continued

| Compound No. | Compound Structure |
| --- | --- |
| S16-7-1 (single diastereomer) | (structure) |
| S16-7-2 (single diastereomer) | (structure) |
| S16-7-3 (single diastereomer) | (structure) |
| S16-7-4 (single diastereomer) | (structure) |
| S16-7-5 (single diastereomer) | (structure) |
| S16-7-6 (single diastereomer) | (structure) |

TABLE 1-continued

| Compound No. | Compound Structure |
| --- | --- |
| S17-3-1 | 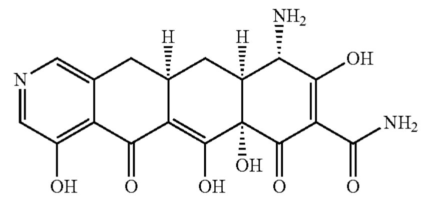 [SMILES: NC(=O)C1=C(O)[C@@H](N)[C@@H]2C[C@@H]3Cc4cncc(O)c4C(=O)C3=C(O)[C@]2(O)C1=O] |
| S17-3-2 | 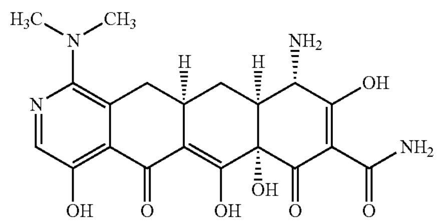 [SMILES: CN(C)c1ncc(O)c2c1C[C@H]1C[C@H]3[C@H](N)C(O)=C(C(N)=O)C(=O)[C@@]3(O)C(O)=C1C2=O] |
| S17-3-3 | 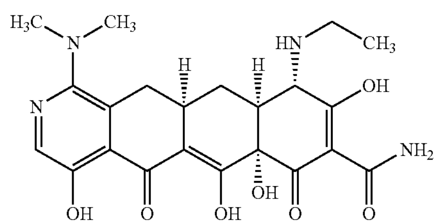 [SMILES: CCN[C@@H]1C(O)=C(C(N)=O)C(=O)[C@@]2(O)C(O)=C3C(=O)c4c(O)cnc(N(C)C)c4C[C@H]3C[C@@H]12] |
| S17-3-4 | 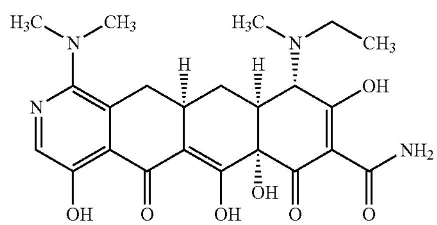 [SMILES: CCN(C)[C@@H]1C(O)=C(C(N)=O)C(=O)[C@@]2(O)C(O)=C3C(=O)c4c(O)cnc(N(C)C)c4C[C@H]3C[C@@H]12] |
| S17-3-5 | 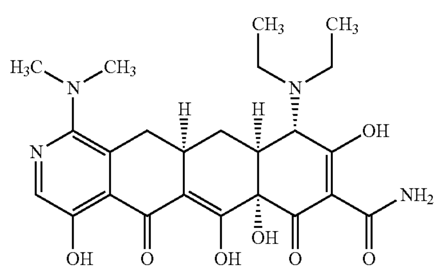 [SMILES: CCN(CC)[C@@H]1C(O)=C(C(N)=O)C(=O)[C@@]2(O)C(O)=C3C(=O)c4c(O)cnc(N(C)C)c4C[C@H]3C[C@@H]12] |
| S17-3-6 | 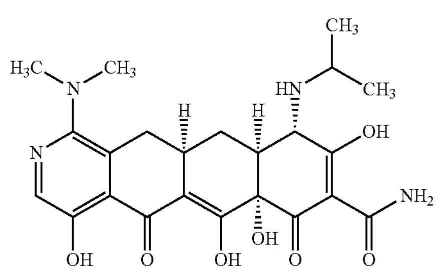 [SMILES: CC(C)N[C@@H]1C(O)=C(C(N)=O)C(=O)[C@@]2(O)C(O)=C3C(=O)c4c(O)cnc(N(C)C)c4C[C@H]3C[C@@H]12] |

TABLE 1-continued

| Compound No. | Compound Structure |
|---|---|
| S17-3-7 | 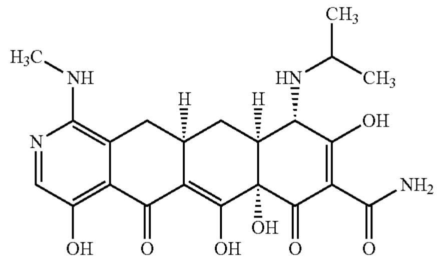 [SMILES: CNc1ncc(O)c2c1C[C@H]1C[C@H]3[C@H](NC(C)C)C(O)=C(C(N)=O)C(=O)[C@@]3(O)C(O)=C1C2=O] |
| S17-3-8 | 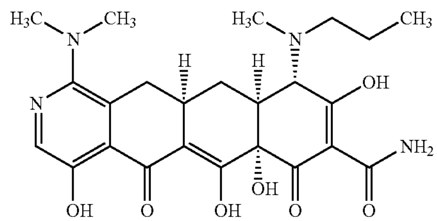 [SMILES: CCCN(C)[C@@H]1C(O)=C(C(N)=O)C(=O)[C@@]2(O)C(O)=C3C(=O)c4c(O)cnc(N(C)C)c4C[C@H]3C[C@@H]12] |
| S17-3-9 | 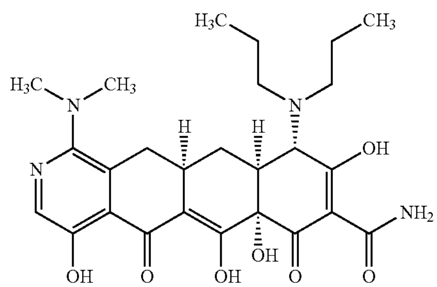 [SMILES: CCCN(CCC)[C@@H]1C(O)=C(C(N)=O)C(=O)[C@@]2(O)C(O)=C3C(=O)c4c(O)cnc(N(C)C)c4C[C@H]3C[C@@H]12] |
| S17-3-10 | 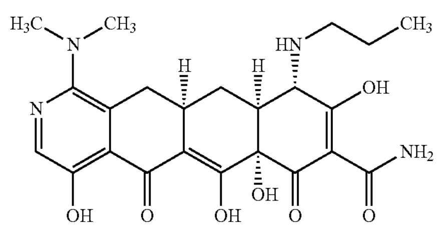 [SMILES: CCCN[C@@H]1C(O)=C(C(N)=O)C(=O)[C@@]2(O)C(O)=C3C(=O)c4c(O)cnc(N(C)C)c4C[C@H]3C[C@@H]12] |
| S17-3-11 | 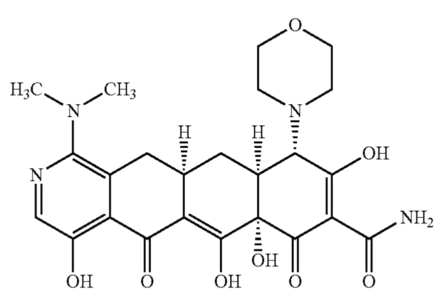 [SMILES: CN(C)c1ncc(O)c2c1C[C@H]1C[C@H]3[C@H](N4CCOCC4)C(O)=C(C(N)=O)C(=O)[C@@]3(O)C(O)=C1C2=O] |
| S18-5-1-1 | 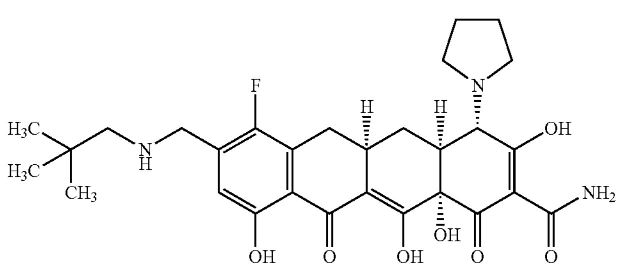 [SMILES: CC(C)(C)CNCc1cc(O)c2c(c1F)C[C@H]1C[C@H]3[C@H](N4CCCC4)C(O)=C(C(N)=O)C(=O)[C@@]3(O)C(O)=C1C2=O] |

TABLE 1-continued

| Compound No. | Compound Structure |
|---|---|
| S18-5-1-2 | 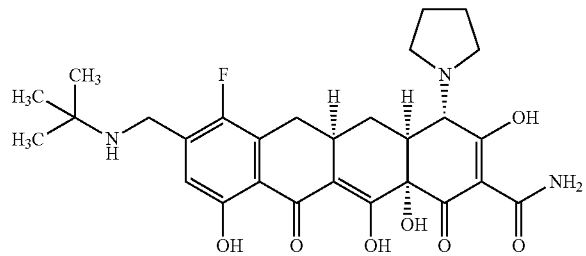 [SMILES: CC(C)(C)NCc1cc(O)c2c(c1F)C[C@H]1C[C@H]3[C@H](N4CCCC4)C(O)=C(C(N)=O)C(=O)[C@@]3(O)C(O)=C1C2=O] |
| S18-5-2-1 | 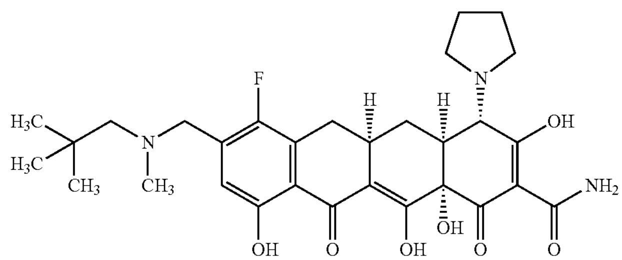 [SMILES: CN(Cc1cc(O)c2c(c1F)C[C@H]1C[C@H]3[C@H](N4CCCC4)C(O)=C(C(N)=O)C(=O)[C@@]3(O)C(O)=C1C2=O)CC(C)(C)C] |
| S18-5-2-2 | 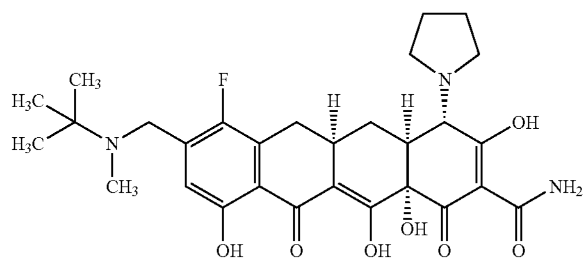 [SMILES: CN(Cc1cc(O)c2c(c1F)C[C@H]1C[C@H]3[C@H](N4CCCC4)C(O)=C(C(N)=O)C(=O)[C@@]3(O)C(O)=C1C2=O)C(C)(C)C] |
| S19-7-1-B (diastereomer B) | 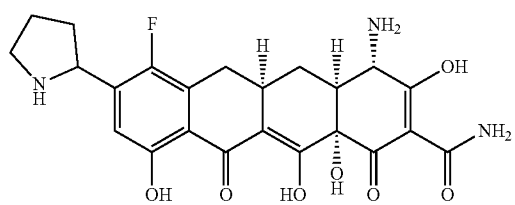 [SMILES: NC(=O)C1=C(O)[C@@H](N)[C@@H]2C[C@@H]3Cc4c(F)c(C5CCCN5)cc(O)c4C(=O)C3=C(O)[C@]2(O)C1=O] |
| S19-7-2 | 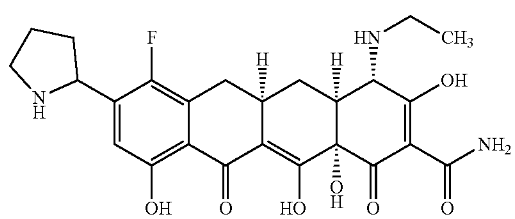 [SMILES: CCN[C@@H]1C(O)=C(C(N)=O)C(=O)[C@@]2(O)C(O)=C3C(=O)c4c(O)cc(C5CCCN5)c(F)c4C[C@H]3C[C@@H]12] |
| S19-7-3-A (diastereomer A) S19-7-3-B (diastereomer B) | 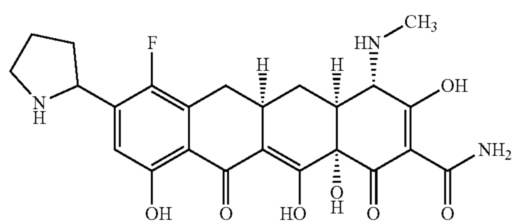 [SMILES: CN[C@@H]1C(O)=C(C(N)=O)C(=O)[C@@]2(O)C(O)=C3C(=O)c4c(O)cc(C5CCCN5)c(F)c4C[C@H]3C[C@@H]12] |

TABLE 1-continued

| Compound No. | Compound Structure |
|---|---|
| S19-7-4-A (diastereomer A) S19-7-4-B (diastereomer B) | 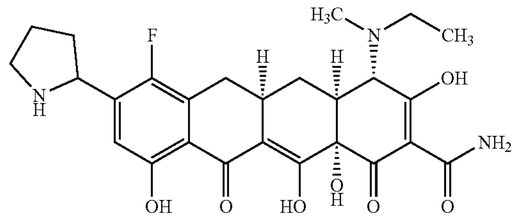 [SMILES: CCN(C)[C@@H]1C(O)=C(C(N)=O)C(=O)[C@@]2(O)C(O)=C3C(=O)c4c(O)cc(C5CCCN5)c(F)c4C[C@H]3C[C@@H]12] |
| S19-7-5-A (diastereomer A) S19-7-5-B (diastereomer B) | 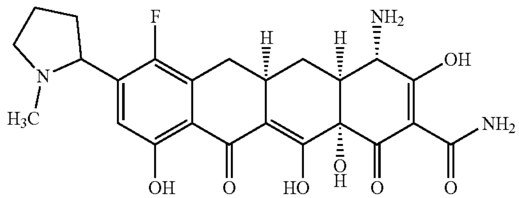 [SMILES: CN1CCCC1c1cc(O)c2c(c1F)C[C@H]1C[C@H]3[C@H](N)C(O)=C(C(N)=O)C(=O)[C@@]3(O)C(O)=C1C2=O] |
| S19-7-6 | 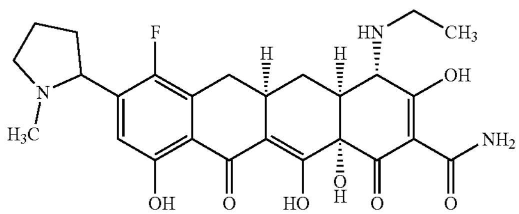 [SMILES: CCN[C@@H]1C(O)=C(C(N)=O)C(=O)[C@@]2(O)C(O)=C3C(=O)c4c(O)cc(C5CCCN5C)c(F)c4C[C@H]3C[C@@H]12] |
| S19-7-7-A (diastereomer A) S19-7-7-B (diastereomer B) | 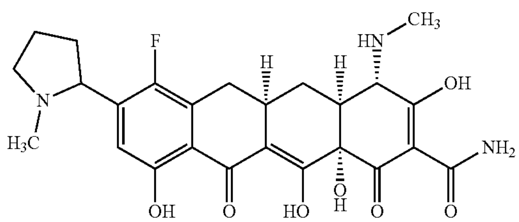 |
| S20-4-1 (single diastereomer) | 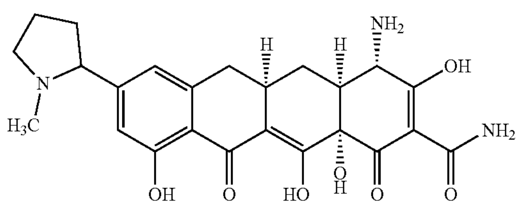 [SMILES: CN1CCCC1c1cc(O)c2c(c1)C[C@H]1C[C@H]3[C@H](N)C(O)=C(C(N)=O)C(=O)[C@@]3(O)C(O)=C1C2=O] |
| S20-4-2 (single diastereomer) | 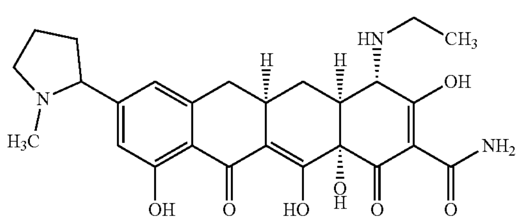 [SMILES: CCN[C@@H]1C(O)=C(C(N)=O)C(=O)[C@@]2(O)C(O)=C3C(=O)c4c(O)cc(C5CCCN5C)cc4C[C@H]3C[C@@H]12] |
| S20-4-3 (single diastereomer) | 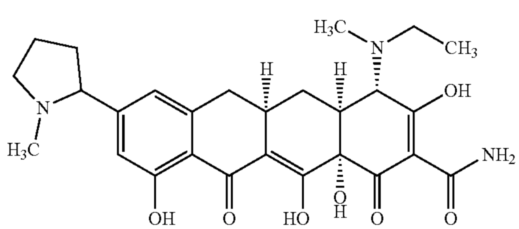 [SMILES: CCN(C)[C@@H]1C(O)=C(C(N)=O)C(=O)[C@@]2(O)C(O)=C3C(=O)c4c(O)cc(C5CCCN5C)cc4C[C@H]3C[C@@H]12] |

TABLE 1-continued

| Compound No. | Compound Structure |
|---|---|
| S20-4-4 (single diastereomer) | 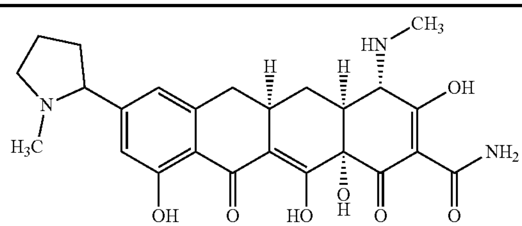 |
| S21-5-1 | 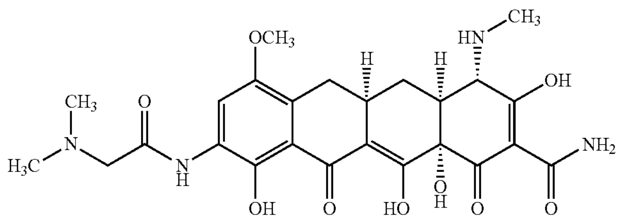 [SMILES: CN[C@@H]1C(O)=C(C(N)=O)C(=O)[C@@]2(O)C(O)=C3C(=O)c4c(O)c(NC(=O)CN(C)C)cc(OC)c4C[C@H]3C[C@@H]12] |
| S21-5-2 | 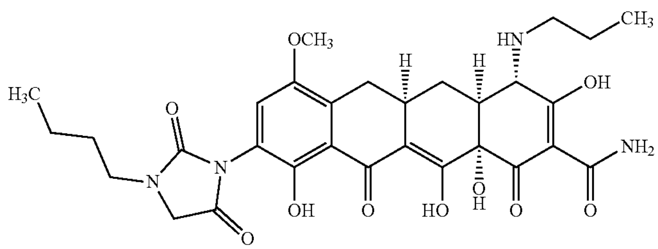 [SMILES: CCCCN1CC(=O)N(c2cc(OC)c3c(c2O)C(=O)C2=C(O)[C@]4(O)C(=O)C(C(N)=O)=C(O)[C@@H](NCCC)[C@@H]4C[C@@H]2C3)C1=O] |
| S21-5-3 | 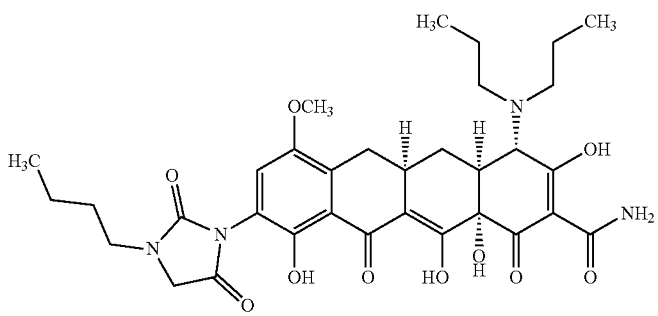 [SMILES: CCCCN1CC(=O)N(c2cc(OC)c3c(c2O)C(=O)C2=C(O)[C@]4(O)C(=O)C(C(N)=O)=C(O)[C@@H](N(CCC)CCC)[C@@H]4C[C@@H]2C3)C1=O] |
| S21-5-4 | 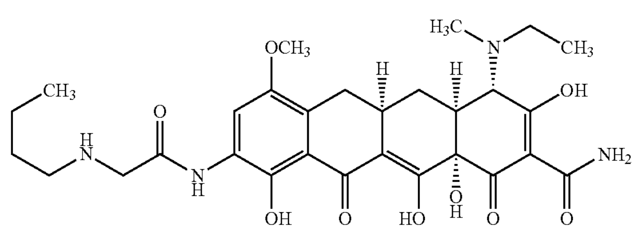 [SMILES: CCCCNCC(=O)Nc1cc(OC)c2c(c1O)C(=O)C1=C(O)[C@]3(O)C(=O)C(C(N)=O)=C(O)[C@@H](N(C)CC)[C@@H]3C[C@@H]1C2] |

An eighth embodiment of the invention is a compound of Formula II:

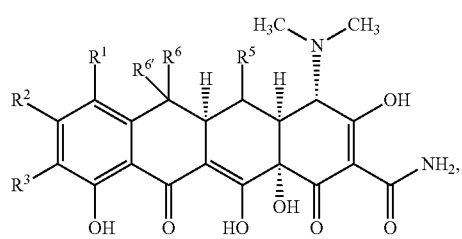

or a pharmaceutically acceptable salt thereof, wherein:

$R^1$ and $R^2$ are taken together with atoms to which they are bound to form a carbocyclyl or heterocyclyl ring and $R^3$ is selected from hydrogen, halo, —($C_1$-$C_6$ alkyl), —$OR^A$, —C(O)$NR^BR^{B'}$, $NR^BR^{B'}$, S(O)$_{0-2}R^C$, —($C_0$-$C_6$ alkylene)-carbocyclyl, and —($C_0$-$C_6$ alkylene)-heterocyclyl; or $R^2$ and $R^3$ are taken together with atoms to which they are bound to form a carbocyclyl or heterocyclyl ring and $R^1$ is selected from hydrogen, halo, —($C_1$-$C_6$ alkyl), —$OR^A$, —C(O)$NR^BR^{B'}$, $NR^BR^{B'}$, S(O)$_{0-2}R^C$, —($C_0$-$C_6$ alkylene)-carbocyclyl, and —($C_0$-$C_6$ alkylene)-heterocyclyl;

each of $R^5$ and $R^6$ is independently selected from hydrogen, halo, —($C_1$-$C_6$ alkyl), —$OR^A$, —C(O)$NR^BR^{B'}$, $NR^BR^{B'}$, S(O)$_{0-2}R^C$, —($C_0$-$C_6$ alkylene)-carbocyclyl, and —($C_0$-$C_6$ alkylene)-heterocyclyl;

$R^{6'}$ is selected from hydrogen, —($C_1$-$C_6$ alkyl) and —($C_3$-$C_6$ cycloalkyl);

each $R^A$ is independently selected from hydrogen, —($C_1$-$C_6$ alkyl), —($C_0$-$C_6$ alkylene)-carbocyclyl, —($C_0$-$C_6$ alkylene)-heterocyclyl, —C(O)—($C_1$-$C_6$ alkyl), —C(O)—($C_0$-$C_6$ alkylene)-carbocyclyl, —C(O)—($C_0$-$C_6$ alkylene)-heterocyclyl, and —C(O)N($R^D$)($R^E$);

each $R^B$ and each $R^{B'}$ is independently selected from hydrogen, —($C_1$-$C_6$ alkyl), —($C_0$-$C_6$ alkylene)-carbocyclyl, —($C_0$-$C_6$ alkylene)-heterocyclyl, —S(O)$_{1-2}$—($C_1$-$C_6$ alkyl), —S(O)$_{1-2}$—($C_0$-$C_6$ alkylene)-carbocyclyl, —S(O)$_{1-2}$—($C_0$-$C_6$ alkylene)-heterocyclyl, —C(O)—($C_1$-$C_6$ alkyl), —C(O)—($C_0$-$C_6$ alkylene)-carbocyclyl, —C(O)H, —C(O)—($C_0$-$C_6$ alkylene)-heterocyclyl, and —C(O)—($C_0$-$C_6$ alkylene)-N($R^D$)($R^E$);

each $R^C$ is independently selected from —($C_1$-$C_6$ alkyl), —($C_0$-$C_6$ alkylene)-carbocyclyl and —($C_0$-$C_6$ alkylene)-heterocyclyl; and each $R^D$ and each $R^E$ is independently selected from hydrogen, —($C_1$-$C_6$ alkyl), —($C_0$-$C_6$ alkylene)-carbocyclyl, and —($C_0$-$C_6$ alkylene)-heterocyclyl, wherein any alkyl, alkylene, carbocyclyl or heterocyclyl portion of $R^1$, $R^2$, $R^3$, $R^5$, $R^6$, $R^{6'}$, $R^A$, $R^B$, $R^{B'}$, $R^C$, $R^D$, or $R^E$ or formed by taking $R^1$ and $R^2$ or $R^2$ and $R^3$ together is optionally and independently substituted. Alternative values for the variables in Formula II are as described and defined in the first through seventh embodiments, or any aspect thereof.

In a first aspect of the eighth embodiment, the compound is represented by Formula IIa:

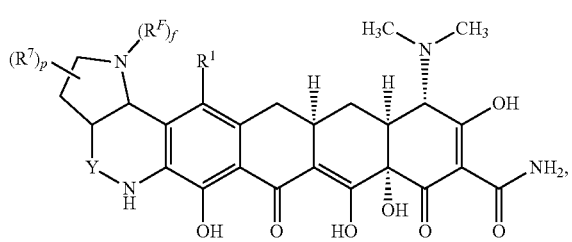

(IIa)

or a pharmaceutically acceptable salt thereof, wherein:

each $R^7$, if present, is independently selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$ alkylene)-$NR^BR^{B'}$, and $S(O)_{0-2}R^C$;

p is 0, 1, 2, 3 or 4;

Y is C(O) or C($R^8$)$_2$ wherein each $R^8$ is independently selected from hydrogen, —($C_1$-$C_6$)alkyl and —($C_3$-$C_6$ cycloalkyl); and f is 0 or 1. The remaining variables are as described and defined in the first through seventh embodiments, or any aspect thereof, or the eighth embodiment.

In a further aspect of the first aspect of the eighth embodiment, p is 0. The remaining variables are as described and defined in the first through seventh embodiments, or any aspect thereof, or the eighth embodiment, or first aspect thereof.

In a second aspect of the eighth embodiment, the compound is represented by Formula IIb:

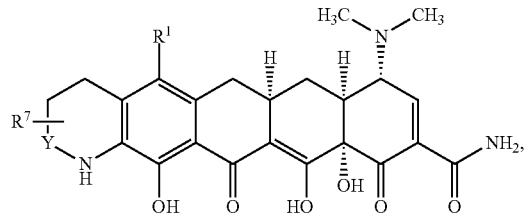

(IIb)

or a pharmaceutically acceptable salt thereof, wherein $R^7$ is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^BR^{B'}$, and $S(O)_{0-2}R^C$; and Y is C(O) or C($R^8$)$_2$ wherein each $R^8$ is independently selected from hydrogen, —($C_1$-$C_6$)alkyl and —($C_3$-$C_6$ cycloalkyl). The remaining variables are as described and defined in the first through seventh embodiments, or any aspect thereof, or the eighth embodiment, or first aspect thereof.

In a third aspect of the eighth embodiment, the compound is represented by Formula IIb-1:

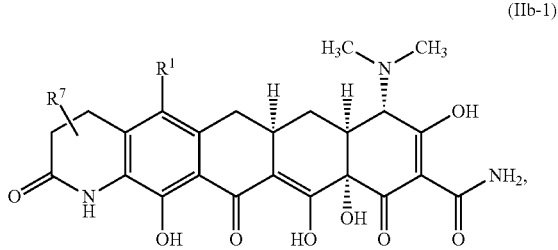

(IIb-1)

or a pharmaceutically acceptable salt thereof, wherein $R^7$ is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^BR^{B'}$, and $S(O)_{0-2}R^C$. The remaining variables are as described and defined in the first through seventh embodiments, or any aspect thereof, or the eighth embodiment, or first or second aspect thereof.

In a fourth aspect of the eighth embodiment, the compound is represented by Formula IId:

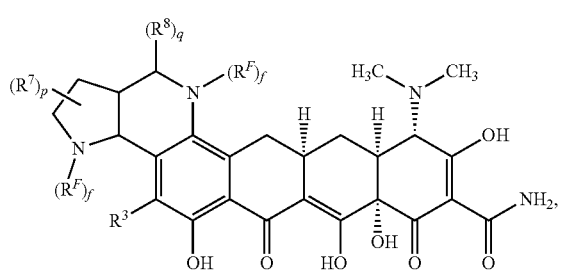

(IId)

or a pharmaceutically acceptable salt thereof, wherein:

each $R^7$ and $R^8$, if present, is independently selected from halo, =O, $C_1$-$C_4$ fluoroalkyl, $C_1$-$C_4$ alkyl, $C_3$-$C_{10}$ carbocyclyl, a 4-13 membered heterocyclyl, $OR^A$, —($C_0$-$C_6$alkylene)-$NR^BR^{B'}$, and $S(O)_{0-2}R^C$;

p is 0, 1, 2, 3 or 4;
q is 0, 1 or 2; and
each f is independently 0 or 1. The remaining variables are as described and defined in the first through seventh embodiments, or any aspect thereof, or the eighth embodiment, or first through third aspects thereof.

In a further aspect of the fourth aspect of the eighth embodiment, p and q are each 0. The remaining variables are as described and defined in the first through seventh embodiments, or any aspect thereof, or the eighth embodiment, or first through fourth aspects thereof.

In a fifth aspect of the eighth embodiment, each $R^F$ is independently selected from —($C_1$-$C_6$ alkyl), —($C_1$-$C_6$ haloalkyl), —($C_1$-$C_6$ hydroxyalkyl), —($C_0$-$C_6$ alkylene)-carbocyclyl, —($C_0$-$C_6$ alkylene)-heterocyclyl, —($C_0$-$C_6$ alkylene)-C(O)$_2$—($C_1$-$C_6$ alkyl) and —($C_1$-$C_6$ alkylene)-$NR^BR^{B'}$. The remaining variables are as described and defined in the first through seventh embodiments, or any aspect thereof, or the eighth embodiment, or first through fourth aspects thereof.

In a sixth aspect of the eighth embodiment, each f is 0. The remaining variables are as described and defined in the first through seventh embodiments, or any aspect thereof, or the eighth embodiment, or first through fifth aspects thereof.

In a seventh aspect of the eighth embodiment, each f is 1. The remaining variables are as described and defined in the first through seventh embodiments, or any aspect thereof, or the eighth embodiment, or first through sixth aspects thereof.

In an eighth aspect of the eighth embodiment, the ring formed by $R^1$ and $R^2$ or $R^2$ and $R^3$ together with atoms to which they are bound is a 4-7 membered non-aromatic heterocyclic ring optionally containing 1-2 heteroatoms independently selected from N, S and O. The remaining variables are as described and defined in the first through seventh embodiments, or any aspect thereof, or the eighth embodiment, or first through seventh aspects thereof.

In a ninth aspect of the eighth embodiment:
any alkyl, or alkylene portion of $R^1$, $R^2$, $R^3$, $R^5$, $R^6$ is optionally and independently substituted with one or more substituents independently selected from halo, =O, $OR^A$, $NR^BR^{B'}$, and S(O)$_{0-2}R^C$;
any alkyl or alkylene portion of $R^{6'}$, $R^A$, or $R^C$, is optionally and independently substituted with one or more fluoro;
any carbocyclyl or heterocyclyl portion of any of $R^1$, $R^2$, $R^3$, $R^5$, $R^6$, or any ring formed by taking together $R^1$ and $R^2$ or $R^2$ and $R^3$ is optionally and independently substituted on a carbon atom with one or more substituents independently selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^BR^{B'}$, and S(O)$_{0-2}R^C$;
any heterocyclyl portion of any of $R^1$, $R^2$, $R^3$, $R^5$, $R^6$, or any ring formed by taking together $R^1$ and $R^2$ or $R^2$ and $R^3$ is optionally and independently substituted on a substitutable nitrogen atom with $R^F$;
each $R^F$ is independently selected from —($C_1$-$C_6$ alkyl), —($C_1$-$C_6$ haloalkyl), —($C_1$-$C_6$ hydroxyalkyl), —($C_0$-$C_6$ alkylene)-carbocyclyl, —($C_0$-$C_6$ alkylene)-heterocyclyl, —S(O)$_{1-2}$—($C_1$-$C_6$ alkyl), —S(O)$_{1-2}$—($C_0$-$C_6$ alkylene)-carbocyclyl, —S(O)$_{1-2}$—($C_0$-$C_6$ alkylene)-heterocyclyl, —C(O)—($C_1$-$C_6$ alkyl), —C(O)—($C_0$-$C_6$ alkylene)-carbocyclyl, —C(O)H, —C(O)—($C_0$-$C_6$ alkylene)-heterocyclyl, —($C_0$-$C_6$ alkylene)-C(O)$_2$—($C_1$-$C_6$ alkyl), —($C_1$-$C_6$ alkylene)-$NR^BR^{B'}$ and —C(O)N($R^D$)($R^E$);

any carbocyclyl or heterocyclyl portion of $R^A$, $R^B$, $R^{B'}$, $R^C$, $R^D$, $R^E$, $R^F$, any cycloalkyl portion of $R^{6'}$, or any substituent of $R^1$, $R^2$, $R^3$, $R^5$, $R^6$ is optionally and independently substituted on a carbon atom with a one or more substituents independently selected from fluoro, chloro, $C_1$-$C_4$ alkyl, $C_1$-$C_4$ fluoroalkyl, —O—$C_1$-$C_4$ alkyl, —O—$C_1$-$C_4$ fluoroalkyl, =O, —OH, —NH$_2$, —NH($C_1$-$C_4$ alkyl), and —N($C_1$-$C_4$ alkyl)$_2$;

any heterocyclyl portion of $R^A$, $R^B$, $R^{B'}$, $R^C$, $R^D$, $R^E$, $R^F$, or any heterocyclyl substituent of $R^1$, $R^2$, $R^3$, $R^5$, or $R^6$ is optionally substituted on a substitutable nitrogen atom with —$C_1$-$C_4$ alkyl, or —S(O)$_{1-2}$—($C_1$-$C_4$ alkyl). The remaining variables are as described and defined in the first through seventh embodiments, or any aspect thereof, or the eighth embodiment, or first through eighth aspects thereof.

In a tenth aspect of the eighth embodiment, the compound is represented by Formula IIa-1:

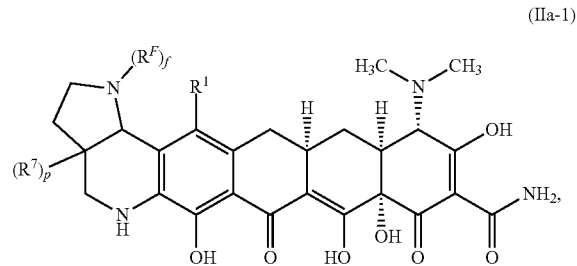

(IIa-1)

or a pharmaceutically acceptable salt thereof, wherein p is 0 or 1 and $R^7$, if present, is —$C_1$-$C_6$ alkyl. The remaining variables are as described and defined in the first through seventh embodiments, or any aspect thereof, or the eighth embodiment, or first through ninth aspects thereof.

In an eleventh aspect of the eighth embodiment, the compound is represented by Formula IIb-2:

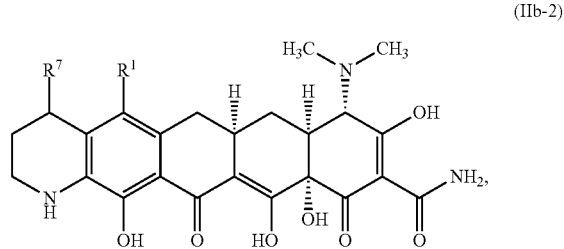

(IIb-2)

or a pharmaceutically acceptable salt thereof, wherein $R^7$ is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^BR^{B'}$, and S(O)$_{0-2}R^C$. The remaining variables are as described and defined in the first through seventh embodiments, or any aspect thereof, or the eighth embodiment, or first through tenth aspects thereof.

In a twelfth aspect of the eighth embodiment, any carbocyclyl or heterocyclyl portion of any ring formed by taking together $R^1$ and $R^2$ or $R^2$ and $R^3$ is optionally and independently substituted on a carbon atom with one or more substituents independently selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl)

and —(C_0-C_6alkylene)-NR^B R^B'. The remaining variables are as described and defined in the first through seventh embodiments, or any aspect thereof, or the eighth embodiment, or first through eleventh aspects thereof.

A ninth embodiment of the invention is a compound represented by Formula IIc:

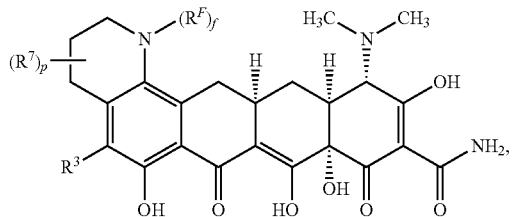

(IIc)

or a pharmaceutically acceptable salt thereof, wherein R^7, if present, is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), OR^A, —($C_0$-$C_6$alkylene)-NR^B R^B', and S(O)_{0-2}R^C; p is 0 or 1; and f is 0 or 1. Values and alternative values for the remaining variables are as described and defined in the first through eighth embodiments, or any aspect thereof.

In a first aspect of the ninth embodiment, p is 1. The remaining variables are as described and defined in the first through eighth embodiments, or any aspect thereof, or the ninth embodiment.

In a second aspect of the ninth embodiment, the compound is represented by Formula IIc-1:

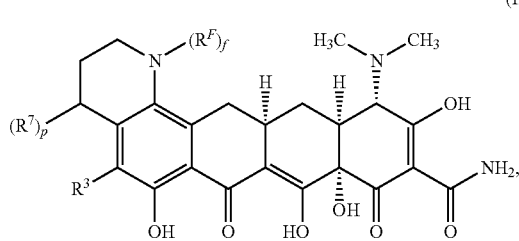

(IIc-1)

or a pharmaceutically acceptable salt thereof. The variables are as described and defined in the first through eighth embodiments, or any aspect thereof, or the ninth embodiment, or first aspect thereof.

In a third aspect of the ninth embodiment, R^7, if present, is selected from —($C_0$-$C_6$ alkylene)-($C_3$-$C_{10}$ carbocyclyl), —($C_0$-$C_6$ alkylene)-(4-13 membered heterocyclyl) and —($C_0$-$C_6$alkylene)-NR^B R^B'. The remaining variables are as described and defined in the first through eighth embodiments, or any aspect thereof, or the ninth embodiment, or first or second aspect thereof.

In a fourth aspect of the ninth embodiment, R^7, if present, is —NR^B R^B'. The remaining variables are as described and defined in the first through eighth embodiments, or any aspect thereof, or the ninth embodiment, or first through third aspects thereof.

In one embodiment, the compound of the invention is one of the compounds set forth in Tables 2A-2F hereinbelow, or a pharmaceutically acceptable salt thereof.

A tenth embodiment of the invention is a compound of Formula Ia:

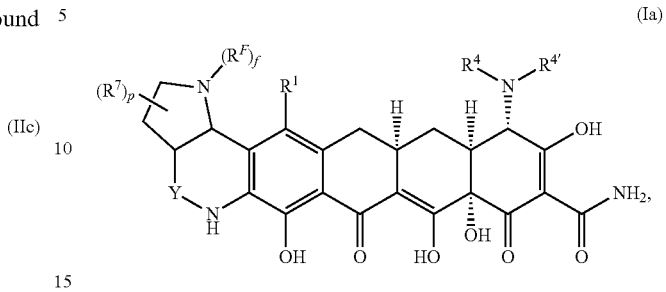

(Ia)

or a pharmaceutically acceptable salt thereof, wherein:

each R^7, if present, is independently selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), OR^A, —($C_0$-$C_6$alkylene)-NR^B R^B', and S(O)_{0-2}R^C;

p is 0, 1, 2, 3 or 4;

Y is C(O) or C(R^8)_2 wherein each R^8 is independently selected from hydrogen, —($C_1$-$C_6$)alkyl and —($C_3$-$C_6$ cycloalkyl); and f is 0 or 1. Values and alternative values for the variables are as described and defined in the first through ninth embodiments, or any aspect thereof.

In a first aspect of the tenth embodiment, p is 0. The remaining variables are as described and defined in the first through ninth embodiments, or any aspect thereof, or the tenth embodiment.

In a second aspect of the tenth embodiment, each R^8 is hydrogen. The remaining variables are as described and defined in the first through ninth embodiments, or any aspect thereof, or the tenth embodiment, or first aspect thereof.

An eleventh embodiment of the invention is a compound of Formula I, or a pharmaceutically acceptable salt thereof, wherein X is C(R^2); R^2 is optionally substituted —($C_0$-$C_1$ alkylene)-(4-6-membered heterocyclyl). Values and alternative values for the variables are as described and defined in the first through tenth embodiments, or any aspect thereof.

In a first aspect of the eleventh embodiment, R^3 is hydrogen. The remaining variables are as described and defined in the first through tenth embodiments, or any aspect thereof, or the eleventh embodiment.

In a second aspect of the eleventh embodiment, R^2 is optionally substituted —($C_0$-$C_1$ alkylene)-pyrrolidinyl. The remaining variables are as described and defined in the first through tenth embodiments, or any aspect thereof, or the eleventh embodiment, or first aspect thereof.

In a third aspect of the eleventh embodiment, R^2 is optionally substituted pyrrolidin-2-yl. The remaining variables are as described and defined in the first through tenth embodiments, or any aspect thereof, or the eleventh embodiment, or first or second aspect thereof.

In a fourth aspect of the eleventh embodiment, R^2 is optionally substituted —($C_1$ alkylene)-(pyrrolidin-1-yl). The remaining variables are as described and defined in the first through tenth embodiments, or any aspect thereof, or the eleventh embodiment, or first through third aspects thereof.

A twelfth embodiment of the invention is a compound of Formula Ib:

(Ib)

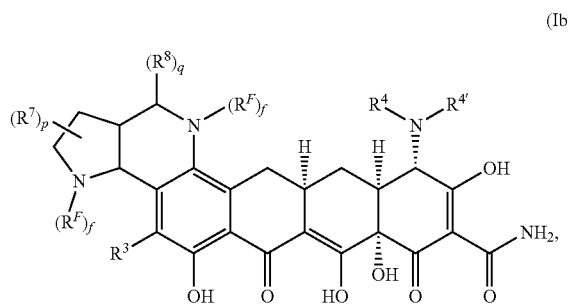

or a pharmaceutically acceptable salt thereof, wherein:

each $R^7$ and $R^8$, if present, is independently selected from halo, =O, $C_1$-$C_4$ fluoroalkyl, $C_1$-$C_4$ alkyl, $C_3$-$C_{10}$ carbocyclyl, a 4-13 membered heterocyclyl, $OR^A$, —($C_0$-$C_6$alkylene)-$NR^B R^{B'}$, and $S(O)_{0-2}R^C$;

p is 0, 1, 2, 3 or 4;

q is 0, 1 or 2; and each f is independently 0 or 1. Values and alternative values for the variables are as described and defined in the first through eleventh embodiments, or any aspect thereof.

In a first aspect of the twelfth embodiment, p and q are each 0. The remaining variables are as described and defined in the first through eleventh embodiments, or any aspect thereof, or the twelfth embodiment.

In a second aspect of the twelfth embodiment, $R^3$ is hydrogen. The remaining variables are as described and defined in the first through eleventh embodiments, or any aspect thereof, or the twelfth embodiment, or first aspect thereof.

A thirteenth embodiment of the invention is a compound represented by Formula Ic:

(Ic)

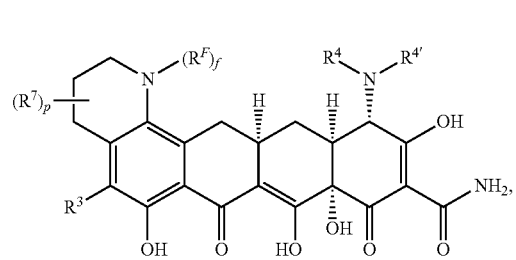

or a pharmaceutically acceptable salt thereof, wherein $R^7$, if present, is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^B R^{B'}$, and $S(O)_{0-2}R^C$; p is 0 or 1; and f is 0 or 1. Values and alternative values for the remaining variables are as described and defined in the first through twelfth embodiments, or any aspect thereof.

In a first aspect of the thirteenth embodiment, p is 1. The remaining variables are as described and defined in the first through twelfth embodiments, or any aspect thereof, or the thirteenth embodiment.

In a second aspect of the thirteenth embodiment, the compound is represented by Formula Ic-1:

(Ic-1)

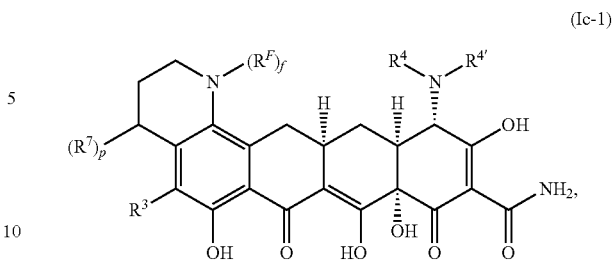

or a pharmaceutically acceptable salt thereof. The variables are as described and defined in the first through twelfth embodiments, or any aspect thereof, or the thirteenth embodiment, or first aspect thereof.

In a third aspect of the thirteenth embodiment, $R^7$, if present, is selected from —($C_0$-$C_6$ alkylene)-($C_3$-$C_{10}$ carbocyclyl), —($C_0$-$C_6$ alkylene)-(4-13 membered heterocyclyl) and —($C_0$-$C_6$ alkylene)-$NR^B R^{B'}$. The remaining variables are as described and defined in the first through twelfth embodiments, or any aspect thereof, or the thirteenth embodiment, or first or second aspect thereof.

In a fourth aspect of the thirteenth embodiment, $R^7$, if present, is —$NR^B R^{B'}$. The remaining variables are as described and defined in the first through twelfth embodiments, or any aspect thereof, or the thirteenth embodiment, or first through third aspects thereof.

In a fourteenth embodiment of the invention, the compound is a compound represented by Formula I, or a pharmaceutically acceptable salt thereof, wherein X is N and $R^3$ is hydrogen. Values and alternative values for the remaining variables are as described and defined in the first through thirteenth embodiments, or any aspect thereof.

In a first aspect of the fourteenth embodiment, $R^1$ is selected from hydrogen and $NR^B R^{B'}$. The remaining variables are as described and defined in the first through thirteenth embodiments, or any aspect thereof, or the fourteenth embodiment.

A fifteenth embodiment of the invention is a compound of Formula I, or a pharmaceutically acceptable salt thereof, wherein X is $C(R^2)$ and $R^2$ is ($C_1$ alkylene)-$NR^B R^{B'}$. Values and alternative values for the remaining variables are as described and defined in the first through fourteenth embodiments, or any aspect thereof.

In a first aspect of the fifteenth embodiment, $R^B$ and $R^{B'}$ are each independently selected from hydrogen and —($C_1$-$C_6$ alkyl). The remaining variables are as described and defined in the first through fourteenth embodiments, or any aspect thereof, or the fifteenth embodiment.

A sixteenth embodiment of the invention is a compound represented by Formula Id:

(Id)

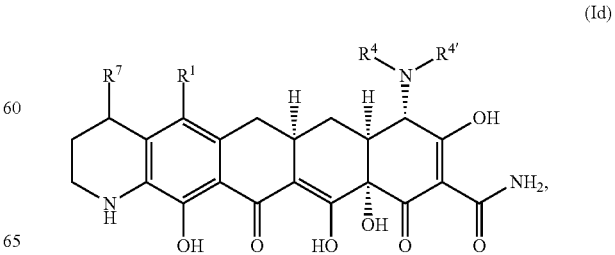

or a pharmaceutically acceptable salt thereof, wherein $R^7$ is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^BR^{B'}$, and $S(O)_{0-2}R^C$. Values and alternative values for the variables are as defined in the first through fifteenth embodiments, or any aspect thereof.

In a first aspect of the sixteenth embodiment, $R^7$ is 4-6 membered heterocyclyl or —$NR^BR^{B'}$. The remaining variables are as described and defined in the first through fifteenth embodiments, or any aspect thereof, or the sixteenth embodiment.

A seventeenth embodiment of the invention is a compound represented by Formula Ie:

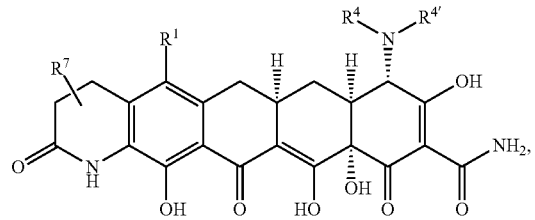

(Ie)

or a pharmaceutically acceptable salt thereof, wherein $R^7$ is selected from halo, =O, $C_1$-$C_4$ fluoroalkyl, $C_1$-$C_4$ alkyl, —($C_0$-$C_6$ alkylene)-($C_3$-$C_{10}$ carbocyclyl), —($C_0$-$C_6$ alkylene)-(4-13 membered heterocyclyl), $OR^A$, —($C_0$-$C_6$alkylene)-$NR^BR^{B'}$, and $S(O)_{0-2}R^C$. Values and alternative values for the variables are as defined in the first through sixteenth embodiments, or any aspect thereof.

In a first aspect of the seventeenth embodiment, $R^7$ is 4-6 membered heterocyclyl or —$NR^BR^{B'}$. The remaining variables are as described and defined in the first through sixteenth embodiments, or any aspect thereof, or the seventeenth embodiment.

In an additional aspect of any of the preceding embodiments, or any aspect thereof, each $R^A$ is independently selected from hydrogen, —($C_1$-$C_6$ alkyl), —($C_0$-$C_6$ alkylene)-carbocyclyl, —($C_0$-$C_6$ alkylene)-heterocyclyl, —S—($C_1$-$C_6$ alkyl), —S—($C_0$-$C_6$ alkylene)-carbocyclyl, —S—($C_0$-$C_6$ alkylene)-heterocyclyl, —C(O)—($C_1$-$C_6$ alkyl), —C(O)—($C_0$-$C_6$ alkylene)-carbocyclyl, —C(O)—($C_0$-$C_6$ alkylene)-heterocyclyl, and —C(O)N($R^D$)($R^E$).

The compounds in Tables 1 and 2A-2F contain stereocenters for which the stereochemistry is not indicated. The compounds of the invention encompass all possible diastereomers resulting from all possible configurations at these stereocenters.

The chemical moiety indicated when f in —N($R^F$)$_f$— is 0 in the structural formulae described herein is —N(H)—. Similarly, when q in —($R^8$)$_q$ is 0, it means that the carbon atom attached to —($R^8$)$_q$ is attached to two hydrogen atoms.

"Alkyl" means an optionally substituted saturated aliphatic branched or straight-chain monovalent hydrocarbon radical having the specified number of carbon atoms. Thus, "($C_1$-$C_6$) alkyl" means a radical having from 1-6 carbon atoms in a linear or branched arrangement. "($C_1$-$C_6$)alkyl" includes methyl, ethyl, propyl, butyl, pentyl and hexyl.

"Alkylene" means an optionally substituted saturated aliphatic branched or straight-chain divalent hydrocarbon radical having the specified number of carbon atoms. Thus, "($C_1$-$C_6$)alkylene" means a divalent saturated aliphatic radical having from 1-6 carbon atoms in a linear arrangement, e.g., —[($CH_2$)$_n$]—, where n is an integer from 1 to 6, "($C_1$-$C_6$)alkylene" includes methylene, ethylene, propylene, butylene, pentylene and hexylene. Alternatively, "($C_1$-$C_6$) alkylene" means a divalent saturated radical having from 1-6 carbon atoms in a branched arrangement, for example: —[($CH_2CH_2CH_2CH_2CH(CH_3)$)]—, —[($CH_2CH_2CH_2CH_2C(CH_3)_2$)]—, —[($CH_2C(CH_3)_2CH(CH_3)$)]—, and the like. A specific branched $C_3$-alkylene is

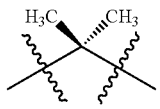

and a specific $C_4$-alkylene is

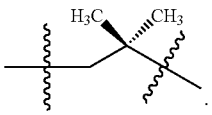

"Aryl" or "aromatic" means an aromatic monocyclic or polycyclic (e.g. bicyclic or tricyclic) carbocyclic ring system. In one embodiment, "aryl" is a 6-12 membered monocylic or bicyclic system. Aryl systems include, but not limited to, phenyl, naphthalenyl, fluorenyl, indenyl, azulenyl, and anthracenyl.

"Carbocyclyl" means a cyclic group, wherein all ring atoms in the ring bound to the rest of the compound (also known as the "first ring") are carbon atoms. "Carbocyclyl" includes 3-12 membered saturated or unsaturated aliphatic cyclic hydrocarbon rings or 6-12 membered aryl rings. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

A fused bicyclic carbocyclyl has two rings which have two adjacent ring atoms in common. The first ring is a monocyclic carbocyclyl and the ring fused to the first ring (also known as the "second ring") is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl.

A spiro bicyclic carbocyclyl has two rings which have only one ring atom in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remainder of the ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "$C_3$-$C_7$ cycloalkyl" means a hydrocarbon radical of a (3-7 membered) saturated aliphatic cyclic hydrocarbon ring. A $C_3$-$C_7$ cycloalkyl includes, but is not limited to cyclopropyl, cyclobutyl, cyclopentyl, cyclohexyl and cycloheptyl.

"Cycloalkene" means an aliphatic cyclic hydrocarbon ring having one or more double bonds in the ring.

"Cycloalkyne" means an aliphatic cyclic hydrocarbon ring having one or more triple bonds in the ring.

"Hetero" refers to the replacement of at least one carbon atom member in a ring system with at least one heteroatom selected from N, S, and O. "Hetero" also refers to the replacement of at least one carbon atom member in a acyclic system. When one heteroatom is S, it can be optionally mono- or di-oxygenated (i.e. —S(O)— or —S(O)$_2$—). A hetero ring system or a hetero acyclic system may have 1, 2, 3 or 4 carbon atom members replaced by a heteroatom.

"Heterocyclyl" means a cyclic 4-12 membered saturated or unsaturated aliphatic or aromatic ring system containing 1, 2, 3, 4 or 5 heteroatoms independently selected from N, O and S, wherein the first ring comprises a ring heteroatom. When one heteroatom is S, it can be optionally mono- or di-oxygenated (i.e. —S(O)— or —S(O)$_2$—). The heterocyclyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0] heptane.

A spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$) cycloalkyl. Alternatively, the second ring is phenyl. Example of spiro bicyclic heterocyclyl includes, but are not limited to, azaspiro[4.4]nonane, 7-azaspiro[4.4]nonane, azasprio[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1] nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

Polycyclic heterocyclyls have more than two rings, wherein the first ring is a heterocyclyl (e.g., three rings resulting in a tricyclic ring system) and adjacent rings having at least one ring atom in common and are heterocyclyl or carbocyclyl. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common. Examples of polycyclic heterocyclyls include

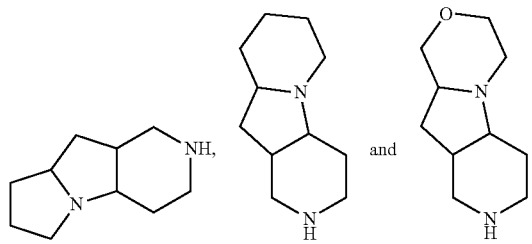

"Heteroaryl" or "heteroaromatic ring" means a 5-12 membered monovalent heteroaromatic monocyclic or bicylic ring radical. A heteroaryl contains 1, 2, 3 or 4 heteroatoms independently selected from N, O, and S. Heteroaryls include, but are not limited to, furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

"Halogen" used herein refers to fluorine, chlorine, bromine, or iodine.

"Alkoxy" means an alkyl radical attached through an oxygen linking atom. "($C_1$-$C_6$)-alkoxy" includes methoxy, ethoxy, propoxy, butoxy, pentoxy and hexoxy.

Haloalkyl and halocycloalkyl include mono, poly, and perhaloalkyl groups where each halogen is independently selected from fluorine, chlorine, and bromine.

"Halogen" and "halo" are interchangeably used herein and each refers to fluorine, chlorine, bromine, or iodine.

"Fluoro" means —F.

"Chloro" means —Cl.

As used herein, "fluoro-substituted-($C_1$-$C_4$)alkyl" or "$C_1$-$C_4$ fluoroalkyl" means a ($C_1$-$C_4$)alkyl substituted with one or more —F groups. Examples of fluoro-substituted-($C_1$-$C_4$) alkyl include, but are not limited to, —CF$_3$, —CH$_2$CF$_3$, —CH$_2$CF$_2$H, —CH$_2$CH$_2$F and —CH$_2$CH$_2$CF$_3$.

"Hydroxyalkyl," as used herein, refers to an alkyl group substituted with one or more hydroxyls. Hydroxyalkyl includes mono, poly, and perhydroxyalkyl groups. Examples of hydroxyalkyls include —$CH_2CH_2OH$ and —$CH_2CH(OH)CH_2OH$.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^°$; —$(CH_2)_{0-4}OR^°$; —$O(CH_2)_{0-4}R^°$, —O—$(CH_2)_{0-4}C(O)OR^°$; —$(CH_2)_{0-4}CH(OR^°)_2$; —$(CH_2)_{0-4}SR^°$; —$(CH_2)_{0-4}Ph$, which may be substituted with $R^°$; —$(CH_2)_{0-4}O(CH_2)_{0-1}Ph$ which may be substituted with $R^°$; —CH=CHPh, which may be substituted with $R^°$; —$(CH_2)_{0-4}O(CH_2)_{0-1}$-pyridyl which may be substituted with $R^°$; —$NO_2$; —CN; —$N_3$; —$(CH_2)_{0-4}N(R^°)_2$; —$(CH_2)_{0-4}N(R^°)C(O)R^°$; —$N(R^°)C(S)R^°$; —$(CH_2)_{0-4}N(R^°)C(O)NR^°_2$; —$N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°_2$; —$N(R^°)N(R^°)C(O)OR^°$; —$(CH_2)_{0-4}C(O)R^°$; —$C(S)R^°$; —$(CH_2)_{0-4}C(O)OR^°$; —$(CH_2)_{0-4}C(O)SR^°$; —$(CH_2)_{0-4}C(O)OSiR^°_3$; —$(CH_2)_{0-4}OC(O)R^°$; —$OC(O)(CH_2)_{0-4}SR$—, $SC(S)SR^°$; —$(CH_2)_{0-4}SC(O)R^°$; —$(CH_2)_{0-4}C(O)NR^°_2$; —$C(S)NR^°_2$; —$C(S)SR^°$; —$SC(S)SR^°$, —$(CH_2)_{0-4}OC(O)NR^°_2$; —$C(O)N(OR^°)R^°$; —$C(O)C(O)R^°$; —$C(O)CH_2C(O)R^°$; —$C(NOR^°)R^°$; —$(CH_2)_{0-4}SSR^°$; —$(CH_2)_{0-4}S(O)_2R^°$; —$(CH_2)_{0-4}S(O)_2OR^°$; —$(CH_2)_{0-4}OS(O)_2R^°$; —$S(O)_2NR^°_2$; —$(CH_2)_{0-4}S(O)R^°$; —$N(R^°)S(O)_2NR^°_2$; —$N(R^°)S(O)_2R^°$; —$N(OR^°)R^°$; —$C(NH)NR^°_2$; —$P(O)_2R^°$; —$P(O)R^°_2$; —$OP(O)R^°_2$; —$OP(O)(OR^°)_2$; $SiR^°_3$; —$(C_{1-4}$ straight or branched alkylene)O—$N(R^°)_2$; or —$(C_{1-4}$ straight or branched)alkylene)C(O)O—$N(R^°)_2$, wherein each $R^°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^°$ (or the ring formed by taking two independent occurrences of $R^°$ together with their intervening atoms), are independently halogen, —$(CH_2)_{0-2}R^•$, —(halo$R^•$), —$(CH_2)_{0-2}OH$, —$(CH_2)_{0-2}OR^•$, —$(CH_2)_{0-2}CH(OR^•)_2$; —O(halo$R^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^°$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^•$, —(halo$R^•$), —OH, —$OR^•$, —O(halo$R^•$), —CN, —C(O)OH, —C(O)O$R^•$, —$NH_2$, —NH$R^•$, —N$R^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, —(halo$R^•$), —OH, —$OR^•$, —O(halo$R^•$), —CN, —C(O)OH, —C(O)O$R^•$, —$NH_2$, —NH$R^•$, —N$R^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Another embodiment of the present invention is a pharmaceutical composition comprising one or more pharmaceutically acceptable carrier and/or diluent and a compound disclosed herein, or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e., a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

"Cis" means on the same side. "Trans" means on opposite sides. The designation "cis" is used when two substituents have an "up-up" or a "down-down" relationship. The designation "trans" is used when two substituents have an "up-down" or "down-up" relationship. Typically, two substituents that are "cis" to one another are arranged on the same side of a molecule. When the term "cis" is used with reference to a fused, saturated or partially saturated ring system, the term is intended to indicate that the two atoms attached to the common ring atoms are cis substituents. For example,

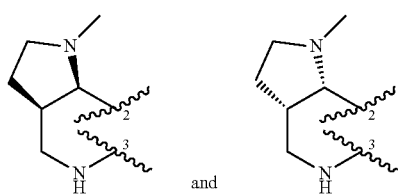

and are cis diastereomers of a moiety having the following structural formula:

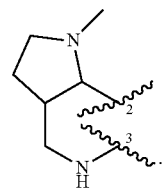 [SMILES: *NCC1CCN(C)C1*]

The present invention also provides a method of treating or preventing a subject with a tetracycline-responsive disease or disorder comprising administering to the subject an effective amount of a compound of the present invention or a pharmaceutically acceptable salt thereof.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, prostatitis, tumor growth and invasion, metastasis, diabetes, diabetic proteinuria, panbronchiolitis, aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold, Wegener's granulomatosis; neutrophilic dermatoses and other inflammatory diseases such as dermatitis herpetiformis, leukocytoclastic vasculitis, bullous lupus erythematosus, pustular psoriasis, erythema elevatum diutinum; vitiligo, discoid lupus erythematosus; pyoderma gangrenosum, pustular psoriasis, blepharitis, or meibomianitis, Alzheimer's disease, degenerative maculopathy; acute and chronic gastroenteritis and colitis; acute and chronic cystitis and urethritis; acute and chronic dermatitis; acute and chronic conjunctivitis, acute and chronic serositis, uremic pericarditis; acute and chronic cholecystis, cystic fibrosis, acute and chronic vaginitis, acute and chronic uveitis, drug reactions, insect bites, burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789, 395; 5,834,450; 6,277,061 and 5,532,227, each of which is expressly incorporated herein by reference).

In addition, a method to treat any disease or disease state that could benefit from modulating the expression and/or function of nitric oxide, metalloproteases, proinflammatory mediators and cytokines, reactive oxygen species, components of the immune response, including chemotaxis, lymphocyte transformation, delayed hypersensitivity, antibody production, phagocytosis, and oxidative metabolism of phagocytes. A method to treat any disease or disease state that could benefit from modulating the expression and/or function of C-reactive protein, signaling pathways (e.g., FAK signaling pathway), and/or augment the expression of COX-2 and PGE$_2$ production is covered. A method to treat any disease or disease state that could benefit from inhibition of neovascularization is covered.

Compounds of the invention can be used to prevent or treat important mammalian and veterinary diseases such as diarrhea, urinary tract infections, infections of skin and skin structure including wounds, cellulitis, and abscesses, ear, nose and throat infections, mastitis and the like. In addition, methods for treating neoplasms using tetracycline compounds of the invention are also included (van der Bozert et al., Cancer Res., 48: 6686-6690 (1988)).

Infections that can be treated using compounds of the invention or a pharmaceutically acceptable salt thereof include, but are not limited to, skin infections, GI infections, urinary tract infections, genito-urinary infections, respiratory tract infections, sinuses infections, middle ear infections, systemic infections, intra-abdominal infections, pyelonephritis, pneumonia, bacterial vaginosis, streptococcal sore throat, chronic bacterial prostatitis, gynecological and pelvic infections, sexually transmitted bacterial diseases, ocular and otic infections, cholera, influenza, bronchitis, acne, psoriasis, rosacea, impetigo, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection is a respiratory infection. In a particular aspect, the respiratory infection is Community-Acquired Bacterial Pneumonia (CABP). In a more particular embodiment, the respiratory infection, for example, CABP is caused by a bacterium selected from *S. aureus, S. pneumoniae, S. pyogenes, H. influenza, M. catarrhalis* and *Legionella pneumophila*.

In another embodiment, the infection is a skin infection. In a particular aspect the skin infection is an acute bacterial skin and skin structure infection (ABSSSI). In a more particular embodiment, the skin infection, for example ABSSSI is caused by a bacterium selected from *S. aureus*, CoNS, *S. pyogenes, S. agalactiae, E. faecalis* and *E. faecium*.

In one embodiment, the infection can be caused by a bacterium (e.g. an anaerobic or aerobic bacterium).

In another embodiment, the infection is caused by a Gram-positive bacterium. In a specific aspect of this embodiment, the infection is caused by a Gram-positive bacterium selected from class Bacilli, including, but not limited to, *Staphylococcus* spp., *Streptococcus* spp., *Enterococcus* spp., *Bacillus* spp., *Listeria* spp.; phylum *Actinobacteria*, including, but not limited to, *Propionibacterium* spp., *Corynebacterium* spp., *Nocardia* spp., *Actinobacteria* spp., and class Clostridia, including, but not limited to, *Clostridium* spp.

In another embodiment, the infection is caused by a Gram-positive bacterium selected from *S. aureus*, CoNS, *S. pneumoniae, S. pyogenes, S. agalactiae, E. faecalis* and *E. faecium*.

In another embodiment, the infection is caused by a Gram-negative bacterium. In one aspect of this embodiment, the infection is caused by a phylum Proteobacteria (e.g., Betaproteobacteria and Gammaproteobacteria), including *Escherichia coli, Salmonella, Shigella*, other Enterobacteriaceae, *Pseudomonas, Moraxella, Helicobacter, Stenotrophomonas, Bdellovibrio*, acetic acid bacteria, *Legionella* or alpha-proteobacteria such as *Wolbachia*. In another aspect, the infection is caused by a Gram-negative bacterium selected from cyanobacteria, spirochaetes, green sulfur or green non-sulfur bacteria. In a specific aspect of this embodiment, the infection is caused by a Gram-negative bacteria selected from Enterobactericeae (e.g., *E. coli, Klebsiella pneumoniae* including those containing extended-spectrum β-lactamases and/or carbapenemases), Bacteroidetes (e.g., *Bacteroides fragilis*), Vibrionaceae (*Vibrio cholerae*), Pasteurellaceae (e.g., *Haemophilus influenzae*), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of Proteeae, *Acinetobacter* spp., *Helicobacter* spp., and *Campylobacter* spp. In a particular embodiment, the infection is caused by Gram-negative bacterium selected from the group consisting of Enterobactericeae (e.g., *E. coli, Klebsiella pneumoniae*), *Pseudomonas*, and *Acinetobacter* spp. In another embodiment, the infection is caused by an organism selected from the group consisting of *K. pneumoniae, Salmonella, E. hirae, A. baumanii, M. catarrhalis, H. influenzae, P. aeruginosa, E. faecium, E. coli, S. aureus*, and *E. faecalis*.

In another embodiment, the infection is cause by a gram negative bacterium selected from *H. influenza, M. catarrhalis* and *Legionella pneumophila*.

In one embodiment, the infection is caused by an organism that grows intracellularly as part of its infection process.

In another embodiment, the infection is caused by an organism selected from the group consisting of order Rickettsiales; phylum Chlamydiae; order Chlamydiales; *Legionella* spp.; class Mollicutes, including, but not limited to, *Mycoplasma* spp. (e.g. *Mycoplasma pneumoniae*); *Mycobacterium* spp. (e.g. *Mycobacterium tuberculosis*); and phylum Spriochaetales (e.g. *Borrelia* spp. and *Treponema* spp.).

In another embodiment, the infection is caused by a Category A Biodefense organism as described at hltp://www.bt.cdc.gov/agent/agentlist-category.asp, the entire teachings of which are incorporated herein by reference. Examples of Category A organisms include, but are not limited to, *Bacillus anthracis* (anthrax), *Yersinia pestis* (plague), *Clostridium botulinum* (botulism) or *Francisella tularensis* (tularemia). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria.

Additional infections that can be treated using compounds of the invention or a pharmaceutically acceptable salt thereof include, but are not limited to, anthrax, botulism, bubonic plague, and tularemia.

In another embodiment, the infection is caused by a Category B Biodefense organism as described at hllp://www.bt.cdc.gov/agent/agentlist-category.asp, the entire teachings of which are incorporated herein by reference. Examples of Category B organisms include, but are not limited to, *Brucella* spp, *Clostridium perfringens*, *Salmonella* spp., *Escherichia coli* O157:H7, *Shigella* spp., *Burkholderia mallei*, *Burkholderia pseudomallei*, *Chlamydia psittaci*, *Coxiella burnetii*, Staphylococcal enterotoxin B, *Rickettsia prowazekii*, *Vibrio cholerae*, and *Cryptosporidium parvum*.

Additional infections that can be treated using compounds of the invention or a pharmaceutically acceptable salt thereof include, but are not limited to, Brucellosis, *Clostridium perfringens*, food-borne illnesses, Glanders, Melioidosis, Psittacosis, Q fever, and water-borne illnesses.

In yet another embodiment, the infection can be caused by one or more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus, Serratia, Staphylococcus* and *Enterococcus* spp., anaerobes (S. E. Dowd, et al., PloS one 2008; 3:e3326, the entire teachings of which are incorporated herein by reference) and respiratory disease (especially in patients that have chronic infections like cystic fibrosis—e.g., *S. aureus* plus *P. aeruginosa* or *H. influenzae*, atypical pathogens), wounds and abscesses (various gram-negative and gram-positive bacteria, notably MSSA/MRSA, coagulase-negative staphylococci, enterococci, *Acinetobacter, P. aeruginosa, E. coli, B. fragilis*), and bloodstream infections (13% were polymicrobial (H. Wisplinghoff, et al., Clin. Infect. Dis. 2004; 39:311-317, the entire teachings of which are incorporated herein by reference)).

In one embodiment, the infection is caused by an organism resistant to one or more antibiotics.

In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline or any other tetracycline derivative. In a particular embodiment, the infection is caused by an organism resistant to tigecycline.

In another embodiment, the infection is caused by an organism resistant to a β-lactam or cephalosporin antibiotic or an organism resistant to penems or carbapenems.

In another embodiment, the infection is caused by an organism resistant to an antimicrobial peptide or a biosimilar therapeutic treatment. Antimicrobial peptides (also called host defense peptides) are an evolutionarily conserved component of the innate immune response and are found among all classes of life. In this case, antimicrobial peptide refers to any naturally occurring molecule or any semi/synthetic molecule that are analogs of anionic peptides, linear cationic α-helical peptides, cationic peptides enriched for specific amino acids (i.e, rich in proline, arginine, phenylalanine, glycine, tryptophan), and anionic and cationic peptides that contain cystein and form disulfide bonds.

In another embodiment, the infection is caused by an organism resistant to macrolides, lincosamides, streptogramin antibiotics, oxazolidinones, and pleuromutilins.

In another embodiment, the infection is caused by an organism resistant to PTK0796 (7-dimethylamino, 9-(2,2-dimethyl-propyl)-aminomethylcycline).

In another embodiment, the infection is caused by a multidrug-resistant pathogen (having intermediate or full resistance to any two or more antibiotics).

In a further embodiment, the tetracycline responsive disease or disorder is not a bacterial infection. In another embodiment, the tetracycline compounds of the invention are essentially non-antibacterial. For example, non-antibacterial compounds of the invention may have MIC values greater than about 4 µg/ml (as measured by assays known in the art and/or the assay given in Example 151. In another embodiment, the tetracycline compounds of the invention have both antibacterial and non-antibacterial effects.

Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, microorganisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity. Examples of matrix metalloproteinase associated states ("MMPAS's") can be treated using compounds of the invention or a pharmaceutically acceptable salt thereof, include, but are not limited to, arteriosclerosis, corneal ulceration, emphysema, osteoarthritis, multiple sclerosis (Liedtke et al., Ann. Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compounds of the present invention or a pharmaceutically acceptable salt thereof include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. Nos. 6,100,248; 5,843,925; 5,837,696; or 5,668,122, incorporated herein by reference in their entirety.

Alternatively, the tetracycline compounds may be useful for preventing or reducing the likelihood of cancer recurrence, for example, to treat residual cancer following surgical resection or radiation therapy. The tetracycline compounds useful according to the invention are especially advantageous as they are substantially non-toxic compared to other cancer treatments.

In a further embodiment, the compounds of the invention are administered in combination with standard cancer therapy, such as, but not limited to, chemotherapy.

Examples of tetracycline responsive states can be treated using the compounds of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e. g., severe bipolar affective (mood) disorder (BP-1), bipolar affective neurological disorders, e. g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compounds of the invention or a pharmaceutically acceptable salt thereof include, but are not limited to, juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e. g., a decrease in bone strength and density), bone fractures, bone formation associated with surgical procedures (e. g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited, to asthma, cystic fibrosis, chronic obstructive pulmonary disease (COPD), and emphysema. In a further embodiment, the acute and/or chronic lung disorders that can be treated using the compounds of the invention or a pharmaceutically acceptable salt thereof include those described in U.S. Pat. Nos. 5,977, 091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the tetracycline compounds of the invention or a pharmaceutically acceptable salt thereof can be used to treat such disorders as described above and in U.S. Pat. Nos. 6,231,894; 5,773,430; 5,919,775 and 5,789,395, incorporated herein by reference.

In still a further embodiment, the tetracycline compounds of the invention or a pharmaceutically acceptable salt thereof can be used to treat pain, for example, inflammatory, nociceptive or neuropathic pain. The pain can be either acute or chronic.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a tetracycline compound of the invention or a pharmaceutically acceptable salt thereof to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e. g., topically). In a further embodiment, the tetracycline compound of the invention or a pharmaceutically acceptable salt thereof is used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The tetracycline compound or a pharmaceutically acceptable salt thereof may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

The compounds of the invention or a pharmaceutically acceptable salt thereof can be used alone or in combination with one or more therapeutic agent in the methods of the invention disclosed herein.

The language "in combination with" another therapeutic agent or treatment includes co-administration of the tetracycline compound and with the other therapeutic agent or treatment as either a single combination dosage form or as multiple, separate dosage forms, administration of the tetracycline compound first, followed by the other therapeutic agent or treatment and administration of the other therapeutic agent or treatment first, followed by the tetracycline compound.

The other therapeutic agent may be any agent that is known in the art to treat, prevent, or reduce the symptoms of a tetracycline-responsive disease or disorder. The choice of additional therapeutic agent(s) is based upon the particular tetracycline-responsive disease or disorder being treated. Such choice is within the knowledge of a treating physician. Furthermore, the other therapeutic agent may be any agent of benefit to the patient when administered in combination with the administration of a tetracycline compound.

The compounds of the invention or a pharmaceutically acceptable salt thereof can be used alone or in combination with one or more antibiotics and/or immunomodulators (e.g. Deoxycholic acid, Macrokine, Abatacept, Belatacept, Infliximab, Adalimumab, Certolizumab pegol, Afelimomab, Golimumab, and FKBP/Cyclophilin/Calcineurin: Tacrolimus, Ciclosporin, Pimecrolimus).

As used herein, the term "subject" means a mammal in need of treatment or prevention, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or 'treatment" refers to obtaining desired pharmacological and/or physiological effect. The effect can include achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome.

As used herein, "preventing" or "prevention" refers to reducing the likelihood of the onset or development of disease, disorder or syndrome.

"Effective amount" means that amount of active compound agent that elicits the desired biological response in a subject. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In another embodiment, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxy-ethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the composition of this invention includes one or more additional agents. The other therapeutic agent may be ay agent that is capable of treating, preventing or reducing the symptoms of a tetracycline-responsive disease or disorder. Alternatively, the other therapeutic agent may be any agent of benefit to a patient when administered in combination with the tetracycline compound in this invention.

While this invention has been particularly shown and described with references to example embodiments thereof, it will be understood by those skilled in the art that various changes in form and details may be made therein without departing from the scope of the invention encompassed by the appended claims.

EXEMPLIFICATION

The following abbreviations are used in throughout the application.

Ac acetyl
aq aqueous
9-BBN 9-borabicyclo[3.3.1]nonane
BHT t-butyl hydroxyl toluene
Bn benzyl
Boc tert-butoxycarbonyl
Bu butyl
dba dibenzylideneacetone
DCE 1,2-dichloroethane
DCM dichloromethane
DEM diethoxymethane
DIBAL-H diisobutylaluminum hydride
DIEA diisopropylethylamine
DMAP 4-(dimethylamino)pyridine
DME dimethoxyethane
DMF N,N-dimethylformamide
DMPU 1,3-dimethyl-3,4,5,6-tetrahydro-2(1H)-pyrimidone
DMSO dimethylsulfoxide
DPPB 1,4-bis(diphenylphosphinebutane)
ESI ESI ionization
Et ethyl
eq equivalent
h hour
HPLC high performance liquid chromatography
i iso
IBX 2-iodoxybenzoic acid
LDA lithium diisopropylamide
LHMDS lithium bis(trimethylsilyl)amide
MHz mega hertz
Ms methylsulfonyl
MS mass spectrometry
MTBE methyl t-butyl ether
m/z mass/charge ratio
MW molecular weight
NCS N-chlorosuccinimide NDMBA 1,3-dimethylbarbituric acid
NMO N-methylmorpholine N-oxide
NMR nuclear magnetic resonance spectrometry
Ph phenyl
Pr propyl
s secondary
t tertiary
TBAF tetrabutylammonium fluoride
TEA triethylamine
Tf trifluoromethanesulfonyl
TFA trifluoroacetic acid
TFAA trifluoroacetic anhydride
THF tetrahydrofuran
TLC thin layer chromatography
TMEDA N,N,N'N'-tetramethylethylenediamine
TMP 2,2,6,6-tetramethylpiperidine
STAB sodium triacetoxyborohydride The compounds described herein were synthesized in accordance with the following Schemes. The specific approaches and compounds shown below are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing the compounds described herein and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

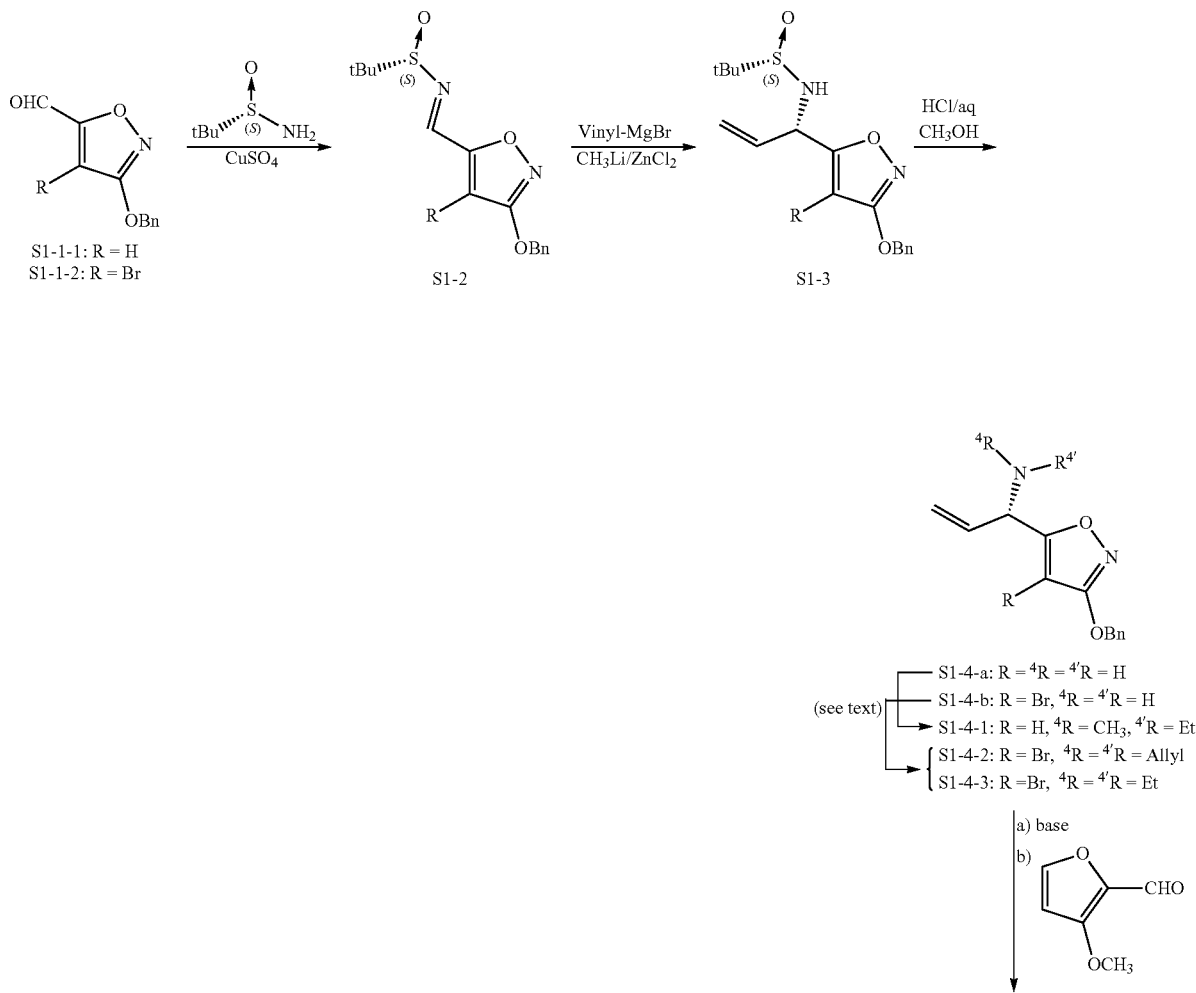

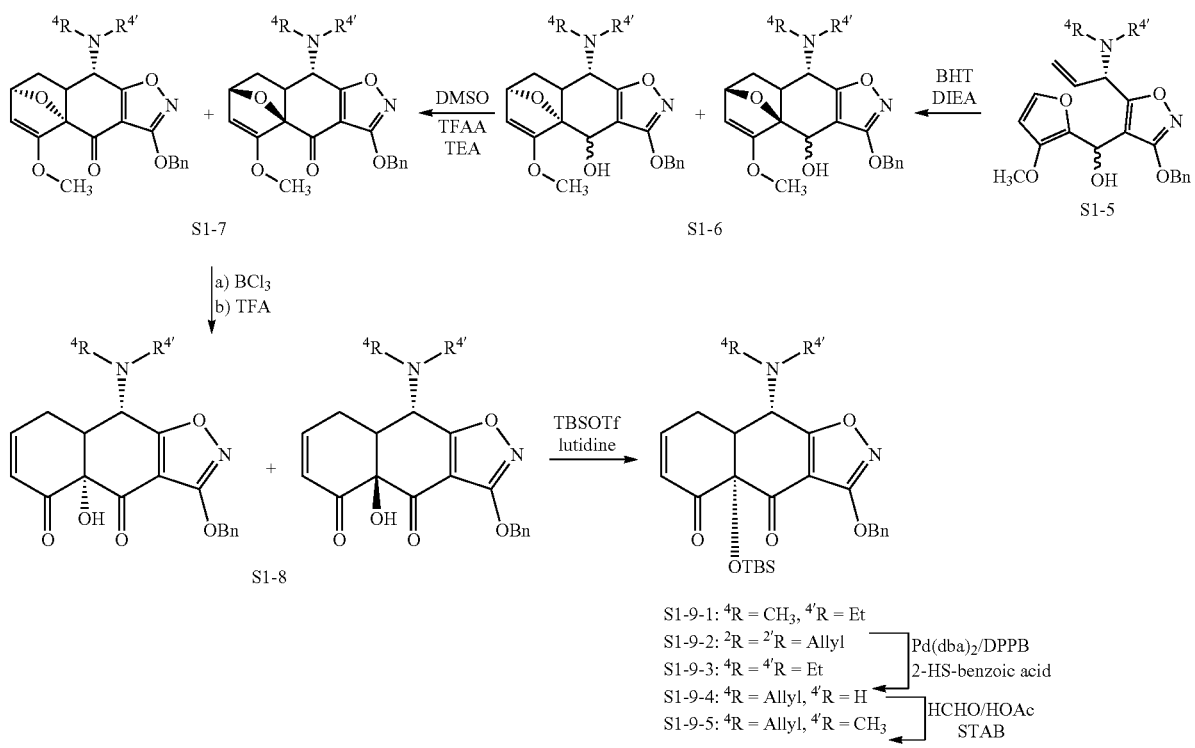

S1-9-1: $^4R = CH_3$, $^{4'}R = Et$
S1-9-2: $^2R = {^{2'}R} = Allyl$ — Pd(dba)$_2$/DPPB, 2-HS-benzoic acid
S1-9-3: $^4R = {^{4'}R} = Et$
S1-9-4: $^4R = Allyl$, $^{4'}R = H$ — HCHO/HOAc, STAB
S1-9-5: $^4R = Allyl$, $^{4'}R = CH_3$ The following compounds were prepared according to Scheme 1.

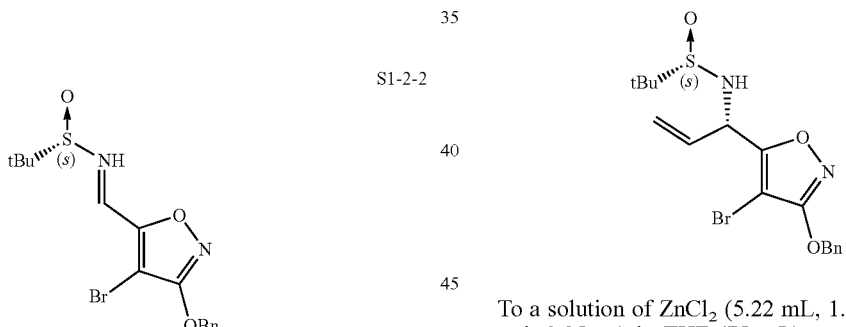

To a mixture of aldehyde S1-1 (12.16 g, 43.11 mmol, 1.0 eq, prepared according to literature procedures including U.S. Pat. No. 7,763,3735), (S)-tert-butylsulfinamide (6.27 g, 51.73 mmol, 1.2 eq) and CuSO$_4$ (4.82 g, 30.16 mmol, 0.7 eq) was added anhydrous toluene (85 mL) under nitrogen. The resulting reaction mixture was heated at 40° C. overnight, then cooled to rt and diluted with water (130 mL). The resulting mixture was extracted with EtOAc (130 mL, then 2×30 mL). The combined organic phase was dried over Na$_2$SO$_4$, filtered and concentrated under reduced pressure. Flash chromatography on silica gel using 5%→15% EtOAc/hexanes yielded the desired product S1-2-2 as a thick yellow oil (15.29 g, 92%): $^1$H NMR (400 MHz, CDCl$_3$) δ 8.47 (s, 1H), 7.48-7.46 (m, 2H), 7.42-7.35 (m, 3H), 5.37 (s, 2H), 1.26 (s, 9H); MS (ESI) m/z 385.02, 387.05 (M+H).

To a solution of ZnCl$_2$ (5.22 mL, 1.9 M in MeTHF, 9.92 mmol, 0.25 eq) in THF (75 mL) was added a solution of MeLi (6.61 mL, 3.0 M in DEM, 19.84 mmol, 0.5 eq) keeping the internal temperature below −58° C. Vinyl magnesium chloride solution (37.2 mL, 1.6 M in THF, 59.53 mmol, 1.5 eq) was added at below −52° C. A solution of imine S1-2-2 (15.29 g, 39.68 mmol, 1.0 eq) in THF (50 mL) was added dropwise via cannula keeping the internal temperature below −76° C. over one hour. The resulting reaction solution was stirred at −78° C. for an additional hour and quenched with citric acid aqueous solution (8 g in 80 mL water) allowing the internal temperature to rise to −3° C. The resulting mixture was extracted with EtOAc (150 mL, then 30 mL). The combined organic phase was dried over Na$_2$SO$_4$, filtered and concentrated under reduced pressure. Flash chromatography on silica gel using 30%→38% EtOAc/hexanes yielded the desired product S1-3-2 (15.46 g) as the major diastereomer: $^1$H NMR (400 MHz, CDCl$_3$) δ 7.45-7.43 (m, 2H), 7.40-7.34 (m, 3H), 5.96-5.88 (m, 1H), 5.39 (d, J=17.7 Hz, 1H), 5.34 (d, J=9.8 Hz, 1H), 5.28 (s, 2H), 5.11 (t, J=6.7 Hz, 1H), 3.78 (d, J=6.1 Hz, 1H), 1.23 (s, 9H); MS (ESI) m/z 413.05, 415.05 (M+H).

S1-4-2

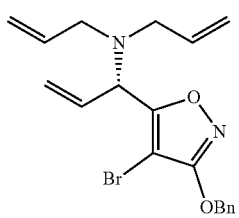

To a solution of compound S1-3-2 (15.46 g, 37.4 mmol, 1 eq) in methanol (122 mL) was added concentrated aqueous hydrochloric acid (6.23 mL, 74.8 mmol, 2.0 eq). After 50 min at room temperature, consumption of starting material was indicated by LC/MS. Solvent was evaporated and the residue was partitioned between EtOAc (150 mL) and saturated aqueous NaHCO$_3$ (150 mL). The organic phase was separated. The aqueous layer was further extracted with EtOAc (2×50 mL). The combined organic phase was washed with brine (50 mL), dried over Na$_2$SO$_4$, filtered and concentrated under reduced pressure to afford crude product S1-4-b: MS (ESI) m/z 309.07, 311.04 (M+H), which was used directly for the next step.

To a mixture of the above intermediate S1-4-b, NaI (560 mg, 3.74 mmol, 0.1 eq) and K$_2$CO$_3$ (12.9 g, 93.5 mmol, 2.5 eq) in THF (110 mL) was added allyl bromide (14.6 mL, 168.3 mmol, 4.5 eq). The resulting reaction mixture was heated at 65° C. overnight. Then more allyl bromide (7 mL, 80.7 mmol, 2.2 eq) was added. The resulting reaction mixture was heated at 65° C. overnight and cooled to rt. The reaction mixture was diluted with EtOAc (300 mL), washed with water and brine. The organic phase was then dried over Na$_2$SO$_4$, filtered and concentrated under reduced pressure. Flash chromatography on silica gel using 1%→10% EtOAc/hexanes yielded the desired product S1-4-2 (11.32 g, 74% over 3 steps): $^1$H NMR (400 MHz, CDCl$_3$) δ 7.47-7.45 (m, 2H), 7.41-7.34 (m, 3H), 6.02-5.94 (m, 1H), 5.84-5.73 (m, 2H), 5.30 (s, 2H), 5.31-5.28 (m, 1H), 5.24-5.16 (m, 3H), 5.14-5.11 (m, 2H), 4.60-4.59 (m, 1H), 3.29 (dd, J=7.3, 14.6 Hz, 2H), 3.04 (dd, J=6.7, 14.6 Hz, 2H); MS (ESI) m/z 389.16, 391.15 (M+H).

S1-5-2

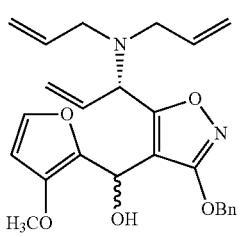

To a solution of bromide S1-4-2 (11.32 g, 29.08 mmol, 1 eq) in THF (110 mL) was added Turbo Grignard solution (1.3 M in THF, 26.8 mL, 34.89 mmol, 1.2 eq) dropwise at ~−10° C. The resulting reaction solution was stirred at that temperature for 30 min, and the cold bath was removed. The reaction was warmed up to 0° C. and then cooled to −30° C. Then a solution of 3-methoxy-2-furaldehyde (4.40 g, 34.89 mmol, 1.2 eq) in THF (20 mL) was added over 10 min at −30° C. to −40° C. The resulting reaction mixture was stirred at −30° C. for 30 min and allowed to warm up to −15° C. Saturated aqueous NH$_4$Cl was added, and the resulting reaction mixture was extracted with EtOAc (120 mL, then 50 mL). The combined organic phase was dried over Na$_2$SO$_4$, filtered and concentrated under reduced pressure. Flash chromatography on silica gel using 1%→20% EtOAc/hexanes yielded the desired product S1-5-2 (~1:1 diastereomers): MS (ESI) m/z 437.25 (M+H).

S1-7-2

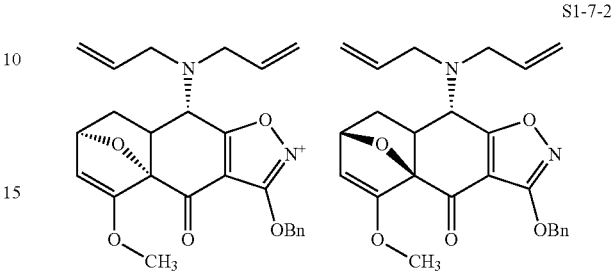

Product S1-5-2 from the previous step was dissolved in 60 mL DMSO. Diisopropylethylamine (5.57 mL, 31.99 mmol, 1.1 eq) and BHT (~100 mg, 0.454 mmol, 0.016 eq) were added. The mixture was vacuumed and then filled with nitrogen. And this degas procedure was repeated four times. The reaction mixture was then stirred at 92° C. for 23 h to yield intermediates S1-6-2. The reaction solution was cooled to room temperature. Ethyl acetate (120 mL) and triethyl amine (12.97 mL, 93.06 mmol, 3.2 eq) were added. The reaction mixture was cooled to 0° C. TFAA (6.47 mL, 46.53 mmol, 1.6 eq) was added at 0 to 4° C. over 5 min. After stirring at 0° C. for 35 min, more TFAA (1.4 mL, 10.07 mmol, 0.35 eq) was added at 0 to 4° C. and the reaction was stirred at 0° C. for another 30 min. Water (120 mL) was added to the reaction. After stirring for 5 min the two layers were separated. The aqueous layer was extracted with ethyl acetate (150 mL). The combined organic layers were washed with water (150 mL) and brine (150 mL), dried over Na$_2$SO$_4$, filtered and concentrated. The residue was purified by flash chromatography on silica gel using 5%→50% EtOAc/hexanes to yield the desired product S1-7-2 (~3:1 diastereomers, 10.8 g, 86% over 3 steps) as a light brownish solid: MS (ESI) m/z 435.24 (M+H).

S1-8-2

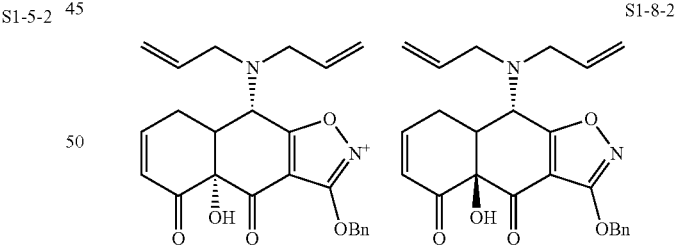

The above compound S1-7-2 was dissolved in DCM (70 mL), and the resulting solution was cooled to −30° C. A solution of BCl$_3$ in DCM (1 M, 29.83 mL, 29.83 mmol, 1.2 eq) was added at −20° C. to −30° C. After stirring for 40 min at the same temperature, more BCl$_3$ in DCM (1 M, 0.5 eq) was added at −20° C. to −30° C. After stirring for 30 min at the same temperature, the reaction was quenched with aq. 20% K$_3$PO$_4$.7H$_2$O (100 mL). The two layers were separated. The aqueous layer was extracted with DCM (30 mL). The combined organic layers were washed with brine (50 mL). The resulting organic layer was concentrated to ~100 mL, and to which was added TFA (9.6 mL, 124.3 mmol, 5.0 eq).

The resulting dark brownish reaction solution was stirred at room temperature for 1.5 h. Aq. 20% K₃PO₄ (250 mL) was added to adjust pH to ~8. The two layers were separated. The aqueous layer was extracted with DCM (2×20 mL). The combined organic layers were washed with brine, dried over Na₂SO₄, filtered and concentrated to give crude product S1-8-2: MS (ESI) m/z 421.21 (M+H).

S1-9-4 (196 mg, 23%) along with SM (138 mg, 15%) and di-deallylation product (239 mg, 31%): ¹H NMR (400 MHz, CDCl₃) δ 7.50-7.46 (m, 2H), 7.38-7.32 (m, 3H), 6.84 (br s, 1H), 6.09 (dt, J=10.4, 1.8 Hz, 1H), 5.85-5.84 (br m, 1H), 5.35 (s, 2H), 5.25 (d, J=14.6 Hz, 1H), 5.15 (d, J=11.0 Hz, 1H), 3.82 (br s, 1H), 3.55 (dd, J=5.5, 13.4 Hz, 1H), 3.42 (br s, 1H), 2.78 (br s, 3H), 0.76 (s, 9H), 0.14 (s, 6H); MS (ESI) m/z 495.24 (M+H).

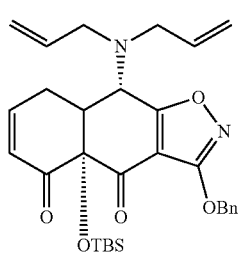

S1-9-2

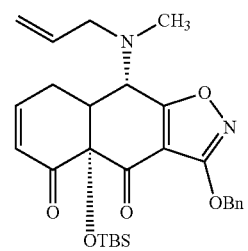

S1-9-5

The crude product S1-8-2 from the previous step was dissolved in EtOAc (80 mL). The reaction solution was cooled with an ice/water bath. 2,6-Lutidine (4.62 mL, 39.8 mmol, 1.6 eq) was added to the reaction mixture followed by TBSOTf (7.42 mL, 32.32 mmol, 1.3 eq). After stirring for 15 min the cold bath was removed. The reaction mixture was stirred at room temperature for 50 min. The reaction was quenched with water. The organic layer was separated and washed with brine, dried over Na₂SO₄, filtered and concentrated. The residue was purified by flash chromatography on silica gel using 1%→10% EtOAc/hexanes to yield a light orange solid, which was then stirred with hexanes (50 mL) overnight and filtered. The filter cake was dried under high vacuum to give the desired product S1-9-2 (7.07 g, 53% over 2 steps): ¹H NMR (400 MHz, CDCl₃) δ 7.46-7.44 (m, 2H), 7.36-7.29 (m, 3H), 6.87-6.83 (m, 1H), 6.03-6.00 (m, 1H), 5.73-5.63 (m, 2H), 5.30 (s, 2H), 5.15 (d, J=17.1 Hz, 2H), 5.10 (d, J=9.8 Hz, 2H), 4.05 (d, J=10.4 Hz, 1H), 3.24-3.17 (m, 4H), 2.87-2.66 (m, 3H), 0.78 (s, 9H), 0.20 (s, 3H), 0.00 (s, 3H); MS (ESI) m/z 535.33 (M+H).

To a solution of compound S1-9-4 (196 mg, 0.396 mmol, 1 eq) in DCM (5 mL) was added HCHO (37 wt % in water, 88 μL, 1.19 mmol, 3.0 eq), HOAc (34 μL, 0.594 mmol, 1.5 eq) and STAB (126 mg, 0.594 mmol, 1.5 eq). The resulting reaction mixture was stirred at rt for 1 h, and more STAB (0.5 eq) was added. The resulting reaction was stirred at rt overnight. Then saturated aq. NaHCO₃ was added. The resulting mixture was extracted with DCM (20 mL, then 10 mL). The combined organic phase was dried over Na₂SO₄, filtered and concentrated under reduced pressure. Flash chromatography on silica gel using 1%→10% EtOAc/hexanes yielded the desired product S1-9-5 (155 mg, 77%) as a white foamy solid: ¹H NMR (400 MHz, CDCl₃) δ 7.45-7.44 (m, 2H), 7.35-7.28 (m, 3H), 6.89-6.86 (m, 1H), 6.03 (d, J=10.4 Hz, 1H), 5.73-5.63 (m, 1H), 5.30 (s, 2H), 5.17 (d, J=17.1 Hz, 1H), 5.10 (d, J=9.8 Hz, 1H), 3.89 (d, J=10.4 Hz, 1H), 3.34-3.26 (m, 2H), 2.83-2.71 (m, 3H), 2.27 (s, 3H), 0.78 (s, 9H), 0.20 (s, 3H), 0.00 (s, 3H); MS (ESI) m/z 509.24 (M+H).

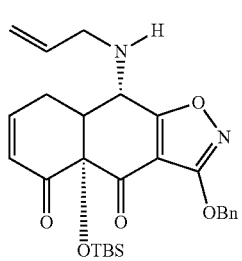

S1-9-4

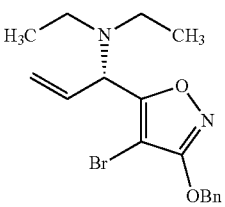

S1-4-3

A mixture of the Pd(dba)₂ (98 mg, 0.171 mmol, 0.1 eq) and DPPB (73 mg, 0.171 mmol, 0.1 eq) was dissolved in THF (1.5 mL). The resulting reaction solution was stirred at rt for 15 min, and added to a solution of enone S1-9-2 (915 mg, 1.71 mmol, 1 eq) and 2-mercaptobenzoic acid (343 mg, 2.22 mmol, 1.3 eq) in THF (8 mL). The resulting orange reaction solution was stirred at rt under nitrogen for 3 overnights. Then saturated aq. NaHCO₃ was added. The resulting mixture was extracted with EtOAc (40 mL, then 20 mL). The combined organic phase was washed with brine, dried over Na₂SO₄, filtered and concentrated under reduced pressure. Flash chromatography on silica gel using 1%→30% EtOAc/hexanes yielded the desired product To a solution of compound S1-3-2 (3.93 g, 9.51 mmol, 1 eq) in methanol (30 mL) was added concentrated aqueous hydrochloric acid (1.59 mL, 19.11 mmol, 2.0 eq). The reaction was stirred at room temperature for 40 min to afford intermediate S1-4-b. The reaction solution was cooled to 0° C. NaOAc (2.44 g, 29.77 mmol, 3.13 eq), acetaldehyde (4.75 mL, 84.64 mmol, 8.9 eq) and picoline-borane (2.00 g, 18.73 mmol, 1.97 eq) were added in sequence. The resulting reaction mixture was stirred at rt for 1 h and 30 min. Water (10 mL) was added and then the solvent was evaporated. To the residue was added concentrated aqueous hydrochloric acid (3.38 mL) and water (10 mL). The resulting solution was extracted with MTBE, and the organic phase was discarded. To the aqueous layer was added toluene (40 mL) followed by aq. NaOH solution (6 N, 7.9 mL) to make the aqueous layer pH=~9. The organic phase was separated, and the aqueous layer was extracted with toluene (20 mL). The combined organic phase was dried over Na$_2$SO$_4$, filtered and concentrated under reduced pressure. Flash chromatography on silica gel using 0%→25% EtOAc/hexanes yielded the desired product S1-4-3 (3.09 g, 89%) as a colorless liquid: $^1$H NMR (400 MHz, CDCl$_3$) δ 7.46-7.44 (m, 2H), 7.40-7.32 (m, 3H), 6.05-5.97 (m, 1H), 5.29 (s, 2H), 5.29-5.21 (m, 2H), 4.52 (d, J=6.7 Hz, 1H), 2.73-2.64 (m, 2H), 2.54-2.46 (m, 2H), 1.02 (t, J=6.7 Hz, 6H); MS (ESI) m/z 365.17, 367.17 (M+H).

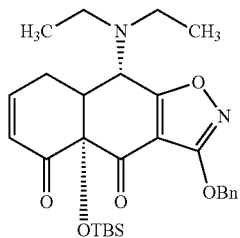

S1-9-3

Compound S1-9-3 was prepared using the same synthetic sequence (addition to furaldehyde, Diels-Alder, oxidation, BCl$_3$ oxo-bridge opening and TBS protection) for compound S1-9-2 from isoxazole S1-4-3 (3.09 g) in 42% overall yield: $^1$H NMR (400 MHz, CDCl$_3$) δ 7.44-7.43 (m, 2H), 7.34-7.27 (m, 3H), 6.90-6.86 (m, 1H), 6.05 (dd, J=3.0, 10.4 Hz, 1H), 5.28 (s, 2H), 3.89 (d, J=10.4 Hz, 1H), 2.91-2.56 (m, 7H), 0.97 (t, J=7.3 Hz, 6H), 0.78 (s, 9H), 0.21 (s, 3H), 0.00 (s, 3H); MS (ESI) m/z 511.34 (M+H).

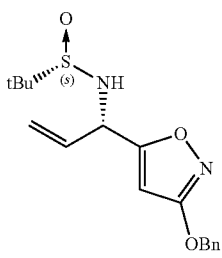

S1-3-1

To a solution of ZnCl$_2$ (12.13 mL, 1.85 M in MeTHF, 22.44 mmol, 0.275 eq) in THF (125 mL) was added a solution of MeLi (13.6 mL, 3.0 M in DEM, 40.80 mmol, 0.5 eq) keeping the internal temperature below −55° C. Vinyl magnesium chloride solution (76.5 mL, 1.6 M in THF, 122.4 mmol, 1.5 eq) was added at below −61° C. A solution of imine S1-2-1 (25 g, 81.60 mmol, 1.0 eq, prepared from S1-1-1 by similar procedures used for S1-2-2) in THF (75 mL) was added dropwise via cannula keeping the internal temperature below −74° C. over 1 h and 20 min. The resulting reaction solution was stirred at −78° C. for an additional 35 min and quenched with citric acid aqueous solution (12.5 g in 125 mL water) allowing the internal temperature to rise to −35° C. The resulting mixture was warmed up to rt and extracted with EtOAc (200 mL). The organic phase was washed with brine, dried over Na$_2$SO$_4$, filtered and concentrated under reduced pressure to give the desired product S1-3-1 (dr=~99.3:0.7) in quantitative yield as a light yellow oil: $^1$H NMR (400 MHz, CDCl$_3$) δ 7.42-7.33 (m, 5H), 5.96-5.87 (m, 1H), 5.92 (s, 1H), 5.43 (d, J=17.1 Hz, 1H), 5.37 (d, J=11.0 Hz, 1H), 5.22 (s, 2H), 5.03 (dt, J=1.2, 6.1 Hz, 1H), 3.77 (d, J=4.3 Hz, 1H), 1.23 (s, 9H); MS (ESI) m/z 335.20 (M+H).

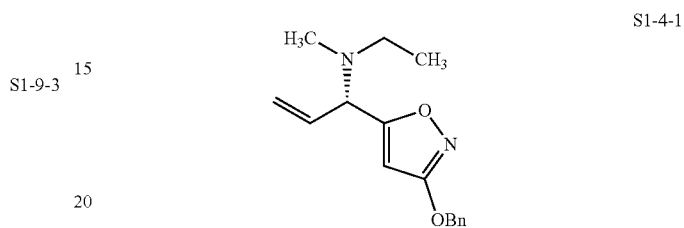

S1-4-1

To a solution of the above crude material S1-3-1 in methanol (200 mL) was added concentrated aqueous hydrochloric acid (13.7 mL, 164 mmol, 2.01 eq) at 10 to 15° C. The reaction as stirred at room temperature for 1 h to afford the primary amine intermediate S1-4-a. The reaction solution was cooled to 0° C. Then NaOAc (20.08 g, 244.8 mmol, 3.0 eq) and picoline-borane (8.37 g, 81.60 mmol, 1 eq) were added in sequence. Then a solution of acetaldehyde in EtOH (50 wt %, 8.15 mL, 81.60 mmol, 1.0 eq) was added dropwise. The resulting reaction mixture was stirred at 0° C. for 1 h and 50 min. An aqueous hydrochloric acid solution (1 N, 280 mL) was added and then the solvent was evaporated. To the residue was added aqueous hydrochloric acid (1 N, 50 mL). The resulting solution was extracted with MTBE (400 mL), and the organic phase was discarded. The aqueous layer was basified with aq. NaOH solution (6 N, 58 mL) to pH=~8. The resulting mixture was extracted with toluene (300 mL, then 150 mL). The combined organic phase was dried over Na$_2$SO$_4$, filtered and concentrated under reduced pressure. Flash chromatography on silica gel using 5%→30% EtOAc/hexanes yielded the desired mono-ethylamine intermediate (15.24 g, 72% over 2 steps) as a yellow oil: $^1$H NMR (400 MHz, CDCl$_3$) δ 7.43-7.31 (m, 5H), 5.91-5.82 (m, 1H), 5.79 (s, 1H), 5.31-5.22 (m, 2H), 5.22 (s, 2H), 4.29 (d, J=6.7 Hz, 1H), 2.69-2.56 (m, 2H), 1.10 (t, J=7.0 Hz, 3H); MS (ESI) m/z 259.14 (M+H).

To a solution of the above mono-ethyl amine (15.24 g, 59.0 mmol, 1 eq) in MeCN (90 mL) was added HCHO (13.2 mL, 177 mmol, 3 eq) at 0° C., followed by HOAc (6.75 mL, 118 mmol, 2 eq) and sodium triacetoxyborohydride (15.0 g, 70.8 mmol, 1.2 eq). The resulting reaction mixture was stirred at rt for 30 min, and quenched by slow addition of saturated aqueous sodium bicarbonate (320 mL). The resulting mixture was stirred at rt for 10 min, and extracted with EtOAc (150 mL, then 100 mL). The organic phase was dried over anhydrous sodium sulfate, filtered, and concentrated. Flash chromatography on silica gel using 10%→25% EtOAc/hexanes yielded the desired product S1-4-1 (15.89 g, 99%) as a pale yellow oil: $^1$H NMR (400 MHz, CDCl$_3$) δ 7.44-7.33 (m, 5H), 5.98-5.89 (m, 1H), 5.78 (s, 1H), 5.30-5.24 (m, 2H), 5.24 (s, 2H), 4.20 (d, J=7.3 Hz, 1H), 2.51-2.40 (m, 2H), 2.22 (s, 3H), 1.05 (t, J=7.3 Hz, 3H); MS (ESI) m/z 273.15 (M+H).

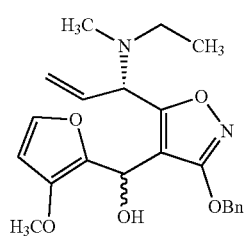

S1-5-1

To a solution of isoxazole S1-4-1 (14.88 g, 54.64 mmol, 1 eq) in DME (29.8 mL) was added a solution of TMPMgCl·LiCl in THF (0.97 M, 81.67 mL, 79.22 mmol, 1.45 eq) at −5° C. to −2° C. over 10 min. The resulting reaction solution was stirred at 0° C. for 1 h, and then cooled to −78° C. A solution of furaldehyde (10.34 g, 81.96 mmol, 1.5 eq) in THF (65 mL) was added dropwise to the reaction mixture via cannula at below −71° C. over 25 min. The resulting reaction mixture was allowed to warm up to −17° C. over 3.5 h, and quenched with saturated NH$_4$Cl (300 mL). The resulting mixture was extracted with ethyl acetate (350 mL). The organic phase was separated, washed with saturated NH$_4$Cl (2×150 mL) and brine (100 mL), dried over Na$_2$SO$_4$, filtered and concentrated. The crude product S1-5-1 (~1:1 diastereomers) was used directly for the next reaction without further purification.

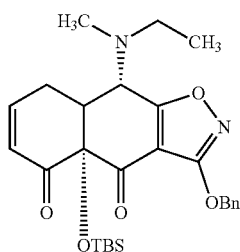

S1-9-1

Compound S1-9-1 was prepared using the same synthetic sequence (Diels-Alder, oxidation, BCl$_3$ oxo-bridge opening and TBS protection) for compound S1-9-2 from the crude addition product S1-5-1 in 26% yield over 5 steps: $^1$H NMR (400 MHz, CDCl$_3$) δ 7.45-7.43 (m, 2H), 7.35-7.28 (m, 3H), 6.90-6.87 (m, 1H), 6.06-6.03 (m, 1H), 5.29 (s, 2H), 3.81 (d, J=11.0 Hz, 1H), 2.84-2.63 (m, 5H), 2.28 (s, 3H), 1.01 (t, J=7.3 Hz, 3H), 0.78 (s, 9H), 0.20 (s, 3H), 0.00 (s, 3H); MS (ESI) m/z 497.18 (M+H).

Scheme 2

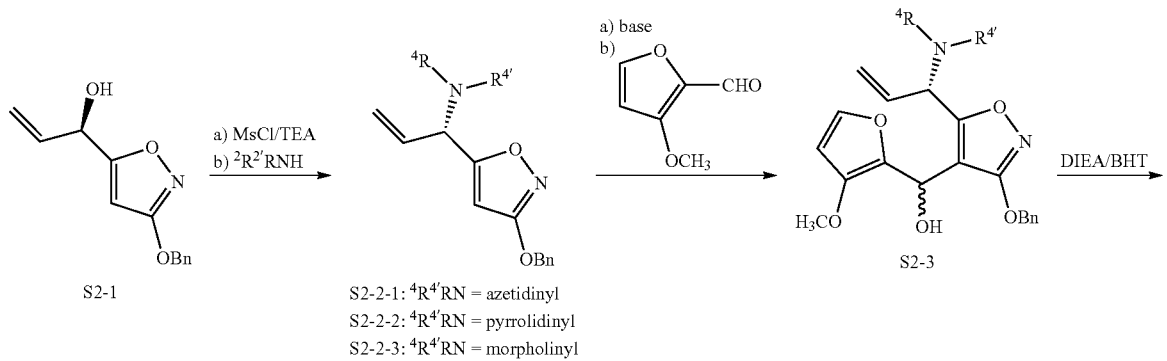

S2-2-1: $^4$R$^{4'}$RN = azetidinyl
S2-2-2: $^4$R$^{4'}$RN = pyrrolidinyl
S2-2-3: $^4$R$^{4'}$RN = morpholinyl

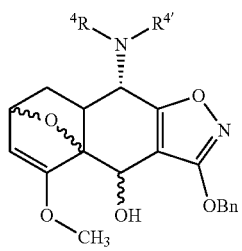

S2-4

DMSO/TEA
SO$_3$-pyridine

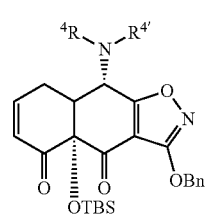 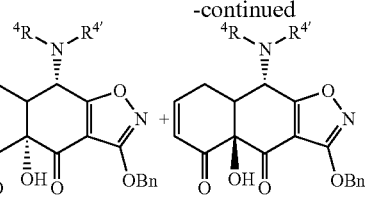 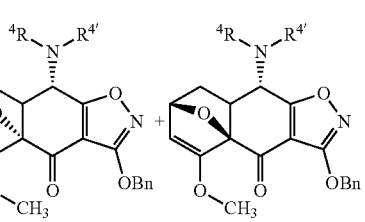

S2-7-1: ⁴R⁴'RN = azetidinyl
S2-7-2: ⁴R⁴'RN = pyrrolidinyl
S2-7-3: ⁴R⁴'RN = morpholinyl The following compounds were prepared according to Scheme 2.

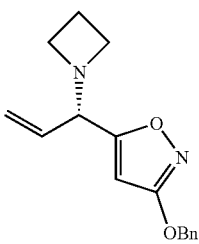

S2-2-1

Azetidine (8.31 g, 88.82 mmol, HCl salt) and sodium hydroxide (3.375 g, 84.38 mmol) were mixed in 25 mL ethanol cooling with an ice water bath. The mixture was stirred at room temperature overnight and then diluted with 10 mL dichloromethane. In another flask, allylic alcohol 1 (3.42 g, 14.8 mmol, 1.0 eq) and triethylamine (1.94 g, 19.24 mmol, 1.3 eq) was dissolved in dichloromethane (34 mL). The solution was cooled to −20 to −15° C. At this temperature MsCl (2.03 g, 17.76 mmol, 1.2 eq) was added. After addition the reaction mixture was stirred at the same temperature for 0.5 h. The above azetidine free base (6 eq) was added to the reaction mixture at −20° C. in 20 min. After the addition, the reaction mixture was placed in a freezer over the weekend. Water (100 mL) was added. The mixture was filtered through a pad of Celite. The organic layer was separated and concentrated to give 5 g crude product. The crude was dissolved in 35 ml of ethyl acetate. The ethyl acetated solution was extracted with aqueous hydrochloric acid (1 N, 20 mL and 0.5 N, 10 mL). The combined aqueous solution was washed with 10 mL of MTBE and then basified with aqueous sodium hydroxide (2 N, 15 mL). The mixture was extracted with MTBE (30 mL and 20 mL). The combined organics were washed with water and brine, and concentrated to give 2.2 g of product. This product was loaded on a 10 g silica gel column, eluted with hexane and ethyl acetate (2:1, 150 mL) to give 1.6 g of product 2-2-1: ¹H NMR (400 MHz, CDCl₃) δ 7.45-7.30 (m, 5H), 5.78 (s, 1H), 5.75-5.66 (m, 1H), 5.29 (d, J=17.1 Hz, 1H), 5.23 (d, J=8.72 Hz, 1H), 5.22 (s, 2H), 3.85 (d, J=8.24 Hz, 1H), 3.21 (m, 4H), 2.06 (m, 2H); MS (ESI) m/z 271.1 (M+H).

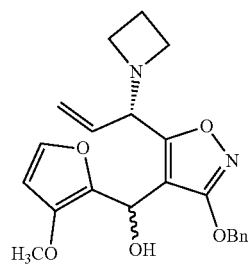

S2-3-1

Compound 2-2-1 (1.6 g, 5.93 mmol) was dissolved in 16 mL of THF, cooled to −100° C. using a liquid nitrogen/ethanol bath. A solution of n-BuLi (2.5 M, 2.84 mL, 7.11 mmol, 1.2 eq) was added at −101° C. to −99° C. to give a golden colored solution. The solution was gradually warmed up to −64° C. The then purple colored solution was cooled to −70° C. A solution of 3-methoxy-2-furaldehyde (0.90 g, 7.11 mmol, 1.2 eq) in 3.5 mL THF was added to the reaction mixture at below −62° C. After addition the reaction mixture was gradually warmed up to −5° C. The reaction was quenched with 20 mL of saturated ammonium chloride solution and extracted with MTBE (30 mL and 20 mL). The combined organics were washed with brine and concentrated to give 2.5 g of crude product. The crude was loaded on a 8 g silica gel column and eluted with hexane and ethyl acetate (5:1) to give 1.8 g of S2-3-1 as a mixture of two diastereomers as (thick oil).

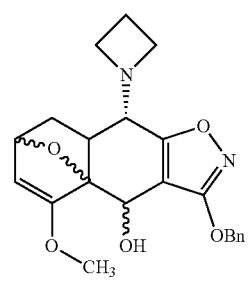

S2-4-1

Compound 2-3-1 (2.5 g, 6.31 mmol) was dissolved in 30 mL of dioxane. To the solution was added diisopropylethylamine (0.90 g, 6.94 mmol, 1.1 eq) and BHT (25 mg). The reaction mixture was stirred at 95° C. for 1 week. The mixture was evaporated to dryness to give 1.94 g of crude product S2-4-1 as a mixture of 4 diastereomers. The crude was directly used in the next step.

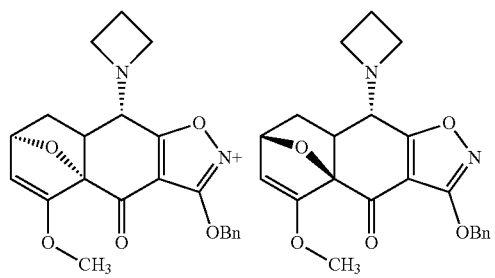

S2-5-1

Compound 2-4-1 (1.94 g, 4.90 mmol) was dissolved in 20 mL of dichloromethane. To the solution was added DMSO (1.53 g, 19.6 mmol, 4.0 eq) and triethylamine (1.98 g, 19.6 mmol, 4.0 eq). The mixture was cooled with an ice water cooling bath. Sulfur trioxide pyridine complex (1.95 g, 12.25 mmol, 2.5 eq) was added. After addition the cooling bath was removed and the reaction mixture was stirred at rt for 2 h. Additional 0.3 g of sulfur trioxide pyridine complex was added. After stirring for another 0.5 h the reaction mixture was cooled with an ice water cooling bath and quenched with water. The organic layer was separated, washed with water and brine, and concentrated to give 1.05 g of compound S2-5-1 as a mixture of 2 diastereomers: MS (ESI) m/z 395.1 (M+H).

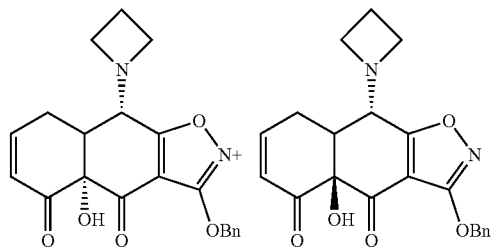

S2-6-1

Compound 2-5-1 (1.0 g, 2.54 mmol) was dissolved in 20 mL of dichloromethane. The solution was cooled. A 1 M solution of BCl$_3$ in dichloromethane (3.81 mL, 3.81 mmol, 1.5 eq) was added at −13° C. to −15° C. After addition the reaction mixture was stirred at the same temperature for 20 min and then quenched with 20 mL 20% aqueous potassium phosphate tribasic solution. The two layers were separated. The aqueous layer was extracted with 10 mL of dichloromethane. The combined organics were washed with brine and concentrated to give 0.7 g of crude product S2-6-1 (mixture of two diastereomers) as a brown oil: MS (ESI) m/z 381.1 (M+H).

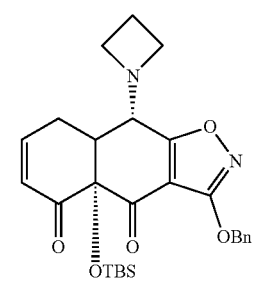

S2-7-1

Compound S2-6-1 (0.7 g, 1.84 mmol) was dissolved in 10 mL dichloromethane. The solution was cooled with an ice water bath. To the solution was added 2,6-lutidine (0.34 mL, 2.94 mmol, 1.6 eq) followed by TBSOTf (0.55 mL, 2.39 mmol, 1.3 eq). The reaction was stirred with ice water cooling for 1 h and then quenched with 10 mL of water. The organic layer was separated, washed with brine and concentrated to give 1 g of crude product. The crude was loaded on a 20 g silica gel column, eluted with hexane and ethyl acetate (6 tol, 280 mL) to give 140 mg product S2-7-1 as a white solid: $^1$H NMR (400 MHz, CDCl$_3$) δ 7.48-7.42 (m, 2H), 7.36-7.26 (m, 3H), 6.91-6.83 (m, 1H), 6.04-5.99 (m, 1H), 5.32 (s, 2H) 3.66-3.56 (m, 3H), 3.30-3.22 (m, 2H), 2.88-2.70 (m, 2H), 2.44-2.38 (m, 1H), 2.12-2.04 (m, 2H), 0.77 (s, 9H), 0.22 (s, 3H), 0.00 (s, 3H); MS (ESI) m/z 495.2 (M+H).

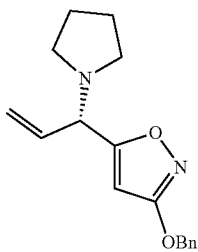

S2-2-2

Compound S2-1 (10 g, 43.3 mmol, 1.0 eq) and triethylamine (7.85 mL, 56.3 mmol, 1.3 eq) were mixed in 150 mL of dichloromethane. The solution was cooled to −27° C. Neat MsCl (3.85 mL, 49.8 mmol, 1.15 eq) was added to the reaction mixture dropwise maintaining the temperature below −20° C. After stirring for additional 30 min, the reaction mixture was further cooled and 2,2,2-trifluoroethanol (24 mL) was added at below −32° C. Pyrrolidine (22.4 mL, 259.8 mmol, 6.0 eq) was added dropwise maintaining temperature at −32° C. to −25° C. After addition the reaction mixture was stirred for 15 min and then stored in a freezer (−23° C.) overnight. Water (100 mL) was added to quench the reaction. The two layers were separated. The organic layer was concentrated to dryness. The residue was dissolved in 200 mL of MTBE. After washing with 100 mL of water 3 times, the MTBE solution was cooled with an ice/water bath. Aqueous HCl (1 M, 100 mL) was added at below 10° C. The two layers were separated. To the aqueous layer was added 2 N NaOH at below 10° C. to adjust the pH to basic. The mixture was extracted with 200 mL of MTBE. The MTBE solution was concentrated to dryness to give 10 g of crude product. The crude was purified using a 40 g silica gel column to give 7 g of product 2-2-2: $^1$H NMR (400 MHz, CDCl$_3$) δ 7.45-7.32 (m, 5H), 6.04-5.95 (m, 1H), 5.84 (s, 1H), 5.34-5.21 (m, 2H), 5.25 (s, 2H), 3.96 (d, J=8.3 Hz, 1H), 2.52-2.49 (m, 4H), 1.85-1.74 (m, 4H); MS (ESI) m/z 285.1 (M+H).

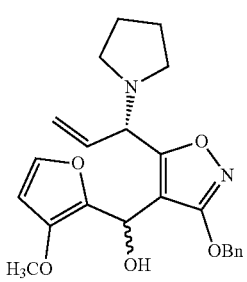

S2-3-2

Compound 2-2-2 (7.0 g, 24.6 mmol, 1.0 eq) was dissolved in THF. The solution was cooled with a water/ice/methanol batch. To the reaction mixture was added TMPMgCl—LiCl (1.0 M, 34.4 mL, 1.4 eq) at 0° C. After addition the reaction mixture was stirred for another 0.5 h and then cooled to −50° C. 3-Methoxy-2-uraldehyde (3.42 g, 27.1 mmol, 1.1 eq) was added at −50° C. The reaction mixture was gradually warmed up to −7° C. in 2.5 h and then quenched with 70 mL of saturated ammonium chloride aqueous solution. The two layers were separated. The aqueous layer was extracted with ethyl acetate twice (30 mL each). The combined organics were washed sequentially with saturated aqueous ammonium chloride (30 mL), water (30 mL) and brine (30 mL). After concentration, the crude was loaded on a 230 g silica gel column, eluted with hexane and ethyl acetate to give 5.8 g of product S2-3-2 as a mixture of the two diastereomers: MS (ESI) m/z 411.2 (M+H).

S2-4-2

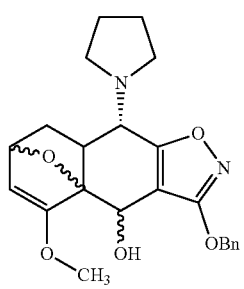

Compound 2-3-2 (5.8 g, 14.15 mmol) was dissolved in 60 mL of dioxane. To the solution was added diisopropylethylamine (2.01 g, 15.56 mmol, 1.1 eq) and BHT (50 mg). The mixture was stirred at 95° C. for 1 week. The mixture was concentrated and then dried under high vacuum to give 6.2 g of crude product S2-4-2 as a mixture of 4 diastereomers: MS (ESI) m/z 411.2 (M+H).

S2-5-2

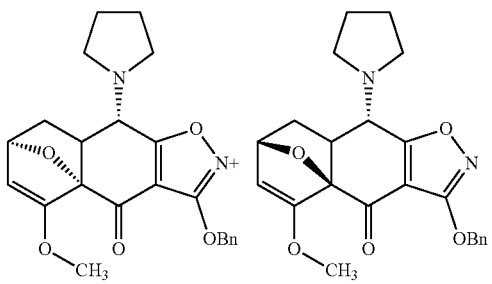

The above crude compound S2-4-2 (14.15 mmol), DMSO (4.42 g, 56.6 mmol, 4.0 eq) and triethylamine (5.72 g, 56.6 mmol, 4.0 eq) were mixed in 60 mL of dichloromethane. After the mixture was cooled with an ice/water cooling bath, sulfur trioxide pyridine complex (4.73 g, 29.7 mmol, 2.1 eq) was added. After addition, the cooling bath was removed. After stirring at rt for 5 h, additional 1 g of sulfur trioxide pyridine was added and the reaction was stirred for another 1 day. The reaction was cooled with an ice/water bath and then quenched with 40 mL of water. The organic layer was separated, washed with brine and concentrated to give 6.8 g of crude product S2-5-2 as a mixture of 2 diastereomers: MS (ESI) m/z 409.2 (M+H).

S2-6-2

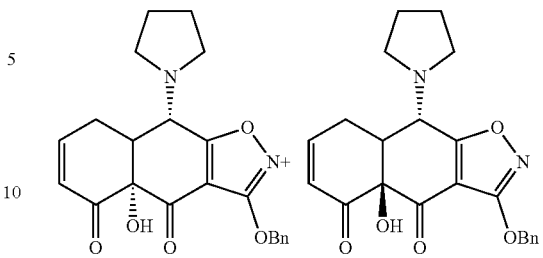

The above crude compound S2-5-2 (~14 mmol) was dissolved in 70 mL of dichloromethane. The solution was cooled with a dry ice/acetone/water bath. A solution of BCl$_3$ (1 M, 19.6 mL, 1.4 eq) was added at −17° C. to −14° C. After addition the reaction mixture was stirred at the same temperature for 20 min and then quenched with 30 mL of 20% aqueous K$_3$PO$_3$ solution. The two layers were separated. The aqueous layer was extracted with 10 mL of dichloromethane. The combined organics were washed with brine and concentrated to give 5.7 g of crude compound S2-6-2 as a brown solid (mixture of 2 diastereomers): MS (ESI) m/z 395.2 (M+H).

S2-7-2

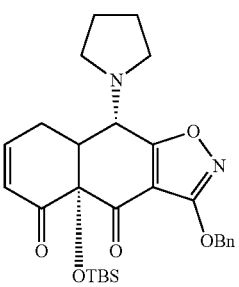

The above crude compound S2-6-2 (~14 mmol) was dissolved in 60 mL of DCM. The solution was cooled with an ice/water bath. To the solution was added 2,6-lutidine (2.4 g, 22.4 mmol, 1.6 eq) followed by TBSOTf (4.9 g, 18.5 mmol, 1.3 eq). The reaction mixture was stirred with the cooling bath for 1 h and then quenched with 50 mL of water. The organic layer was separated, washed with brine and concentrated. The crude was loaded on a 50 g silica gel column, eluted with hexane and ethyl acetate (9:1, 500 mL) to give 2.1 g of compound S2-7-2 as a yellow solid: $^1$H NMR (400 MHz, CDCl$_3$) δ7.46-7.40 (m, 2H), 7.34-7.24 (m, 3H), 6.91-6.84 (m, 1H), 6.06-6.02 (m, 1H), 5.29 (s, 2H), 4.05 (d, J=11.0 Hz, 1H), 3.00-2.94 (m, 2H), 2.82-2.72 (m, 3H), 2.60-2.54 (m, 2H), 0.77 (s, 9H), 0.20 (s, 3H), 0.00 (s, 3H); MS (ESI) m/z 509.3 (M+H).

S2-2-3

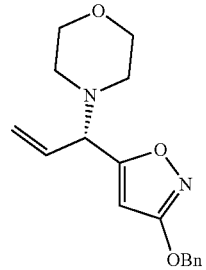

Compound S2-1 (10 g, 43.3 mmol, 1.0 eq) and triethylamine (7.85 mL, 56.3 mmol, 1.3 eq) were mixed in 150 mL of dichloromethane. The solution was cooled to below −20°

C. Neat MsCl (3.85 mL, 49.8 mmol, 1.15 eq) was added to the reaction mixture dropwise maintaining the temperature below −20° C. After addition the reaction mixture was stirred for 30 min. The reaction mixture was further cooled to −28° C. Morpholine (22.7 mL, 259.8 mmol, 6.0 eq) was added dropwise keeping the temperature below −25° C. The reaction mixture was gradually warmed up to 5° C. over a period of 5 h. Water (150 mL) was added to quench the reaction. The organic layer was separated and concentrated to dryness. The residue was dissolved in 200 mL of toluene, washed with water (100 mL×2) and brine (100 mL), and again concentrated to dryness. The crude was loaded on an 80 g silica gel column and eluted with hexane and ethyl acetate (2:1 to 3:2). The fractions containing the product were combined and then concentrated to 200 mL. After the solution was cooled to 0° C., 1 N HCl (60 mL) was added. The two layers were separated. To the aqueous layer was added MTBE (300 mL) and 2 N NaOH (40 mL) while cooling with an ice/water bath. The organic layer was separated and concentrated to dryness to give 8.9 g of product S2-2-3: $^1$H NMR (400 MHz, CDCl$_3$) δ 7.45-7.32 (m, 5H), 5.95-5.85 (m, 1H), 5.81 (s, 1H), 5.35-5.29 (m, 2H), 5.23 (s, 2H), 3.98 (d, J=8.2 Hz, 1H), 3.69 (t, J=4.6 Hz, 4H), 2.55-2.41 (m, 4H); MS (ESI) m/z 301.1 (M+H).

S2-3-3

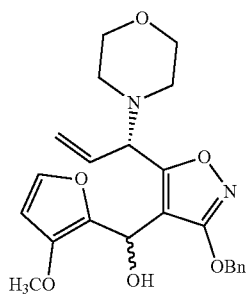

Compound S2-2-3 (8.9 g, 29.6 mmol, 1.0 eq) was dissolved in 150 mL of THF. The solution was cooled to −102° C. using a liquid nitrogen/ethanol bath. n-BuLi (2.5 M in hexane, 15.4 mL, 38.48 mmol, 1.3 eq) was added slowly maintaining the temperature below −98° C. The reaction mixture was stirred at −102° C. to −80° C. for 1 h. Solid MgBr$_2$-Et$_2$O (9.94 g, 35.52 mmol, 1.2 eq) was added via a solid additional funnel over a period of 10 min maintaining temperature below −70° C. The resulting slurry was stirred at −70° C. for 30 min. At the same temperature solid 3-methoxy-2furaldehyde (4.48 g, 38.48 mmol, 1.3 eq) was added. The reaction mixture was gradually warmed up to −20° C. over a period of 1.5 h and then quenched with 80 mL of saturated NH$_4$Cl. The organic layer was separated and concentrated to dryness. The residue was dissolved in 200 mL of ethyl acetate, washed with water and brine and again concentrated to dryness. The crude was purified by silica gel (300 g) column eluting with hexane and ethyl acetate (4:1 to 3:1) to give 4.84 g of compound S2-3-3 as a 1 to 1 mixture of the 2 diastereomers: MS (ESI) m/z 427.2 (M+H).

S2-4-3

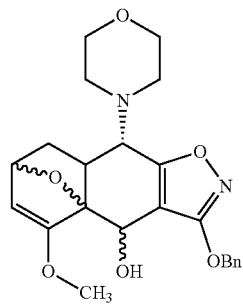

Compound S2-3-3 (4.84 g, 11.4 mmol), diiospropylethylamine (4.5 mL, 25.8 mmol) and BHT (10 mg) were mixed in 150 mL 2-propanol. The reaction mixture was refluxed for 1 week. The mixture was concentrated to dryness. The residue was purified by silica gel column eluting with hexane and acetone (4:1 to 2:1) to give 0.93 g product S2-4-3 as a mixture of 4 diastereomers: MS (ESI) m/z 427.2 (M+H).

S2-5-3

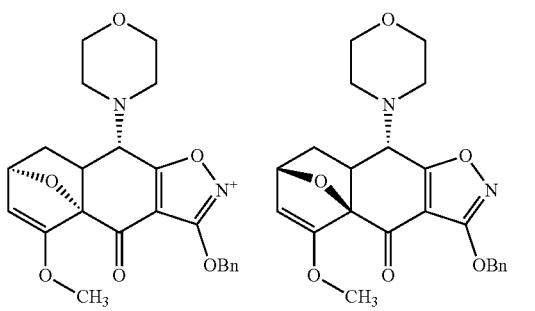

Compound S2-4-3 (0.9 g, 2.11 mmol, 1.0 eq) was dissolved in 4 mL of dichloromethane. To the solution was added triethylamine (1.2 mL, 8.44 mmol, 4.0 eq). The solution was cooled with an ice/water bath. A mixture of sulfur trioxide pyridine complex (705 mg, 4.43 mmol, 2.1 eq) in DMSO (2.33 mL) was added at temperature below 5° C. The water bath was removed and the reaction mixture was stirred at room temperature overnight. The reaction was cooled with an ice/water cooling bath and quenched with 20 mL of water. The organic layer was separated and concentrated to dryness. The residue was dissolved in 100 mL of ethyl acetate, washed with water (25 mL×3) and brine (25 mL) and concentrated to dryness. The residue was dissolved in 20 mL of toluene and then evaporated to dryness to give 0.86 g crude product s2-5-3 as a mixture of 2 diastereomers: MS (ESI) m/z 425.2 (M+H).

S2-6-3

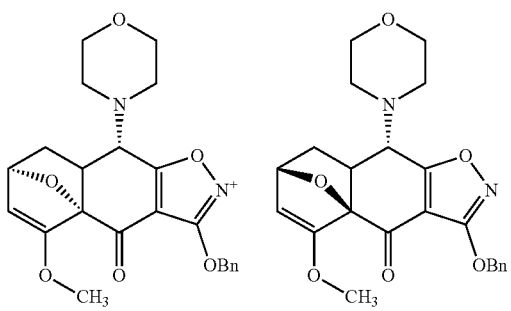

Compound S2-5-3 (0.86 g, 2 mmol, 1.0 eq) was dissolved in 12 mL of dichloromethane. The solution was cooled to −17° C. To the solution was added BCl$_3$ (1 M, 3 mL, 3 mmol, 1.5 eq) was added at below −15° C. After addition the reaction mixture was stirred at −16° C. to −13° C. for 30 min. Aqueous 15% K$_3$PO$_4$ was added to quench the reaction. The reaction mixture was extracted with 100 mL of dichloromethane, washed with water (30 mL×3) and brine. After concentration to dryness, 0.83 g of crude product S2-6-3 was obtained: MS (ESI) m/z 411.2 (M+H).

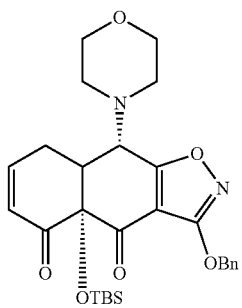

S2-7-3

Compound S2-6-3 (0.83 g, 3 mmol, 1.0 eq) was dissolved in 10 mL of dichloromethane. To this solution was added 2,6-lutidine (0.46 mL, 4 mmol, 2.0 eq). After the solution was cooled with an ice/water bath, TBSOTf (0.69 mL, 3 mmol, 1.5 eq) was added. After addition the reaction mixture was stirred at 0° C. for 1.5 h. Water (10 mL) was added to quench the reaction. The mixture was extracted with 100 mL of toluene. The organics was washed with water (20 mL×3) and brine (20 mL), and concentrated. The crude was purified by a silica gel (20 g) column eluting with toluene followed by dichloromethane and acetone (9:1) to give 0.66 g of product S2-7-3 as a yellow solid: $^1$H NMR (400 MHz, CDCl$_3$) δ 7.46-7.42 (m, 2H), 7.36-7.28 (m, 3H), 6.92-6.86 (m, 1H), 6.06 (m, 1H), 5.30 (d, J=2.8 Hz, 2H), 3.71 (d, J=11 Hz, 1H), 2.98-2.92 (m, 2H), 2.86-2.74 (m, 3H), 2.56-2.50 (m, 2), 0.78 (s, 9H), 0.20 (s, 3H), 0.00 (s, 3H); MS (ESI) m/z 525.2 (M+H).

The following compounds were prepared according to Scheme 3.

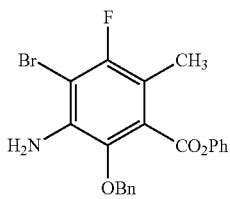

S3-2

To a solution of aniline S3-1 (15.0 g, 42.69 mmol, 1 eq, prepared according to literature procedures including *J. Med. Chem.*, 2012, 55, 606-622) and NaOAc (10.5 g, 128.07 mmol, 3 eq) in HOAc (100 mL) was added a solution of Br$_2$ (2.20 mL, 42.69 mmol, 1 eq) in HOAc (10 mL) dropwise via syringe at 17→19° C. while cooled in a cold water bath. After stirring at 20° C. for 20 min, more Br$_2$ (66 µL) in HOAc (1 mL) was added. After stirring for 5 min, the reaction was poured into ice/water. The resulting mixture was extracted with EtOAc (600 mL). The organic phase was separated, washed with 10% aqueous Na$_2$S$_2$O$_3$ solution, water, saturated aqueous sodium bicarbonate and brine. The resulting organic phase was dried over sodium sulfate, filtered and concentrated under reduced pressure. Flash chromatography on silica gel using 5%→6% EtOAc/hexanes yielded the desired product S3-2 as thick pale Scheme 3

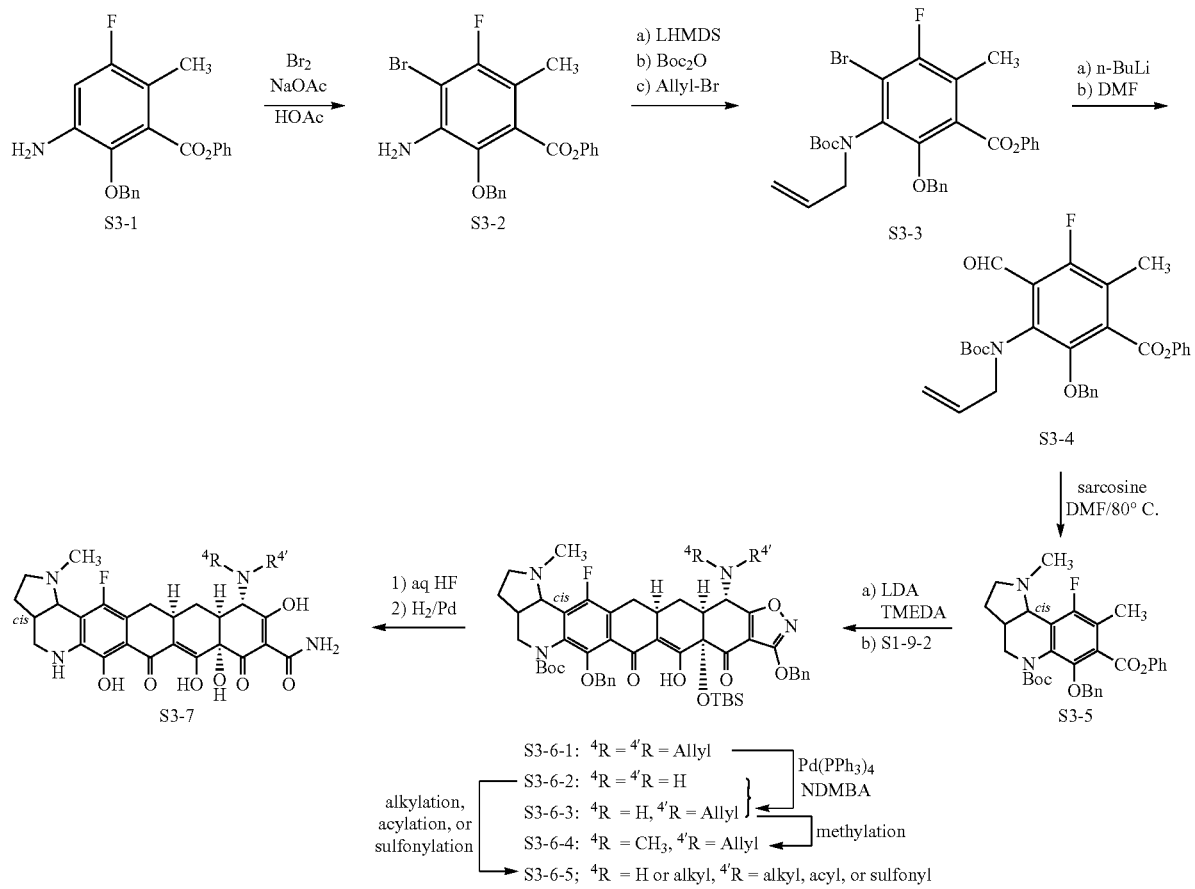

yellow oil (15.59 g, 85%): ¹H NMR (400 MHz, CDCl₃) δ 7.44-7.35 (m, 7H), 7.28-7.25 (m, 1H), 7.15-7.13 (m, 2H), 5.01 (s, 2H), 4.27 (br s, 2H), 2.32 (d, J=2.4 Hz, 3H); MS (ESI) m/z 429.94, 431.92 (M+H).

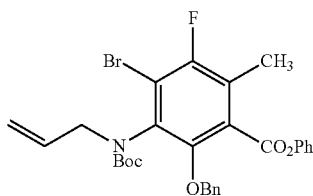

S3-3

To a solution of aniline S3-2 (908 mg, 2.11 mmol, 1 eq) in anhydrous THF (8 mL) was added a solution of LHMDS in THF (4.43 mL, 1.0 M, 4.43 mmol, 2.1 eq) at below −70° C. over 7 min. The resulting reaction solution was stirred at −78° C. for 15 min. A solution of Boc₂O (484 mg, 2.22 mmol, 1.05 eq) in THF (1 mL) was added at below −71° C. The reaction was stirred at −78° C. for 30 min, and then the dry ice was removed from the cold bath. The reaction was then warmed up to −50° C., and allyl bromide (0.201 mL, 2.32 mmol, 1.1 eq) was added. The reaction was warmed up to rt in 20 min, then it was heated at 50° C. for 3 h. More allyl bromide (0.201 mL, 2.32 mmol, 1.1 eq) was added. The resulting reaction was heated at 50° C. for 2 h, and then cooled to rt. The reaction was diluted with EtOAc (40 mL), washed with saturated aqueous NH₄Cl (2×30 mL) and brine (30 mL). The resulting organic phase was dried over sodium sulfate, filtered, and concentrated under reduced pressure. Flash chromatography on silica gel using 2%→5% EtOAc/hexanes yielded the desired product S3-3 (1.06 g, 88%, ~3:1 rotamers): ¹H NMR (400 MHz, CDCl₃) δ 7.39-7.34 (m, 7H), 7.29-7.25 (m, 1H), 7.04-7.00 (m, 2H), 6.00-5.90 (m, 1H), 5.09-5.04 (m, 1H), 5.03-5.00 (m, 2.25H), 4.92 (d, J=10.4 Hz, 0.75H), 4.50 (dd, J=6.1, 14.6 Hz, 0.75H), 4.24 (dd, J=6.1, 15.3 Hz, 0.25H), 4.04-3.97 (m, 1H), 2.42 (d, J=2.4 Hz, 2.25H), 2.40 (d, J=2.4 Hz, 0.75H), 1.54 (s, 2.25H), 1.44 (s, 6.75H); MS (ESI) m/z 591.99, 593.98 (M+Na).

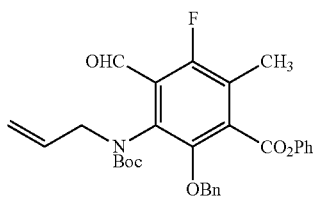

S3-4

To a solution of bromide S3-3 (1.06 g, 1.86 mmol, 1 eq) in anhydrous THF (30 mL) was added a solution of nBuLi in hexanes (1.16 mL, 1.6 M, 1.86 mmol, 1.0 eq) dropwise at below −100° C. After stirring for 3 min, a solution of DMF (0.215 mL, 2.79 mmol, 1.5 eq) in THF (1 mL) was added at below −100° C. The resulting reaction solution was then allowed to warm up to −78° C. and stirred at that temperature for 35 min. Then saturated aqueous NH₄Cl was added. The resulting mixture was allowed to warm up to rt and extracted with EtOAc (40 mL). The organic phase was washed with brine, dried over sodium sulfate, filtered, and concentrated under reduced pressure. Flash chromatography on silica gel using 3%→12% EtOAc/hexanes yielded the desired product S3-4 (0.91 g, 94%, ~2:1 rotamers): ¹H NMR (400 MHz, CDCl₃) δ 10.22 (s, 1H), 7.38-7.33 (m, 7H), 7.28-7.24 (m, 1H), 7.02-6.99 (m, 2H), 5.93-5.79 (m, 1H), 5.04-4.96 (m, 3.35H), 4.89 (d, J=9.8 Hz, 0.65H), 4.64 (dd, J=5.5, 14.6 Hz, 0.65H), 4.32 (dd, J=5.5, 14.6 Hz, 0.35H), 3.97 (dd, J=7.9, 14.6 Hz, 0.35H), 3.90 (dd, J=8.5, 14.6 Hz, 0.65H), 2.40 (d, J=1.8 Hz, 2H), 2.37 (d, J=1.8 Hz, 1H), 1.51 (s, 3H), 1.36 (s, 6H); MS (EST) m/z 542.11 (M+Na).

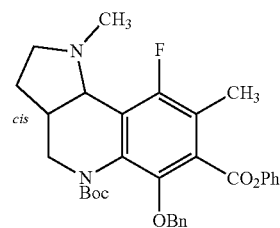

S3-5

To a mixture of compound S3-4 (4.52 g, 8.71 mmol, 1 eq) and sarcosine (1.16 g, 13.06 mmol, 1.5 eq) was added DMF (72 mL) under nitrogen. The resulting reaction mixture was stirred at 80° C. for 1 h 30 min, and cooled to rt. The resulting reaction mixture was then partitioned between EtOAc (500 mL) and water (720 mL). The organic phase was separated, washed with water (2×500 mL), brine (250 mL), dried over Na₂SO₄, filtered and concentrated under reduced pressure. Flash chromatography on silica gel using 10%→60% EtOAc/hexanes yielded the desired product S3-5 as a white solid (4.68 g, 98%). ¹H NMR (400 MHz, CDCl₃) δ 7.38-7.28 (m, 7H), 7.25-7.22 (m, 1H), 7.06-7.04 (m, 2H), 4.96-4.84 (m, 2H), 4.25 (br s, 1H), 3.60 (br s, 1H), 2.98 (br t, J=7.3 Hz, 1H), 2.78-2.64 (m, 2H), 2.35 (d, J=1.8 Hz, 3H), 2.26 (br s, 4H), 2.17-2.02 (m, 2H), 1.32 (br s, 9H); MS (ESI) m/z 547.14 (M+H).

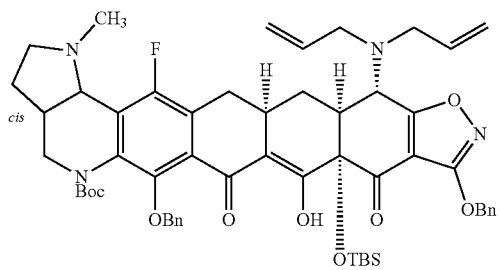

S3-6-1

General Procedure A (Michael-Dieckmann annulation). n-BuLi (170 μL, 1.6 M in hexanes, 0.272 mmol, 1.4 eq) was added dropwise to a solution of diisopropylamine (41 μL, 0.291 mmol, 1.5 eq) in THF (1 mL) at −50° C. The reaction mixture was warmed up to −20° C. and re-cooled to below −70° C. TMEDA (44 μL, 0.291 mmol, 1.5 eq) was added. The reaction solution was stirred at −78° C. for 5 min. A solution of racemic compound S3-5 (106 mg, 0.194 mmol, 1 eq) in THF (1 mL) was added dropwise via a cannula at below −72° C. The resulting red orange solution was stirred at −78° C. for 30 min, and cooled to −100° C. using a EtOH/liquid N₂ bath. A solution of enone S1-9-2 (104 mg, 0.194 mmol, 1 eq) in THF (1 mL) was added to the reaction mixture. The reaction mixture was allowed to gradually warm up and then LHMDS (194 μL, 1.0 M in THF, 0.194 mmol, 1 eq) was added at ~-90° C. The reaction mixture was gradually warmed up to -10° C. A saturated aqueous NH₄Cl (20 mL) solution was added to the reaction. The reaction mixture was extracted with EtOAc (40 mL). The organic phase was washed with brine (20 mL), dried over Na₂SO₄, and concentrated under reduced pressure. Flash chromatography on silica gel using 1%→50% EtOAc/hexanes yielded the desired product S3-6-1 as a yellow solid (179 mg, 94%, ~1:1 diastereomers plus rotamers for each diastereomer): MS (ESI) m/z 987.52 (M+H).

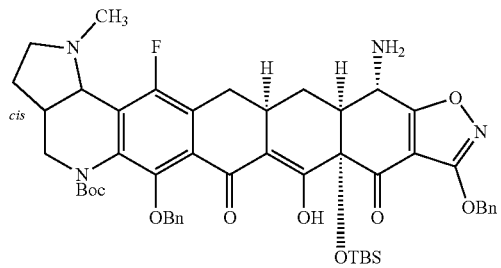

S3-6-2

General Procedure B (de-allylation). To a mixture of compound S3-6-1 (234 mg, 0.237 mmol, 1 eq), 1,3-dimethylbarbituric acid (370 mg, 2.37 mmol, 10 eq) and Pd(PPh₃)₄ (14 mg, 0.024 mmol, 0.1 eq) was added DCM (5 mL) under nitrogen. The resulting reaction solution was stirred at rt overnight. The reaction mixture was quenched with aqueous saturated sodium bicarbonate (bubbling). The resulting reaction mixture was stirred at rt for 10 min, and extracted with dichloromethane (3×10 mL). The combined organic extracts were dried over anhydrous sodium sulfate, filtered and concentrated under reduced pressure. The residue was purified by flash chromatography on silica gel using 20%→100% EtOAc/hexanes to yield the desired product S3-6-2 (159 mg, 74%, ~1:1 diastereomers plus rotamers for each diastereomer) as a yellow solid: MS (ESI) m/z 907.51 (M+H).

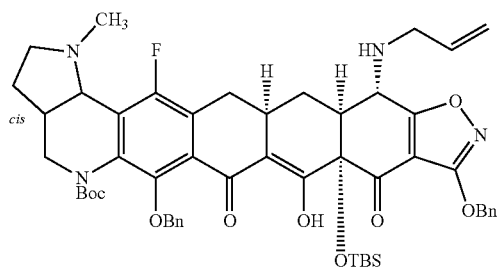

S3-6-3

Compound S3-6-3 was also isolated in 15% yield along with compound S3-6-2 (41% yield) and starting material (18% recovered) by using the general procedure B when only half of the amounts of the reagents were used. S3-6-3: MS (ESI) m/z 947.49 (M+H).

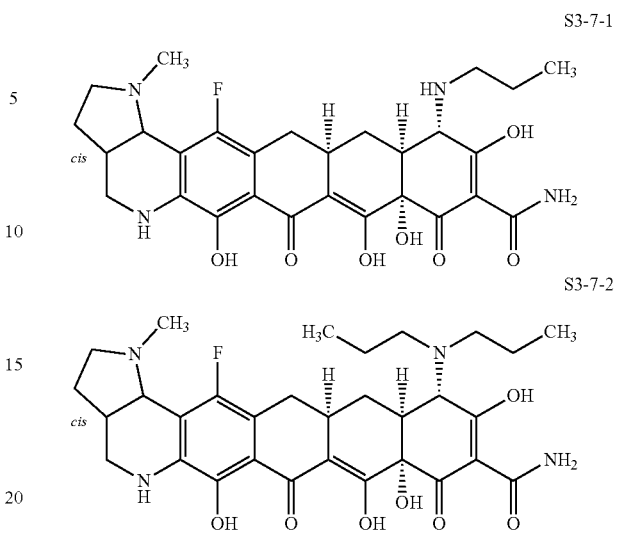

General Procedure C (HF desilylation and hydrogenation). Aqueous HF (48-50%, 0.5 mL) was added to a solution of compound S3-6-1 (27 mg, 0.028 mmol, 1 eq) in dioxane (0.5 mL) in a polypropylene reaction vessel at rt. The mixture was stirred vigorously at rt overnight and poured slowly into saturated aqueous NaHCO₃ (15 mL) (vigorously bubbling). The resulting mixture was extracted with EtOAc (30 mL). The organic phase was washed with brine, dried over anhydrous sodium sulfate and concentrated under reduced pressure. The residue was used directly in the next step without further purification (MS (ESI) m/z 773.35 (M+H)).

Pd—C (10 wt %, 10 mg) was added in one portion into a solution of the above crude product in a mixture of CH₃OH (1 mL) and HCl/water (1 N, 84 μL, 0.084 mmol, 3 eq) at rt. The reaction vessel was sealed and purged with hydrogen by briefly evacuating the flask followed by flushing with hydrogen gas (1 atm). The reaction mixture was stirred under a hydrogen atmosphere (1 atm) at rt for 40 min, and filtered through a small Celite pad. The cake was washed with MeOH. The filtrate was concentrated. The residue was purified by preparative reverse phase HPLC on a Waters Autopurification system using a Phenomenex Polymerx 10μ RP-γ 100 A column [10 μm, 150×21.20 mm; flow rate, 20 mL/min; Solvent A: 0.05 NHCl/water; Solvent B: CH₃CN; injection volume: 3.0 mL (0.05 NHCl/water); gradient: 0→35% B in A over 20 min; mass-directed fraction collection]. Fractions containing the desired product were collected and freeze-dried to yield compound S3-7-1 (6.63 mg) and compound S3-7-2 (3.33 mg). The two diastereomers of compound S3-7-1 was separated by a second HPLC purification (5→30% B in A over 20 min). The early eluting diastereomer is S3-7-1-A, and the later one is S3-7-1-B.

S3-7-1-A: ¹H NMR (400 MHz, CD₃OD, hydrochloride salt) δ 4.76 (d, J=6.4 Hz, 1H), 3.86 (s, 1H), 3.77-3.71 (m, 1H), 3.44 (dd, J=5.5, 13.3 Hz, 1H), 3.35-3.17 (m, 3H), 3.12-3.04 (m, 5H), 2.99-2.93 (m, 1H), 2.84 (d, J=12.4 Hz, 1H), 2.78-2.71 (m, 1H), 2.57-2.47 (m, 1H), 2.25-2.17 (m, 2H), 2.09-2.01 (m, 1H), 1.83-1.72 (m, 2H), 1.60-1.50 (m, 1H), 1.03 (t, J=7.3 Hz, 3H); MS (ESI) m/z 557.28 (M+H).

S3-7-1-B: ¹H NMR (400 MHz, CD₃OD, hydrochloride salt) δ 4.76 (d, J=6.0 Hz, 1H), 3.87 (s, 1H), 3.78-3.71 (m, 1H), 3.45 (dd, J=5.5, 13.3 Hz, 1H), 3.36-3.19 (m, 3H), 3.12-3.04 (m, 5H), 3.00-2.93 (m, 1H), 2.86 (d, J=12.4 Hz, 1H), 2.78-2.70 (m, 1H), 2.58-2.48 (m, 1H), 2.23-2.14 (m, 2H), 2.07-1.99 (m, 1H), 1.82-1.72 (m, 2H), 1.58-1.48 (m, 1H), 1.02 (t, J=7.3 Hz, 3H); MS (ESI) m/z 557.28 (M+H).

S3-7-2: $^1$H NMR (400 MHz, CD$_3$OD, hydrochloride salt, mixture of diastereomers) δ 4.76 (d, J=6.0 Hz, 1H), 4.22 (s, 1H), 3.78-3.72 (m, 1H), 3.53-3.17 (m, 5H), 3.14-2.93 (m, 8H), 2.78-2.70 (m, 1H), 2.58-2.48 (m, 1H), 2.25-2.15 (m, 2H), 2.08-1.99 (m, 1H), 1.89-1.76 (m, 4H), 1.66-1.56 (m, 1H), 1.02 (t, J=6.9 Hz, 3H), 0.99 (t, J=7.3 Hz, 3H); MS (ESI) m/z 599.37 (M+H).

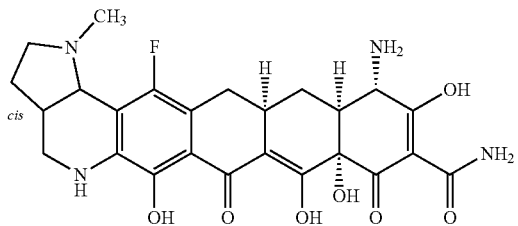

S3-7-3

Compound S3-7-3 was prepared from compound S3-6-2 by using the general procedure C.

S3-7-3-A: $^1$H NMR (400 MHz, CD$_3$OD, hydrochloride salt) δ 4.76 (d, J=6.4 Hz, 1H), 3.87 (s, 1H), 3.78-3.71 (m, 1H), 3.44 (dd, J=5.5, 12.8 Hz, 1H), 3.36-3.29 (m, 1H), 3.13-3.02 (m, 5H), 2.97-2.87 (m, 1H), 2.80-2.71 (m, 1H), 2.65-2.62 (m, 1H), 2.56-2.48 (m, 1H), 2.26-2.19 (m, 2H), 2.08-2.03 (m, 1H), 1.61-1.52 (m, 1H); MS (ESI) m/z 515.25 (M+H).

S3-7-3-B: $^1$H NMR (400 MHz, CD$_3$OD, hydrochloride salt) δ 4.75 (d, J=6.4 Hz, 1H), 3.87 (s, 1H), 3.78-3.71 (m, 1H), 3.45 (dd, J=5.5, 13.3 Hz, 1H), 3.37-3.29 (m, 1H), 3.12-3.02 (m, 5H), 2.98-2.91 (m, 1H), 2.76-2.70 (m, 1H), 2.65-2.62 (m, 1H), 2.56-2.50 (m, 1H), 2.24-2.17 (m, 2H), 2.07-2.00 (m, 1H), 1.61-1.52 (m, 1H); MS (ESI) m/z 515.25 (M+H).

General Procedure D-1 (Reductive Alkylation). To a solution of compound S3-6-3 (22 mg, 0.023 mmol, 1 eq) in DCM (1 mL) was added a solution of HCHO in water (37 wt %, 5.2 μL, 0.070 mmol, 3 eq), HOAc (2.6 μL, 0.046 mmol, 2 eq) and sodium triacetoxyborohydride (10 mg, 0.046 mmol, 2 eq) subsequently. The resulting reaction mixture was stirred at rt overnight. More HCHO in water (37 wt %, 5.2 μL, 0.070 mmol, 3 eq), HOAc (2.6 μL, 0.046 mmol, 2 eq) and sodium triacetoxyborohydride (10 mg, 0.046 mmol, 2 eq) were added. The resulting mixture was further stirred at rt for 6 h, and quenched by the addition of saturated aqueous sodium bicarbonate and potassium phosphate buffer solution (pH=7). The resulting mixture was extracted with DCM (2×20 mL). The combined organic phase was dried over anhydrous sodium sulfate, filtered, and concentrated to give the crude reductive alkylation product S3-6-4: MS (ESI) m/z 961.52 (M+H).

The crude reductive alkylation product S3-6-4 was subjected to the general procedure C for HF desilylation and hydrogenation to yield the desired compound S3-7-4-A (3.50 mg, 24% over 3 steps), S3-7-4-B (2.59 mg, 18% over 3 steps) and S3-7-5 (2.12 mg, 14% over 3 steps, a mixture of diastereomers).

S3-7-4-A: $^1$H NMR (400 MHz, CD$_3$OD, hydrochloride salt) δ 4.76 (d, J=6.4 Hz, 1H), 3.81 (s, 1H), 3.78-3.71 (m, 1H), 3.44 (dd, J=6.4, 12.8 Hz, 1H), 3.35-3.31 (m, 1H), 3.11-3.04 (m, 5H), 2.99-2.91 (m, 1H), 2.91 (s, 3H), 2.82-2.72 (m, 2H), 2.57-2.50 (m, 1H), 2.24-2.17 (m, 2H), 2.08-2.01 (m, 1H), 1.59-1.49 (m, 1H); MS (ESI) m/z 529.29 (M+H).

S3-7-4-B: $^1$H NMR (400 MHz, CD$_3$OD, hydrochloride salt) δ 4.76 (d, J=6.4 Hz, 1H), 3.80 (s, 1H), 3.78-3.71 (m, 1H), 3.45 (dd, J=5.0, 12.8 Hz, 1H), 3.35-3.30 (m, 1H), 3.12-3.03 (m, 5H), 3.01-2.94 (m, 1H), 2.91 (s, 3H), 2.81 (d, J=12.4 Hz, 1H), 2.76-2.71 (m, 1H), 2.58-2.48 (m, 1H), 2.22-2.15 (m, 2H), 2.07-1.99 (m, 1H), 1.59-1.50 (m, 1H); MS (ESI) m/z 529.29 (M+H).

S3-7-5: $^1$H NMR (400 MHz, CD$_3$OD, hydrochloride salt, mixture of diastereomers) δ 4.76 (d, J=6.4 Hz, 1H), 4.20 (s, 0.5H), 4.11 (s, 0.5H), 3.78-3.72 (m, 1H), 3.48-3.43 (m, 1H), 3.36-3.29 (m, 2H), 3.13-2.91 (m, 11H), 2.79-2.71 (m, 1H), 2.56-2.50 (m, 1H), 2.26-2.16 (m, 2H), 2.08-1.99 (m, 1H), 1.89-1.76 (m, 2H), 1.66-1.56 (m, 1H), 1.05-0.99 (m, 3H); MS (ESI) m/z 571.33 (M+H).

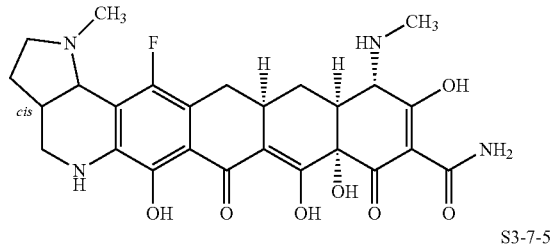

S3-7-4

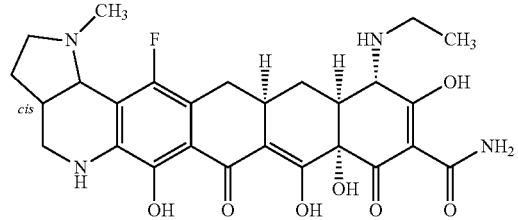

S3-7-6

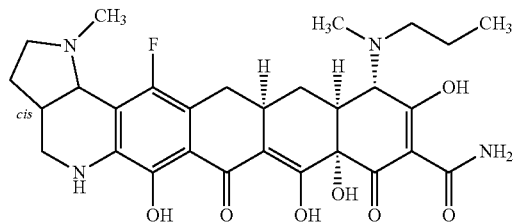

S3-7-5

Compound S3-7-6 was prepared from compound S3-6-2 by using the general procedure D-1 (with acetaldehyde) and C.

S3-7-6-A: $^1$H NMR (400 MHz, CD$_3$OD, hydrochloride salt) δ 4.76 (d, J=6.4 Hz, 1H), 3.86 (s, 1H), 3.78-3.71 (m, 1H), 3.47-3.40 (m, 2H), 3.36-3.29 (m, 2H), 3.12-3.04 (m, 5H), 2.98-2.90 (m, 1H), 2.83 (d, J=12.8 Hz, 1H), 2.78-2.71 (m, 1H), 2.55-2.49 (m, 1H), 2.24-2.17 (m, 2H), 2.07-2.00 (m, 1H), 1.58-1.49 (m, 1H), 1.36 (t, J=6.9 Hz, 3H); MS (ESI) m/z 543.26 (M+H).

S3-7-6-B: $^1$H NMR (400 MHz, CD$_3$OD, hydrochloride salt) δ 4.76 (d, J=6.0 Hz, 1H), 3.86 (s, 1H), 3.78-3.71 (m, 1H), 3.48-3.41 (m, 2H), 3.36-3.29 (m, 2H), 3.13-3.04 (m, 5H), 3.00-2.92 (m, 1H), 2.84 (d, J=12.4 Hz, 1H), 2.76-2.70 (m, 1H), 2.58-2.48 (m, 1H), 2.22-2.15 (m, 2H), 2.07-0.99 (m, 1H), 1.59-1.49 (m, 1H), 1.36 (t, J=7.3 Hz, 3H); MS (ESI) m/z 543.26 (M+H).

S3-7-7

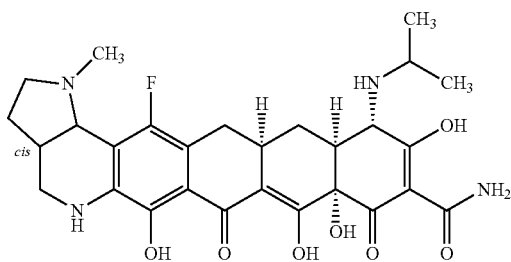

Compound S3-7-7 was prepared from compound S3-6-2 by using the general procedure D-1 (with acetone) and C. The two diastereomers were separated by HPLC.

S3-7-7-A: ¹H NMR (400 MHz, CD₃OD, hydrochloride salt) δ 4.76 (d, J=6.4 Hz, 1H), 3.95 (s, 1H), 3.86-3.71 (m, 2H), 3.45 (dd, J=5.5, 12.8 Hz, 1H), 3.38-3.29 (m, 1H), 3.13-3.02 (m, 5H), 2.96-2.92 (m, 1H), 2.82 (d, J=12.8 Hz, 1H), 2.78-2.71 (m, 1H), 2.58-2.49 (m, 1H), 2.25-2.18 (m, 2H), 2.09-2.00 (m, 1H), 1.61-1.51 (m, 1H), 1.42 (d, J=6.9 Hz, 3H), 1.38 (d, J=6.4 Hz, 3H); MS (ESI) m/z 557.27 (M+H).

S3-7-7-B: ¹H NMR (400 MHz, CD₃OD, hydrochloride salt) δ 4.76 (d, J=6.0 Hz, 1H), 3.95 (s, 1H), 3.86-3.71 (m, 2H), 3.45 (dd, J=5.5, 12.8 Hz, 1H), 3.35-3.29 (m, 1H), 3.12-2.92 (m, 6H), 2.83 (d, J=12.4 Hz, 1H), 2.78-2.71 (m, 1H), 2.57-2.48 (m, 1H), 2.26-2.15 (m, 2H), 2.07-1.99 (m, 1H), 1.60-1.51 (m, 1H), 1.43 (d, J=6.9 Hz, 3H), 1.39 (d, J=6.4 Hz, 3H); MS (ESI) m/z 557.27 (M+H).

S3-7-8

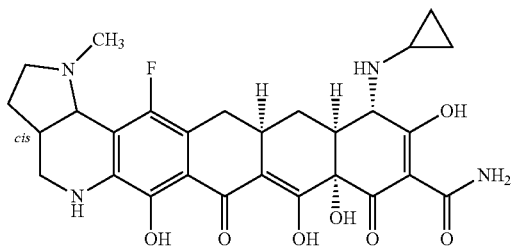

General Procedure D-2 (cyclopropylation). To a solution of compound S3-6-2 (20 mg, 0.022 mmol, 1 eq) in MeOH (1 mL) was added 4 Å molecular sieves, HOAc (7.6 μL, 0.132 mmol, 6 eq), [(1-ethoxycyclopropyl)oxy]trimethylsilane (26.4 μL, 0.132 mmol, 6 eq), and sodium cyanoborohydride (5.6 mg, 0.088 mmol, 4 eq) subsequently. The resulting reaction mixture was stirred at 55° C. overnight. The resulting mixture was cooled to rt, and filtered through a pad of Celite. The cake was washed with DCM. The filtrate was washed with a mixture of saturated aqueous sodium bicarbonate and potassium phosphate buffer solution (pH=7). The resulting organic phase was dried over anhydrous sodium sulfate, filtered, and concentrated. The residue was purified by preparative reverse phase HPLC on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 3.0 mL (CH₃CN); gradient: 20→100% B in A over 13 min; mass-directed fraction collection]. Fractions containing the desired product were collected and freeze-dried to yield the desired product (7.8 mg, 37%). MS (ESI) m/z 947.53 (M+H).

The above product was subjected to the general procedure C for HF desilylation and hydrogenation to yield the desired compound S3-7-8.

S3-7-8-A: ¹H NMR (400 MHz, CD₃OD, hydrochloride salt) δ 4.75 (d, J=6.9 Hz, 1H), 3.98 (s, 1H), 3.77-3.71 (m, 1H), 3.44 (dd, J=5.0, 10.3 Hz, 1H), 3.38-3.29 (m, 1H), 3.12-2.95 (m, 8H), 2.78-2.72 (m, 1H), 2.58-2.49 (m, 1H), 2.25-2.18 (m, 2H), 2.09-2.01 (m, 1H), 1.61-1.51 (m, 1H), 1.10-0.95 (m, 4H); MS (ESI) m/z 555.26 (M+H).

S3-7-8-B: ¹H NMR (400 MHz, CD₃OD, hydrochloride salt) δ 4.75 (d, J=6.4 Hz, 1H), 3.98 (s, 1H), 3.77-3.70 (m, 1H), 3.44 (dd, J=6.6, 13.3 Hz, 1H), 3.35-3.24 (m, 1H), 3.11-2.95 (m, 8H), 2.76-2.69 (m, 1H), 2.57-2.48 (m, 1H), 2.25-2.15 (m, 2H), 2.06-1.98 (m, 1H), 1.60-1.50 (m, 1H), 1.08-0.93 (m, 4H); MS (ESI) m/z 555.26 (M+H).

S3-7-9

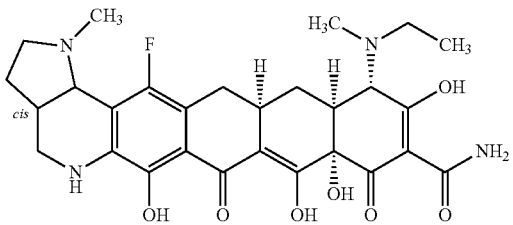

Compound S3-7-9 was prepared from compound S3-6-2 by using the general procedure D-1 twice (with acetaldehyde followed by formaldehyde) and general procedure C.

S3-7-9-A: ¹H NMR (400 MHz, CD₃OD, hydrochloride salt) δ 4.76 (d, J=6.0 Hz, 1H), 4.21 (s, 0.5H), 4.12 (s, 0.5H), 3.78-3.71 (m, 1H), 3.53-3.42 (m, 2H), 3.36-3.30 (m, 2H), 3.12-2.90 (m, 10H), 2.78-2.70 (m, 1H), 2.57-2.49 (m, 1H), 2.25-2.17 (m, 2H), 2.09-2.01 (m, 1H), 1.68-1.54 (m, 1H), 1.43-1.34 (m, 3H); MS (ESI) m/z 557.31 (M+H).

S3-7-9-B: ¹H NMR (400 MHz, CD₃OD, hydrochloride salt, ~1:1 conformers) δ 4.76 (d, J=6.0 Hz, 1H), 4.21 (s, 0.5H), 4.12 (s, 0.5H), 3.78-3.72 (m, 1H), 3.52-3.43 (m, 2H), 3.36-3.30 (m, 2H), 3.13-2.94 (m, 10H), 2.78-2.70 (m, 1H), 2.58-2.49 (m, 1H), 2.25-2.16 (m, 2H), 2.08-1.99 (m, 1H), 1.68-1.56 (m, 1H), 1.43-1.36 (m, 3H); MS (ESI) m/z 557.31 (M+H).

S3-7-10

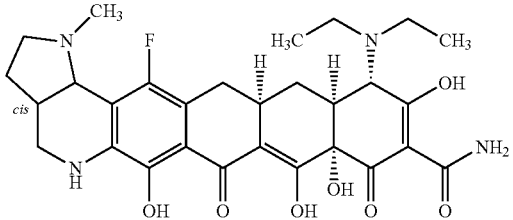

Compound S3-7-10 was prepared from compound S3-6-2 by using the general procedure D (with excess acetaldehyde) and C.

S3-7-10-A: ¹H NMR (400 MHz, CD₃OD, hydrochloride salt) δ 4.76 (d, J=6.0 Hz, 1H), 4.23 (s, 1H), 3.78-3.71 (m, 1H), 3.61-3.54 (m, 1H), 3.48-3.42 (m, 3H), 3.34-3.30 (m, 1H), 3.14-2.96 (m, 7H), 2.92 (d, J=12.8 Hz, 1H), 2.78-2.72

(m, 1H), 2.57-2.48 (m, 1H), 2.25-2.18 (m, 2H), 2.08-1.99 (m, 2H), 1.66-1.56 (m, 1H), 1.40 (t, J=6.9 Hz, 6H); MS (ESI) m/z 571.31 (M+H).

S3-7-10-B: $^1$H NMR (400 MHz, CD$_3$OD, hydrochloride salt) δ 4.76 (d, J=6.0 Hz, 1H), 4.24 (s, 1H), 3.78-3.72 (m, 1H), 3.62-3.57 (m, 1H), 3.50-3.43 (m, 3H), 3.34-3.30 (m, 1H), 3.12-2.98 (m, 7H), 2.92 (d, J=12.8 Hz, 1H), 2.78-2.72 (m, 1H), 2.58-2.49 (m, 1H), 2.22-2.16 (m, 2H), 2.06-1.99 (m, 2H), 1.66-1.56 (m, 1H), 1.41 (t, J=7.3 Hz, 6H); MS (ESI) m/z 571.31 (M+H).

S3-7-11

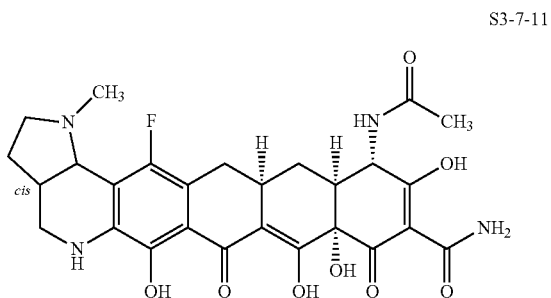 [SMILES: CC(=O)N[C@@H]1C(O)=C(C(N)=O)C(=O)[C@@]2(O)C(O)=C3C(=O)c4c(O)c5c(c(F)c4C[C@H]3C[C@@H]12)C1C(CCN1C)CN5]

To a solution of compound S3-6-2 (21 mg, 0.023 mmol, 1 eq) and $^i$Pr$_2$NEt (11.9 μL, 0.069 mmol, 3 eq) in DCM (1 mL) was added acetyl chloride (2.5 μL, 0.035 mmol, 1.5 eq) at 0° C. The resulting reaction mixture was stirred at 0° C. for 25 min. Potassium phosphate buffer solution (pH=7) was added. The resulting mixture was extracted with DCM (3×10 mL). The combined organic phase was dried over anhydrous sodium sulfate, filtered, and concentrated. LC-MS showed a mixture of the desired product and diacylation by-product. The residue was dissolved in MeOH (0.5 mL). Potassium carbonate (6.4 mg, 0.46 mmol, 2 eq) was added. The resulting reaction mixture was stirred at rt for 45 min and quenched with saturated aqueous NH$_4$Cl and potassium phosphate buffer solution (pH=7). The resulting mixture was extracted with DCM (3×10 mL). The combined organic phase was dried over anhydrous sodium sulfate, filtered, and concentrated.

The above crude product, MS (ESI) m/z 949.56 (M+H), was subjected to the general procedure C for HF desilylation and hydrogenation to yield the desired compound S3-7-11 (3.95 mg, 27% over 3 steps): $^1$H NMR (400 MHz, CD$_3$OD, hydrochloride salt, mixture of diastereomers) δ 4.75 (d, J=5.5 Hz, 1H), 4.70-4.65 (m, 1H), 3.77-3.70 (m, 1H), 3.46-3.41 (m, 1H), 3.35-3.29 (m, 2H), 3.12-3.00 (m, 5H), 2.96-2.89 (m, 1H), 2.78-2.72 (m, 1H), 2.54-2.46 (m, 1H), 2.41-2.33 (m, 2H), 2.07-2.04 (m, 4H), 1.60-1.54 (m, 1H); MS (ESI) m/z 557.26 (M+H).

S3-7-12

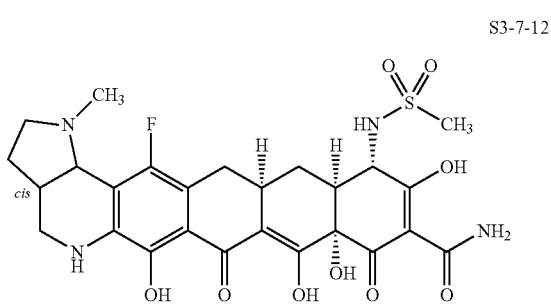 [SMILES: CN1CCC2CNc3c(O)c4c(c(F)c3C21)C[C@H]1C[C@H]2[C@H](NS(C)(=O)=O)C(O)=C(C(N)=O)C(=O)[C@@]2(O)C(O)=C1C4=O]

To a solution of compound S3-6-2 (21 mg, 0.023 mmol, 1 eq) and $^i$Pr$_2$NEt (11.9 μL, 0.069 mmol, 3 eq) in DCM (1 mL) was added methane sulfonic anhydride (6 mg, 0.035 mmol, 1.5 eq) at 0° C. The resulting reaction mixture was stirred at 0° C. for 1 h and 35 min and then rt overnight. More $^i$Pr$_2$NEt (11.9 μL, 0.069 mmol, 3 eq) and methane sulfonic anhydride (6 mg, 0.035 mmol, 1.5 eq) were added at 0° C. The resulting reaction mixture was stirred at that temperature for 1 h. Saturated aqueous NH$_4$Cl and potassium phosphate buffer solution (pH=7) were added. The resulting mixture was extracted with DCM (3×10 mL). The combined organic phase was dried over anhydrous sodium sulfate, filtered, and concentrated to yield the crude product: MS (ESI) m/z 985.52 (M+H). This crude product was subjected to the general procedure C for HF desilyllation and hydrogenation to yield the desired compound S3-7-12 (3.39 mg, 22% over 3 steps): $^1$H NMR (400 MHz, CD$_3$OD, hydrochloride salt, mixture of diastereomers) δ 4.77-4.75 (m, 1H), 4.08 (d, J=4.6 Hz, 1H), 3.76-3.70 (m, 1H), 3.44 (d, J=5.5, 13.3 Hz, 1H), 3.33-3.29 (m, 1H), 3.18-3.01 (m, 8H), 2.96-2.92 (m, 1H), 2.78-2.72 (m, 1H), 2.53-2.38 (m, 3H), 2.29-2.23 (m, 1H), 2.08-2.00 (m, 1H), 1.70-1.62 (m, 1H); MS (ESI) m/z 593.17 (M+H).

S3-7-13

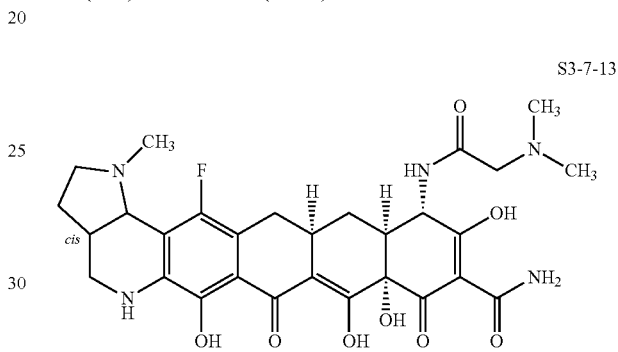

To a solution of compound S3-6-2 (30 mg, 0.033 mmol, 1 eq) and $^i$Pr$_2$NEt (40 μL, 0.23 mmol, 7 eq) in DCM (1.5 mL) was added dimethylaminoacetyl chloride hydrochloride (26 mg, 0.165 mmol, 5 eq) at rt. The resulting reaction mixture was stirred at rt overnight. Potassium phosphate buffer solution (pH=7) was added. The resulting mixture was extracted with DCM (3×10 mL). The combined organic phase was dried over anhydrous sodium sulfate, filtered, and concentrated to yield the crude product: MS (ESI) m/z 992.59 (M+H).

General Procedure E (global deprotection). To a solution of the above crude product in DCM (0.2 mL) was added dimethyl sulfide (7.3 μL, 0.099 mmol, 3 eq) at 0° C., followed by methane sulfonic acid (0.1 mL). The resulting reaction solution was stirred at rt for 2 h, and DCM was evaporated by blowing nitrogen to the reaction with stirring. Then DCM (50 μL) and dimethyl sulfide (10 μL) were added, and the resulting reaction solution was stirred at rt for 3 days. Again solvent was evaporated and the residue was diluted with 0.05 N HCl in water solution. The resulting solution was purified by preparative reverse phase HPLC on a Waters Autopurification system using a Phenomenex Polymerx 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water); gradient: 0→30% B in A over 20 min; mass-directed fraction collection]. Fractions containing the desired product were collected and freeze-dried to yield compound S3-7-13-A (3.25 mg, 15% over 2 steps) as the early eluting diastereomer and compound S3-7-13-B (8.02 mg, 36% over 2 steps) as the later eluting diastereomer.

S3-7-13-A: $^1$H NMR (400 MHz, CD$_3$OD, hydrochloride salt, rotamers) δ 4.75 (d, J=6.4 Hz, 1H), 4.71-4.70 (m, 1H), 4.08, 4.03 (ABq, J=15.6 Hz, 2H), 3.78-3.72 (m, 1H), 3.44 (dd, J=5.4, 12.9 Hz, 1H), 3.36-3.29 (m, 1H), 3.09-3.04 (m, 5H), 2.99-2.90 (m, 7H), 2.79-2.72 (m, 1H), 2.57-2.47 (m, 2H), 2.39-2.32 (m, 2H), 2.08-2.00 (m, 1H), 1.64-1.56 (m, 1H); MS (ESI) m/z 600.31 (M+H).
S3-7-13-B: $^1$H NMR (400 MHz, CD$_3$OD, hydrochloride salt, rotamers) δ 4.77-4.76 (m, 1H), 4.72-4.71 (m, 1H), 4.14-4.03 (m, 2H), 3.78-3.72 (m, 1H), 3.44 (dd, J=5.0, 12.8 Hz, 1H), 3.36-3.29 (m, 1H), 3.14-2.91 (m, 12H), 2.79-2.72 (m, 1H), 2.56-2.48 (m, 2H), 2.36-2.34 (m, 2H), 2.07-1.98 (m, 1H), 1.64-1.56 (m, 1H); MS (ESI) m/z 600.31 (M+H).
Scheme 4
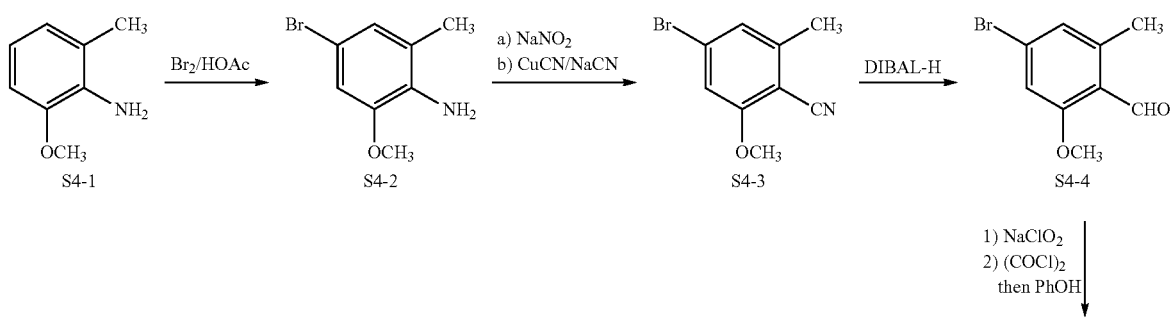
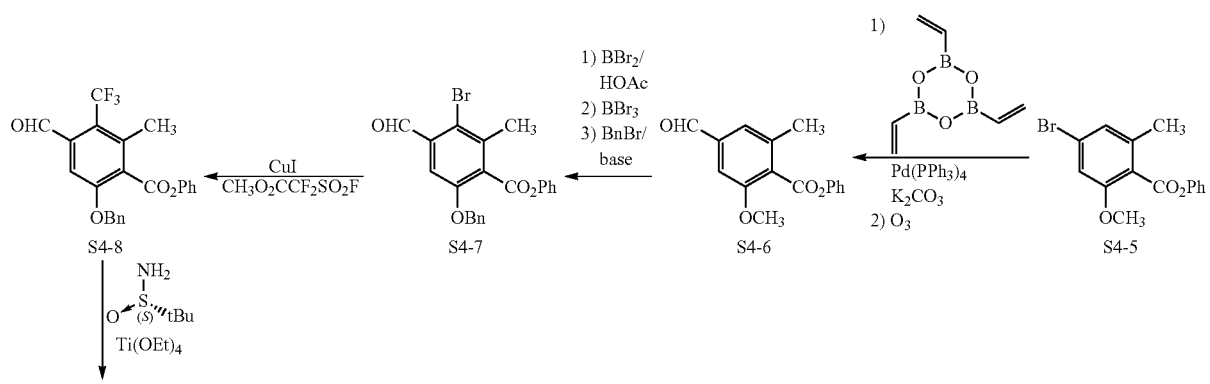
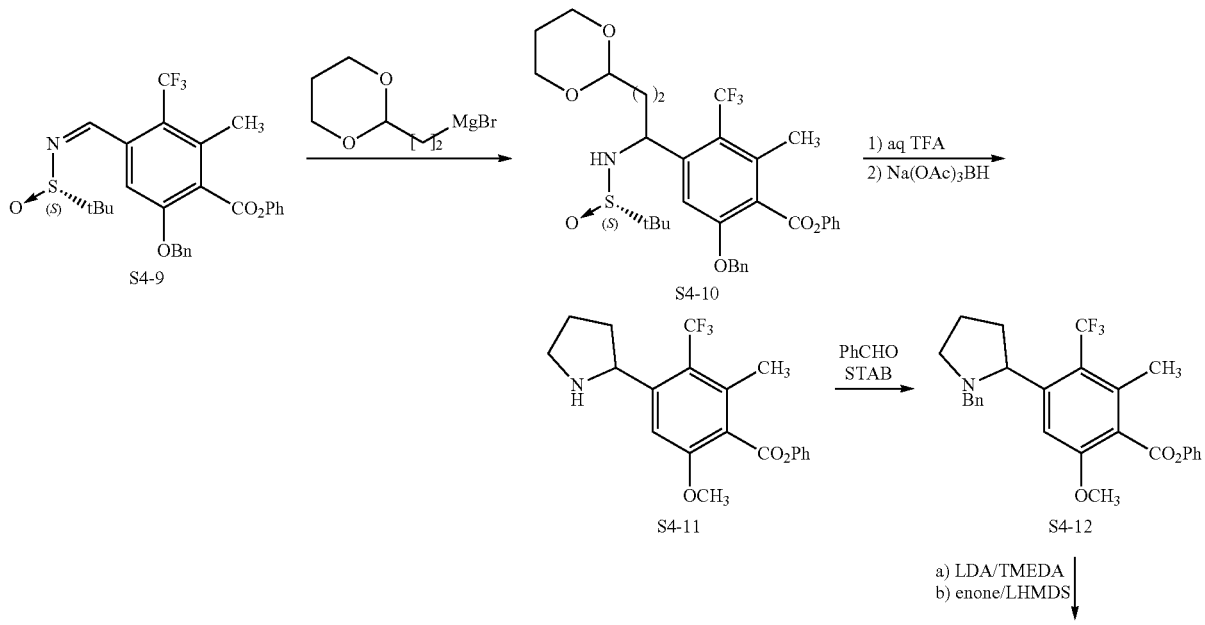

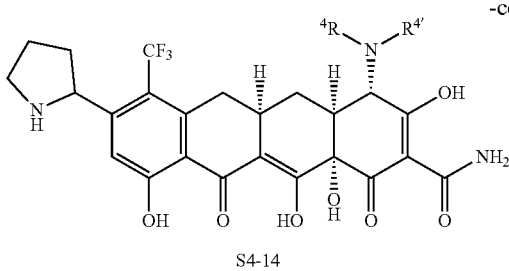

S4-14

1) aq HF
2) H₂/Pd-C

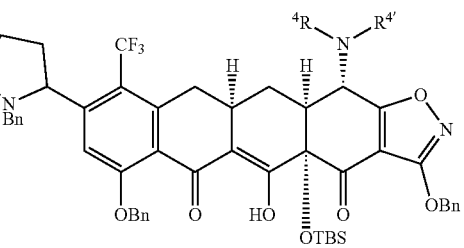

| | |
|---|---|
| S4-13-1: ⁴R⁴'RN = (Allyl)₂N | de-allylation |
| S4-13-2: ⁴R⁴'RN = NH₂ | |
| alkylation → S4-13-3: ⁴R⁴'RN = mono- or dialkylamino | |
| S4-13-4: ⁴R⁴'RN = Et(CH₃)N | |
| S4-13-5: ⁴R⁴'RN = Et₂N | |
| S4-13-6: ⁴R⁴'RN = azetidinyl | |
| S4-13-7: ⁴R⁴'RN = pyrrolidinyl | |

The following compounds were prepared according to Scheme 4.

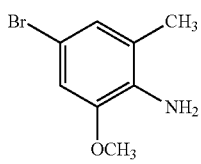

S4-2

To an ice-cooled solution of 2-methoxy-6-methylaniline (S4-1, 25.12 g, 183.10 mmol, 1 eq) in CH₃OH (79 mL) and HOAc (25 mL) was added a solution of bromine (9.41 mL, 183.10 mmol, 1 eq) in HOAc (79 mL) drop wise via an addition funnel. The reaction mixture was allowed to warm to rt and stirred for 2 h after complete addition. EtOAc (150 mL) was added, and the solid was collected by filtration and washed with more EtOAc, yielding 37.20 g of compound S4-2 as an off-white solid (HBr salt).

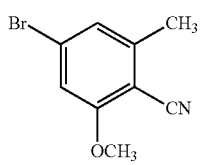

S4-3

4-Bromo-2-methoxy-6-methylaniline (S4-2, HBr salt, 20.00 g, 92.70 mmol, 1 eq) was suspended in concentrated aqueous HCl (22 mL) and crushed ice (76 g) cooled in an ice-bath. A solution of NaNO₂ (6.52 g, 94.60 mmol, 1.02 eq) in H₂O (22 mL) was added drop wise. The resulting mixture was stirred at 0° C. for 30 min and neutralized with aqueous Na₂CO₃. A suspension of CuCN (10.40 g, 115.90 mmol, 1.25 eq) in H₂O (44 mL) was mixed with a solution of NaCN (14.40 g, 294.80 mmol, 3.18 eq) in 22 mL of H₂O and cooled in an ice-bath. The initial diazonium salt mixture was then added to the CuCN and NaCN mixture with vigorous stirring while maintaining the temperature at 0° C. (toluene (180 mL) was also added in portions during the addition). The reaction mixture was stirred at 0° C. for 1 h, at rt for 2 h, and at 50° C. for another 1 h. After cooling to rt, the layers were separated. The aqueous layer was extracted with toluene. The combined organic layers were washed with brine, dried over magnesium sulfate, and concentrated. The residue was passed through a silica gel plug, washed with toluene, and concentrated to yield 14.50 g of compound S4-3 as a light yellow solid.

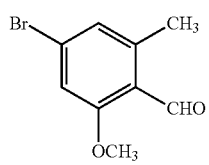

S4-4

To a solution of S4-3 (11.34 g, 50.20 mmol, 1 eq) in THF (100 mL) was added 1.5 M DIBAL-H in toluene (40.10 mL, 60.20 mmol, 1.2 eq) slowly at −78° C. The reaction was allowed to warm to rt gradually and stirred overnight. After re-cooled to 0° C., the reaction was carefully quenched by 1 N aqueous HCl. The resulting mixture was stirred at rt for 1 h and extracted three times with EtOAc. The combined EtOAc layers were washed with H₂O, saturated aqueous NaHCO₃ and brine, dried over magnesium sulfate, and concentrated to provide compound S4-4 as a yellow solid, which was used directly in the next step.

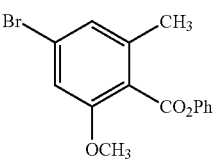

S4-5

To a suspension of S4-4 (50.20 mmol, 1 eq) in t-BuOH (200 mL) was added a solution of NaClO₂ (11.34 g, 100.30 mmol, 2 eq) and NaH₂PO₄ (34.6 g, 250.80 mmol, 5 eq) in H₂O (100 mL) via an addition funnel. After complete addition, 2-methyl-2-butene (42.40 mL, 0.40 mol, 8 eq) was added. The resulting homogenous solution was stirred at rt for 30 min, and volatiles were removed. The residue was suspended in 150 mL of H₂O. The solution was acidified to pH=1 with 1 N aqueous HCl and extracted three times with t-butyl methyl ether. The combined organic solution was extracted three times with 1 N aqueous NaOH. The combined aqueous solution was acidified with 6 N aqueous HCl, and extracted three times with EtOAc. The combined EtOAc extracts were washed with brine, dried over magnesium sulfate, and concentrated to provide 8.64 g of the benzoic acid intermediate (4-4-a) as an off-white solid, which was used directly in the next step.

To a solution of the above benzoic acid (8.64 g, 35.20 mmol, 1 eq) in dichloromethane (70 mL) was added oxalyl chloride (3.76 mL, 42.30 mmol, 1.2 eq), followed by a couple of drops of DMF (caution: gas evolution). The mixture was stirred at rt for 30 min and the volatiles were evaporated under reduce pressure. The residue was further dried under high vacuum to afford the crude benzoyl chloride. The crude benzoyl chloride was re-dissolved in dichloromethane (70 mL). Triethylamine (12.3 mL, 88.10 mmol, 2.5 eq), phenol (3.98 g, 42.30 mmol, 1.2 eq) and DMAP (0.43 g, 3.52 mmol, 0.1 eq) were added. The mixture was stirred at rt for 1 h. The solvent was evaporated. The residue was suspended in EtOAc, and the precipitate was filtered off The organic solution was then washed with 1 N aqueous HCl (three times), $H_2O$, saturated aqueous $NaHCO_3$, and brine, dried over sodium sulfate, filtered and concentrated. Purification of the residue by flash chromatography gave compound S4-5 (10.05 g, 89%) as an off-white solid: $^1$H NMR (400 MHz, $CDCl_3$) δ 7.41-7.45 (m, 2H), 7.22-7.27 (m, 3H), 7.04 (d, J=0.9 Hz, 1H), 6.97 (d, J=0.9 Hz, 1H), 3.87 (s, 3H), 2.42 (s, 3H); MS (ESI) m/z 319.0 (M–H).

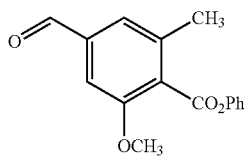

S4-6

Compound S4-5 (20 g, 62.5 mmol, 1.0 eq), 2,4,6-trivinylcyclotriboroxane-pyridine complex (7.8 g, 31.25 mmol, 0.50 eq), $Pd(PPh_3)_4$ (2.2 g, 1.88 mmol, 0.030 eq) and $K_2CO_3$ (17.25 g, 125 mmol, 2.0 eq) were added to a vessel in 1.4 mL dioxane:$H_2O$ (3:1, V:V). The mixture was bubbled with $N_2$ to remove $O_2$ for 6 times. The mixture was heated to reflux for 19 h. The mixture was concentrated. The residue partitioned between EtOAc and water. The organic layer was dried over $Na_2SO_4$ and evaporated to dryness. The crude compound was purified by column chromatography on silica gel, eluting with (petroleum ether:EtOAc=200:1 to 100:1 to 50:1 gradient). This yielded 14.8 g (88.3%) compound S4-5-a as a light yellow solid: $^1$H NMR (400 MHz, $CDCl_3$) δ 7.38-7.34 (m, 2H), 7.27-7.16 (m, 3H), 6.83-6.76 (m, 2H), 6.65-6.60 (m, 1H), 5.72 (d, J=17.6 Hz, 1H), 5.25 (d, J=11.2 Hz, 1H), 3.83 (s, 3H), 2.38 (s, 3H); MS (ESI) m/z 269.1 (M+H).

An ozone-enriched steam of oxygen was bubbled through a cold (–78° C.) solution of compound S4-5-a (21 g, 78.3 mmol, 1.0 eq) in anhydrous $CH_2Cl_2$ until it turned light blue. The reaction was followed by TLC. The solution was purged with argon at –78° C. for 10 min to remove the excess $O_3$. $CH_3SCH_3$ (50 mL) was added into the reaction mixture and was stirred for 5 hours from –78° C. to 25° C. The reaction was concentrated. The crude compound was purified by column chromatography on silica gel, eluting with (petroleum ether:EtOAc=100:1 to 50:1 to 30:1 gradient) to yield 13 g (61.6%) compound S4-6 as a light yellow solid: $^1$H NMR (400 MHz, $CDCl_3$) δ 9.97 (s, 1H), 7.46-7.41 (m, 2H), 7.36-7.22 (m, 5H), 3.92 (s, 3H), 2.51 (s, 3H); MS (ESI) m/z 271.1 (M+H).

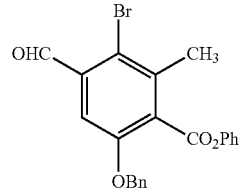

S4-7

Compound S4-6 (1.8 g, 6.62 mmol, 1 eq) was dissolved in HOAc. Bromine (1.6 mL, 26.5 mmol, 4 eq) was added dropwise into the solution. The reaction mixture was stirred for 1 hour at rt. The mixture was concentrated. The residue was dissolved in EtOAc and washed with saturated $NaHCO_3$, brine and water. The organics were dried over $Na_2SO_4$ and concentrated to dryness to afford 1.9 g bromo compound S4-6-a as a light yellow solid.

$BBr_3$ (4.9 g, 1.9 mL, 19.5 mmol, 1.5 eq) was added to a $CH_2Cl_2$ solution (30 mL) of S4-6-a (3.5 g, 13.0 mmol, 1.0 eq) at –78° C. The reaction was stirred from –78° C. to 25° C. for 1.5 h, was quenched with saturated $NaHCO_3$ and was extracted with EtOAc. The combined EtOAc extracts were dried ($Na_2SO_4$) and concentrated to yield 3.3 g of crude phenol S4-6-b.

$K_2CO_3$ (3.6 g, 26.0 mmol, 2.0 eq) and benzylbromide (4.2 g, 26.0 mmol, 2.0 eq) were added to a solution of compound S4-6-b (3.3 g, 13.0 mmol, 1.0 eq) in DMF (15 mL). The reaction mixture was stirred at rt for 2 h. The reaction mixture was filtered (EtOAc wash). Water (150 mL) was added, and the mixture was extracted with EtOAc. The organic layer was dried over $Na_2SO_4$ and concentrated. The crude compound was purified by column chromatography on silica gel, eluting with (petroleum ether:EtOAc=100:1 to 50:1 gradient). This gave 3.5 g (61.7% for 3 steps) of compound S4-7 as a light yellow solid: $^1$H NMR (400 MHz, $CDCl_3$) δ 10.43 (s, 1H), 7.46-7.30 (m, 9H), 7.08-7.05 (m, 2H), 5.17 (s, 2H), 2.52 (s, 3H); MS (ESI) m/z 425.1 (M+H).

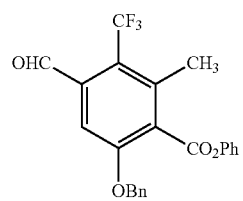

S4-8

To a solution of compound S4-7 (5 g, 11.8 mmol, 1.0 eq) in anhydrous DMF was added $CH_3O_2CCF_2SO_2F$ (11.3 g, 59 mmol, 5.0 eq) and CuI (4.5 g, 23.6 mmol, 2.0 eq). The reaction was heated to 100° C. for 20 h. The mixture was filtered and washed with EtOAc. The solution was concentrated and extracted with EtOAc and water. The organic layer was dried over $Na_2SO_4$ and concentrated to give 7 g of the crude compound S4-8 as brown oil: $^1$H NMR (400 MHz, $CDCl_3$) δ 10.35-10.32 (m, 1H), 7.40-7.28 (m, 9H), 7.02-6.83 (m, 2H), 5.17 (s, 2H), 2.55-2.51 (m, 3H); MS (EST) m/z 415.1 (M+H).

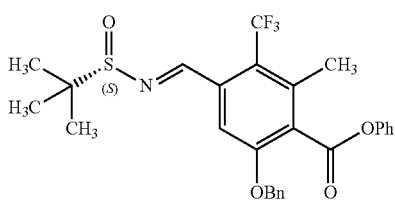

S4-9

To a solution of S4-8 (4.02 g, 9.70 mmol) in THF (39 mL) was added a solution of Ti(OEt)$_4$ (technical grade, ~20% Ti; 20.1 mL, 19.4 mmol, 2.0 eq) under N$_2$ atmosphere, followed by (S)-tert-butanesulfinamide (1.76 g, 14.6 mmol, 1.5 eq). The resulting yellow solution was stirred at rt and conversion was followed by LC-MS. Upon completion, the reaction mixture was poured into 80 mL brine while rapidly stirring, and stirring was continued for another 30 min. The resulting suspension was filtered through a plug of Celite, and the filter cake was washed with EtOAc. The filtrate was transferred to a separation funnel where the organic layer was washed with brine, dried over sodium sulfate, and concentrated under reduced pressure. Purification of the residue by Biotage flash chromatography gave compound S4-9 as an off-white foam (4.07 g, 81%): $^1$H NMR (400 MHz, CDCl$_3$) δ 8.96 (br. s, 1H), 7.23-7.45 (m, 9H), 7.08 (d, J=7.3 Hz, 2H), 5.25 (s, 2H), 2.58 (q, J=3.2 Hz, 3H), 1.24 (s, 9H); MS (ESI) m/z 518.5 (M+H).

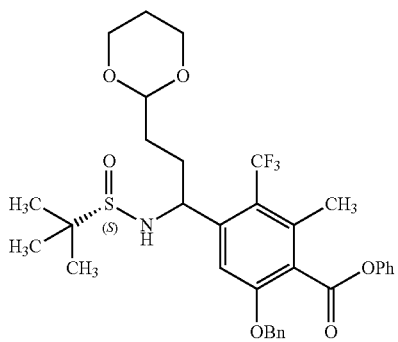

S4-10

A flame dried flask was charged with magnesium turnings (10.94 g, 450 mmol) and catalytic amounts of I$_2$ (761.4 mg, 3 mmol), which was heated with heat gun under N$_2$ for 2 min. Once they were cooled to rt, THF (150 mL) was added. A small portion solution of 2-(2-bromoethyl)-1,3-dioxane (20.3 mL, 150 mmol) in THF (50 mL) was added. After the reaction commenced, the rest of 2-(2-bromoethyl)-1,3-dioxane solution was added via cannula. The reaction mixture was periodically cooled in a rt water bath to prevent refluxing. After addition of the 2-(2-bromoethyl)-1,3-dioxane solution was completed, the reaction mixture was stirred for 2 h. The solution was then transferred to a sure-sealed bottle to remove the remaining Mg and stored in fridge for future use.

To a solution of compound S4-9 (2.32 g, 4.49 mmol) in THF (18 mL) was added the Grignard solution (11.2 mL) prepared above at −78° C. in 10 min. After the mixture was stirred at this temperature for 1 h 30 min, the cold bath was removed. When the inner temperature reached −48° C., sat. aq. NH$_4$Cl (30 mL) was added. The layers were separated. The aqueous layer was extracted with EtOAc (×2). The combined organic layers were washed with brine, dried over sodium sulfate, and concentrated under reduced pressure to yield the crude product as a white solid, which was suspended in 25 mL heptane. The mixture was stirred at rt for 1 h 30 min, the solid was collected by filtration and washed with small portion of heptane. Further dried under high vacuum provided compound S4-10 as a white solid (2.70 g, 95%, single diastereomer): $^1$H NMR (400 MHz, CDCl$_3$) δ 7.41 (d, J=7.3 Hz, 2H), 7.31-7.37 (m, 5H), 7.22 (t, J=7.3 Hz, 1H), 7.15 (s, 1H), 7.05 (d, J=7.3 Hz, 2H), 5.20 (s, 2H), 4.88 (dd, J=7.8, 11.2 Hz, 1H), 4.47 (t, J=4.6 Hz, 1H), 4.04-4.09 (m, 2H), 3.71-3.75 (m, 3H), 2.52 (q, J=3.2 Hz, 3H), 1.98-2.09 (m, 1H), 1.81-1.90 (m, 2H), 1.62-1.71 (m, 1H), 1.47-1.57 (m, 1H), 1.30 (d, J=11.9 Hz, 1H), 1.17 (s, 9H); MS (ESI) m/z 634.6 (M+H).

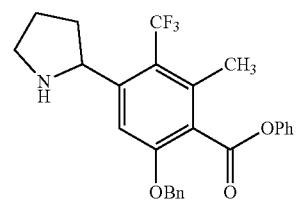

S4-11

Compound S4-10 (2.70 g, 4.26 mmol) was added to the mixture of TFA-H$_2$O (21 mL-21 mL) cooled in an ice bath. The resulting mixture was then stirred at 6° C. and conversion was followed by LC-MS. Upon completion, the reaction mixture was cooled to −20° C., and NaBH(OAc)$_3$ was added. Temperature was then allowed to warm to rt. After the mixture was stirred at rt for 1 h, it was re-cooled to 0° C. The pH of the solution was adjusted to ~8 with 45% aq. KOH. The aqueous solution was extracted with MTBE (×3). The combined organic layers were washed with brine, dried over sodium sulfate, and concentrated under reduced pressure. Purification of the residue by Biotage flash chromatography gave compound S4-11 as a light yellow oil (1.29 g, 66%, single enantiomer A): $^1$H NMR (400 MHz, CDCl$_3$) δ 7.67 (s, 1H), 7.22-7.46 (m, 8H), 7.08 (d, J=7.3 Hz, 2H), 5.22 (ABq, J=11.4, 18.4 Hz, 2H), 4.64-4.69 (m, 1H), 3.02-3.16 (m, 2H), 2.53 (q, J=3.2 Hz, 3H), 2.21-2.30 (m, 1H), 1.85 (br s, 1H), 1.73-1.80 (m, 2H), 1.44-1.52 (m, 1H); MS (ESI) m/z 456.5 (M+H).

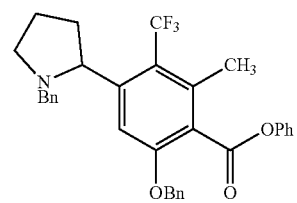

S4-12

To a solution of compound S4-11 (164 mg, 0.36 mmol, 1 eq) in MeCN (1.5 mL) was added HOAc (82 μL, 1.44 mmol, 4.0 eq) followed by benzaldehyde (109 μL, 1.08 mmol, 3.0 eq) and STAB (229 mg, 1.08 mmol, 3.0 eq). The resulting reaction mixture was stirred at rt overnight, diluted with EtOAc. Saturated aqueous sodium bicarbonate was added. The organic phase was separated and washed with brine. The resulting organic phase was dried over anhydrous sodium sulfate, filtered, and concentrated under reduced pressure. Flash chromatography on silica gel using 0%→10% EtOAc/ hexanes yielded the desired product S4-12 (194 mg, 99%, single enantiomer A) as a white solid: $^1$H NMR (400 MHz, CDCl$_3$) δ 7.90 (s, 1H), 7.47-7.45 (m, 2H), 7.40-7.35 (m, 5H), 7.30-7.24 (m, 6H), 7.11-7.09 (m, 2H), 5.25, 5.21 (ABq, J=11.6 Hz, 2H), 3.95 (t, J=7.9 Hz, 1H), 3.78 (d, J=13.4 Hz, 1H), 3.19-3.13 (m, 2H), 2.57 (q, J=1.8 Hz, 3H), 2.35-2.26 (m, 2H), 1.84-1.78 (m, 2H), 1.64-1.55 (m, 1H); MS (ESI) m/z 546.30 (M+H).

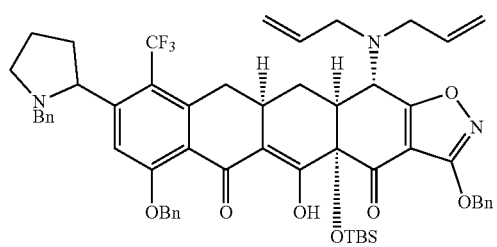

S4-13-1

Compound S4-13-1 was prepared in 98% yield from S4-12 (single enantiomer A) and N-diallyl enone S1-9-2 using general procedure A. S4-13-1 (single diastereomer A, light yellow solid): $^1$H NMR (400 MHz, CDCl$_3$) δ 15.76 (s, 1H), 7.85 (s, 1H), 7.53-7.48 (m, 4H), 7.42-7.34 (m, 5H), 7.31-7.19 (m, 6H), 5.88-5.78 (m, 2H), 5.39 (s, 2H), 5.28 (s, 2H), 5.24 (d, J=17.7 Hz, 2H), 5.15 (d, J=9.8 Hz, 2H), 4.13 (d, J=10.4 Hz, 1H), 3.84 (t, J=8.4 Hz, 1H), 3.65 (d, J=13.4 Hz, 1H), 3.36 (br d, J=11.0 Hz, 2H), 3.28-3.10 (m, 5H), 3.00 (t, J=15.3 Hz, 1H), 2.87-2.81 (m, 1H), 2.55-2.45 (m, 2H), 2.35-2.29 (m, 2H), 2.15 (d, J=14.0 Hz, 1H), 1.81-1.50 (m, 3H), 0.86 (s, 9H), 0.29 (s, 3H), 0.17 (s, 3H); MS (ESI) m/z 986.55 (M+H).

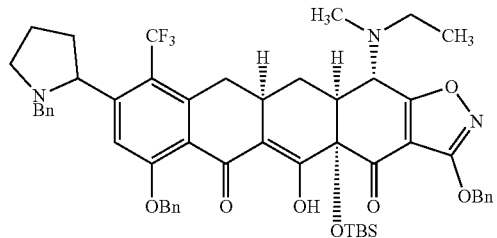

S4-13-4

Compound S4-13-4 was prepared in 79% yield from racemic S4-12 and N-methylethyl enone S1-9-1 using general procedure A. S4-13-4 (~1:1 mixture of two diastereomers, light yellow foam): $^1$H NMR (400 MHz, CDCl$_3$) δ 15.78 (br s, 1H), 7.94 (s, 0.5H), 7.84 (s, 0.5H), 7.52-7.44 (m, 4H), 7.41-7.19 (m, 11H), 5.37 (s, 2H), 5.29-5.27 (m, 2H), 4.06-4.03 (m, 0.5H), 3.85-3.78 (m, 1H), 3.64 (d, J=12.8 Hz, 0.5H), 3.31-3.15 (m, 4H), 2.92-2.65 (m, 4H), 2.58-2.44 (m, 2H), 2.379 (s, 1.5H), 2.376 (s, 1.5H), 2.34-2.27 (m, 2H), 2.18 (d, J=14.6 Hz, 1H), 1.79-1.72 (m, 2H), 1.55-1.48 (m, 1H), 1.13 (t, J=7.3 Hz, 3H), 0.86 (s, 4.5H), 0.85 (s, 4.5H), 0.29 (s, 3H), 0.18 (s, 1.5H), 0.17 (s, 1.5H); MS (ESI) m/z 948.56 (M+H).

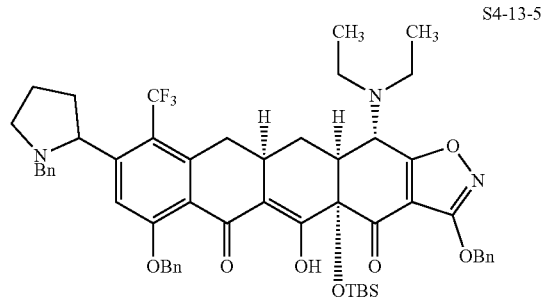 [SMILES: CCN(CC)[C@@H]1c2onc(OCc3ccccc3)c2C(=O)[C@@]2(O[Si](C)(C)C(C)(C)C)C(O)=C3C(=O)c4c(OCc5ccccc5)cc(C5CCCN5Cc5ccccc5)c(C(F)(F)F)c4C[C@H]3C[C@@H]12]

S4-13-5

Compound S4-13-5 was prepared in 64% yield from racemic S4-12 and N-diethyl enone S1-9-3 using the general procedure A. S4-13-5: (~1:1 mixture of diastereomers, light yellow foam): $^1$H NMR (400 MHz, CDCl$_3$) δ 15.73 (s, 0.5H), 15.72 (s, 0.5H), 7.90 (s, 0.5H), 7.80 (s, 0.5H), 7.51-7.45 (m, 4H), 7.40-7.19 (m, 11H), 5.37 (s, 2H), 5.37-5.27 (m, 2H), 4.19 (t, J=8.5 Hz, 0.5H), 4.05 (d, J=10.4 Hz, 1H), 4.00 (t, J=7.9 Hz, 0.5H), 3.88 (d, J=13.4 Hz, 0.5H), 3.76 (d, J=13.4 Hz, 0.5H), 3.60 (d, J=12.8 Hz, 0.5H), 3.48 (t, J=7.3 Hz, 0.5H), 3.41 (d, J=13.4 Hz, 0.5H), 3.36 (t, J=8.5 Hz, 0.5H), 3.28 (d, J=15.9 Hz, 0.5H), 3.16 (d, J=12.8 Hz, 0.5H), 2.93-2.73 (m, 6H), 2.54-2.46 (m, 3H), 2.37-2.31 (m, 1H), 2.26-2.22 (m, 1H), 1.99-1.64 (m, 3H), 1.13-1.09 (m, 6H), 0.87 (s, 4.5H), 0.86 (s, 4.5H), 0.30 (s, 1.5H), 0.29 (s, 1.5H), 0.18 (s, 1.5H), 0.17 (s, 1.5H); MS (ESI) m/z 962.57 (M+H).

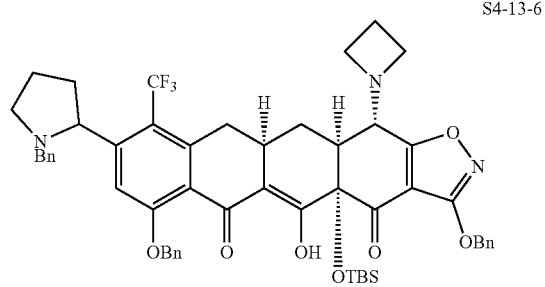 [SMILES: CC(C)(C)[Si](C)(C)O[C@@]12C(=O)c3c(OCc4ccccc4)noc3[C@@H](N3CCC3)[C@@H]1C[C@@H]1Cc3c(c(OCc4ccccc4)cc(C4CCCN4Cc4ccccc4)c3C(F)(F)F)C(=O)C1=C2O]

S4-13-6

Compound S4-13-6 was prepared in 33% yield from S4-12 (single diastereomer A) and azetidinyl enone S2-7-1 using general procedure A. S4-13-6 (single diastereomer A): $^1$H NMR (400 MHz, CDCl$_3$) δ 15.94 (s, 1H), 7.75 (s, 1H), 7.41-7.37 (m, 4H), 7.31-7.15 (m, 8H), 7.12-7.10 (m, 3H), 5.32-5.13 (m, 4H), 3.72 (t, J=6.7 Hz, 1H), 3.56-3.51 (m, 2H), 3.40 (q, J=6.7 Hz, 2H), 3.27 (q, J=6.7 Hz, 2H), 3.12 (d, J=12.8 Hz, 1H), 3.05-2.97 (m, 2H), 2.69-2.59 (m, 1H), 2.47 (t, J=15.8 Hz, 1H), 2.25-2.16 (m, 3H), 2.10-1.98 (m, 3H), 1.73-1.64 (m, 3H), 1.46-1.39 (m, 1H), 0.71 (s, 9H), 0.07 (s, 3H), 0.06 (s, 3H); MS (ESI) m/z 946.14 (M+H).

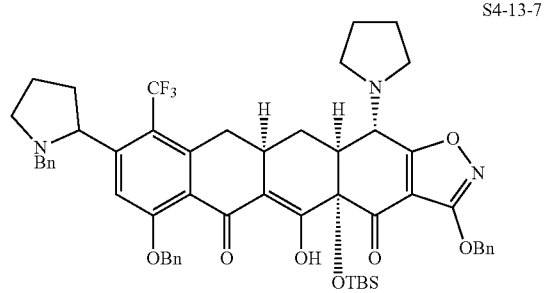 [SMILES: CC(C)(C)[Si](C)(C)O[C@@]12C(=O)c3c(OCc4ccccc4)noc3[C@@H](N3CCCC3)[C@@H]1C[C@@H]1Cc3c(c(OCc4ccccc4)cc(C4CCCN4Cc4ccccc4)c3C(F)(F)F)C(=O)C1=C2O]

S4-13-7

Compound S4-13-7 was prepared in 60% yield from S4-12 (single diastereomer A) and pyrrolidinyl enone S2-7-2 using general procedure A. S4-13-7 (single diastereomer A): ¹H NMR (400 MHz, CDCl₃) δ 15.82 (s, 1H), 7.84 (s, 1H), 7.52-7.47 (m, 4H), 7.41-7.33 (m, 5H), 7.31-7.24 (m, 3H), 7.21-7.19 (m, 3H), 5.37 (s, 2H), 5.28 (s, 2H), 4.28 (d, J=11.0 Hz, 1H), 3.81 (t, J=6.7 Hz, 1H), 3.64 (d, J=13.4 Hz, 1H), 3.24 (d, J=12.8 Hz, 1H), 3.17-3.14 (m, 2H), 3.06-3.01 (m, 2H), 2.88-2.77 (m, 2H), 2.71-2.66 (m, 2H), 2.62-2.58 (m, 1H), 2.49-2.41 (m, 1H), 2.32-2.26 (m, 2H), 2.12 (d, J=14.0 Hz, 1H), 1.87-1.84 (m, 4H), 1.79-1.75 (m, 2H), 1.56-1.48 (m, 1H), 0.85 (s, 9H), 0.28 (s, 3H), 0.17 (s, 3H); MS (ESI) m/z 960.18 (M+H).

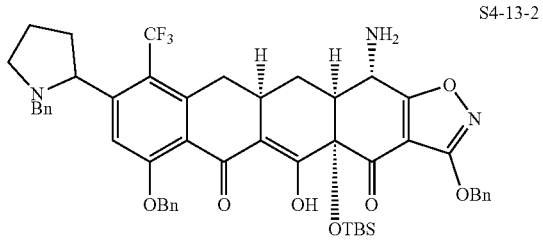 [SMILES: CC(C)(C)[Si](C)(C)O[C@@]12C(=O)c3c(OCc4ccccc4)noc3[C@@H](N)[C@@H]1C[C@@H]1Cc3c(c(OCc4ccccc4)cc(C4CCCN4Cc4ccccc4)c3C(F)(F)F)C(=O)C1=C2O]

S4-13-2

Compound S13-2 was prepared in 88% yield from compound S4-13-1 by using the general procedure B. S4-13-2 (single diastereomer A, light yellow solid): ¹H NMR (400 MHz, CDCl₃) δ 16.14 (s, 1H), 7.77 (s, 1H), 7.42-7.37 (m, 4H), 7.30-7.21 (m, 6H), 7.18-7.15 (m, 2H), 7.12-7.08 (m, 3H), 5.30, 5.26 (ABq, J=12.2 Hz, 2H), 5.21, 5.14 (ABq, J=12.2 Hz, 2H), 3.82 (br s, 1H), 3.71 (t, J=7.9 Hz, 1H), 3.54 (d, J=13.4 Hz, 1H), 3.11 (d, J=13.4 Hz, 1H), 3.06-3.02 (m, 1H), 2.91 (d, J=15.9 Hz, 1H), 2.63-2.50 (m, 2H), 2.36 (d, J=15.3 Hz, 1H), 2.21-2.15 (m, 2H), 2.04-1.98 (m, 1H), 1.67-1.62 (m, 2H), 1.46-1.38 (m, 2H), 0.64 (s, 9H), 0.11 (s, 3H), 0.00 (s, 3H); MS (ESI) m/z 906.50 (M+H).

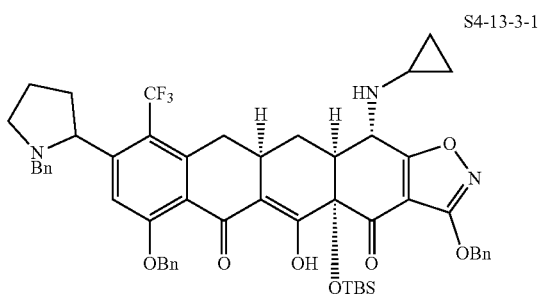 [SMILES: CC(C)(C)[Si](C)(C)O[C@@]12C(=O)c3c(OCc4ccccc4)noc3[C@@H](NC3CC3)[C@@H]1C[C@@H]1Cc3c(c(OCc4ccccc4)cc(C4CCCN4Cc4ccccc4)c3C(F)(F)F)C(=O)C1=C2O]

S4-13-3-1

Compound S4-13-3-1 was prepared from compound S4-13-2 using general procedure D-2. S4-13-3-1 (single diastereomer A): ¹H NMR (400 MHz, CDCl₃) δ 16.24 (s, 1H), 7.86 (s, 1H), 7.53-7.47 (m, 4H), 7.40-7.30 (m, 6H), 7.28-7.18 (m, 5H), 5.40, 5.37 (ABq, J=12.2 Hz, 2H), 5.32, 5.26 (ABq, J=12.8 Hz, 2H), 3.87-3.83 (m, 2H), 3.68 (dJ=13.4 Hz, 1H), 3.34-3.24 (m, 2H), 2.78 (d, J=15.9 Hz, 1H), 2.69-2.62 (m, 2H), 2.48-2.42 (m, 2H), 2.36-2.26 (m, 2H), 2.10-2.04 (m, 1H), 1.86-1.77 (m, 2H), 1.62-1.55 (m, 1H), 1.51-1.41 (m, 1H), 0.76 (s, 9H), 0.57-0.52 (m, 2H), 0.47-0.42 (m, 2H), 0.22 (s, 3H), 0.12 (s, 3H); MS (ESI) m/z 946.06 (M+H).

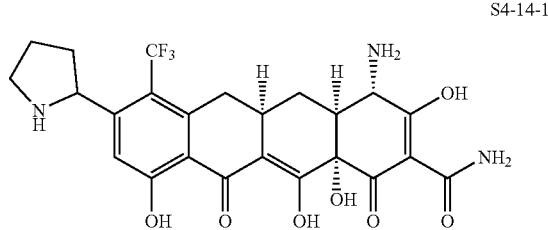 [SMILES: NC(=O)C1=C(O)[C@@H](N)[C@@H]2C[C@@H]3Cc4c(c(O)cc(C5CCCN5)c4C(F)(F)F)C(=O)C3=C(O)[C@]2(O)C1=O]

S4-14-1

Compound S4-14-1 was prepared from compound S4-13-2 using general procedure C. S4-14-1 (single diastereomer A): ¹H NMR (400 MHz, CD₃OD, hydrochloride salt) δ 7.22 (s, 1H), 4.97 (t, J=8.7 Hz, 1H), 3.90 (s, 1H), 3.63-3.57 (m, 1H), 3.52-3.45 (m, 1H), 3.29-3.24 (m, 1H), 2.98-2.89 (m, 1H), 2.68-2.55 (m, 3H), 2.34-2.12 (m, 4H), 1.63-1.54 (m, 1H); MS (ESI) m/z 524.24 (M+H).

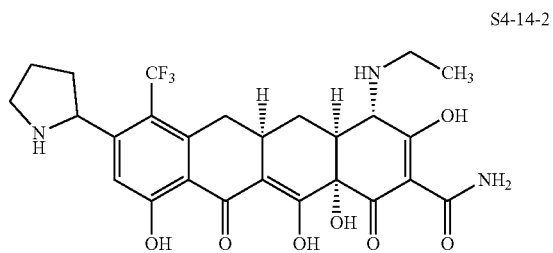 [SMILES: CCN[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12]

S4-14-2

Compound S4-14-2 was prepared from compound S4-13-2 using the general procedures D-1 (with acetaldehyde) and C. S4-14-2 (single diastereomer A): ¹H NMR (400 MHz, CD₃OD, hydrochloride salt) δ 7.22 (s, 1H), 4.96 (t, J=8.2 Hz, 1H), 3.88 (s, 1H), 3.63-3.57 (m, 1H), 3.51-3.41 (m, 2H), 3.35-3.32 (m, 1H), 3.27-3.23 (m, 1H), 2.98-2.92 (m, 1H), 2.86 (d, J=13.3 Hz, 1H), 2.65-2.55 (m, 2H), 2.34-2.11 (m, 4H), 1.60-1.51 (m, 1H), 1.35 (t, J=7.3 Hz, 3H); MS (ESI) m/z 552.26 (M+H).

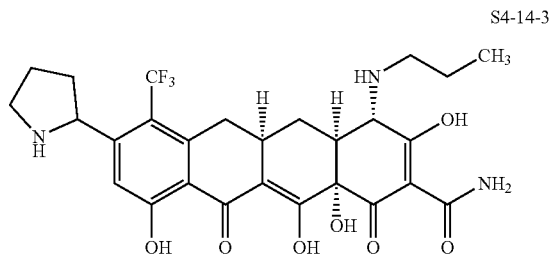 [SMILES: CCCN[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12]

S4-14-3

Compound S4-14-3 was prepared from compound S4-13-2 using the general procedures D-1 (with propionaldehyde) and C. S4-14-3 (single diastereomer A): ¹H NMR (400 MHz, CD₃OD, hydrochloride salt) δ 7.21 (s, 1H), 4.96 (t, J=9.2 Hz, 1H), 3.89 (s, 1H), 3.63-3.56 (m, 1H), 3.51-3.45 (m, 1H), 3.30-3.17 (m, 3H), 2.98-2.86 (m, 2H), 2.65-2.54 (m, 2H), 2.33-2.11 (m, 4H), 1.82-1.72 (m, 2H), 1.61-1.51 (m, 1H), 1.02 (t, J=7.3 Hz, 3H); MS (ESI) m/z 566.04 (M+H).

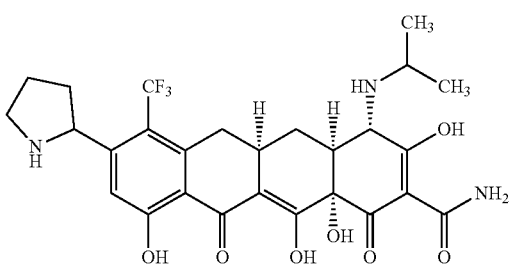
S4-14-4

Compound S4-14-4 was prepared from compound S4-13-2 using the general procedures D-1 (with acetone) and C. S4-14-4 (single diastereomer A): $^1$H NMR (400 MHz, CD$_3$OD, hydrochloride salt) δ 7.21 (s, 1H), 4.96 (t, J=9.2 Hz, 1H), 3.97 (s, 1H), 3.86-3.79 (m, 1H), 3.63-3.56 (m, 1H), 3.51-3.44 (m, 1H), 3.30-3.24 (m, 1H), 3.00-2.91 (m, 1H), 2.85 (d, J=12.4 Hz, 1H), 2.65-2.54 (m, 2H), 2.33-2.11 (m, 4H), 1.62-1.53 (m, 1H), 1.42 (d, J=6.4 Hz, 3H), 1.38 (d, J=6.4 Hz, 3H); MS (ESI) m/z 566.26 (M+H).

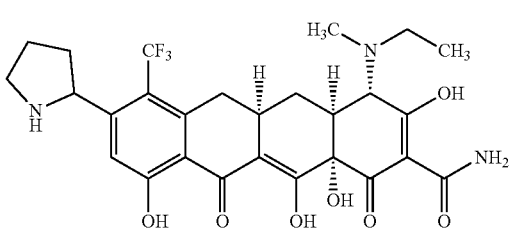
S4-14-5-A

Compound S4-14-5-A was prepared from compound S4-13-2 by using the general procedures D-1 (twice, with acetaldehyde followed by formaldehyde) and C. S4-14-5-A (single diastereomer A): $^1$H NMR (400 MHz, CD$_3$OD, hydrochloride salt, ~1:1 conformers) δ 7.23 (s, 1H), 4.97 (t, J=9.2 Hz, 1H), 4.25 (s, 0.5H), 4.16 (s, 0.5H), 3.64-3.57 (m, 1H), 3.51-3.46 (m, 2H), 3.37-3.31 (m, 1H), 3.29-3.26 (m, 1H), 3.02-2.93 (m, 5H), 2.67-2.56 (m, 2H), 2.34-2.12 (m, 4H), 1.71-1.59 (m, 1H), 1.43-1.36 (m, 3H); MS (ESI) m/z 566.28 (M+H).

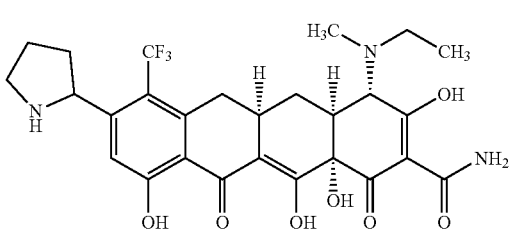
S4-14-5-B

Compound S4-14-5-B was prepared from compound S4-13-4 using general procedure C and separated from compound S4-14-5-A by preparative HPLC. S4-14-5-B (single diastereomer B): $^1$H NMR (400 MHz, CD$_3$OD, hydrochloride salt, ~1:1 conformers) δ 7.34 (s, 1H), 5.05 (t, J=8.2 Hz, 1H), 4.24 (s, 0.5H), 4.19 (s, 0.5H), 3.65-3.59 (m, 1H), 3.52-3.46 (m, 2H), 3.36-3.31 (m, 1H), 3.29-3.26 (m, 1H), 3.04-2.94 (m, 5H), 2.61-2.46 (m, 2H), 2.31-2.14 (m, 4H), 1.74-1.62 (m, 1H), 1.42-1.37 (m, 3H); MS (ESI) m/z 566.36 (M+H).

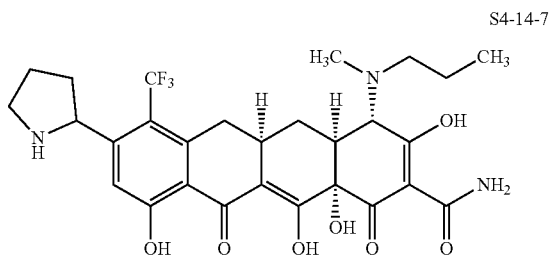 [SMILES: CCCN(C)[C@@H]1C(O)=C(C(N)=O)C(=O)[C@@]2(O)C(O)=C3C(=O)c4c(O)cc(C5CCCN5)c(C(F)(F)F)c4C[C@H]3C[C@@H]12]
S4-14-7

Compound S4-14-7 was prepared from compound S4-13-2 using general procedures D-1 (twice, with propionaldehyde followed by formaldehyde) and C. S4-14-7 (single diastereomer A): $^1$H NMR (400 MHz, CD$_3$OD, hydrochloride salt, ~1:1 conformers) δ 7.22 (s, 1H), 4.97 (t, J=9.2 Hz, 1H), 4.22 (s, 0.5H), 4.15 (s, 0.5H), 3.63-3.57 (m, 1H), 3.51-3.45 (m, 1H), 3.29-3.15 (m, 1H), 3.03-2.94 (m, 5H), 2.66-2.55 (m, 2H), 2.36-2.12 (m, 4H), 1.87-1.73 (m, 2H), 1.68-1.59 (m, 1H), 1.05-0.98 (m, 3H); MS (ESI) m/z 580.05 (M+H).

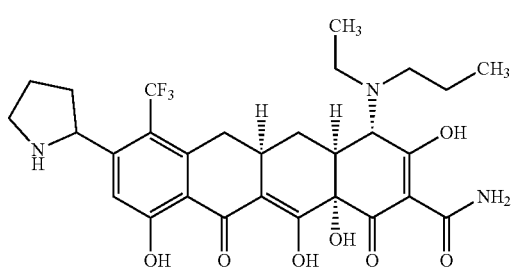
S4-14-8

Compound S4-14-8 was prepared from compound S4-13-2 using general procedures D-1 (twice, with propionaldehyde followed by acetaldehyde) and C. S4-14-8 (single diastereomer A): $^1$H NMR (400 MHz, CD$_3$OD, hydrochloride salt, ~1:1 conformers) δ 7.21 (s, 1H), 4.97 (t, J=9.2 Hz, 1H), 4.26 (s, 0.5H), 4.23 (s, 0.5H), 3.63-3.56 (m, 2H), 3.51-3.45 (m, 2H), 3.29-3.25 (m, 1H), 3.05-2.93 (m, 2H), 2.67-2.55 (m, 2H), 2.34-2.11 (m, 4H), 1.88-1.78 (m, 2H), 1.68-1.59 (m, 1H), 1.41 (t, J=6.9 Hz, 3H), 1.04-0.96 (m, 3H); MS (ESI) m/z 594.33 (M+H).

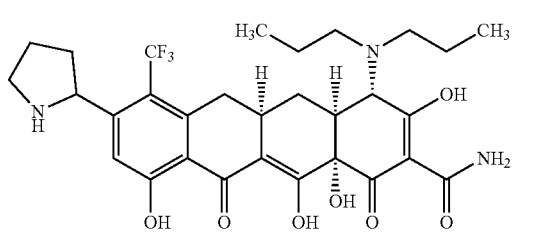
S4-14-9

Compound S4-14-9 was prepared from compound S4-13-2 using general procedures D-1 (with excess propionaldehyde) and C. S4-14-9 (single diastereomer A): $^1$H NMR (400 MHz, CD₃OD, hydrochloride salt) δ 7.21 (s, 1H), 4.96 (t, J=9.2 Hz, 1H), 4.16 (s, 1H), 3.63-3.56 (m, 1H), 3.51-3.45 (m, 1H), 3.34-3.24 (m, 5H), 3.05-2.96 (m, 1H), 2.92 (d, J=12.8 Hz, 1H), 2.67-2.55 (m, 2H), 2.33-2.27 (m, 1H), 2.24-2.12 (m, 3H), 1.86-1.76 (m, 4H), 1.69-1.60 (m, 1H), 0.99 (t, J=7.3 Hz, 6H); MS (ESI) m/z 608.35 (M+H).

S4-14-10

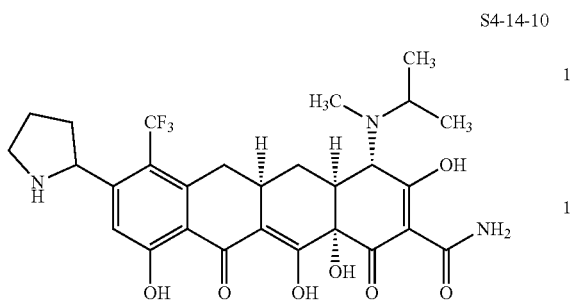

Compound S4-14-10 was prepared from compound S4-13-2 using general procedures D-1 (twice, with acetone followed by formaldehyde) and C. S4-14-10 (single diastereomer A): ¹H NMR (400 MHz, CD₃OD, hydrochloride salt, ~2:3 conformers) δ 7.22 (s, 1H), 4.96 (t, J=9.2 Hz, 1H), 4.32 (s, 0.4H), 4.16-4.14 (m, 0.6H), 4.04 (0.6H), 3.83-3.80 (m, 0.4H), 3.63-3.56 (m, 1H), 3.51-3.45 (m, 1H), 3.29-3.23 (m, 1H), 3.03-2.90 (m, 5H), 2.67-2.55 (m, 2H), 2.36-2.12 (m, 4H), 1.68-1.53 (m, 1H), 1.44 (d, J=6.4 Hz, 4H), 1.38 (d, J=6.0 Hz, 2H); MS (ESI) m/z 580.31 (M+H).

S4-14-11

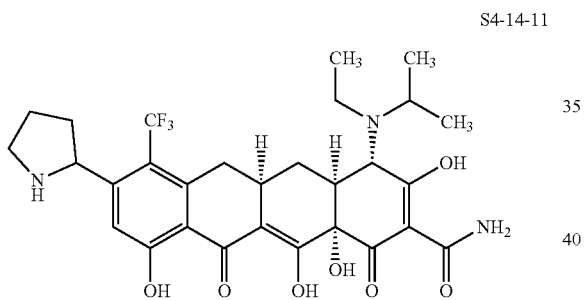

Compound S4-14-11 was prepared from compound S4-13-2 using general procedures D-1 (twice, with acetone followed by acetaldehyde) and C. S4-14-11 (single diastereomer A): ¹H NMR (400 MHz, CD₃OD, hydrochloride salt, ~1:3 conformers) δ 7.21 (s, 1H), 4.96 (t, J=9.2 Hz, 1H), 4.32 (s, 0.25H), 4.14 (m, 0.75H), 4.04-3.97 (m, 1H), 3.62-3.38 (m, 4H), 3.29-3.24 (m, 1H), 3.00-2.85 (m, 2H), 2.66-2.54 (m, 2H), 2.33-2.27 (m, 2H), 2.24-2.11 (m, 2H), 1.60-1.50 (m, 1H), 1.50-1.37 (m, 6.75H), 1.34 (t, J=6.9 Hz, 2.25H); MS (ESI) m/z 594.30 (M+H).

S4-14-12

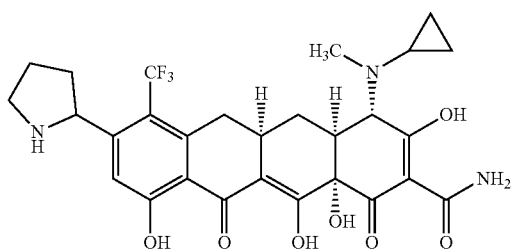

Compound S4-14-12 was prepared from compound S4-13-3-1 using general procedures D-1 (with formaldehyde) and C. S4-14-12 (single diastereomer A): ¹H NMR (400 MHz, CD₃OD, hydrochloride salt) δ 7.21 (s, 1H), 4.96 (t, J=9.2 Hz, 1H), 4.89-4.81 (m, 1H), 4.34 (s, 1H), 3.62-3.56 (m, 1H), 3.51-3.45 (m, 1H), 3.29-3.25 (m, 1H), 3.12-3.05 (m, 5H), 2.67-2.55 (m, 2H), 2.33-2.25 (m, 2H), 2.23-2.12 (m, 2H), 1.72-1.62 (m, 1H), 1.30 (br s, 1H), 1.09-0.99 (m, 3H); MS (ESI) m/z 578.07 (M+H).

S4-14-13

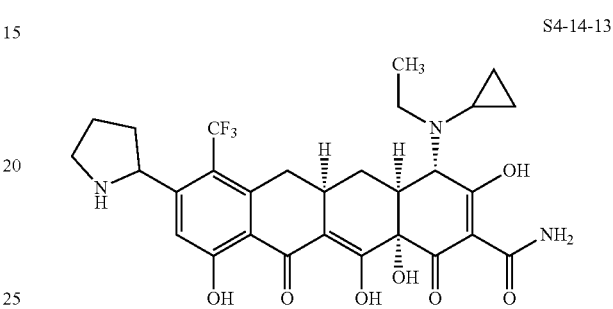

Compound S4-14-13 was prepared from compound S4-13-3-1 using general procedures D-1 (with acetaldehyde) and C. S4-14-13 (single diastereomer A): ¹H NMR (400 MHz, CD₃OD, hydrochloride salt) δ 7.21 (s, 1H), 4.96 (t, J=9.2 Hz, 1H), 4.89-4.81 (m, 1H), 4.35 (s, 1H), 3.62-3.44 (m, 4H), 3.29-3.25 (m, 1H), 3.11-3.01 (m, 2H), 2.67-2.55 (m, 2H), 2.33-2.25 (m, 2H), 2.23-2.12 (m, 2H), 1.72-1.62 (m, 1H), 1.45 (t, J=7.3 Hz, 3H), 1.41-1.00 (m, 3H); MS (ESI) m/z 592.11 (M+H).

S4-14-14-A

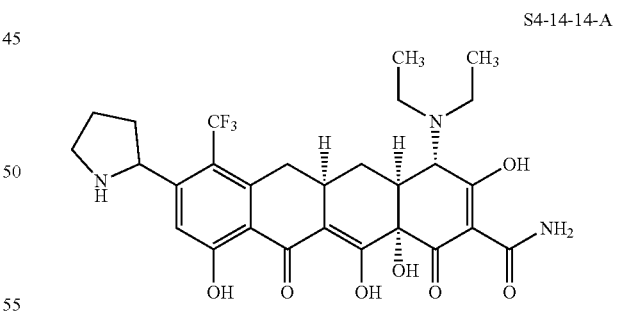

Compound S4-14-14-A was prepared from compound S4-13-2 using general procedures D-1 (with excess acetaldehyde) and C. S4-14-14-A (single diastereomer A): ¹H NMR (400 MHz, CD₃OD, hydrochloride salt) δ 7.21 (s, 1H), 4.98 (t, J=8.7 Hz, 1H), 4.26 (s, 1H), 3.63-3.54 (m, 2H), 3.51-3.43 (m, 3H), 3.34-3.26 (m, 2H), 3.04-2.92 (m, 2H), 2.67-2.55 (m, 2H), 2.36-2.10 (m, 4H), 1.68-1.59 (m, 1H), 1.41 (t, J=6.9 Hz, 6H); MS (ESI) m/z 580.08 (M+H).

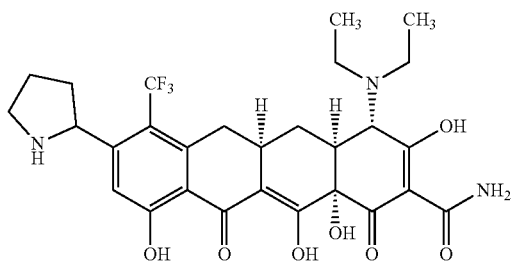

S4-14-14-B

Compound S4-14-14-B was prepared from compound S4-13-5 using general procedure C and separated from compound S4-14-14 by preparative HPLC. S4-14-14-B (single diastereomer B): $^1$H NMR (400 MHz, CD$_3$OD, hydrochloride salt) δ 7.30 (s, 1H), 5.05 (t, J=9.2 Hz, 1H), 4.26 (s, 1H), 3.63-3.58 (m, 2H), 3.52-3.46 (m, 3H), 3.37-3.31 (m, 1H), 3.29-3.26 (m, 1H), 3.02-2.94 (m, 2H), 2.59 (t, J=14.6 Hz, 1H), 2.52-2.46 (m, 1H), 2.31-2.18 (m, 4H), 1.69-1.60 (m, 1H), 1.42 (t, J=6.4 Hz, 6H); MS (ESI) m/z 580.37 (M+H).

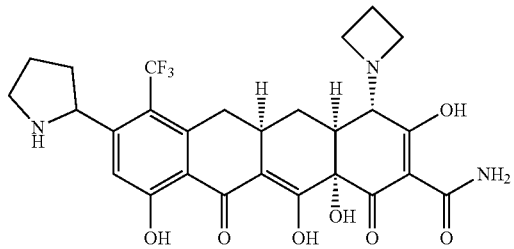

S4-14-17

Compound S4-14-17 was prepared from compound S4-13-6 using general procedure C. S4-14-17 (single diastereomer A): $^1$H NMR (400 MHz, CD$_3$OD, trifluoroacetic acid salt) δ 7.19 (s, 1H), 4.96 (t, J=8.7 Hz, 1H), 4.60-4.25 (m, 4H), 4.05 (s, 1H), 3.62-3.55 (m, 1H), 3.51-3.44 (m, 1H), 3.25-3.22 (m, 1H), 2.98-2.90 (m, 1H), 2.68-2.54 (m, 4H), 2.34-2.11 (m, 5H), 1.60-1.50 (m, 1H); MS (EST) m/z 564.08 (M+H).

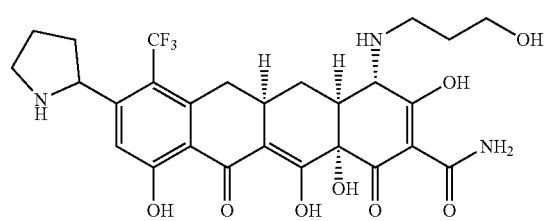

S4-14-16

Compound S4-14-16 was prepared from compound S4-13-2 using the general procedures D-1 (with 3-Rtert-butyldimethylsilyl)oxyl-1-propanal) and C. S4-14-16 (single diastereomer A): $^1$H NMR (400 MHz, CD$_3$OD, hydrochloride salt) δ 7.20 (s, 1H), 4.96 (t, J=9.2 Hz, 1H), 3.89 (s, 1H), 3.78-3.69 (m, 2H), 3.62-3.56 (m, 1H), 3.52-3.41 (m, 3H), 3.27-3.23 (m, 1H), 2.99-2.91 (m, 1H), 2.85 (d, J=12.8 Hz, 1H), 2.66-2.54 (m, 2H), 2.33-2.27 (m, 1H), 2.24-2.09 (m, 3H), 1.98-1.92 (m, 2H), 1.61-1.52 (m, 1H), 1.41 (t, J=6.9 Hz, 6H); MS (ESI) m/z 582.05 (M+H).

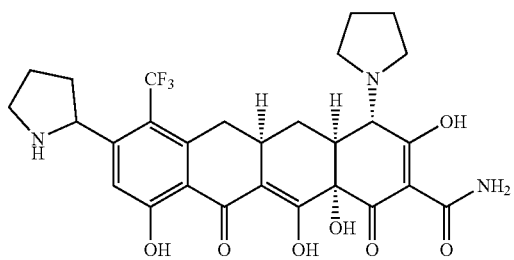

S4-14-18

Compound S4-14-18 was prepared from compound S4-13-7 using general procedure C. S4-14-18 (single diastereomer A): $^1$H NMR (400 MHz, CD$_3$OD, hydrochloride salt) δ 7.22 (s, 1H), 4.96 (t, J=9.2 Hz, 1H), 4.04 (s, 1H), 3.63-3.57 (m, 5H), 3.51-3.47 (m, 1H), 3.26-3.22 (m, 1H), 3.01-2.94 (m, 2H), 2.65-2.54 (m, 2H), 2.33-2.27 (m, 1H), 2.22-2.09 (m, 7H), 1.63-1.54 (m, 1H); MS (ESI) m/z 578.11 (M+H).

Scheme 5

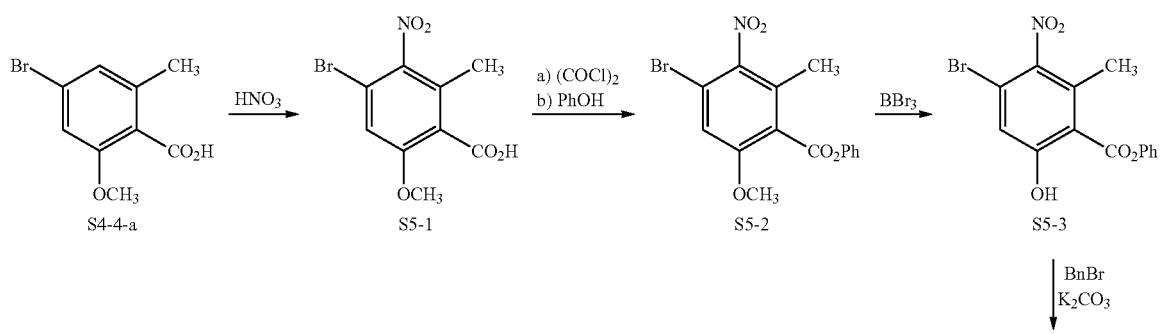

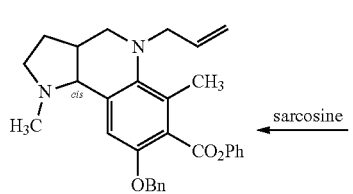
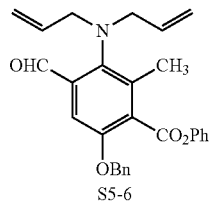
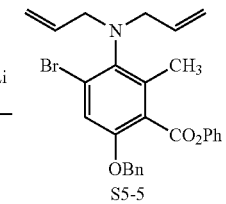
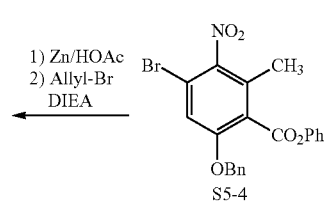

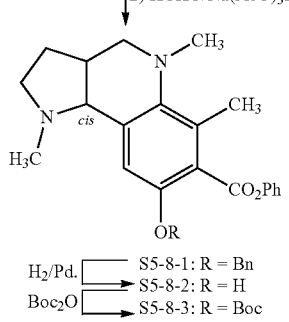

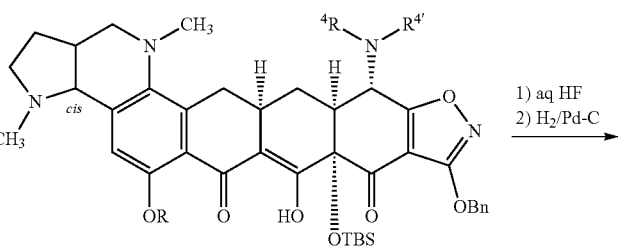

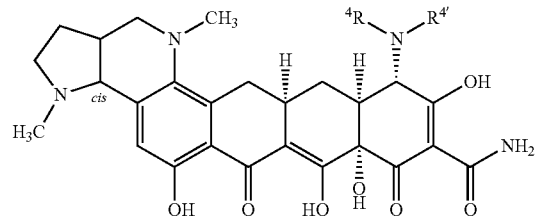

The following compounds were prepared according to Scheme 5.

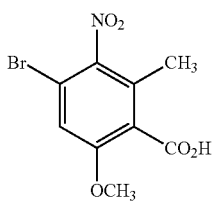

A solution of HNO$_3$ (68-70%, 0.56 mL, 8.57 mmol, 1.05 eq) in concentrated H$_2$SO$_4$ (2 mL) was added dropwise to a solution of compound S4-4-a (2.00 g, 8.16 mmol, 1.0 eq) in concentrated H$_2$SO$_4$ (20 mL) at 0° C. The reaction mixture was stirred at 0° C. for 10 min and poured onto ice (~200 mL). The mixture was extracted with EtOAc (150 mL). The organic phase was separated, washed with brine (2×50 mL), dried over magnesium sulfate, filtered, and concentrated to give crude S5-1 as an orange solid: $^1$H NMR (400 MHz, CDCl$_3$) δ 11.5 (br s, 1H), 7.06 (s, 1H), 3.90 (s, 3H), 2.32 (s, 3H); MS (ESI) m/z 288.01, 289.99 (M–H).

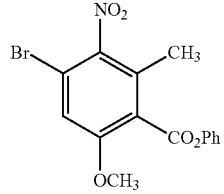

Compound S5-1 was dissolved in dichloromethane (16 mL). Oxalyl chloride (0.85 mL, 9.79 mmol, 1.2 eq) was added, followed by a few drops of DMF. The reaction mixture was stirred at rt for 30 min, concentrated, and further dried under high vacuum. The residue was re-dissolved in dichloromethane (16 mL). Phenol (0.92 g, 9.79 mmol, 1.2 eq), triethylamine (2.84 mL, 20.40 mmol, 2.5 eq), and DMAP (100 mg, 0.82 mmol, 0.1 eq) were added. The reaction was stirred at rt for 1 h and concentrated under reduced pressure. The residue was dissolved in EtOAc (150 mL), washed with 1 N aqueous HCl (50 mL), brine (50 mL), 1 N aqueous NaOH (50 mL), and then brine (50 mL), dried over anhydrous magnesium sulfate, filtered, and concentrated to afford the desired product S5-2 as a light yellow solid: ¹H NMR (400 MHz, CDCl₃) δ 7.45-7.41 (m, 2H), 7.30-7.26 (m, 1H), 7.21-7.16 (m, 2H), 7.09 (s, 1H), 3.94 (s, 3H), 2.38 (s, 3H); MS (ESI) m/z 364.05, 366.06 (M−H).

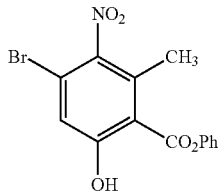

S5-3

A solution of BBr₃ in dichloromethane (1.0 M, 8.16 mL, 8.16 mmol, 1.0 eq) was added slowly to a solution of compound S5-2 in dichloromethane (32 mL) at −78° C. The reaction was stirred at −78° C. for 15 min and then allowed to warm to 0° C. in 50 min and kept at that temperature for 10 min. The reaction mixture was poured into saturated aqueous NaHCO₃ solution (50 mL) and stirred at rt for 10 min. The dichloromethane was evaporated. The residue was extracted with EtOAc (100 mL, then 30 mL). The organic extracts were combined and dried over anhydrous magnesium sulfate. The dried solution was filtered, and the filtrate was concentrated to give crude S5-3 (2.20 g): ¹H NMR (400 MHz, CDCl₃) δ 11.2 (br s, 1H), 7.48-7.44 (m, 2H), 7.36-7.32 (m, 1H), 7.25 (s, 1H), 7.18-7.16 (m, 2H), 2.63 (s, 3H); MS (ESI) m/z 350.01, 352.03 (M−H).

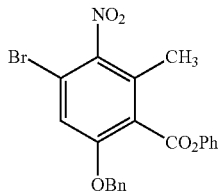

S5-4

Benzylbromide (0.78 mL, 6.56 mmol, 1.05 eq) and K₂CO₃ powder (1.73 g, 12.50 mmol, 2.0 eq) were added to a solution of compound S5-3 (2.20 g, 6.25 mmol, 1.0 eq) in acetone (12 mL). The mixture was stirred at rt overnight. The solid was filtered off and further washed with EtOAc (30 mL). The filtrate was concentrated. The residue was purified by flash column chromatography (2-20% EtOAc/hexanes) to afford the desired product S5-4 as a white solid (1.68 g, 47% over four steps): ¹H NMR (400 MHz, CDCl₃) δ 7.40-7.32 (m, 8H), 7.15 (s, 1H), 7.03-7.01 (m, 2H), 5.18 (s, 2H), 2.39 (s, 3H); MS (ESI) m/z 440.09, 442.06 (M−H).

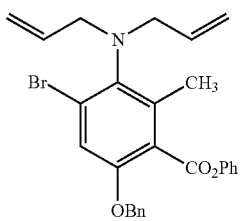

S5-5

Zinc dust (12.1 g, 186 mmol) was added portionwise to a solution of compound S5-4 (8.24 g, 18.6 mmol) in THF (70 mL) and acetic acid (20 mL). After 1 h, the reaction mixture was filtered through Celite (EtOAc wash), and the filtrate was concentrated under reduced pressure. The material was diluted with EtOAc, and was washed with NaHCO₃ (saturated, aqueous solution, 3×) and brine (1×). The EtOAc layer was dried over Na₂SO₄, was filtered, and was concentrated to give 7.30 g (95%) of the crude aniline S5-4-a as a thick oil.

A DMF (15 mL) solution of crude aniline intermediate S5-4-a (4.52 mmol), diisopropylethylamine (3.94 mL, 22.6 mmol, 5 eq) and allylbromide (1.62 mL, 18.1 mmol, 4 eq) was heated in a sealed tube at 90° C. for 4 h, cooled down to rt, and diluted with EtOAc (100 mL). The organic phase was washed with water (50 mL×2) and aqueous NH₄Cl solution (50 mL), dried over sodium sulfate, and concentrated to yield the compound S5-5: MS (ESI) m/z 492.04, 494.04 (M+H). This crude product was used directly in the next step without further purification.

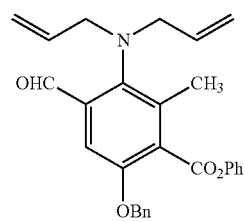

S5-6

A solution of n-BuLi in hexanes (4.22 mL, 2.5 M, 1.2 eq) was added dropwise to a solution of compound S5-5 (4.33 g, 8.8 mmol, 1 eq) in THF (30 mL) at −78° C. under a N₂ atmosphere. The resulting red solution was stirred at −78° C. for 5 min and then DMF (2.04 mL, 3 eq) was added dropwise. The reaction was slowly warmed to 0° C. in 1 h. Saturated aqueous NH₄Cl was added. The resulting mixture was extracted three times with EtOAc. The combined EtOAc extracts were washed with brine, dried (sodium sulfate), and concentrated. Purification of the residue by flash chromatography (5% to 15%, EtOAc/hexane) gave compound S5-6 (1.92 g, 50%): ¹H NMR (400 MHz, CDCl₃) δ 10.40 (s, 1H), 7.44-7.30 (m, 8H), 7.25-7.22 (m, 1H), 7.21 (d, J=6.8 Hz, 2H), 5.86-5.75 (m, 2H), 5.14 (s, 2H), 5.15-5.06 (m, 4H), 3.73 (d, J=6.4 Hz, 4H), 2.41 (s, 3H); MS (ESI) m/z 440.14 (M−H).

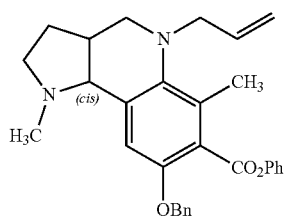

S5-7

Compound S5-6 (577 mg, 1.31 mmol, 1 eq) was dissolved in 6 mL dry DMF. Sarcosine (202 mg, 1.5 eq) was added. The resulting suspension was heated to 80° C. for 4 h until it became a homogeneous dark yellow solution. The reaction solution was cooled down to rt, diluted with ethyl acetate, washed with water and brine, dried (sodium sulfate), and concentrated to afford compound S5-7 (727 mg, crude): ¹H NMR (400 MHz, CDCl₃) δ 7.48-7.19 (m, 10H), 6.66 (s, 1H), 6.02-5.86 (m, 1H), 5.36-4.99 (m, 4H), 3.35 (s, 2H), 3.19-

2.78 (m, 3H), 2.42-2.31 (m, 3H), 2.35 (s, 3H), 2.24 (s, 3H), 2.09-1.95 (m, 1H), 1.70-1.50 (m, 1H); MS (ESI) m/z 469.15 (M+H).

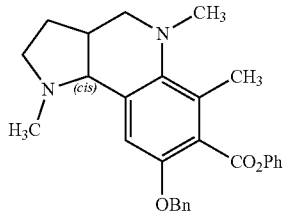
S5-8-1

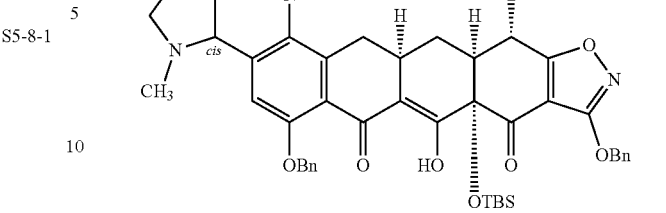
S5-9-1

Compound S5-9-1 was prepared in 95% yield from compound S5-9-5 using general procedure B. S5-9-1 (mixture of diastereomers): MS (ESI) m/z 803.48 (M+H).

To a solution of compound S5-7 (727 mg, crude 1.3 mmol, 1 eq) in 6 mL dry DCM was added tetrakis(triphenylphosphine) palladium (75 mg, 0.05 eq) and 1,3-dimethylbarbituric acid (609 mg, 3 eq) under nitrogen. The reaction mixture was purged with nitrogen, stirred at rt for 2 h, dilute with 25 mL saturated aqueous NaHCO₃ solution, and extracted with DCM (25 mL×3). The combined organic extracts were dried over anhydrous sodium sulfate, filtered, and concentrated to yield the aniline intermediate S5-7-a (crude): MS (ESI) m/z 429.10 (M+H).

Formaldehyde (290 µL, 37% aqueous solution, 3 eq), sodium triacetoxyborohydride (551 mg, 2 eq), and acetic acid (223 µL, 3 eq) were added sequentially to a solution of intermediate S5-7-a in dichloromethane (5 mL) at 25° C. After stirring for 30 min, the reaction mixture was quenched by the addition of saturated aqueous sodium bicarbonate (15 mL) and extracted with dichloromethane (3×10 mL). The combined organic extracts were dried over anhydrous sodium sulfate, filtered, and concentrated. Purification of the residue by flash chromatography (15% to 50%, EtOAc/hexane) gave compound S5-8-1 (441 mg, 41% for 3 steps): ¹H NMR (400 MHz, CDCl₃) δ 7.47-7.42 (m, 2H), 7.40-7.32 (m, 5H), 7.28-7.20 (m, 1H), 7.19-7.13 (m, 2H), 6.68 (s, 1H), 5.15 (s, 2H), 3.12-3.00 (m, 2H), 2.92-2.81 (m, 2H), 2.66 (s, 3H), 2.54-2.46 (m, 1H), 2.41 (s, 3H), 2.36 (s, 3H), 2.33-2.22 (m, 1H), 2.12-2.00 (m, 1H), 1.45-1.32 (m, 1H); MS (ESI) m/z 443.16 (M+H).

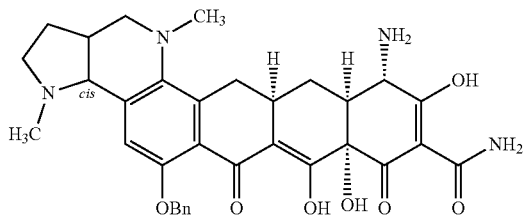
S5-10-1

Compound S5-10-1 was prepared from compound S5-9-1 using general procedure C, and the two diastereomers were separated by preparative HPLC.

S5-10-1-A: ¹H NMR (400 MHz, CD₃OD, hydrochloride salt) δ 7.17 (s, 1H), 4.70 (d, J=6.0 Hz, 1H), 3.91 (s, 1H), 3.88-3.81 (m, 1H), 3.64-3.38 (m, 4H), 3.19-3.05 (m, 8H), 2.70-2.47 (m, 3H), 2.34-2.24 (m, 1H), 2.03-1.96 (m, 1H), 1.66-1.57 (m, 1H); MS (ESI) m/z 511.30 (M+H).

S5-10-1-B: ¹H NMR (400 MHz, CD₃OD, hydrochloride salt) δ 7.12 (s, 1H), 4.56 (d, J=6.0 Hz, 1H), 3.91 (s, 1H), 3.84-3.78 (m, 1H), 3.43-3.34 (m, 4H), 3.29-3.25 (m, 1H), 3.14 (s, 3H), 2.98-2.90 (m, 1H), 2.83 (s, 3H), 2.69-2.60 (m, 2H), 2.42 (t, J=14.6 Hz, 1H), 2.28-2.24 (m, 1H), 1.91-1.84 (m, 1H), 1.69-1.59 (m, 1H); MS (ESI) m/z 511.30 (M+H).

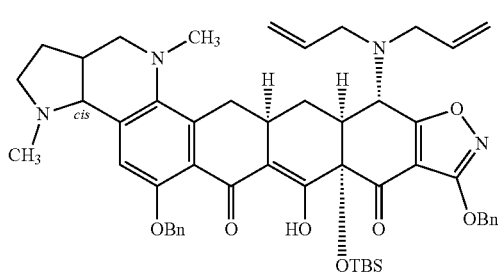
S5-9-5

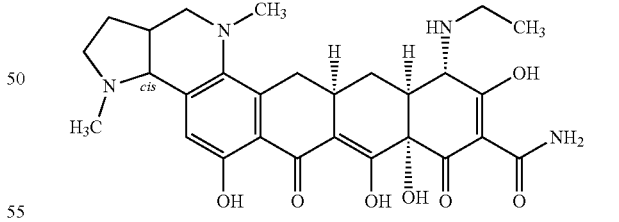
S5-10-2

Compound S5-9-5 was prepared in 50% yield from S5-8-1 and N-diallyl enone S1-9-2 using general procedure A. S5-9-5 (~1:1 mixture of diastereomers, yellow foam): ¹H NMR (400 MHz, CDCl₃) δ 15.90 (br s, 1H), 7.42-7.18 (m, 10H), 6.59 (s, 0.5H), 6.53 (s, 0.5H), 5.75-5.67 (m, 2H), 5.27 (s, 2H), 5.13-4.96 (m, 6H), 4.06 (d, J=10.4 Hz, 1H), 3.31-3.08 (m, 6H), 3.02-2.92 (m, 2H), 2.80-2.69 (m, 4H), 2.48-2.28 (m, 6H), 2.22-2.14 (m, 1H), 2.09-2.03 (m, 4H), 1.53-1.48 (m, 1H), 0.722 (s, 4.5H), 0.718 (s, 4.5H), 0.163 (s, 1.5H), 0.156 (s, 1.5H), 0.026 (s, 3H); MS (ESI) m/z 883.56 (M+H).

Compound S5-10-2 was prepared from compound S5-9-1 using general procedures D-1 (with acetaldehyde) and C, and the two diastereomers were separated preparative HPLC.

S5-10-2-A: ¹H NMR (400 MHz, CD₃OD, hydrochloride salt) δ 7.16 (s, 1H), 4.68 (d, J=5.5 Hz, 1H), 3.89 (s, 1H), 3.86-3.80 (m, 1H), 3.54-3.52 (m, 1H), 3.48-3.33 (m, 5H), 3.17-3.07 (m, 8H), 2.86 (d, J=12.8 Hz, 1H), 2.68-2.62 (m, 1H), 2.47 (t, J=14.6 Hz, 1H), 2.33-2.30 (m, 1H), 2.00-1.93 (m, 1H), 1.64-1.55 (m, 1H), 1.36 (t, J=6.9 Hz, 3H); MS (ESI) m/z 539.33 (M+H).

S5-10-2-B: ¹H NMR (400 MHz, CD₃OD, hydrochloride salt) δ 7.16 (s, 1H), 4.61 (d, J=5.9 Hz, 1H), 3.91 (s, 1H), 3.87-3.80 (m, 1H), 3.49-3.32 (m, 7H), 3.15 (s, 3H), 3.03-2.94 (m, 1H), 2.91 (s, 3H), 2.85 (d, J=12.4 Hz, 1H), 2.71-2.62 (m, 1H), 2.45 (t, J=14.2 Hz, 1H), 2.28-2.24 (m, 1H), 1.94-1.88 (m, 1H), 1.67-1.58 (m, 1H), 1.36 (t, J=7.3 Hz, 3H); MS (ESI) m/z 539.33 (M+H).

S5-10-3

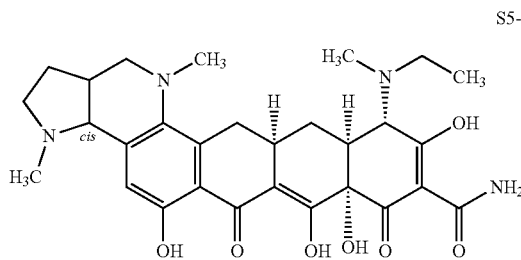

Compound S5-10-3 was prepared from compound S5-9-1 using general procedures D-1 (twice, with acetaldehyde followed by formaldehyde) and C, and the two diastereomers were separated by preparative HPLC.

S5-10-3-A: ¹H NMR (400 MHz, CD₃OD, hydrochloride salt, ~1:1 conformers) δ 7.15 (s, 1H), 4.67 (br s, 1H), 4.26 (s, 0.5H), 4.17 (s, 0.5H), 3.86-3.79 (m, 1H), 3.54-3.37 (m, 7H), 3.18-2.94 (m, 11H), 2.67-2.62 (m, 1H), 2.46 (t, J=14.2 Hz, 1H), 2.34 (br t, J=11.0 Hz, 1H), 1.99-1.92 (m, 1H), 1.72-1.61 (m, 1H), 1.45-1.37 (m, 3H); MS (ESI) m/z 553.34 (M+H).

S5-10-3-B: ¹H NMR (400 MHz, CD₃OD, hydrochloride salt, ~1:1 conformers) δ 7.12 (s, 1H), 4.56 (d, J=5.5 Hz, 1H), 4.25 (s, 0.5H), 4.16 (s, 0.5H), 3.85-3.78 (m, 1H), 3.53-3.26 (m, 7H), 3.14 (s, 3H), 3.02-2.94 (m, 5H), 2.82 (s, 3H), 2.68-2.59 (m, 1H), 2.40 (t, J=14.6 Hz, 1H), 2.29-2.22 (m, 1H), 1.91-1.84 (m, 1H), 1.75-1.63 (m, 1H), 1.44-1.36 (m, 3H); MS (ESI) m/z 553.34 (M+H).

S5-8-3

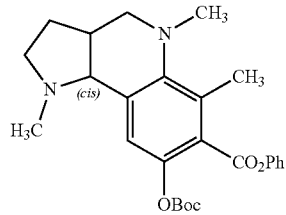

To a solution of S5-8-1 (1.63 g, 3.67 mmol, 1 eq) in MeOH (18 mL), was added palladium on carbon (Degussa, 10 wt %, 161 mg). An atmosphere of hydrogen was introduced and the reaction mixture was stirred at room temperature. After 30 min, the hydrogen balloon had deflated, so another portion of palladium catalyst (50 mg) was added, followed by reintroduction of hydrogen atmosphere. After an additional hour, the reaction mixture was filtered through a small Celite pad and the filtrate was concentrated under reduced pressure to give intermediate S5-8-2. To a solution of the above crude oil S5-8-2 in dichloromethane (20 mL) was added di-tent-butyl dicarbonate (890 mg, 4.08 mmol, 1.1 eq) and dimethylaminopyridine (54 mg, 0.44 mmol, 0.1 eq) and the reaction mixture was stirred at ambient temperature. After 50 min, the mixture was concentrated under reduced pressure. Purification of the resulting residue via flash column chromatography (Biotage, 50 g silica gel column, 20% to 90% acetonitrile in dichloromethane gradient) provided an impure fraction containing desired product. A second purification via flash column chromatography (Biotage, 50 g silica gel column, 2% to 70% acetonitrile in dichloromethane gradient) provided the desired compound S5-8-3 (1.57 g, 94%) as a colorless oil: ¹H NMR (400 MHz, CDCl₃) δ 7.45-7.39 (m, 2H), 7.30-7.22 (m, 3H), 6.97 (s, 1H), 3.14-3.07 (m, 2H), 2.94-2.87 (m, 2H), 2.70 (s, 3H), 2.44 (s, 3H), 2.41 (s, 3H), 2.30 (q, J=9.2 Hz, 1H), 2.13-2.02 (m, 1H), 1.44 (s, 9H), 1.43-1.34 (m, 1H); MS (ESI) m/z 453.99 (M–H).

S5-9-4

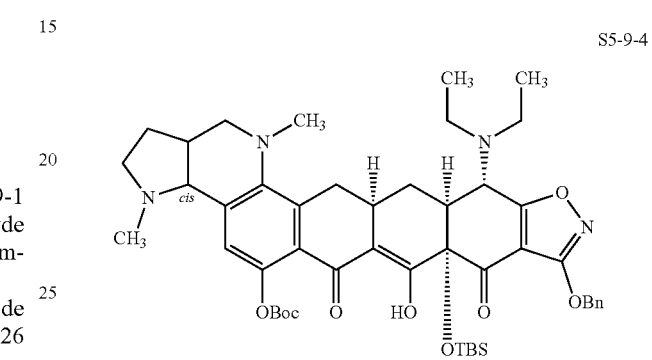

Compound S5-9-4 was prepared in 75% yield from S5-8-3 and N-diethyl enone S1-9-3 using general procedure A. S5-9-4 (yellow foam, ~1:1 diastereomers): MS (ESI) m/z 869.92 (M+H).

S5-10-4

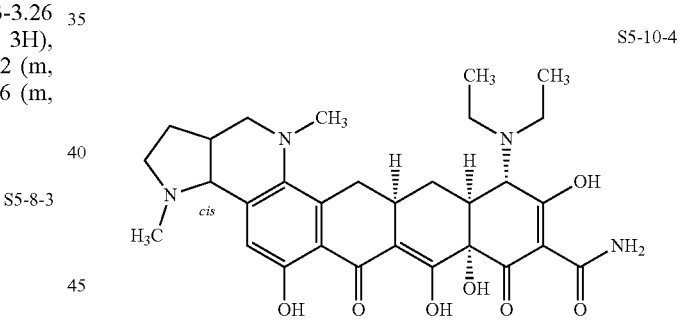

Compound S5-10-4 was prepared from compound S5-9-4 using general procedure C, and the two diastereomers were separated by preparative HPLC.

S5-10-4-A: ¹H NMR (400 MHz, CD₃OD, hydrochloride salt) δ 7.26 (s, 1H), 4.83 (d, J=5.5 Hz, 1H), 4.30 (s, 1H), 3.92-3.85 (m, 1H), 3.82-3.71 (m, 2H), 3.62-3.56 (m, 3H), 3.53-3.42 (m, 3H), 3.38-3.32 (m, 1H), 3.32 (s, 3H), 3.20 (s, 3H), 3.11 (d, J=15.1 Hz, 1H), 2.96 (d, J=13.3 Hz, 1H), 2.74-2.55 (m, 2H), 2.42-2.39 (m, 1H), 2.05-1.98 (m, 1H), 1.71-1.62 (m, 1H), 1.43 (t, J=7.3 Hz, 3H), 1.41 (t, J=7.3 Hz, 3H); MS (ESI) m/z 567.53 (M+H).

S5-10-4-B: ¹H NMR (400 MHz, CD₃OD, hydrochloride salt) δ 7.28 (s, 1H), 4.78 (d, J=5.5 Hz, 1H), 4.31 (s, 1H), 3.93-3.80 (m, 2H), 3.72-3.68 (m, 1H), 3.62-3.46 (m, 6H), 3.38-3.30 (m, 1H), 3.21-3.14 (m, 1H), 3.16 (s, 3H), 3.14 (s, 3H), 2.96 (d, J=12.8 Hz, 1H), 2.78-2.66 (m, 1H), 2.58 (t, J=14.2 Hz, 1H), 2.32-2.29 (m, 1H), 2.02-1.95 (m, 1H), 1.75-1.65 (m, 1H), 1.414 (t, J=7.3 Hz, 3H), 1.409 (t, J=7.3 Hz, 3H); MS (ESI) m/z 567.53 (M+H).

Scheme 6
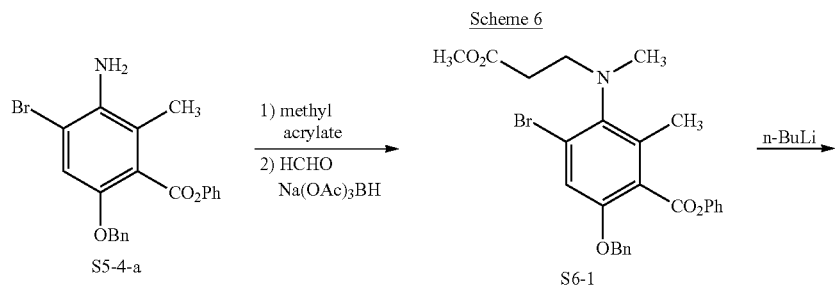
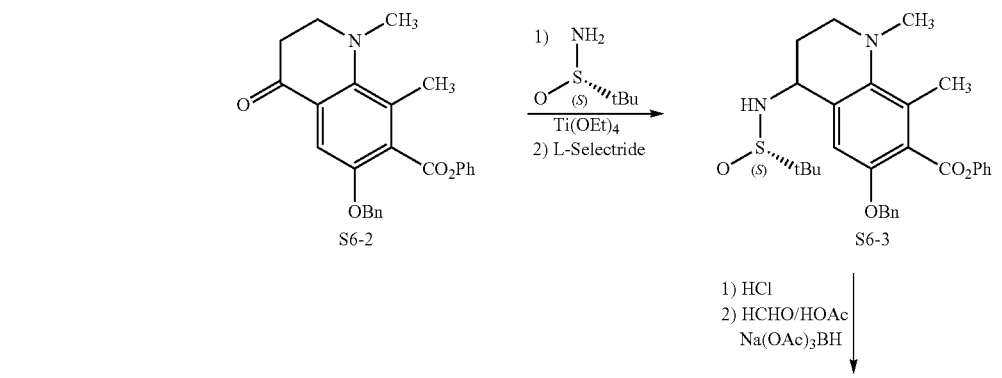
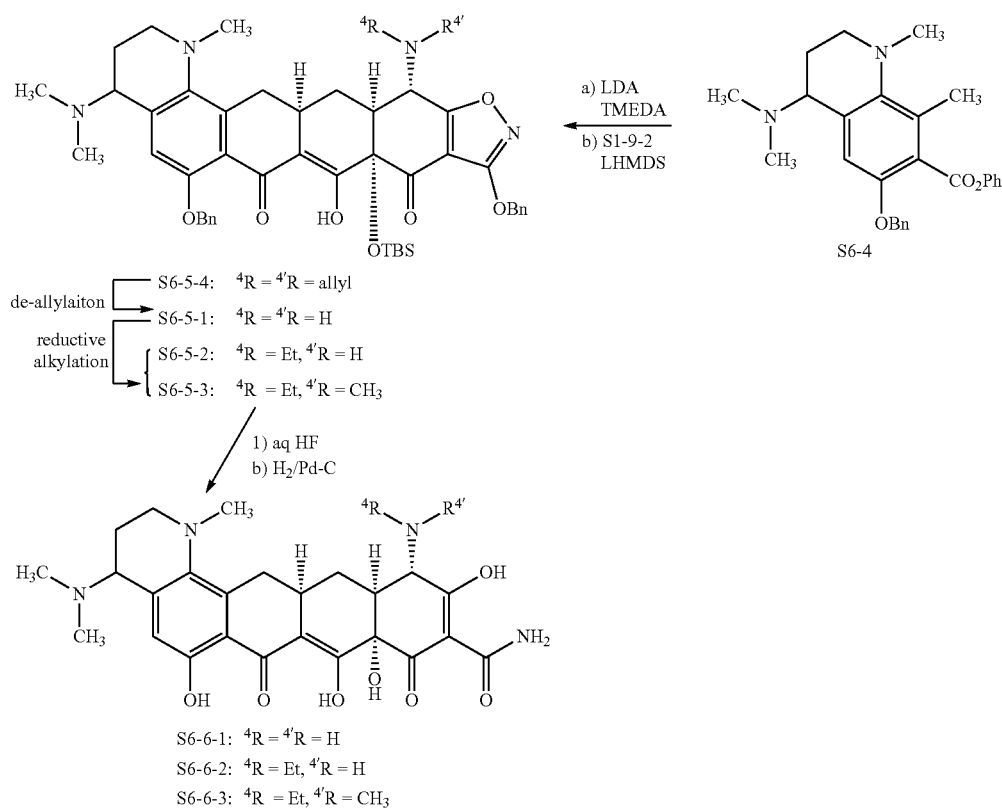

The following compounds were prepared according to Scheme 6.

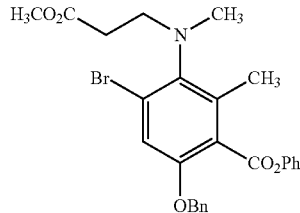
S6-1

Compound S5-4-a (crude) was dissolved in methyl acrylate (10 mL) and acetic acid (20 mL) and was heated to 110° C. in a sealed vessel. After stirring overnight, additional methyl acrylate (5 mL) was added, and heating was continued at 110° C. overnight. Upon cooling to rt, the reaction mixture was concentrated. The material was dissolved in EtOAc and was washed with NaHCO$_3$ (saturated, aqueous solution, 3×) and brine (1×). The EtOAc layer was dried over Na$_2$SO$_4$, was filtered, and was concentrated to give the corresponding aniline intermediate. This intermediate was dissolved in CH$_2$Cl$_2$ (100 mL) and acetic acid (5 mL) and formaldehyde (37%, aqueous, 5 mL) were added. Na(OAc)$_3$BH (5.6 g, 26.4 mmol) was then added. After 1 h, the reaction mixture was quenched with NaHCO$_3$ (saturated, aqueous solution) and the layers were separated. The organic layer was washed with NaHCO$_3$ (saturated, aqueous solution, 2×) and brine (1×), was dried over Na$_2$SO$_4$, was filtered, and was concentrated. The material was purified by column chromatography (100 g Biotage column, 0 to 12% EtOAc in hexanes gradient) to give 3.94 g (44%, 3 steps) of the product S6-1: R$_f$=0.20 in 10% EtOAc/hexanes: $^1$H NMR (400 MHz, CDCl$_3$) δ 7.45-7.32 (m, 7H), 7.26-7.21 (m, 1H), 7.11-7.04 (m, 3H), 5.10 (s, 2H), 3.66 (s, 3H), 3.48-3.41 (m, 2H), 2.80 (s, 3H), 2.50 (dt, J=6.9 Hz, 2.3 Hz, 2H), 2.38 (s, 3H); MS (ESI) m/z 512.33, 514.33 (M+H).

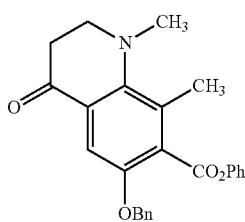
S6-2 n-BuLi (2.5 M solution, 5.2 mL, 13.0 mmol) was added dropwise to a −78° C. solution of S6-1 (3.94 g, 7.69 mmol) in THF (30 mL). After 5 min, the reaction was quenched with NH$_4$Cl (saturated, aqueous solution) and was extracted with EtOAc (2×). The combined extracts were dried over Na$_2$SO$_4$, were filtered, and were concentrated. The material was purified by column chromatography (100 g Biotage column, 5 to 30% EtOAc in hexanes gradient) to give 0.854 g (28%) of the product S6-2 as a bright yellow oil: $^1$H NMR (400 MHz, CDCl$_3$) δ 7.48 (s, 1H), 7.45-7.41 (m, 2H), 7.38-7.30 (m, 5H), 7.26-7.22 (m, 1H), 7.10-7.06 (m, 2H), 5.15 (s, 2H), 3.55 (t, J=6.4 Hz, 2H), 2.87 (s, 3H), 2.77 (t, J=6.4 Hz, 2H), 2.41 (s, 3H); MS (ESI) m/z 402.00 (M+H).

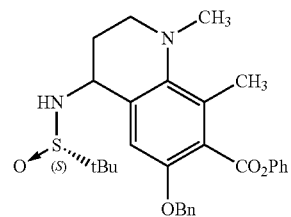
S6-3

Ti(OEt)$_4$ (3.82 mL, 18.40 mmol) was added to a solution of compound S6-2 (2.46 g, 6.12 mmol) and (S)-(−)-t-butylsulfinamide (2.23 g, 18.40 mmol) in toluene (20 mL), and the reaction mixture was heated to 75° C. After stirring overnight, the reaction mixture was diluted with EtOAc and was quenched with NaHCO$_3$ (saturated, aqueous solution). The mixture was filtered through Celite (EtOAc wash), and the filtrate was washed with NaHCO$_3$ (saturated, aqueous solution, 3×) and brine. The organics were dried over Na$_2$SO$_4$, were filtered, and were concentrated. The material was purified by column chromatography (100 g Biotage column, 15 to 60% EtOAc in hexanes gradient) to give 1.943 g (63%) of the sulfinimine intermediate as a yellow solid: $^1$H NMR (400 MHz, CDCl$_3$) δ 7.56 (s, 1H), 7.43-7.22 (m, 8H), 7.14-7.08 (m, 2H), 5.14 (s, 2H), 3.47-3.37 (m, 1H), 3.36-3.30 (m, 2H), 3.08-2.99 (m, 1H), 2.75 (s, 3H), 2.38 (s, 3H), 1.27 (s, 9H); MS (ESI) m/z 505.16 (M+H).

L-Selectride (1.0 M solution in THF, 19.30 mL, 19.30 mmol) was added dropwise to a 0° C. solution of the above sulfinimine (1.94 g, 3.85 mmol) in THF (20 mL). After complete addition, the ice bath was removed, and the reaction mixture was stirred for 4 h. The reaction mixture was quenched with NaHCO$_3$ (saturated, aqueous solution) and was diluted with EtOAc. The mixture was washed with NaHCO$_3$ (saturated, aqueous solution, 3×) and brine. The organics were dried over Na$_2$SO$_4$, were filtered, and were concentrated. The material was purified by column chromatography (50 g Biotage column, 40 to 100% EtOAc in hexanes gradient) to give 1.65 g (85%) of the desired sulfonamide S6-3 (single diastereomer A) as a white solid: $^1$H NMR (400 MHz, CDCl$_3$) δ 7.41-7.26 (m, 7H), 7.24-7.19 (m, 1H), 7.12-7.07 (m, 2H), 6.86 (s, 1H), 5.07 (AB$_q$, J=15.6 Hz, 11.9 Hz, 2H), 4.42-4.34 (m, 1H), 3.38 (d, J=10.1 Hz, 1H), 3.18-3.12 (m, 2H), 2.65 (s, 3H), 2.37 (s, 3H), 2.36-2.25 (m, 1H), 2.13-2.03 (m, 1H), 1.21 (s, 9H); MS (ESI) m/z 507.19 (M+H).

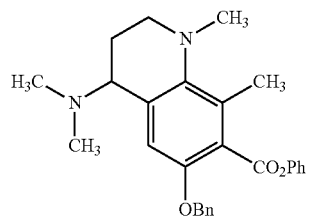
S6-4

The above sulfonamide S6-3 (1.65 g, 3.27 mmol) was stirred in HCl (4 M solution in 1,4-dioxane, 4 mL) and MeOH (16 mL). After 1 h, the reaction mixture was concentrated and was re-dissolved in CH$_2$Cl$_2$ (25 mL). Na(OAc)$_3$BH (2.08 g, 9.80 mmol) and formaldehyde (37% aqueous solution, 5 mL) were added. After 15 min, the reaction mixture was quenched with NaHCO$_3$ (saturated, aqueous solution) and was diluted with EtOAc. The mixture was washed with NaHCO$_3$ (saturated, aqueous solution, 3×) and brine. The organics were dried over Na$_2$SO$_4$, were filtered, and were concentrated. The material was purified by column chromatography (50 g Biotage column, 50 to 100% EtOAc in hexanes gradient) to give 1.33 g (94%) of single enantiomer S6-4 (single enantiomer A) as a solid: $R_f$=0.26 in 5% MeOH/CH$_2$Cl$_2$; $^1$H NMR (400 MHz, CDCl$_3$) δ 7.46-7.41 (m, 2H), 7.37-7.18 (m, 7H), 7.12-7.06 (m, 2H), 5.10 (s, 2H), 3.79 (dd, J=9.2 Hz, 6.9 Hz, 1H), 3.16-3.10 (m, 2H), 2.62 (s, 3H), 2.37 (s, 3H), 2.24 (s, 6H), 2.12-2.02 (m, 1H), 1.56-1.68 (m, 1H); MS (ESI) m/z 431.34 (M+H).

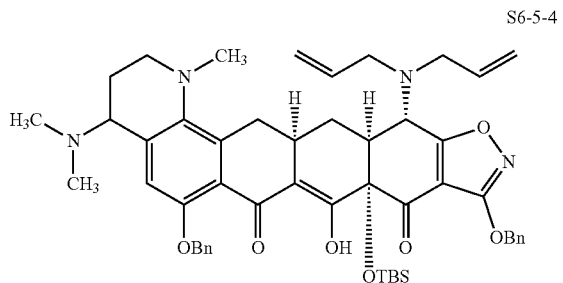 [SMILES: C=CCN(CC=C)[C@@H]1c2onc(OCc3ccccc3)c2C(=O)[C@@]2(O[Si](C)(C)C(C)(C)C)C(O)=C3C(=O)c4c(OCc5ccccc5)cc5c(c4C[C@H]3C[C@@H]12)N(C)CCC5N(C)C]

S6-5-4

Compound S6-5-4 was prepared in 57% yield from S6-4 and N-diallyl enone S1-9-2 using general procedure A. S6-5-4 (single diastereomer, yellow foamy solid): $^1$H NMR (400 MHz, CDCl$_3$) δ 15.90 (br s, 1H), 7.41-7.36 (m, 4H), 7.29-7.14 (m, 7H), 5.77-5.67 (m, 2H), 5.27 (s, 2H), 5.13-4.96 (m, 6H), 4.07 (d, J=10.4 Hz, 1H), 3.57 (br s, 1H), 3.26-3.01 (m, 6H), 2.94-2.88 (m, 1H), 2.82-2.76 (m, 1H), 2.50 (s, 3H), 2.47-2.28 (m, 3H), 2.17-2.03 (m, 7H), 1.88-1.76 (m, 2H), 0.72 (s, 9H), 0.16 (s, 3H), 0.04 (s, 3H); MS (ESI) m/z 871.56 (M+H).

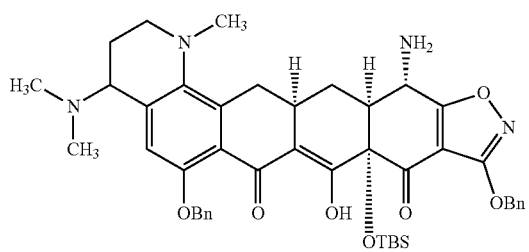

S6-5-1

Compound S6-5-1 was prepared in 79% yield from compound S6-5-4 using general procedure B. S6-5-1 (single diastereomer): $^1$H NMR (400 MHz, CDCl$_3$) δ 16.57 (br s, 1H), 7.66-7.61 (m, 1H), 7.54-7.51 (m, 2H), 7.47-7.42 (m, 2H), 7.36-7.26 (m, 6H), 5.38, 5.34 (ABq, J=12.2 Hz, 2H), 5.22, 5.12 (ABq, J=12.2 Hz, 2H), 3.92 (d, J=2.4 Hz, 1H), 3.67 (t, J=5.5 Hz, 1H), 3.14-2.93 (m, 2H), 2.72-2.66 (m, 1H), 2.60-2.57 (m, 1H), 2.48 (s, 3H), 2.38-2.21 (m, 7H), 2.14-2.04 (m, 2H), 1.96-1.84 (m, 2H), 1.57-1.48 (m, 1H), 0.73 (s, 9H), 0.20 (s, 3H), 0.10 (s, 3H); MS (ESI) m/z 791.48 (M+H).

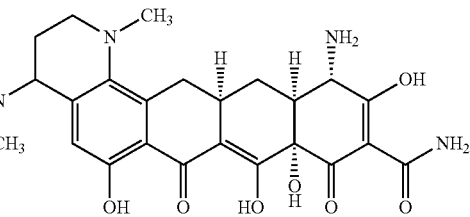

S6-6-1

Compound S6-6-1 was prepared from compound S6-5-1 using general procedure C.

S6-6-1 (single diastereomer): $^1$H NMR (400 MHz, CD$_3$OD, hydrochloride salt) δ 7.34 (s, 1H), 5.01 (d, J=6.0 Hz, 1H), 3.92 (s, 1H), 3.74-3.67 (m, 1H), 3.64-3.58 (m, 1H), 3.29-3.26 (m, 1H), 3.15-3.06 (m, 7H), 2.76 (br s, 3H), 2.69-2.64 (m, 3H), 2.53 (t, J=14.6 Hz, 1H), 2.35-2.30 (m, 1H), 1.68-1.59 (m, 1H); MS (ESI) m/z 499.32 (M+H).

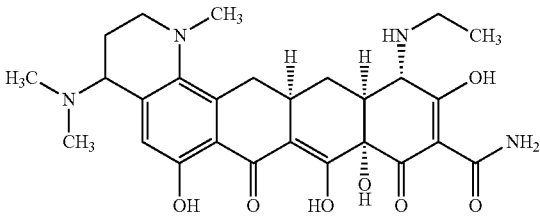

S6-6-2

Compound S6-6-2 was prepared from compound S6-5-1 using general procedures D-1 (with acetaldehyde) and C. S6-6-2 (single diastereomer): $^1$H NMR (400 MHz, CD$_3$OD, hydrochloride salt) δ 7.33 (s, 1H), 4.99 (d, J=6.9 Hz, 1H), 3.91 (s, 1H), 3.71-3.65 (m, 1H), 3.62-3.56 (m, 1H), 3.46-3.40 (m, 1H), 3.38-3.32 (m, 1H), 3.30-3.25 (m, 1H), 3.12-3.09 (m, 7H), 2.86 (d, J=12.8 Hz, 1H), 2.76 (br s, 3H), 2.66-2.61 (m, 2H), 2.50 (t, J=14.6 Hz, 1H), 2.33-2.30 (m, 1H), 1.66-1.57 (m, 1H), 1.36 (t, J=6.9 Hz, 3H); MS (ESI) m/z 527.28 (M+H).

S6-6-3

Compound S6-6-3 was prepared from compound S6-5-1 using general procedures D-1 (twice, with acetaldehyde followed by formaldehyde) and C. S6-6-3 (single diastereomer): $^1$H NMR (400 MHz, CD$_3$OD, hydrochloride salt, ~1:1 conformers) δ 7.30 (s, 1H), 4.98 (t, J=6.4 Hz, 1H), 4.26 (s, 0.5H), 4.17 (s, 0.5H), 3.65-3.50 (m, 3H), 3.37-3.30 (m, 2H), 3.09-2.94 (m, 11H), 2.75 (br s, 3H), 2.63-2.58 (m, 2H), 2.49 (t, J=14.2 Hz, 1H), 2.35-2.29 (m, 1H), 1.74-1.63 (m, 1H), 1.44-1.37 (m, 3H); MS (ESI) m/z 541.35 (M+H).

Scheme 7

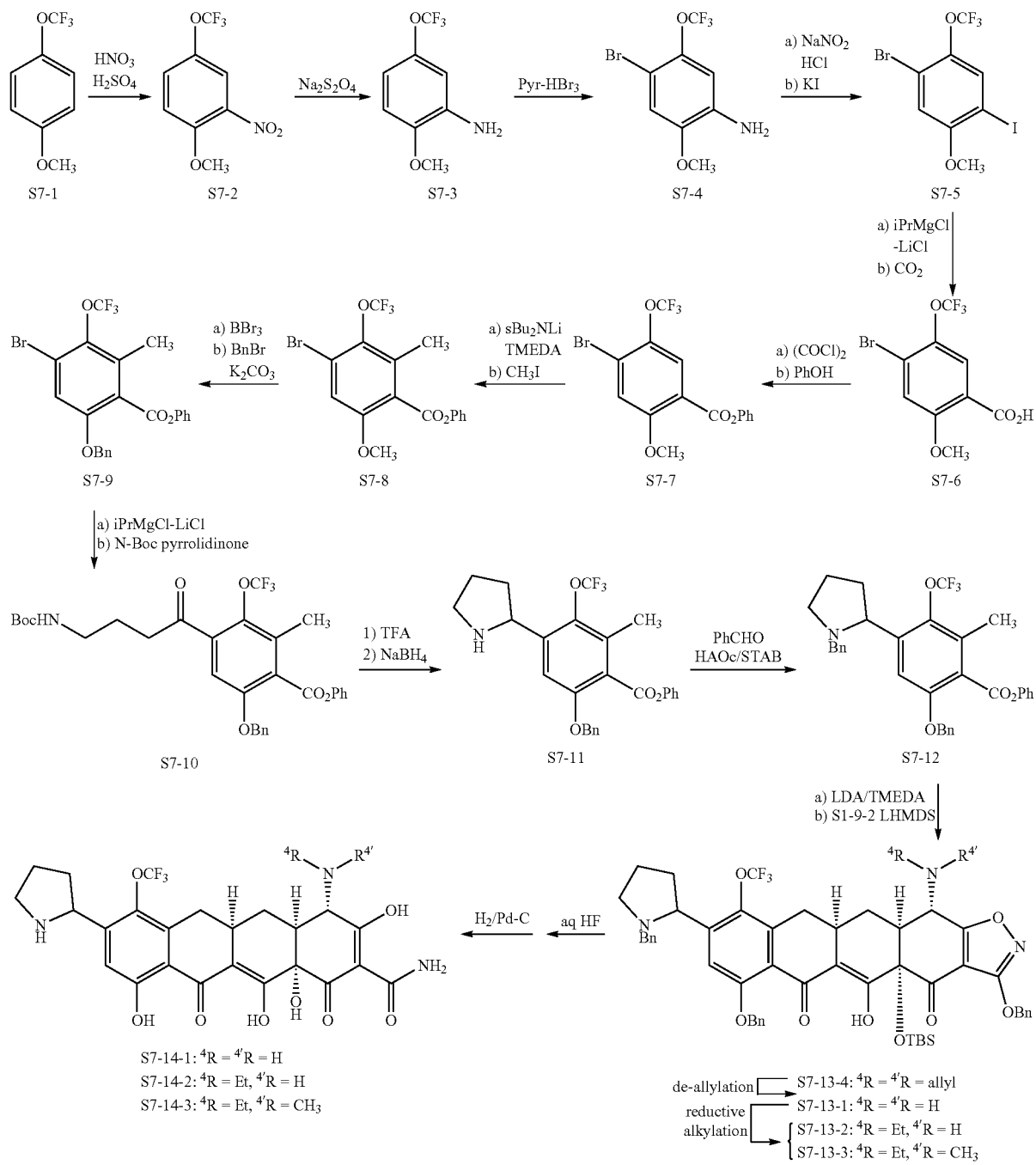

The following compounds were prepared according to Scheme 7.

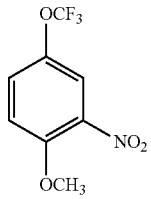

S7-2

To p-trifluoromethoxyanisole (S7-1, 19.20 g, 0.10 mol, 1 eq) in methylene chloride (200 mL) at 0° C. was added a pre-cooled (0° C.) solution of nitric acid (14.29 mL, 69%, 0.22 mol, 2.2 eq) in sulfuric acid (17.86 mL) dropwise within 15 min. The reaction was stirred from 0° C. to rt for overnight. The aqueous layer was removed. The organic layer was washed with saturated aqueous sodium bicarbonate (100 mL×2) and brine (100 mL×1), dried over sodium sulfate, and concentrated to dryness to yield the desired compound S7-2 as a pale liquid (24.20 g, quantitative): $R_f$=0.45 (20% EtOAc/hexane): $^1$H NMR (400 MHz, CDCl$_3$)

δ 7.75 (d, J=2.4 Hz, 1H), 7.42 (dd, J=3.0, 9.2 Hz, 1H), 7.10 (d, J=9.2 Hz, 1H), 3.97 (s, 3H).

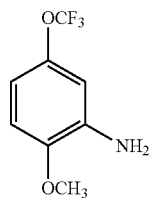

S7-3

To a solution of compound S7-2 (0.10 mol, 1 eq) in THF (600 mL) at 0° C. was added a solution of $Na_2S_2O_4$ (102.4 g, 85%, 0.50 mol, 5 eq) in water (400 mL). The reaction was stirred at rt for 16 h. The organic layer was collected. The aqueous later was extracted with EtOAc (100 mL×3). The combined organic layers were dried over sodium sulfate and concentrated. EtOAc (200 mL) was added to the residue. The insoluble material was filtered. The filtrate was collected. Aqueous HCl (150 mL, 2 N) and methanol (150 mL) were added to the solid. The mixture was stirred at rt for 2 h, neutralized with aqueous NaOH (6 N), and extracted with EtOAc (100 mL×3). The extracts were combined with the previously saved EtOAc filtrate, dried over sodium sulfate, and concentrated to dryness to yield the desired product S7-3 as a deep yellow liquid (16.69 g, 81%): $R_f$=0.50 (20% EtOAc/hexane): $^1$H NMR (400 MHz, $CDCl_3$) δ 6.70 (d, J=9.2 Hz, 1H), 6.59 (s, 1H), 6.57 (d, J=9.2 Hz, 1H), 3.83 (s, 3H); MS (ESI) m/z 208.0 (M+H).

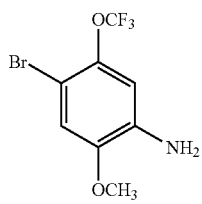

S7-4

To compound S7-3 (16.69 g, 0.081 mol, 1 eq) in methylene chloride (250 mL) at 0° C. was added pridine-$HBr_3$ (31.09 g, 0.097 mol, 1.2 eq) in small portions. The reaction mixture was stirred at 0° C. for 1 h, washed with aqueous $Na_2S_2O_3$ (1 M, 100 mL×3) and brine (100 mL×1), dried over sodium sulfate, and concentrated. Flash column chromatography on slica gel with 0% to 20% EtOAc/hexane gave the desired product S7-4 as a pale liquid (21.30 g, 92%): $R_f$=0.30 (20% EtOAc/hexane): $^1$H NMR (400 MHz, $CDCl_3$) δ 6.90 (s, 1H), 6.66 (d, J=1.2 Hz, 1H), 4.01 (br s, 2H), 3.83 (s, 3H); MS (ESI) m/z 286.0 (M+H).

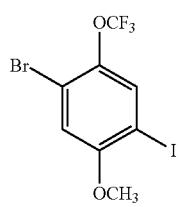

S7-5

To compound S7-4 (19.84 g, 69.58 mmol, 1 eq) in dioxane (70 mL) and aqueous HCl (70 mL, 8.5 N) at 0° C. was added a solution of $NaNO_2$ (5.26 g, 76.23 mmol, 1.1 eq) in water (28 mL) slowly. The reaction mixture was stirred at rt for 30 min and added slowly into a stirred solution of KI (115.50 g, 0.70 mol, 10 eq) in water (140 mL) at 0° C. (gas evolution!). The reaction mixture was stirred at rt for 72 h and extracted with EtOAc (200 mL×1, 50 mL×2). The extracts were combined and concentrated. The residue was re-dissolved in EtOAc (100 mL). The solution was washed with aqueous $Na_2SO_3$ (2 M, 100 mL×2), saturated aqueous sodium bicarbonate (100 mL×1), and brine (100 mL×1), dried over sodium sulfate, and concentrated. Flash column chromatography on slica gel with 0% to 5% EtOAc/hexane afforded the desired compound S7-5 as a colorless liquid (19.80 g, 72%): $R_f$=0.66 (10% EtOAc/hexane): $^1$H NMR (400 MHz, $CDCl_3$) δ 7.67 (s, 1H), 6.99 (s, 1H), 3.87 (s, 3H).

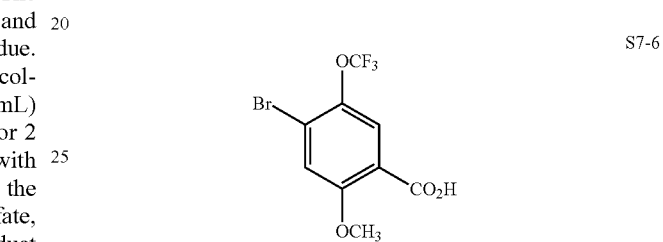

S7-6

A solution of compound S7-5 (18.80 g, 47.36 mmol, 1 eq) in THF (100 mL) was cooled to −78° C. and added with iPrMgCl—LiCl (43.72 mL, 1.3 M in THF, 56.84 mmol, 1.2 eq) dropwise within 30 min. The reaction was stirred at −78° C. for 30 min. Dry carbon dioxide was bubbled through the reaction mixture at −78° C. for 30 min. The reaction mixture was stirred from −78° C. to rt for 2 h, added with aqueous HCl (1 N, 100 mL), and concentrated. The aqueous mixture was extracted with EtOAc (50 mL×4). The combined extracts were dried over sodium sulfate and concentrated to dryness to yield the desired product S7-6 as a pale solid (15.37 g, quantitative): MS (ESI) m/z 312.9 (M−H).

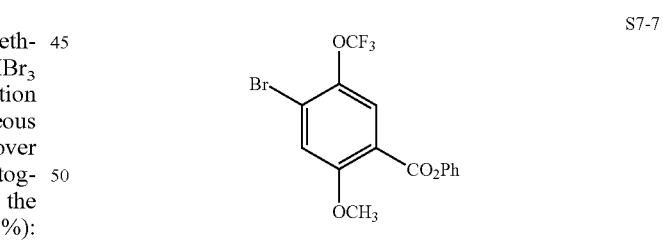

S7-7

To compound S7-6 (crude, 47.36 mmol, 1 eq) in methylene chloride (100 mL) at 0° C. was added DMF (0.10 mL, 1.30 mmol, 0.027 eq) and oxalyl chloride (19.64 mL, 122.00 mmol, 2.5 eq) dropwise (gas evolution). The reaction was stirred at rt for 1.5 h and concentrated to dryness. The residue was redissolved in methylene chloride (100 mL). Phenol (5.51 g, 58.55 mmol, 1.2 eq), DIEA (12.67 mL, 72.74 mmol, 1.5 eq), and DMAP (0.60 g, 4.91 mmol, 0.10 eq) were added. The reaction solution was stirred at rt for overnight and concentrated. The residue was redissolved in EtOAc. The solution was washed with saturated aqueous sodium bicarbonate (50 mL×2) and brine (50 mL×1), dried over sodium sulfate, and concentrated to dryness. Flash column chromatography on slica gel with 0% to 20%

EtOAc/hexane gave the desired product S7-7 as a colorless oil (17.00 g, 90%): R$_f$=0.33 (10% EtOAc/hexane): $^1$H NMR (400 MHz, CDCl$_3$) δ 7.95 (d, J=1.2 Hz, 1H), 7.45-7.37 (m, 2H), 7.29-7.16 (m, 4H), 3.86 (s, 3H); MS (ESI) m/z 391.0 (M+H).

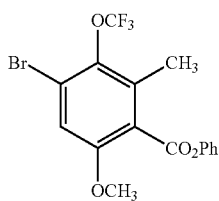

S7-8 s-Bu$_2$NH (14.64 mL, 84.85 mmol, 2 eq) and Et$_3$N—HCl (146 mg, 1.06 mmol, 0.025 eq) were dissolved in anhydrous THF (150 mL) and cooled to −78° C. n-BuLi (34.00 mL, 2.5 M in hexane, 85.00 mmol, 2 eq) was added dropwise. The solution was stirred at 0° C. for 10 min and recolled to −78° C. TMEDA (12.75 mL, 85.00 mmol, 2 eq) was added, followed by the dropwise addition of compound S7-7 (16.61 g, 42.47 mmol, 1 eq) in THF (100 mL) over 30 min. The reaction was stirred at −78° C. for 1 h. Methyl iodide (18.50 mL, 0.30 mol, 7 eq) was added rapidly over one min. The reaction was stirred from −78° C. to rt for 2 h, added with saturated aqueous ammonium chloride (200 mL), and concentrated. The aqueous solution was extracted with EtOAc (100 mL×3). The combined extracts were dried over sodium sulfate and concentrated. Flash column chromatography on slica gel with 0% to 10% EtOAc/hexane yielded the desired product S7-8 as a pale oil (11.76 g, 69%): R$_f$=0.60 (20% EtOAc/hexane): $^1$H NMR (400 MHz, CDCl$_3$) δ 7.48-7.41 (m, 2H), 7.32-7.25 (m, 1H), 7.23 (d, J=7.3 Hz, 2H), 7.10 (s, 1H), 3.91 (s, 3H), 2.44 (s, 3H); MS (ESI) m/z 402.9 (M−H).

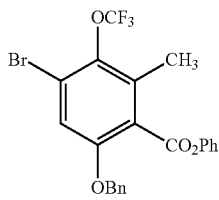

S7-9

To compound S7-8 (12.26 g, 30.26 mmol, 1 eq) in methylene chloride (60 mL) at −78° C. was added BBr$_3$ (33.30 mL, 1.0 M in methylene chloride, 33.30 mmol, 1.1 eq) dropwise. The reaction was stirred from −78° C. to 0° C. for 1 h. Saturated aqueous sodium bicarbonte (200 mL) was added. The mixture was stirred at rt for 15 min and extracted with methylene chloride (50 mL×4). The combined extracts were dried over sodium sulfate and concentrated to yield the crude phenol intermediate S7-8-a as a pale oil (12.00 g, quantitative): R$_f$=0.70 (20% EtOAc/hexane): $^1$H NMR (400 MHz, CDCl$_3$) δ 10.97 (s, 1H), 7.50-7.44 (m, 2H), 7.38-7.30 (m, 1H), 7.25-7.15 (m, 3H), 2.68 (s, 3H); MS (ESI) m/z 388.9 (M−H).

The above crude phenol S7-8-a (30.26 mmol, 1 eq) was dissolved in DMF (30 mL). Potassium carbonate (8.35 g, 60.50 mmol, 2 eq) and benzylbromide (4.31 mL, 36.28 mmol, 1.2 eq) were added. The reaction mixture was stirred at rt for 1 h, diluted with EtOAc (300 mL), washed with water (600 mL×1, 100 mL×1) and brine (100 mL×1), dried over sodium sulfate, and concentrated. Flash column chromatography on slica gel with 0% to 10% EtOAc/hexane afforded the desired product S7-9 as a white solid (13.20 g, 91% over two steps): R$_f$=0.70 (20% EtOAc/hexane): $^1$H NMR (400 MHz, CDCl$_3$) δ 7.43-7.20 (m, 8H), 7.16 (s, 1H), 7.03 (d, J=9.1 Hz, 2H), 5.12 (s, 2H), 2.43 (s, 3H); MS (ESI) m/z 479.0 (M−H).

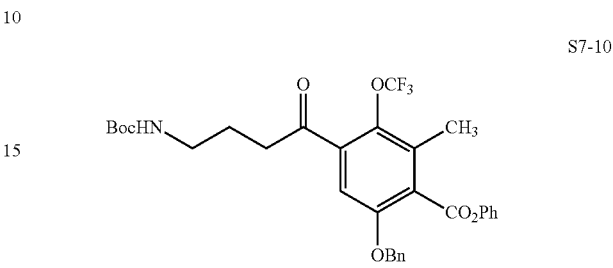

S7-10

To compound S7-9 (4.81 g, 10.00 mmol, 1 eq) in THF at 0° C. was added iPrMgCl—LiCl (11.54 mL, 1.3 M in THF, 15.00 mmol, 1.5 eq) dropwise over 10 min. The reaction was stirred at 0° C. for 2 h and cooled to −78° C. N-Boc pyrrolidinone (3.41 mL, 20.00 mmol, 2 eq) was added. The reaction was warmed from −78° C. to rt over 1 h with stirring. Saturated aqueous ammonium chloride (200 mL) was added. The mixture was extracted with EtOAc (100 mL×1, 50 mL×2). The combined EtOAc extracts were dried over sodium sulfate and concentrated under reduced pressure. Flash column chromatography on silica gel with 0-15% EtOAc/hexane yielded the desired product S7-10 as a white solid (3.20 g, 56%): R$_f$ 0.40 (20% EtOAc/hexane): $^1$H NMR (400 MHz, CDCl$_3$) δ 7.47.45-7.30 (m, 6H), 7.28-7.20 (m, 1H), 7.08-7.02 (m, 3H), 6.87 (s, 1H), 5.14 (s, 2H), 4.00 (br t, J=8.9 Hz, 2H), 2.63 (dt, J=2.5, 9.2 Hz, 2H), 2.40 (s, 3H), 1.30-1.10 (m, 2H); MS (ESI) m/z 588.2, (M−H).

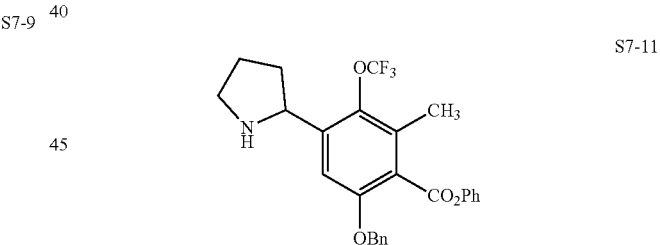

S7-11

To compound S7-10 (3.25 g, 5.53 mmol, 1 eq) in methylene chloride (5 mL) at 0° C. was added TFA-methylene chloride (10 mL, 1:1, v/v). The reaction solution was stirred at rt for 30 min and concentrated to dryness under reduced pressure. Saturated aqueous sodium bicarbonate (100 mL) was added to the residue. The mixture was extracted with methylene chloride (50 mL×4). The combined methylene chloride extracts were dried over sodium sulfate and concentrated under reduced pressure to yield the cyclic imine intermediate as a pale oil (2.73 g): $^1$H NMR (400 MHz, CDCl$_3$) δ 7.45-7.20 (m, 9H), 7.06 (d, J=10.3 Hz, 2H), 5.17 (s, 2H), 4.03 (t, J=7.4 Hz, 2H), 2.92 (t, J=8.0 Hz, 2H), 2.44 (s, 3H), 2.11-2.00 (m, 2H); MS (ESI) m/z 470.0 (M+H).

The above intermediate was redissolved in methanol (40 mL) and cooled to 0° C. Sodium borohydride (1.05 g, 27.76 mmol, 5 eq) was added. The reactoin was stirred at rt for 30 min. Additional sodium borohydride (1.00 g×2) was added.

The reaction was stirred at rt for 30 min. Aqueous HCl (2 N) was added until pH=2-3. Saturated aqueous sodium bicarbonate (100 mL) was added. The mixture was extracted with methylene chloride (50 mL×4). The combined methylene chloride extracts were dried over sodium sulfate and concentrated to yield S7-11 as a pale oil (2.71 g, crude): MS (ESI) m/z 472.1 (M+H).

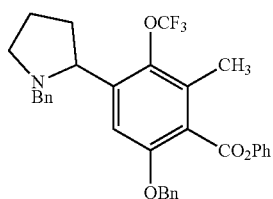

S7-12

To a solution of compound S7-11 (crude product of the previous steps, 0.87 mmol, 1 eq) in DCM (3 mL) was added PhCHO (106 µL, 1.044 mmol, 1.2 eq), HOAc (100 µL, 1.74 mmol, 2.0 eq) and STAB (369 mg, 1.74 mmol, 2.0 eq). The resulting reaction mixture was stirred at rt for 1 h and 25 min. Then saturated aq. NaHCO₃ was added. The resulting mixture was extracted with DCM (20 mL, then 10 mL). The combined organic phase was dried over Na₂SO₄, filtered and concentrated under reduced pressure. Flash chromatography on silica gel using 2%→10% EtOAc/hexanes yielded the desired product S7-12 (272 mg, 56% over 3 steps) as a white solid: $^1$H NMR (400 MHz, CDCl₃) δ 7.49-7.46 (m, 3H), 7.41-7.35 (m, 5H), 7.32-7.24 (m, 6H), 7.11-7.10 (m, 2H), 5.22, 5.18 (ABq, J=11.6 Hz, 2H), 3.84 (t, J=8.5 Hz, 1H), 3.77 (d, J=13.4 Hz, 1H), 3.17-3.10 (m, 2H), 2.43 (s, 3H), 2.31-2.24 (m, 2H), 1.91-1.80 (m, 2H), 1.64-1.55 (m, 1H); MS (ESI) m/z 562.23 (M+H).

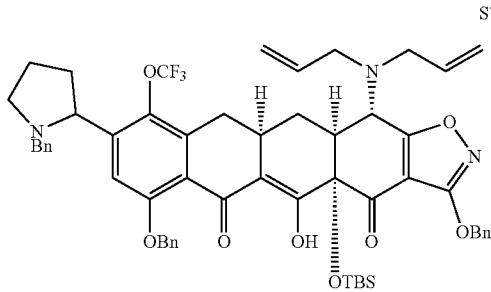

S7-13-4

Compound S7-13-4 was prepared in 88% yield from S7-12 and N-diallyl enone S1-9-2 using general procedure A. S7-13-4 (mixture of diastereomers, yellow foam): $^1$H NMR (400 MHz, CDCl₃, ~1:1 diastereomers) δ 16.02 (s, 0.5H), 16.00 (s, 0.5H), 7.56-7.14 (m, 11H), 5.86-5.76 (m, 2H), 5.38 (s, 2H), 5.28-5.20 (m, 4H), 5.12 (d, J=10.4 Hz, 2H), 3.88-3.76 (m, 2H), 3.59 (d, J=12.8 Hz, 1H), 3.36-3.08 (m, 7H), 2.99-2.88 (m, 1H), 2.75-2.64 (m, 1H), 2.55-2.45 (m, 2H), 2.35-2.24 (m, 2H), 2.15 (d, J=14.0 Hz, 1H), 1.92-1.79 (m, 2H), 1.64-1.58 (m, 1H), 0.86 (s, 4.5H), 0.85 (s, 4.5), 0.28 (s, 3H), 0.16 (s, 3H); MS (ESI) m/z 1002.49 (M+H).

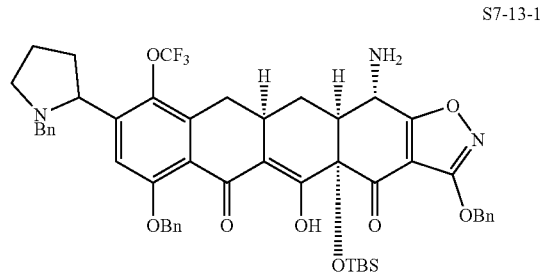 [SMILES: CC(C)(C)[Si](C)(C)O[C@@]12C(=O)c3c(OCc4ccccc4)noc3[C@@H](N)[C@@H]1C[C@@H]1Cc3c(OC(F)(F)F)c(C4CCCN4Cc4ccccc4)cc(OCc4ccccc4)c3C(=O)C1=C2O]

S7-13-1

Compound S7-13-1 was prepared from compound S7-13-4 using general procedure B and the two diastereomers were separated by preparative HPLC on a C-18 column.

S7-13-1-A (47%, early eluting diastereomer A): $^1$H NMR (400 MHz, CDCl₃) δ 16.28 (br s, 1H), 7.62-7.60 (m, 1H), 7.38-7.16 (m, 9H), 5.52 (br s, 2H), 5.30, 5.26 (ABq, J=12.2 Hz, 2H), 4.26 (br s, 1H), 4.05-3.86 (m, 3H), 2.79-2.71 (m, 2H), 2.60-2.57 (m, 2H), 2.40-2.02 (m, 7H), 1.47-1.28 (m, 1H), 0.66 (s, 9H), 0.14 (s, 3H), 0.00 (s, 3H); MS (ESI) m/z 922.43 (M+H).

S7-13-1-B (39%, later eluting diastereomer B): $^1$H NMR (400 MHz, CDCl₃) δ 16.29 (br s, 1H), 7.53 (s, 1H), 7.44-7.42 (m, 2H), 7.36-7.35 (m, 2H), 7.29-7.11 (m, 4H), 7.08-7.06 (m, 2H), 5.52 (br s, 2H), 5.30-5.11 (m, 4H), 4.05-3.98 (m, 1H), 3.83 (d, J=13.4 Hz, 1H), 3.62 (d, J=13.4 Hz, 1H), 3.54 (t, J=8.5 Hz, 1H), 2.82 (dd, J=3.7, 15.3 Hz, 1H), 2.69-2.58 (m, 2H), 2.51-2.48 (m, 1H), 2.29-2.24 (m, 1H), 2.16-2.00 (m, 3H), 1.89-1.84 (3H), 1.42-1.32 (m, 1H), 0.64 (s, 9H), 0.13 (s, 3H), 0.00 (s, 3H); MS (ESI) m/z 922.43 (M+H).

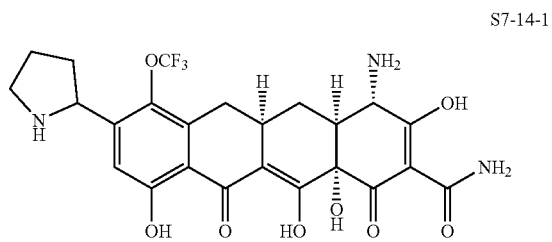 [SMILES: NC(=O)C1=C(O)[C@@H](N)[C@@H]2C[C@@H]3Cc4c(OC(F)(F)F)c(C5CCCN5)cc(O)c4C(=O)C3=C(O)[C@]2(O)C1=O]

S7-14-1

Compounds S7-14-1-A and S7-14-1-B were prepared from the corresponding compounds S7-13-1-A and S7-13-1-B separately using general procedure C.

S7-14-1-A: $^1$H NMR (400 MHz, CD₃OD, hydrochloride salt) δ 7.20 (s, 1H), 4.91-4.83 (m, 1H), 3.90 (s, 1H), 3.52-3.46 (m, 2H), 3.20 (dd, J=4.1, 15.6 Hz, 1H), 3.01-2.92 (m, 1H), 2.54-2.48 (m, 1H), 2.68-2.65 (m, 1H), 2.40 (t, J=14.6 Hz, 1H), 2.35-2.18 (m, 4H), 1.64-1.55 (m, 1H); MS (ESI) m/z 540.17 (M+H).

S7-14-1-B: $^1$H NMR (400 MHz, CD₃OD, hydrochloride salt) δ 7.17 (s, 1H), 4.91 (t, J=9.6 Hz, 1H), 3.89 (s, 1H), 3.59-3.47 (m, 2H), 3.18 (dd, J=4.1, 15.6 Hz, 1H), 3.01-2.92 (m, 1H), 2.68-2.64 (m, 1H), 2.59-2.52 (m, 1H), 2.40 (t, J=14.6 Hz, 1H), 2.34-2.06 (m, 4H), 1.64-1.54 (m, 1H); MS (ESI) m/z 540.18 (M+H).

S7-14-2

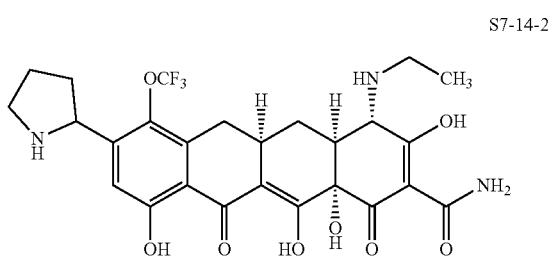 [SMILES: CCN[C@@H]1C(O)=C(C(N)=O)C(=O)[C@@]2(O)C(O)=C3C(=O)c4c(O)cc(C5CCCN5)c(OC(F)(F)F)c4C[C@H]3C[C@@H]12]

Compound S7-14-2-A was prepared from compound S7-13-1-A using general procedures D-1 (with acetalde- Compound S7-14-3-A was prepared from compound S7-13-1-A using general procedures D-1 (twice, with acetaldehyde followed by formaldehyde) and C. S7-14-3-A: $^1$H NMR (400 MHz, CD$_3$OD, hydrochloride salt, ~1:1 conformers) δ 7.20 (s, 1H), 4.91-4.85 (m, 1H), 4.24 (s, 0.5H), 4.15 (s, 0.5H), 3.54-3.44 (m, 3H), 3.38-3.33 (m, 1H), 3.22-3.19 (m, 1H), 3.05-2.93 (m, 5H), 2.54-2.48 (m, 1H), 2.40 (t, J=14.6 Hz, 1H), 2.35-2.16 (m, 4H), 1.72-1.60 (m, 1H), 1.44-1.36 (m, 3H); MS (ESI) m/z 582.21 (M+H).

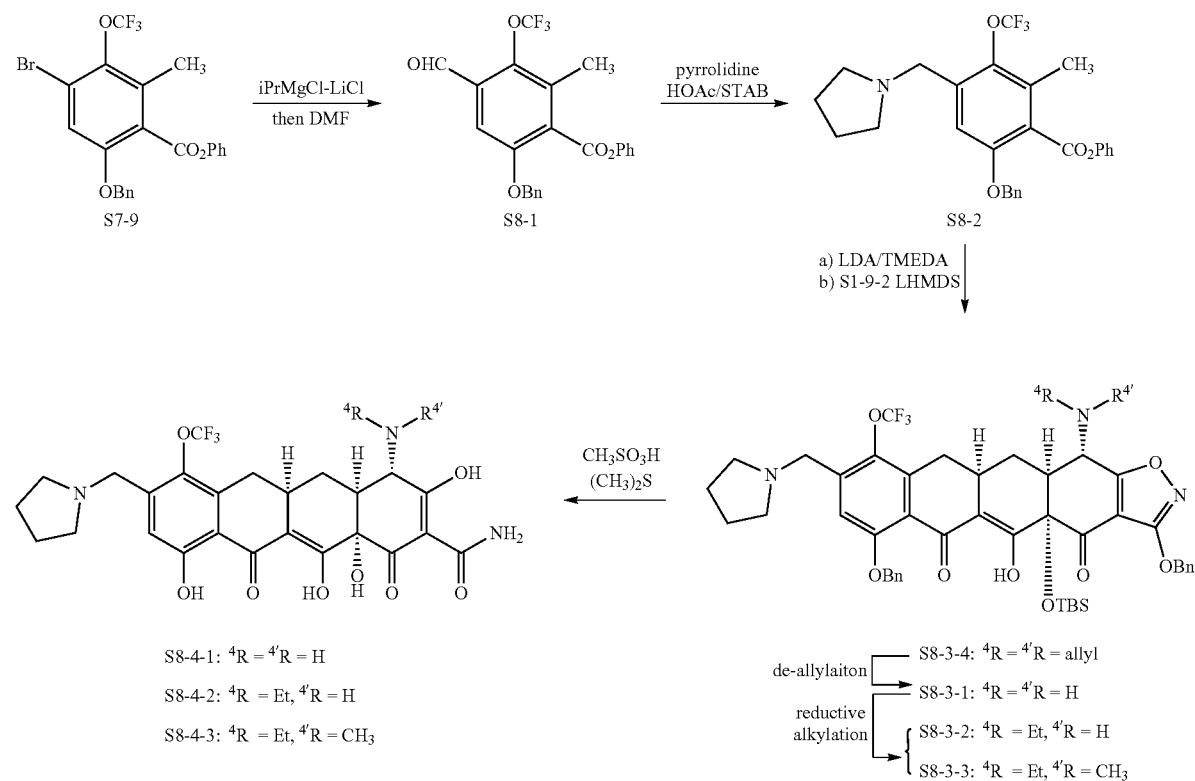

hyde) and C. S7-14-2-A: $^1$H NMR (400 MHz, CD$_3$OD, hydrochloride salt) δ 7.19 (s, 1H), 4.89-4.85 (m, 1H), 3.88 (s, 1H), 3.52-3.39 (m, 3H), 3.38-3.32 (m, 1H), 3.19 (dd, J=4.1, 16.0 Hz, 1H), 3.01-2.93 (m, 1H), 2.87-2.84 (m, 1H), 2.54-2.48 (m, 1H), 2.40 (t, J=14.6 Hz, 1H), 2.34-2.16 (m, 4H), 1.63-1.54 (m, 1H), 1.36 (t, J=7.3 Hz, 3H); MS (ESI) m/z 568.18 (M+H).

The following compounds were prepared according to Scheme 8.

S7-14-3

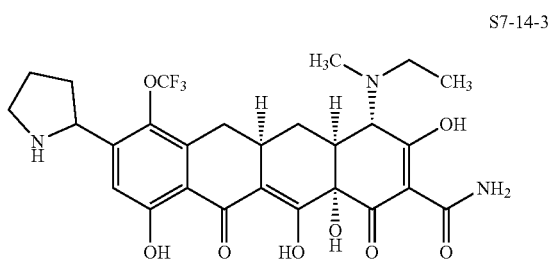 [SMILES: CCN(C)[C@@H]1C(O)=C(C(N)=O)C(=O)[C@@]2(O)C(O)=C3C(=O)c4c(O)cc(C5CCCN5)c(OC(F)(F)F)c4C[C@H]3C[C@@H]12]

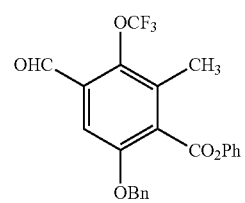

To a solution of bromide S7-9 (500 mg, 1.04 mmol, 1 eq) in THF (5 mL) was added Turbo Grignard solution (1.3 M in THF, 1.04 mL, 1.35 mmol, 1.3 eq) dropwise at ~−3° C.

The resulting reaction solution was stirred at 0° C. for 1 h, then cooled to −78° C. A solution of DMF (160 μL, 2.08 mmol, 2.0 eq) in THF (0.6 mL) was added dropwise at below −73° C. The resulting reaction mixture was allowed to warm up to rt slowly over 1 h and 40 min. Saturated aqueous NH₄Cl was added, and the resulting reaction mixture was extracted with EtOAc (50 mL). The organic phase was dried over $Na_2SO_4$, filtered and concentrated under reduced pressure. The crude product S8-1 (503 mg), MS (ESI) m/z 429.16 (M−H), was used directly for the next reaction without further purification.

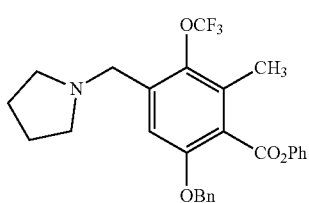

To a solution of the above crude product S8-1 (260 mg, 0.537 mmol, 1 eq) in DCE (2 mL) was added pyrrolidine (67 μL, 0.806 mmol, 1.5 eq), HOAc (92 μL, 1.61 mmol, 3.0 eq) and STAB (228 mg, 1.07 mmol, 2.0 eq). The resulting reaction mixture was stirred at rt for 30 min. Then saturated aq. $NaHCO_3$ was added. The resulting mixture was extracted with DCM (3×15 mL). The combined organic phase was dried over $Na_2SO_4$, filtered and concentrated under reduced pressure. Flash chromatography on silica gel using 1%→30% EtOAc/hexanes yielded the desired product S8-2 (236 mg, 90% over 2 steps) as a white solid: MS (ESI) m/z 486.27 (M+H).

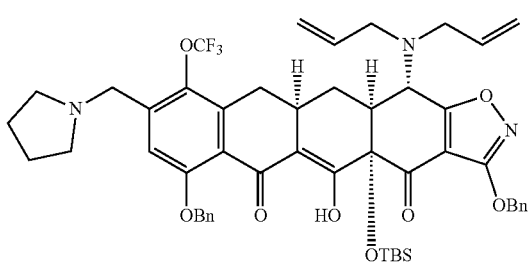

Compound S8-3-4 was prepared in 89% yield from S8-2 and N-diallyl enone S1-9-2 using general procedure A. S8-3-4 (yellow solid): ¹H NMR (400 MHz, CDCl₃) δ 16.00 (s, 1H), 7.52-7.50 (m, 2H), 7.46-7.44 (m, 2H), 7.40-7.31 (m, 5H), 7.26-7.24 (m, 2H), 5.84-5.74 (m, 2H), 5.38 (s, 2H), 5.29, 5.24 (ABq, J=12.8 Hz, 2H), 5.21 (d, J=18.6 Hz, 2H), 5.10 (d, J=10.4 Hz, 2H), 3.71, 3.62 (ABq, J=15.3 Hz, 2H), 3.36-3.32 (m, 2H), 3.23-3.11 (m, 3H), 2.96-2.90 (m, 1H), 2.69 (t, J=15.3 Hz, 1H), 2.54-2.40 (m, 7H), 2.14 (d, J=14.0 Hz, 1H), 1.73-1.76 (m, 4H), 0.84 (s, 9H), 0.28 (s, 3H), 0.15 (s, 3H); MS (ESI) m/z 926.56 (M+H).

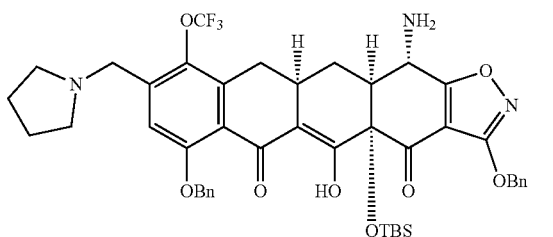

Compound S8-3-1 was prepared in 86% yield from compound S8-3-4 using general procedure B. S8-3-1: ¹H NMR (400 MHz, CDCl₃) δ 16.44 (s, 1H), 7.44-7.37 (m, 4H), 7.29-7.18 (m, 6H), 7.15 (br s, 1H), 5.30, 5.26 (ABq, J=12.2 Hz, 2H), 5.22, 5.14 (ABq, J=12.8 Hz, 2H), 3.82 (br s, 1H), 3.55 (s, 2H), 2.91 (dd, J=3.7, 15.9 Hz, 1H), 2.69-2.61 (m, 1H), 2.52 (d, J=12.2 Hz, 1H), 2.32 (br s, 4H), 2.14 (t, J=15.3 Hz, 1H), 2.02-1.99 (m, 1H), 1.65 (br s, 4H), 1.46-1.38 (m, 1H), 0.64 (s, 9H), 0.12 (s, 3H), 0.00 (s, 3H); MS (ESI) m/z 846.49 (M+H).

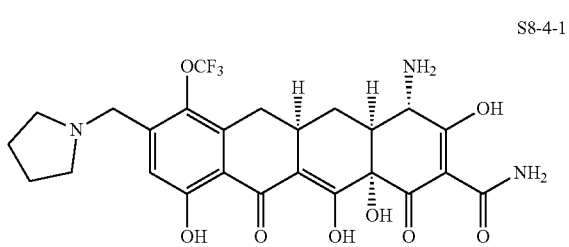 [SMILES: NC(=O)C1=C(O)[C@@H](N)[C@@H]2C[C@@H]3Cc4c(OC(F)(F)F)c(CN5CCCC5)cc(O)c4C(=O)C3=C(O)[C@]2(O)C1=O]

Compound S8-4-1 was prepared from compound S8-3-1 using general procedure E. S8-4-1: ¹H NMR (400 MHz, CD₃OD, hydrochloride salt) δ 7.27 (s, 1H), 4.52 (s, 2H), 3.91 (s, 1H), 3.68-3.62 (m, 1H), 3.58-3.52 (m, 1H), 3.27-3.13 (m, 3H), 3.04-2.95 (m, 1H), 2.70-2.66 (m, 1H), 2.40 (t, J=14.6 Hz, 1H), 2.28-2.17 (m, 3H), 2.07-2.04 (m, 2H), 1.64-1.55 (m, 1H); MS (ESI) m/z 554.19 (M+H).

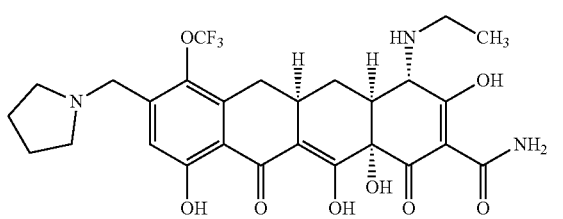

Compound S8-4-2 was prepared from compound S8-4-1 using general procedures D-1 (with acetaldehyde) and E. S8-4-2: ¹H NMR (400 MHz, CD₃OD, hydrochloride salt) δ 7.25 (s, 1H), 4.51 (s, 2H), 3.88 (s, 1H), 3.66-3.60 (m, 1H), 3.57-3.52 (m, 1H), 3.46-3.42 (m, 1H), 3.38-3.33 (m, 1H), 3.26-3.12 (m, 3H), 3.05-2.96 (m, 1H), 2.88-2.85 (m, 1H), 2.40 (t, J=15.1 Hz, 1H), 2.27-2.16 (m, 3H), 2.09-2.02 (m, 2H), 1.63-1.53 (m, 1H), 1.36 (t, J=7.3 Hz, 3H); MS (ESI) m/z 582.23 (M+H).

S8-4-3

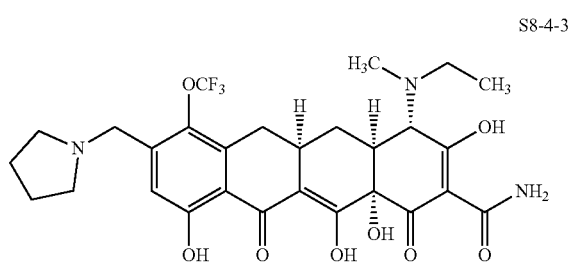 [SMILES: CCN(C)[C@@H]1C(O)=C(C(N)=O)C(=O)[C@@]2(O)C(O)=C3C(=O)c4c(O)cc(CN5CCCC5)c(OC(F)(F)F)c4C[C@H]3C[C@@H]12]

Compound S8-4-3 was prepared from compound S8-4-1 using general procedures D (twice, with acetaldehyde followed formaldehyde) and E. S8-4-3: [1]-1 NMR (400 MHz, CD$_3$OD, hydrochloride salt, ~1:1 conformers) δ 7.27 (s, 1H), 4.52 (s, 2H), 4.25 (s, 0.5H), 4.16 (s, 0.5H), 3.68-3.62 (m, 1H), 3.58-3.45 (m, 2H), 3.38-3.33 (m, 1H), 3.27-3.11 (m, 3H), 3.08-2.94 (m, 5H), 2.40 (t, J=14.6 Hz, 1H), 2.30-2.18 (m, 3H), 2.10-2.03 (m, 2H), 1.71-1.60 (m, 1H), 1.44-1.37 (m, 3H); MS (ESI) m/z 596.24 (M+H).

0.26 mmol, 2.6 eq) was added, followed by the addition of a THF solution (3 mL) of compound S9-1 (133 mg, 0.25 mmol, 2.5 eq, WO2010126607) drop-wise over 5 min. The reaction solution was stirred at −78° C. for 30 min. Compound S2-7-1 (45 mg, 0.10 mmol, 1 eq, $^4$R$^{4'}$RN=azetidinyl, in 2 mL THF) was added drop-wise. The reaction solution was stirred from −78° C. to 0° C. for 1 h, added with saturated aqueous sodium bicarbonate (50 mL), and extracted with EtOAc (50 mL×3). The EtOAc extracts were combined, dried over sodium sulfate, and concentrated. The residue was purified by column chromatography on silica gel with 0%-8% EtOAc-hexane to yield the desired product S9-2-1 as a yellow solid (43 mg, 51%): $^1$H NMR (400 MHz, CDCl$_3$) δ 16.44 (s, 1H), 7.60-7.10 (m, 20H), 6.64 (d, J=10.4 Hz, 1H), 5.39 (d, J=12.2 Hz, 1H), 5.35 (d, J=12.2 Hz, 1H), 5.20 (d, J=9.8 Hz, 1H), 5.07 (d, J=9.9 Hz, 1H), 4.33 (d, J=14.6 Hz, 2H), 4.20 (d, J=14.6 Hz, 2H), 3.61 (d, J=6.1 Hz, 1H), 3.55-3.45 (m, 2H), 3.40-3.32 (m, 2H), 3.01 (dd, J=4.4, 15.2 Hz, 1H), 2.85-2.75 (m, 1H), 2.35-1.55 (m, 6H), 0.80 (s, 9H), 0.15 (s, 6H); MS (ESI) m/z 932.5 (M+H).

Scheme 9

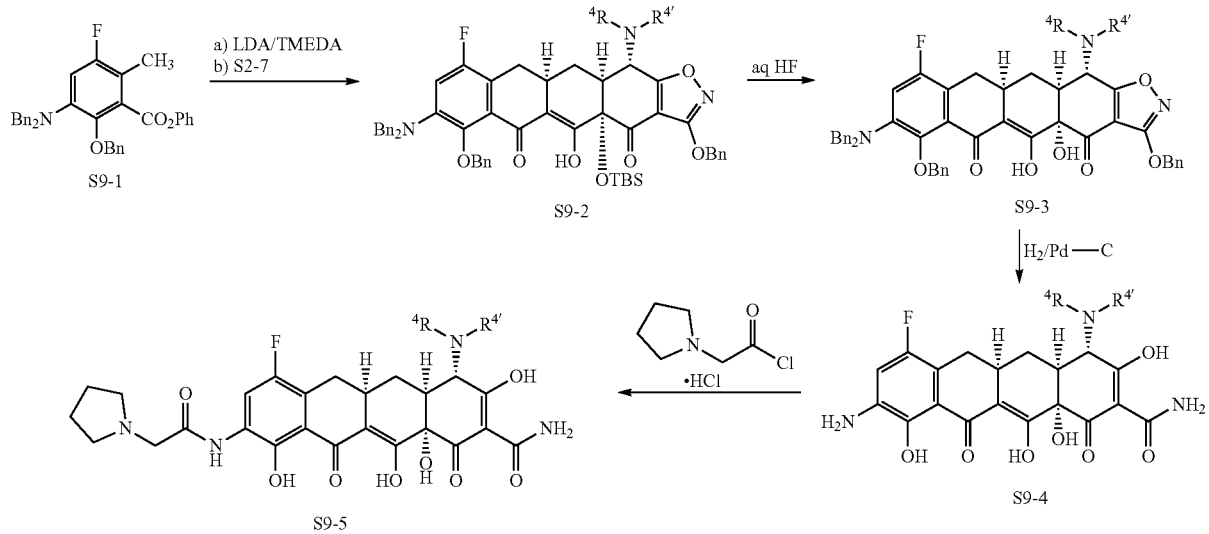

The following compounds were prepared according to Scheme 9.

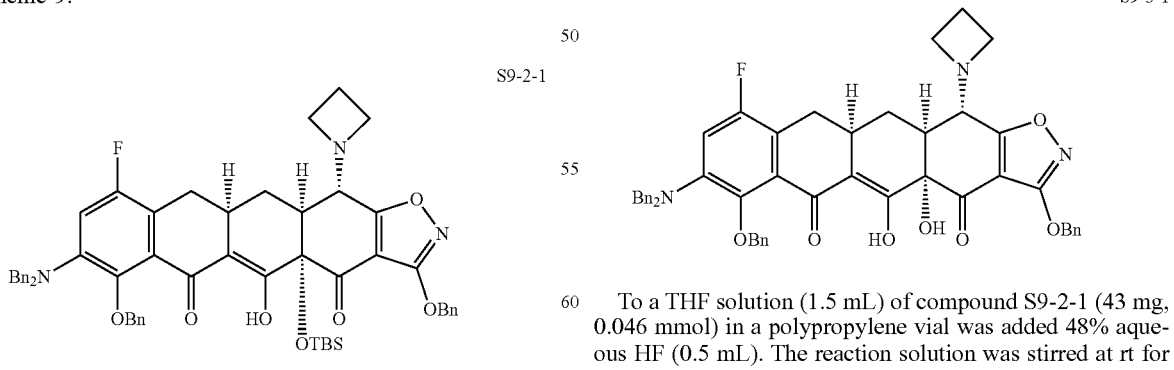

To diisopropylamine (36 μL, 0.25 mmol, 2.5 eq) in THF at −78° C. was added n-BuLi (0.16 mL, 1.6 M/hexanes, 0.25 mmol, 2.5 eq) drop-wise. The reaction solution was stirred at 0° C. for 10 min and cooled to −78° C. TMEDA (39 μL, To a THF solution (1.5 mL) of compound S9-2-1 (43 mg, 0.046 mmol) in a polypropylene vial was added 48% aqueous HF (0.5 mL). The reaction solution was stirred at rt for 2 h and added into aqueous K$_2$HPO$_4$ (5 g in 20 mL water) with stirring. The mixture was extracted with EtOAc (20 mL×3). The EtOAc extracts were combined, dried over sodium sulfate, and concentrated to yield compound S9-3-1 as an orange solid: MS (ESI) m/z 818.5 (M+H).

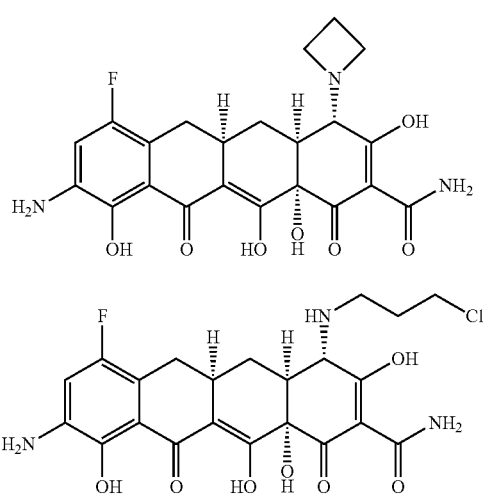

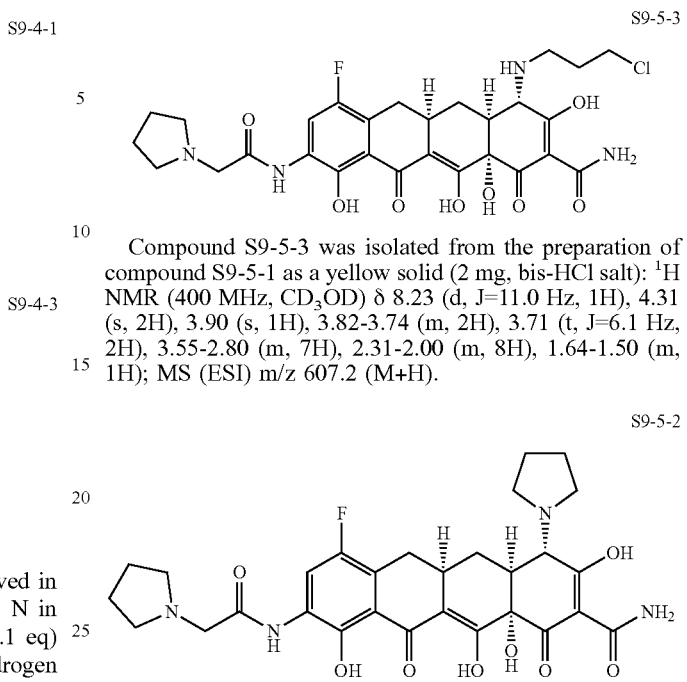

Compound S9-5-3 was isolated from the preparation of compound S9-5-1 as a yellow solid (2 mg, bis-HCl salt): $^1$H NMR (400 MHz, CD$_3$OD) δ 8.23 (d, J=11.0 Hz, 1H), 4.31 (s, 2H), 3.90 (s, 1H), 3.82-3.74 (m, 2H), 3.71 (t, J=6.1 Hz, 2H), 3.55-2.80 (m, 7H), 2.31-2.00 (m, 8H), 1.64-1.50 (m, 1H); MS (ESI) m/z 607.2 (M+H).

Compound S9-3-1 (0.046 mmol, 1 eq) was dissolved in methanol-dioxane (4 mL, 7:1, v/v). HCl (1 mL, 0.5 N in methanol) and 10% Pd—C (11 mg, 0.005 mmol, 0.1 eq) were added. The reaction mixture was purged with hydrogen and stirred under a hydrogen atmosphere (1 atm) for 2 h. The catalyst was filtered off with a Celite pad and washed with methanol (2 mL×3). The filtrate was concentrated. The residue was purified by preparative HPLC on a PolymerX column with 0%-35% acetonitrile-0.05 N aqueous HCl over 20 min to yield the desired compound S9-4-1 as a yellow solid (15 mg, 61%): MS (ESI) m/z 460.2 (M+H). The sample contained a small amount of ring-opened product S9-4-3: MS (ESI) m/z 496.3 (M+H).

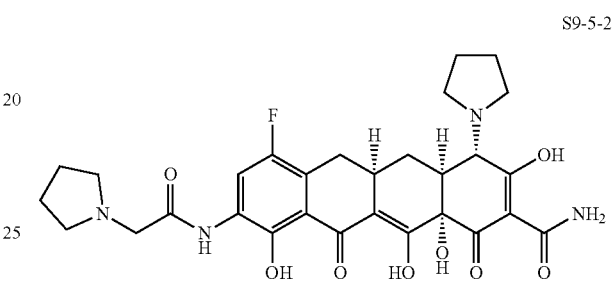

Using similar procedures, compound S9-5-2 was prepared from D-ring precursor S9-1 and enone S2-7-2 as a yellow solid (bis-HCl salt): $^1$H NMR (400 MHz, CD$_3$OD) δ 8.23 (d, J=10.4 Hz, 1H), 4.32 (s, 2H), 4.00 (s, 1H), 3.98-3.65 (m, 4H), 3.50-2.95 (m, 7H), 2.45-1.95 (m, 10H), 1.68-1.55 (m, 1H); MS (ESI) m/z 585.3 (M+H).

The following compounds were prepared from a fully assembled D-ring precuror and N-di-allyl enone S1-9-2 using general procedures A, B, D-1, and E.

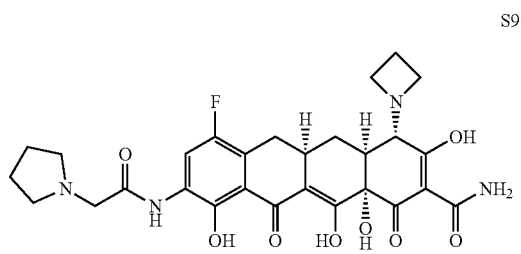

Compound S9-4-1 (15 mg, 0.028 mmol, 1 eq) was dissolved in acetonitrile-DMPU (1 mL, 1:3, v/v). Pyrrolidinylacetyl chloride (6 mg, HCl salt, 0.032 mmol, 1.2 eq) was added. The reaction solution was stirred at rt for 1 h and added into dithyl ether (50 mL) with rapid stirring. The precipiate was collected on a small Celite pad, washed with more dithyl ether (5 mL×4), and eluted with methanol (5 mL×3). The methanol eluent was collected and concentrated. The residue was purified by preparative HPLC on a PolymerX column with 0%-35% acetonitrile-0.05 N aqueous HCl over 20 min to yield the desired product S9-5-1 as a yellow solid (5 mg, bis-HCl salt, 31%): $^1$H NMR (400 MHz, CD$_3$OD) δ 8.21 (d, J=11.0 Hz, 1H); 4.64-4.54 (m, 2H), 4.34 (s, 2H), 4.27-4.15 (m, 2H), 4.12 (s, 1H), 3.83-3.75 (m, 2H), 3.55-2.50 (m, 6H), 2.40-2.00 (m, 6H), 1.60-1.48 (m, 1H); MS (ESI) m/z 571.2 (M+H).

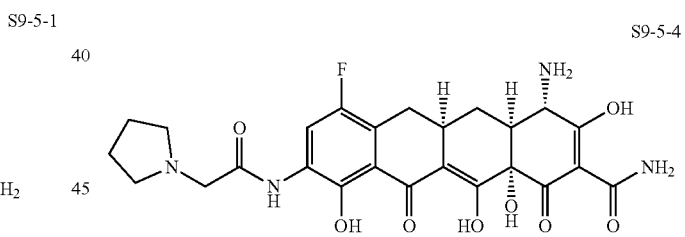

S9-5-4: $^1$H NMR (400 MHz, CD$_3$OD, hydrochloride salt) δ 8.22 (d, J=11.0 Hz, 1H), 4.33 (s, 2H), 3.89 (s, 1H), 3.82-3.76 (m, 2H), 3.23-3.12 (m, 3H), 3.02-2.94 (m, 1H), 2.67-2.64 (m, 1H), 2.32-2.14 (m, 4H), 2.12-2.02 (m, 2H), 1.63-1.54 (m, 1H); MS (ESI) m/z 531.31 (M+H).

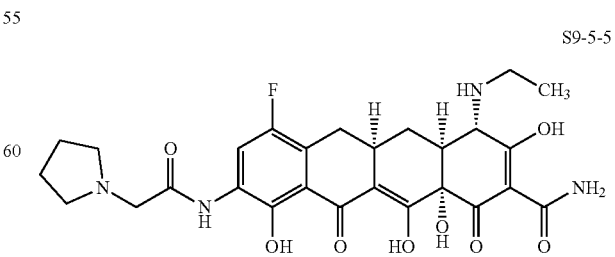

S9-5-5: $^1$H NMR (400 MHz, CD$_3$OD, hydrochloride salt) δ 8.22 (d, J=11.0 Hz, 1H), 4.33 (s, 2H), 3.87 (s, 1H), 3.82-3.76 (m, 2H), 3.47-3.32 (m, 2H), 3.24-3.11 (m, 3H), 3.04-2.97 (m, 1H), 2.86-2.82 (m, 1H), 2.31-2.14 (m, 4H), 2.12-2.03 (m, 2H), 1.62-1.52 (m, 1H), 1.36 (t, J=7.3 Hz, 3H); MS (ESI) m/z 559.27 (M+H).

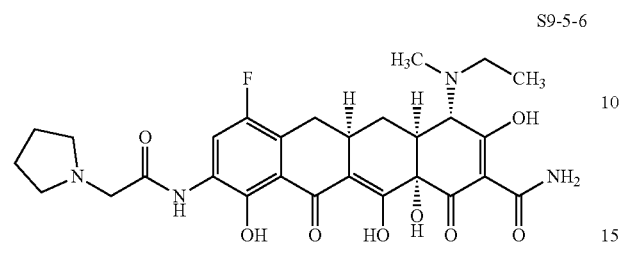

S9-5-6

S9-5-6: ¹H NMR (400 MHz, CD₃OD, hydrochloride salt, ~1:1 conformers) δ 8.23 (d, J=11.0 Hz, 1H), 4.32 (s, 2H), 4.22 (s, 0.5H), 4.13 (s, 0.5H), 3.82-3.76 (m, 2H), 3.50-3.46 (m, 1H), 3.37-3.30 (m, 1H), 3.23-3.13 (m, 3H), 3.06-2.93 (m, 5H), 2.32-2.14 (m, 4H), 2.12-2.06 (m, 2H), 1.70-1.59 (m, 1H), 1.43-1.36 (m, 3H); MS (ESI) m/z 573.33 (M+H).

according the similar procedures used for the preparation of S4-12. Compound S10-2: ¹H NMR (400 MHz, CDCl₃) δ 7.47-7.45 (m, 2H), 7.38-7.31 (m, 5H), 7.26-7.22 (m, 1H), 7.20 (br s, 1H), 7.12-7.09 (m, 2H), 5.16 (s, 2H), 3.70 (s, 3H), 3.64 (t, J=7.9 Hz, 1H), 3.39 (t, J=7.9 Hz, 1H), 2.64-2.55 (m, 1H), 2.39 (s, 3H), 2.28-2.17 (m, 2H), 2.11-2.03 (m, 1H), 1.93-1.83 (m, 2H), 1.64-1.55 (m, 1H), 1.03 (t, J=7.3 Hz, 3H); MS (ESI) m/z 446.42 (M+H).

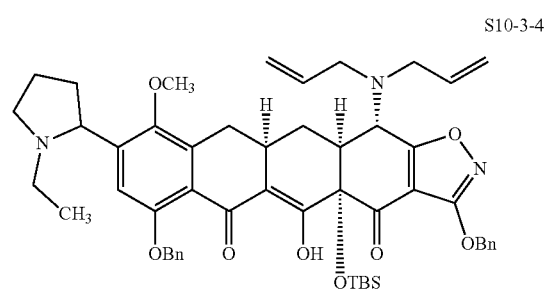 [SMILES: C=CCN(CC=C)[C@@H]1c2onc(OCc3ccccc3)c2C(=O)[C@@]2(O[Si](C)(C)C(C)(C)C)C(O)=C3C(=O)c4c(OCc5ccccc5)cc(C5CCCN5CC)c(OC)c4C[C@H]3C[C@@H]12]

S10-3-4

Scheme 10

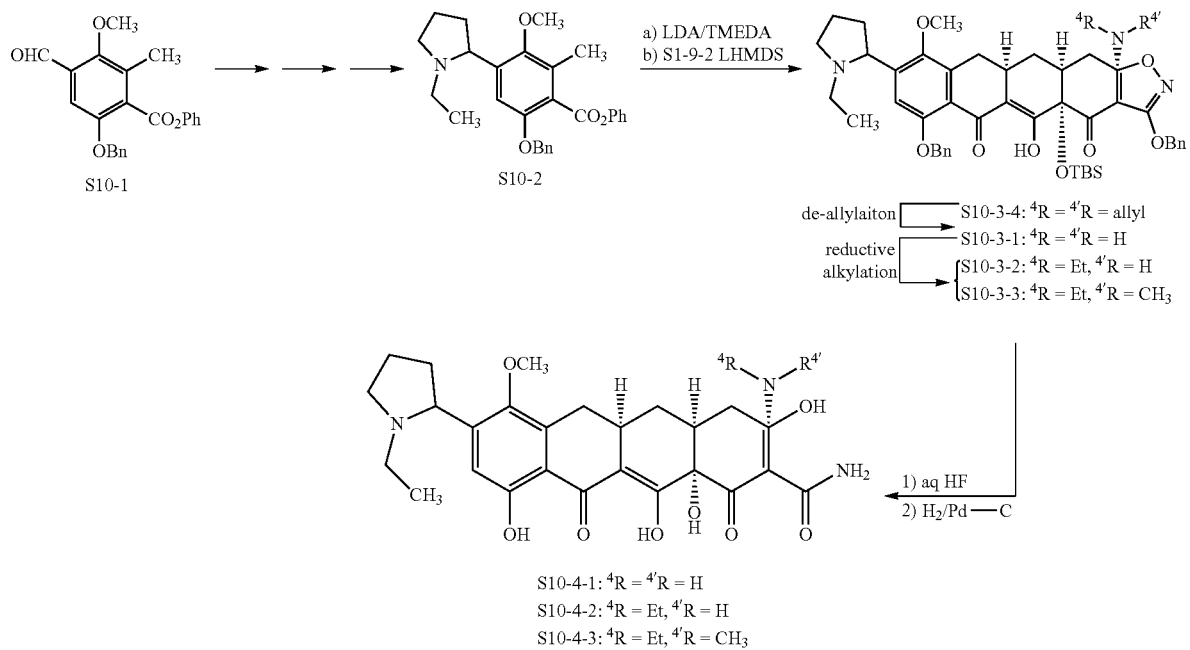

The following compounds were prepared according to Scheme 10.

S10-2

Compound S10-2 was synthesized from S10-1 (prepared using literature procedures including WO 2010129057)

Compound S10-3-4 was prepared in 68% yield from S10-2 and N-diallyl enone S1-9-2 using general procedure A. S10-3-4 (single diastereomer): ¹H NMR (400 MHz, CDCl₃) δ 16.16 (s, 1H), 7.51-7.46 (m, 4H), 7.40-7.21 (m, 7H), 5.86-5.76 (m, 2H), 5.36 (s, 2H), 5.23-5.07 (m, 6H), 4.12 (d, J=9.7 Hz, 1H), 3.66 (s, 3H), 3.68-3.61 (m, 1H), 3.35-3.33 (m, 3H), 3.24-3.14 (m, 3H), 2.96-2.90 (m, 1H), 2.61 (t, J=15.3 Hz, 1H), 2.52-2.40 (m, 3H), 2.25-2.11 (m, 4H), 1.94-1.82 (m, 2H), 1.62-1.54 (m, 1H), 0.98 (t, J=7.3 Hz, 3H), 0.82 (s, 9H), 0.26 (s, 3H), 0.13 (s, 3H); MS (ESI) m/z 886.60 (M+H).

S10-3-1

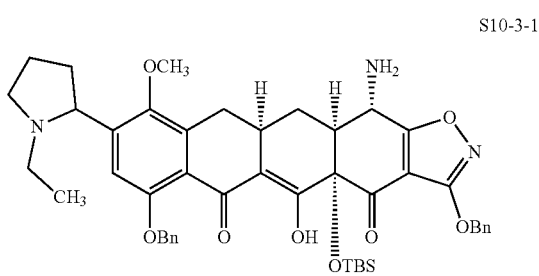 [SMILES: CCN1CCCC1c1cc(OCc2ccccc2)c2c(c1OC)C[C@H]1C[C@H]3[C@H](N)c4onc(OCc5ccccc5)c4C(=O)[C@@]3(O[Si](C)(C)C(C)(C)C)C(O)=C1C2=O]

Compound S10-3-1 was prepared in 78% yield from compound S10-3-4 using general procedure B. S10-3-1 (single diastereomer) ¹H NMR (400 MHz, CDCl₃) δ 16.54 (s, 1H), 7.42-7.41 (m, 2H), 7.37-7.34 (m, 2H), 7.27-7.15 (m, 7H), 5.29, 5.25 (ABq, J=12.2 Hz, 2H), 5.16, 5.07 (ABq, J=12.2 Hz, 2H), 3.82 (br s, 1H), 3.61 (t, J=8.5 Hz, 1H), 3.48 (s, 3H), 3.32-3.28 (m, 1H), 2.95 (dd, J=4.3, 15.3 Hz, 1H), 2.69-2.59 (m, 1H), 2.52-2.43 (m, 2H), 2.18-1.98 (m, 5H), 1.88-1.73 (m, 2H), 1.56-1.38 (m, 2H), 0.90 (t, J=7.3 Hz, 3H), 0.63 (s, 9H), 0.11 (s, 3H), 0.00 (s, 3H); MS (ESI) m/z 806.51 (M+H).

S10-4-1

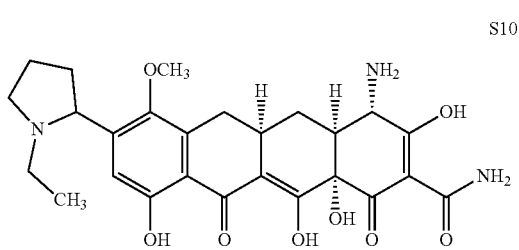

Compound S10-4-1 was prepared from compound S10-3-1 using general procedure C. S10-4-1 (single diastereomer): ¹H NMR (400 MHz, CD₃OD, hydrochloride salt) δ 7.09 (s, 1H), 3.90 (s, 1H), 3.86-3.80 (m, 1H), 3.68 (s, 3H), 3.37-3.30 (m, 1H), 3.28-3.07 (m, 3H), 3.00-2.91 (m, 1H), 2.67-2.54 (m, 2H), 2.41 (t, J=14.2 Hz, 1H), 2.34-2.21 (m, 5H), 1.66-1.57 (m, 1H), 1.25 (t, J=7.3 Hz, 3H); MS (ESI) m/z 514.28 (M+H).

S10-4-2

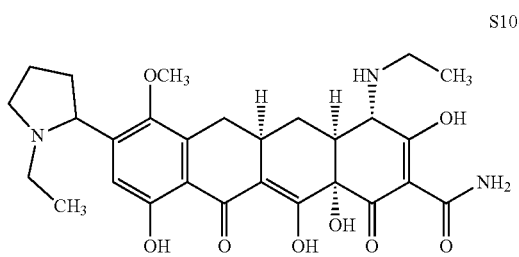

Compound S10-4-2 was prepared from compound S10-3-1 using general procedures D-1 (with acetaldehyde) and C. S10-4-2 (single diastereomer): ¹H NMR (400 MHz, CD₃OD, hydrochloride salt) δ 7.10 (s, 1H), 3.88 (s, 1H), 3.85-3.80 (m, 1H), 3.68 (s, 3H), 3.46-3.31 (m, 3H), 3.27-3.07 (m, 3H), 3.01-2.92 (m, 1H), 2.86-2.83 (m, 1H), 2.62-2.55 (m, 1H), 2.39 (t, J=14.2 Hz, 1H), 2.34-2.22 (m, 5H), 1.64-1.55 (m, 1H), 1.36 (t, J=7.3 Hz, 3H), 1.25 (t, J=7.3 Hz, 3H); MS (ESI) m/z 542.35 (M+H).

S10-4-3

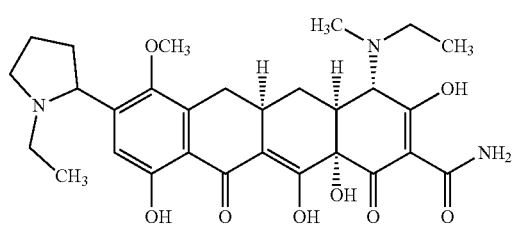

Compound S10-4-3 was prepared from compound S10-3-1 using general procedures D-1 (twice, with acetaldehyde followed by formaldehyde) and C. S10-4-3 (single diastereomer): ¹H NMR (400 MHz, CD₃OD, hydrochloride salt, ~1:1 conformers) δ 7.11 (s, 1H), 4.24 (s, 0.5H), 4.14 (s, 0.5H), 3.86-3.80 (m, 1H), 3.69 (s, 3H), 3.53-3.47 (m, 1H), 3.38-3.30 (m, 2H), 3.29-3.07 (m, 3H), 3.02-2.94 (m, 5H), 2.62-2.57 (m, 1H), 2.40 (t, J=15.1 Hz, 1H), 2.34-2.24 (m, 5H), 1.73-1.61 (m, 1H), 1.44-1.37 (m, 3H), 1.25 (t, J=7.3 Hz, 3H); MS (ESI) m/z 556.37 (M+H).

Scheme 11

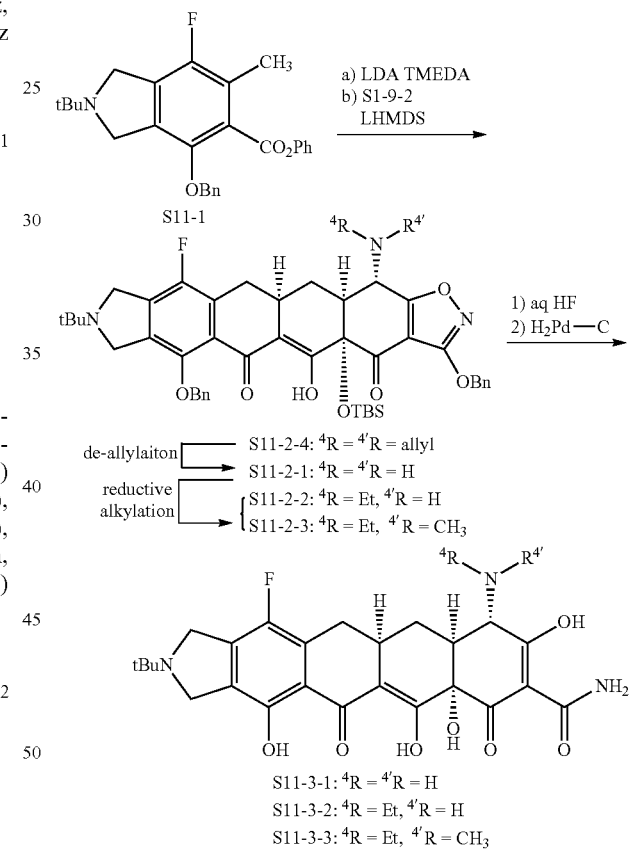

The following compounds were prepared according to Scheme 11.

S11-2-4

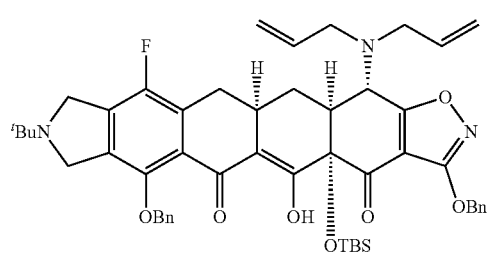

Compound S11-2-4 was synthesized in 71% yield from S11-1 (prepared according to literature procedures including WO 2011123536) and N-diallyl enone S1-9-2 using general procedure A. S11-2-4: $^1$H NMR (400 MHz, CDCl$_3$) δ 16.00 (s, 1H), 7.51-7.49 (m, 2H), 7.40-7.31 (m, 8H), 5.86-5.76 (m, 2H), 5.37 (s, 2H), 5.22 (d, J=17.1 Hz, 2H), 4.12 (d, J=9.8 Hz, 2H), 4.90 (s, 2H), 4.13-4.03 (m, 3H), 3.93-3.80 (m, 2H), 3.34-3.12 (m, 5H), 3.02-2.96 (m, 1H), 2.62 (t, J=15.3 Hz, 1H), 2.55-2.41 (m, 2H), 2.14 (d, J=14.6 Hz, 1H), 1.12 (s, 9H), 0.82 (s, 9H), 0.26 (s, 3H), 0.12 (s, 3H); MS (ESI) m/z 874.57 (M+H).

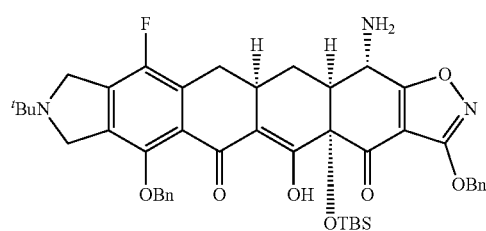

S11-2-1

Compound S11-2-1 was prepared in 44% yield from compound S11-2-4 using general procedure B. S11-2-1: $^1$H NMR (400 MHz, CDCl$_3$) δ 16.45 (s, 1H), 7.39-7.33 (m, 4H), 7.30-7.23 (m, 6H), 7.16 (s, 1H), 5.30, 5.26 (ABq, J=12.2 Hz, 2H), 4.98, 4.84 (ABq, J=11.0 Hz, 2H), 4.03 (br s, 2H), 3.84 (br s, 3H), 2.95-2.91 (m, 1H), 2.72-2.64 (m, 1H), 2.53-2.51 (m, 1H), 2.14-2.02 (m, 2H), 1.50-1.42 (m, 1H), 1.04 (s, 9H), 0.65 (s, 9H), 0.11 (s, 3H), 0.00 (s, 3H); MS (ESI) m/z 794.49 (M+H).

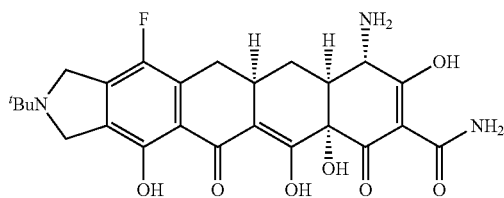

S11-3-1

Compound S11-3-1 was prepared from compound S11-2-1 using general procedure C. S11-3-1: $^1$H NMR (400 MHz, CD$_3$OD, hydrochloride salt) δ 4.87 (s, 2H), 4.74 (s, 2H), 3.88 (s, 1H), 3.20-3.16 (m, 1H), 3.03-2.97 (m, 1H), 2.65 (d, J=12.4 Hz, 1H), 2.33 (t, J=14.6 Hz, 1H), 2.26-2.22 (m, 1H), 1.64-1.54 (m, 1H), 1.52 (s, 9H); MS (ESI) m/z 502.27 (M+H).

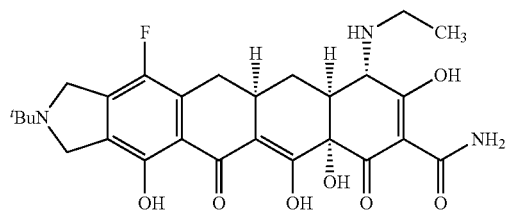

S11-3-2

Compound S11-3-2 was prepared from compound S11-2-1 using general procedures D-1 (with acetaldehyde) and C. S11-3-2: $^1$H NMR (400 MHz, CD$_3$OD, hydrochloride salt) δ 4.87 (s, 2H), 4.74 (s, 2H), 3.86 (s, 1H), 3.47-3.30 (m, 2H), 3.19-3.15 (m, 1H), 3.05-2.98 (m, 1H), 2.84 (d, J=12.8 Hz, 1H), 2.32 (t, J=15.1 Hz, 1H), 2.25-2.21 (m, 1H), 1.62-1.52 (m, 1H), 1.52 (s, 9H), 1.36 (t, J=6.9 Hz, 3H); MS (ESI) m/z 530.28 (M+H).

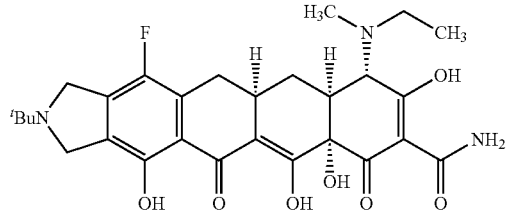

S11-3-3

Compound S11-3-3 was prepared from compound S11-2-1 using general procedure D-1 (twice, with acetaldehyde followed by formaldehyde) and C. S11-3-3: $^1$H NMR (400 MHz, CD$_3$OD, hydrochloride salt, ~1:1 conformers) δ 4.87 (s, 2H), 4.75 (s, 2H), 4.22 (s, 0.5H), 4.13 (s, 0.5H), 3.52-3.44 (m, 1H), 3.38-3.30 (m, 1H), 3.22-3.18 (m, 1H), 3.11-2.93 (m, 5H), 2.36-2.21 (m, 2H), 1.70-1.59 (m, 1H), 1.52 (s, 9H), 1.43-1.36 (m, 3H); MS (ESI) m/z 544.33 (M+H).

Scheme 12

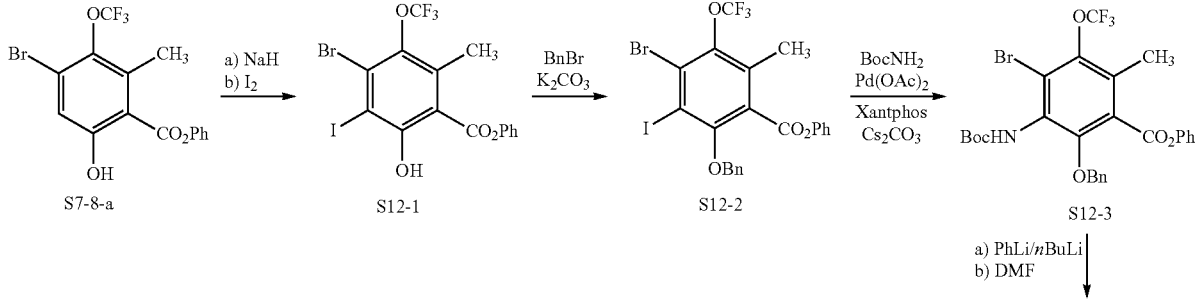

-continued

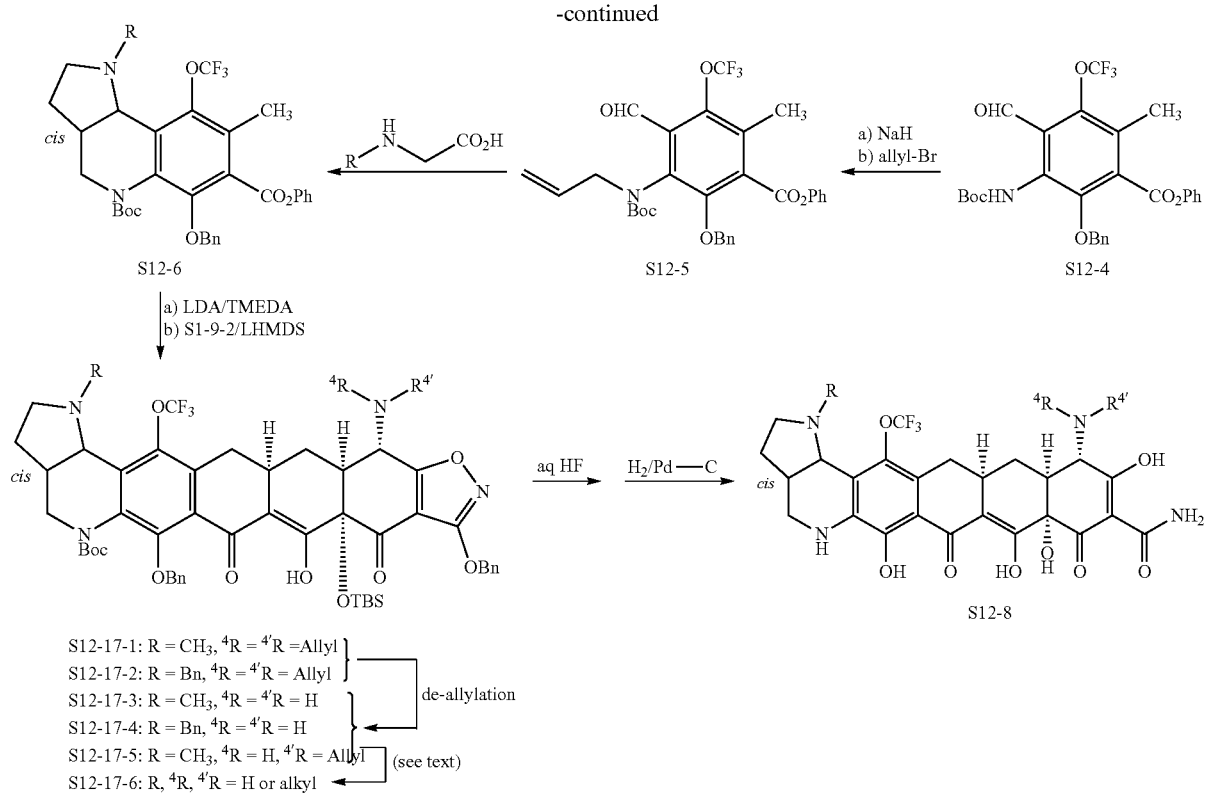

S12-17-1: R = CH₃, ⁴R = ⁴'R = Allyl
S12-17-2: R = Bn, ⁴R = ⁴'R = Allyl   } de-allylation
S12-17-3: R = CH₃, ⁴R = ⁴'R = H
S12-17-4: R = Bn, ⁴R = ⁴'R = H
S12-17-5: R = CH₃, ⁴R = H, ⁴'R = Allyl   (see text)
S12-17-6: R, ⁴R, ⁴'R = H or alkyl The following compounds were prepared according to Scheme 12.

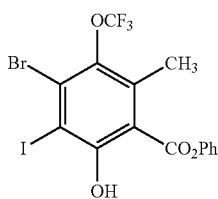

S12-1

To phenol S7-8-a (5.20 mmol, 1 eq, obtained from treatment of 2.50 g of the corresponding benzyl ether with TFA/anisole, containing inseparable impurities, ~75% pure) in toluene (20 mL) at rt was added NaH (0.83 g, 20.80 mmol, 60% in mineral oil, 4 eq) in small portions. The mixture was stirred at rt for 20 min. Iodine (5.28 g, 20.80 mmol, 4 eq) was added. The reaction mixture was stirred at rt overnight, diluted with EtOAc (200 mL), washed with 1 N aqueous HCl (100 mL×1), 5% aqueous Na₂S₂O₃ (100 mL×2), and brine (100 mL×1), dried over sodium sulfate, and concentrated under reduced pressure to yield the crude product S12-1 as a pale oil: $R_f$ 0.45 (10% EtOAc/hexane); MS (ESI) m/z 514.8 (M–H).

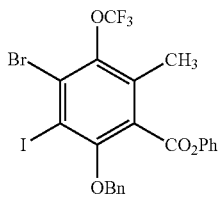

S12-2

To the above crude phenol S12-1 (5.20 mmol, 1 eq) in DMF (10 mL) at rt was added potassium carbonate (1.44 g, 10.44 mmol, 2 eq) and benzyl bromide (0.74 mL, 6.23 mmol, 1.2 eq). The reaction mixture was stirred at rt for 3 h, diluted with EtOAc (200 mL), washed with water (200 mL×1, 100 mL×1) and brine (50 mL×1), dried over sodium sulfate, and concentrated under reduced pressure. Flash column chromatography on silica gel with 0-3% EtOAc/hexane yielded the desired product S12-2 as a pale oil (3.48 g): $R_f$ 0.55 (10% EtOAc/hexane): ¹H NMR (400 MHz, CDCl₃) δ 7.55-7.00 (m, 10H), 5.11 (s, 2H), 2.44 (s, 3H); MS (ESI) m/z 604.8 (M–H).

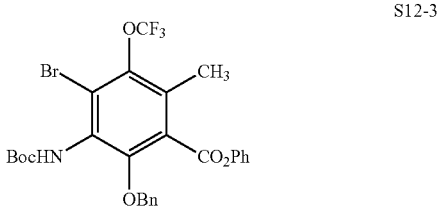

S12-3

To compound S12-2 (5.20 mmol, 90% pure) was added cesium carbonate (2.54 g, 7.80 mmol, 1.5 eq), BocNH₂ (0.67 g, 5.70 mmol, 1.1 eq), Xantphos (1.20 g, 2.07 mmol, 0.4 eq), Pd(OAc)₂ (224 mg, 1.00 mmol, 0.2 eq), and anhydrous dioxane (10 mL). Nitrogen gas was bubbled through the mixture for 5 min. The reaction vessel was sealed and heated at 80° C. for 48 h with vigorous stirring. After cooling down to rt, water (100 mL) was added. The reaction mixture was extracted with methylene chloride (100 mL×1, 50 mL×2). The combined extracts were dried over sodium sulfate and concentrated under reduced pressure. Flash column chromatography on silica gel with 0-15% EtOAc/hexane yielded the desired product S12-3 as a white solid (0.87 g, 28% overall yield): $R_f$ 0.25 (10% EtOAc/hexane): $^1$H NMR (400 MHz, CDCl$_3$) δ 7.45-7.20 (m, 8H), 7.03 (d, J=7.3 Hz, 2H), 6.07 (br s, 1H), 5.03 (s, 2H), 2.46 (s, 3H), 1.46 (s, 9H); MS (ESI) m/z 594.0 (M–H).

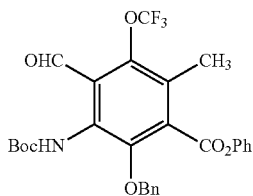

S12-4

To compound S12-3 (0.68 g, 1.14 mmol, 1 eq) in anhydrous THF (6 mL) at −78° C. was added PhLi (0.95 mL, 1.80 M/nBu$_2$O, 1.71 mmol, 1.5 eq) dropwise over 1 min. After stirring at −78° C. for 10 min, nBuLi (0.86 mL, 1.60 M/hexane, 1.38 mmol, 1.2 eq) was added dropwise over 2 min. The reaction was stirred at −78° C. for 5 min. Dry DMF (0.26 mL, 3.36 mmol, 3 eq) was added dropwise. The reaction was stirred from −78° C. to 0° C. over 1 h and quenched with saturated aqueous sodium bicarbonate (50 mL). The reaction mixture was extracted with methylene chloride (50 mL×3). The combined extracts were dried over sodium sulfate and concentrated under reduced pressure. Flash column chromatography on silica gel with 0-15% EtOAc/hexane yielded the desired product S12-4 as a pale solid (232 mg, 37%): $R_f$ 0.33 (10% EtOAc/hexane): $^1$H NMR (400 MHz, CDCl$_3$) δ 10.21 (s, 1H), 7.90 (br s, 1H), 7.45-7.20 (m, 8H), 7.05 (d, J=7.3 Hz, 2H), 5.00 (s, 2H), 2.42 (s, 3H), 1.43 (s, 9H); MS (ESI) m/z 544.2 (M–H). Note: use of reduced amounts of PhLi and n-BuLi can potentially increase product yield.

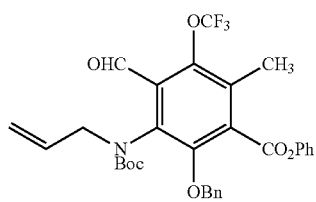

S12-5

To compound S12-4 (232 mg, 0.43 mmol, 1 eq) in dry DMF (2 mL) at rt was added NaH (21 mg, 60% in mineral oil, 0.52 mmol, 1.2 eq). After stirring at rt for 30 min, allyl bromide (56 μL, 0.64 mmol, 1.5 eq) was added. The reaction mixture was stirred at rt for 1 h, diluted with EtOAc (50 mL), washed with water (50 mL×2) and brine (50 mL×1), dried over sodium sulfate, and concentrated under reduced pressure. Flash column chromatography on silica gel with 0-8% EtOAc/hexane yielded the desired product S12-5 as a pale oil (206 mg, 82%): $R_f$ 0.45 (10% EtOAc/hexane): $^1$H NMR (400 MHz, CDCl$_3$) δ 10.16 (s, 1H), 7.40-6.95 (m, 10H), 5.95-5.75 (m, 1H), 5.10-4.85 (m, 4H), 4.64, 4.28 (dd, dd, J=5.5, 12.8 Hz, J=4.9, 12.2 Hz, 1H), 4.00, 3.89 (dd, dd, J=8.1, 10.2 Hz, J=8.6, 12.8 Hz, 1H), 2.46, 2.43 (s, s, 3H), 1.53, 1.50 (s, s, 9H); MS (ESI) m/z 584.2 (M–H).

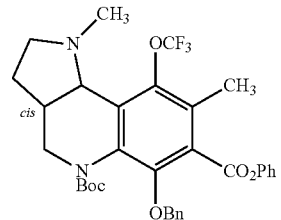

S12-6-1

To compound S12-5 (206 mg, 0.35 mmol) in DMF (2 mL) was added N-methyl glycine (47 mg, 0.53 mmol, 1.5 eq). The mixture was heated at 100° C. for 24 h. After cooling down to rt, the reaction mixture was diluted with EtOAc (50 mL), washed with aqueous saturated sodium bicarbonate (50 mL×2) and brine (50 mL×1), dried over sodium sulfate, and concentrated under reduced pressure. Flash column chromatography on silica gel with 0-15% EtOAc/hexane yielded the desired product S12-6-1 as a white foam (190 mg, 89%): $R_f$ 0.50 (10% EtOAc/hexane): $^1$H NMR (400 MHz, CDCl$_3$), broad and complex due to presence of various rotamers and/or conformers: MS (ESI) m/z 613.3 (M+H).

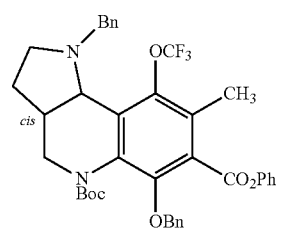

S12-6-2

Compound S12-6-2 was prepared similarly from S12-5 and N-benzyl glycine: $^1$H NMR (400 MHz, CDCl$_3$), broad and complex due to presence of various rotamers and/or conformers: MS (ESI) m/z 689.3 (M+H).

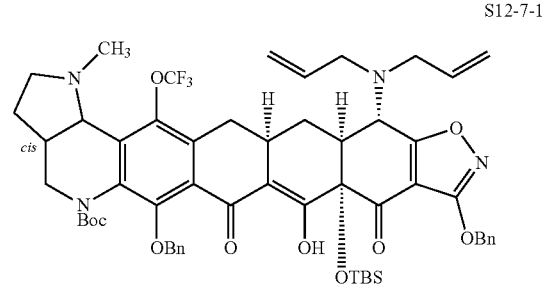 [SMILES: C=CCN(CC=C)[C@@H]1c2onc(OCc3ccccc3)c2C(=O)[C@@]2(O[Si](C)(C)C(C)(C)C)C(O)=C3C(=O)c4c(c(OC(F)(F)F)c5c(c4OCc4ccccc4)N(C(=O)OC(C)(C)C)CC4CCN(C)C54)C[C@H]3C[C@@H]12]

S12-7-1

Compound S12-7-1 was prepared from S12-6-1 and N-diallyl enone S1-9-2 using general procedure A and the two diastereomers were separated.

S12-7-1-A (52% yield, less polar diastereomer on TLC, rotamers): MS (ESI) m/z 1053.55 (M+H).

S12-7-1-B (18% yield, more polar diastereomer on TLC, rotamers): MS (ESI) m/z 1053.55 (M+H).

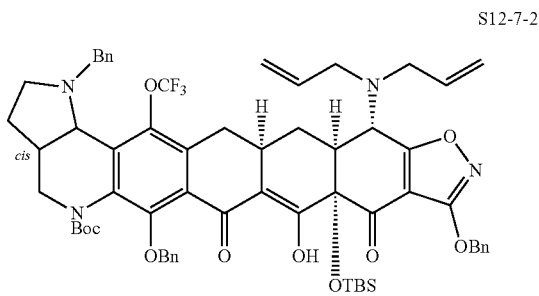 [SMILES: C=CCN(CC=C)[C@@H]1c2onc(OCc3ccccc3)c2C(=O)[C@@]2(O[Si](C)(C)C(C)(C)C)C(O)=C3C(=O)c4c(c(OC(F)(F)F)c5c(c4OCc4ccccc4)N(C(=O)OC(C)(C)C)CC4CCN(Cc6ccccc6)C54)C[C@H]3C[C@@H]12]

S12-7-2

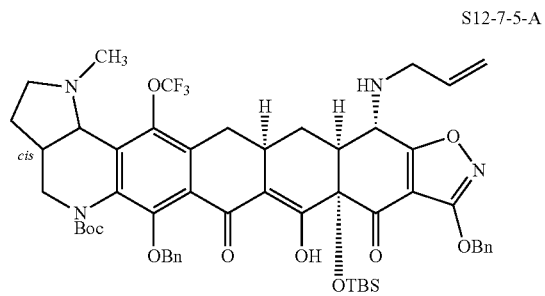 [SMILES: C=CCN[C@@H]1c2onc(OCc3ccccc3)c2C(=O)[C@@]2(O[Si](C)(C)C(C)(C)C)C(O)=C3C(=O)c4c(c(OC(F)(F)F)c5c(c4OCc4ccccc4)N(C(=O)OC(C)(C)C)CC4CCN(C)C54)C[C@H]3C[C@@H]12]

S12-7-5-A

Compound S12-7-2 was prepared from S12-6-2 and N-diallyl enone S1-9-2 using general procedure A and the two diastereomers were separated.

S12-7-2-A (52% yield, less polar diastereomer on TLC, rotamers): MS (ESI) m/z 1129.58 (M+H).

S12-7-2-B (18% yield, more polar diastereomer on TLC, rotamers): MS (ESI) m/z 1129.58 (M+H).

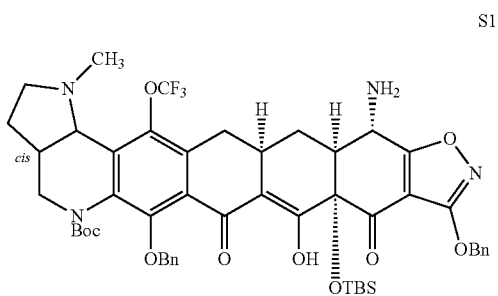

S12-7-3

Compounds S12-7-3-A and S12-7-3-B were prepared from the corresponding compounds S12-7-1-A and S12-7-1-B separately using general procedure B.

S12-7-3-A (92% yield, rotamers): MS (ESI) m/z 973.54 (M+H).

S12-7-3-B (42% yield, rotamers): MS (ESI) m/z 973.51 (M+H).

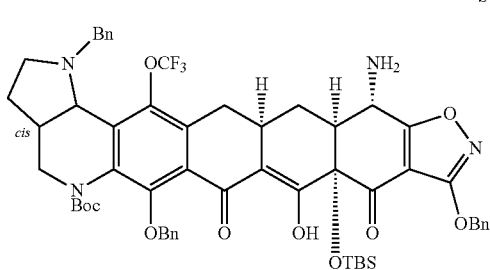

S12-7-4

Compounds S12-7-4-A and S12-7-4-B were prepared from the corresponding compounds S12-7-2-A and S12-7-2-B separately using general procedure B.

S12-7-4-A (54% yield, rotamers): MS (ESI) m/z 1049.60 (M+H).

S12-7-4-B (25% yield, rotamers): MS (ESI) m/z 1049.61 (M+H).

A mixture of Pd(dba)$_2$ (5.6 mg, 0.0097 mmol, 0.1 eq) and DPPB (4.1 mg, 0.0097 mmol, 0.1 eq) was dissolved in THF (1 mL). The resulting reaction solution was stirred at rt under nitrogen for 10 min, and added to a solution of compound S12-7-1-A (102 mg, 0.097 mmol, 1 eq) and 2-mercaptobenzoic acid (19.4 mg, 0.126 mmol, 1.3 eq) in THF (1 mL). The resulting orange reaction solution was stirred at rt under nitrogen overnight. More Pd(dba)$_2$ (5.6 mg, 0.0097 mmol, 0.1 eq) and DPPB (4.1 mg, 0.0097 mmol, 0.1 eq) were added. The resulting reaction mixture was stirred at rt overnight. Then saturated aq. NaHCO$_3$ was added. The resulting mixture was extracted with EtOAc (30 mL). The organic phase was washed with brine, dried over Na$_2$SO$_4$, filtered and concentrated under reduced pressure. The residue was purified by preparative reverse phase HPLC on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 3.0 mL (CH$_3$CN); gradient: 20→100% B in A over 10 min; mass-directed fraction collection]. Fractions containing the desired product were collected and freeze-dried to yield the desired product S12-7-5-A (13.6 mg, 14%, MS (ESI) m/z 1013.51 (M+H)) along with di-deallylation product S12-7-3-A (23.6 mg) and starting material (61.7 mg).

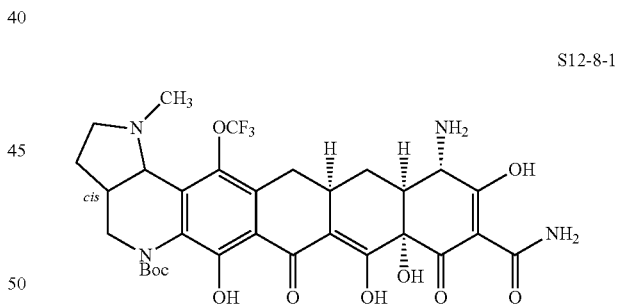

S12-8-1

Compounds S12-8-1-A and S12-8-1-B were prepared from the corresponding compounds S12-7-3-A and S12-7-3-B separately using general procedure C.

S12-8-1-A: $^1$H NMR (400 MHz, CD$_3$OD, hydrochloride salt) δ 4.74 (d, J=6.9 Hz, 1H), 3.88 (s, 1H), 3.73-3.67 (m, 1H), 3.38-3.30 (m, 2H), 3.16-3.07 (m, 2H), 2.99 (s, 3H), 2.94-2.87 (m, 2H), 2.66 (d, J=13.3 Hz, 1H), 2.56-2.47 (m, 1H), 2.28-2.22 (m, 2H), 2.12-2.04 (m, 1H), 1.60-1.50 (m, 1H); MS (ESI) m/z 581.24 (M+H).

S12-8-1-B: $^1$H NMR (400 MHz, CD$_3$OD, hydrochloride salt) δ 4.75 (d, J=7.3 Hz, 1H), 3.88 (s, 1H), 3.73-3.65 (m, 1H), 3.36-3.30 (m, 2H), 3.14-3.06 (m, 2H), 2.97 (s, 3H), 3.01-2.90 (m, 2H), 2.64 (d, J=11.9 Hz, 1H), 2.56-2.47 (m, 1H), 2.28 (t, J=14.8 Hz, 1H), 2.22-2.18 (m, 1H), 2.14-2.05 (m, 1H), 1.61-1.52 (m, 1H); MS (ESI) m/z 581.29 (M+H).

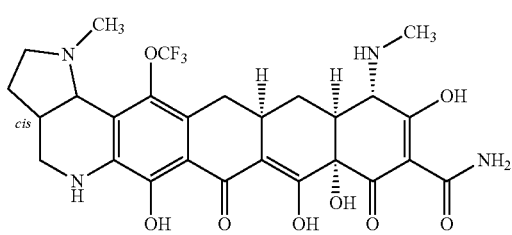

S12-8-2-A

Compound S12-8-2-A was prepared from the corresponding compound S12-7-5-A using general procedures D-1 (with formaldehyde), B and C. S12-8-2-A: $^1$H NMR (400 MHz, CD$_3$OD, hydrochloride salt) δ 4.76 (d, J=6.9 Hz, 1H), 3.81 (s, 1H), 3.73-3.68 (m, 1H), 3.39-3.30 (m, 2H), 3.15-3.07 (m, 2H), 3.00 (s, 3H), 2.96-2.92 (m, 2H), 2.92 (s, 3H), 2.85-2.79 (m, 1H), 2.56-2.48 (m, 1H), 2.30-2.19 (m, 2H), 2.14-2.05 (m, 1H), 1.60-1.50 (m, 1H); MS (ESI) m/z 595.27 (M+H).

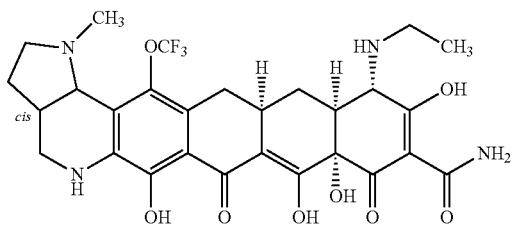

S12-8-3

Compounds S12-8-3-A and S12-8-3-B were prepared from the corresponding compounds S12-7-3-A and S12-7-3-B separately using general procedures D1 (with acetaldehyde) and C.

S12-8-3-A: $^1$H NMR (400 MHz, CD$_3$OD, hydrochloride salt) δ 4.75 (d, J=6.9 Hz, 1H), 3.87 (s, 1H), 3.73-3.67 (m, 1H), 3.48-3.32 (m, 4H), 3.16-3.06 (m, 2H), 3.00 (s, 3H), 2.96-2.89 (m, 2H), 2.85 (d, J=12.4 Hz, 1H), 2.56-2.47 (m, 1H), 2.28-2.21 (m, 2H), 2.13-2.04 (m, 1H), 1.59-1.49 (m, 1H), 1.36 (t, J=7.3 Hz, 3H); MS (ESI) m/z 609.27 (M+H).

S12-8-3-B: $^1$H NMR (400 MHz, CD$_3$OD, hydrochloride salt) δ 4.75 (d, J=6.9 Hz, 1H), 3.86 (s, 1H), 3.70-3.64 (m, 1H), 3.44-3.30 (m, 4H), 3.13-3.05 (m, 2H), 3.00 (s, 3H), 3.00-2.94 (m, 2H), 2.82 (d, J=12.8 Hz, 1H), 2.54-2.47 (m, 1H), 2.27 (t, J=14.6 Hz, 1H), 2.21-2.16 (m, 1H), 2.12-2.06 (m, 1H), 1.60-1.50 (m, 1H), 1.36 (t, J=7.3 Hz, 3H); MS (ESI) m/z 609.29 (M+H).

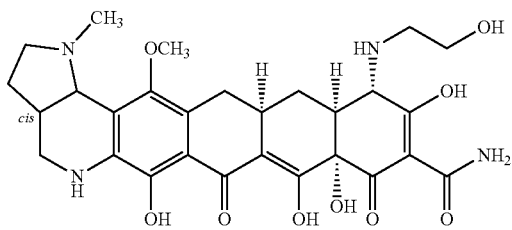

S12-8-4-A

Compound S12-8-4-A was prepared from compound S12-7-3-A using general procedures D-1 (with (tert-butyldimethylsilyloxy)acetaldehyde) and C. S12-8-4-A: $^1$H NMR (400 MHz, CD$_3$OD, hydrochloride salt) δ 4.75 (d, J=6.9 Hz, 1H), 4.00 (s, 1H), 3.90-3.82 (m, 2H), 3.72-3.66 (m, 1H), 3.49-3.41 (m, 2H), 3.38-3.32 (m, 2H), 3.14-3.06 (m, 2H), 2.99 (s, 3H), 2.96-2.86 (m, 3H), 2.56-2.47 (m, 1H), 2.29-2.20 (m, 2H), 2.13-2.04 (m, 1H), 1.60-1.51 (m, 1H); MS (ESI) m/z 625.30 (M+H).

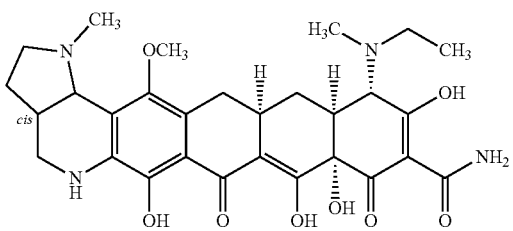

S12-8-5-A

Compound S12-8-5-A was prepared from compound S12-7-3-A using general procedures D-1 (twice, with acetaldehyde followed by formaldehyde) and C.

S12-8-5-A: $^1$H NMR (400 MHz, CD$_3$OD, hydrochloride salt, ~1:1 conformers) δ 4.75 (d, J=7.3 Hz, 1H), 4.23 (s, 0.5H), 4.14 (s, 0.5H), 3.74-3.68 (m, 1H), 3.53-3.44 (m, 1H), 3.39-3.32 (m, 3H), 3.16-3.09 (m, 2H), 3.02-2.90 (m, 9H), 2.56-2.47 (m, 1H), 2.30-2.20 (m, 2H), 2.13-2.04 (m, 1H), 1.68-1.56 (m, 1H), 1.43-1.36 (m, 3H); MS (ESI) m/z 623.32 (M+H).

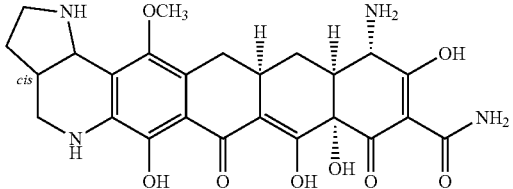

S12-8-6

Compounds S12-8-6A and S12-8-6B were prepared from the corresponding compounds S12-7-4-A and S12-7-4-B separately using general procedure C.

S12-8-6-A: $^1$H NMR (400 MHz, CD$_3$OD, hydrochloride salt) δ 4.83 (d, J=6.9 Hz, 1H), 3.88 (s, 1H), 3.45-3.36 (m, 3H), 3.07 (dd, J=4.1, 15.1 Hz, 1H), 2.97 (dd, J=11.2, 12.8 Hz, 1H), 2.90-2.75 (m, 2H), 2.66-2.64 (m, 1H), 2.44-2.35 (m, 1H), 2.32-2.21 (m, 2H), 2.15-2.07 (m, 1H), 1.62-1.52 (m, 1H); MS (ESI) m/z 567.28 (M+H).

S12-8-6-B: $^1$H NMR (400 MHz, CD$_3$OD, hydrochloride salt) δ 4.81 (d, J=6.9 Hz, 1H), 3.89 (s, 1H), 3.44-3.37 (m, 3H), 3.05 (dd, J=3.7, 15.1 Hz, 1H), 2.98-2.91 (m, 2H), 2.80-2.72 (m, 1H), 2.65 (d, J=12.8 Hz, 1H), 2.42-2.33 (m, 1H), 2.28-2.18 (m, 2H), 2.14-2.06 (m, 1H), 1.60-1.51 (m, 1H); MS (ESI) m/z 567.26 (M+H).

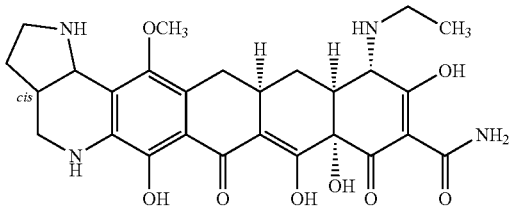

S12-8-7-A

Compound S12-8-7-A was prepared from compound S12-7-4-A using general procedures D-1 (with acetaldehyde) and C. S12-8-7-A: ¹H NMR (400 MHz, CD₃OD, hydrochloride salt) δ 4.81 (d, J=6.9 Hz, 1H), 3.86 (s, 1H), 3.45-3.33 (m, 5H), 3.04 (dd, J=4.1, 15.1 Hz, 1H), 2.96 (dd, J=11.0, 12.4 Hz, 1H), 2.90-2.74 (m, 3H), 2.42-2.33 (m, 1H), 2.29-2.19 (m, 2H), 2.13-2.05 (m, 1H), 1.58-1.48 (m, 1H), 1.35 (t, J=7.3 Hz, 3H); MS (ESI) m/z 595.31 (M+H).

0.5H), 3.53-3.35 (m, 5H), 3.07 (dd, J=4.1, 15.6 Hz, 1H), 3.02-2.93 (m, 6H), 2.82-2.77 (m, 1H), 2.43-2.34 (m, 1H), 2.31-2.20 (m, 2H), 2.14-2.06 (m, 1H), 1.68-1.56 (m, 1H), 1.42-1.34 (m, 3H); MS (ESI) m/z 609.33 (M+H).

Scheme 13

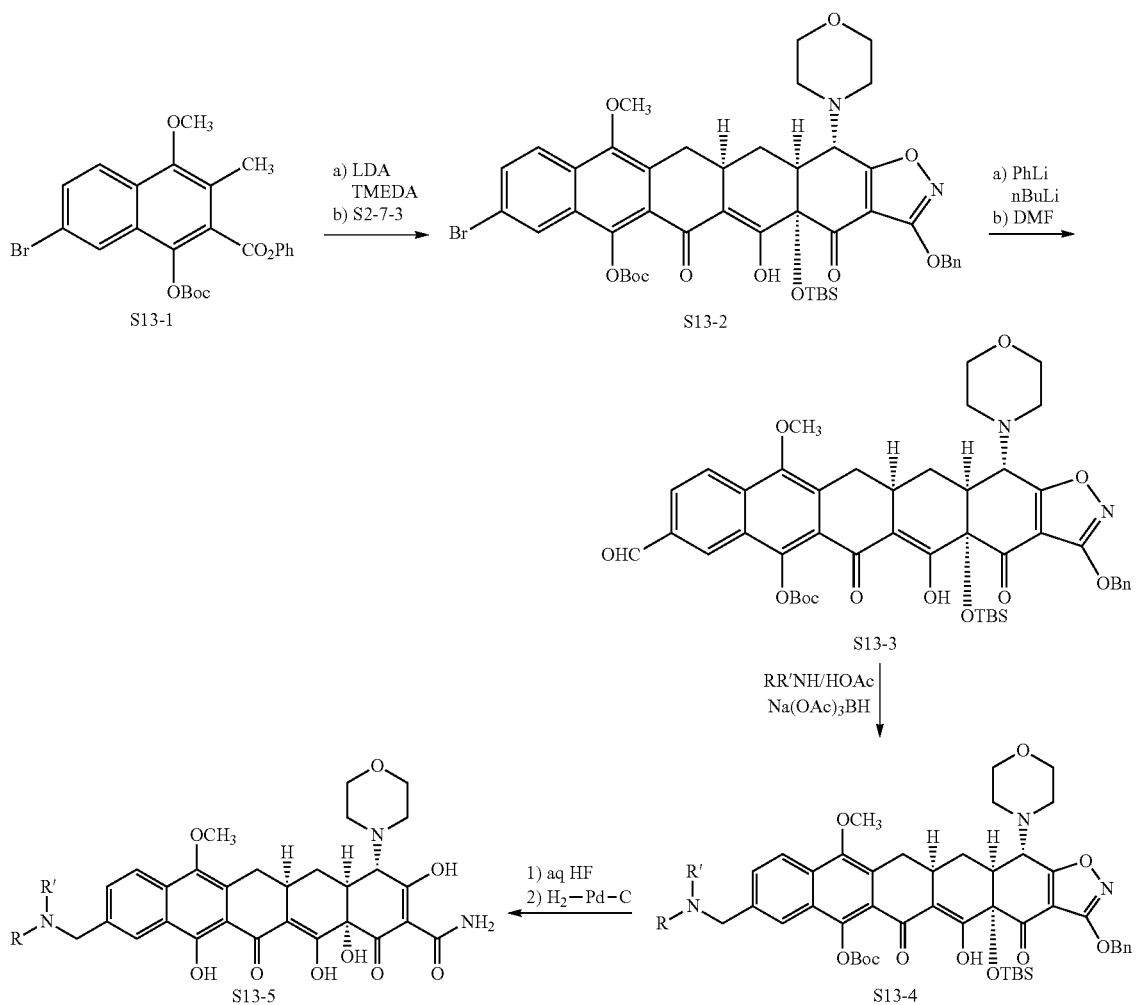

The following compounds were prepared according to Scheme 13.

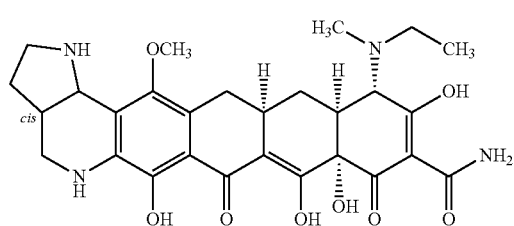

S12-8-8-A

Compound S12-8-8-A was prepared from compound S12-7-4-A using general procedures D-1 (twice, with acetaldehyde followed by formaldehyde) and C. S12-8-8-A: ¹H NMR (400 MHz, CD₃OD, hydrochloride salt, ~1:1 conformers) δ 4.82 (d, J=7.3 Hz, 1H), 4.22 (s, 0.5H), 4.13 (s,

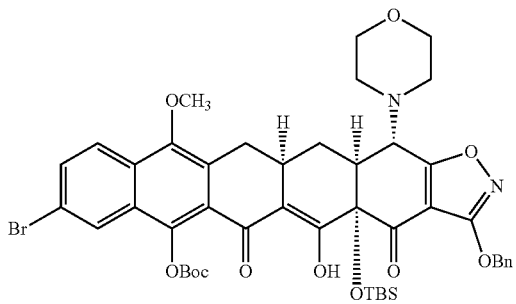

S13-2

To a solution of compound S13-1 (100 mg, 0.205 mmol, 1.5 eq, prepared according to literature procedures including J. Med. Chem., 2011, 54, 3704) and enone S2-7-3 (72 mg, 0.136 mmol, 1.0 eq) in THF (3 mL) was added LDA solution in THF (~1.2 M, 2.73 mL, 0.34 mmol, 2.5 eq) dropwise via a syringe at −78° C. The resulting red orange solution was allowed to gradually warm up to −10° C. A saturated aqueous NH$_4$Cl (20 mL) solution was added to the reaction. The reaction mixture was extracted with DCM (3×15 mL). The combined organic phase was dried over Na$_2$SO$_4$, and concentrated under reduced pressure. The residue was purified by preparative reverse phase HPLC on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 3.0 mL (CH$_3$CN); gradient: 85→100% B in A over 8 min; mass-directed fraction collection]. Fractions containing the desired product were collected and concentrated to yield the desired product S13-2 (52.8 mg, 42%, yellow solid): $^1$H NMR (400 MHz, CDCl$_3$) δ 15.94 (s, 1H), 8.24 (br s, 1H), 7.94 (d, J=8.5 Hz, 1H), 7.69 (dd, J=1.8, 8.5 Hz, 1H), 7.50-7.48 (m, 2H), 7.39-7.32 (m, 3H), 5.37, 5.33 (ABq, J=12.2 Hz, 2H), 3.96 (d, J=10.4 Hz, 1H), 3.85 (s, 3H), 3.77-3.71 (m, 4H), 3.46 (dd, J=4.3, 15.3 Hz, 1H), 3.08-3.02 (m, 3H), 2.65-2.49 (m, 5H), 2.24 (d, J=14.0 Hz, 1H), 1.58 (s, 9H), 0.81 (s, 9H), 0.25 (s, 3H), 0.12 (s, 3H); MS (ESI) m/z 917.36, 919.34 (M+H).

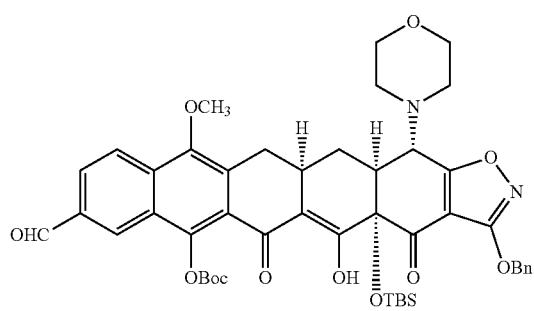

S13-3

A solution of phenyllithium in di-n-butyl ether (1.03 M, 112 μL, 0.115 mmol, 2.0 eq) was added dropwise to a solution of compound S13-2 (52.8 mg, 0.058 mmol, 1.0 eq) in tetrahydrofuran (2 mL) at −78° C., forming a red solution. After 5 min, a solution of n-butyllithium in hexanes (1.84 M, 47 μL, 0.086 mmol, 1.5 eq) was added dropwise at −78° C. followed 1 min later by N,N-dimethylformamide (22 μL, 0.288 mmol, 5.0 eq). The deep red reaction mixture was stirred at −78° C. for 1 h. Saturated aqueous ammonium chloride solution (10 mL) was added dropwise at −78° C., followed by aqueous potassium phosphate buffer solution (pH 7.0, 0.2 M, 10 mL). The reaction mixture was allowed to warm up to rt, then was extracted with dichloromethane (3×15 mL). The organic extracts were combined and the combined solution was dried over anhydrous sodium sulfate. The dried solution was filtered and the filtrate was concentrated. The residue was purified by preparative reverse phase HPLC on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 90→95% B over 10 min, then 100% B for 5 min; mass-directed fraction collection]. Fractions with the desired MW were collected and concentrated to afford the desired product S13-3 (28.3 mg, 57%) as a yellow solid: $^1$H NMR (400 MHz, CDCl$_3$) δ 15.92 (br s, 1H), 10.17 (s, 1H), 8.59 (br s, 1H), 8.19 (d, J=8.5 Hz, 1H), 8.10 (dd, J=4.3, 8.5 Hz, 1H), 7.51-7.49 (m, 2H), 7.39-7.33 (m, 3H), 5.38, 5.34 (ABq, J=12.2 Hz, 2H), 3.96 (d, J=10.4 Hz, 1H), 3.89 (s, 3H), 3.79-3.71 (m, 4H), 3.52 (dd, J=4.3, 15.3 Hz, 1H), 3.10-3.02 (m, 3H), 2.67-2.51 (m, 5H), 2.25 (d, J=14.8 Hz, 1H), 1.59 (s, 9H), 0.81 (s, 9H), 0.24 (s, 3H), 0.13 (s, 3H); MS (ESI) m/z 867.44 (M+H).

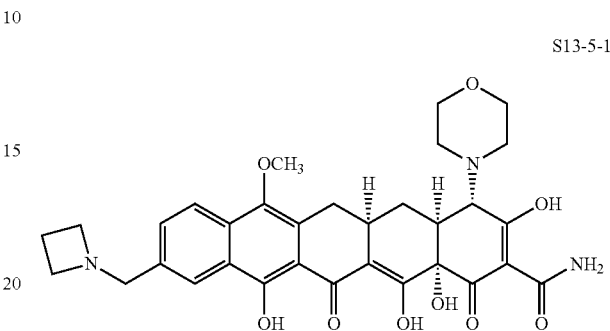

S13-5-1

General Procedure F for reductive amination. Azetidine (3.2 μL, 0.048 mmol, 3.0 eq), acetic acid (3 μL, 0.048 mmol, 3.0 eq) and sodium triacetoxyborohydride (6.8 mg, 0.032 mmol, 2.0 eq) were added in sequence to a solution of aldehyde S13-3 (14 mg, 0.016 mmol, 1.0 eq) in 1,2-dichloroethane (1 mL) at rt. After stirring for 1 h, the reaction mixture was poured into saturated aqueous sodium bicarbonate solution. The product was extracted into dichloromethane (3×15 mL). The combined organic extracts were dried over anhydrous sodium sulfate. The dried solution was filtered and the filtrate was concentrated to yield intermediate S13-4-1, which was deprotected using general procedure C to give compound S13-5-1: $^1$H NMR (400 MHz, CD$_3$OD, hydrochloride salt) δ 8.53 (br s, 1H), 8.12 (d, J=8.7 Hz, 1H), 7.75 (dd, J=1.4, 8.7 Hz, 1H), 4.56 (s, 2H), 4.29-4.22 (m, 2H), 4.14-4.08 (m, 2H), 4.08 (s, 1H), 4.07-3.98 (m, 4H), 3.80 (s, 3H), 3.62-3.57 (m, 4H), 3.14-3.10 (m, 1H), 3.05-2.99 (m, 1H), 2.85-2.75 (m, 1H), 2.62-2.54 (m, 1H), 2.52-2.45 (m, 1H), 2.41 (t, J=13.7 Hz, 1H), 2.28-2.24 (m, 1H), 1.73-1.63 (m, 1H); MS (ESI) m/z 606.38 (M+H).

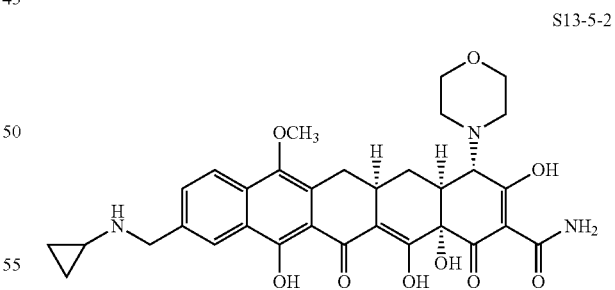

S13-5-2

Compound S13-5-2 was prepared from aldehyde S13-3 using general procedures F (with cyclopropylamine) and C. S13-5-2: $^1$H NMR (400 MHz, CD$_3$OD, hydrochloride salt) δ 8.57 (d, J=1.4 Hz, 1H), 8.11 (d, J=8.2 Hz, 1H), 7.81 (dd, J=1.8, 8.7 Hz, 1H), 4.51 (s, 2H), 4.11 (s, 1H), 4.07-3.95 (m, 4H), 3.81 (s, 3H), 3.62-3.57 (m, 4H), 3.41 (dd, J=4.6, 15.1 Hz, 1H), 3.12 (d, J=12.8 Hz, 1H), 3.06-2.98 (m, 1H), 2.86-2.81 (m, 1H), 2.39 (t, J=13.7 Hz, 1H), 2.28-2.26 (m, 1H), 1.72-1.62 (m, 1H), 0.95-0.90 (m, 4H); MS (ESI) m/z 606.34 (M+H).

Scheme 14

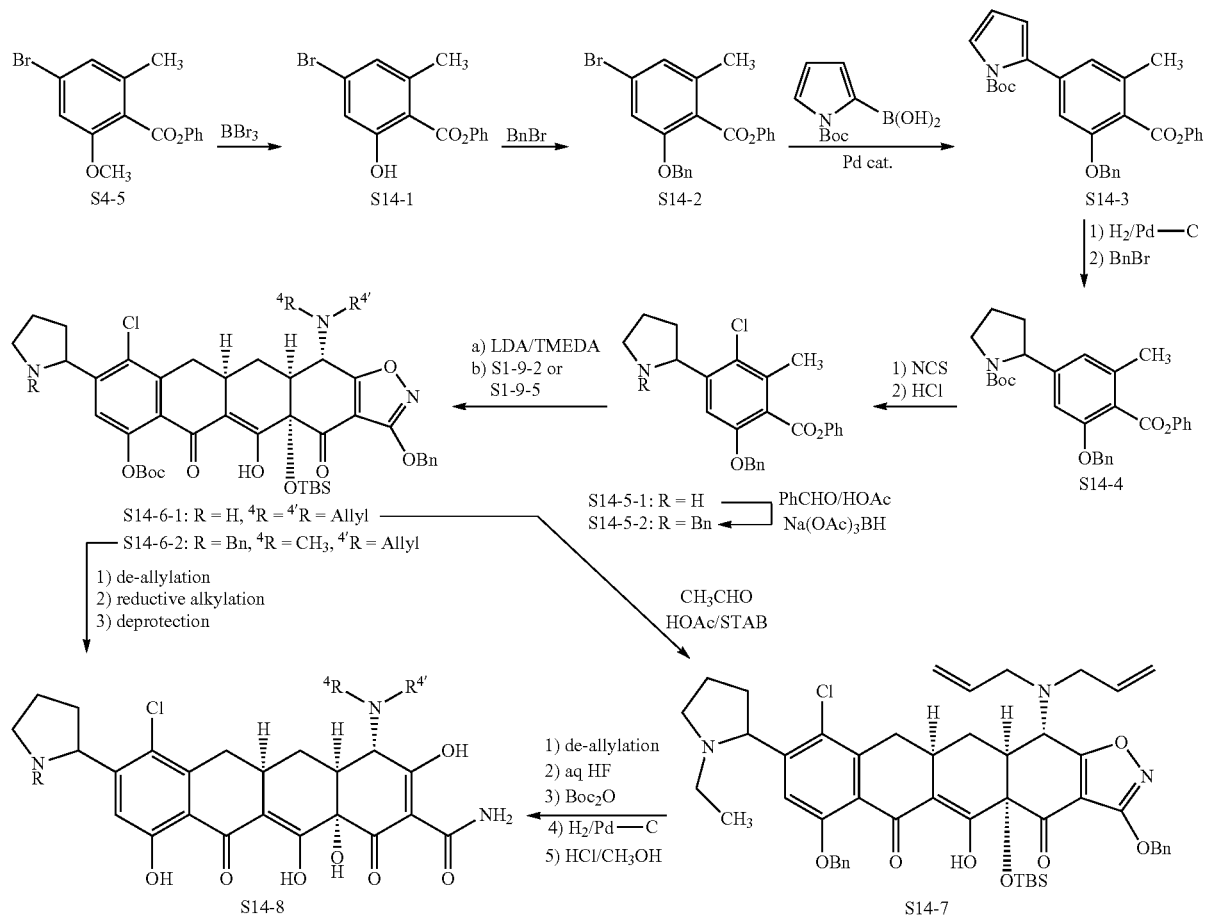

The following compounds were prepared according to Scheme 14.

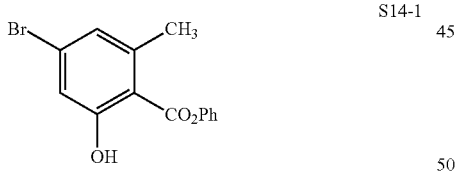

S14-1

To a solution of S4-5 (3.06 g, 9.53 mmol, 1 eq) in methylene chloride (19 mL) at −78° C. was added BBr$_3$ (9.53 mL, 1.0 M/CH$_2$Cl$_2$, 9.53 mmol, 1 eq) drop wise. The reaction mixture was stirred at −78° C. for 15 min and at 0° C. for 30 min. Saturated aqueous NaHCO$_3$ was added. The mixture was stirred at rt for 10 min and extracted with EtOAc (2 times). The organic extracts were combined, washed with brine, dried over sodium sulfate, and concentrated under reduced pressure to yield the desired product S14-1 as a white solid, which was used in the next reaction without further purification: $^1$H NMR (400 MHz, CDCl$_3$) δ 11.13 (s, 1H), 7.42-7.48 (m, 2H), 7.29-7.33 (m, 1H), 7.15-7.20 (m, 2H), 7.08 (s, 1H), 6.97 (s, 1H), 2.66 (s, 3H); MS (ESI) m/z 305.0 (M−H).

S14-2

To a solution of S14-1 (9.53 mmol, 1 eq) in acetone (19 mL) was added K$_2$CO$_3$ (2.63 g, 15.00 mmol, 1.5 eq) and BnBr (1.19 mL, 10.00 mmol, 1.05 eq). The mixture was stirred at rt overnight and filtered through a Celite pad. The Celite pad was washed with EtOAc. The combined filtrate was concentrated under reduced pressure. Flash chromatography on silica gel with 0%-5% EtOAc/hexanes yielded the desired product S14-2 as a white solid (3.61 g, 96% over 2 steps): $^1$H NMR (400 MHz, CDCl$_3$) δ 7.20-7.45 (m, 8H), 7.03-7.09 (m, 4H), 5.13 (s, 2H), 2.43 (s, 3H) MS (ESI) m/z 419.1 (M+Na).

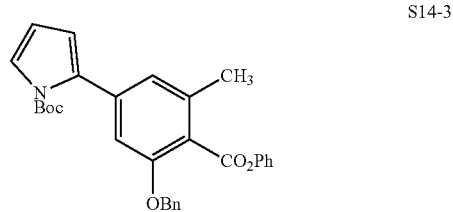

To a pressure vial was charged with compound S14-2 (852 mg, 2.14 mmol, 1 eq), N-Boc-2-pyrroleboronic acid (543 mg, 2.57 mmol, 1.2 eq), dichloro[1,1'-bis(diphenylphosphino)ferrrocene] palladium(II) dichloromethane adduct (88 mg, 0.11 mmol, 0.05 eq), and sodium carbonate (1.14 g, 10.7 mmol, 5 eq). The vial was briefly evacuated and filled with $N_2$. Toluene (5 mL), 1,4-dioxane (5 mL), and $H_2O$ (1 mL) were added. The reaction mixture was heated with a 90° C. oil bath for 2 h, cooled to rt, diluted with EtOAc, washed with aqueous phosphate buffer (pH=7) and brine, dried over $Na_2SO_4$, and concentrated. Purification of the residue by Biotage flash chromatography gave compound S14-3 as a colorless oil (621 mg, 60%): $^1$H NMR (400 MHz, $CDCl_3$) δ 7.22-7.48 (m, 9H), 7.12 (d, J=7.8 Hz, 2H), 6.89 (d, J=7.8 Hz, 2H), 6.20-6.26 (m, 2H), 5.15 (s, 2H), 2.48 (s, 3H), 1.41 (s, 9H); MS (ESI) m/z 484.4 (M+H).

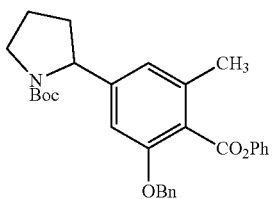

S14-4

Compound S14-3 (621 mg, 1.28 mmol, 1 eq) was dissolved in methanol. Pd—C (10% w/w, 186 mg) was added. The reaction flask was briefly evacuated and re-filled with hydrogen. The reaction mixture was stirred under 1 atm $H_2$ at rt for 2 h and filtered through a Celite pad. The Celite pad was washed with methanol. The filtrate was concentrated to give the intermediate as a white foam.

The above intermediate was dissolved in acetone (12 mL). $K_2CO_3$ (350 mg, 2.54 mmol, 2 eq) and BnBr (0.16 mL, 1.33 mmol, 1.04 eq) were added. After stirring for an overnight at rt, the reaction mixture was filtered through a Celite pad. The Celite pad was washed with three portions of EtOAc. The combined filtrate was concentrated. Purification of the residue by Biotage flash chromatography gave compound S14-4 as colorless oil (504 mg, 81%): $^1$H NMR (400 MHz, $CDCl_3$, rotamer) δ 7.22-7.48 (m, 8H), 7.05-7.15 (m, 2H), 6.63-6.70 (m, 2H), 5.13 (s, 2H), 4.90 and 4.76 (br s, 1H), 3.50-3.65 (m, 2H), 2.43 (s, 3H), 2.25-2.28 (m, 1H), 1.72-1.90 (m, 3H), 1.48 (s, 3H), 1.26 (s, 6H); MS (ESI) m/z 488.4 (M+H).

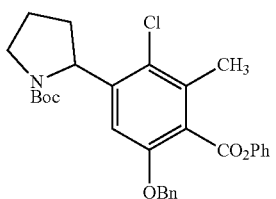

S14-4-a

To a solution of compound S14-4 (556 mg, 1.14 mmol, 1 eq) in 5 mL of $CH_3CN$ was added NCS (160 mg, 1.20 mmol, 1.05 eq) in one portion. The reaction mixture was heated with a 60° C. oil bath for 18 h, cooled to rt, and evaporated to dryness. The residue was suspended in 200 mL $CH_2Cl_2$, washed with aqueous NaOH (1 N), $H_2O$ and brine, dried over $Na_2SO_4$, and concentrated. Purification of the residue by Biotage flash chromatography gave compound S14-4-a as a white solid (447 mg, 75%): $^1$H NMR (400 MHz, $CDCl_3$, mixtures of rotamers) δ 7.22-7.48 (m, 8H), 7.05-7.15 (m, 2H), 6.63-6.70 (m, 1H), 5.06-5.26 (m, 3H), 3.47-3.58 (m, 2H), 2.46 (s, 3H), 2.25-2.28 (m, 1H), 1.55-1.88 (m, 3H), 1.48 (s, 3H), 1.26 (s, 6H); MS (ESI) m/z 522.4 (M+H).

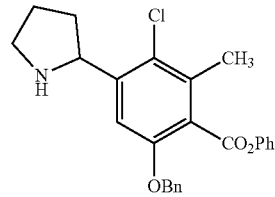

S14-5-1

Compound S14-4-a (447 mg, 0.86 mmol) was suspended in HCl/1,4-dioxane (4.0 M, 9 mL). After stirring at rt for 1 h, the volatiles were evaporated. The residue was suspended in EtOAc, washed with saturated aqueous $NaHCO_3$ and brine, dried over $Na_2SO_4$, and concentrated. Purification of the residue by Biotage flash chromatography gave compound S14-5-1 as an off-white solid (338 mg, 93%): $^1$H NMR (400 MHz, $CDCl_3$) δ 7.48 (dd, J=1.8, 7.8 Hz, 2H), 7.34-7.42 (m, 6H), 7.26 (t, J=7.8 Hz, 1H), 7.14 (d, J=7.8 Hz, 2H), 5.20 (s, 2H), 4.57 (t, J=7.4 Hz, 1H), 3.04-3.18 (m, 2H), 2.52 (s, 3H), 2.34-2.45 (m, 1H), 2.06 (br s, 1H), 1.78-1.85 (m, 2H), 1.44-1.54 (m, 1H); MS (ESI) m/z 422.4 (M+H).

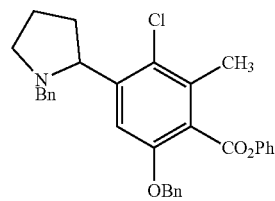

S14-5-2

To a solution of compound S14-5-1 (100 mg, 0.237 mmol, 1 eq) in DCM (3 mL) was added benzaldehyde (36 μL, 0.356 mmol, 1.5 eq), acetic acid (27 μL, 0.474 mmol, 2.0 eq) and sodium triacetoxyborohydride (100 mg, 0.474 mmol, 2.0 eq) in sequence. The resulting reaction mixture was stirred at rt for 1.5 h, and quenched with saturated aqueous sodium bicarbonate solution. The product was extracted into dichloromethane (3×15 mL). The combined organic extracts were dried over anhydrous sodium sulfate. The dried solution was filtered and the filtrate was concentrated. Flash chromatography on silica gel using 1%→15% EtOAc/hexanes yielded the desired product S14-5-2 (60 mg, 49%) as a white solid: $^1$H NMR (400 MHz, $CDCl_3$) δ 7.53 (s, 1H), 7.44-7.42 (m, 2H), 7.38-7.28 (m, 9H), 7.26-7.22 (m, 2H), 7.10-7.08 (m, 2H), 5.19, 5.14 (ABq, J=11.6 Hz, 2H), 3.97 (t, J=7.9 Hz, 1H), 3.85 (d, J=13.4 Hz, 1H), 3.20 (d, J=13.4 Hz, 1H), 3.18-3.13 (m, 1H), 2.49 (s, 3H), 2.46-2.36 (m, 1H), 2.31 (q, J=8.5 Hz, 1H), 1.86-1.78 (m, 2H), 1.56-1.45 (m, 1H); MS (ESI) m/z 512.27 (M+H).

S14-6-2

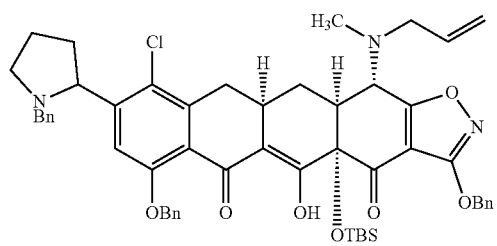

Compound S14-6-2 was prepared in 89% yield from S14-5-2 and N-methylallyl enone S1-9-5 using general procedure A. S14-6-2: ¹H NMR (400 MHz, CDCl₃, ~1:1 diastereomers) δ 16.08 (s, 0.5H), 16.07 (s, 0.5H), 7.57 (d, J=7.3 Hz, 1H), 7.52-7.44 (m, 4H), 7.41-7.21 (m, 11H), 5.91-5.82 (m, 1H), 5.38 (s, 2H), 5.30-5.17 (m, 4H), 4.09 (d, J=10.4 Hz, 1H), 3.96 (q, J=8.5 Hz, 1H), 3.80 (t, J=14.0 Hz, 1H), 3.48-3.40 (m, 2H), 3.33-3.14 (m, 3H), 3.07-2.96 (m, 1H), 2.65-2.29 (m, 7H), 2.20 (d, J=14.0 Hz, 1H), 1.85-1.77 (m, 3H), 1.53-1.43 (m, 1H), 0.87 (s, 4.5H), 0.86 (s, 4.5H), 0.30 (s, 3H), 0.18 (s, 1.5H), 0.17 (s, 1.5H); MS (ESI) m/z 926.53 (M+H).

Compound S14-8-2 was prepared from compound S14-6-2-a using general procedures D-1 (with acetaldehyde) and E. S14-8-2: ¹H NMR (400 MHz, CD₃OD, hydrochloride salt, ~1:1 diastereomers) δ 7.42-7.40 (m, 2H), 7.36-7.31 (m, 3H), 7.23 (s, 0.5H), 7.22 (s, 0.5H), 5.19-5.11 (m, 1H), 4.50, 4.36 (ABq, J=12.2 Hz, 1H), 4.48, 4.35 (ABq, J=12.2 Hz, 1H), 4.25 (s, 0.5H), 4.17 (s, 0.5H), 3.82-3.74 (m, 1H), 3.58-3.46 (m, 2H), 3.38-3.32 (m, 2H), 3.10-2.94 (m, 5H), 2.69-2.63 (m, 1H), 2.36-2.23 (m, 4H), 2.12-2.03 (m, 1H), 1.71-1.59 (m, 1H), 1.46-1.37 (m, 3H); MS (ESI) m/z 622.33 (M+H).

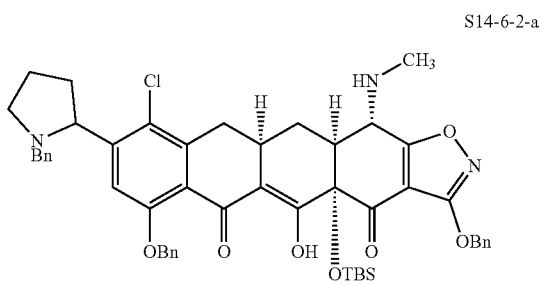 [SMILES: CN[C@@H]1c2onc(OCc3ccccc3)c2C(=O)[C@@]2(O[Si](C)(C)C(C)(C)C)C(O)=C3C(=O)c4c(OCc5ccccc5)cc(C5CCCN5Cc5ccccc5)c(Cl)c4C[C@H]3C[C@@H]12]

S14-6-2-a

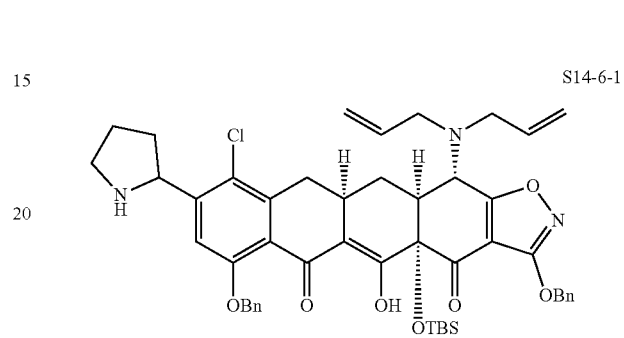

S14-6-1

Compound S14-6-2-a was prepared in 70% yield from compound 514-6-2 using general procedure B. S14-6-2-a: ¹H NMR (400 MHz, CDCl₃, ~1:1 diastereomers) δ 16.57 (s, 1H), 7.55 (d, J=6.7 Hz, 1H), 7.51-7.47 (m, 4H), 7.38-7.22 (m, 11H), 5.40, 5.36 (ABq, J=12.2 Hz, 2H), 5.29-5.13 (m, 2H), 7.92 (dt, J=1.8, 7.9 Hz, 1H), 3.81 (d, J=13.4 Hz, 0.5H), 3.76 (d, J=13.4 Hz, 0.5H), 3.66 (d, J=1.8 Hz, 1H), 3.28-3.12 (m, 3H), 2.86-2.76 (m, 1H), 2.72 (d, J=12.2 Hz, 1H), 2.60 (s, 3H), 2.43-2.19 (m, 2H), 2.10-2.03 (m, 1H), 1.82-1.76 (m, 2H), 1.62-1.43 (m, 3H), 0.74 (s, 9H), 0.21 (s, 3H), 0.11 (s, 3H); MS (ESI) m/z 886.51 (M+H).

Compound S14-6-1 was prepared in 24% yield from S14-5-1 and N-diallyl enone S1-9-2 using general procedure A (with the exception that 2.6 equivalents of LDA were used). S14-6-1 (~1:1 diastereomers): MS (ESI) m/z 862.44 (M+H).

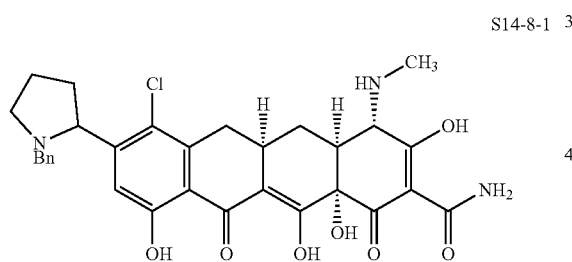

S14-8-1

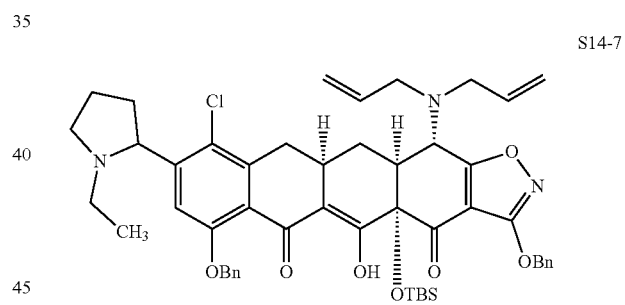

S14-7

Compound S14-8-1 was prepared from compound S14-6-2-a using general procedure E. S14-8-1: ¹H NMR (400 MHz, CD₃OD, hydrochloride salt, ~1:1 diastereomers) δ 7.42-7.40 (m, 2H), 7.35-7.30 (m, 3H), 7.224 (s, 0.5H), 7.222 (s, 0.5H), 5.19-5.11 (m, 1H), 4.49, 4.36 (ABq, J=13.3 Hz, 1H), 4.48, 4.35 (ABq, J=13.3 Hz, 1H), 3.85 (s, 0.5H), 3.84 (s, 0.5H), 3.82-3.73 (m, 1H), 3.57-3.50 (m, 1H), 3.36-3.27 (m, 1H), 3.03-3.29 (m, 1H), 3.94 (s, 1.5H), 3.92 (s, 1.5H), 2.85 (t, J=13.7 Hz, 1H), 2.71-2.63 (m, 1H), 2.35-2.21 (m, 4H), 2.13-2.01 (m, 1H), 1.61-1.50 (m, 1H); MS (ESI) m/z 594.27 (M+H).

Compound S14-7 was prepared from compound S14-6-1 using general procedure D-1 (with acetaldehyde). MS (ESI) m/z 890.52 (M+H).

S14-8-2

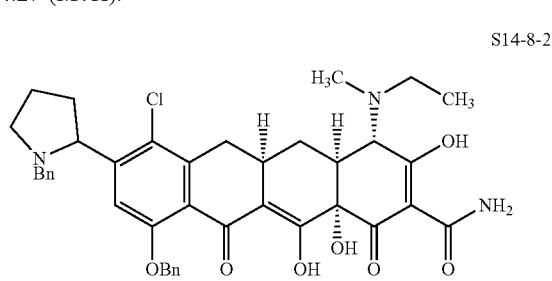

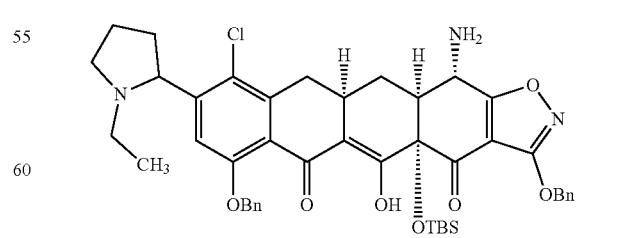

S14-7-a

Compound S14-7-a was prepared in 80% yield over 2 steps from crude compound S14-7 using general procedure B. S14-7-a: MS (ESI) m/z 810.43 (M+H).

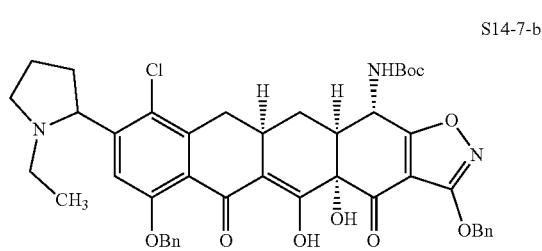 [SMILES: CCN1CCCC1c1cc(OCc2ccccc2)c2c(c1Cl)C[C@H]1C[C@H]3[C@H](NC(=O)OC(C)(C)C)c4onc(OCc5ccccc5)c4C(=O)[C@@]3(O)C(O)=C1C2=O]

Compound S14-7-b was prepared from compound S14-7-a using the first step of general procedure C followed by Boc protection. Thus, the crude desilyllation product (MS (ESI) m/z 696.31 (M+H)) was dissolved in DCM (2 mL). Boc$_2$O (16 mg, 0.072 mmol, 3.0 eq) and DMAP (cat.) were added. The resulting reaction solution was stirred at rt overnight. The reaction was concentrated to yield compound S14-7-b, which was used directly for the hydrogenation reaction below. S14-7-b: MS (ESI) m/z 796.39 (M+H).

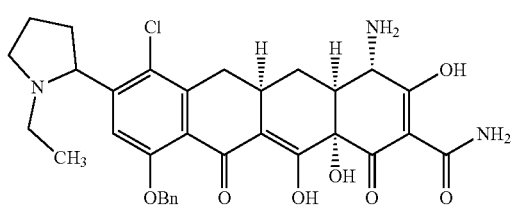

Compound S14-8-3 was prepared from compound S14-7-b using the second step of general procedure C followed by HCl/MeOH treatment. Thus the crude hydrogenation product was dissolved in 1 M HCl/MeOH (1 mL). The resulting reaction solution was stirred at rt for 30 min and concentrated. The residue was purified by preparative reverse phase HPLC on a Waters Autopurification system using a Phenomenex Polymerx 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water); gradient: 0→35% B in A over 20 min; mass-directed fraction collection]. Fractions containing the desired product were collected and freeze-dried to yield compound S14-8-3-A (1.07 mg, early eluting product) and compound S14-8-3-B (1.11 mg, later eluting product).

S14-8-3-A: $^1$H NMR (400 MHz, CD$_3$OD, hydrochloride salt) δ 7.22 (s, 1H), 5.10-5.05 (m, 1H), 3.93-3.89 (m, 2H), 3.44-3.15 (m, 3H), 3.06-2.99 (m, 1H), 2.68-2.62 (m, 2H), 2.44 (t, J=14.2 Hz, 1H), 2.36-2.23 (m, 4H), 2.16-2.08 (m, 1H), 1.65-1.56 (m, 1H), 1.29 (t, J=7.3 Hz, 3H); MS (ESI) m/z 518.22 (M+H).

S14-8-3-B: $^1$H NMR (400 MHz, CD$_3$OD, hydrochloride salt) δ 7.22 (s, 1H), 5.08-5.04 (m, 1H), 3.94-3.88 (m, 2H), 3.44-3.15 (m, 3H), 3.06-2.99 (m, 1H), 2.70-2.64 (m, 2H), 2.43 (t, J=16.0 Hz, 1H), 2.36-2.25 (m, 4H), 2.17-2.10 (m, 1H), 1.66-1.57 (m, 1H), 1.29 (t, J=7.3 Hz, 3H); MS (ESI) m/z 518.22 (M+H).

Scheme 15

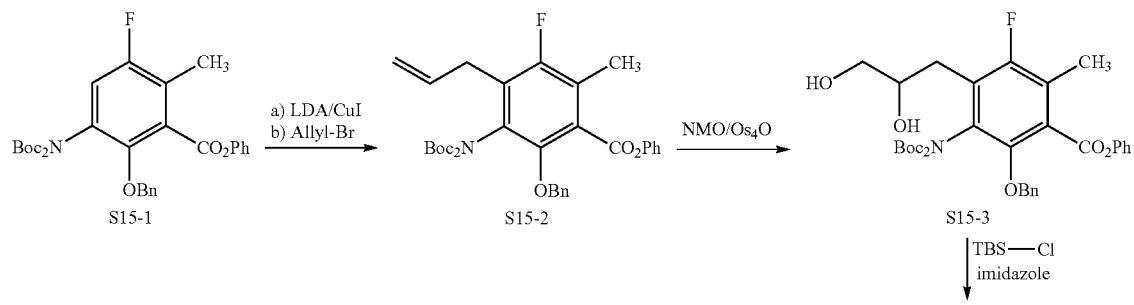

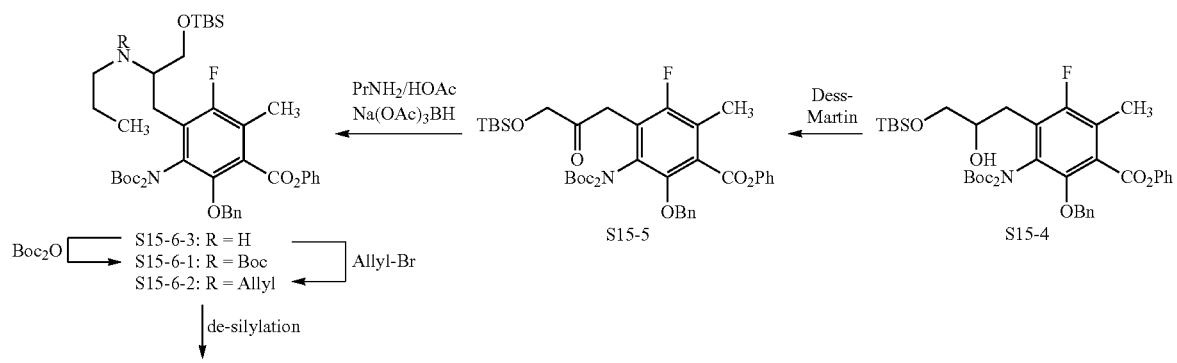

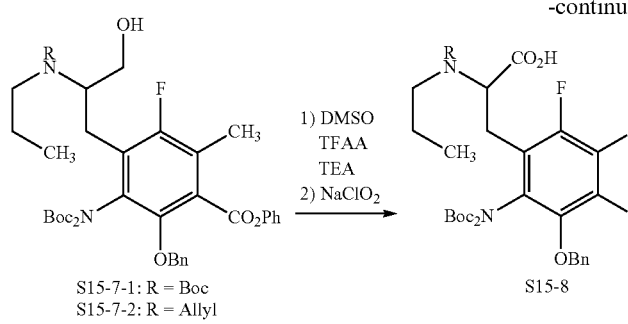

S15-7-1: R = Boc
S15-7-2: R = Allyl

1) DMSO
TFAA
TEA
2) NaClO₂

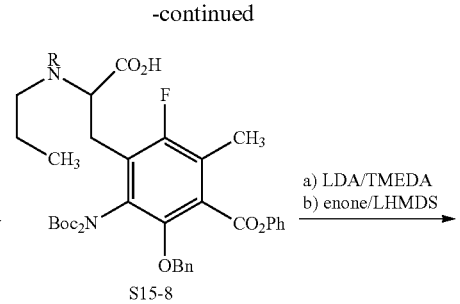

S15-8 a) LDA/TMEDA
b) enone/LHMDS

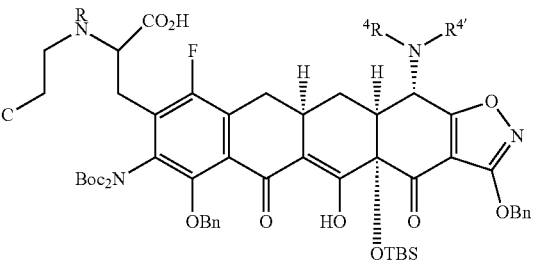

S15-9-1: R = Boc, ⁴R = ⁴'R = Allyl
S15-9-2: R = Allyl, ⁴R = CH₃, ⁴'R = Et (see text)

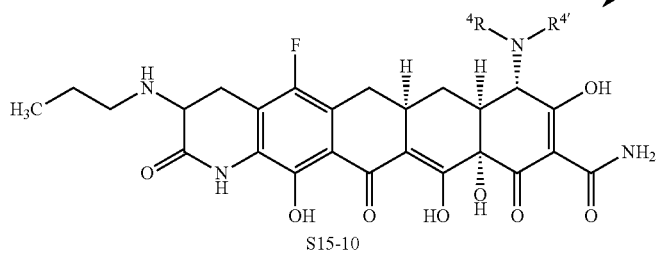

S15-10

The following compounds were prepared according to Scheme 15.

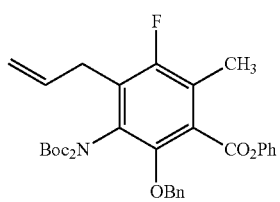

S15-2

To a solution of diisopropylamine (0.57 mL, 4.07 mmol, 1.5 eq) in THF (5 mL) at −78° C. was added "BuLi (2.54 mL, 1.6 M in hexane, 4.07 mmol, 1.5 eq) dropwise. The reaction was stirred at 0° C. for 10 min and cooled to −78° C. A solution of compound S15-1 (1.49 g, 2.70 mmol, 1 eq, prepared according to literature procedures including WO2011123536) in THF (5 mL) was added dropwise over 5 min. The reaction was stirred at −78° C. for 30 min. CuI powder (0.39 g, 2.05 mmol, 0.75 eq) was added. The reaction was stirred at −78° C. for 1 h. Allylbromide (0.48 mL, 5.36 mmol, 2 eq) was added. The reaction was stirred from −78° C. to rt overnight and quenched with saturated aqueous ammonium chloride (100 mL). The reaction mixture was extracted with methylene chloride (50 mL×3). The combined methylene chloride extracts were dried over sodium sulfate and concentrated. Flash chromatography on silica gel with 0→10% EtOAc/hexanes yielded compound S15-2 as a pale oil (1.32 g, 93%): $^1$H NMR (400 MHz, CDCl₃) δ 7.30-7.40 (m, 7H), 7.19-7.28 (m, 1H), 6.99 (d, J=8.0 Hz, 2H), 5.78-5.90 (m, 1H), 5.08 (d, J=21.0 Hz, 1H), 5.03 (d, J=10.4 Hz, 1H), 4.95 (s, 2H), 3.33 (d, J=6.1 Hz, 2H), 2.37 (d, J=2.4 Hz, 3H), 1.37 (s, 18H); MS (ESI) m/z 590.3 (M−H).

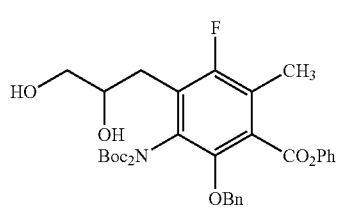

S15-3

To a solution of compound S15-2 (1.32 g, 2.23 mmol, 1 eq) in acetone (10 mL) was added water (0.57 mL), NMO (0.31 g, 2.65 mmol, 1.2 eq), and OsO4 (0.14 mL, 4% in water, 0.022 mmol, 0.01 eq). The resulting reaction mixture was stirred at 40° C. for 3 h and cooled to rt. Aqueous Na$_2$S$_2$O$_3$ solution (20 mL, 2 M) and water (20 mL) were added. The mixture was extracted with EtOAc (40 mL×3). The combined EtOAc extracts were dried over sodium sulfate and concentrated. Flash chromatography on silica gel with 0→80% EtOAc/hexanes yielded compound S15-3 as a white solid (1.27 g, 91%): $^1$H NMR (400 MHz, CDCl$_3$) δ 7.30-7.40 (m, 7H), 7.20-7.27 (m, 1H), 7.01 (d, J=7.3 Hz, 2H), 4.94 (s, 2H), 4.02-4.10 (m, 1H), 3.68 (dd, J=3.6, 11.6 Hz, 1H), 3.53 (dd, J=6.1, 10.0 Hz, 1H), 2.72-2.85 (m, 2H), 2.38 (d, J=2.4 Hz, 3H), 1.40 (s, 18H); MS (ESI) m/z 626.2 (M+H).

S15-4

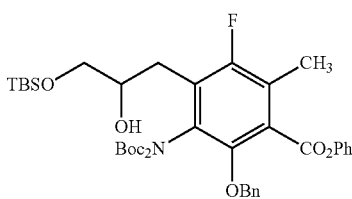

To a solution of compound S15-3 (2.22 g, 3.55 mmol, 1 eq) and imidazole (0.36 g, 5.29 mmol, 1.5 eq) in methylene chloride (20 mL) at rt was added a solution of TBSCl (0.64 g, 4.25 mmol, 1.2 eq) in methylene chloride (5 mL) dropwise over 5 min. The reaction was stirred at rt overnight. Saturated aqueous sodium bicarbonate solution (50 mL) was added. The mixture was extracted with methylene chloride (50 mL×3). The combined methylene chloride extracts were dried over sodium sulfate and concentrated. Flash chromatography on silica gel with 0→20% EtOAc/hexanes yielded compound S15-4 as a colorless oil (2.25 g, 86%): $^1$H NMR (400 MHz, CDCl$_3$) δ7.30-7.40 (m, 7H), 7.22-7.28 (m, 1H), 7.02 (d, J=7.3 Hz, 2H), 4.96 (s, 2H), 3.93-4.01 (m, 1H), 3.54-3.64 (m, 2H), 2.82-2.88 (m, 1H), 2.71-2.78 (m, 1H), 2.39 (d, J=2.4 Hz, 3H), 1.40 (s, 9H), 1.39 (s, 9H), 0.92 (s, 9H), 0.09 (s, 3H), 0.08 (s, 3H); MS (ESI) m/z 740.2 (M+H).

S15-5

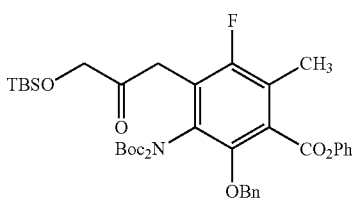

To a solution of compound S15-4 (2.25 g, 3.04 mmol, 1 eq) in methylene chloride (20 mL) was added Dess-Martin reagent (3.87 g, 9.12 mmol, 3 eq) at rt. After stirring for 5 min, methylene chloride (140 mL) containing water (0.164 mL, 9.12 mmol, 3 eq) was added. The resulting reaction was stirred at rt for 1 h and quenched with saturated aqueous sodium bicarbonate (50 mL) and aqueous Na$_2$S$_2$O$_3$ solution (50 mL, 2 M). The organic layer was separated. The aqueous layer was extracted with methylene chloride (100 mL×3). The combined organic layers were dried over sodium sulfate and concentrated. Flash chromatography on silica gel with 0→15% EtOAc/hexanes yielded compound S15-5 (2.11 g, 94%): $^1$H NMR (400 MHz, CDCl$_3$) δ 7.28-7.40 (m, 7H), 7.20-7.25 (m, 1H), 6.99 (d, J=7.9 Hz, 2H), 4.94 (s, 2H), 4.25 (s, 2H), 3.82 (d, J=1.6 Hz, 2H), 2.38 (d, J=1.5 Hz, 3H), 1.36 (s, 18H), 0.93 (s, 9H), 0.11 (s, 6H); MS (ESI) m/z 736.2 (M−H).

S15-6-3

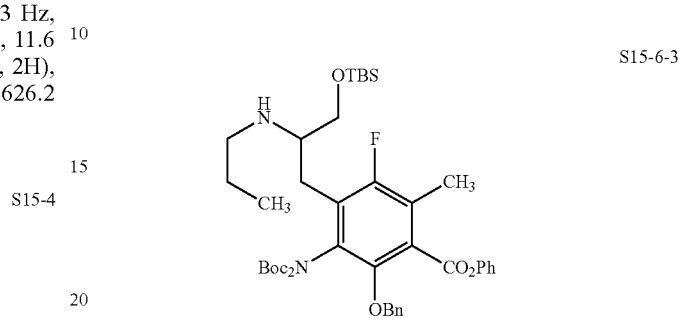

To a solution of compound S15-5 (1.01 g, 1.37 mmol, 1 eq) in dichloroethane (4 mL) was added acetic acid (0.47 mL, 8.22 mmol, 6 eq), propylamine (0.56 mL, 6.84 mmol, 5 eq), and Na(OAc)$_3$BH (1.45 g, 6.84 mmol, 5 eq). The resulting reaction mixture was stirred at rt for 3 days. Saturated aqueous sodium bicarbonate (15 mL) was added. The resulting mixture was stirred at rt for 15 min, and extracted with methylene chloride (30 mL, then 2×15 mL). The combined methylene chloride extracts were dried over sodium sulfate, filtered and concentrated to yield compound S15-6-3 as a pale yellow oil: MS (ESI) m/z 781.43 (M+H).

S15-6-1

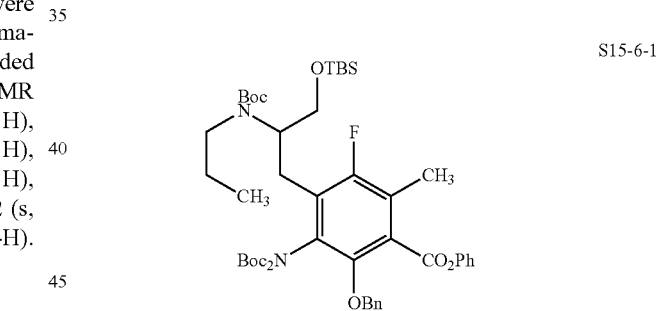

To a solution of the above crude compound S15-6-3 (1.37 mmol, 1 eq) in DCM (10 mL) was added Boc$_2$O (329 mg, 1.51 mmol, 1.1 eq) and DMAP (17 mg, 0.14 mmol, 0.1 eq). The resulting reaction solution was stirred at rt for 1.5 h. More Boc$_2$O (60 mg, 0.271 mmol, 0.2 eq) was added. The resulting reaction was stirred at rt for 1 h and stored in fridge over the weekend. The reaction was concentrated. The residue was purified by flash chromatography on silica gel with 0→15% EtOAc/hexanes to yield a mixture of products (835 mg), which were dissolved in MeCN (22.5 mL) in a polypropylene reaction vessel. A solution of HF in MeCN (1 M in aqueous acetonitrile, prepared from 48% aqueous HF and acetonitrile, 2.84 mL, 2.84 mmol) was added. The resulting reaction solution was stirred at rt for 30 min and quenched with saturated sodium bicarbonate and brine. The resulting mixture was extracted with EtOAc (50 mL×3). The combined organic extracts were dried over sodium sulfate, filtered and concentrated to yield compound S15-6-1: MS (ESI) m/z 879.51 (M−H).

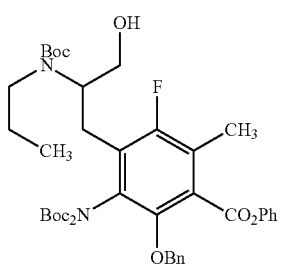

S15-7-1

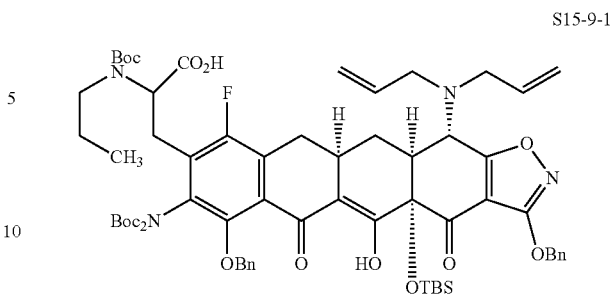

S15-9-1

To a solution of crude compound S15-6-1 (0.948 mmol, 1 eq) in THF (10 mL) was added HOAc (108 μL, 1.90 mmol, 2 eq) followed by TBAF (1.0 M in THF, 1.04 mL, 1.04 mmol, 1.1 eq). The resulting reaction was stirred at rt for 4 h and more TBAF (0.9 eq) was added. The resulting reaction was stirred at rt for 5 days and quenched with saturated aqueous sodium bicarbonate. The mixture was extracted with EtOAc (60 mL). The organic phase was dried over sodium sulfate, filtered and concentrated. The residue was purified by flash chromatography on silica gel with 1→50% EtOAc/hexanes to yield compound S15-7-1 (631 mg, 60% over 3 steps) as a white foamy solid: MS (ESI) m/z 765.37 (M−H).

Compound S15-9-1 was prepared in 20% yield from S15-8-1 and N-diallyl enone S1-9-2 using general procedure A (except that 3.5 equivalents of LDA were used). S15-9-1 (~1:1 diastereomers): MS (ESI) m/z 1221.53 (M+H).

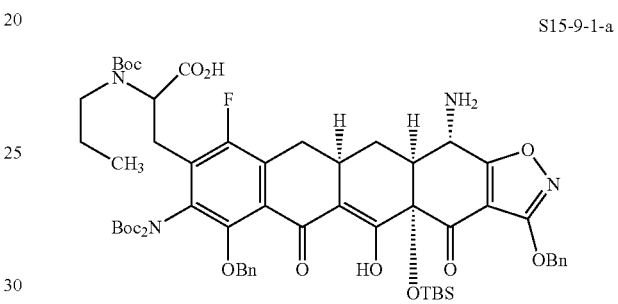

S15-9-1-a

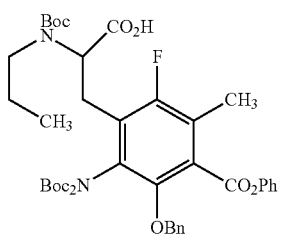

S15-8-1

Compound S15-9-1-a was prepared in 64% yield from compound S15-9-1 using general procedure B. S15-9-1-a (~1:1 diastereomers): MS (ESI) m/z 1141.44 (M+H).

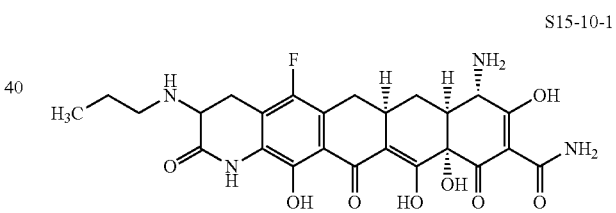

S15-10-1

To a solution of DMSO (0.88 mL, 12.34 mmol, 15 eq) in methylene chloride (10 mL) at −78° C. was added TFAA (1.15 mL, 8.23 mmol, 10 eq). The resulting suspension was warmed up to −40° C. and then cooled back to −78° C. A solution of compound S15-7-1 (631 mg, 0.823 mmol, 1 eq) in methylene chloride (3 mL) was added dropwise. The reaction was stirred at −78° C. for 3 h. Triethylamine (2.29 mL, 16.46 mmol, 20 eq) was added. The reaction was stirred at −78° C. for 10 min and warmed up to rt over 2 h, quenched with saturated aqueous sodium bicarbonate. The resulting mixture was extracted with DCM (30 mL, then 10 mL). The combined organic phase was dried over sodium sulfate, filtered and concentrated to yield the crude aldehyde intermediate: MS (ESI) m/z 765.31 (M+H).

The above aldehyde intermediate was dissolved in t-butanol (6 mL) and water (6 mL). NaH$_2$PO$_4$·H$_2$O (565 mg, 4.11 mmol, 5 eq) was added. The resulting solution was cooled to 0° C., followed by the addition of 2-methyl-2-butylene (435 μL, 4.11 mmol, 5 eq) and NaClO$_2$ (4.94 mL, 0.5 M in t-butanol/water (2:1, v/v), 2.46 mmol, 3 eq). The reaction was stirred at 0° C. for 30 min. Saturated aqueous ammonium chloride was added. The mixture was extracted with EtOAc (60 mL). The organic phase was washed with brine, dried over sodium sulfate, filtered and concentrated. Flash chromatography on silica gel with 10→80% EtOAc/hexanes yielded compound S15-8-1 as a yellow solid (640 mg, 100% over 2 steps): MS (ESI) m/z 779.33 (M−H).

Compound S15-10-1 was prepared from compound S15-9-1-a using general procedure E. S15-10-1: $^1$H NMR (400 MHz, CD$_3$OD, hydrochloride salt, ~1:1 diastereomers) δ 4.37-4.32 (m, 1H), 3.88 (s, 1H), 3.70-3.63 (m, 1H), 3.21-2.98 (m, 5H), 2.65 (d, J=12.8 Hz, 1H), 2.23-2.22 (m, 2H), 1.86-1.76 (m, 2H), 1.66-1.54 (m, 1H), 1.073 (t, J=7.3 Hz, 1.5H), 1.069 (t, J=7.3 Hz, 1.5H); MS (ESI) m/z 531.12 (M+H).

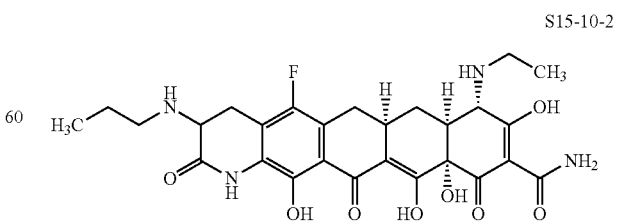

S15-10-2

Compound S15-10-2 was prepared from compound S15-9-1-a using general procedures D-1 (with acetaldehyde) and E. S15-10-2: $^1$H NMR (400 MHz, CD$_3$OD, hydrochloride salt, ~1:1 diastereomers) δ 4.34 (dd, J=5.5, 14.6 Hz, 1H), 3.86 (s, 1H), 3.70-3.63 (m, 1H), 3.47-3.30 (m, 2H), 3.25-3.12 (m, 3H), 3.06-2.98 (m, 2H), 2.84 (d, J=12.8 Hz, 1H), 2.31-2.21 (m, 2H), 1.86-1.75 (m, 2H), 1.61-1.52 (m, 1H), 1.362 (t, J=7.3 Hz, 1.5H), 1.358 (t, J=7.3 Hz, 1.5H), 1.072 (t, J=7.3 Hz, 1.5H), 1.068 (t, J=7.3 Hz, 1.5H); MS (ESI) m/z 559.16 (M+H).

S15-10-3

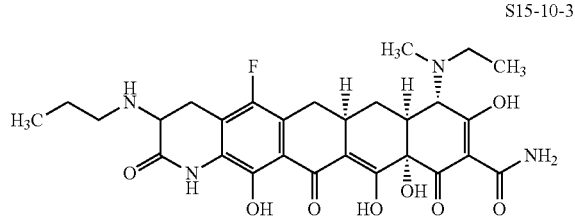 [SMILES: CCCNC1Cc2c(F)c3c(c(O)c2NC1=O)C(=O)C1=C(O)[C@]2(O)C(=O)C(C(N)=O)=C(O)[C@@H](N(C)CC)[C@@H]2C[C@@H]1C3]

Compound S15-10-3 was prepared from compound S15-9-1-a using general procedure D-1 (twice, with acetaldehyde followed by formaldehyde) and E. S15-10-3: $^1$H NMR (400 MHz, CD$_3$OD, hydrochloride salt, ~1:1 diastereomers) δ 4.35 (dd, J=6.4, 14.6 Hz, 1H), 4.22 (s, 0.5H), 4.13 (s, 0.5H), 3.71-3.64 (m, 1H), 3.52-3.44 (m, 1H), 3.38-3.30 (m, 1H), 3.23-3.12 (m, 3H), 3.07-2.93 (m, 6H), 2.32-2.21 (m, 2H), 1.86-1.75 (m, 2H), 1.70-1.58 (m, 1H), 1.43-1.36 (m, 3H), 1.07 (t, J=7.3 Hz, 3H); MS (ESI) m/z 573.16 (M+H).

S15-6-2

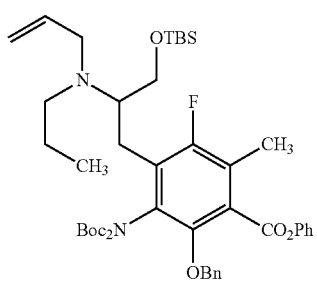

To a solution of compound S15-6-3 (0.686 mmol, crude, 1 eq) in acetonitrile (2 mL) was added potassium carbonate (190 mg, 1.37 mmol, 2 eq) and allylbromide (74 μL, 0.823 mmol, 1.2 eq). The resulting reaction mixture was stirred at rt for 2 days. Brine (50 mL) was added. The mixture was extracted with EtOAc (40 mL). The organic phase was washed with brine, dried over sodium sulfate, filtered and concentrated. Flash chromatography on silica gel with 0→10% EtOAc/hexanes yielded compound S15-6-2 as a colorless oil (415 mg, 74% for two steps): $^1$H NMR (400 MHz, CDCl$_3$) δ 7.34-7.26 (m, 7H), 7.21 (t, J=7.3 Hz, 1H), 6.99 (d, J=7.9 Hz, 2H), 5.81-5.71 (m, 1H), 5.12 (d, J=17.1 Hz, 1H), 4.96 (d, J=9.2 Hz, 1H), 4.86, 4.82 (AB q, J=10.4 Hz, 2H), 3.59 (dd, J=6.7, 10.4 Hz, 1H), 3.50 (dd, J=3.7, 10.4 Hz, 1H), 3.30 (dd, J=6.1, 14.6 Hz, 1H), 3.17 (dd, J=6.1, 14.6 Hz, 1H), 3.10-3.04 (m, 1H), 2.80 (dd, J=9.2, 13.4 Hz, 1H), 2.59-2.44 (m, 3H), 2.32 (d, J=1.8 Hz, 3H), 1.39 (s, 9H), 1.38-1.33 (m, 2H), 1.26 (s, 9H), 0.82 (s, 9H), 0.78 (t, J=7.3 Hz, 3H), -0.032 (s, 3H), -0.057 (s, 3H); MS (ESI) m/z 590.3 (M−H). MS (ESI) m/z 821.23 (M+H).

S15-7-2

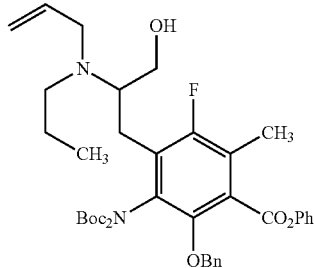

To a solution of compound S15-6-2 (415 mg, 0.505 mmol, 1 eq) in acetonitrile (24 mL) in a polypropylene reaction vessel was added HF (1.52 mL, 1 M in aqueous acetonitrile, prepared from 48% aqueous HF and acetonitrile, 1.52 mmol, 3 eq). The reaction was stirred at rt for 2 h and quenched with saturated aqueous sodium bicarbonate (5 mL). The resulting reaction mixture was evaporated, and the residue was extracted with EtOAc (40 mL). The organic phase was washed with brine, dried over sodium sulfate, filtered and concentrated to yield compound S15-7-2 as a white foamy solid (crude): $^1$H NMR (400 MHz, CDCl$_3$) δ 7.39-7.30 (m, 7H), 7.24 (t, J=7.3 Hz, 1H), 6.99 (d, J=7.9 Hz, 2H), 5.84-5.74 (m, 1H), 5.28 (d, J=17.1 Hz, 1H), 5.14 (d, J=10.4 Hz, 1H), 4.92, 4.88 (ABq, J=10.4 Hz, 2H), 3.41-3.36 (m, 2H), 3.26-3.15 (m, 3H), 3.01 (dd, J=7.9, 14.0 Hz, 1H), 2.71 (dt, J=12.8, 3.0 Hz, 1H), 2.64-2.54 (m, 2H), 2.50-2.43 (m, 1H), 2.37 (d, J=1.8 Hz, 3H), 1.61-1.51 (m, 2H), 1.46 (s, 9H), 1.33 (s, 9H), 0.92 (t, J=7.3 Hz, 3H); MS (ESI) m/z 707.18 (M+H).

S15-8-2

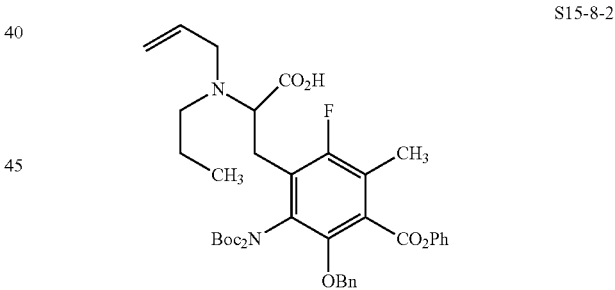

To a solution of DMSO (0.54 mL, 7.58 mmol, 15 eq) in methylene chloride (5 mL) at −78° C. was added TFAA (0.71 mL, 5.05 mmol, 10 eq). The resulting suspension was stirred at −78° C. for 20 min. A solution of the above crude compound S15-7-2 (0.505 mmol, 1 eq) in methylene chloride (5 mL) was added dropwise. The reaction was stirred at −78° C. for 3 h. Triethylamine (1.41 mL, 10.1 mmol, 20 eq) was added. The reaction was stirred at −78° C. for 10 min and warmed up to rt over 2 h, quenched with saturated aqueous sodium bicarbonate. The resulting mixture was extracted with EtOAc (50 mL). The organic phase was dried over sodium sulfate, filtered and concentrated to yield the crude aldehyde intermediate: MS (ESI) m/z 705.15 (M+H).

The above aldehyde intermediate was dissolved in t-butanol (7.5 mL) and water (7.5 mL). NaH$_2$PO$_4$.H$_2$O (348 mg, 2.52 mmol, 5 eq) was added. The resulting solution was cooled to 0° C., followed by the addition of 2-methyl-2-butylene (267 μL, 2.52 mmol, 5 eq) and NaClO₂ (3.03 mL, 0.5 M in t-butanol-water (2:1, v/v), 1.52 mmol, 3 eq). The reaction was stirred at 0° C. for 1 h. Saturated aqueous ammonium chloride was added. The mixture was extracted with EtOAc (60 mL). The organic phase was washed with brine, dried over sodium sulfate, filtered and concentrated. Flash chromatography on silica gel with 10→100% EtOAc/hexanes yielded compound S15-8-2 as a colorless oil (76 mg, 21% over 3 steps): ¹H NMR (400 MHz, CDCl₃) δ 7.37-7.30 (m, 7H), 7.26-7.22 (m, 1H), 7.03-7.00 (m, 2H), 5.84-5.74 (m, 1H), 5.22 (d, J=10.4 Hz, 1H), 5.18 (d, J=18.9 Hz, 1H), 4.92 (s, 2H), 4.04 (t, J=6.7 Hz, 1H), 3.68 (dd, J=6.1, 14.6 Hz, 1H), 3.35 (dd, J=5.5, 14.0 Hz, 1H), 3.21 (dd, J=7.3, 14.0 Hz, 1H), 2.81 (dd, J=7.6, 15.3 Hz, 1H), 2.63 (t, J=6.7 Hz, 2H), 2.38 (s, 3H), 1.60-1.49 (m, 2H), 1.45 (s, 9H), 1.33 (s, 9H), 0.90 (t, J=7.3 Hz, 3H); MS (ESI) m/z 721.18 (M+H).

S15-9-2

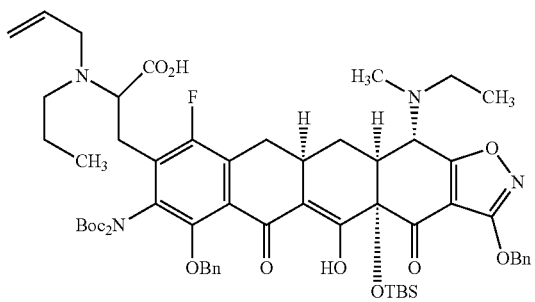

Compound S15-9-2 was prepared in 44% yield from S15-8-2 and N-methylethyl enone S1-9-1 using general procedure A (except that 2.2 equivalents of LDA were used) as a mixture of two diastereomers, which were separated by preparative reverse phase HPLC on a Waters Autopurification system using a Sunfire Prep C18 OBD column [5 μm, 19×50 mm; flow rate, 20 mL/min; Solvent A: H₂O with 0.1% HCO₂H; Solvent B: MeOH with 0.1% HCO₂H; gradient: 85→92% B over 15 min, then 100% B for 5 min; mass-directed fraction collection]. Fractions with the desired MW were collected and concentrated to afford the desired product S15-9-2-A (20.3 mg, 17%, early eluting product) and S15-9-2-B (19.7 mg, 17%, later eluting product).

S15-9-2-A: ¹H NMR (400 MHz, CDCl₃, ~1:1 rotamers) δ 16.02 (br s, 1H), 7.51-7.48 (m, 4H), 7.38-7.32 (m, 6H), 5.85-5.75 (m, 1H), 5.35 (s, 2H), 5.25-5.17 (m, 2H), 5.04 (dd, J=3.0, 9.2 Hz, 2H), 4.72 (dd, J=2.4, 9.2 Hz, 1H), 4.06-4.03 (m, 1H), 3.98 (dd, J=3.0, 10.4 Hz, 1H), 3.52-3.38 (m, 2H), 3.28-3.24 (m, 2H), 3.05-2.98 (m, 1H), 2.84-2.80 (m, 2H), 2.66 (br s, 3H), 2.58-2.39 (m, 6H), 2.17 (d, J=14.6 Hz, 1H), 1.59-1.53 (m, 2H), 1.46 (s, 4.5H), 1.45 (s, 4.5H), 1.28 (s, 4.5H), 1.27 (s, 4.5H), 1.14-1.10 (m, 3H), 0.90-0.87 (m, 3H), 0.82 (s, 4.5H), 0.81 (s, 4.5H), 0.27 (s, 1.5H), 0.26 (s, 1.5H), 0.14 (s, 1.5H), 0.13 (s, 1.5H); MS (ESI) m/z 1123.18 (M+H).

S15-9-2-B: ¹H NMR (400 MHz, CDCl₃) δ 15.89 (br s, 1H), 7.50-7.48 (m, 2H), 7.44-7.42 (m, 2H), 7.39-7.30 (m, 6H), 5.89-5.79 (m, 1H), 5.35 (s, 2H), 5.32 (d, J=10.4 Hz, 1H), 5.22 (d, J=17.1 Hz, 1H), 4.82, 4.77 (ABq, J=9.2 Hz, 2H), 4.14 (t, J=6.1 Hz, 1H), 3.97 (d, J=10.4 Hz, 1H), 3.61 (dt, J=4.9, 15.9 Hz, 1H), 3.41 (dd, J=7.3, 13.4 Hz, 1H), 3.24 (dd, J=7.9, 15.9 Hz, 1H), 3.06-2.99 (m, 1H), 2.96-2.86 (m, 2H), 2.85-2.74 (m, 2H), 2.69-2.63 (m, 1H), 2.60-2.56 (m, 1H), 2.51-2.43 (m, 2H), 2.39 (s, 3H), 2.19 (d, J=14.0 Hz, 1H), 1.65-1.59 (m, 2H), 1.39 (s, 9H), 1.35 (s, 9H), 1.17 (t, J=7.3 Hz, 3H), 0.87 (t, J=7.3 Hz, 3H), 0.82 (s, 9H), 0.27 (s, 3H), 0.13 (s, 3H); MS (ESI) m/z 1123.18 (M+H).

S15-9-2-a

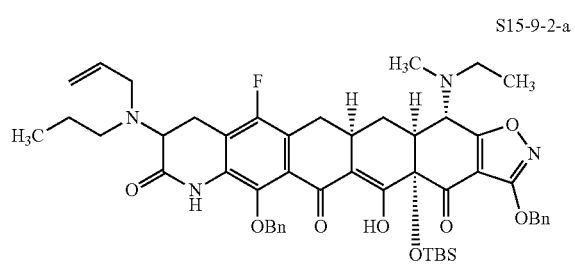 [SMILES: C=CCN(CCC)C1Cc2c(F)c3c(c(OCc4ccccc4)c2NC1=O)C(=O)C1=C(O)[C@]2(O[Si](C)(C)C(C)(C)C)C(=O)c4c(OCc5ccccc5)noc4[C@@H](N(C)CC)[C@@H]2C[C@@H]1C3]

Single diastereomer S15-9-2-B (19.7 mg, 0.018 mmol, 1 eq) was dissolved in dioxane (0.25 mL). HCl-dioxane (0.25 mL, 4 N) was added dropwise. The resulting reaction solution was stirred at rt for 3 h and quenched with saturated sodium bicarbonate solution (~3 mL). The resulting reaction mixture was extracted with EtOAc (30 mL). The organic phase was dried over sodium sulfate, filtered and concentrated to yield compound S15-9-2-a-B (crude): MS (ESI) m/z 905.31 (M+H).

Single diastereomer S15-9-2-A was similarly converted to the corresponding single diastereomer S15-9-2-a-A: MS (ESI) m/z 905.25 (M+H).

S15-10-3

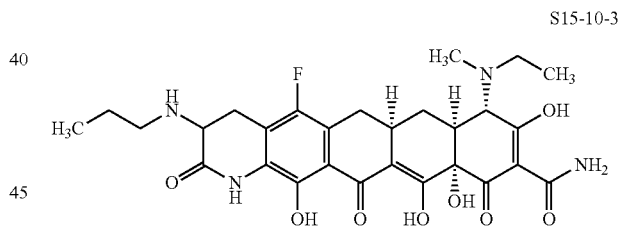

Single diastereomers S15-10-3-A and S15-10-3-B were prepared from the corresponding compounds S15-9-2-a-A and S15-9-2-a-B separately using general procedures B and C.

S15-10-3-A: ¹H NMR (400 MHz, CD₃OD, hydrochloride salt, ~1:1 conformers) δ 4.35 (dd, J=6.9, 14.6 Hz, 1H), 4.22 (s, 0.5H), 4.13 (s, 0.5H), 3.69 (dd, J=6.9, 15.6 Hz, 1H), 3.53-3.46 (m, 1H), 3.38-3.31 (m, 1H), 3.23-3.14 (m, 3H), 3.07-2.94 (m, 6H), 2.31-2.21 (m, 2H), 1.86-1.76 (m, 2H), 1.70-1.58 (m, 1H), 1.44-1.37 (m, 3H), 1.07 (t, J=7.3 Hz, 3H); MS (ESI) m/z 573.09 (M+H).

S15-10-3-B: ¹H NMR (400 MHz, CD₃OD, hydrochloride salt, ~1:1 conformers) δ 4.35 (dd, J=6.4, 14.6 Hz, 1H), 4.22 (s, 0.5H), 4.13 (s, 0.5H), 3.67 (dd, J=6.9, 16.0 Hz, 1H), 3.54-3.46 (m, 1H), 3.38-3.30 (m, 1H), 3.23-3.12 (m, 3H), 3.07-2.93 (m, 6H), 2.32-2.21 (m, 2H), 1.86-1.76 (m, 2H), 1.70-1.58 (m, 1H), 1.43-1.36 (m, 3H), 1.07 (t, J=7.3 Hz, 3H); MS (ESI) m/z 573.09 (M+H).

Scheme 16

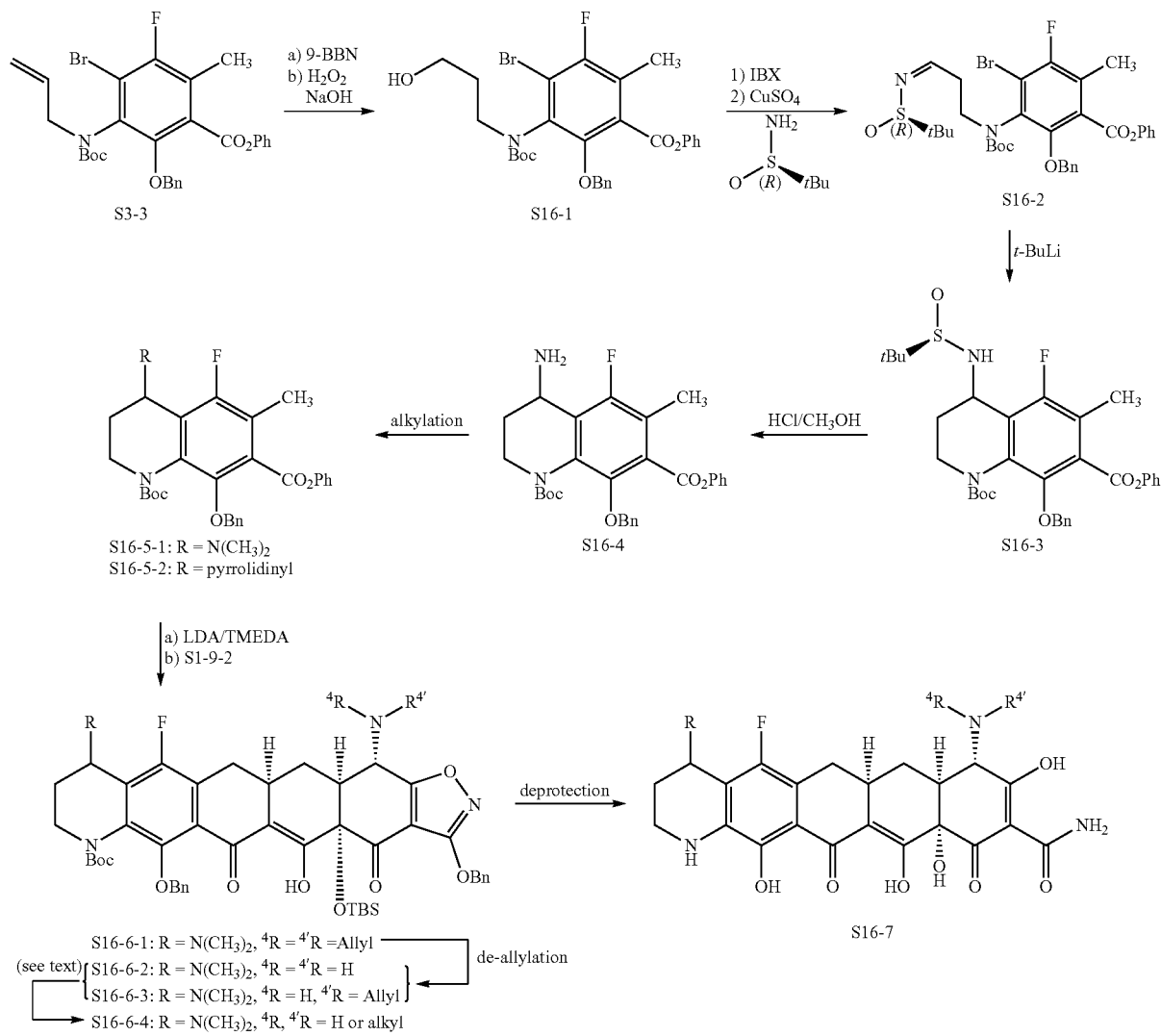

The following compounds were prepared according to Scheme 16.

S16-1

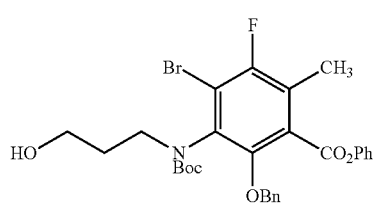

9-Borabicyclo[3.3.1]nonane solution (0.5 M in THF, 27.0 mL, 13.5 mmol) was added to a solution of compound S3-3 (2.56 g, 0.4.49 mmol) in THF (20 mL). After 1 h, the reaction mixture was cooled to 0° C. and NaOH (6 N aqueous solution, 6.75 mL, 40.4 mmol) was carefully added followed by hydrogen peroxide (30% aqueous solution, 4.6 mL, 40.4 mmol). After 10 min, the reaction mixture was diluted with EtOAc and was washed with water (2×) and brine (1×). The organics were dried over $Na_2SO_4$, were filtered, and were concentrated under reduced pressure to yield the crude product S16-1: $^1H$ NMR (400 MHz, $CDCl_3$) δ 7.38-7.32 (m, 7H), 7.28-7.22 (m, 1H), 7.02-6.97 (m, 2H), 4.92 (ABq, J=27.5 Hz, 10.1 Hz, 2H), 3.99-3.90 (m, 1H), 3.88-3.80 (m, 1H), 3.70-3.63 (m, 1H), 3.59-3.51 (m, 1H), 2.41 (d, J=2.3 Hz, 3H), 1.74-1.62 (m, 2H), 1.42 (s, 9H); MS (ESI) m/z 587.93, 589.93 (M+H).

S16-2

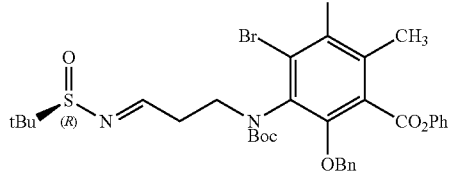

2-Iodoxybenzoic acid (stabilized, 45 wt %, 3.07 g, 4.93 mmol) was added to a solution of compound S16-1 (2.64 g, 4.49 mmol) in DMSO (12 mL). After 3 h, the reaction mixture was diluted with EtOAc and was filtered through Celite (EtOAc wash). The filtrate was washed with NaHCO$_3$ (saturated, aqueous solution, 3×) and brine (1×). The organics were dried over Na$_2$SO$_4$, were filtered, and were concentrated under reduced pressure. The material was dissolved in toluene (10 mL), and copper(II) sulfate (2.15 g, 13.5 mmol) and (R)-(+)-t-butylsulfinamide (1.09 g, 8.98 mmol) were added. After stirring for 2 days, the reaction mixture was diluted with EtOAc and was washed with water (3×) and brine (2×). The organics were dried over Na$_2$SO$_4$, were filtered, and were concentrated under reduced pressure. The material was purified by column chromatography (50 g Biotage column, 5 to 40% EtOAc in Hexanes gradient). This gave 1.165 mg (38%, 3 steps) of the desired product S16-2 as a thick oil: $^1$H NMR (400 MHz, CDCl$_3$) mixture of rotamers or E/Z isomers, δ 8.09-7.98 (m, 1H), 7.38-7.32 (m, 7H), 7.28-7.22 (m, 1H), 7.04-6.97 (m, 2H), 5.04-4.89 (m, 2H), 4.10-4.00 (m, 1H), 3.87-3.74 (m, 1H), 3.00-2.72 (m, 2H), 2.44-2.38 (m, 3H), 1.53 (s, 3H), 1.42 (s, 6H), 1.15-1.07 (m, 9H); MS (ESI) m/z 688.98, 690.98 (M+H).

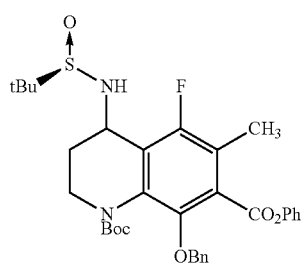

S16-3 t-Butyllithium (1.7 M solution, 1.98 mL, 3.37 mmol) was added dropwise to a −100° C. solution of compound S16-2 (1.165 g, 1.689 mmol) in THF (20 mL). After 5 min, the reaction mixture was quenched with NH$_4$Cl (saturated, aqueous solution), was diluted with EtOAc and was washed with water (1×) and brine (1×). The organics were dried over Na$_2$SO$_4$, were filtered, and were concentrated under reduced pressure. The material was purified by column chromatography (50 g Biotage column, 30 to 90% EtOAc in Hexanes gradient). This gave 505 mg (49%) of the desired product S16-3 as a white solid (single diastereomer): $^1$H NMR (400 MHz, CDCl$_3$) δ 7.42-7.34 (m, 2H), 7.33-7.22 (m, 6H), 7.10-7.04 (m, 2H), 4.93-4.76 (m, 3H), 3.42-3.34 (m, 1H), 2.37-2.27 (m, 4H), 2.10-1.90 (m, 2H), 1.33 (s, 9H), 1.16 (s, 9H); MS (ESI) m/z 611.74 (M+H).

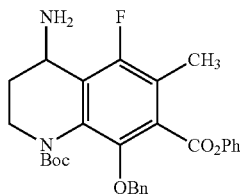

S16-4

Compound S16-3 (158 mg, 0.258 mmol) was stirred in HCl (4 M solution in 1,4-dioxane, 0.5 mL) and MeOH (2.5 mL). After 4 h, the reaction mixture was diluted with EtOAc and was washed with NaHCO$_3$ (saturated, aqueous solution, 3×) and brine (1×). The organics were dried over Na$_2$SO$_4$, were filtered, and were concentrated under reduced pressure to give compound S16-4 (single enantiomer): MS (ESI) m/z 507.19 (M+H).

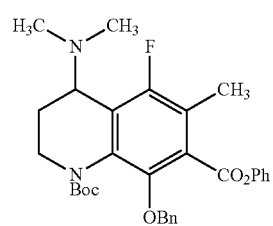

S16-5-1

Crude S16-4 (0.258 mmol) was dissolved in CH$_2$Cl$_2$ (5 mL) and Na(OAc)$_3$BH (219 mg, 1.03 mmol) and formaldehyde (37% aqueous solution, 1 mL) were added. After 30 min, the reaction mixture was diluted with EtOAc. The mixture was washed with NaHCO$_3$ (saturated, aqueous solution, 3×) and brine (1×), was dried over Na$_2$SO$_4$, was filtered, and was concentrated. The material was purified by column chromatography (25 g Biotage column, 20 to 80% EtOAc in Hexanes gradient) to give 117 mg (85%, 2 steps) of the product S16-5-1 (single diastereomer): $^1$H NMR (400 MHz, CDCl$_3$) δ 7.44-7.20 (m, 8H), 7.08-7.02 (m, 2H), 4.98-4.76 (m, 2H), 4.22-4.10 (m, 1H), 3.90-3.82 (m, 1H), 3.10-2.98 (m, 1H), 2.38-2.27 (m, 4H), 2.20 (s, 6H), 1.70-1.56 (m, 1H), 1.30 (s, 9H); MS (ESI) m/z 535.32 (M+H).

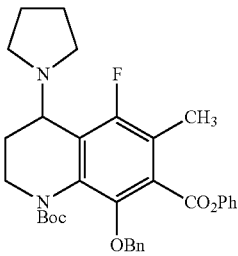

S16-5-2

Crude S16-4 (0.247 mmol) was dissolved in CH$_3$CN (2 mL) and triethylamine (0.103 mL, 0.741 mmol) and 1,4-dibromobutane (0.0292 mL, 0.247 mmol) were added. The reaction mixture was heated to 130° C. for 15 min in a microwave reactor. Additional 1,4-dibromobutane (0.050 mL, 0.42 mmol) was added, and the mixture was again heated to 130° C. for 15 min by microwave reactor. The reaction mixture was diluted with EtOAc, was washed with NaHCO$_3$ (saturated, aqueous solution, 2×) and brine (1×), was dried over Na$_2$SO$_4$, was filtered, and was concentrated. The material was purified by column chromatography (10 g Biotage column, 20 to 60% EtOAc in Hexanes gradient) to give 41.2 mg (30%, 2 steps) of the product S16-5-2 (single enantiomer): $^1$H NMR (400 MHz, CDCl$_3$) δ 7.40-7.20 (m, 8H), 7.08-7.01 (m, 2H), 5.00 and 4.79 (ABq, J=10.6 Hz, 2H), 4.22-4.10 (m, 1H), 3.84-3.80 (m, 1H), 3.20-3.08 (m, 1H), 2.68-2.58 (m, 2H), 2.42-2.30 (m, 6H), 1.76-1.55 (m, 5H), 1.30 (s, 9H); MS (ESI) m/z 561.23 (M+H).

S16-6-1

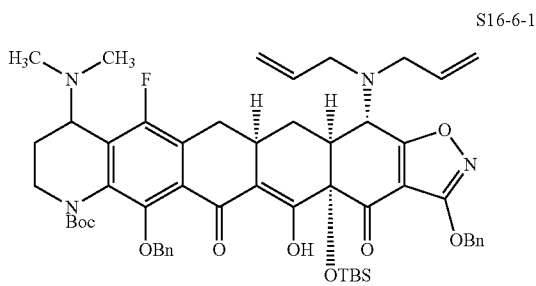 [SMILES: C=CCN(CC=C)[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)N(C(=O)OC(C)(C)C)CCC5N(C)C)C[C@H]3C[C@@H]12]

Lithium diisopropylamide was prepared from diisopropylamine (0.0382 mL, 0.270 mmol) and n-BuLi (1.6 M solution, 0.169 mL, 0.270 mmol) in THF (3 mL) at −40° C. The reaction mixture was cooled to −78° C., and TMEDA (0.125 mL, 0.832 mmol) was added. A solution of compound S16-5-1 (117 mg, 0.219 mmol) in THF (1 mL) was then added dropwise, resulting in an orange-red solution. The reaction mixture was stirred at −78° C. for 30 min. A solution of enone S1-9-2 (111 mg, 0.208 mmol) in THF (1 mL) was added dropwise, followed by LHMDS (1.0 M solution, 0.25 mL, 0.25 mmol). The reaction mixture was allowed to warm to −10° C. over 1 h. The reaction was quenched by the addition of ammonium chloride (saturated, aqueous solution) and was diluted with EtOAc. The mixture was washed with water (3×) and brine (1×), was dried over $Na_2SO_4$, was filtered, and was concentrated under reduced pressure. The material was purified by column chromatography (25 g Biotage column, 15 to 50% EtOAc in Hexanes gradient). This gave 116 mg of S16-6-1 (57%, single diastereomer): $^1$H NMR (400 MHz, $CDCl_3$) δ 15.9 (s, 1H), 7.44-7.36 (m, 2H), 7.36-7.12 (m, 8H), 5.87-5.65 (m, 2H), 5.26 (s, 2H), 5.20-5.00 (m, 4H), 4.96-4.84 (m, 1H), 4.66-4.48 (m, 1H), 4.12-3.95 (m, 2H), 3.82-3.72 (m, 1H), 3.28-3.18 (m, 2H), 3.17-3.00 (m, 3H), 2.95-2.80 (m, 2H), 2.51 (t, J=14.7 Hz, 1H), 2.44-2.16 (m, 3H), 2.10 (s, 6H), 2.25-1.96 (m, 1H), 1.58-1.44 (m, 1H), 1.33 (s, 2.7H), 1.07 (s, 5.3H), 0.68 (s, 9H), 0.15 (s, 3H), 0.00 (s, 3H); MS (ESI) m/z 975.39 (M+H).

S16-6-2

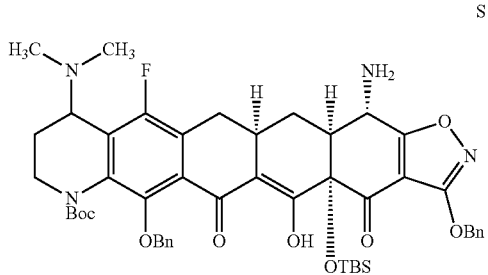

Compound S16-6-1 (42.2 mg, 0.0433 mmol), 1,3-dimethylbarbituric acid (27.0 mg, 0.173 mmol), and $Pd(Ph_3P)_4$ (5.0 mg, 0.0043 mmol) were dissolved in $CH_2Cl_2$ (2 mL), and the reaction mixture was evacuated and backfilled with nitrogen (3×). After 6 h, the reaction mixture was diluted with EtOAc, was washed with $NaHCO_3$ (saturated, aqueous, 3×) and pH 7 phosphate buffer (1×), was dried over $Na_2SO_4$, was filtered, and was concentrated under reduced pressure. The material was purified by column chromatography (10 g Biotage column, 50 to 100% EtOAc in Hexanes gradient). This gave 30.9 mg of S16-6-2 (80%, single diastereomer): MS (ESI) m/z 895.38 (M+H).

S16-6-4-1

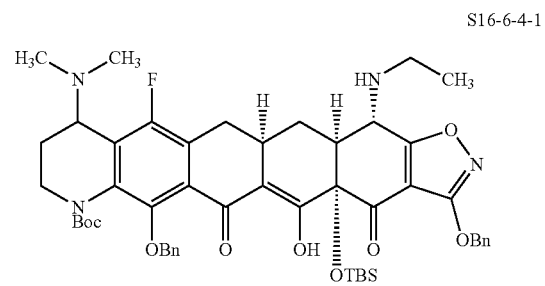 [SMILES: CCN[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)N(C(=O)OC(C)(C)C)CCC5N(C)C)C[C@H]3C[C@@H]12]

Compound S16-6-2 (30.9 mg, 0.0345 mmol) and acetic acid (0.0039 mL, 0.069 mmol) were dissolved in MeOH (1 mL), and the reaction mixture was cooled to 0° C. $Na(OAc)_3BH$ (14.6 mg, 0.069 mmol) and acetaldehyde (50 wt % solution in EtOH, 0.0026 mL, 0.0518 mmol) were added. After 10 min, ~90% conversion was observed by LC/MS. Additional $Na(OAc)_3BH$ (14.6 mg, 0.069 mmol) and acetaldehyde (50 wt % solution in EtOH, 0.0026 mL, 0.0518 mmol) were added. After 5 min, the reaction mixture was quenched with $NaHCO_3$ (saturated, aqueous) and was diluted with EtOAc. The mixture was washed with $NaHCO_3$ (saturated, aqueous, 2×) and pH 7 phosphate buffer (1×), was dried over $Na_2SO_4$, was filtered, and was concentrated under reduced pressure. This gave 28.5 mg (90%) of crude S16-6-4-1, which was used without further purification: MS (ESI) m/z 923.36 (M+H).

S16-6-4-2

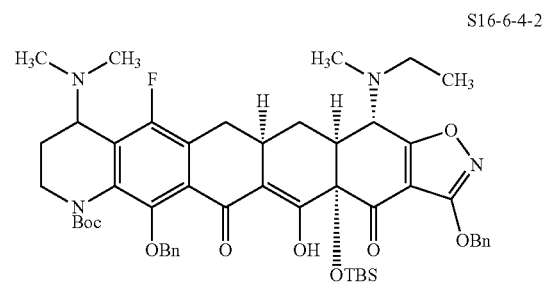 [SMILES: CCN(C)[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)N(C(=O)OC(C)(C)C)CCC5N(C)C)C[C@H]3C[C@@H]12]

Formaldehyde (37% aqueous solution, 0.5 mL) was added to a mixture of compound S16-6-4-1 (14.3 mg, 0.0155 mmol) and $Na(OAc)_3BH$ (9.8 mg, 0.046 mmol) in $CH_2Cl_2$ (1 mL). After 1 h, the reaction mixture was diluted with EtOAc, was washed with $NaHCO_3$ (saturated, aqueous, 2×) and pH 7 phosphate buffer (1×), was dried over $Na_2SO_4$, was filtered, and was concentrated under reduced pressure to give the crude compound S16-6-4-2, which was used without further purification: MS (ESI) m/z 937.49 (M+H).

S16-7-1

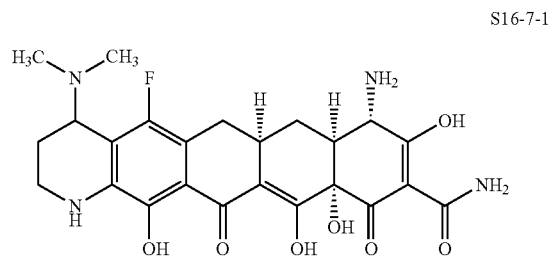 [SMILES: CN(C)C1CCNc2c(O)c3c(c(F)c21)C[C@H]1C[C@H]2[C@H](N)C(O)=C(C(N)=O)C(=O)[C@@]2(O)C(O)=C1C3=O]

Compound S16-6-2 (19.5 mg, 0.0218 mmol) was stirred in methanesulfonic acid (0.10 mL), dimethylsulfide (0.020 mL), and $CH_2Cl_2$ (0.20 ml). After stirring overnight, the reaction mixture was concentrated under a flow of air. Dimethylsulfide (0.020 mL), and $CH_2Cl_2$ (0.040 ml) were added, and the mixture was stirred overnight. Additional dimethylsulfide (0.040 mL) was added, and the mixture was stirred for 5 h. The reaction mixture was diluted with 0.05 N aqueous HCl (2 mL) and was purified directly on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→50% B; mass-directed fraction collection]. Fractions with the desired MW were collected and freeze-dried to yield 7.6 mg (57%) of S16-7-1 as a yellow solid (single diastereomer): ¹H NMR (400 MHz, CD₃OD) δ 4.73 (s, 1H), 3.87 (s, 1H), 3.70-3.60 (m, 1H), 3.40-3.30 (m, 1H), 3.12-3.00 (m, 1H), 2.99-2.82 (m, 7H), 2.68-2.56 (m, 2H), 2.26-2.15 (m, 2H), 2.04-1.90 (m, 1H), 1.62-1.50 (m, 1H); MS (ESI) m/z 503.11 (M+H).

The following compounds were prepared from S16-6-4-1 and S16-6-4-2 according to the procedures for compound S16-7-1:

S16-7-2

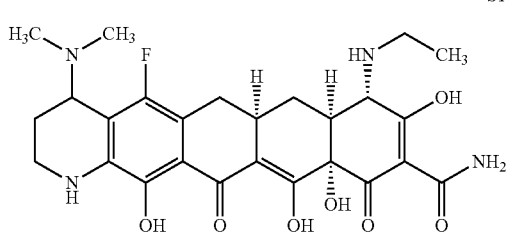

S16-7-2 (single diastereomer): ¹H NMR (400 MHz, CD₃OD) δ 4.73 (s, 1H), 3.85 (s, 1H), 3.70-3.60 (m, 1H), 3.48-3.30 (m, 3H), 3.20-2.78 (m, 9H), 2.65-2.56 (m, 1H), 2.24-2.14 (m, 2H), 2.04-1.90 (m, 1H), 1.60-1.49 (m, 1H), 1.36 (t, J=7.3 Hz, 3H); MS (ESI) m/z 531.18 (M+H).

S16-7-3

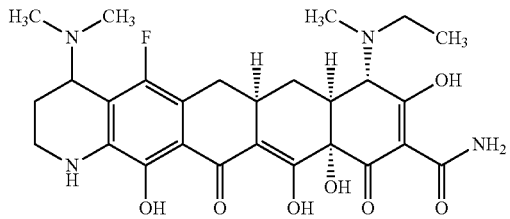

S16-7-3 (single diastereomer): ¹H NMR (400 MHz, CD₃OD) δ 4.76-4.70 (m, 1H), 4.21 (s, 0.5H), 4.11 (s, 0.5H), 3.70-3.60 (m, 1H), 3.56-3.43 (m, 1H), 3.40-3.30 (m, 2H), 3.11-2.84 (m, 12H), 2.65-2.56 (m, 1H), 2.27-2.13 (m, 2H), 2.03-1.90 (m, 1H), 1.69-1.54 (m, 1H), 1.45-1.34 (m, 3H); MS (ESI) m/z 545.23 (M+H).

The following compounds were prepared according to the procedures for Example S16-7-1 substituting compound S16-5-2 for compound S16-5-1:

S16-7-4

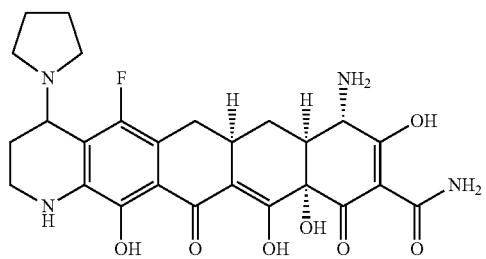

S16-7-4 (single diastereomer): ¹H NMR (400 MHz, CD₃OD) δ 4.76-4.70 (m, 1H), 3.87 (s, 1H), 3.86-3.76 (m, 1H), 3.67 (dd, J=13.7, 5.04 Hz, 1H), 3.48-3.24 (m, 4H), 3.07 (dd, J=14.2, 4.6 Hz, 1H), 3.00-2.85 (m, 1H), 2.66-2.61 (m, 1H), 2.57-2.48 (m, 1H), 2.28-2.10 (m, 4H), 2.10-1.90 (m, 3H), 1.63-1.52 (m, 1H); MS (ESI) m/z 529.14 (M+H).

S16-7-5

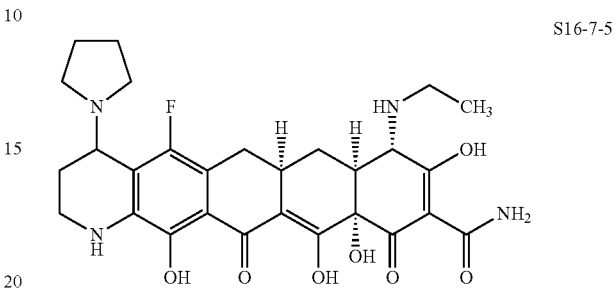

S16-7-5 (single diastereomer): ¹H NMR (400 MHz, CD₃OD) δ 4.77-4.72 (m, 1H), 3.87-3.77 (m, 2H), 3.67 (dd, J=13.7, 5.5 Hz, 1H), 3.50-3.26 (m, 6H), 3.06 (dd, J=14.2, 4.6 Hz, 1H), 3.00-2.90 (m, 1H), 2.86-2.79 (m, 1H), 2.57-2.49 (m, 1H), 2.28-2.12 (m, 4H), 2.11-1.90 (m, 3H), 1.60-1.48 (m, 1H), 1.36 (t, J=7.3 Hz, 3H); MS (ESI) m/z 557.14 (M+H).

S16-6-3

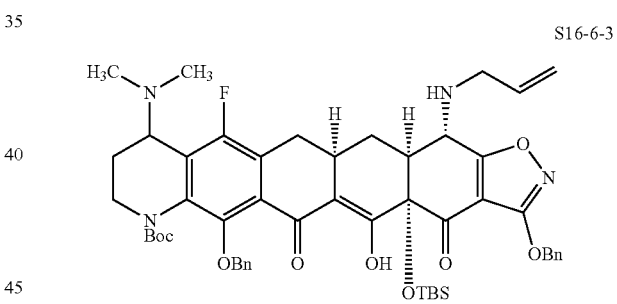

Compound S16-6-1 (116 mg, 0.119 mmol) and 2-mercaptobenzoic acid (22.0 mg, 0.143 mmol) were weighed into a flask. This was evacuated and backfilled with nitrogen (3×). THF (2 mL) was added followed by a solution of Pd(dba)₂ (6.9 mg, 0.012 mmol) and 1,4-bis(diphenylphosphino)butane (5.1 mg, 0.012 mmol) in THF (0.20 mL). After 6 h, additional Pd(dba)₂ (6.9 mg, 0.012 mmol) and 1,4-bis(diphenylphosphino)butane (5.1 mg, 0.012 mmol) in THF (0.20 mL) was added. After stirring overnight, the reaction mixture was diluted with EtOAc, was washed with NaHCO₃ (saturated, aqueous, 2×) and pH 7 phosphate buffer (1×), was dried over Na₂SO₄, was filtered, and was concentrated under reduced pressure. The material was purified by column chromatography (10 g Biotage column, 20 to 100% EtOAc in Hexanes gradient). This gave 33.9 mg (30%) of S16-6-3, 42.2 mg (36%) of recovered S16-6-1, and 19.5 mg (18%) of the fully de-allylated product, S16-6-2. MS for S16-6-3: (ESI) m/z 935.34 (M+H).

S16-6-4-3

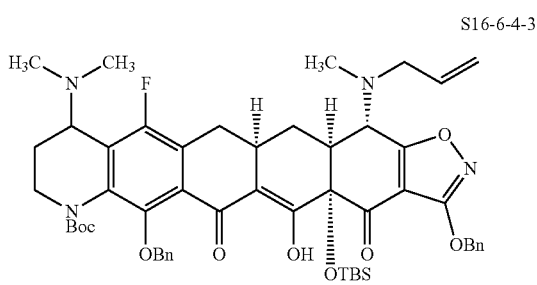 [SMILES: C=CCN(C)[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)N(C(=O)OC(C)(C)C)CCC5N(C)C)C[C@H]3C[C@@H]12]

Formaldehyde (37% aqueous solution, 0.5 mL) was added to a mixture of compound S16-6-3 (33.9 mg, 0.0363 mmol) and Na(OAc)$_3$BH (23.0 mg, 0.109 mmol) in CH$_2$Cl$_2$ (2 mL). After 1 h, ~50% conversion was observed by LC/MS. Additional formaldehyde (37% aqueous solution, 0.5 mL) and Na(OAc)$_3$BH (25 mg, 0.12 mmol) were added. After stirring overnight, additional Na(OAc)$_3$BH (50 mg, 0.24 mmol) was added. After 2 h, the reaction mixture was diluted with EtOAc, was washed with NaHCO$_3$ (saturated, aqueous, 3×) and pH 7 phosphate buffer (1×), was dried over Na$_2$SO$_4$, was filtered, and was concentrated under reduced pressure. The crude S16-6-4-3 was used without further purification: MS (ESI) m/z 949.41 (M+H).

S16-6-4-4

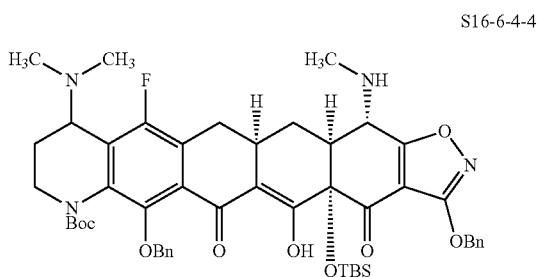 [SMILES: CN[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)N(C(=O)OC(C)(C)C)CCC5N(C)C)C[C@H]3C[C@@H]12]

Compound S16-6-4-3 (34.4 mg, 0.0363 mmol), 1,3-dimethylbarbituric acid (22.7 mg, 0.145 mmol), and Pd(Ph$_3$P)$_4$ (4.2 mg, 0.0036 mmol) were dissolved in CH$_2$Cl$_2$ (4 mL), and the reaction mixture was evacuated and backfilled with nitrogen (3×). After 6 h, the reaction mixture was diluted with EtOAc, was washed with NaHCO$_3$ (saturated, aqueous, 3×) and pH 7 phosphate buffer (1×), was dried over Na$_2$SO$_4$, was filtered, and was concentrated under reduced pressure. The material was purified by column chromatography (10 g Biotage column, 50 to 100% EtOAc in Hexanes gradient). This gave 32.8 mg (99%) of S16-6-4-4: MS (ESI) m/z 909.36 (M+H).

S16-7-6

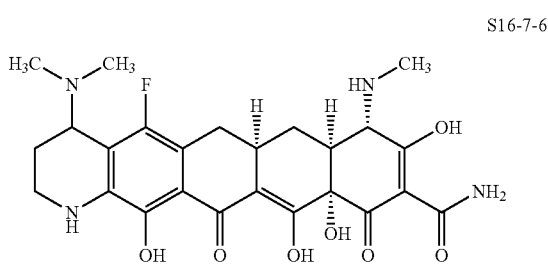 [SMILES: CN[C@@H]1C(O)=C(C(N)=O)C(=O)[C@@]2(O)C(O)=C3C(=O)c4c(O)c5c(c(F)c4C[C@H]3C[C@@H]12)C(N(C)C)CCN5]

Compound S16-6-4-4 (32.8 mg, 0.0361 mmol) was stirred in methanesulfonic acid (0.10 mL), dimethylsulfide (0.020 mL), and CH$_2$Cl$_2$ (0.20 ml). After stirring overnight, the reaction mixture was concentrated. Dimethylsulfide (0.040 mL), and CH$_2$Cl$_2$ (0.040 ml) were added. After 4 h, the reaction mixture was diluted with 1:1 MeOH:0.05 N aqueous HCl (2 mL) and was purified directly on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH$_3$CN; gradient: 0→50% B; mass-directed fraction collection]. Fractions with the desired MW were collected and freeze-dried to yield 10.7 mg (47%) of S16-7-6 as an orange-red solid (single diastereomer): $^1$H NMR (400 MHz, CD$_3$OD) δ 4.76-4.71 (m, 1H), 3.81 (s, 1H), 3.68-3.60 (m, 1H), 3.42-3.32 (m, 1H), 3.06 (dd, J=15.1, 4.6 Hz, 1H), 3.02-2.78 (m, 11H), 2.66-2.56 (m, 1H), 2.24-2.12 (m, 2H), 2.04-1.92 (m, 1H), 1.58-1.46 (m, 1H); MS (ESI) m/z 517.22 (M+H).

Scheme 17

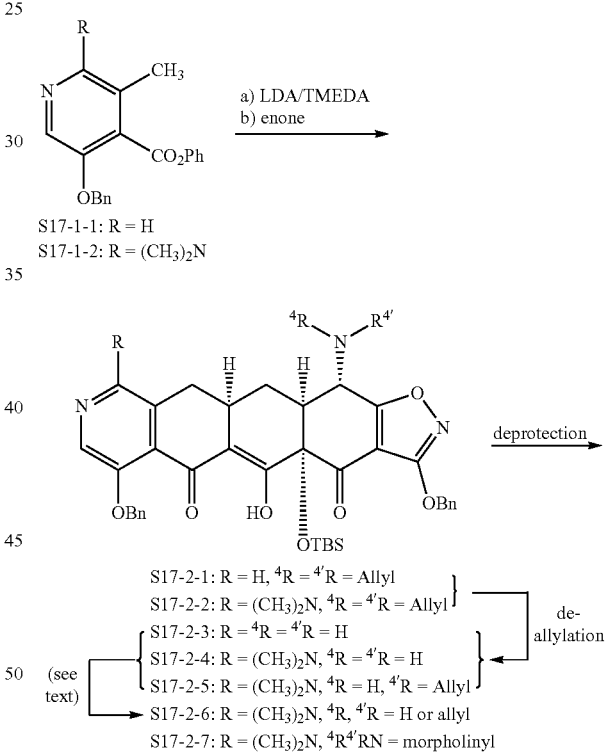

S17-1-1: R = H
S17-1-2: R = (CH$_3$)$_2$N

S17-2-1: R = H, $^4$R = $^{4'}$R = Allyl
S17-2-2: R = (CH$_3$)$_2$N, $^4$R = $^{4'}$R = Allyl
S17-2-3: R = $^4$R = $^{4'}$R = H
S17-2-4: R = (CH$_3$)$_2$N, $^4$R = $^{4'}$R = H
S17-2-5: R = (CH$_3$)$_2$N, $^4$R = H, $^{4'}$R = Allyl
S17-2-6: R = (CH$_3$)$_2$N, $^4$R, $^{4'}$R = H or allyl
S17-2-7: R = (CH$_3$)$_2$N, $^4$R$^{4'}$RN = morpholinyl

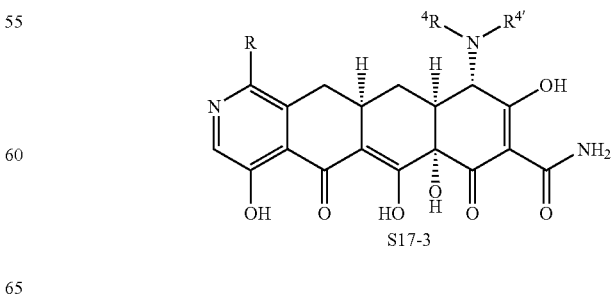

S17-3

The follow compounds were prepared according to Scheme 17.

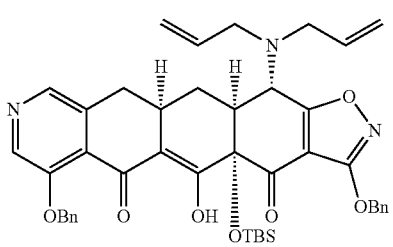

S17-2-1

Lithium diisopropylamide was prepared from diisopropylamine (0.0393 mL, 0.278 mmol) and n-BuLi (1.6 M solution, 0.174 mL, 0.278 mmol) in THF (3 mL) at −40° C. The reaction mixture was cooled to −78° C., and TMEDA (0.128 mL, 0.856 mmol) was added. A solution of compound S17-1-1 (75.0 mg, 0.235 mmol, prepared according to literature procedures including *J. Med. Chem.*, 2011, 54, 1511) in THF (1 mL) was then added dropwise, resulting in a deep red solution. The reaction mixture was stirred at −78° C. for 30 min. A solution of enone S1-9-2 (114 mg, 0.214 mmol) in THF (1 mL) was added dropwise, followed by LHMDS (1.0 M solution, 0.257 mL, 0.257 mmol). The reaction mixture was allowed to warm to −20° C. over 1 h. The reaction was quenched by the addition of ammonium chloride (saturated, aqueous solution) and was diluted with EtOAc. The mixture was washed with water (3×), 1 N aq. NaOH (3×), pH 7 phosphate buffer (1×), and brine (1×), was dried over $Na_2SO_4$, was filtered, and was concentrated under reduced pressure. The material was purified by column chromatography (25 g Biotage column, 10 to 50% EtOAc in Hexanes gradient). This gave 28.6 mg (18%) of S17-2-1: $^1$H NMR (400 MHz, $CDCl_3$) δ 15.7 (s, 1H), 8.36 (s, 1H), 8.17 (s, 1H), 7.54-7.24 (m, 10H), 5.85-5.73 (m, 2H), 5.37 (s, 2H), 5.32-5.04 (m, 6H), 4.06 (d, J=10.4 Hz, 1H), 3.36-3.16 (m, 4H), 2.90-2.82 (m, 2H), 2.60-2.40 (m, 1H), 2.14-2.05 (m, 1H), 1.64-1.50 (m, 1H), 1.30-1.20 (m, 1H), 0.81 (s, 9H), 0.24 (s, 3H), 0.12 (s, 3H); MS (ESI) m/z 760.24 (M+H).

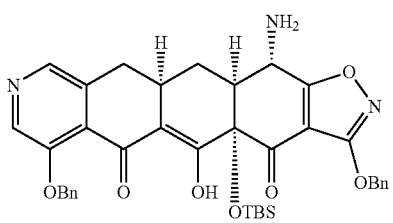

S17-2-3

Compound S17-2-1 (28.6 mg, 0.0376 mmol), 1,3-dimethylbarbituric acid (23.4 mg, 0.150 mmol), and $Pd(Ph_3P)_4$ (4.3 mg, 0.0038 mmol) were dissolved in $CH_2Cl_2$ (2 mL), and the reaction mixture was evacuated and backfilled with nitrogen (3×). After 5 h, the reaction mixture was diluted with EtOAc, was washed with $NaHCO_3$ (saturated, aqueous, 3×) and brine (1×), was dried over $Na_2SO_4$, was filtered, and was concentrated under reduced pressure. The material was purified by column chromatography (10 g Biotage column, 50 to 100% EtOAc in Hexanes gradient). This gave 4.8 mg (19%) of S17-2-3: MS (ESI) m/z 680.18 (M+H).

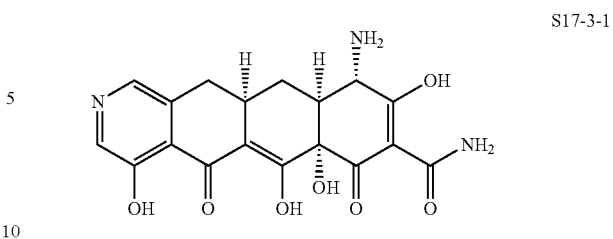

S17-3-1

Compound S17-2-3 (4.8 mg, 0.0706 mmol) was stirred in methanesulfonic acid (0.10 mL), dimethylsulfide (0.020 mL), and $CH_2Cl_2$ (0.20 ml). After stirring overnight, the reaction mixture was concentrated. Dimethylsulfide (0.040 mL), and $CH_2Cl_2$ (0.040 ml) were added. After 4 h, additional methanesulfonic acid (0.040 mL) was added, and the mixture was stirred overnight. The reaction mixture was purified directly on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→50% B; mass-directed fraction collection]. Fractions with the desired MW were collected and freeze-dried to yield 3.0 mg (92%) of S17-3-1 as a yellow solid: $^1$H NMR (400 MHz, $CD_3OD$) δ 8.53 (s, 1H), 8.31 (s, 1H), 3.91 (s, 1H), 3.42-3.008 (m, 2H), 2.80-2.65 (m, 1H), 2.34-2.24 (m, 2H), 1.70-1.60 (m, 1H); MS (ESI) m/z 388.03 (M+H).

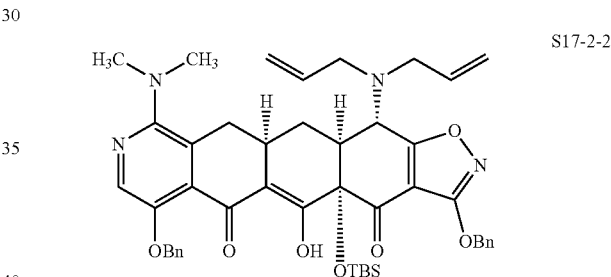

S17-2-2

Lithium diisopropylamide was prepared from diisopropylamine (0.107 mL, 0.754 mmol) and n-BuLi (1.6 M solution, 0.471 mL, 0.754 mmol) in THF (5 mL) at −40° C. The reaction mixture was cooled to −78° C., and TMEDA (0.377 mL, 2.51 mmol) was added. A solution of compound S17-1-2 (239 mg, 0.659 mmol, prepared according to literature procedures including *J. Med. Chem.*, 2011, 54, 1511) in THF (2 mL) was then added dropwise, resulting in an orange-red solution. The reaction mixture was stirred at −78° C. for 30 min. A solution of enone S1-9-2 (336 mg, 0.628 mmol) in THF (1 mL) was added dropwise, followed by LHMDS (1.0 M solution, 0.816 mL, 0.816 mmol). The reaction mixture was allowed to warm to −20° C. over 1 h. The reaction was quenched by the addition of ammonium chloride (saturated, aqueous solution) and was diluted with EtOAc. The mixture was washed with water (3×) and brine (1×), was dried over $Na_2SO_4$, was filtered, and was concentrated under reduced pressure. The material was purified by column chromatography (25 g Biotage column, 10 to 40% EtOAc in Hexanes gradient). This gave 338.5 mg (67%) of S17-2-2: $^1$H NMR (400 MHz, $CDCl_3$) δ 15.5 (s, 1H), 8.01 (s, 1H), 7.54-7.48 (m, 2H), 7.45-7.24 (m, 7H), 7.14-7.08 (m, 1H), 5.88-5.75 (m, 2H), 5.37 (s, 2H), 5.26-5.07 (m, 6H), 4.12 (d, J=10.1 Hz, 1H), 3.40-3.18 (m, 4H), 3.01 (dd, J=15.3, 4.9 Hz, 1H), 2.97-2.86 (m, 1H), 2.76 (s, 6H), 2.63 (t, J=15.3 Hz, 1H), 2.57-2.50 (m, 1H), 2.48-2.36 (m, 1H), 2.19-2.12 (m, 1H), 0.80 (s, 9H), 0.25 (s, 3H), 0.12 (s, 3H); MS (ESI) m/z 803.27 (M+H).

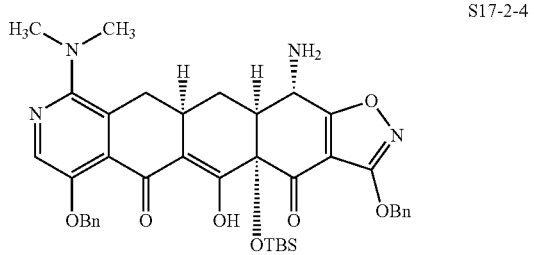 [SMILES: CN(C)c1ncc(OCc2ccccc2)c2c1C[C@H]1C[C@H]3[C@H](N)c4onc(OCc5ccccc5)c4C(=O)[C@@]3(O[Si](C)(C)C(C)(C)C)C(O)=C1C2=O]

S17-2-4

Compound S17-2-2 (149 mg, 0.185 mmol), 1,3-dimethylbarbituric acid (115 mg, 0.740 mmol), and Pd(Ph₃P)₄ (21.4 mg, 0.0185 mmol) were dissolved in CH₂Cl₂ (5 mL), and the reaction mixture was evacuated and backfilled with nitrogen (3×). After stirring overnight, the reaction mixture was diluted with EtOAc, was washed with NaHCO₃ (saturated, aqueous, 3×), pH 7 phosphate buffer (1×), and brine (1×), was dried over Na₂SO₄, was filtered, and was concentrated under reduced pressure. The material was purified by column chromatography (25 g Biotage column, 0 to 10% MeOH in EtOAc gradient). This gave 98.1 mg (73%) of S17-2-4: MS (ESI) m/z 723.21 (M+H).

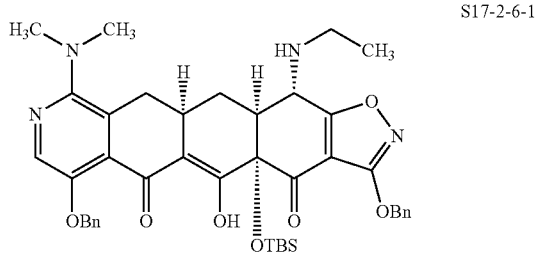 [SMILES: CCN[C@@H]1c2onc(OCc3ccccc3)c2C(=O)[C@@]2(O[Si](C)(C)C(C)(C)C)C(O)=C3C(=O)c4c(OCc5ccccc5)cnc(N(C)C)c4C[C@H]3C[C@@H]12]

S17-2-6-1

Compound S17-2-4 (78.5 mg, 0.109 mmol) and acetic acid (0.0124 mL, 0.217 mmol) were dissolved in MeOH (2 mL), and the reaction mixture was cooled to 0° C. Na(OAc)₃BH (46 mg, 0.217 mmol) and acetaldehyde (50 wt % solution in EtOH, 0.0217 mL, 0.217 mmol) were added. After 10 min, complete conversion was observed by LC/MS. The reaction mixture was quenched with NaHCO₃ (saturated, aqueous) and was diluted with EtOAc. The mixture was washed with NaHCO₃ (saturated, aqueous, 2×), pH 7 phosphate buffer (1×), and brine (1×), was dried over Na₂SO₄, was filtered, and was concentrated under reduced pressure to give crude product S17-2-6-1, which was used without further purification: MS (ESI) m/z 751.30 (M+H).

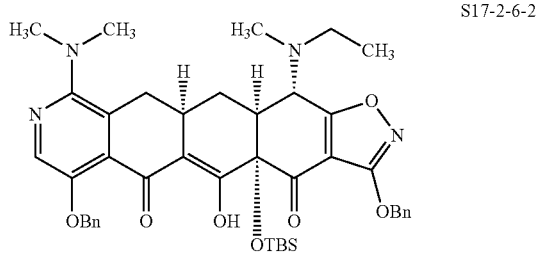 [SMILES: CCN(C)[C@@H]1c2onc(OCc3ccccc3)c2C(=O)[C@@]2(O[Si](C)(C)C(C)(C)C)C(O)=C3C(=O)c4c(OCc5ccccc5)cnc(N(C)C)c4C[C@H]3C[C@@H]12]

S17-2-6-2

Formaldehyde (37% aqueous solution, 0.5 mL) was added to a mixture of compound S17-2-6-1 (20.4 mg, 0.0272 mmol) and Na(OAc)₃BH (17.3 mg, 0.0816 mmol) in CH₂Cl₂ (2 mL). After 1 h, the reaction mixture was diluted with EtOAc, was washed with NaHCO₃ (saturated, aqueous, 2×), pH 7 phosphate buffer (1×), and brine, was dried over Na₂SO₄, was filtered, and was concentrated under reduced pressure to give crude product S17-2-6-2, which was used without further purification: MS (ESI) m/z 765.34 (M+H).

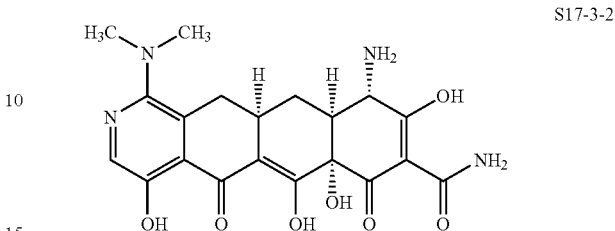

S17-3-2

Compound S17-2-4 (19.6 mg, 0.0271 mmol) was stirred in methanesulfonic acid (0.10 mL), dimethylsulfide (0.020 mL), and CH₂Cl₂ (0.20 ml). After stirring overnight, the reaction mixture was concentrated. Dimethylsulfide (0.080 mL), and CH₂Cl₂ (0.040 ml) were added. After stirring overnight, the reaction mixture was concentrated and purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→50% B; mass-directed fraction collection]. Fractions with the desired MW were collected and freeze-dried to yield 1.78 mg (13%) of S17-3-2 as a yellow solid: ¹H NMR (400 MHz, CD₃OD) δ 8.17 (s, 1H), 3.92 (s, 1H), 3.24-3.04 (m, 8H), 2.74-2.64 (m, 1H), 2.58 (t, J=14.6 Hz, 1H), 2.36-2.26 (m, 1H), 1.70-1.60 (m, 1H); MS (ESI) m/z 431.08 (M+H).

The following compounds were prepared from S17-2-6-1 and S17-2-6-2 according to the procedures for compound S17-3-2:

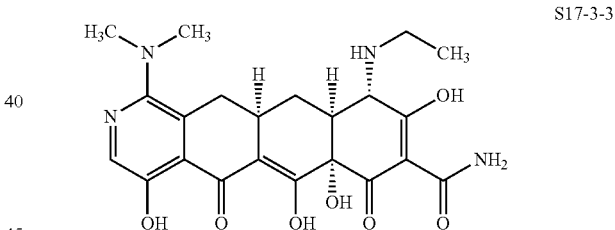

S17-3-3

S17-3-3: ¹H NMR (400 MHz, CD₃OD) δ 8.20 (s, 1H), 3.92 (s, 1H), 3.46-3.30 (m, 2H), 3.26-3.08 (m, 8H), 2.93-2.84 (m, 1H), 2.60 (t, J=14.6 Hz, 1H), 2.36-2.26 (m, 1H), 1.70-1.60 (m, 1H), 1.37 (t, J=6.8 Hz, 3H); MS (ESI) m/z 459.13 (M+H).

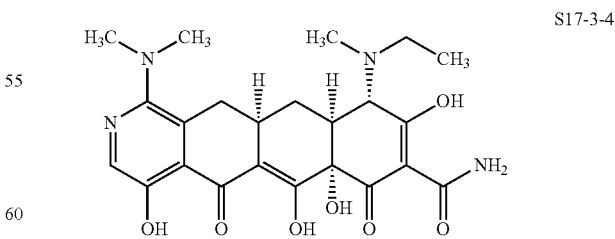

S17-3-4

S17-3-4: ¹H NMR (400 MHz, CD₃OD) δ 8.21 (s, 1H), 3.92 (d, J=34.4 Hz, 1H), 3.58-3.44 (m, 1H), 3.43-3.28 (m, 1H), 3.24-3.12 (m, 8H), 3.06-2.93 (m, 4H), 2.60 (t, J=13.7 Hz, 1H), 2.40-2.26 (m, 1H), 1.78-1.64 (m, 1H), 1.47-1.34 (m, 3H); MS (ESI) m/z 473.15 (M+H).

The following compounds were prepared from S17-2-4 according to similar procedures for S17-3-3:

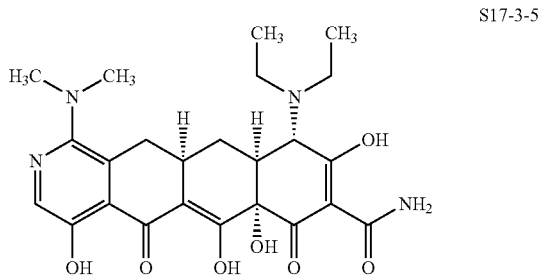 [SMILES: CCN(CC)[C@@H]1C(O)=C(C(N)=O)C(=O)[C@@]2(O)C(O)=C3C(=O)c4c(O)cnc(N(C)C)c4C[C@H]3C[C@@H]12]

S17-3-5

S17-3-5: ¹H NMR (400 MHz, CD₃OD) δ 8.21 (s, 1H), 4.30 (s, 1H), 3.66-3.53 (m, 1H), 3.53-3.42 (m, 2H), 3.40-3.30 (m, 1H), 3.24-3.12 (m, 8H), 3.00-2.93 (m, 1H), 2.59 (t, J=15.1 Hz, 1H), 2.37-2.29 (m, 1H), 1.76-1.64 (m, 1H), 1.41 (t, J=7.4 Hz, 6H); MS (ESI) m/z 487.13 (M+H).

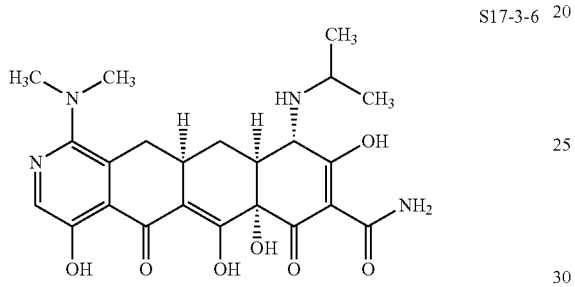

S17-3-6

S17-3-6: ¹H NMR (400 MHz, CD₃OD) δ 8.20 (s, 1H), 4.01 (s, 1H), 3.83 (hept, J=6.4 Hz, 1H), 3.24-3.10 (m, 8H), 2.94-2.84 (m, 1H), 2.65-2.55 (m, 1H), 2.38-2.28 (m, 1H), 1.70-1.60 (m, 1H), 1.46-1.34 (m, 6H); MS (ESI) m/z 473.11 (M+H).

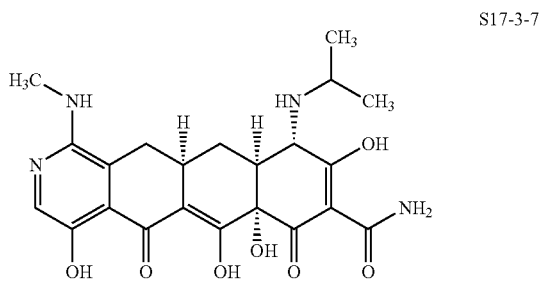 [SMILES: CNc1ncc(O)c2c1C[C@H]1C[C@H]3[C@H](NC(C)C)C(O)=C(C(N)=O)C(=O)[C@@]3(O)C(O)=C1C2=O]

S17-3-7

Compound S17-3-7 was isolated as a side-product from the methanesulfonic acid deprotection step of S17-3-6. S17-3-7: ¹H NMR (400 MHz, CD₃OD) δ 7.53 (s, 1H), 3.99 (s, 1H), 3.82 (hept, J=6.4 Hz, 1H), 3.36-3.26 (m, 1H), 3.02 (s, 3H), 2.94-2.84 (m, 2H), 2.36-2.26 (m, 2H), 1.70-1.60 (m, 1H), 1.41 (dd, J=15.1, 6.4 Hz, 6H); MS (ESI) m/z 459.05 (M+H).

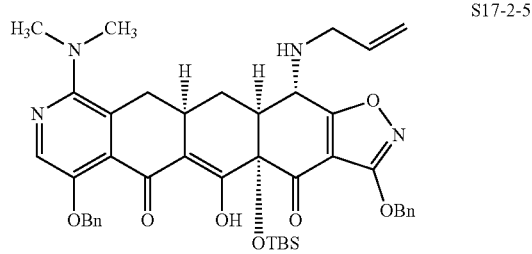 [SMILES: C=CCN[C@@H]1c2onc(OCc3ccccc3)c2C(=O)[C@@]2(O[Si](C)(C)C(C)(C)C)C(O)=C3C(=O)c4c(OCc5ccccc5)cnc(N(C)C)c4C[C@H]3C[C@@H]12]

S17-2-5

Compound S17-2-2 (165 mg, 0.205 mmol) and 2-mercaptobenzoic acid (37.9 mg, 0.246 mmol) were weighed into a flask. This was evacuated and backfilled with nitrogen (3×). THF (2 mL) was added followed by a solution of Pd(dba)₂ (12 mg, 0.021 mmol) and 1,4-bis(diphenylphosphino)butane (9.0 mg, 0.021 mmol) in THF (0.20 mL). After 4 h, the reaction mixture was diluted with EtOAc, was washed with NaHCO₃ (saturated, aqueous, 2×), pH 7 phosphate buffer (1×), and brine (1×), was dried over Na₂SO₄, was filtered, and was concentrated under reduced pressure. The material was purified by column chromatography (25 g Biotage column, 20 to 100% EtOAc in Hexanes gradient). This gave 52.3 mg (34%) of S17-2-5 and 17.0 mg (11%) of the fully de-allylated product, S17-2-4. Data for S17-2-5: MS (ESI) m/z 763.23 (M+H).

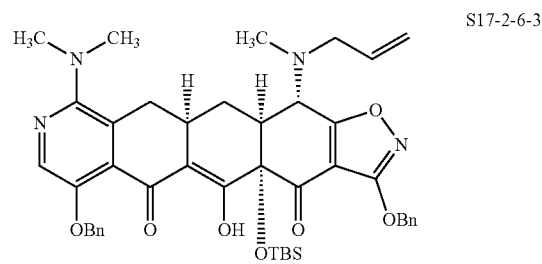 [SMILES: C=CCN(C)[C@@H]1c2onc(OCc3ccccc3)c2C(=O)[C@@]2(O[Si](C)(C)C(C)(C)C)C(O)=C3C(=O)c4c(OCc5ccccc5)cnc(N(C)C)c4C[C@H]3C[C@@H]12]

S17-2-6-3

Formaldehyde (37% aqueous solution, 0.5 mL) was added to a mixture of compound S17-2-5 (26.1 mg, 0.0342 mmol) and Na(OAc)₃BH (21.7 mg, 0.103 mmol) in CH₂Cl₂ (2 mL). Additional portions of Na(OAc)₃BH (22 mg, 0.11 mmol) were added approximately every 10 min over the next 1 h (6 total). The reaction mixture was diluted with EtOAc, was washed with NaHCO₃ (saturated, aqueous, 2×) and brine (1×), was dried over Na₂SO₄, was filtered, and was concentrated under reduced pressure to yield the crude product S17-2-6-3, which was used without further purification: MS (ESI) m/z 777.24 (M+H).

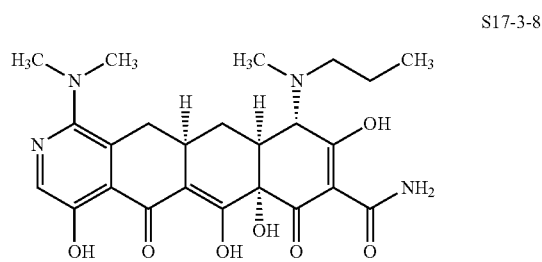 [SMILES: CCCN(C)[C@@H]1C(O)=C(C(N)=O)C(=O)[C@@]2(O)C(O)=C3C(=O)c4c(O)cnc(N(C)C)c4C[C@H]3C[C@@H]12]

S17-3-8

Compound S17-2-6-3 (13.3 mg, 0.0171 mmol) was stirred in aqueous HF (48-50% solution, 0.40 mL) and 1,4-dioxane (1 ml). After stirring overnight, the reaction mixture was poured into a solution of K₂HPO₄ (4.8 g) in water (20 mL) and was extracted with EtOAc (2×). The organics were concentrated and re-dissolved in MeOH (1 mL), 1,4-dioxane (1 mL), and 6 N aqueous HCl (0.2 mL). 10% Pd on carbon (Degussa, 5 mg) was added, and an atmosphere of hydrogen (balloon) was introduced. After 1 h, the reaction mixture was purged with nitrogen and filtered through Celite (MeOH wash). The filtrate was concentrated and was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN;

gradient: 0→50% B; mass-directed fraction collection]. Fractions with the desired MW were collected and freeze-dried to yield 2.4 mg (25%) of S17-3-8 as a yellow solid: $^1$H NMR (400 MHz, CD$_3$OD) δ 4.76-4.71 (m, 1H), 3.81 (s, 1H), 3.68-3.60 (m, 1H), 3.42-3.32 (m, 1H), 3.06 (dd, J=15.1, 4.6 Hz, 1H), 3.02-2.78 (m, 11H), 2.66-2.56 (m, 1H), 2.24-2.12 (m, 2H), 2.04-1.92 (m, 1H), 1.58-1.46 (m, 1H); MS (ESI) m/z 487.17 (M+H).

S17-3-9

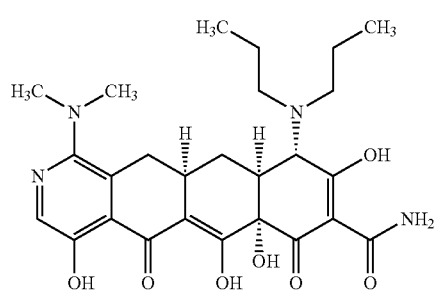

Compound S17-2-2 (16.4 mg, 0.0204 mmol) was stirred in aqueous HF (48-50% solution, 0.40 mL) and 1,4-dioxane (1 ml). After 2 h, the reaction mixture was poured into a solution of K$_2$HPO$_4$ (4.8 g) in water (20 mL) and was extracted with EtOAc (2×). The organics were concentrated and re-dissolved in MeOH (2 mL), 1,4-dioxane (2 mL), and 6 N aqueous HCl (0.2 mL). 10% Pd on carbon (Degussa, 5 mg) was added, and an atmosphere of hydrogen (balloon) was introduced. After 1 h, the reaction mixture was purged with nitrogen and filtered through Celite (MeOH wash). The filtrate was concentrated and was purified on a Waters Autopurification system equipped with a Phenomenex Polymerx 10µ RP 100 A column [10 µm, 30×21.20 mm; flow rate, 20 mL/min; Solvent A: 0.05 N HCl in water; Solvent B: CH$_3$CN; gradient: 0→50% B; mass-directed fraction collection]. Fractions with the desired MW were collected and freeze-dried to yield 0.88 mg (7%) of S17-3-9 as a yellow solid and 6.8 mg (61%) of the mono-propyl compound S17-3-10. Data for S17-3-9: $^1$H NMR (400 MHz, CD$_3$OD) δ 8.14 (s, 1H), 4.26 (s, 1H), 3.65-3.45 (m, 4H), 3.24-2.90 (m, 9H), 2.54 (t, J=14.6 Hz, 1H), 2.32-2.20 (m, 1H), 1.94-1.60 (m, 5H), 1.12-0.92 (m, 6H); MS (ESI) m/z 515.21 (M+H).

S17-3-10

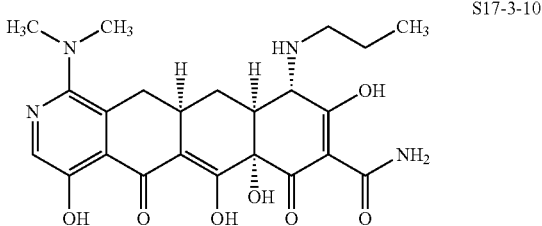 [SMILES: CCCN[C@@H]1C(O)=C(C(N)=O)C(=O)[C@@]2(O)C(O)=C3C(=O)c4c(O)cnc(N(C)C)c4C[C@H]3C[C@@H]12]

S17-3-10: $^1$H NMR (400 MHz, CD$_3$OD) δ 8.20 (s, 1H), 3.93 (s, 1H), 3.26-3.08 (m, 10H), 2.96-2.88 (m, 1H), 2.59 (t, J=14.6 Hz, 1H), 2.37-2.27 (m, 1H), 1.84-1.72 (m, 2H), 1.70-1.60 (m, 1H), 1.03 (t, J=7.8 Hz, 3H); MS (ESI) m/z 473.12 (M+H).

S17-2-7

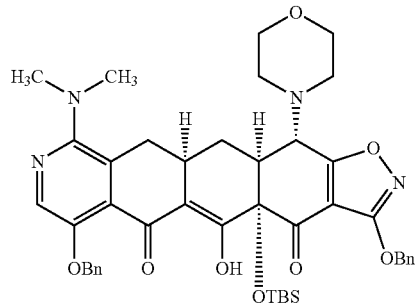

Lithium diisopropylamide was prepared from diisopropylamine (0.024 mL, 0.167 mmol) and n-BuLi (1.84 M solution, 0.091 mL, 0.167 mmol) in THF (2 mL) at −40° C. The reaction mixture was cooled to −78° C., and TMEDA (0.091 mL, 0.608 mmol) was added. A solution of compound S17-1-2 (55.3 mg, 0.152 mmol) in THF (0.5 mL) was then added dropwise, resulting in a deep orange solution. The reaction mixture was stirred at −78° C. for 5 min. A solution of enone S2-7-3 (40 mg, 0.076 mmol) in THF (0.5 mL) was added dropwise. The reaction mixture was allowed to warm to −20° C. over 45 min. The reaction was quenched by the addition of ammonium chloride (saturated, aqueous solution) and was extracted with EtOAc (2×). The combined extracts were dried over Na$_2$SO$_4$, were filtered, and were concentrated under reduced pressure. The material was purified by preparative reverse phase HPLC purification on a Waters Autopurification system using a Sunfire Prep C18 OBD column [5 µm, 19×50 mm; flow rate, 20 mL/min; Solvent A: H$_2$O with 0.1% HCO$_2$H; Solvent B: CH$_3$CN with 0.1% HCO$_2$H; gradient: 80→100% B over 15 min; mass-directed fraction collection]. This gave 28.9 mg (48%) of S17-2-7: $^1$H NMR (400 MHz, CDCl$_3$) δ 15.5 (s, 1H), 8.02 (s, 1H), 7.52-7.22 (m, 10H), 5.36 (s, 2H), 5.22-5.12 (m, 2H), 4.03 (d, J=10.4 Hz, 1H), 3.74-3.70 (m, 4H), 3.12-2.86 (m, 4H), 2.72 (s, 6H), 2.66-2.54 (m, 4H), 2.51-2.38 (m, 1H), 2.24-2.16 (m, 1H), 0.81 (s, 9H), 0.25 (s, 3H), 0.13 (s, 3H); MS (ESI) m/z 793.45 (M+H).

S17-3-11

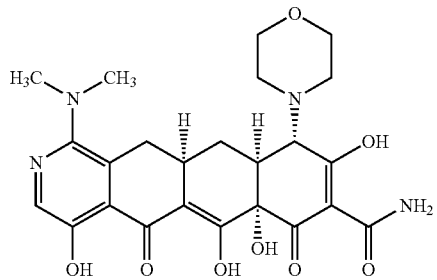

Compound S17-2-7 (28.9 mg, 0.0364 mmol) was stirred in aqueous HF (48-50% solution, 0.40 mL) and acetonitrile (0.6 ml). After stirring overnight, the reaction mixture was poured into a solution of K$_2$HPO$_4$ (4.8 g) in water (15 mL) and was extracted with EtOAc (3×). The organics were dried over Na$_2$SO$_4$, were filtered, and were concentrated. The material was dissolved in MeOH (1 mL) and 1,4-dioxane (1 mL), 10% Pd on carbon (Degussa, 5 mg) was added, and an atmosphere of hydrogen (balloon) was introduced. After 2 h, the reaction mixture was purged with nitrogen and filtered through Celite (MeOH wash). The filtrate was concentrated and was purified on a Waters Autopurification system equipped with a Phenomenex Polymerx 10µ RP 100 A column [10 µm, 30×21.20 mm; flow rate, 20 mL/min;

Solvent A: 0.05 N HCl in water; Solvent B: CH$_3$CN; gradient: 0→100% B; mass-directed fraction collection]. Fractions with the desired MW were collected and freeze-dried to yield 12.6 mg (60%) of S17-3-11 as an orange solid: $^1$H NMR (400 MHz, CD$_3$OD) δ 8.21 (s, 1H), 4.21 (s, 1H), 4.12-3.94 (m, 3H), 3.93-3.74 (m, 2H), 3.70-3.52 (m, 3H), 3.34-3.18 (m, 9H), 2.61 (t, J=14.6 Hz, 1H), 2.43-2.35 (m, 1H), 1.74-1.62 (m, 1H); MS (ESI) m/z 501.29 (M+H).

Lithium diisopropylamide was prepared from diisopropylamine (0.0807 mL, 0.571 mmol) and n-BuLi (2.5 M solution, 0.228 mL, 0.571 mmol) in THF (10 mL) at −40° C. The reaction mixture was cooled to −78° C., and TMEDA (0.367 mL, 2.45 mmol) was added. A solution of compound S18-1 (240 mg, 0.489 mmol, prepared according to literature procedures including WO2011123536) in THF (5 mL) was added dropwise, resulting in a deep red solution. The

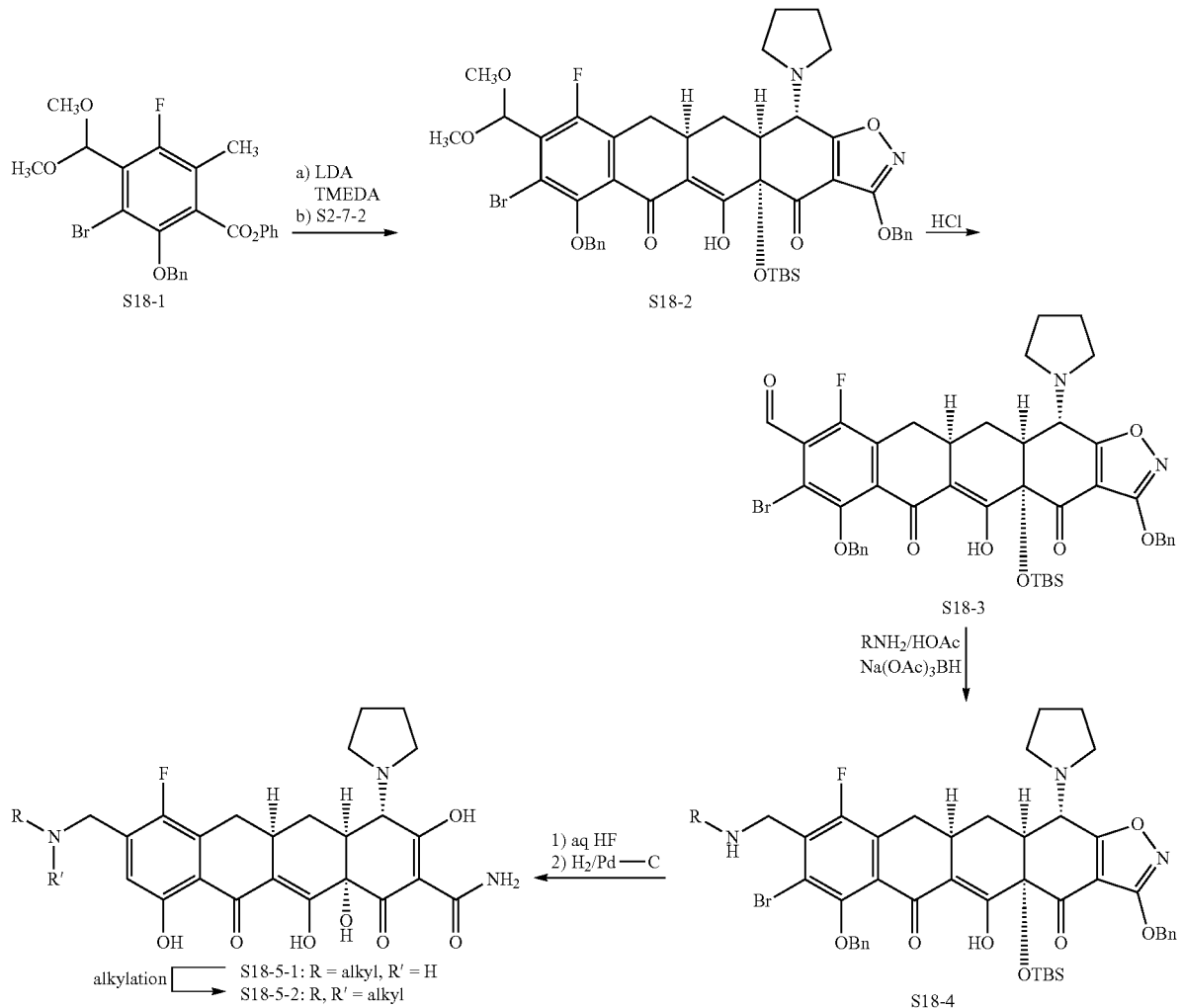

Scheme 18

The following compounds were prepared according to Scheme 18.

S18-2 reaction mixture was stirred at −78° C. for 5 min. A solution of enone S2-7-2 (208 mg, 0.408 mmol) in THF (2 mL) was added dropwise. The reaction mixture was allowed to warm to −20° C. over 1 h. The reaction was quenched by the addition of ammonium chloride (saturated, aqueous solution) and was extracted with EtOAc (2×). The combined extracts were dried over Na$_2$SO$_4$, were filtered, and were concentrated under reduced pressure. The material was purified by column chromatography (25 g Biotage column, 5 to 40% EtOAc in Hexanes gradient). This gave 198 mg (54%) of S18-2: $^1$H NMR (400 MHz, CDCl$_3$) δ 15.96 (s, 1H), 7.55 (d, J=6.7 Hz, 2H), 7.48 (d, J=6.7 Hz, 2H), 7.40-7.29 (m, 6H), 5.78 (s, 1H), 5.35 (s, 2H), 4.95 (ABq, J=26.2, 9.2 Hz, 2H), 4.19 (d, J=10.4 Hz, 1H), 3.52 (s, 6H), 3.21 (dd, J=16.5, 5.5 Hz, 1H), 3.07-2.92 (m, 3H), 2.70-2.58 (m, 3H), 2.48-2.32 (m, 2H), 2.15-2.08 (m, 1H), 1.88-1.80

(m, 4H), 0.80 (s, 9H), 0.25 (s, 3H), 0.12 (s, 3H); MS (ESI) m/z 903.25, 905.25 (M+H).

S18-3

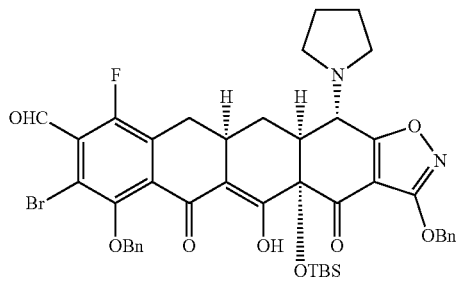

Compound S18-2 (198 mg, 0.219 mmol) was dissolved in THF (5 mL), and 6 N aqueous HCl (0.5 mL) was added. After 4 h, the reaction mixture was concentrated under reduced pressure to give crude S18-3, which was used for the next step without further purification: MS (ESI) m/z 857.23, 859.20 (M+H).

S18-4-1

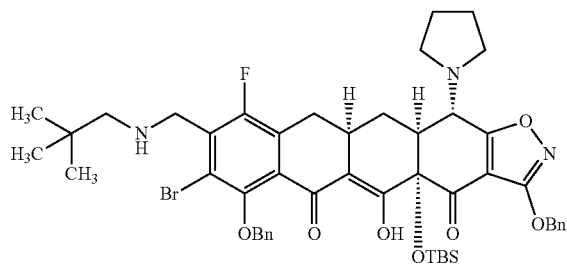

Compound S18-3 (78.2 mg, 0.0874 mmol) was dissolved in $CH_2Cl_2$ (4 mL). HOAc (0.015 mL, 0.262 mmol) and 2,2-dimethylpropan-1-amine (22.8 mg, 0.262 mmol) were added. The mixture was stirred for 30 min, and $Na(OAc)_3BH$ (37 mg, 0.175 mmol) was added. After stirring overnight, the reaction mixture was diluted with pH 7.4 phosphate buffer and was extracted with $CH_2Cl_2$ (3×). The combined extracts were dried over $Na_2SO_4$, were filtered, and were concentrated to give crude S18-4-1, which was used for the next step without further purification: MS (ESI) m/z 928.32, 930.35 (M+H).

S18-5-1-1

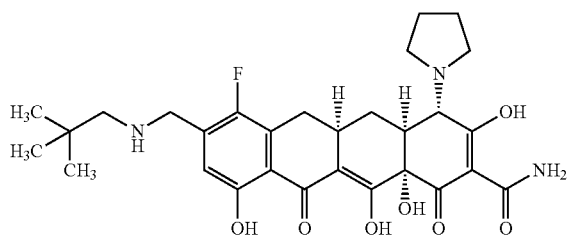

Compound S18-4-1 (crude, 0.0874 mmol) was stirred in aqueous HF (48-50% solution, 0.40 mL) and 1,4-dioxane (1 mL). After stirring overnight, the reaction mixture was poured into a solution of $K_2HPO_4$ (4.8 g) in water (15 mL) and was extracted with EtOAc (2×). The organics were dried over $Na_2SO_4$, were filtered, and were concentrated. The material was dissolved in MeOH (2 mL) and 1,4-dioxane (2 mL), and 10% Pd—C (5 mg) was added. An atmosphere of hydrogen (balloon) was introduced, and 0.5 M HCl in MeOH (0.2 mL) was added. After 2 h, the reaction mixture was purged with nitrogen and was filtered through Celite. The filtrate was concentrated, and the material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 20→100% B; mass-directed fraction collection]. Fractions with the desired MW were collected and freeze-dried to yield 30.5 mg (55%) of S18-5-1-1 as a yellow solid: $^1$H NMR (400 MHz, $CD_3OD$) δ 7.13 (d, J=5.5 Hz, 1H), 4.33 (s, 2H), 4.09 (s, 1H), 4.00-3.90 (m, 1H), 3.80-3.68 (m, 1H), 3.60-3.40 (m, 2H), 3.28-3.02 (m, 3H), 2.92 (s, 2H), 2.38-1.95 (m, 6H), 1.68-1.54 (m, 1H), 1.06 (s, 9H); MS (ESI) m/z 558.31 (M+H).

The following Example was prepared according to procedures similar to those described for Example S18-5-1-1:

S18-5-1-2

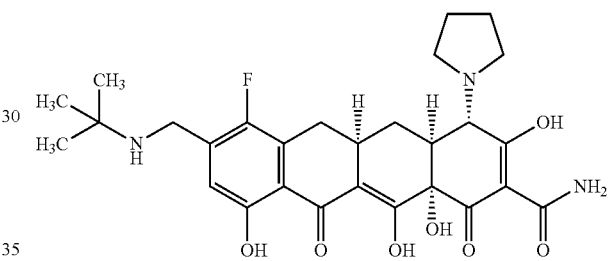

S18-5-1-2: $^1$H NMR (400 MHz, $CD_3OD$) δ 7.09 (d, J=6.0 Hz, 1H), 4.22 (s, 2H), 4.09 (s, 1H), 3.98-3.88 (m, 1H), 3.78-3.68 (m, 1H), 3.60-3.40 (m, 2H), 3.28-3.00 (m, 3H), 2.38-1.95 (m, 6H), 1.66-1.54 (m, 1H), 1.47 (s, 9H); MS (ESI) m/z 544.28 (M+H).

S18-5-2-1

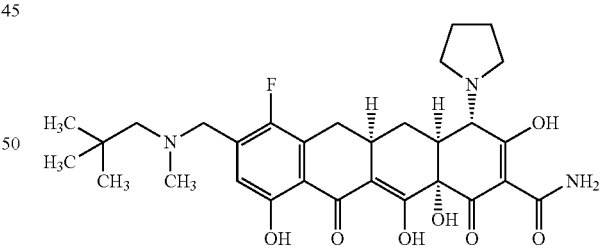

Compound S18-5-1-1 (11.6 mg, 0.0184 mmol) was dissolved in DMF (0.5 mL) and triethylamine (0.0051 mL, 0.0368 mmol), $InCl_3$ (0.41 mg, 0.0018 mmol), and formaldehyde (0.0041 mL, 0.0552 mmol) were added. After 30 min, the reaction mixture was diluted with 0.5 M HCl in MeOH (0.5 mL) and was added dropwise to diethyl ether (125 mL). The resulting solid was collected by filtration through Celite (diethyl ether wash, 3×). The solid was dissolved in MeOH and was concentrated. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 20→100% B; mass-directed fraction collection]. Fractions with the desired MW were collected and freeze-dried to yield 2.9 mg (24%) of S18-5-2-1 as a yellow solid: $^1$H NMR (400 MHz, CD$_3$OD) δ 7.09 (d, J=6.0 Hz, 1H), 4.56 (d, J=12.8 Hz, 1H), 4.33 (d, J=12.8 Hz, 1H), 3.99 (s, 1H), 3.98-3.90 (m, 1H), 3.78-3.65 (m, 1H), 3.51-3.36 (m, 2H), 3.25-3.10 (m, 2H), 3.10-2.90 (m, 5H), 2.46-2.32 (m, 1H), 2.26-1.94 (m, 6H), 1.70-1.58 (m, 1H), 1.07 (s, 9H); MS (ESI) m/z 572.31 (M+H).

The following Example was prepared according to procedures similar to those described for Example S18-5-2-1:

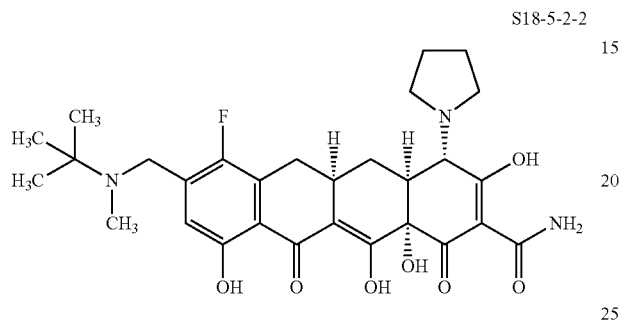

S18-5-2-2

S18-5-2-2: $^1$H NMR (400 MHz, CD$_3$OD) δ 7.21-7.17 (m, 1H), 4.13-4.02 (m, 3H), 3.90-3.78 (m, 1H), 3.62-3.50 (m, 2H), 3.35-28 (m, 1H), 3.23-3.09 (m, 1H), 2.92-2.80 (m, 4H), 2.56-2.42 (m, 1H), 2.38-2.03 (m, 6H), 1.80-1.60 (m, 10H); MS (ESI) m/z 558.34 (M+H).

Scheme 19
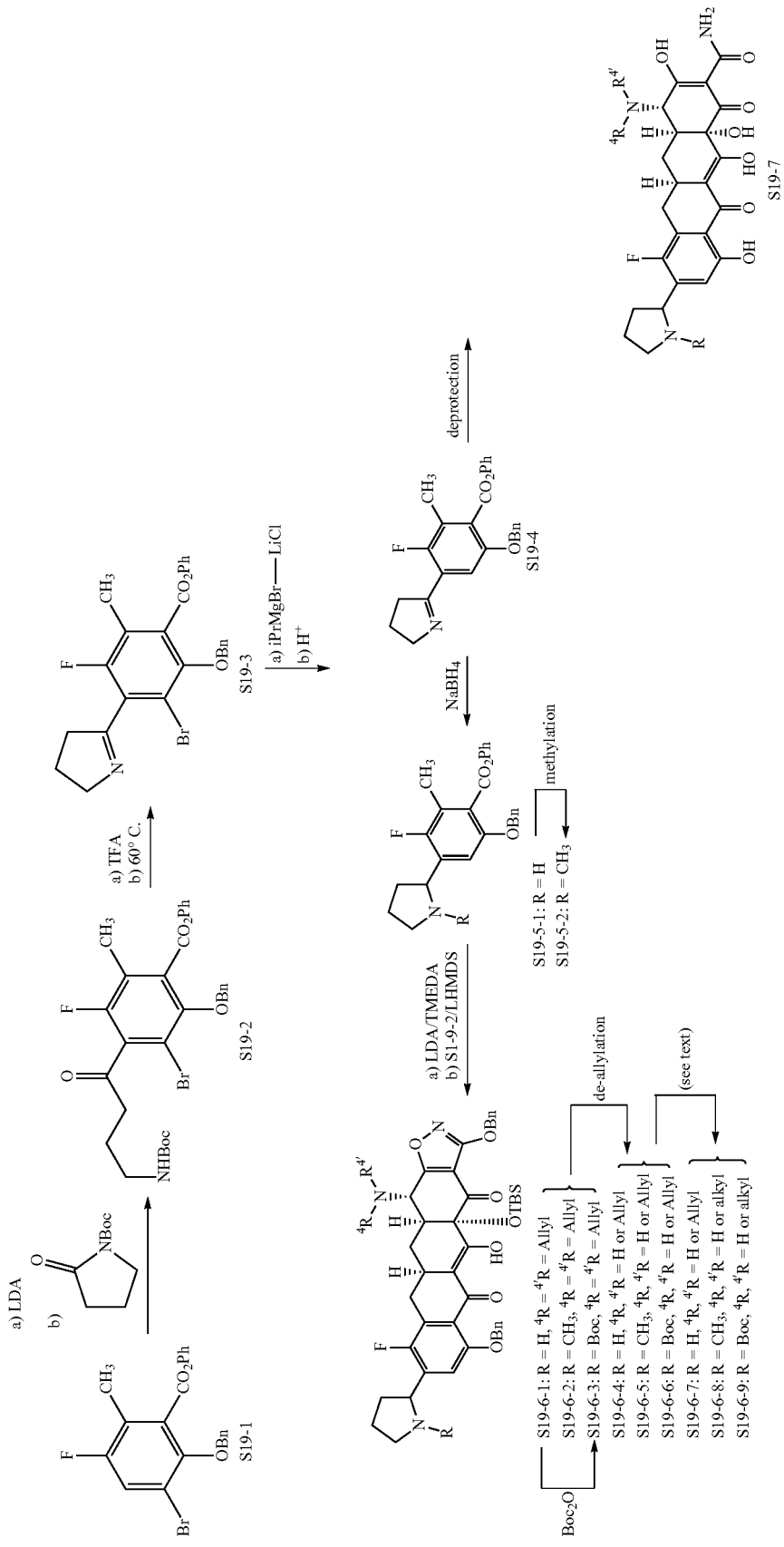

The following compounds were prepared according to Schemed 19.

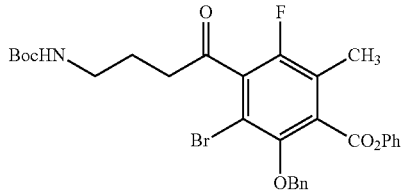
S19-2

To a solution of i-Pr$_2$NH (0.56 mL, 3.97 mmol, 1.5 eq) in THF (25 mL) was added n-BuLi (2.34 mL, 1.7 M/hexanes, 3.97 mmol, 1.5 eq) drop wise at −78° C. The reaction was allowed to warm to 0° C. and then cooled to −78° C. A solution of ester S19-1 (1.10 g, 2.65 mmol, 1 eq, prepared according to literature procedures including WO2011123536) in THF (3 mL) was added at −78° C., and the mixture was stirred for 25 min. A solution of N-Boc-2-pyrrolidinone (1.23 g, 6.63 mmol, 2.5 eq) in THF (3 mL) was added at −78° C. The reaction mixture was stirred at −78° C. for 25 min, slowly warmed to −30° C., and stirred at −30° C. for 20 min. The reaction was quenched with aqueous phosphate buffer (5 mL, pH=7). The mixture was extracted with EtOAc (3×15 mL). The organic extracts were combined, dried over Na$_2$SO$_4$, and concentrated. The residue was purified by flash chromatography on silica gel, eluting with hexanes/EtOAc (1:0 to 7:1) to afford S19-2 (800 mg, 50%): $^1$H NMR (400 MHz, CDCl$_3$) δ 7.24-7.50 (m, 8H), 7.01-7.06 (m, 2H), 5.09 (s, 2H), 4.61-4.70 (br, 1H), 3.20-3.27 (m, 2H), 2.88 (t, J=7.0 Hz, 2H), 2.34 (d, J=1.8 Hz, 3H), 1.94 (dq, J=6.7, 6.7 Hz, 2H), 1.43 (s, 9H); MS (ESI) m/z 624.44 (M+Na).

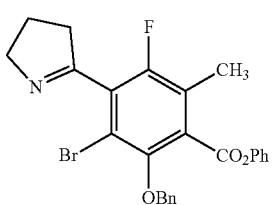
S19-3

To a solution of ketone S19-2 (800 mg, 1.33 mmol) in CH$_2$Cl$_2$ (8 mL) was added TFA (2 mL). The reaction mixture was stirred at rt for 1 h and concentrated. A solution of K$_2$CO$_3$ (5.0 g) in water (10 mL) was added, and the mixture was extracted with EtOAc (3×10 mL). The organic layers were combined, dried over Na$_2$SO$_4$, and concentrated. The residue was re-dissolved in toluene/EtOAc (1:1, 25 mL), stirred at 60° C. for 20 h, and concentrated. The residue was purified by flash chromatography on silica gel, eluting with hexanes/EtOAc (1:0 to 3:1) to afford S19-3 (600 mg, 93%): $^1$H NMR (400 MHz, CDCl$_3$) δ 7.24-7.50 (m, 8H), 7.02-7.07 (m, 2H), 5.10 (s, 2H), 4.12-4.17 (m, 2H), 2.82-2.89 (m, 2H), 2.34 (d, J=2.4 Hz, 3H), 2.06-2.15 (m, 2H); MS (ESI) m/z 480.31 (M−H).

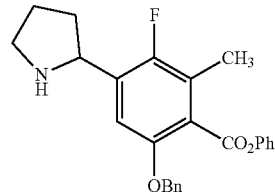
S19-5-1

To a solution of S19-3 (500 mg, 1.04 mmol, 1 eq) in THF (20 mL) was added i-PrMgBr—LiCl (3.50 mL, 1.2 M/THF, 4.16 mmol, 4 eq) at −50° C. The reaction mixture was slowly warmed to 0° C. over 1 h and stirred at 0° C. for 2 h. The reaction mixture was added with aqueous phosphate buffer (10 mL, pH=7) and extracted with EtOAc (100 mL). The organic extract was washed with brine (3×20 mL), dried over Na$_2$SO$_4$, and concentrated to dryness to give intermediate S19-4.

S19-4 was re-dissolved in CH$_3$OH (20 mL) and added with NaBH4 (100 mg, 2.64 mmol, 2.5 eq). The solution was stirred at rt for 40 min. HCl/1,4-dioxane (4 mL, 4 N) was added. The mixture was stirred at rt for 10 min and concentrated. Aqueous NaOH (10 mL, 1 N) was added. The aqueous layer was extracted with EtOAc (3×15 mL). The organic extracts were combined, dried over Na$_2$SO$_4$, and concentrated. The residue was purified by flash chromatography on silica gel, eluting with hexanes/EtOAc (1:0 to 0:1) to afford S19-5-1 (330 mg, 79% over 2 steps): $^1$H NMR (400 MHz, CDCl$_3$) δ 7.05-7.45 (m, 11H), 5.13 (s, 2H), 4.41 (t, J=7.6 Hz, 1H), 3.01-3.18 (m, 2H), 2.34 (d, J=1.8 Hz, 3H), 2.20-2.32 (m, 1H), 1.52-1.80 (comp, 3H); MS (ESI) m/z 405.97 (M+H).

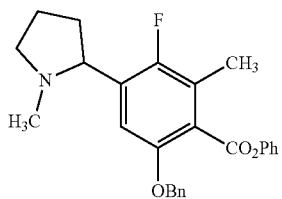
S19-5-2

To a solution of S19-5-1 (350 mg, 0.864 mmol, 1 eq) in dichloroethane (5 mL) was added aqueous formaldehyde (37%, 322 μL, 4.32 mmol, 5 eq), followed by acetic acid (247 μL, 4.32 mmol, 5 eq). After 10 min, sodium triacteoxyborohydride (905 mg, 4.27 mmol, 5 eq) was added. After 110 min, the reaction solution was diluted slowly with aqueous sodium bicarbonate solution (4 mL) and stirred 20 min, then was diluted further with aqueous sodium bicarbonate solution (20 mL), water (5 mL) and extracted with EtOAc (2×50 mL). The combined organic layers were dried over Na$_2$SO$_4$, were filtered, and were concentrated under reduced pressure. Purification of the resulting residue via flash column chromatography (Biotage, 25 g silica gel column, 20% to 60% EtOAc in hexanes gradient) provided the desired compound S19-5-2 (292 mg, 80%) as a white solid. $^1$H NMR (400 MHz, CDCl$_3$) δ 7.48-7.40 (m, 2H), 7.39-7.27 (m, 5H), 7.25-7.22 (m, 1H), 7.12-7.02 (m, 1H), 5.15 (s, 2H), 3.46 (t, J=7.9 Hz, 1H), 3.25 (t, J=7.9 Hz, 1H), 2.35 (s, 3H), 2.33-2.24 (m, 2H), 2.20 (s, 3H), 1.98-1.78 (m, 2H), 1.69-1.50 (m, 1H); MS (ESI) m/z 418.27 (M−H).

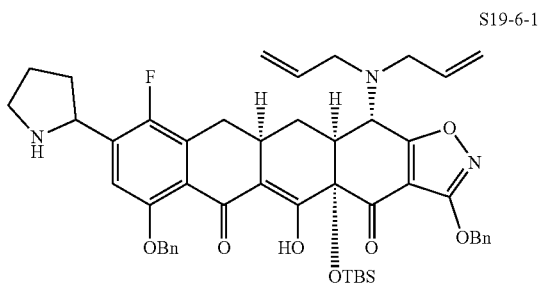 [SMILES: C=CCN(CC=C)[C@@H]1c2onc(OCc3ccccc3)c2C(=O)[C@@]2(O[Si](C)(C)C(C)(C)C)C(O)=C3C(=O)c4c(OCc5ccccc5)cc(C5CCCN5)c(F)c4C[C@H]3C[C@@H]12]

S19-6-1

Lithium diisopropylamide (3.2 eq) was prepared at −40° C. from n-butyllithium (1.6 M solution in hexane, 1.23 mL, 1.96 mmol) and diisopropylamine (287 μL, 2.03 mmol) in THF (15 mL). The solution was cooled to −78° C. and TMEDA (304 μL, 2.03 mmol, 3.2 eq) was added, followed by drop wise addition of compound S19-5-1 (766 mg, 1.89 mmol, 3.0 eq) in THF (2 mL) with a 500 μL THF rinse forward, maintaining internal temp below −70° C. The solution became a deep red color. After 30 min at this temperature, a solution of diallylenone S1-9-2 (339 mg, 0.634 mmol, 1 eq) in THF (2 mL) was added drop wise via syringe with a 500 μL THF rinse forward. After complete addition, the reaction mixture was allowed to warm over 75 min. Excess base was quenched at −10° C. by the addition of saturated aqueous NH$_4$Cl (6 mL). The reaction mixture was diluted with pH 7 phosphate buffer (40 mL) and extracted with EtOAc (2×40 mL). Combined organic extracts were dried over Na$_2$SO$_4$, were filtered, and were concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 40→60% B; mass-directed fraction collection], yielding 89.8 mg of an early eluting diastereomer (S19-6-1-A: diastereomer A), 120 mg of a later eluting diastereomer ((S19-6-1-B: diastereomer B), and 34 mg of a diastereomeric mixture (45% total yield). S19-6-1-A: $^1$H NMR (diastereomer A: 400 MHz, CDCl$_3$) δ 7.52-7.46 (m, 4H), 7.41-7.30 (m, 5H), 7.28-7.25 (m, 1H), 7.14 (d, J=5.5 Hz, 1H), 5.87-5.72 (m, 2H), 7.36 (s, 2H), 5.25-5.12 (m, 4H), 5.10 (d, J=10.4 Hz, 2H), 4.43 (t, J=7.9 Hz, 1H), 4.07 (d, J=7.9 Hz, 1H), 3.36-3.28 (m, 2H), 3.25-3.02 (m, 5H), 2.99-2.91 (m, 1H), 2.62-2.53 (m, 1H), 2.52-2.48 (m, 2H), 2.32-2.21 (m, 2H), 2.16-2.08 (m, 1H), 1.89-1.80 (m, 2H), 1.67-1.57 (m, 1H), 0.81 (s, 9H), 0.24 (s, 3H), 0.12 (s, 3H); MS (ESI) m/z 846.54 (M+H). S19-6-1-B: $^1$H NMR (diastereomer B: 400 MHz, CDCl$_3$) δ 7.57-7.47 (m, 4H), 7.40-7.22 (m, 7H), 5.84-5.73 (m, 2H), 5.37 (s, 2H), 5.36 (s, 2H), 5.16 (d, J=16.5 Hz, 2H), 5.11 (d, J=9.8 Hz, 2H), 4.75 (t, J=7.9 Hz, 1H), 4.04 (d, J=10.3 Hz, 1H, 3.43-3.34 (m, 1H), 3.42-3.08 (m, 6H), 3.03-2.91 (m, 1H), 2.66-2.53 (m, 1H), 2.52-2.30 (m, 3H), 2.14-2.07 (m, 1H), 2.02-1.82 (m, 3H), 0.82 (s, 9H), 0.24 (s, 3H), 0.12 (s, 3H); MS (ESI) m/z 846.54 (M+H).

A solution of S19-6-1-B (13 mg, 0.016 mmol, 1 eq), tetrakis(triphenylphosphine)-palladium (1.8 mg, 0.0016 mmol, 0.1 eq) and dimethylbarbituric acid (12.3 mg, 0.079 mmol, 5 eq) in dichloromethane (750 μL) was degassed with bubbling nitrogen gas for two minutes and then stirred at ambient temperature for 17 h. Additional solvent (1 mL) and Pd catalyst (3 mg, 0.25 mmol, 0.2 eq) were added and the solution degassed as above. After an additional 42 h, the reaction mixture was diluted with saturated aqueous sodium bicarbonate solution (15 mL) and extracted with EtOAc (2×20 mL). The organic layer was dried over Na$_2$SO$_4$, was filtered, and was concentrated under reduced pressure. Purification of the resulting residue via flash column chromatography (Biotage, 10 g silica gel column, 1% to 10% MeOH in dichloromethane gradient) provided the desired compound S19-6-4-1-B (4.8 mg, 40%, diastereomer B): $^1$H NMR (400 MHz, CDCl$_3$) δ 7.60-7.41 (m, 4H), 7.40-7.23 (m, 6H), 7.18-7.12 (m, 1H), 5.43-5.32 (m, 2H), 5.28-5.14 (m, 2H), 4.42-4.36 (m, 1H), 3.91 (brs, 1H), 3.14-2.98 (m, 2H), 2.83-2.72 (m, 1H), 2.64-2.58 (m, 1H), 2.30-2.02 (m, 2H), 1.87-1.77 (m, 2H), 1.24 (brs, 1H), 0.90-0.82 (m, 1H), 0.75 (s, 9H), 0.20 (s, 3H), 0.09 (s, 3H); MS (ESI) m/z 766.47 (M+H).

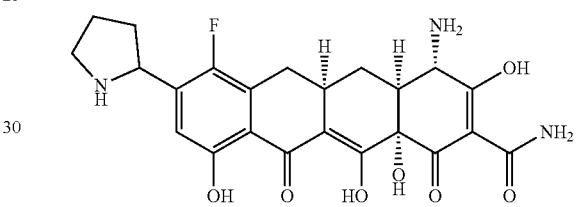

S19-7-1-B

A solution of S19-6-1-B (4.8 mg, 0.0063 mmol) in dichloromethane (200 μL) was cooled to 0° C. was added dimethylsulfide (10 μL), followed by drop wise addition of methanesulfonic acid. The reaction mixture was allowed to warm and was stirred at ambient temperature for 21 h. Dichloromethane solvent was evaporated under an N$_2$ stream, another 50 μL of dichloromethane and 10 μL of dimethylsulfide were added. After an additional 5 d, the solvent was evaporated and the resulting red-orange residue was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH$_3$CN; gradient: 0→30% B; mass-directed fraction collection]. Fractions with the desired MW were collected and freeze-dried to yield the desired compound S19-7-1-B (1.4 mg, 42%) as a yellow solid: $^1$H NMR (400 MHz, CD$_3$OD) δ 6.97 (d, J=5.5 Hz, 1H), 3.88 (s, 1H), 3.53-3.39 (m, 2H), 3.22-3.16 (m, 1H), 3.08-2.96 (m, 1H), 2.71-2.62 (m, 2H), 2.58-2.45 (m, 1H), 2.40-2.12 (m, 5H), 2.67-2.53 (m, 1H); MS (ESI) m/z 474.10 (M+H).

S19-6-4-1-B

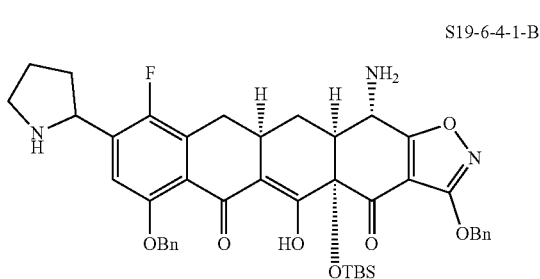 [SMILES: CC(C)(C)[Si](C)(C)O[C@@]12C(=O)c3c(OCc4ccccc4)noc3[C@@H](N)[C@@H]1C[C@@H]1Cc3c(F)c(C4CCCN4)cc(OCc4ccccc4)c3C(=O)C1=C2O]

S19-6-3

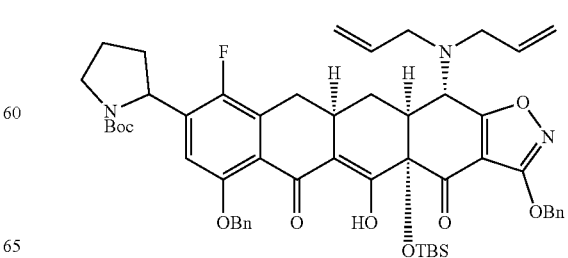

To a solution of S19-6-1-A (diastereomer A, 89.8 mg, 0.106 mmol, 1 eq) in dichloromethane (1 mL) was added di-tent-butyl dicarbonate (28.5 mg, 0.130 mmol, 1.2 eq) and dimethylaminopyridine (1.3 mg, 0.011 mmol, 0.1 eq) and the reaction mixture was stirred at ambient temperature. After 70 min, the mixture was placed in the fridge (4° C.) overnight, then diluted with saturated aqueous ammonium chloride (10 mL), water (2 mL) and extracted with EtOAc (2×20 mL). The combined organic layers were dried over Na$_2$SO$_4$, were filtered, and were concentrated under reduced pressure. Purification of the resulting residue via flash column chromatography (Biotage, 10 g silica gel column, 5% to 40% EtOAc in hexanes gradient) provided the desired compound S19-6-3-A (80.7 mg, 80%) as an oil. Similar conditions were applied to S19-6-1-B (diastereomer B, 120 mg, 0.142 mmol) to provide 58 mg of desired S19-6-3-B (43%). S19-6-3-A: $^1$H NMR (diastereomer A, rotamers: 400 MHz, CDCl$_3$) δ 16.05 (m, 1H), 7.52-7.25 (m, 10H), 6.66-6.51 (m, 1H), 5.87-5.72 (m, 2H), 5.36 (s, 2H), 5.25-4.90 (m, 6H), 3.65-2.88 (m, 8H), 2.63-2.17 (m, 3H), 2.15-2.07 (m, 1H), 1.88-1.62 (m, 2H), 1.47, 1.19 (m, 9H), 0.81 (s, 9H), 0.24 (s, 3H), 0.12 (s, 3H); MS (ESI) m/z 946.64 (M+H). S19-6-3-B: $^1$H NMR (diastereomer B, rotamers: 400 MHz, CDCl$_3$) δ 7.53-7.25 (m, 10H), 6.49-6.41 (m, 1H), 5.35 (s, 2H), 5.25-4.89 (m, 6H), 3.57-3.01 (m, 8H), 2.67-2.37 (m, 3H), 2.29-2.15 (m, 1H), 1.48-1.10 (m, 9H), 0.88-0.79 (m, 9H), 0.27-0.09 (m, 6H); MS (ESI) m/z 946.67 (M+H).

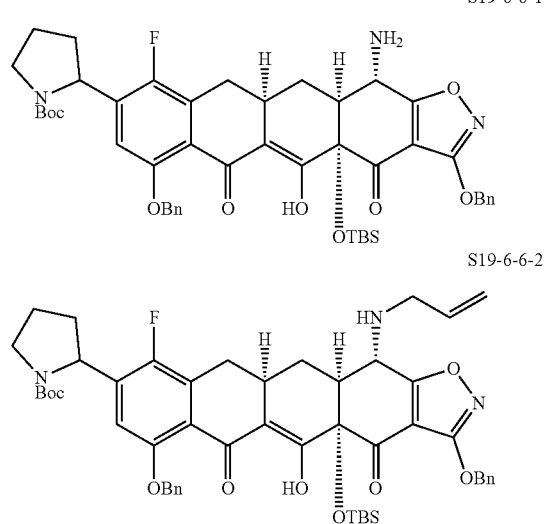

To a solution of S19-6-3-A (diastereomer A, 80.7 mg, 0.085 mmol, 1 eq) and 2-mercaptobenzoic acid (15.8 mg, 0.102 mmol, 1.2 eq) in THF (1 mL) under N$_2$ was added 100 µL of a dry, air-free prepared solution of bis(dibenzylideneacetone)palladium(0) and 1,4-bis(diphenylphosphinebutane) in THF (0.086 M of catalyst/ligand, 1 mL) drop wise via syringe. After 24 h, another aliquot of catalyst/ligand solution was added. After an additional 28 h, the reaction mixture was diluted with saturated aqueous sodium bicarbonate solution (10 mL) and pH 7 phosphate buffer (15 mL) and extracted with EtOAc (2×20 mL). The combined organic layers were dried over Na$_2$SO$_4$, were filtered, and were concentrated under reduced pressure. Purification of the resulting residue via flash column chromatography (Biotage, 10 g silica gel column, 7% to 60% EtOAc in hexanes gradient) provided the monoallyl compound S19-6-6-2-A (25 mg, 32%), the amino compound S19-6-6-1-A (12.5 mg, 17%) and recovered diallyl starting material S19-6-3-A (26.5 mg, 33%). Similar conditions were applied to S19-6-3-B (diastereomer B, 58 mg, 0.061 mmol) to provide monoallyl S19-6-6-2-B (15.3 mg, 28%), amino S19-6-6-1-B (10.7 mg, 20%), and recovered diallyl S19-6-3-B (19.3, 33%). Monoallyl S19-6-6-2-A: $^1$H NMR (diastereomer A, 400 MHz, CDCl$_3$, rotamers) δ 16.71-16.56 (m, 1H), 7.45-7.20 (m, 10H), 6.56-6.42 (m, 1H), 5.36-5.27 (m, 2H), 5.26-4.83 (m, 4H), 3.67-3.21 (m, 4H), 2.97-2.85 (m, 1H), 3.78-3.62 (m, 1H), 3.58-2.90 (m, 4H), 2.87-2.59 (m, 2H), 2.58-1.09 (m, 11H), 0.82-0.58 (m, 9H), 0.21-0.12 (m, 3H), 0.09-0.05 (m, 3H); MS (ESI) m/z 906.59 (M+H). Amino S19-6-6-1-A: $^1$H NMR (diastereomer A, 400 MHz, CDCl$_3$, rotamers); MS (ESI) m/z 866.57 (M+H). Monoallyl S19-6-6-2-B: $^1$H NMR (diastereomer B, 400 MHz, CDCl$_3$, rotamers) δ 7.48-7.23 (m, 10H, 6.37-6.29 (m, 1H), 5.91-5.74 (m, 1H), 5.36-4.81 (m, 6H), 377-2.62 (m, 6H), 2.31-2.03 (m, 2H), 1.70-1.07 (m, 15H), 0.83-0.62 (m, 9H), 0.26-0.15 (m, 3H), 0.04-0.23 (m, 3H); MS (ESI) m/z 906.59 (M+H). Amino S19-6-6-1-B: $^1$H NMR (diastereomer B, 400 MHz, CDCl$_3$, rotamers); MS (ESI) m/z 866.57 (M+H).

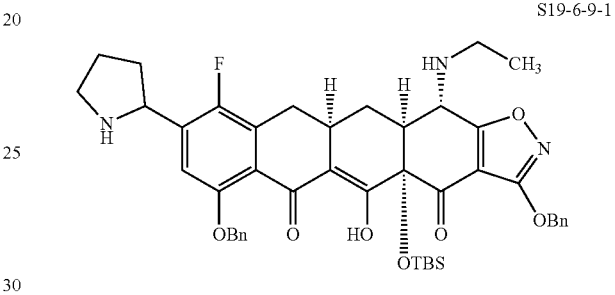

To a solution of S19-6-6-1-A (diastereomer A, 12.5 mg, 0.014 mmol, 1 eq) in methanol (750 µL) was added acetic acid (4 µL, 0.072 mmol, 3 eq) and the mixture cooled to 0° C. Sodium triacetoxyborohydride (12.3 mg, 0.058 mmol, 4 eq) was added, followed by a prepared solution of acetaldehyde in methanol (50 µL in 950 µL; 48 µL, 0.043 mmol, 3 eq). After 50 min at 0° C., the solution was diluted with saturated aqueous sodium bicarbonate solution (1 mL), pH 7 phosphate buffer (1 mL) and EtOAc (500 µL). Stirred 5 min, then extracted with EtOAc (10 mL, 5 mL). Combined organic layers were dried over Na$_2$SO$_4$, were filtered, and were concentrated under reduced pressure. The resulting crude oil, S19-6-9-1-A, was used without further purification: MS (ESI) m/z 894.40 (M+H). Similar results observed with diastereomer B S19-6-6-1-B and a diastereomeric mixture of S19-6-6-1.

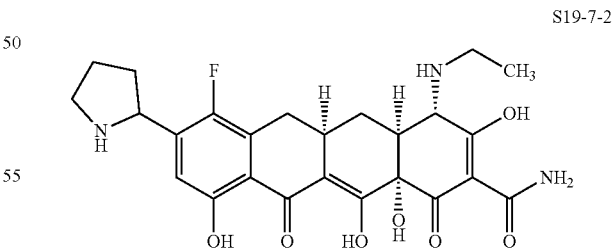

S19-7-2 (diastereomeric mixture) was prepared similarly to compound S19-7-1-B from S19-6-9-1 (diastereomeric mixture) via treatment with dimethylsulfide in methanesulfonic acid: $^1$H NMR (400 MHz, CD$_3$OD) δ 7.01-6.95 (m, 1H), 3.87 (s, 1H), 3.57-3.38 (m, 5H), 3.19 (dd, J=15.9, 4.3 Hz, 1H), 3.08-2.92 (m, 1H), 2.88-2.81 (m, 1H), 2.55-2.46 (m, 1H), 2.41-2.07 (5H), 1.64-1.50 (m, 1H), 1.45-1.32 (m, 3H); MS (ESI) m/z 502.13 (M+H).

S19-6-9-2

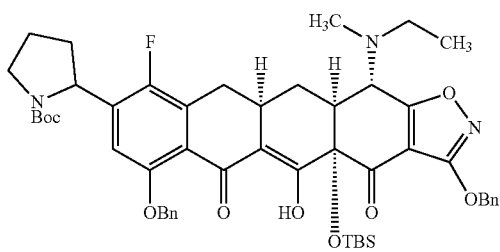

To a solution of S19-6-9-1-A (diastereomer A, 0.014 mmol, 1 eq) in dichloroethane (750 µL) was added aqueous formaldehyde (37%, 5.6 µL, 0.072 mmol, 5 eq), followed by acetic acid (4 µL, 0.072 mmol, 5 eq). After fifteen minutes, sodium triacteoxyborohydride (14.8 mg, 0.072 mmol, 5 eq) was added. After 70 min, the reaction solution was diluted with aqueous sodium bicarbonate solution (1 mL) and stirred five minutes, then diluted further with aqueous sodium bicarbonate solution (6 mL) and extracted with EtOAc (2×8 mL). The combined organic layers were dried over $Na_2SO_4$, were filtered, and were concentrated under reduced pressure. The resulting crude oil, S19-6-9-2-A, was used without further purification. S19-6-9-2-B (diastereomer B) was prepared similarly to compound S19-6-9-2-A from S19-6-9-1-B (diastereomer B) via reductive alkylation as above. S19-6-9-2-A: MS (ESI) m/z 908.60 (M+H). S19-6-9-2-B: MS (ESI) m/z 908.61 (M+H).

S19-6-9-3

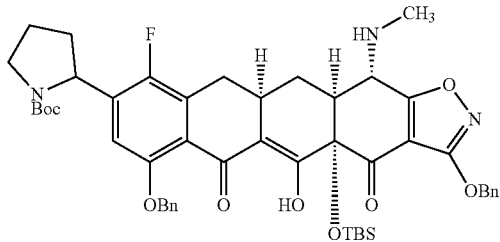

To a solution of S19-6-6-2-A (diastereomer A, 15.3 mg, 0.017 mmol, 1 eq) in dichloroethane (1.5 mL) was added aqueous formaldehyde (37%, 6.3 µL, 0.084 mmol, 5 eq), followed by acetic acid (4.8 µL, 0.084 mmol, 5 eq). After five minutes, sodium triacteoxyborohydride (17.9 mg, 0.084 mmol, 5 eq) was added. After 2.5 h, another portion of sodium triacetoxyborohydride (20 mg, 0.094 mmol, 5.5 eq) was added. After an additional 1.75 h, the reaction solution was diluted with aqueous sodium bicarbonate solution (2 mL) and stirred 15 min, then was diluted further with aqueous sodium bicarbonate solution (10 mL) and extracted with EtOAc (2×25 mL). The combined organic layers were dried over $Na_2SO_4$, were filtered, and were concentrated under reduced pressure. The resulting crude oil was used for the following reaction without further purification.

A solution of the above crude oil (0.017 mmol, 1 eq), tetrakis(triphenylphosphine)-palladium (3.1 mg, 0.0027 mmol, 0.1 eq) and dimethylbarbituric acid (20.0 mg, 0.128 mmol, 5 eq) in dichloromethane (1 mL) was degassed with bubbling nitrogen gas for two minutes and then stirred at ambient temperature for 24 h. The reaction mixture was diluted with saturated aqueous sodium bicarbonate solution (15 mL) and extracted with EtOAc (2×25 mL). The organic layer was dried over $Na_2SO_4$, was filtered, and was concentrated under reduced pressure. Purification of the resulting residue via flash column chromatography (Biotage, 10 g silica gel column, 17% to 70% EtOAc in hexanes gradient) provided the desired compound S19-6-9-3-A (11.9 mg, 49%): $^1$H NMR (diastereomer A, 400 MHz, $CDCl_3$: rotamers); MS (ESI) m/z 880.47 (M+H).

S19-6-9-3-B (diastereomer B) was prepared similarly to compound S19-6-9-3-A from S19-6-6-2-B (diastereomer B) via reductive alkylation and deallylation as above: $^1$H NMR (diastereomer B, 400 MHz, $CDCl_3$: rotamers); MS (ESI) m/z 880.47 (M+H).

S19-7-3

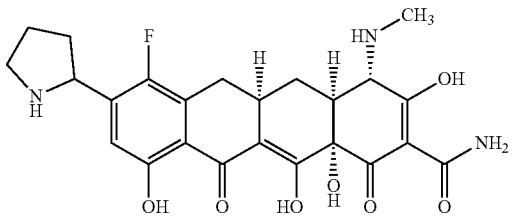

S19-7-3-A (diastereomer A) was prepared similarly to compound S19-7-1-B from S19-6-9-3-A (diastereomer A) via treatment with dimethylsulfide in methanesulfonic acid. $^1$H NMR (400 MHz, $CD_3OD$) δ 6.98 (d, J=5.5 Hz, 1H), 4.87-4.76 (m, 2H), 3.81 (s, 1H), 3.50-3.39 (m, 2H), 3.19 (dd, J=15.3, 4.3 Hz, 1H), 3.09-2.96 (m, 1H), 2.91 (s, 3H), 2.81 (d, J=12.2 Hz, 1H), 2.55-2.45 (m, 1H), 2.38-2.09 (m, 6H), 1.63-1.51 (m, 1H); MS (ESI) m/z 488.26 (M+H).

S19-7-3-B (diastereomer B) was prepared similarly to compound S19-7-1-B from S19-6-9-3-B (diastereomer B) via treatment with dimethylsulfide in methanesulfonic acid. $^1$H NMR (400 MHz, $CD_3OD$) δ 6.99 (d, J=6.1 Hz, 1H), 4.86-4.77 (m, 2H), 3.81 (s, 1H), 3.50-3.40 (m, 2H), 3.19 (dd, J=15.3, 4.3 Hz, 1H), 3.09-2.97 (m, 1H), 2.91 (s, 3H), 2.81 (d, J=12.9 Hz, 1H), 2.54-2.45 (m, 1H), 2.38-2.11 (m, 6H), 1.63-1.51 (m, 1H); MS (ESI) m/z 488.25 (M+H).

S19-7-4

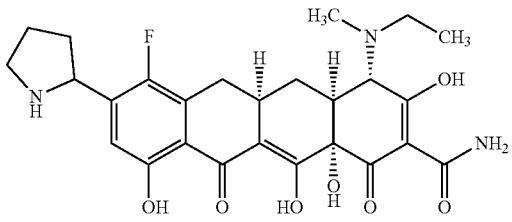

S19-7-4-A (diastereomer A) was prepared similarly to compound S19-7-1-B from S19-6-9-2-A (diastereomer A) via treatment with dimethylsulfide in methanesulfonic acid. $^1$H NMR (400 MHz, $CD_3OD$) δ 6.99 (d, J=6.1 Hz, 1H), 4.23, 4.14 (s, s, 1H), 3.55-3.42 (m, 2H), 3.39-3.31 (m, 1H), 3.25-3.16 (m, 1H), 3.14-2.90 (m, 6H), 2.56-2.47 (m, 1H), 2.39-2.10 (m, 6H), 1.72-1.58 (m, 1H), 1.45-1.34 (m, 3H); MS (ESI) m/z 516.29 (M+H).

S19-7-4-B (diastereomer B) was prepared similarly to compound S19-7-1-B from S19-6-9-2-B (diastereomer B) via treatment with dimethylsulfide in methanesulfonic acid. $^1$H NMR (400 MHz, $CD_3OD$) δ 6.99 (d, J=6.1 Hz, 1H), 4.21, 4.12 (s, s, 1H), 3.54-3.40 (m, 3H), 3.25-3.15 (m, 1H), 3.14-2.86 (m, 6H), 2.56-2.42 (m, 1H), 2.42-2.09 (m, 6H), 1.72-1.56 (m, 1H), 1.45-1.34 (m, 3H); MS (ESI) m/z 516.30 (M+H).

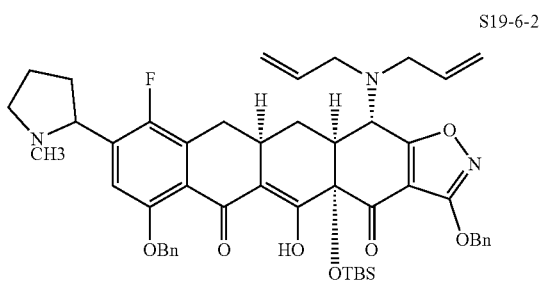 [SMILES: C=CCN(CC=C)[C@@H]1c2onc(OCc3ccccc3)c2C(=O)[C@@]2(O[Si](C)(C)C(C)(C)C)C(O)=C3C(=O)c4c(OCc5ccccc5)cc(C5CCCN5C)c(F)c4C[C@H]3C[C@@H]12]

S19-6-2

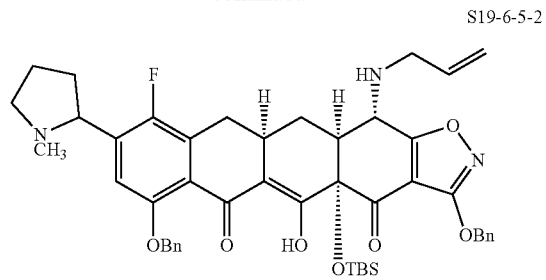 [SMILES: CN[C@@H]1c2onc(OCc3ccccc3)c2C(=O)[C@@]2(O[Si](C)(C)C(C)(C)C)C(O)=C3C(=O)c4c(OCc5ccccc5)cc(C5CCCN5C)c(F)c4C[C@H]3C[C@@H]12]

S19-6-5-2

Lithium diisopropylamide (2.1 eq) was prepared at −40° C. from n-butyllithium (1.6 M solution in hexane, 324 µL, 0.519 mmol) and diisopropylamine (77 µL, 0.543 mmol) in THF (4 mL). The solution was cooled to −78° C. and TMEDA (81.5 µL, 0.543 mmol, 2.2 eq) was added, followed by drop wise addition of compound S19-5-2 (210 mg, 0.500 mmol, 2.0 eq) in THF (900 µL) with a 200 µL THF rinse forward, maintaining the internal temp below −70° C. The solution became red-orange in color. After 30 min at this temperature, a solution of diallylenone S1-9-2 (132 mg, 0.247 mmol, 1 eq) in THF (900 µL) was added drop wise via syringe with a 200 µL THF rinse forward, maintaining the internal temperature below −70° C. Lithium hexamethyldisilazane (1 M in THF, 247 µL, 0.247 mmol, 1 eq). After complete addition, the reaction mixture was allowed to warm to −10° C. over 1 h. Excess base was quenched at −10° C. by the addition of saturated aqueous NH$_4$Cl solution (5 mL) and the mixture was allowed to warm to ambient temperature. The reaction mixture was diluted with saturated aqueous NH$_4$Cl solution (15 mL) and water (3 mL), and extracted with EtOAc (2×25 mL). Combined organic extracts were dried over Na$_2$SO$_4$, were filtered, and were concentrated under reduced pressure. The material was purified via flash column chromatography (Biotage, 50 g silica gel column, 8% to 80% EtOAc in hexanes gradient), which produced a mixture of product S19-6-2 and remaining S19-5-2. Further purification on a Waters Autopurification system equipped with a Sunfire Prep C18 OBD column [5 µm, 19×50 mm; flow rate, 20 mL/min; Solvent A: H$_2$O with 0.1% HCO$_2$H; Solvent B: CH$_3$CN with 0.1% HCO$_2$H; gradient: 10→100% B; mass-directed fraction collection], provided desired compound S19-6-2 (103 mg, 49%): $^1$H NMR (400 MHz, CDCl$_3$) δ 16.13 (s, 1H), 7.56-7.45 (4H), 7.44-7.29 (m, 5H), 7.28-7.23 (m, 1H), 7.19-7.09 (m, 1H), 5.90-5.71 (m, 2H), 5.36 (s, 2H), 5.33-5.03 (m, 8H), 3.57-3.44 (m, 1H), 3.40-3.27 (m, 2H), 3.27-3.10 (m, 4H), 3.07-2.95 (m, 1H), 2.72-2.55 (m, 1H), 2.54-2.04 (m, 8H), 2.01-1.79 (m, 1H), 1.75-1.57 (m, 1H), 1.02-0.75 (m, 9H), 0.27 (s, 3H), 0.14 (s, 3H); MS (ESI) m/z 860.59 (M+H).

S19-6-5-1 and S19-6-5-2 were prepared similarly to S19-6-6-1 and S19-6-6-2 from S19-6-2 (103 mg, 0.121 mmol) via treatment with catalytic bis(dibenzylideneacetone)palladium(0) and 1,4-bis(diphenylphosphinebutane) in the presence of 2-mercaptobenzoic acid. S19-6-5-2 (monoallyl, mixture of diastereomers, 34.8 mg, 35%): MS (ESI) m/z 820.53 (M+H). S19-6-5-1 (amino, mixture of diastereomers, 27.1 mg, 29%): MS (ESI) m/z 780.47 (M+H). Unreacted starting material was also recovered (S19-6-2, 21.6 mg, 21%).

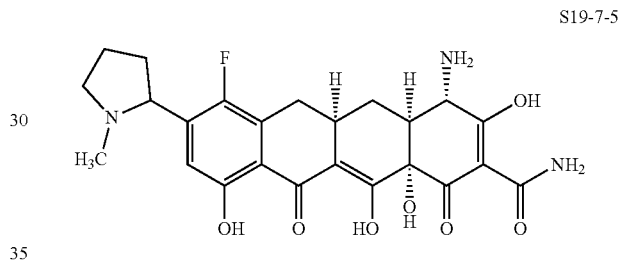

S19-7-5

S19-7-5-A (diastereomer A) and S19-7-5-B (diastereomer B) were prepared similarly to compound S19-7-1-B from S19-6-5-1 (diastereomeric mixture) via treatment with dimethylsulfide in methanesulfonic acid. Diastereomers were separated on purification. S19-7-5-A (diastereomer A): $^1$H NMR (400 MHz, CD$_3$OD) δ 7.07 (d, J=5.5 Hz, 1H), 4.72-4.66 (m, 1H), 3.91-3.80 (m, 2H), 3.41-3.30 (m, 1H), 3.21 (dd, J=15.9, 3.7 Hz, 1H), 3.07-2.96 (m, 1H), 2.87 (s, 3H), 2.65 (d, J=12.8 Hz, 1H), 2.61-2.51 (m, 1H), 2.42-2.20 (m, 5H), 1.66-1.54 (m, 1H); MS (ESI) m/z 488.22 (M+H). S19-7-5-B (diastereomer B): $^1$H NMR (400 MHz, CD$_3$OD) δ $^1$H NMR (400 MHz, CD$_3$OD) δ 7.07 (d, J=6.1 Hz, 1H), 4.76-4.67 (m, 1H), 3.91-3.79 (m, 2H), 3.41-3.30 (m, 1H), 3.20 (dd, J=15.3, 4.9 Hz, 1H), 3.07-2.96 (m, 1H), 2.87 (s, 3H), 2.65 (d, J=12.8 Hz, 1H), 2.61-2.51 (m, 1H), 2.42-2.20 (m, 5H), 1.66-1.54 (m, 1H); MS (ESI) m/z 488.22 (M+H).

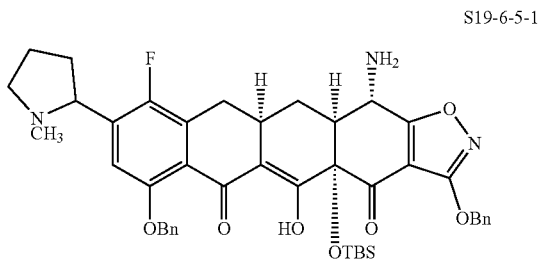

S19-6-5-1

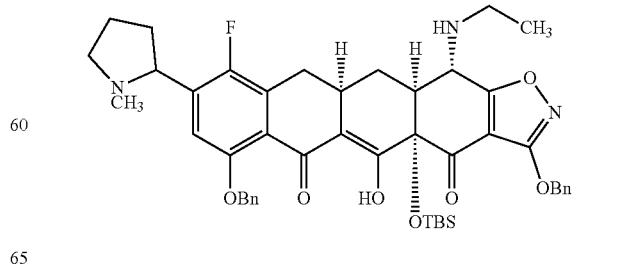

S19-6-8-1

S19-6-8-1 (diastereomeric mixture) was prepared similarly to compound S19-6-9-1 from S19-6-5-1 (diastereomeric mixture) via treatment with acetaldehyde and sodium triacetoxyborohydride. S19-6-8-1 (diastereomeric mixture): MS (ESI) m/z 808.51 (M+H).

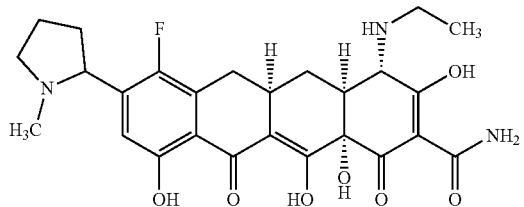

S19-7-6

S19-7-6 (diastereomeric mixture) was prepared similarly to compound S19-7-1-B from S19-6-8-1 (diastereomeric mixture) via treatment with dimethylsulfide in methanesulfonic acid. $^1$H NMR (400 MHz, CD$_3$OD) δ 7.10 (d, J=5.5 Hz, 1H), 4.78-4.68 (m, 1H), 3.92-3.81 (m, 2H), 3.48-3.32 (m, 3H), 3.25-3.14 (m, 1H), 3.10-2.98 (m, 1H), 2.92-2.82 (m, 4H), 2.62-51 (m, 1H), 2.40-2.22 (m, 5H), 1.65-1.50 (m, 1H), 1.36 (t, J=7.3 Hz, 3H); MS (ESI) m/z 516.26 (M+H).

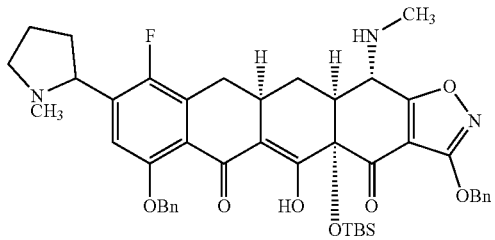

S19-6-8-2

S19-6-8-2 was prepared from S19-6-5-2 similarly to compound S19-6-9-3 via reductive alkylation with aqueous formaldehyde with triacetoxyborohydride followed by allyl deprotection with tetrakis(triphenylphosphine)palladium and dimethylbarbituric acid. S19-6-8-2 (diastereomeric mixture): MS (ESI) m/z 794.53 (M+H).

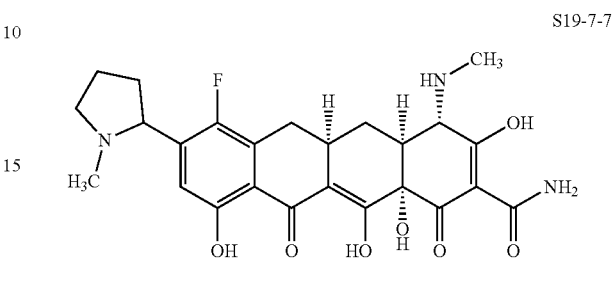

S19-7-7

S19-7-7-A (diastereomer A) and S19-7-7-B (diastereomer B) were prepared similarly to compound S19-7-1-B from S19-6-8-2 (diastereomeric mixture) via treatment with dimethylsulfide in methanesulfonic acid. Diastereomers were separated on purification. S19-7-7-A (diastereomer A): $^1$H NMR (400 MHz, CD$_3$OD) δ 7.07 (d, J=5.5 Hz, 1H), 4.71 (t, J=7.9 Hz, 1H), 3.89-3.77 (m, 2H), 3.40-3.35 (m, 1H), 3.20 (dd, J=15.2, 4.9 Hz, 1H), 3.10-2.97 (m, 1H), 2.91 (s, 3H), 2.87 (s, 3H), 2.80 (d, J=12.2 Hz, 1H), 2.62-2.50 (m, 1H), 2.42-2.16 (m, 5H), 1.64-1.51 (m, 1H); MS (ESI) m/z 502.30 (M+H). S19-7-7-B (diastereomer B): $^1$H NMR (400 MHz, CD$_3$OD) δ 7.07 (d, J=5.5 Hz, 1H), 4.74-4.64 (m, 1H), 3.89-3.77 (m, 2H), 3.40-3.35 (m, 1H), 3.18 (dd, J=15.2, 4.9 Hz, 1H), 3.09-2.97 (m, 1H), 2.90 (s, 3H), 2.86 (s, 3H), 2.80 (d, J=12.2 Hz, 1H), 2.62-2.50 (m, 1H), 2.40-2.17 (m, 5H), 1.64-1.52 (m, 1H); MS (ESI) m/z 502.30 (M+H).

Scheme 20

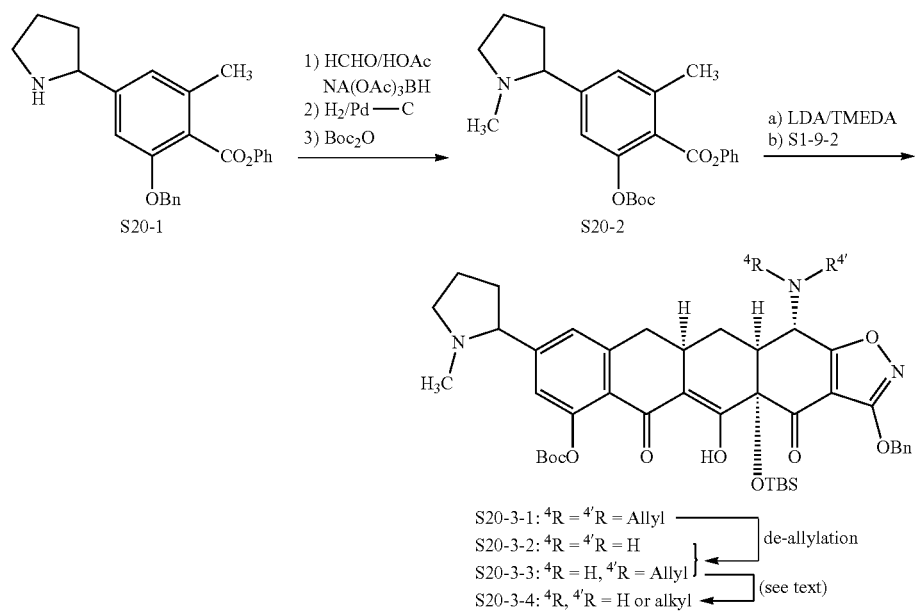

-continued

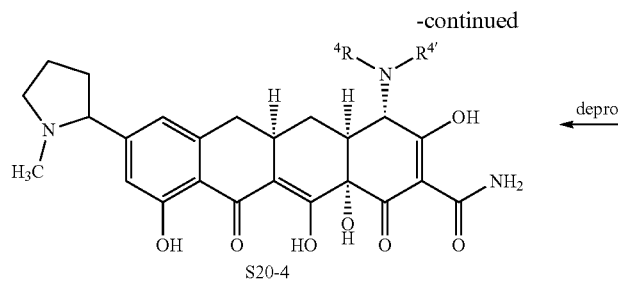

S20-4

The following compounds were prepared according to Scheme 20.

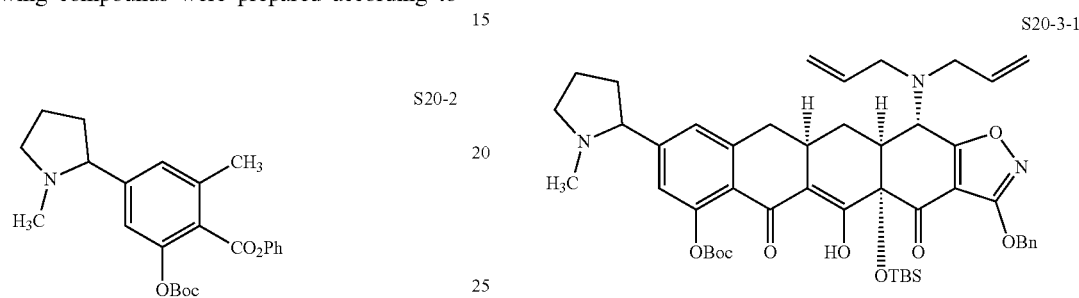

To a solution of S20-1 (single enantiomer, 257 mg, 0.528 mmol, 1 eq, prepared from S4-6 with similar procedures used for the preparation of S4-11 without the bromination and trifluoromethylation steps) in dichloroethane (5 mL) was added aqueous formaldehyde (37%, 196 μL, 2.64 mmol, 5 eq), followed by acetic acid (150 μL, 2.64 mmol, 5 eq). After 25 min, sodium triacetoxyborohydride (555 mg, 2.64 mmol, 5 eq) was added. After 55 min, the reaction solution was diluted with aqueous sodium bicarbonate solution (4 mL) and stirred 20 min, then was diluted further with aqueous sodium bicarbonate solution (15 mL), water (5 mL) and extracted with EtOAc (2×30 mL). The combined organic layers were dried over $Na_2SO_4$, were filtered, and were concentrated under reduced pressure to produce a crude oil.

The material was dissolved in dioxane:MeOH (1:1, 2 mL), and palladium on carbon (Degussa, 10 wt %, 55 mg) was added. An atmosphere of hydrogen was introduced and the reaction mixture was stirred for 5.5 h. Another portion of palladium catalyst (40 mg) was added, followed by reintroduction of hydrogen atmosphere. After an additional hour, the reaction mixture was filtered through a small Celite pad and the filtrate was concentrated under reduced pressure.

To a solution of the above crude oil in dichloromethane (2.6 mL) was added di-tert-butyl dicarbonate (166 mg, 0.761 mmol, 1.5 eq) and dimethylaminopyridine (3 mg, 0.024 mmol, 0.05 eq) and the reaction mixture was stirred at ambient temperature. After 90 min, the mixture was diluted with saturated aqueous ammonium chloride (20 mL), water (1 mL) and extracted with EtOAc (2×25 mL). The combined organic layers were dried over $Na_2SO_4$, were filtered, and were concentrated under reduced pressure. Purification of the resulting residue via flash column chromatography (Biotage, 25 g silica gel column, 2% to 50% EtOAc in hexanes gradient) provided the desired compound S20-2 (166 mg, 77%) as a white solid. $^1$H NMR (400 MHz, $CDCl_3$) δ 7.44-7.38 (m, 2H), 7.28-7.21 (m, 3H), 7.19-7.16 (m, 1H), 7.09 (s, 1H), 3.29-3.21 (m, 1H), 3.13-3.04 (m, 1H), 2.51 (s, 3H), 2.36-3.28 (m, 1H), 2.23-2.04 (m, 4H), 2.02-1.88 (m, 1H), 1.86-1.68 (m, 2H), 1.42 (s, 9H); MS (ESI) m/z 410.27 (M−H).

Lithium diisopropylamide (2.5 eq) was prepared at −40° C. from n-butyllithium (1.6 M solution in hexane, 484 μL, 0.775 mmol) and diisopropylamine (114 μL, 8.06 mmol) in THF (5 mL). The solution was cooled to −78° C. and TMEDA (120 μL, 0.806 mmol, 2.6 eq) was added, followed by drop wise addition of compound S20-2 (166 mg, 0.403 mmol, 1.3 eq) in THF (1 mL) with a 500 μL THF rinse forward, maintaining the internal temperature below −70° C. The solution became a deep red color. After 30 min at this temperature, the solution was cooled to −100° C. A solution of diallylenone S1-9-2 (165 mg, 0.308 mmol, 1 eq) in THF (1 mL) was added drop wise via syringe with a 500 μL THF rinse forward, maintaining the internal temperature below −90° C. After complete addition, the reaction mixture was allowed to warm slowly in the bath. When the solution reached −78° C., lithium hexamethyldisilazane (1 M in hexanes, 310 μL, 1 eq) was added. After 70 min, excess base was quenched at −10° C. by the addition of a saturated aqueous $NH_4Cl$ solution (3 mL) and the mixture was warmed to ambient temperature. The reaction mixture was diluted with saturated aqueous $NH_4Cl$ solution (15 mL) and water (2 mL) and was extracted with EtOAc (2×25 mL). Combined organic extracts were dried over $Na_2SO_4$, were filtered, and were concentrated under reduced pressure. Purification of the resulting residue via flash column chromatography (Biotage, 25 g silica gel column, 7% to 60% EtOAc in hexanes gradient) provided the desired compound S20-3-1 (single diastereomer, 203.8 mg, 70%) as a yellow foam (>90% purity): $^1$H NMR (400 MHz, $CDCl_3$) δ 15.61 (s, 1H), 7.40-7.34 (m, 2H), 7.30-7.19 (m, 3H), 7.06-6.98 (m, 1H), 6.90 (s, 1H), 5.74-5.61 (m, 2H), 5.24 (s, 2H), 5.12 (d, J=17.1 Hz, 2H), 5.00 (d, J=9.8 Hz, 2H), 3.26-3.05 (m, 4H), 3.05-2.79 (m, 3H), 2.76-2.68 (m, 1H), 2.41-2.26 (m, 2H), 2.25-2.02 (m, 5H), 2.01-1.93 (m, 1H), 1.90-1.54 (m, 3H), 1.53-1.43 (m, 1H), 1.42 (s, 9H), 0.71 (s, 9H), 0.14 (s, 3H), 0.00 (s, 3H); MS (ESI) m/z 850.53 (M−H).

S20-3-2

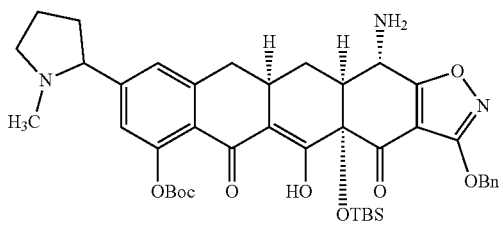

A solution of S20-3-1 (103 mg, 0.121 mmol, 1 eq), tetrakis(triphenylphosphine)-palladium (7.0 mg, 0.0061 mmol, 0.05 eq) and dimethylbarbituric acid (95.5 mg, 0.612 mmol, 5 eq) under nitrogen was dissolved in dichloromethane (1.5 mL) and stirred at ambient temperature. After 22 h, additional solvent (500 µL) and Pd catalyst (8 mg, 0.007 mmol, 0.06 eq) were added. After an additional 2.5 h, the reaction mixture was diluted with saturated aqueous sodium bicarbonate solution (15 mL) and water (2 mL) and extracted with EtOAc (2×35 mL). The organic layer was dried over $Na_2SO_4$, was filtered, and was concentrated under reduced pressure. Purification of the resulting residue via flash column chromatography (Biotage, 25 g silica gel column, 40% to 100% EtOAc in hexanes, then 10% MeOH in dichloromethane gradient) provided the desired compound S20-3-2 (single diastereomer, 80.6 mg, 86%). $^1$H NMR (rotamers, 400 MHz, $CDCl_3$) δ 16.33 (s, 1H), 7.72-7.63 (m, 2H), 7.59-7.43 (m, 2H), 7.42-7.31 (m, 1H), 7.13 (s, 1H), 7.04 (s, 1H), 5.44-5.33 (m, 2H), 3.97 (brs, 1H), 3.28-3.21 (m, 1H), 3.15-3.05 (m, 1H), 3.04-2.89 (m, 1H), 2.82-2.72 (m, 1H), 2.68-2.56 (m, 1H), 2.38-2.27 (m, 1H), 2.26-2.08 (m, 6H), 2.01-1.90 (m, 1H), 1.89-1.67 (m, 2H), 1.65-1.51 (m, 9H), 0.91-0.72 (m, 9H), 0.26-0.08 (m, 6H); MS (ESI) m/z 772.47 (M+H).

S20-3-3

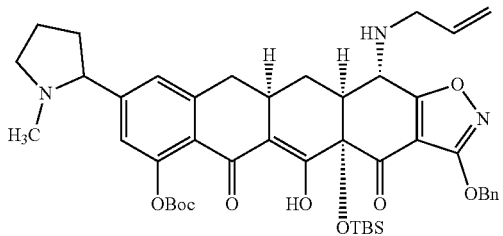

To a solution of S20-3-1 (100 mg, 0.117 mmol, 1 eq) and 2-mercaptobenzoic acid (23 mg, 0.149 mmol, 1.2 eq) in THF (1 mL) under $N_2$ was added 500 µL of a dry, air-free, prepared solution of bis(dibenzylideneacetone)palladium(0) and 1,4-bis(diphenylphosphinebutane) in THF (0.02 M in catalyst/ligand, 1 mL) drop wise via syringe. After 19 h, another portion of palladium catalyst (6.7 mg, 0.012 mmol, 0.1 eq), ligand (6 mg, 0.014 mmol, 1.2 eq) and 2-mercaptobenzoic acid (25 mg, 0.16 mmol, 1.4 eq) was added. After an additional 24 h, the reaction mixture was diluted with saturated aqueous sodium bicarbonate solution (20 mL) and water (2 mL) and extracted with EtOAc (2×25 mL). The combined organic layers were dried over $Na_2SO_4$, were filtered, and were concentrated under reduced pressure. Purification of the resulting residue via flash column chromatography (Biotage, 25 g silica gel column, 5% to 80% EtOAc in hexanes gradient) provided the monoallyl compound S20-3-3 (25 mg, 26%), and recovered diallyl S20-3-1 (52.7 mg, 53%). Monoallyl S20-3-3: $^1$H NMR (400 MHz, $CDCl_3$, single diastereomer, rotamers) δ 16.30 (s, 1H), 7.43-7.37 (m, 2H), 7.33-7.23 (m, 3H), 7.02 (s, 1H), 6.94 (s, 1H), 5.86-5.74 (m, 1H), 5.33 (d, J=12.2 Hz, 1H), 5.29 (d, J=12.2 Hz, 1H), 5.21 (d, J=17.7 Hz, 1H), 5.08 (d, J=9.8 Hz, 1H), 3.68 (s, 1H), 3.48 (dd, J=13.4, 6.1 Hz, 1H), 3.35 (dd, J=13.4, 6.1 Hz, 1H), 3.18-3.11 (m, 1H), 3.03-2.95 (m, 1H), 2.90-2.75 (m, 1H), 2.69-2.60 (m, 2H), 2.52-2.41 (m, 1H), 2.30-2.05 (m, 5H), 2.00-1.57 (m, 4H), 1.56-1.36 (m, 10H), 0.66 (s, 9H), 0.10 (s, 3H), 0.00 (s, 3H); MS (ESI) m/z 812.55 (M+H).

S20-4-1

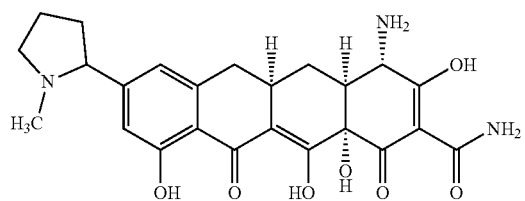

S20-4-1 (single diastereomer) was prepared similarly to compound S19-7-1-B from S20-3-2 (single diastereomer) via treatment with dimethylsulfide in methanesulfonic acid: $^1$H NMR (400 MHz, $CD_3OD$, methanesulfonic acid salt) δ 6.98 (s, 1H), 6.92 (s, 1H), 4.37-4.27 (m, 1H), 3.90-3.78 (m, 2H), 3.07-2.97 (m, 1H), 2.93 (dd, J=15.2, 4.3 Hz, 1H), 2.80 (s, 3H), 2.66-2.47 (m, 3H), 2.34-2.16 (m, 4H), 2.02 (s, 3H, MeSO3H), 1.62-1.50 (m, 1H); MS (ESI) m/z 470.21 (M+H).

S20-3-4-1

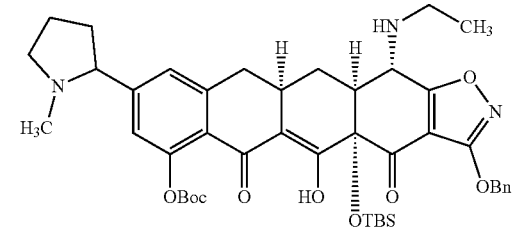

S20-3-4-1 (single diastereomer) was prepared similarly to compound 519-6-9-1 from S20-3-2 (single diastereomer) via treatment with acetaldehyde and sodium triacetoxyborohydride. $^1$H NMR (400 MHz, $CDCl_3$, single diastereomer) δ 16.26 (s, 1H), 7.41-7.34 (m, 3H), 7.31-7.21 (m, 3H), 6.94 (s, 1H), 5.33-5.24 (m, 2H), 3.66 (d, J=2.4 Hz, 1H), 3.02-2.89 (m, 1H), 2.88-2.77 (m, 1H), 2.73-2.58 (m, 2H), 2.53-2.41 (m, 1H), 2.30-2.05 (m, 3H), 2.00-1.92 (m, 2H), 1.56-1.37 (m, 11H), 1.34-1.23 (m, 1H), 1.05 (t, J=7.3 Hz, 3H), 0.67 (s, 9H), 0.09 (s, 3H), 0.00 (s, 3H); MS (ESI) m/z 800.51 (M+H).

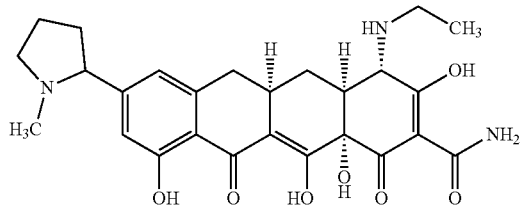

S20-4-2

S20-4-2 (single diastereomer) was prepared similarly to compound S19-7-1-B from S20-3-4-1 (single diastereomer) via treatment with dimethylsulfide in methanesulfonic acid. $^1$H NMR (400 MHz, CD$_3$OD) δ 6.99 (s, 1H), 6.96 (s, 1H), 4.36-4.29 (m, 1H), 3.89-3.80 (m, 2H), 3.48-3.33 (m, 1H), 3.08-2.98 (m, 1H), 2.92 (dd, J=15.2, 4.3 Hz, 1H), 2.84-2.78 (m, 5H), 2.64-2.50 (m, 2H), 2.34-2.17 (m, 5H), 1.59-1.46 (m, 1H), 1.35 (t, J=6.7 Hz, 3H); MS (ESI) m/z 498.27 (M+H).

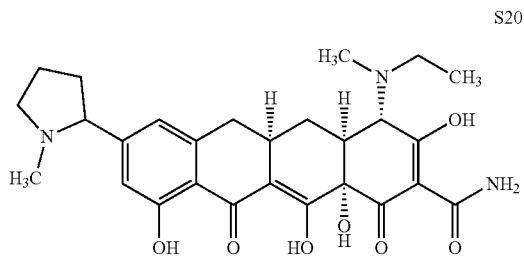

S20-4-3

S20-4-3 (single diastereomer) was prepared similarly to compound 519-7-4 from S20-3-4-1 (single diastereomer) via reductive alkylation with aqueous formaldehyde followed by deprotection via treatment with dimethylsulfide in methanesulfonic acid: $^1$H NMR (400 MHz, CD$_3$OD) δ 7.00 (s, 1H), 6.97 (s, 1H), 4.38-4.29 (m, 1H), 4.22, 4.12 (s, s, 1H), 3.89-3.80 (m, 1H), 3.53-3.42 (m, 1H), 3.15-3.03 (m, 1H), 3.02-2.89 (m, 4H), 2.81 (s, 3H), 2.65-2.47 (m, 2H), 2.34-2.15 (m, 4H), 1.66-1.54 (m, 1H), 1.45-1.33 (m, 3H); MS (ESI) m/z 512.30 (M+H).

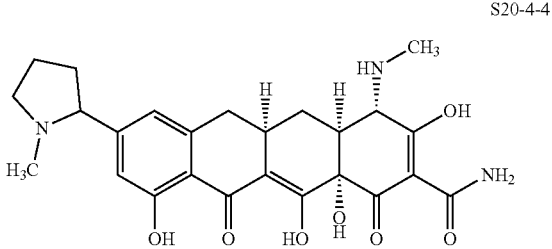 [SMILES: CN[C@@H]1C(O)=C(C(N)=O)C(=O)[C@@]2(O)C(O)=C3C(=O)c4c(O)cc(C5CCCN5C)cc4C[C@H]3C[C@@H]12]

S20-4-4

S20-4-4 (single diastereomer) was prepared similarly to compound S19-7-3 from S20-3-3 (single diastereomer) via reductive alkylation with aqueous formaldehyde followed by allyl deprotection and treatment with dimethylsulfide in methanesulfonic acid. $^1$H NMR (400 MHz, CD$_3$OD) δ 6.99 (s, 1H), 6.96 (s, 1H), 4.36-4.29 (m, 1H), 3.89-3.78 (m, 2H), 3.09-2.98 (m, 1H), 2.96-2.87 (m, 4H), 2.83-2.76 (m, 4H), 2.64-2.47 (m, 2H), 2.33-2.14 (m, 4H), 1.60-1.48 (m, 1H); MS (ESI) m/z 484.25 (M+H).

Scheme 21

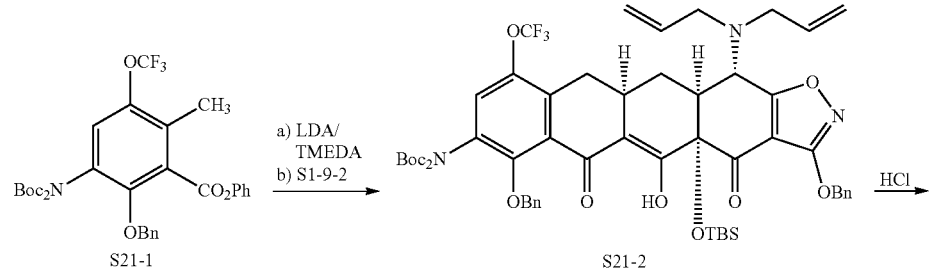

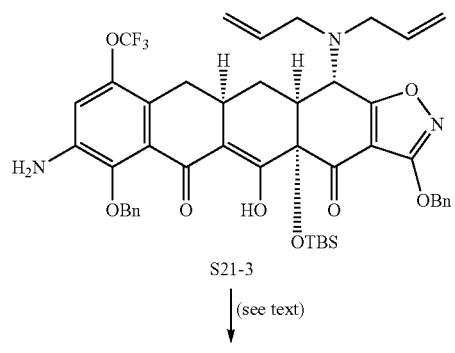

(see text)

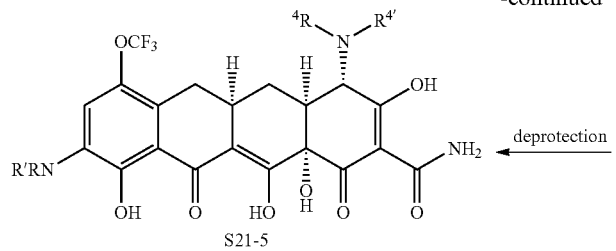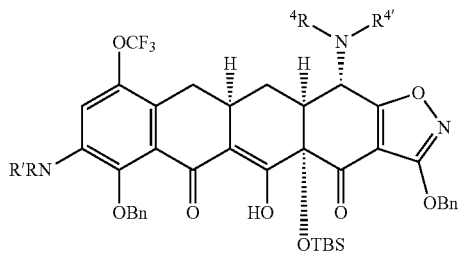

The following compounds were prepared according to Scheme 21.

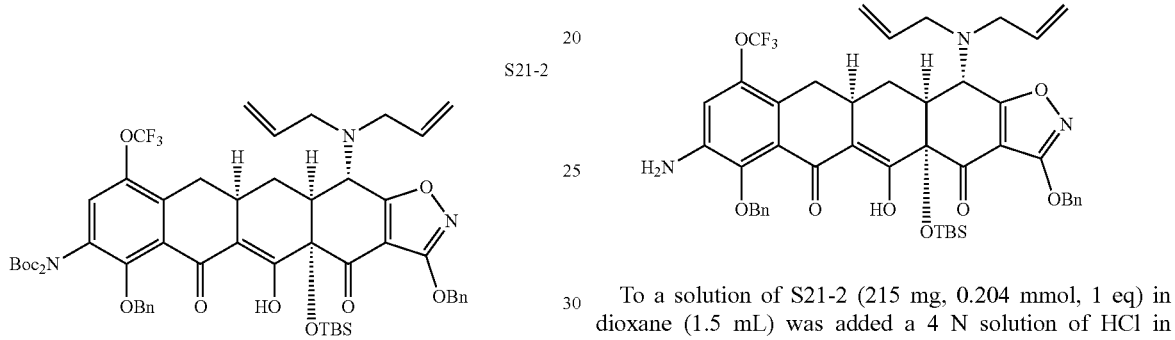

Lithium diisopropylamide (1.6 eq) was prepared at −40° C. from n-butyllithium (1.6 M solution in hexane, 382 μL, 0.611 mmol) and diisopropylamine (91.7 μL, 0.649 mmol) in THF (5 mL). The solution was cooled to −78° C. and TMEDA (97.3 μL, 0.649 mmol, 1.7 eq) was added, followed by drop wise addition of compound S21-1 (346.8 mg, 0.561 mmol, 1.5 eq, prepared according to literature procedures including WO2011025982) in THF (1 mL) with a 500 μL THF rinse forward, maintaining the internal temperature below −70° C. The solution became a deep red color. After 30 min at this temperature, the solution was cooled to −100° C. A solution of diallylenone S1-9-2 (204 mg, 0.382 mmol, 1 eq) in THF (1 mL) was added drop wise via syringe with a 400 μL THF rinse forward, maintaining the internal temperature below −90° C. After complete addition, the reaction mixture was allowed to warm slowly in the bath. When the solution reached −78° C., lithium hexamethyldisilazane (1 M in hexanes, 382 μL, 1 eq) was added. After 90 min, excess base was quenched at −10° C. by the addition of a saturated aqueous $NH_4Cl$ solution (3 mL) and the mixture was warmed to ambient temperature. The reaction mixture was diluted with saturated aqueous $NH_4Cl$ solution (20 mL) and water (2 mL) and was extracted with EtOAc (2×25 mL). Combined organic extracts were dried over $Na_2SO_4$, were filtered, and were concentrated under reduced pressure. Purification of the resulting residue on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 90→100% B; mass-directed fraction collection], provided desired compound S21-2 (218 mg, 54%, >85% desired, impurity is mono-Boc protected aniline): MS (ESI) m/z 1058.03 (M+H).

To a solution of S21-2 (215 mg, 0.204 mmol, 1 eq) in dioxane (1.5 mL) was added a 4 N solution of HCl in dioxane (1.5 mL). After 3.5 h, the reaction was cooled to 0° C. and a saturated sodium bicarbonate solution (6 mL) was added dropwise, followed by EtOAc (5 mL). After 10 min, the heterogeneous solution was warmed to ambient temperature and further diluted with saturated sodium bicarbonate solution (15 mL) and extracted with EtOAc (2×25 mL). The combined organic extracts were dried over $Na_2SO_4$, were filtered, and were concentrated under reduced pressure to yield intermediate S21-3, which was used without further purification: MS (ESI) m/z 858.44 (M+H).

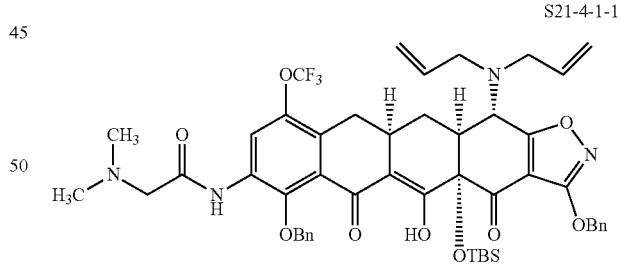

To a solution of S21-3 (0.101 mmol, 1 eq) in THF (2 mL) was added bromoacetylbromide (11.5 μL, 0.132 mmol, 1.3 eq). After 19 h, a solution of dimethylamine in ethanol (5.6 M, 150 μL, 0.84 mmol, 8.4 eq) was added. After 3 h, the reaction was diluted with EtOAc (20 mL) and washed with a saturated aqueous sodium bicarbonate solution (15 mL). The aqueous layer was extracted with EtOAc (20 mL), and the combined organic extracts were dried over $Na_2SO_4$, were filtered, and were concentrated under reduced pressure. Purification of the resulting residue via flash column chromatography (Biotage, 25 g silica gel column, 5% to 40% EtOAc in hexanes gradient) provided the desired product S21-4-1-1 (43.6 mg, 46%): $^1$H NMR (400 MHz, CDCl$_3$, rotamers) δ 15.82, 15.72 (s, s, 1H), 9.87 (brs, 1H), 8.65 (brs, 1H), 7.54-7.45 (m, 2H), 7.44-7.28 (m, 9H), 5.87-5.69 (m, 2H), 5.38-5.34 (m, 2H), 5.22 (d, J=17.1 Hz, 2H), 5.17-5.06 (m, 2H), 5.03-4.91 (m, 2H), 4.82 (d, J=10.3 Hz, 1H), 4.10-4.01 (m, 1H), 3.37-3.25 (m, 1H), 3.25-3.08 (m, 4H), 3.07-2.91 (m, 3H), 2.71-2.60 (m, 1H), 2.57-2.10 (m, 10H), 0.88-0.77 (m, 9H), 0.29-0.21 (m, 3H), 0.13-0.09 (s, 3H); MS (ESI) m/z 941.52 (M–H).

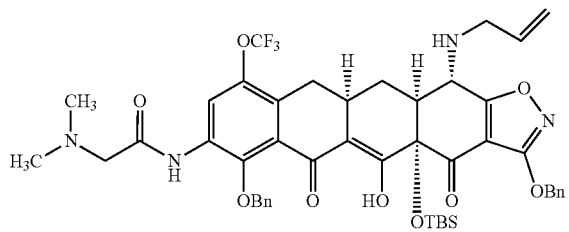

S21-4-2-1

S21-4-2-1 was prepared similarly to S19-6-6-2 via deallylation of S21-4-1-1 with bis(dibenzylideneacetone)palladium(0) and 1,4-bis(diphenylphosphinebutane) in the presence of 2-mercaptobenzoic acid: MS (ESI) m/z 903.48 (M+H).

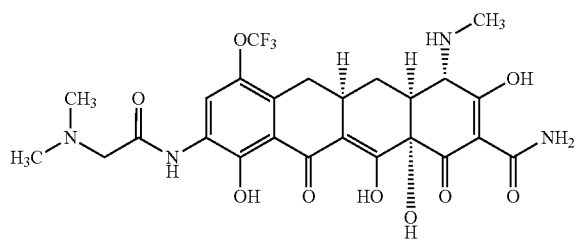

S21-5-1

S21-5-1 was prepared similarly to compound S19-7-3 from S21-4-2-1 via reductive alkylation with aqueous formaldehyde followed by allyl deprotection and treatment with dimethylsulfide in methanesulfonic acid: $^1$H NMR (400 MHz, CD$_3$OD) δ 8.43 (s, 1H), 4.24 (s, 2H), 3.80 (s, 1H), 3.07-2.92 (m, 8H), 2.91 (s, 3H), 2.82-2.75 (m, 1H), 2.37-2.27 (m, 1H), 2.24-2.15 (m, 1H), 1.66-1.51 (m, 1H); MS (ESI) m/z 585.28 (M+H).

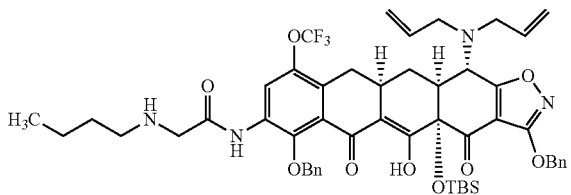

S21-4-1-2

S21-4-1-2 was prepared similarly to S21-4-1-1 via treatment with bromoacetylbromide followed by addition of n-butylamine. Rotamers were observed by $^1$H NMR (CDCl$_3$). MS (ESI) m/z 972.13 (M+H).

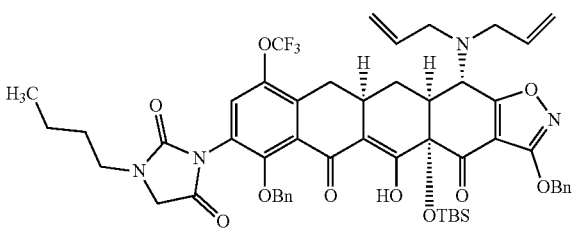

S21-4-1-3

To a solution of S21-4-1-2 (35.4 mg, 0.036 mmol, 1 eq) in dichloromethane (800 µL) was added di-tent-butyl dicarbonate (10 mg, 0.046 mmol, 1.2 eq) and dimethylaminopyridine (2 mg, 0.016 mmol, 0.4 eq) and the reaction mixture was stirred at ambient temperature. After 22 h, the mixture was diluted with saturated aqueous ammonium chloride (10 mL), water (1 mL) and extracted with EtOAc (2×25 mL). The combined organic layers were dried over Na$_2$SO$_4$, were filtered, and were concentrated under reduced pressure. A crude $^1$H NMR spectrum of the resulting residue indicated incomplete reaction and it was resubmitted to the above reaction conditions and work up. Purification of the resulting residue via flash column chromatography (Biotage, 10 g silica gel column, 1% to 35% EtOAc in hexanes gradient) provided compound S21-4-1-3 (15 mg, 39%). Rotamers observed in $^1$H NMR (400 MHz, CDCl$_3$). MS (ESI) m/z 997.53 (M+H).

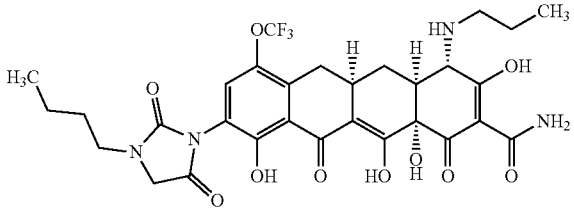

S21-5-2

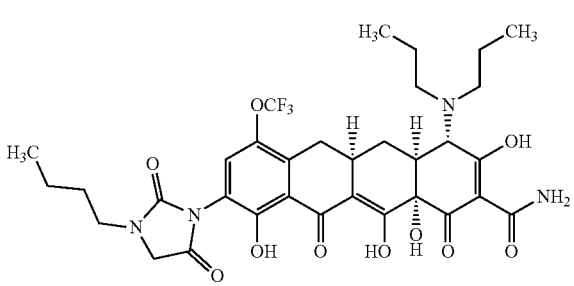

S21-5-3

Aqueous HF (48%, 150 µL) was added to a solution of S21-4-1-3 (15 mg, 0.013 mmol) in dioxane (500 µL) in a plastic vial. After 23 h the reaction mixture was poured into a solution of K$_2$HPO$_4$ (1.8 g) in water (10 mL). The mixture was extracted with EtOAc (2×25 mL). The combined EtOAc extracts were dried over Na$_2$SO$_4$, were filtered, and were and concentrated under reduced pressure. The material was dissolved in MeOH (1 mL) and aqueous HCl (1 M, 50 µL), and palladium on carbon (Degussa, 10 wt %, 10 mg) was added. An atmosphere of hydrogen was introduced and the reaction mixture was stirred for 2 h. The reaction mixture was filtered through a small Celite pad and the filtrate was concentrated under reduced pressure. The material was purified on a Waters Autopurification system equipped with a Phenomenex Polymerx 10µ RP 100 A column [10 µm, 30×21.20 mm; flow rate, 20 mL/min; Solvent A: 0.05 N HCl in water; Solvent B: CH₃CN; gradient: 5→60% B; mass-directed fraction collection]. Fractions with the desired MW were collected and freeze-dried to yield compound S21-5-2 (monopropylamino, 1.78 mg, 18%) and compound S21-5-3 (dipropylamino, 0.83 mg, 8%) as yellow solids. S21-5-2: ¹H NMR (400 MHz, CD₃OD, monopropylamino,) δ 7.56 (s, 1H), 4.17 (s, 2H), 3.87 (s, 1H), 3.52-3.40 (m, 2H), 3.28-3.14 (m, 4H), 3.08-2.97 (m, 1H), 2.83 (d, J=12.8 Hz, 1H), 2.46-2.35 (m, 1H), 2.25-2.16 (m, 1H), 1.82-1.70 (m, 2H), 1.68-1.56 (m, 3H), 1.46-1.34 (m, 2H), 1.03 (t, J=7.32 Hz, 3H), 0.98 (t, J=7.32 Hz, 3H); MS (ESI) m/z 667.30 (M+H). S21-5-3: ¹H NMR (400 MHz, CD₃OD, dipropylamino,) δ 7.57 (s, 1H), 4.23 (s, 1H), 4.19 (s, 2H), 3.56-3.40 (m, 4H), 3.23-3.03 (m, 1H), 2.97-2.90 (m, 1H), 2.47-2.37 (m, 1H), 2.25-2.17 (m, 1H), 1.92-1.79 (m, 5H), 1.70-1.58 (m, 4H), 1.48 (s, 1H), 1.46-1.35 (m, 2H), 1.08-0.94 (m, 9H); MS (ESI) m/z 709.34 (M+H).

S21-4-1-4

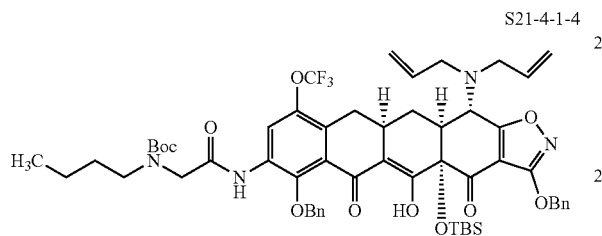

To a solution of S21-4-1-2 (32.4 mg, 0.033 mmol, 1 eq) in dichloromethane (1.5 mL) and methanol (600 μL) was added di-tent-butyl dicarbonate (8 mg, 0.037 mmol, 1.1 eq) and the reaction mixture was stirred at ambient temperature. After 4.5 h, the mixture was diluted with saturated aqueous ammonium chloride (10 mL), water (3 mL) and extracted with EtOAc (2×25 mL). The combined organic layers were dried over Na₂SO₄, were filtered, and were concentrated under reduced pressure. Combined with a second reaction (0.011 mmol of S21-4-1-2) and purified via flash column chromatography (Biotage, 10 g silica gel column, 1% to 35% EtOAc in hexanes gradient) to provide compound S21-4-1-4 (30.3 mg, 64%). Rotamers observed in ¹H NMR (400 MHz, CDCl₃). MS (ESI) m/z 1071.66 (M+H).

S21-4-2-2

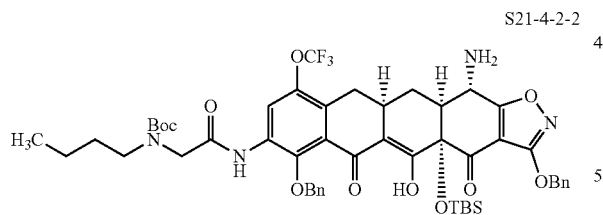

S21-4-2-2 was prepared similarly to S20-3-2 from S21-4-1-4 via deallylation with tetrakis(triphenylphosphine)palladium and dimethylbarbituric acid. ¹H NMR (400 MHz, CDCl₃) indicates rotamers. MS (ESI) m/z 991.58 (M+H).

S21-5-4

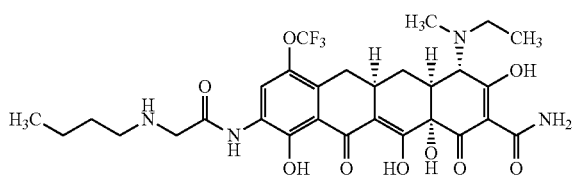

S21-5-4 was prepared similarly to S19-7-4 from S21-4-2-2 via successive reductive alkylation with acetaldehyde and formaldehyde, then global deprotection via successive aqueous HF treatment and reduction over palladium on carbon: ¹H NMR (400 MHz, CD₃OD) δ 8.44 (s, 1H), 4.28-4.10 (m, 1H), 4.09 (s, 2H), 3.58-3.30 (m, 2H), 3.22-2.87 (m, 8H), 2.37-2.17 (m, 2H), 1.78-1.59 (m, 3H), 1.53-1.32 (m, 5H), 1.01 (t, J=7.3 Hz, 3H); MS (ESI) m/z 641.34 (M+H).

Scheme 22

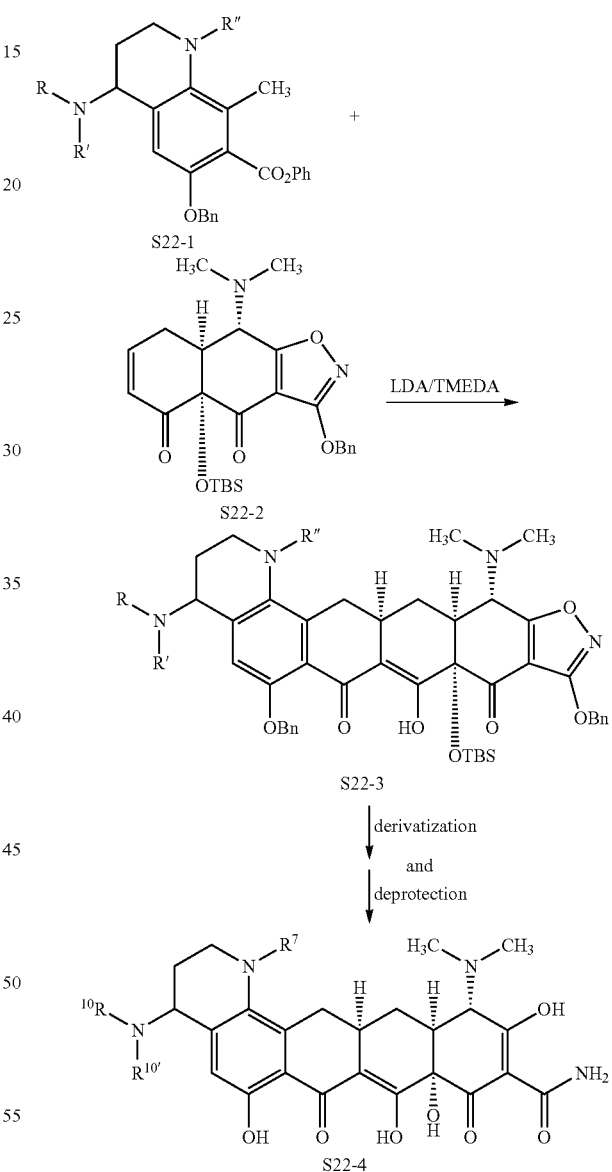

The compounds in Table 2A were synthesized according to Scheme 22 from dimethylamino enone S22-2 and a properly substituted and protected D-ring intermediate S22-1. A synthesis of enone S22-2 is described in U.S. Pat. No. 7,807,842 and Org. Lett., 2007, 9(18), 3523-3525, the relevant portions of which are incorporated herein by reference. S22-1 was prepared by a procedure similar to that used to prepare S6-4.

TABLE 2A

| Compound No. | Compound Structure | MS (ESI) m/z (M + H) |
|---|---|---|
| S22-4-1-A (diastereomer A) S22-4-1-B (diastereomer B) | 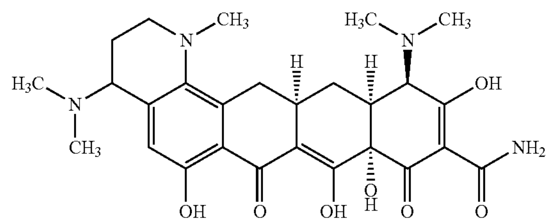 [SMILES: CN1CCC(N(C)C)c2cc(O)c3c(c21)C[C@H]1C[C@H]2[C@@H](N(C)C)C(O)=C(C(N)=O)C(=O)[C@@]2(O)C(O)=C1C3=O] | 527.36 (A) 527.34 (B) |
| S22-4-2-A (diastereomer A) S22-4-2-B (diastereomer B) | 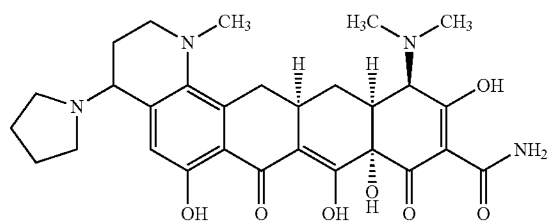 [SMILES: CN1CCC(N2CCCC2)c2cc(O)c3c(c21)C[C@H]1C[C@H]2[C@@H](N(C)C)C(O)=C(C(N)=O)C(=O)[C@@]2(O)C(O)=C1C3=O] | 533.42 (A) 553.33 (B) |
| S22-4-3-A (diastereomer A) S22-4-3-B (diastereomer B) | 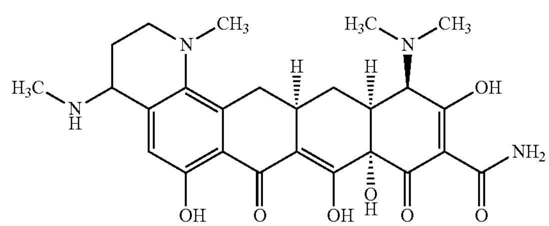 [SMILES: CNC1CCN(C)c2c1cc(O)c1c2C[C@H]2C[C@H]3[C@@H](N(C)C)C(O)=C(C(N)=O)C(=O)[C@@]3(O)C(O)=C2C1=O] | 513 31 (A) 513.33 (B) |
| S22-4-4-A (diastereomer A) S22-4-2-B (diastereomer B) | 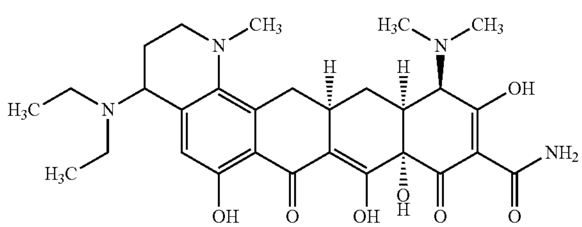 [SMILES: CCN(CC)C1CCN(C)c2c1cc(O)c1c2C[C@H]2C[C@H]3[C@@H](N(C)C)C(O)=C(C(N)=O)C(=O)[C@@]3(O)C(O)=C2C1=O] | 555.1 |
| S22-4-5-A (diastereomer A) S22-4-5-B (diastereomer B) | 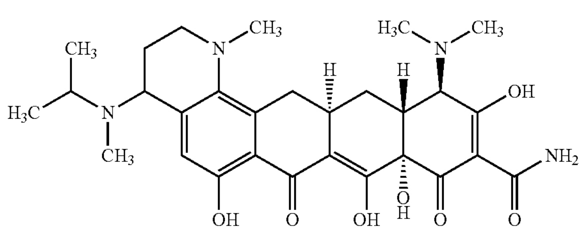 [SMILES: CC(C)N(C)C1CCN(C)c2c1cc(O)c1c2C[C@H]2C[C@@H]3[C@@H](N(C)C)C(O)=C(C(N)=O)C(=O)[C@@]3(O)C(O)=C2C1=O] | 555.34 (A) 555.39 (B) |
| S22-4-6-B (diastereomer B) | 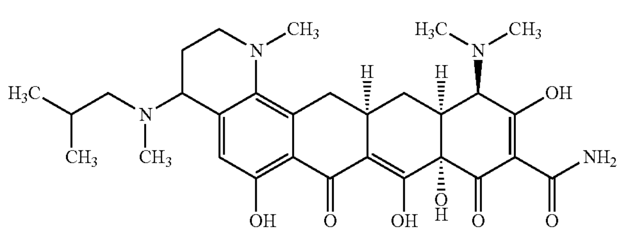 [SMILES: CC(C)CN(C)C1CCN(C)c2c1cc(O)c1c2C[C@H]2C[C@H]3[C@@H](N(C)C)C(O)=C(C(N)=O)C(=O)[C@@]3(O)C(O)=C2C1=O] | 569.39 |

TABLE 2A-continued

| Compound No. | Compound Structure | MS (ESI) m/z (M + H) |
|---|---|---|
| S22-4-7 | 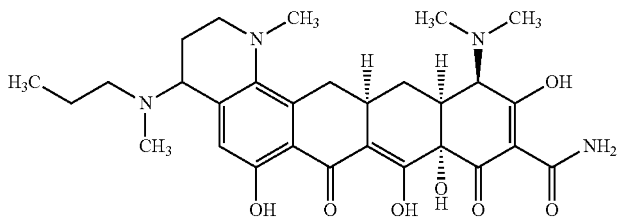 [SMILES: CCCN(C)C1CCN(C)c2c1cc(O)c1c2C[C@H]2C[C@H]3[C@@H](N(C)C)C(O)=C(C(N)=O)C(=O)[C@@]3(O)C(O)=C2C1=O] | 555.2 |
| S22-4-8-A (diastereomer A) | 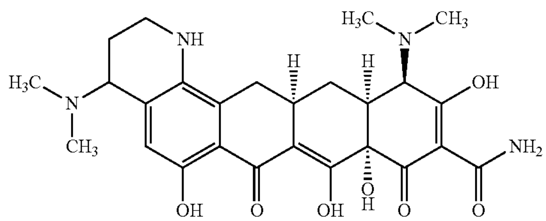 [SMILES: CN(C)C1CCNc2c1cc(O)c1c2C[C@H]2C[C@H]3[C@@H](N(C)C)C(O)=C(C(N)=O)C(=O)[C@@]3(O)C(O)=C2C1=O] | 513.32 (A) |
| S22-4-9-A (diastereomer A) | 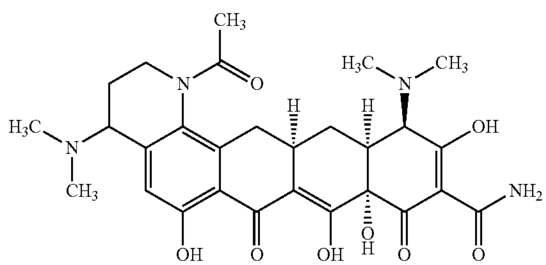 [SMILES: CC(=O)N1CCC(N(C)C)c2cc(O)c3c(c21)C[C@H]1C[C@H]2[C@@H](N(C)C)C(O)=C(C(N)=O)C(=O)[C@@]2(O)C(O)=C1C3=O] | 555.32 |
| S22-4-10-A (diastereomer A) S22-4-10-B (diastereomer B) | 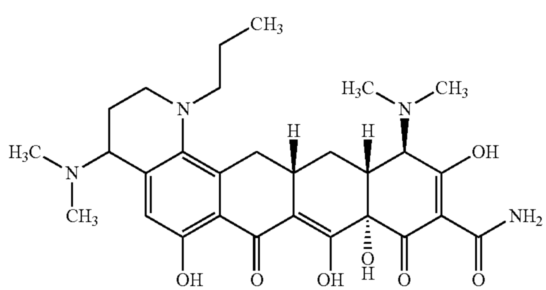 [SMILES: CCCN1CCC(N(C)C)c2cc(O)c3c(c21)C[C@@H]1C[C@@H]2[C@@H](N(C)C)C(O)=C(C(N)=O)C(=O)[C@@]2(O)C(O)=C1C3=O] | 555.2 |
| S22-4-11-A (diastereomer A) S22-4-11-B (diastereomer B) | 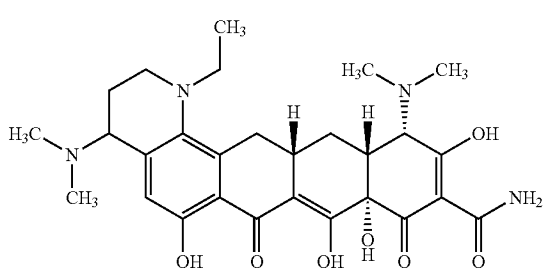 [SMILES: CCN1CCC(N(C)C)c2cc(O)c3c(c21)C[C@@H]1C[C@@H]2[C@H](N(C)C)C(O)=C(C(N)=O)C(=O)[C@@]2(O)C(O)=C1C3=O] | 541.1 |

TABLE 2A-continued

| Compound No. | Compound Structure | MS (ESI) m/z (M + H) |
|---|---|---|
| S22-4-12-A (diastereomer A) S22-4-12-B (diastereomer B) | 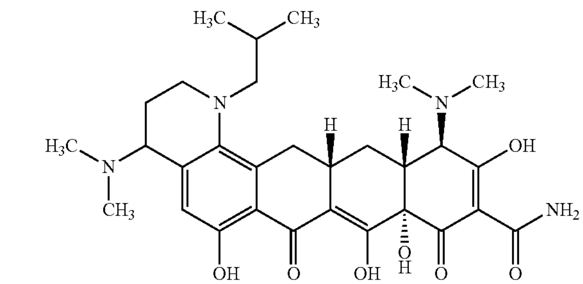 [SMILES: CC(C)CN1CCC(N(C)C)c2cc(O)c3c(c21)C[C@@H]1C[C@@H]2[C@@H](N(C)C)C(O)=C(C(N)=O)C(=O)[C@@]2(O)C(O)=C1C3=O] | 569.1 |
| S22-4-13-A (diastereomer A) | 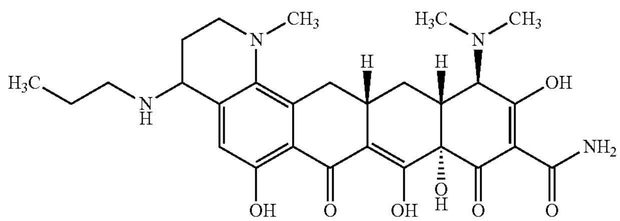 [SMILES: CCCNC1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 541.34 |
| S22-4-14-A (diastereomer A) | 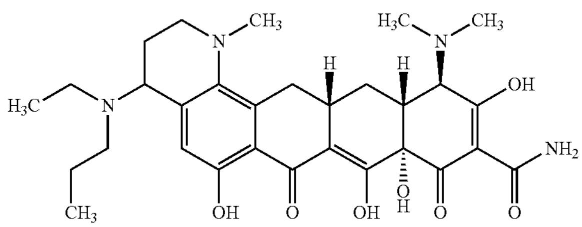 [SMILES: CCCN(CC)C1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 569.35 |
| S22-4-15-A (diastereomer A) | 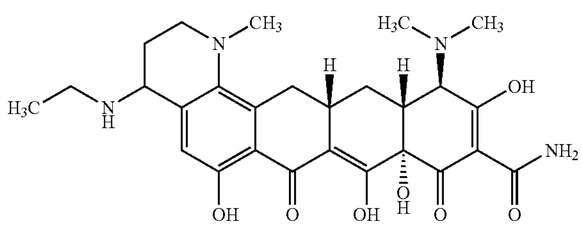 [SMILES: CCNC1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 527.32 |
| S22-4-16-A (diastereomer A) | 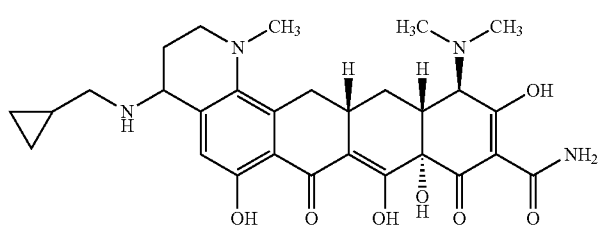 [SMILES: CN1CCC(NCC2CC2)c2cc(O)c3c(c21)C[C@@H]1C[C@@H]2[C@@H](N(C)C)C(O)=C(C(N)=O)C(=O)[C@@]2(O)C(O)=C1C3=O] | 553.37 |
| S22-4-17-A | 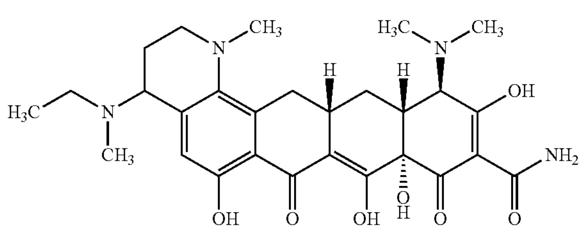 [SMILES: CCN(C)C1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 541.32 |

TABLE 2A-continued
| Compound No. | Compound Structure | MS (ESI) m/z (M + H) |
|---|---|---|
| S22-4-18-A (diastereomer A) | 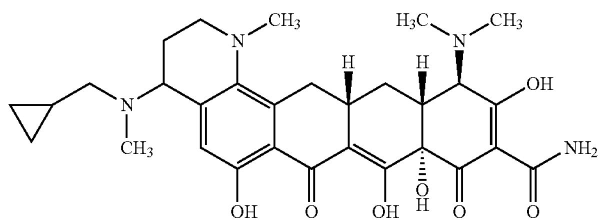 [SMILES: CN1CCC(N(C)CC2CC2)c2cc(O)c3c(c21)C[C@@H]1C[C@@H]2[C@@H](N(C)C)C(O)=C(C(N)=O)C(=O)[C@@]2(O)C(O)=C1C3=O] | 567.36 |
| S22-4-19-A (diastereomer A) | 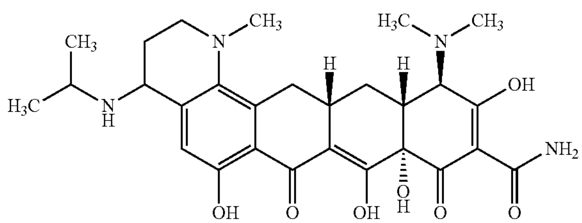 [SMILES: CC(C)NC1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 541.33 |
| S22-4-20-A (diastereomer A) | 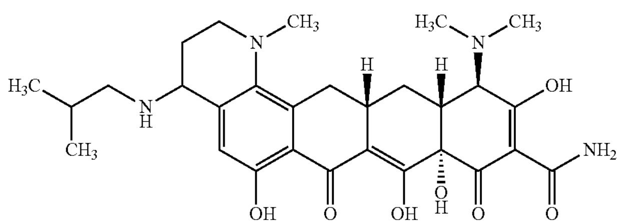 [SMILES: CC(C)CNC1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 555.35 |
| S22-4-21-A (diastereomer A) | 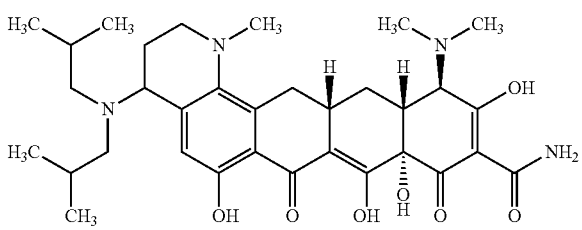 [SMILES: CC(C)CN(CC(C)C)C1CCN(C)c2c1cc(O)c1c2C[C@@H]2C[C@@H]3[C@@H](N(C)C)C(O)=C(C(N)=O)C(=O)[C@@]3(O)C(O)=C2C1=O] | 611.44 |
| S22-4-22-A (diastereomer A) | 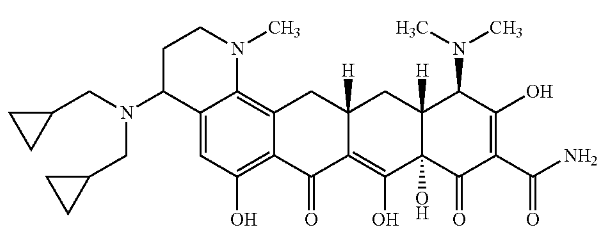 [SMILES: CN1CCC(N(CC2CC2)CC2CC2)c2cc(O)c3c(c21)C[C@@H]1C[C@@H]2[C@@H](N(C)C)C(O)=C(C(N)=O)C(=O)[C@@]2(O)C(O)=C1C3=O] | 607.38 |
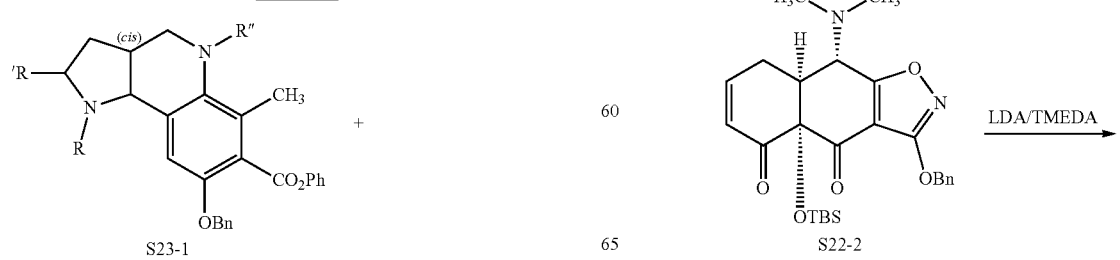
Scheme 23

-continued

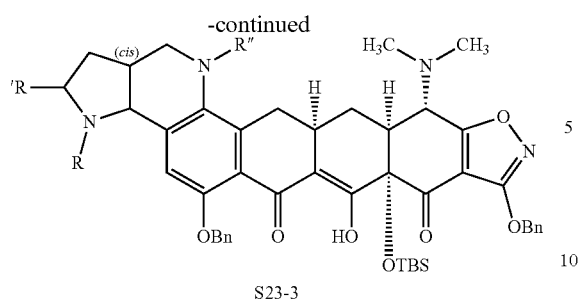

S23-3

| derivatization
| and
↓ deprotection

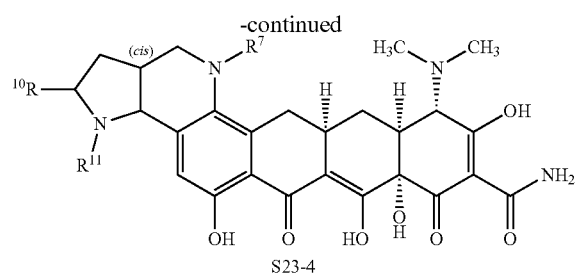

S23-4

The compounds in Table 2B were synthesized according to Scheme 23 from dimethylamino enone S22-2 and a properly substituted and protected D-ring intermediate S23-1. S23-1 was prepared by a procedure similar to that used to prepare S5-8.

TABLE 2B

| Compound No. | Compound Structure | MS (ESI) m/z (M + H) |
|---|---|---|
| S23-4-1-A (diastereomer A) S23-4-1-B (diastereomer B) | 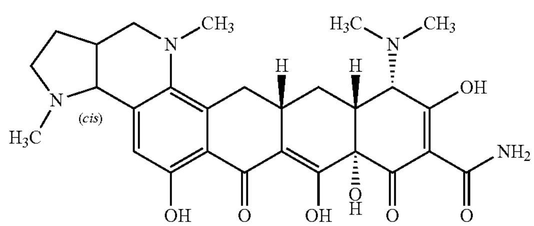 [SMILES: CN1CC2CCN(C)C2c2cc(O)c3c(c21)C[C@@H]1C[C@@H]2[C@H](N(C)C)C(O)=C(C(N)=O)C(=O)[C@@]2(O)C(O)=C1C3=O] | 539.15 |
| S23-4-2-A (diastereomer A) S23-4-2-B (diastereomer B) | 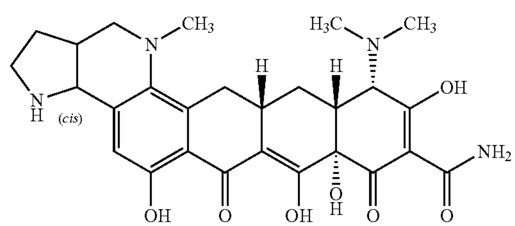 [SMILES: CN1CC2CCNC2c2cc(O)c3c(c21)C[C@@H]1C[C@@H]2[C@H](N(C)C)C(O)=C(C(N)=O)C(=O)[C@@]2(O)C(O)=C1C3=O] | 525.12 |
| S23-4-3-B (diastereomer B) | 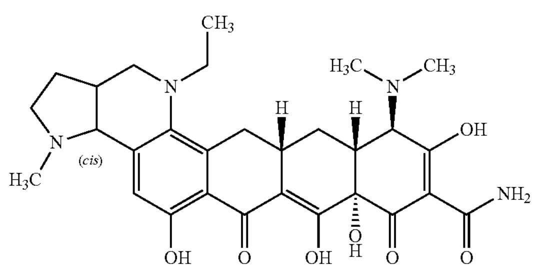 [SMILES: CCN1CC2CCN(C)C2c2cc(O)c3c(c21)C[C@@H]1C[C@@H]2[C@@H](N(C)C)C(O)=C(C(N)=O)C(=O)[C@@]2(O)C(O)=C1C3=O] | 533.17 |
| S23-4-4-A (diastereomer A) S23-4-4-B (diastereomer B) | 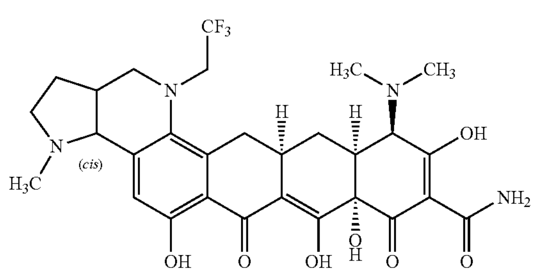 [SMILES: CN1CCC2CN(CC(F)(F)F)c3c(cc(O)c4c3C[C@H]3C[C@H]5[C@@H](N(C)C)C(O)=C(C(N)=O)C(=O)[C@@]5(O)C(O)=C3C4=O)C21] | 657.14 |

TABLE 2B-continued
| Compound No. | Compound Structure | MS (ESI) m/z (M + H) |
|---|---|---|
| S23-4-5-B (diastereomer B) | 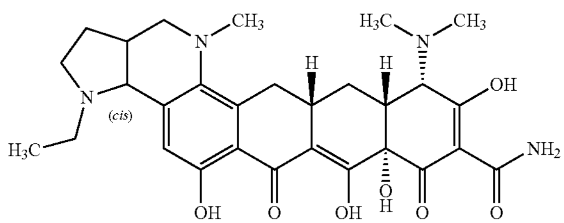 [SMILES: CCN1CCC2CN(C)c3c(cc(O)c4c3C[C@@H]3C[C@@H]5[C@H](N(C)C)C(O)=C(C(N)=O)C(=O)[C@@]5(O)C(O)=C3C4=O)C21] | 553.11 |
| S23-4-6-A (diastereomer A) S23-4-6-B (diastereomer B) | 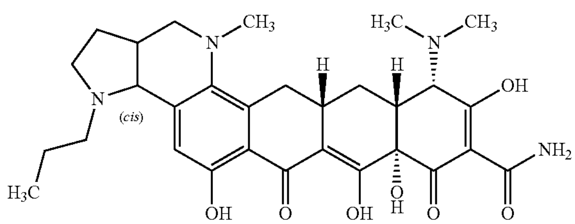 [SMILES: CCCN1CCC2CN(C)c3c(cc(O)c4c3C[C@@H]3C[C@@H]5[C@H](N(C)C)C(O)=C(C(N)=O)C(=O)[C@@]5(O)C(O)=C3C4=O)C21] | 567.42 (A) 567.37 (B) |
| S23-4-7-A (diastereomer A) S23-4-7-B (diastereomer B) | 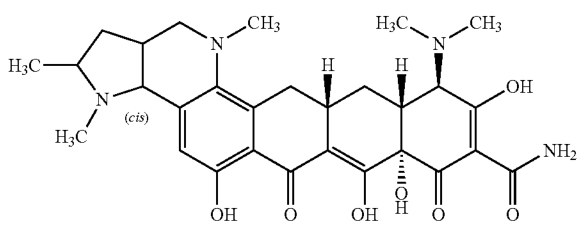 [SMILES: CC1CC2CN(C)c3c(cc(O)c4c3C[C@@H]3C[C@@H]5[C@@H](N(C)C)C(O)=C(C(N)=O)C(=O)[C@@]5(O)C(O)=C3C4=O)C2N1C] | 533.42 (A) 533.26 (B) |
| S23-4-8-A (diastereomer A) S23-4-8-B (diastereomer B) | 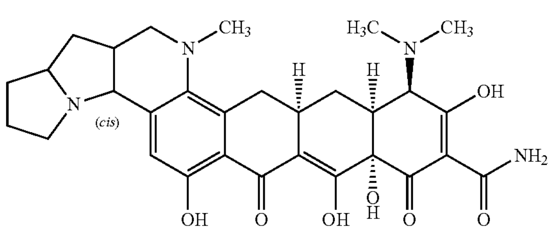 [SMILES: CN1CC2CC3CCCN3C2c2cc(O)c3c(c21)C[C@H]1C[C@H]2[C@@H](N(C)C)C(O)=C(C(N)=O)C(=O)[C@@]2(O)C(O)=C1C3=O] | 565.35 |
Scheme 24
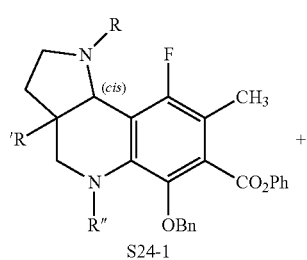
S24-1
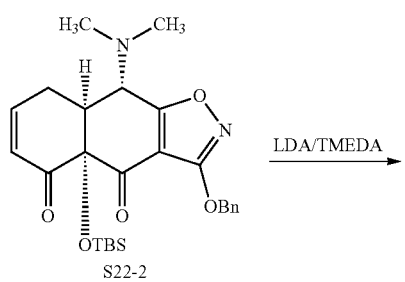
S22-2
LDA/TMEDA

251
-continued

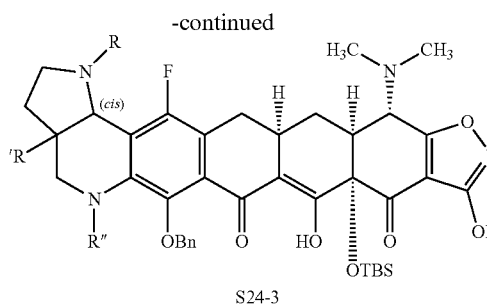

S24-3

↓ derivatization and deprotection

252
-continued

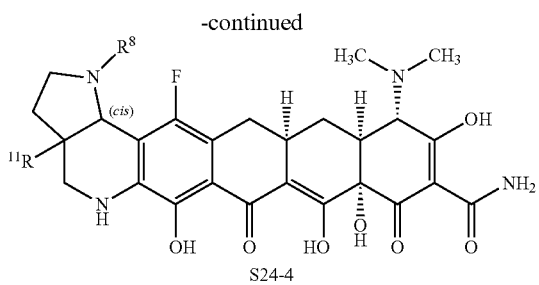

S24-4

The compounds in Table 2C were synthesized according to Scheme 24 from dimethylamino enone S22-2 and a properly substituted and protected D-ring intermediate S24-1. S24-1 was prepared by a procedure similar to that used to prepare S3-5.

TABLE 2C

| Compound No. | Compount Structure | MS (ESI) m/z (M + H) |
|---|---|---|
| S24-4-1-A (diastereomer A) 524-4-1-B (diastereomer B) | | 543.07 |
| S24-42-2-A (diastereomer A) S24.4-2-B (diastereomer B) | | 529.07 |
| S24-4-3-A (diastereomer A) S24-4-3-B (diastereomer B) | | 557.15 |
| S24-4-4-A (diastereomer A) S24-4-4-B (diastereomer B) | | 557.13 (A) 557.10 (B) |

TABLE 2C-continued

| Compound No. | Compound Structure | MS (ESI) m/z (M + H) |
|---|---|---|
| S24-4-5-A (diastereomer A) S24-4-5-B (diastereomer B) | | 543.14 |
| S24-4-6-A (diastereomer A) S24-4-6-B (diastereomer B) | | 585.26 |
| S24-4-7-A (diasteremer A) S24-4-7-B (diastereomer B) | | 571.2 |
| S24-4-8-A (diasteremer A) S24-4-8-B (diastereomer B) | | 585.18 |
| S24-4-9-A S24-4-9-B S24-4-9-C S24-4-9-D (diastereomer A, B, C, D) | | 603.1 |
| S24-4-10-A (diasteremer A) S24-4-10-B (diastereomer B) | | 573.1 |

TABLE 2C-continued

| Compound No. | Compound Structure | MS (ESI) m/z (M + H) |
|---|---|---|
| S24-4-11-A (diasteremer A) S24-4-11-B (diastereomer B) | | 615.1 |
| S24-4-1-12-A (diasteremer A) S24-4-12-B (diastereomer B) | | 600.1 |
| S24-4-13-B (diastereomer B) | | 642.2 |
| S24-4-14-A (diasteremer A) S24-4-14-B (diasteromer B) | | 636.2 |
| S24-4-15 | | 628.1 |

Scheme 25

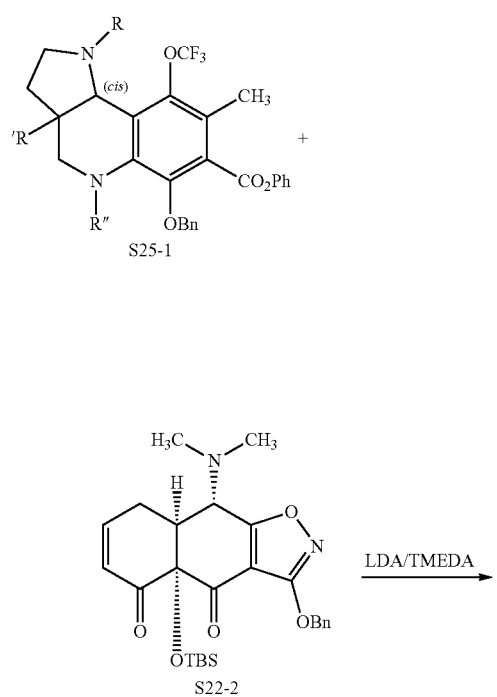

S25-1

S22-2

LDA/TMEDA

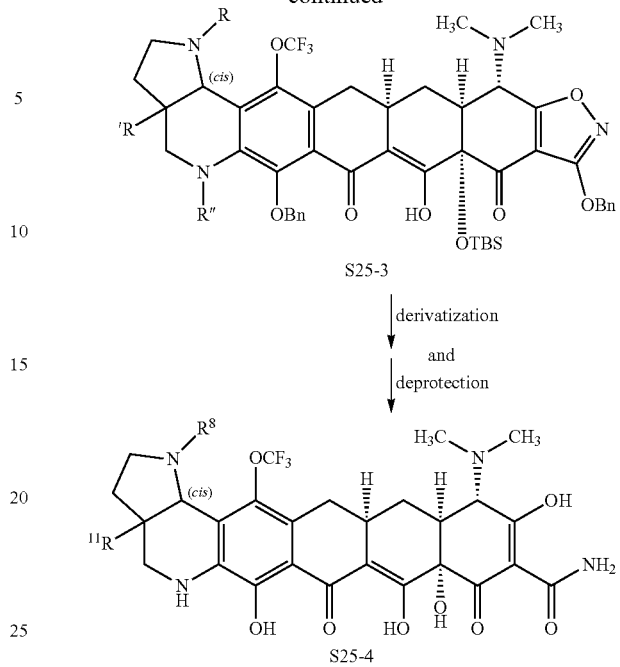

S25-3 derivatization and deprotection

S25-4

The compounds in Table 2D were synthesized according to Scheme 25 from dimethylamino enone S22-2 and a properly substituted and protected D-ring intermediate S25-1. S25-1 was prepared by a procedure similar to that used to prepare S12-6.

TABLE 2D

| Compound No. | Compound Structure | MS (ESI) m/z (M + H) |
|---|---|---|
| S25-4-1-A (diastereomer A) S25-4-1-B (diastereomer B) | 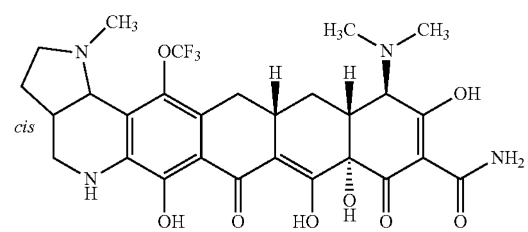 [SMILES: CN1CCC2CNc3c(O)c4c(c(OC(F)(F)F)c3C21)C[C@@H]1C[C@@H]2[C@@H](N(C)C)C(O)=C(C(N)=O)C(=O)[C@@]2(O)C(O)=C1C4=O] | 609.3 |
| S25-4-2-A (diastereomer A) S25-4-2-B (diastereomer B) | 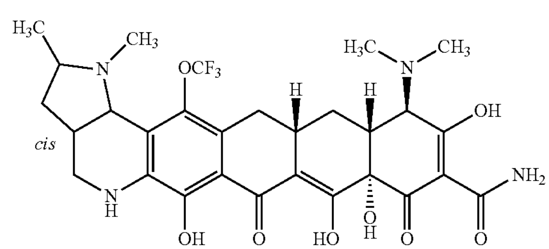 [SMILES: CC1CC2CNc3c(O)c4c(c(OC(F)(F)F)c3C2N1C)C[C@@H]1C[C@@H]2[C@@H](N(C)C)C(O)=C(C(N)=O)C(=O)[C@@]2(O)C(O)=C1C4=O] | 623.1 (A) 623.4 (B) |
| S25-4-3-A (diastereomer A) S25-4-3-B (diastereomer B) | 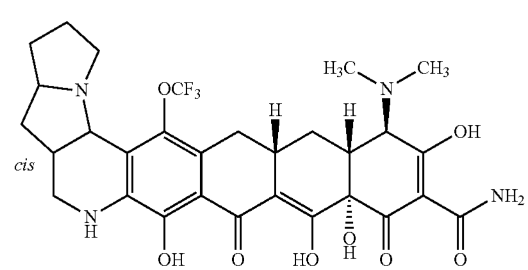 [SMILES: CN(C)[C@H]1C(O)=C(C(N)=O)C(=O)[C@@]2(O)C(O)=C3C(=O)c4c(O)c5c(c(OC(F)(F)F)c4C[C@@H]3C[C@H]12)C1C(CN5)CC2CCCN21] | 635.1 |

TABLE 2D-continued
| Compound No. | Compound Structure | MS (ESI) m/z (M + H) |
|---|---|---|
| S25-4-4-A (diastereomer A) S25-4-4-B (diastereomer B) | 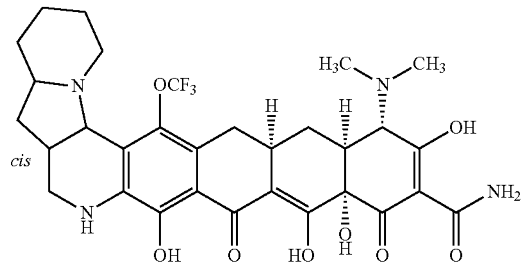 [SMILES: CN(C)[C@@H]1C(O)=C(C(N)=O)C(=O)[C@@]2(O)C(O)=C3C(=O)c4c(O)c5c(c(OC(F)(F)F)c4C[C@H]3C[C@@H]12)C1C(CN5)CC2CCCCN21] | 649.1 |
| S25-4-5-A (diastereomer A) S25-4-5-B (diastereomer B) | 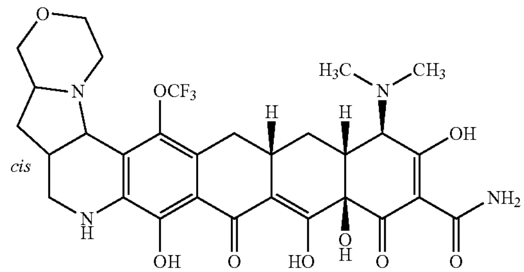 [SMILES: CN(C)[C@H]1C(O)=C(C(N)=O)C(=O)[C@]2(O)C(O)=C3C(=O)c4c(O)c5c(c(OC(F)(F)F)c4C[C@@H]3C[C@H]12)C1C(CN5)CC2COCCN21] | 651.1 |
| S25-4-6 | 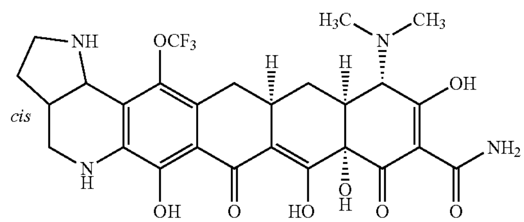 [SMILES: CN(C)[C@@H]1C(O)=C(C(N)=O)C(=O)[C@@]2(O)C(O)=C3C(=O)c4c(O)c5c(c(OC(F)(F)F)c4C[C@H]3C[C@@H]12)C1NCCC1CN5] | 595.2 |
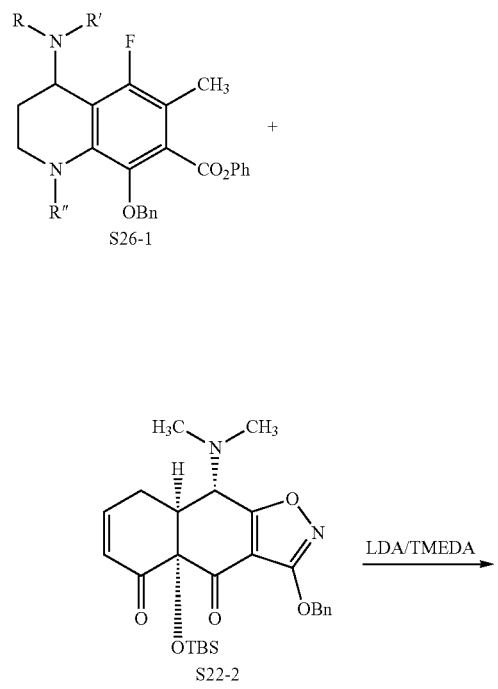
Scheme 26
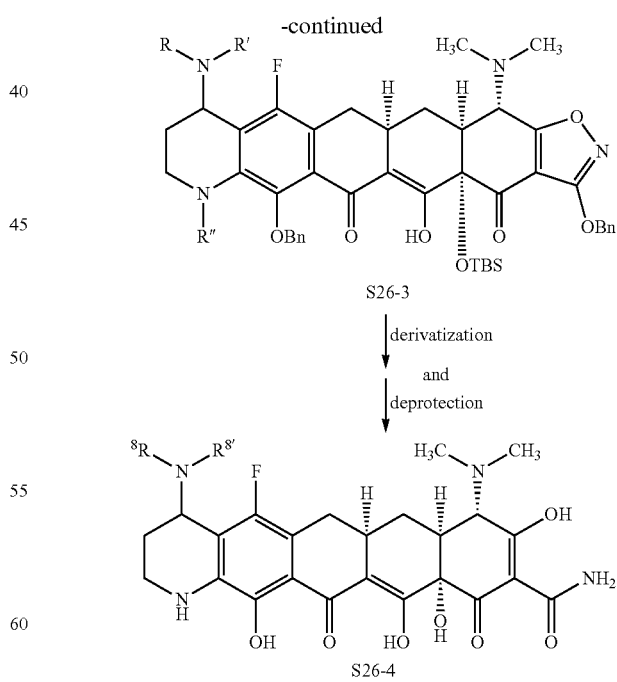
The compounds in Table 2E were synthesized according to Scheme 26 from dimethylamino enone S22-2 and a properly substituted and protected D-ring intermediate S26-1. S26-1 was prepared by a procedure similar to that used to prepare S16-5-1.

TABLE 2E
| Compound No. | Compound Structure | MS (ESI) m/z (M + H) |
|---|---|---|
| S26-4-1-A (diastereomer A) S26-4-1-B (diastereomer B) | 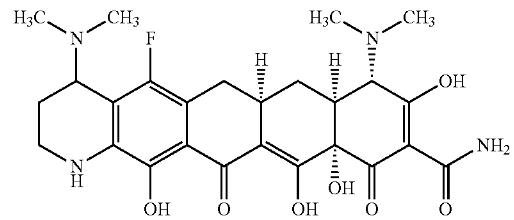 [SMILES: CN(C)C1CCNc2c(O)c3c(c(F)c21)C[C@H]1C[C@H]2[C@H](N(C)C)C(O)=C(C(N)=O)C(=O)[C@@]2(O)C(O)=C1C3=O] | 531.25 |
| S26-4-2-A (diastereomer A) | 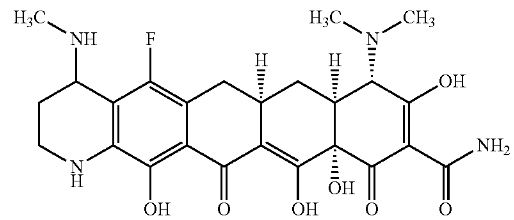 [SMILES: CNC1CCNc2c(O)c3c(c(F)c21)C[C@H]1C[C@H]2[C@H](N(C)C)C(O)=C(C(N)=O)C(=O)[C@@]2(O)C(O)=C1C3=O] | 517.27 |
| S26-4-3-A (diastereomer A) | 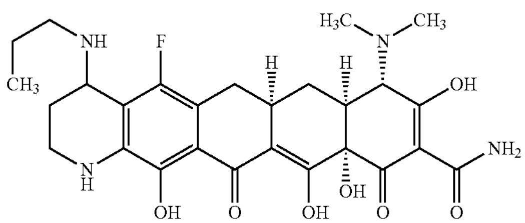 [SMILES: CCCNC1CCNc2c(O)c3c(c(F)c21)C[C@H]1C[C@H]2[C@H](N(C)C)C(O)=C(C(N)=O)C(=O)[C@@]2(O)C(O)=C1C3=O] | 545.30 |
| S26-4-4-A (diastereomer A) | 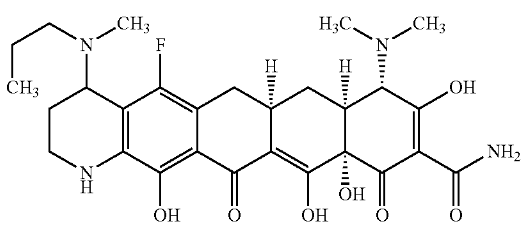 [SMILES: CCCN(C)C1CCNc2c(O)c3c(c(F)c21)C[C@H]1C[C@H]2[C@H](N(C)C)C(O)=C(C(N)=O)C(=O)[C@@]2(O)C(O)=C1C3=O] | 559.36 |
| S26-4-5-A (diastereomer A) | 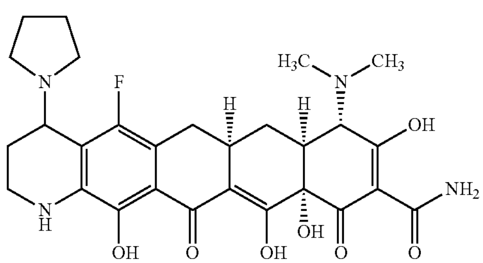 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)C(N1CCCC1)CCN5] | 557.19 |
Scheme 27
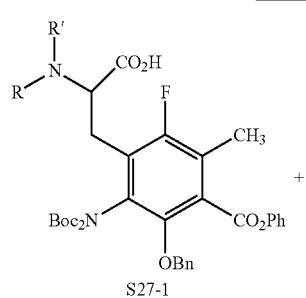
S27-1
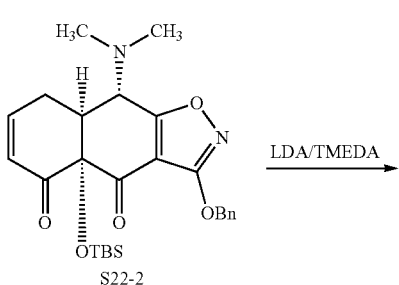
S22-2
LDA/TMEDA →

263
-continued

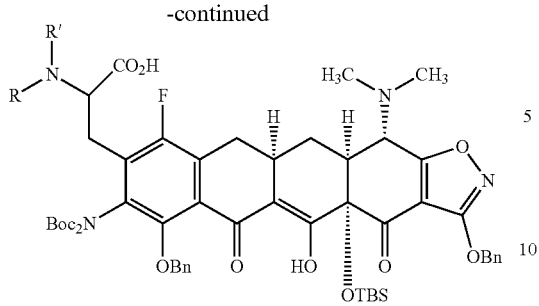

S27-3

↓ cyclization,
↓ derivatization, and
↓ deprotection

264
-continued

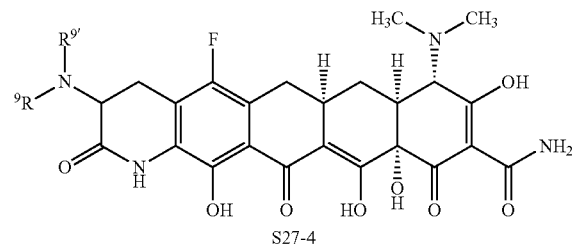

S27-4

The compounds in Table 2F were synthesized according to Scheme 27 from dimethylamino enone S22-2 and a properly substituted and protected D-ring intermediate S27-1. S27-1 was prepared by a procedure similar to that used to prepare S15-8.

TABLE 2F

| Compound No. | Compound Structure | MS (ESI) m/z (M + H) |
|---|---|---|
| S27-4-1-A (diastereomer A) S27-4-1-B (diastereomer B) | 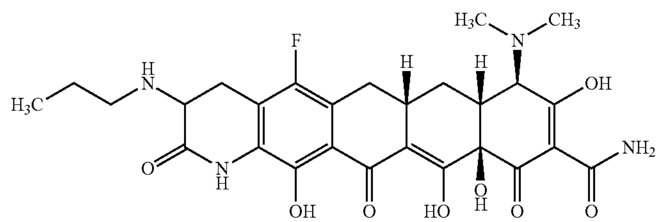 [SMILES: CCCNC1Cc2c(F)c3c(c(O)c2NC1=O)C(=O)C1=C(O)[C@@]2(O)C(=O)C(C(N)=O)=C(O)[C@H](N(C)C)[C@H]2C[C@H]1C3] | 599.2 |
| S27-4-2 | 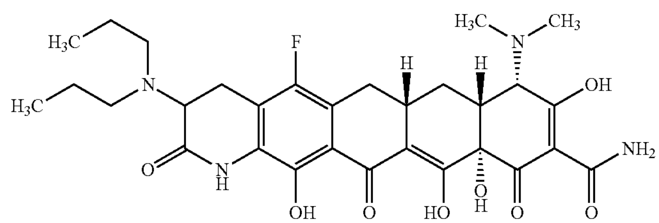 [SMILES: CCCN(CCC)C1Cc2c(F)c3c(c(O)c2NC1=O)C(=O)C1=C(O)[C@]2(O)C(=O)C(C(N)=O)=C(O)[C@@H](N(C)C)[C@H]2C[C@H]1C3] | 601.1 |
| S27-4-3 | 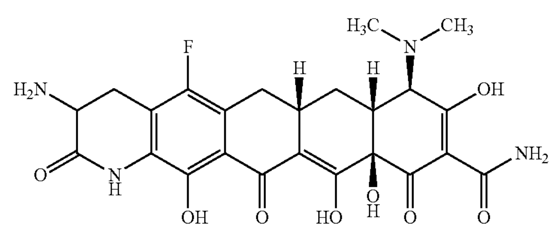 [SMILES: CN(C)[C@H]1C(O)=C(C(N)=O)C(=O)[C@]2(O)C(O)=C3C(=O)c4c(O)c5c(c(F)c4C[C@@H]3C[C@H]12)CC(N)C(=O)N5] | 517.1 |
| S27-4-4 | 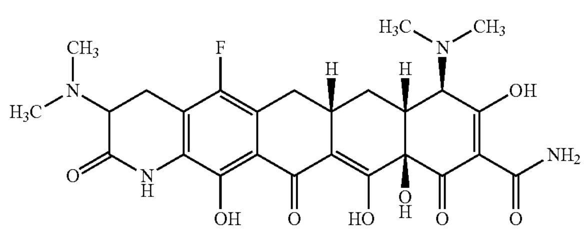 [SMILES: CN(C)C1Cc2c(F)c3c(c(O)c2NC1=O)C(=O)C1=C(O)[C@@]2(O)C(=O)C(C(N)=O)=C(O)[C@H](N(C)C)[C@H]2C[C@H]1C3] | 545.1 |

TABLE 2F-continued

| Compound No. | Compound Structure | MS (ESI) m/z (M + H) |
|---|---|---|
| S27-4-5 | 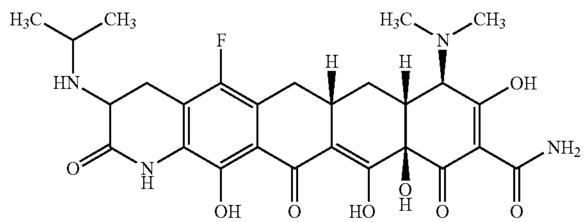 [SMILES: CC(C)NC1Cc2c(F)c3c(c(O)c2NC1=O)C(=O)C1=C(O)[C@@]2(O)C(=O)C(C(N)=O)=C(O)[C@H](N(C)C)[C@H]2C[C@H]1C3] | 559.3 |
| S27-4-6 | 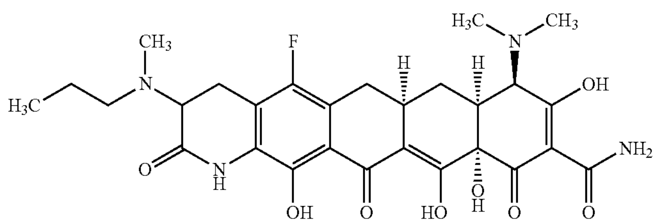 [SMILES: CCCN(C)C1Cc2c(F)c3c(c(O)c2NC1=O)C(=O)C1=C(O)[C@]2(O)C(=O)C(C(N)=O)=C(O)[C@H](N(C)C)[C@@H]2C[C@@H]1C3] | 573.1 |
| S27-4-7 | 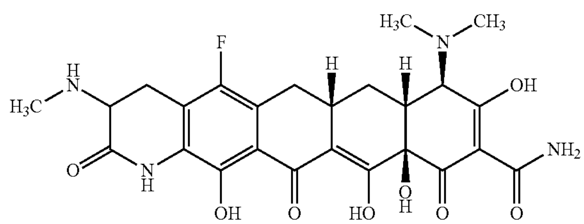 [SMILES: CNC1Cc2c(F)c3c(c(O)c2NC1=O)C(=O)C1=C(O)[C@@]2(O)C(=O)C(C(N)=O)=C(O)[C@H](N(C)C)[C@H]2C[C@H]1C3] | 531.1 |
| S27-4-8-B (diastereomer B) | 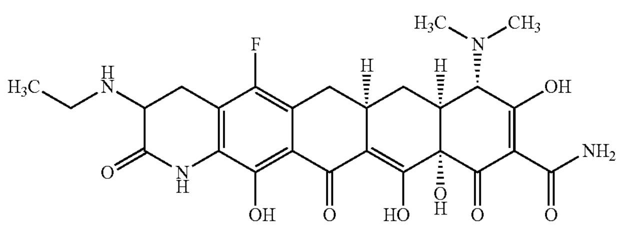 [SMILES: CCNC1Cc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3] | 545.3 |
| S27-4-9-B (diastereomer B) | 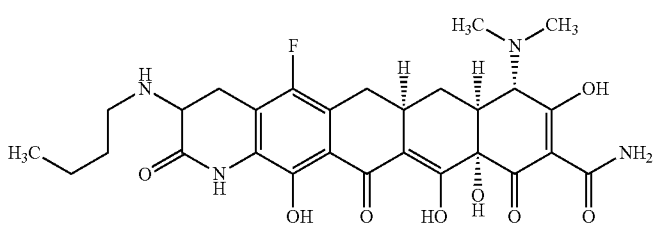 [SMILES: CCCCNC1Cc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3] | 573.3 |
| S27-4-10-B (diastereomer B) | 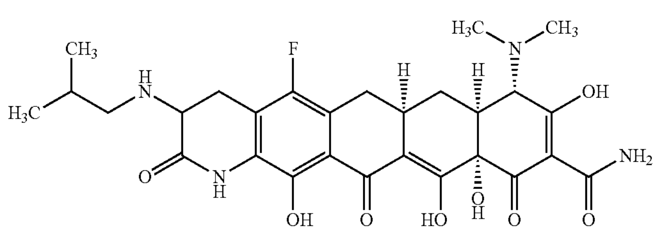 [SMILES: CC(C)CNC1Cc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3] | 573.3 |

TABLE 2F-continued

| Compound No. | Compound Structure | MS (ESI) m/z (M + H) |
|---|---|---|
| S27-4-11-B (diastereomer B) | 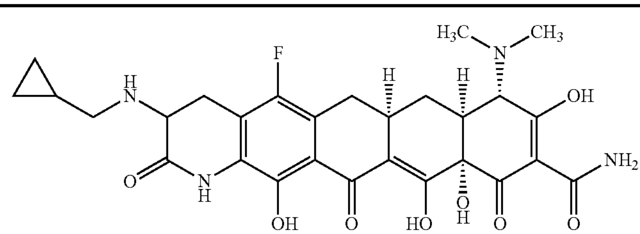 | 571.3 |
| S27-4-12-B (diastereomer B) | 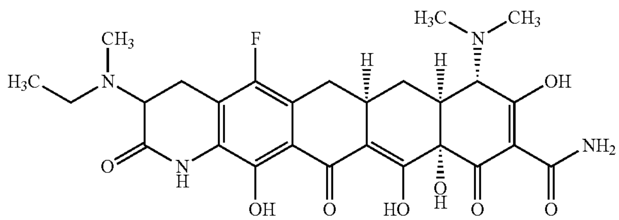 [SMILES: CCN(C)C1Cc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3] | 559.3 |
| S27-4-13-A (diastereomer A) S27-4-13-B (diastereomer B) | 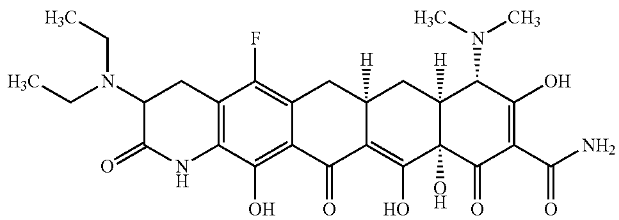 [SMILES: CCN(CC)C1Cc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3] | 573.3 |
| S27-4-14-B (diastereomer B) | 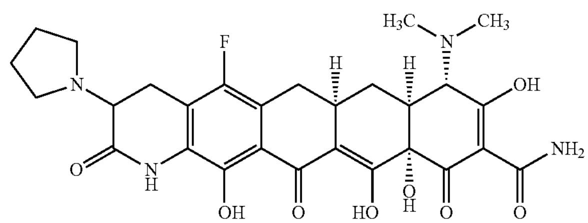 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CC(N1CCCC1)C(=O)N5] | 570.3 |

Antibacterial Activity.

The antibacterial activities for the compounds of the invention were studied according to the following protocols.

Minimum Inhibitory Concentration (MIC) Assay

MICs were determined according to the Clinical and Laboratory Standards Institute (CLSI) guidances (e.g., CLSI. Performance standards for antimicrobial susceptibility testing; nineteenth information supplement. CLSI document M100-S19, CLSI, 940 West Valley Road, Suite 1400, Wayne, Pa. 19087-1898, USA, 2009). Briefly, frozen bacterial strains were thawed and subcultured onto Mueller Hinton Broth (MHB) or other appropriate media (*Streptococcus* requires blood and *Haemophilus* requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 (this is the working inoculum) using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty μL of MHB was added to wells 2-12 of a 96-well plate. One hundred μL of appropriately diluted antibiotics was added to well 1. Fifty μL of antibiotics was removed from well 1 and added to well 2 and the contents of well 2 mixed by pipetting up and down five times. Fifty μL of the mixture in well 2 was removed and added to well 3 and mixed as above. Serial dilutions were continued in the same manner through well 12. Fifty μL was removed from well 12 so that all contained 50 μL. Fifty μL of the working inoculum was then added to all test wells. A growth control well was prepared by adding 50 μL of working inoculum and 50 μL of MHB to an empty well. The plates were then incubated at 37° C. overnight, removed from the incubator and each well was read on a plate reading mirror. The lowest concentration (MIC) of test compound that inhibited the growth of the bacteria was recorded.

Example

| | 1 | 2 | 3 | 4 | 5 | 6 | 7 | 8 | 9 | 10 | 11 | 12 |
|---|---|---|---|---|---|---|---|---|---|---|---|---|
| [Abt] | 32 | 16 | 8 | 4 | 2 | 1 | 0.5 | 0.25 | 0.125 | 0.06 | 0.03 | 0.015 |
| Growth | − | − | − | − | − | + | + | + | + | + | + | + |

[abt] = antibiotic concentration in the well in μg/ml
Growth = bacterial growth (cloudiness)

Interpretation: MIC=2 μg/mL

Protocol for Determining Inoculum Concentration (Viable Count)

Fifty 50 μl of the inoculum was pipetted into well 1. Ninety μl of sterile 0.9% NaCl was pipetted into wells 2-6 of a 96-well microtiter plate. Ten μL from was removed from well 1 and added it to well 2 followed by mixing. Ten μL was removed from well two and mixed with the contents of well 3 and so on creating serial dilutions through well 6. Ten μL was removed from each well and spotted onto an appropriate agar plate. The plate was placed into an incubator overnight. The colonies in spots that contain distinct colonies were counted. Viable count was calculated by multiplying the number of colonies by the dilution factor.

| Spot from Well | 1 | 2 | 3 | 4 | 5 | 6 |
|---|---|---|---|---|---|---|
| Dilution Factor | $10^2$ | $10^3$ | $10^4$ | $10^5$ | $10^6$ | $10^7$ |

Bacterial Strains

The following bacterial strains, listed below, were examined in minimum inhibitory concentration (MIC) assays.

| ORGANISM | STRAIN DESIGNATION | KEY PROPERTIES |
|---|---|---|
| Staphylococcus aureus | SA100 | ATCC 13709, MSSA, Smith strain |
| Staphylococcus aureus | SA101 | ATCC 29213, CLSI quality control strain, MSSA |
| Staphylococcus aureus | SA191 | HA-MRSA, tetracycline-resistant, lung infection model isolate |
| Staphylococcus aureus | SA161 | HA-MRSA, tetracycline-resistant, tet(M) |
| Staphylococcus aureus aaaureusaureus | SA158 | Tetracycline-resistant tet(K) |
| Staphylococcus epidermidis | SE164 | ATCC 12228, CLSI quality control strain, tetracycline-resistant |
| Enterococcus faecalis | EF103 | ATCC 29212, tet-I/R, control strain |
| Enterococcus faecalis | EF159 | Tetracycline-resistant, tet(M) |
| Enterococcus faecalis | EF327 | Wound isolate (US) tet(M) |
| Enterococcus faecium | EF404 | Blood isolate (US) tet(M) |
| Streptococcus pneumoniae | SP106 | ATCC 49619, CLSI quality control strain |
| Streptococcus pneumoniae | SP160 | Tetracycline-resistant, tet(M) |
| Streptococcus pyogenes | SP312 | 2009 clinical isolate, tet(M) |
| Streptococcus pyogenes | SP193 | S. pyogenes for efficacy models; tetS; sensitive to sulfonamides |
| Haemophilus influenzae | HI262 | Tetracycline-resistant, ampicillin-resistant |
| Moraxella catarrhalis | MC205 | ATCC 8176, CLSI quality control strain |
| Escherichia coli | EC107 | ATCC 25922, CLSI quality control strain |
| Escherichia coli | EC155 | Tetracycline-resistant, tet(A) |
| Enterobacter cloacae | EC108 | ATCC 13047, wt |
| Enterobacter cloacae | EC603 | Urine isolate (Spain) |
| Escherichia coli | EC878 | MG1655 tolC::kan |
| Klebsiella pneumoniae | KP109 | ATCC 13883, wt |
| Klebsiella pneumoniae | KP153 | Tetracycline-resistant, tet(A), MDR, ESBL+ |
| Klebsiella pneumoniae | KP457 | 2009 ESBL+, CTX-M, OXA |
| Proteus mirabilis | PM112 | ATCC 35659 |
| Proteus mirabilis | PM385 | Urine ESBL+ isolate |
| Pseudomonas aeruginosa | PA111 | ATCC 27853, wt, control strain |
| Pseudomonas aeruginosa | PA169 | Wt, parent of PA170-173 |
| Pseudomonas aeruginosa | PA173 | PA170 ΔmexX; MexXY-(missing a functional efflux pump) |
| Pseudomonas aeruginosa | PA555 | ATCC BAA-47, wild type strain PAO1 |
| Pseudomonas aeruginosa | PA556 | Multiple-Mex efflux pump knockout strain |
| Pseudomonas aeruginosa | PA673 | 2009 urine isolate from catheter in male from East North Central US |
| Pseudomonas aeruginosa | PA669 | 2009 clinical isolate from tracheal aspirate |
| Pseudomonas aeruginosa | PA693 | 2009 isolate from corneal scraping of female from Pacific US |
| Pseudomonas aeruginosa | PA1145 | Strain used in murine pneumonia model |
| Acinetobacter baumannii | AB110 | ATCC 19606, wt |
| Acinetobacter baumannii | AB250 | Cystic fibrosis isolate, MDR |
| Stenotrophomonas maltophilia | SM256 | Cystic fibrosis isolate, MDR |
| Burkholderia cenocepacia | BC240 | Cystic fibrosis isolate, MDR |

*MDR, multidrug-resistant;
MRSA, methicillin-resistant S. aureus;
MSSA, methicillin-sensitive S. aureus;
HA-MRSA, hospital-associated MRSA;
tet(K), major gram-positive tetracycline efflux mechanism;
tet(M), major gram-positive tetracycline ribosome-protection mechanism;
ESBL+, extended spectrum β-lactamase Results Values of minimum inhibition concentration (MIC) for tested compounds of the invention are provided in Tables 3, 4, 5, 6, 7 and 8. In Tables 3-8, A=lower than or equal to lowest MIC among three control compounds; B=greater than lowest MIC among three control compounds, but lower than or equal to the highest MIC among three control compounds; C=greater than MIC of all three control compounds; and ND=not determined. MIC values for sancycline, minocycline and tigecycline are reported in μg/mL.

TABLE 3

MIC Values for Compounds of the Invention Compared to Sancycline, Minocycline and Tigecycline.

MIC (μg/mL)

| Cmpd. No. | SA 101 29213 | SA 161 tetM | SA 158 tetK | EF 327 tetM | EF 404 tetM | SP 160 tetM | EC 107 25922 | EC 155 tetA | EC 878 tolC | KP 457 CTX-M-15 | PM 385 | PA 555 BAA-47 | PA 556 | PA 1145 | PA 669 | PA 673 | PA 693 | EC 603 tetA | AB 250 | SM 256 | BC 240 |
|---|---|---|---|---|---|---|---|---|---|---|---|---|---|---|---|---|---|---|---|---|---|
| S6-6-1 | C | C | B | B | B | B | B | B | B | A | A | A | A | A | A | A | A | B | C | C | C |
| S6-6-2 | C | C | B | B | B | B | B | B | B | A | A | A | A | A | A | A | A | A | B | C | C |
| S6-6-3 | B | B | B | B | B | B | A | B | B | A | A | A | B | A | A | A | A | A | A | A | B |
| S5-10-1-A | C | C | B | C | C | C | B | C | B | B | B | C | B | C | B | B | A | B | C | C | C |
| S5-10-1-B | C | B | B | B | B | B | B | B | B | B | A | A | A | A | A | A | A | B | C | C | C |
| S5-10-2-A | C | C | B | C | C | C | B | C | B | B | B | C | B | C | B | B | A | B | C | C | C |
| S5-10-2-B | C | B | B | B | B | B | B | A | B | A | A | A | A | B | A | A | A | A | B | C | C |
| S5-10-3-A | C | C | B | B | C | B | B | B | B | A | A | B | B | B | B | B | A | B | A | C | C |
| S5-10-3-B | B | A | B | B | B | A | A | A | A | A | A | A | A | A | A | A | A | A | A | A | B |
| S5-10-4-A | C | C | B | B | C | B | B | B | B | A | A | C | B | C | C | C | C | B | A | C | C |
| S5-10-4-B | ND | ND | ND | ND | ND | ND | ND | ND | ND | ND | ND | ND | ND | ND | ND | ND | ND | ND | ND | ND | ND |
| S4-14-1 | C | C | B | B | C | B | B | C | B | B | A | B | A | A | A | A | A | B | C | C | C |
| S4-14-2 | C | C | B | B | B | B | B | B | B | A | A | A | A | A | A | A | A | B | A | C | C |
| S4-14-3 | C | C | B | B | B | B | A | B | A | A | A | A | A | A | A | A | A | A | A | C | A |
| S4-14-4 | C | C | B | B | B | B | A | B | A | A | A | A | A | A | A | A | A | B | A | C | B |
| S4-14-5-A | A | B | A | B | B | A | A | A | A | A | A | A | A | A | A | A | A | A | A | A | A |
| S4-14-5-B | B | C | A | B | B | B | A | B | A | A | A | A | A | A | A | A | A | A | A | A | A |
| S4-14-7 | A | B | A | B | B | A | A | A | A | A | A | A | A | A | A | A | A | A | A | A | A |
| S4-14-8 | B | B | B | B | B | A | A | A | A | A | A | A | B | A | A | A | A | A | A | A | A |
| S4-14-9 | C | B | B | B | B | B | B | A | B | B | A | A | C | C | B | B | A | B | A | C | C |
| S4-14-10 | B | B | B | B | B | B | A | B | A | A | A | C | B | A | A | A | A | B | A | A | A |
| S4-14-11 | B | B | B | B | B | A | A | A | A | A | A | A | B | A | A | A | A | A | A | A | A |
| S4-14-12 | B | B | B | B | B | B | B | B | B | B | A | C | C | C | B | B | A | B | A | A | C |
| S4-14-13 | C | B | B | B | B | B | B | B | B | A | A | C | C | C | B | B | A | B | A | B | C |
| S4-14-14-A | A | B | A | B | A | A | A | A | A | A | A | A | A | A | A | A | A | A | A | A | A |
| S4-14-14-B | B | C | B | B | B | B | A | A | A | A | A | A | B | A | A | A | A | A | A | A | A |
| S4-14-16 | C | C | C | C | C | C | C | C | C | C | C | C | C | C | B | B | A | B | C | C | C |
| S4-14-17 | C | C | B | B | B | B | B | B | A | A | A | A | A | A | A | A | A | B | B | C | C |
| S4-14-18 | C | C | B | B | B | B | A | B | A | A | A | A | A | A | A | A | A | B | A | C | B |
| S8-4-1 | C | C | B | B | B | B | A | B | A | A | A | A | A | A | A | A | A | B | A | C | A |
| S7-14-1-A | C | C | B | C | C | B | B | C | B | B | A | B | A | B | B | A | A | B | C | C | C |
| S7-14-1-B | C | C | B | C | C | C | B | C | B | B | B | A | B | A | A | A | A | B | C | C | C |
| S21-5-1 | C | C | C | B | B | B | B | C | B | C | C | C | C | C | B | B | A | B | C | C | C |
| S8-4-2 | C | C | B | B | B | B | A | B | A | A | A | A | B | A | A | A | A | B | A | B | B |
| S7-14-2-A | C | C | B | B | B | B | B | B | B | A | A | A | A | B | A | A | A | B | B | C | C |
| S21-5-2 | C | C | C | B | C | C | C | C | C | C | C | C | C | C | B | B | A | B | C | C | C |
| S8-4-3 | A | B | A | B | B | A | A | A | A | A | A | A | B | B | A | A | A | A | A | A | B |
| S7-14-3-A | A | B | A | B | B | A | A | B | A | A | A | A | A | A | A | A | A | A | A | A | A |
| S21-5-4 | C | B | B | B | B | A | B | B | B | B | B | C | C | C | B | B | A | B | A | B | A |
| S21-5-3 | C | B | B | B | C | C | C | C | C | C | C | C | C | C | B | B | A | B | C | C | C |
| S14-8-3-A | C | C | B | B | B | B | B | B | B | B | B | B | C | B | A | B | A | B | C | C | C |
| S14-8-3-B | C | C | B | B | B | B | B | B | B | B | B | B | C | A | A | A | A | B | A | C | B |
| S14-8-1 | C | B | B | B | B | B | C | C | C | C | C | C | C | C | B | B | A | B | C | C | C |
| S14-8-2 | C | B | B | B | B | B | C | C | C | C | C | C | C | C | B | B | A | B | C | C | C |
| S19-7-1-B | C | C | C | C | C | C | C | C | C | B | A | C | B | C | B | A | A | B | C | C | C |
| S19-7-3-A | C | C | B | C | C | C | B | B | B | B | A | C | B | B | B | A | A | B | C | C | C |
| S19-7-3-B | C | C | C | C | C | C | B | B | B | B | A | C | B | B | B | A | A | B | C | C | C |
| S19-7-2 | C | C | B | C | C | B | B | B | B | A | A | C | B | C | B | A | A | B | C | C | C |
| S19-7-4-A | B | B | B | B | B | B | A | B | B | A | A | A | A | A | A | A | A | A | A | C | B |
| S19-7-4-B | C | C | B | B | B | B | B | B | B | A | A | A | A | A | A | A | A | A | C | C | C |
| S19-7-5-A | C | C | B | B | B | B | B | B | B | B | A | A | B | A | A | A | B | C | C | B |
| S19-7-5-B | C | C | B | B | B | B | B | B | B | A | A | A | B | A | A | A | A | B | C | C | B |
| S19-7-7-A | C | C | B | B | B | B | B | B | B | B | A | A | B | B | A | A | A | B | C | C | C |
| S19-7-7-B | C | C | B | B | B | B | B | B | B | A | A | A | B | A | A | A | A | B | B | C | B |
| S19-7-6 | C | B | B | B | B | B | B | B | B | A | A | B | B | B | A | A | A | A | C | A | B |
| S9-5-4 | C | B | B | B | B | B | B | B | A | A | A | A | A | A | A | A | A | B | C | C | C |
| S9-5-5 | C | B | B | B | B | B | B | B | A | A | A | B | A | A | A | A | A | B | B | C | B |
| S9-5-6 | B | B | B | A | B | A | A | A | A | A | A | B | A | A | A | A | A | A | A | A | A |
| S20-4-1 | C | C | B | B | C | B | B | B | B | B | A | A | A | A | A | A | A | B | C | C | C |
| S20-4-4 | C | C | B | B | B | B | B | B | B | A | A | A | A | A | A | A | A | B | C | C | C |
| S20-4-2 | C | C | B | B | B | B | B | A | B | A | A | B | A | B | B | B | A | B | B | C | B |
| S20-4-3 | B | C | B | B | B | B | B | A | B | A | A | A | A | B | B | B | A | A | A | A | B |
| S10-3-1 | B | C | B | B | B | B | A | B | B | A | A | A | A | A | A | A | A | A | C | C | C |
| S10-3-2 | B | C | B | C | B | B | A | B | B | A | A | A | A | A | B | A | A | B | B | C | C |
| S10-3-3 | B | B | B | B | B | A | A | A | A | A | A | A | B | A | A | A | A | A | A | A | B |
| S3-7-3-A | C | C | B | C | C | B | B | B | B | B | A | C | B | C | B | A | A | B | C | C | C |
| S3-7-3-B | C | B | B | B | B | B | B | B | B | B | A | A | A | B | B | A | A | B | C | C | C |
| S3-7-4-A | C | C | B | B | B | B | B | B | B | B | A | B | B | B | B | A | A | B | C | C | C |
| S3-7-4-B | C | B | B | B | B | B | B | B | B | B | A | B | A | B | B | A | A | B | C | C | C |
| S3-7-6-A | C | C | B | B | B | B | B | B | B | A | A | B | B | B | B | A | A | B | C | C | C |
| S3-7-6-B | C | B | B | B | B | B | B | B | B | A | A | A | A | B | B | A | A | A | C | C | C |

TABLE 3-continued

MIC Values for Compounds of the Invention Compared to Sancycline, Minocycline and Tigecycline.

MIC (µg/mL)

| Cmpd. No. | SA 101 29213 | SA 161 tetM | SA 158 tetK | EF 327 tetM | EF 404 tetM | SP 160 tetM | EC 107 25922 | EC 155 tetA | EC 878 tolC | KP 457 CTX-M-15 | PM 385 | PA 555 BAA-47 | PA 556 | PA 1145 | PA 669 | PA 673 | PA 693 | EC 603 tetA | AB 250 | SM 256 | BC 240 |
|---|---|---|---|---|---|---|---|---|---|---|---|---|---|---|---|---|---|---|---|---|---|
| S3-7-1-A | C | C | B | B | B | B | B | B | B | B | A | C | B | C | B | B | A | B | C | C | C |
| S3-7-1-B | C | B | B | B | B | B | B | A | B | A | A | B | A | B | B | B | A | A | A | C | B |
| S3-7-7-A | C | C | B | B | B | B | B | B | B | A | A | C | B | C | B | B | A | B | C | C | C |
| S3-7-7-B | C | B | B | B | B | B | B | A | B | A | A | B | A | B | B | B | A | A | A | C | C |
| S3-7-8-A | C | C | B | B | B | B | B | B | B | B | B | C | B | C | B | B | A | B | A | C | C |
| S3-7-8-B | C | B | B | B | B | B | B | A | C | A | A | C | B | C | B | B | A | A | A | A | C |
| S3-7-9-A | B | B | B | B | B | B | B | B | B | A | A | B | B | B | B | B | A | A | A | C | C |
| S3-7-9-B | B | B | A | B | B | A | B | A | B | A | A | A | A | A | A | A | A | A | A | A | A |
| S3-7-5 | C | B | B | B | B | B | B | B | B | B | A | B | B | B | B | B | A | A | A | A | C |
| S3-7-10-A | C | B | B | B | B | B | B | B | B | A | A | C | B | C | B | B | A | A | A | C | C |
| S3-7-10-B | B | B | B | B | B | B | A | A | B | A | A | A | B | B | A | B | A | A | A | A | B |
| S3-7-2 | C | C | B | B | B | B | B | B | B | B | B | C | C | C | B | B | A | B | A | C | C |
| 53-7-11 | C | C | C | C | C | C | C | C | C | C | C | C | C | C | B | B | A | B | C | C | C |
| 53-7-12 | C | C | C | C | C | C | C | C | C | C | C | C | C | C | B | B | A | B | C | C | C |
| S3-7-13-A | C | C | C | C | C | C | C | C | C | C | C | C | C | C | B | B | A | B | C | C | C |
| S3-7-13-B | C | C | C | B | C | B | C | C | C | C | C | C | C | C | B | B | A | B | C | C | C |
| S12-8-6-A | C | C | B | B | C | B | B | B | B | C | C | C | B | C | B | B | A | B | C | C | C |
| S12-8-6-B | C | C | C | C | C | C | C | C | C | C | C | C | B | C | B | B | A | B | C | C | C |
| S12-8-1-A | B | B | A | B | B | A | B | A | A | A | A | A | A | A | A | A | A | B | A | C | C |
| S12-8-1-B | C | C | B | C | C | C | B | C | B | B | B | B | B | B | A | A | A | B | C | C | C |
| S12-8-2-A | C | B | B | B | B | B | B | B | B | B | B | B | B | B | B | B | A | B | C | C | C |
| S12-8-7-A | C | B | B | B | B | B | B | B | B | B | B | B | B | B | B | B | A | B | C | C | C |
| S12-8-3-A | B | B | A | B | A | A | A | A | A | A | A | A | A | B | A | A | A | A | A | A | B |
| S12-8-3-B | C | C | C | C | C | B | C | C | B | C | C | C | C | C | B | B | A | B | C | C | C |
| S12-8-4-A | C | C | B | B | B | B | B | B | B | C | C | C | B | C | B | B | A | B | C | C | C |
| S12-8-5-A | A | A | A | A | A | A | A | A | A | A | A | A | B | A | A | A | A | A | A | A | B |
| S12-8-8-A | B | B | B | A | B | A | A | A | A | A | A | A | A | A | A | A | A | A | A | B | B |
| S11-3-1 | C | C | C | B | B | B | B | B | B | C | B | A | C | A | A | A | A | B | C | C | B |
| S11-3-2 | C | B | B | B | B | B | B | B | B | B | B | C | C | C | B | B | A | B | A | C | C |
| S11-3-3 | B | B | B | B | B | B | B | B | B | B | C | C | C | C | B | B | A | B | A | C | B |
| S16-7-1 | C | B | B | B | B | B | B | B | B | B | A | B | B | B | B | B | A | B | C | C | C |
| S16-7-4 | C | B | B | B | B | B | B | B | B | B | A | A | B | B | B | B | A | B | C | C | C |
| S16-7-6 | C | B | B | B | B | B | B | B | B | B | A | A | A | B | B | B | A | B | C | C | C |
| S16-7-2 | C | B | B | B | B | B | B | B | B | A | A | A | A | A | B | B | A | B | B | C | C |
| S16-7-5 | C | B | B | B | B | B | B | A | B | A | A | A | B | B | B | B | A | A | A | C | C |
| S16-7-3 | B | B | B | B | B | A | B | A | B | A | A | A | B | A | A | A | A | A | A | A | B |
| S17-3-1 | C | C | C | C | C | C | C | C | C | C | C | C | C | C | B | B | A | B | C | C | C |
| S17-3-2 | C | C | C | C | C | C | B | C | B | C | C | C | C | C | B | A | A | B | C | C | C |
| S17-3-3 | C | C | C | C | C | C | B | C | B | C | B | C | B | C | B | B | A | B | C | C | C |
| S17-3-10 | C | C | C | C | C | C | B | C | B | B | B | C | B | C | B | B | A | B | B | C | B |
| S17-3-7 | C | C | C | C | C | C | C | C | C | C | C | B | B | C | B | B | A | B | C | C | C |
| S17-3-6 | C | C | C | C | C | C | B | C | B | C | C | C | B | C | B | B | A | B | C | C | C |
| S17-3-4 | B | C | B | B | C | B | B | C | B | B | B | A | B | B | B | A | A | B | B | A | A |
| S17-3-5 | B | C | B | B | C | B | C | B | A | B | A | B | B | B | B | A | A | B | A | A | A |
| S17-3-8 | B | C | B | B | C | B | B | C | B | B | B | B | B | C | B | B | A | B | A | B | B |
| S17-3-9 | C | C | C | B | C | B | C | C | B | C | C | C | C | C | B | B | A | B | B | C | C |
| S15-10-1 | C | C | B | B | B | B | B | B | B | B | B | B | B | B | A | A | A | B | C | C | C |
| S15-10-2 | C | B | B | B | B | B | B | B | B | B | B | C | B | C | B | B | A | B | C | C | C |
| S15-10-3-A | A | A | A | A | A | A | A | A | A | A | A | A | A | A | A | A | A | A | A | A | A |
| S15-10-3-B | A | A | A | A | A | A | A | A | A | A | A | A | A | A | A | A | A | A | A | A | A |
| Sancycline | 0.5 | 2 | 4 | 4 | 4 | 8 | 8 | 32 | 1 | 8 | 8 | 32 | 1 | 32 | 33 | 33 | 33 | 32 | 16 | 1 | 4 |
| Minocycline | 0.06 | 8 | 0.03 | 32 | 8 | 2 | 0.5 | 8 | 0.25 | 8 | 16 | 16 | 0.13 | 32 | 33 | 33 | 33 | 33 | 8 | 0.5 | 8 |
| Tigecycline | 0.06 | 0.13 | 0.06 | 0.06 | 0.03 | 0.02 | 0.03 | 0.5 | 0.03 | 1 | 4 | 16 | 0.25 | 16 | 32 | 32 | 33 | 2 | 8 | 1 | 16 |

TABLE 4

MIC Values for Compounds of the Invention Compared to Sancycline, Minocycline and Tigecycline.

MIC (µg/mL)

| Compound No. | SA 101 29213 | SA 100 13709 | SA 161 MRSA, tetM | SA 158 tetK | EF 103 29212 | EF 159 tetM | SP 106 49619 | SP 160 tetM | EC107 25922 | E0155 tetA | AB110 19606 | PA111 27853 | E01108 13047 | KP109 13883 | KP153 tetA |
|---|---|---|---|---|---|---|---|---|---|---|---|---|---|---|---|
| S13-5-1 | C | C | C | C | C | C | C | C | C | C | C | B | C | C | C |
| S13-5-2 | C | C | B | C | B | B | C | B | C | C | C | B | C | C | C |
| S17-3-11 | C | C | B | C | C | B | C | C | B | C | C | B | C | C | C |

TABLE 4-continued

MIC Values for Compounds of the Invention Compared to Sancycline, Minocycline and Tigecycline.

MIC (µg/mL)

| Compound No. | SA 101 29213 | SA 100 13709 | SA 161 MRSA, tetM | SA 158 tetK | EF 103 29212 | EF 159 tetM | SP 106 49619 | SP 160 tetM | EC107 25922 | E0155 tetA | AB110 19606 | PA111 27853 | E01108 13047 | KP109 13883 | KP153 tetA |
|---|---|---|---|---|---|---|---|---|---|---|---|---|---|---|---|
| S9-4-1 | B | B | B | B | B | B | B | B | B | B | B | B | B | B | B |
| S9-5-2 | B | B | B | B | B | B | B | B | B | B | B | B | B | B | A |
| S9-5-1 | C | C | B | B | B | B | B | B | B | B | C | B | A | B | B |
| S9-5-3 | C | B | B | B | B | B | B | B | B | A | A | B | B | B | A |
| S18-5-1-1 | C | C | C | B | B | C | C | B | B | B | C | B | B | B | B |
| S18-5-2-1 | B | B | B | B | B | B | C | B | B | B | C | B | C | B | B |
| S18-5-1-2 | C | C | B | B | B | B | C | B | B | B | A | B | B | B | B |
| S18-5-2-2 | C | C | C | B | B | B | B | B | B | B | B | B | B | B | B |
| Sancycline | 0.5 | 1 | 2 | 4 | 8 | 8 | 0.25 | 8 | 8 | 32 | 0.25 | 33 | 8 | 8 | 32 |
| Minocycline | 0.063 | 0.063 | 8 | 0.031 | 1 | 16 | 0.015 | 2 | 0.5 | 8 | 0.063 | 16 | 2 | 1 | 8 |
| Tigecycline | 0.063 | 0.063 | 0.125 | 0.063 | 0.031 | 0.063 | 0.016 | 0.016 | 0.031 | 0.5 | 0.25 | 8 | 0.25 | 0.125 | 1 |

TABLE 5

MIC Values for Compounds of the Invention Compared to Sancycline, Minocycline and Tigecycline.

MIC (µg/mL)

| Cmpd. No. | SA 101 29213 | SA 191 | SA 161 tetM | SA 158 tetK | SE 164 12228 | EF 159 tetM | SP 106 49619 | SP 160 tetM | SP 312 | HI 262 33929 | MC 205 8176 | EC 107 25922 | EC 155 tetA | KP 153 tetA | KP 194 7E + 05 | PM 112 35659 | PA 555 | PA 556 | AB 250 | SM 256 | BC 240 |
|---|---|---|---|---|---|---|---|---|---|---|---|---|---|---|---|---|---|---|---|---|---|
| S22-4-5-A | C | C | C | B | B | C | B | B | C | C | C | B | B | B | B | C | C | C | A | C | C |
| S22-4-6-B | C | B | B | B | A | B | A | B | B | C | B | B | B | B | B | C | C | | A | C | C |
| S22-4-5-B | B | B | B | B | A | B | A | B | B | C | B | B | B | A | B | B | B | | A | B | C |
| Sancycline | 0.5 | 8 | 2 | 4 | 4 | 8 | 0.25 | 8 | 4 | 0.5 | 0.13 | 8 | 32 | 32 | 32 | 4 | 32 | 1 | 16 | 1 | 4 |
| Minocycline | 0.0625 | 8 | 8 | 0.03 | 0.125 | 16 | 0.015 | 2 | 16 | 1 | 0.02 | 0.5 | 8 | 8 | 32 | 8 | 16 | 0.125 | 8 | 0.5 | 8 |
| Tigecycline | 0.0625 | 0.5 | 0.13 | 0.06 | 0.125 | 0.06 | 0.016 | 0.20 | 0.02 | 1 | 0.02 | 0.03 | 0.5 | 1 | 8 | 1 | 16 | 0.25 | 8 | 1 | 16 |

TABLE 6

MIC Values for Compounds of the Invention Compared to Sancycline, Minocycline and Tigecycline.

MIC (µg/mL)

| Cmpd. No. | SA 101 29213 | SA 161 tetM | SA 158 tetK | EF 327 tetM | EF 404 tetM | SP 160 | SP 312 tetM | EC 107 25922 | EC 155 tetA | EC 878 tolC | EC 880 ipxC |
|---|---|---|---|---|---|---|---|---|---|---|---|
| S22-4-1-A | B | B | B | B | B | B | B | B | B | A | B |
| S22-4-1-B | C | B | B | B | B | B | B | B | B | B | C |
| S22-4-2-A | B | B | B | B | B | B | B | B | B | A | B |
| S22-4-2-B | C | B | B | B | B | B | B | B | B | B | B |
| S22-4-3-B | B | B | B | B | B | B | B | C | B | C | B |
| S22-4-3-A | C | B | C | C | B | B | B | C | B | C | C |
| S22-4-8-A | B | B | B | B | B | B | B | B | B | B | B |
| S22-4-9-A | C | B | B | B | B | B | B | C | B | C | C |
| Sancycline | 0.5 | 2 | 4 | 4 | 4 | 8 | 4 | 8 | 32 | 1 | 0.25 |
| Minocycline | 0.063 | 8 | 0.03 | 32 | 8 | 2 | 16 | 0.5 | 8 | 0.25 | 0.015 |
| Tigecycline | 0.063 | 0.125 | 0.063 | 0.063 | 0.031 | 0.015 | 0.015 | 0.03 | 0.5 | 0.031 | 0.015 |

TABLE 6-continued

MIC Values for Compounds of the Invention Compared to Sancycline, Minocycline and Tigecycline.

| | MIC (μg/mL) | | | | | | | | | | |
|---|---|---|---|---|---|---|---|---|---|---|---|
| Cmpd. No. | EC 882 imp | KP 457 CTX-M-15 | PM 385 | PA5 55 BAA-47 | PA 556 | PA 884 35151 | PA 689 | EC 603 tetA | AB 250 | SM 256 | BC 240 |
| S22-4-1-A | A | A | A | A | B | A | A | A | A | B | C |
| S22-4-1-B | B | B | B | A | B | B | B | A | C | C | C |
| S22-4-2-A | A | A | A | A | B | A | A | A | A | B | C |
| S22-4-2-B | A | A | B | A | B | B | A | A | B | C | C |
| S22-4-3-B | B | A | A | B | B | A | B | C | C | C | C |
| S22-4-3-A | B | B | B | B | B | A | B | C | C | C | C |
| S22-4-8-A | B | A | A | B | B | B | B | C | C | B | C |
| S22-4-9-A | B | B | A | B | B | B | B | C | C | C | C |
| Sancycline | 0.25 | 8 | 8 | 32 | 1 | 4 | 16 | 32 | 16 | 1 | 4 |
| Minocycline | 0.015 | 8 | 16 | 16 | 0.125 | 1 | 8 | 33 | 8 | 0.5 | 8 |
| Tigecycline | 0.015 | 1 | 4 | 16 | 0.25 | 0.063 | 1 | 2 | 8 | 1 | 16 |

TABLE 7

MIC Values for Compounds of the Invention Compared to Sancycline, Minocycline and Tigecycline.

| | MIC (μg/mL) | | | | | | | | | | | | | | | | | | |
|---|---|---|---|---|---|---|---|---|---|---|---|---|---|---|---|---|---|---|---|
| Cmpd. No. | SA 101 29213 | SA 161 tetM | SA 158 tetK | EF 327 tetM | EF 404 tetM | SP 160 tetM | EC 07 25922 | EC 155 tetA | EC 878 tolC | EC 880 ipxC | EC 882 imp | KP 457 CTX-M-15 | PM 385 | PA 555 BAA-47 | PA 556 | PA 1145 Vivi-source | EC 603 tetA | AB 250 | SM 256 | BC 240 |
| S23-4-1-A | C | B | B | B | B | B | A | B | B | B | B | A | A | A | A | A | A | A | B |
| S23-4-1-B | C | B | C | B | B | C | B | B | B | B | B | B | A | A | B | C | B | A | C |
| S23-4-2-A | C | C | C | C | C | C | C | B | C | C | C | C | C | C | B | C | B | C | C |
| S23-4-2-B | C | C | C | B | B | B | B | B | B | B | C | C | B | B | B | C | B | C | C |
| Sancycline | 0.5 | 2 | 4 | 4 | 4 | 8 | 8 | 32 | 1 | 0.25 | 0.25 | 8 | 8 | 32 | 1 | | 32 | 16 | 1 | 4 |
| Minocycline | 0.06 | 8 | 0.03 | 32 | 8 | 2 | 0.5 | 8 | 0.25 | 0.02 | 0.02 | 8 | 16 | 16 | 0.13 | | 33 | 8 | 0.5 | 8 |
| Tigecycline | 0.06 | 0.13 | 0.06 | 0.06 | 0.03 | 0.02 | 0.03 | 0.5 | 0.03 | 0.02 | 0.02 | 1 | 4 | 16 | 0.25 | 16 | 2 | 8 | 1 | 16 |

TABLE 8

MIC Values for Compounds of the Invention Compared to Sancycline, Minocycline and Tigecycline.

| | MIC (μg/mL) | | | | | | | | | | |
|---|---|---|---|---|---|---|---|---|---|---|---|
| Cmpd. No. | SA 101 tetM 29213 | SA 161 tetM | SA 158 tetK | EF 327 tetM | EF 404 tetM | SP 160 tetM | EC 107 25922 | EC 155 tetA | EC 878 tolC | KP 457 CTX-M-15 | PM 385 |
| S22-4-4-A | C | C | B | B | C | B | B | B | C | C | C |
| S22-4-4-B | B | B | B | B | B | A | B | B | B | A | A |
| S22-4-7 | C | B | B | B | B | B | B | B | B | B | B |
| S22-4-10-A | C | C | B | B | B | B | B | B | B | B | B |
| S22-4-10-B | B | B | B | B | B | A | B | B | B | A | A |
| S22-4-11-A | B | B | B | B | B | B | B | B | B | A | A |
| S22-4-11-B | C | C | B | C | C | B | B | C | B | B | A |
| S22-4-12-A | C | C | B | B | C | B | B | B | B | C | C |
| S22-4-12-B | A | B | A | B | B | B | A | B | B | B | B |
| S22-4-15-A | B | B | B | B | B | B | B | B | B | A | A |
| S22-4-17-A | B | B | B | B | B | B | B | B | B | A | A |
| S22-4-13-A | B | B | B | B | B | B | B | B | B | A | A |
| S22-4-14-A | B | B | B | B | B | A | B | A | B | B | A |
| S22-4-20A | B | B | B | A | A | A | B | B | B | B | A |
| S22-4-21-A | C | B | B | B | B | B | C | C | C | C | C |
| S22-4-16-A | B | B | B | B | B | B | B | B | B | A | A |
| S22-4-18-A | A | B | B | B | B | A | B | B | A | A | A |

TABLE 8-continued

| | | | | | | | | | | | |
|---|---|---|---|---|---|---|---|---|---|---|---|
| S22-4-22-A | C | B | B | B | B | A | B | B | B | B | B |
| S22-4-19-A | B | B | B | B | B | B | B | B | B | A | A |
| S23-4-3-B | B | B | B | B | B | B | B | B | B | A | A |
| S23-4-4-A | C | C | B | B | C | B | B | B | B | B | C |
| S23-4-4-B | B | B | B | B | B | A | B | A | A | B | A |
| S23-4-5-B | C | B | B | B | B | B | B | B | B | B | B |
| S23-4-6-A | C | C | B | C | C | B | B | B | C | C | C |
| S23-4-6-B | B | B | B | A | B | A | B | B | B | B | A |
| S23-4-7-A | C | C | B | B | C | B | B | B | C | B | C |
| S23-4-7-B | C | B | B | B | B | B | B | B | B | B | B |
| S23-4-8-A | C | C | B | C | C | C | B | C | C | B | C |
| S23-4-8-B | C | B | B | B | B | B | B | B | C | C | C |
| S24-4-2-A | C | C | B | B | B | B | B | B | B | B | A |
| S24-4-2-B | C | B | B | B | B | B | B | B | B | B | A |
| S24-4-1-A | B | B | B | B | B | B | B | B | B | A | A |
| S24-4-1-B | B | B | B | B | B | A | B | A | B | A | A |
| S24-4-3-A | C | B | B | B | B | B | B | B | B | B | A |
| S24-4-3-B | B | B | B | B | B | A | B | A | B | A | A |
| S24-4-9-A | C | C | C | B | C | B | C | C | C | C | C |
| S24-4-9-B | C | C | B | B | B | B | C | C | C | C | C |
| S24-4-9-C | C | C | C | C | C | C | C | C | C | C | C |
| S24-4-9-D | C | C | B | C | C | B | C | B | C | C | C |
| S24-4-11-A | C | B | B | B | B | B | C | C | C | C | C |
| S24-4-11-B | C | C | B | B | C | C | C | C | C | C | C |
| S24-4-10-A | C | B | B | B | B | B | B | B | B | B | B |
| S24-4-10-B | C | C | B | B | B | B | B | B | B | B | B |
| S24-4-12-A | C | C | B | C | C | C | C | C | C | C | C |
| S24-4-12-B | C | B | B | B | B | B | B | C | C | C | C |
| S24-5-13-B | C | B | B | B | B | B | B | B | B | C | C |
| S24-4-14-A | B | B | B | B | B | A | B | B | B | B | B |
| S24-4-14-B | C | B | B | B | B | B | B | B | B | B | C |
| S24-4-15 | C | C | B | C | C | B | B | B | C | C | C |
| S24-4-5-A | C | C | B | B | B | B | B | B | B | B | A |
| S24-4-5-B | C | C | B | B | B | B | B | B | C | C | B |
| S24-4-4-A | B | B | B | B | B | B | B | B | B | B | B |
| S24-4-4-B | C | B | B | B | B | B | B | B | C | B | C |
| S24-4-7-A | B | C | B | B | B | B | B | B | B | B | B |
| S24-4-7-B | C | B | B | B | B | B | B | B | B | C | C |
| S24-4-6-A | B | B | B | B | B | B | B | B | B | C | C |
| S24-4-6-B | C | B | B | B | B | A | B | B | C | C | C |
| S24-4-8-A | C | C | B | B | B | B | B | B | B | B | B |
| S24-4-8-B | C | B | B | B | B | B | B | B | B | C | C |
| S25-4-3-A | C | C | B | B | C | B | B | B | B | C | C |
| S25-4-3-B | B | B | B | B | B | A | B | A | A | B | A |
| S25-4-4-A | C | C | B | B | B | B | B | B | B | C | C |
| S25-4-4-B | A | B | A | A | A | A | A | A | A | B | A |
| S25-4-5-A | C | C | B | B | B | B | B | B | C | C | C |
| S25-4-5-B | C | B | B | B | B | B | B | B | B | C | C |
| S25-4-2-A | A | A | A | A | A | A | A | A | A | A | A |
| S25-4-2-B | A | A | A | A | A | A | A | A | A | B | A |
| S25-4-1-A | A | A | A | A | A | A | A | A | A | A | A |
| S25-4-1-B | B | C | B | B | B | B | B | B | B | B | B |
| S25-4-6 | B | B | B | B | B | B | B | B | B | B | A |
| S26-4-1-A | B | B | B | B | B | A | B | B | B | A | A |
| S26-4-1-B | C | B | B | B | B | B | B | B | B | A | A |
| S26-4-2-A | C | C | B | B | B | B | B | C | C | B | A |
| S26-4-3-A | B | B | B | B | B | A | B | B | B | A | A |
| S26-4-4-A | B | B | A | B | B | A | B | A | B | A | A |
| S26-4-5-A | B | B | B | B | B | B | B | A | B | A | A |
| S27-4-3 | C | B | B | B | B | B | B | C | B | B | B |
| S27-4-7 | C | B | B | B | B | B | B | B | B | B | B |
| S27-4-8-B | A | B | B | A | B | A | B | B | A | A | A |
| S27-4-1-A | A | A | A | A | A | A | A | B | A | A | A |
| S27-4-1-B | A | A | A | A | A | A | A | B | A | A | A |
| S27-4-9-B | A | A | A | A | A | A | A | A | A | A | A |
| S27-4-10-B | A | A | A | A | A | A | A | A | A | A | A |
| S27-4-11-B | A | A | A | A | A | A | A | B | A | A | A |
| S27-4-5 | B | B | A | A | A | A | B | B | A | B | A |
| S27-4-4 | B | B | B | A | A | A | B | B | B | B | B |
| S27-4-12-B | A | A | A | A | A | A | A | B | A | A | A |
| S27-4-6 | B | B | A | A | A | A | B | B | B | B | C |
| S27-4-13-A | B | A | A | A | A | A | A | A | A | A | A |
| S27-4-13-B | B | A | B | A | A | A | A | A | A | A | A |
| S27-4-2 | C | B | B | B | B | B | B | B | B | C | B |
| S27-4-14-B | A | A | A | A | A | B | B | A | A | A | A |
| Sancycline | 0.5 | 2 | 4 | 4 | 4 | 8 | 8 | 32 | 1 | 8 | 8 |

TABLE 8-continued

| | | | | | | | | | | | |
|---|---|---|---|---|---|---|---|---|---|---|---|
| Minocycline | 0.06 | 8 | 0.03 | 32 | 8 | 2 | 0.5 | | 8 | 0.25 | 8 | 16 |
| Tigecycline | 0.06 | 0.1 | 0.06 | 0.06 | 0.06 | 0.03 | 0.02 | | 0.5 | 0.03 | 1 | 4 |

MIC Values for Compounds of the Invention Compared to Sancycline, Minocycline and Tigecycline.

| | MIC (µg/mL) | | | | | | | | |
|---|---|---|---|---|---|---|---|---|---|
| Cmpd. No. | PA 555 BAA-47 | PA 556 | PA 1145 Vivi-source | PA 669 | PA 673 | PA 693 | EC 603 tetA | AB 250 | SM 256 | BC 240 |
| S22-4-4-A | C | C | C | B | B | A | B | B | C | C |
| S22-4-4-B | B | B | B | B | B | A | A | A | A | B |
| S22-4-7 | C | B | C | B | B | A | B | A | B | C |
| S22-4-10-A | C | B | C | B | B | A | B | A | B | C |
| S22-4-10-B | A | B | B | B | B | A | A | A | A | B |
| S22-4-11-A | A | B | A | A | A | A | A | A | A | B |
| S22-4-11-B | B | B | B | B | A | A | B | C | C | C |
| S22-4-12-A | C | C | C | B | B | A | B | A | C | C |
| S22-4-12-B | B | B | C | B | B | A | B | A | B | C |
| S22-4-15-A | A | B | A | A | A | A | B | B | C | C |
| S22-4-17-A | A | B | A | A | A | A | B | A | A | B |
| S22-4-13-A | A | B | A | A | A | A | B | A | C | B |
| S22-4-14-A | B | B | B | B | B | A | B | A | A | B |
| S22-4-20A | B | B | B | B | B | A | B | A | A | A |
| S22-4-21-A | C | C | C | B | B | A | B | C | C | C |
| S22-4-16-A | A | A | A | A | A | A | B | A | C | B |
| S22-4-18-A | A | B | B | A | A | A | B | A | A | A |
| S22-4-22-A | C | C | C | B | B | A | B | A | C | C |
| S22-4-19-A | A | B | A | A | A | A | B | A | C | B |
| S23-4-3-B | A | B | B | B | B | A | A | A | B | B |
| S23-4-4-A | C | C | C | B | B | A | B | A | C | C |
| S23-4-4-B | A | B | B | B | B | A | A | A | A | B |
| S23-4-5-B | B | B | B | B | B | A | B | B | C | C |
| S23-4-6-A | C | C | C | B | B | A | B | C | C | C |
| S23-4-6-B | B | B | B | B | B | A | B | A | B | B |
| S23-4-7-A | C | C | C | B | B | A | B | C | C | C |
| S23-4-7-B | B | B | B | B | B | A | B | C | C | C |
| S23-4-8-A | C | B | C | B | B | A | B | C | C | C |
| S23-4-8-B | C | C | C | B | B | A | B | C | C | C |
| S24-4-2-A | B | B | B | B | B | A | B | C | C | C |
| S24-4-2-B | B | B | B | B | B | A | B | C | C | C |
| S24-4-1-A | A | A | A | A | A | A | A | A | C | C |
| S24-4-1-B | A | A | A | A | A | A | A | A | B | B |
| S24-4-3-A | B | B | B | B | B | A | A | B | C | C |
| S24-4-3-B | A | A | A | A | A | A | A | A | B | B |
| S24-4-9-A | C | C | C | B | B | A | B | C | C | C |
| S24-4-9-B | C | B | C | B | B | A | B | C | C | C |
| S24-4-9-C | C | C | C | B | B | A | B | C | C | C |
| S24-4-9-D | C | B | C | B | B | A | B | C | C | C |
| S24-4-11-A | C | C | C | B | B | A | B | C | C | C |
| S24-4-11-B | C | C | C | B | B | A | B | C | C | C |
| S24-4-10-A | B | B | B | B | B | A | B | C | C | C |
| S24-4-10-B | B | B | C | B | B | A | B | C | C | C |
| S24-4-12-A | C | C | C | B | B | A | B | C | C | C |
| S24-4-12-B | C | B | C | B | B | A | B | C | C | C |
| S24-5-13-B | C | C | C | B | B | A | B | C | C | C |
| S24-4-14-A | C | B | C | B | B | A | B | A | C | C |
| S24-4-14-B | C | B | C | B | B | A | B | C | C | C |
| S24-4-15 | C | C | C | B | B | A | B | C | C | C |
| S24-4-5-A | B | B | B | B | B | A | B | C | C | C |
| S24-4-5-B | C | B | C | B | B | A | B | C | C | C |
| S24-4-4-A | B | B | B | B | B | A | B | A | C | C |
| S24-4-4-B | C | B | C | B | B | A | B | C | C | C |
| S24-4-7-A | B | B | C | B | B | A | B | A | C | C |
| S24-4-7-B | C | B | C | B | B | A | B | C | C | C |
| S24-4-6-A | C | C | C | B | B | A | B | B | C | C |
| S24-4-6-B | C | C | C | B | B | A | B | C | C | C |
| S24-4-8-A | C | C | C | B | B | A | B | B | C | C |
| S24-4-8-B | C | C | C | B | B | A | B | C | C | C |
| S25-4-3-A | C | B | C | B | B | A | B | C | C | C |
| S25-4-3-B | A | B | A | A | A | A | B | B | C | C |
| S25-4-4-A | C | C | C | B | B | A | B | B | C | C |
| S25-4-4-B | A | B | A | A | A | A | B | A | B | B |
| S25-4-5-A | C | C | C | B | B | A | B | B | C | C |
| S25-4-5-B | C | C | C | B | B | A | B | B | C | C |
| S25-4-2-A | A | B | A | A | A | A | A | A | A | B |
| S25-4-2-B | A | B | A | A | A | A | A | A | A | B |
| S25-4-1-A | A | A | A | A | A | A | A | A | A | B |

TABLE 8-continued

| | | | | | | | | | | |
|---|---|---|---|---|---|---|---|---|---|---|
| S25-4-1-B | B | B | C | B | B | A | B | A | C | C |
| S25-4-6 | B | B | A | B | B | A | B | C | C | C |
| S26-4-1-A | A | A | A | A | A | A | A | A | B | B |
| S26-4-1-B | A | B | A | A | A | A | B | A | C | C |
| S26-4-2-A | C | C | C | B | B | A | B | C | C | C |
| S26-4-3-A | A | A | A | A | A | A | A | A | B | B |
| S26-4-4-A | A | B | B | B | B | A | A | A | A | B |
| S26-4-5-A | A | B | A | A | A | A | A | A | A | B |
| S27-4-3 | C | B | B | B | B | A | B | C | C | C |
| S27-4-7 | B | B | B | B | B | A | B | C | C | C |
| S27-4-8-B | A | A | A | A | A | A | B | B | C | C |
| S27-4-1-A | A | A | A | A | A | A | B | A | C | A |
| S27-4-1-B | A | A | A | A | A | A | B | A | C | B |
| S27-4-9-B | A | A | A | A | A | A | B | A | B | A |
| S27-4-10-B | A | A | A | A | A | A | B | A | B | A |
| S27-4-11-B | A | A | A | A | A | A | B | A | C | B |
| S27-4-5 | A | B | A | A | A | A | B | A | C | C |
| S27-4-4 | A | B | A | A | A | A | B | B | C | C |
| S27-4-12-B | A | A | A | A | A | A | B | A | C | C |
| S27-4-6 | B | B | B | B | B | A | B | A | C | C |
| S27-4-13-A | A | B | A | A | A | A | B | A | C | B |
| S27-4-13-B | A | B | A | A | A | A | B | A | C | B |
| S27-4-2 | C | C | C | B | B | A | B | A | C | C |
| S27-4-14-B | A | B | A | A | A | A | B | A | C | B |
| Sancycline | 32 | 1 | 32 | 33 | 33 | 33 | 32 | 16 | 1 | 4 |
| Minocycline | 16 | 0.13 | 32 | 33 | 33 | 33 | 33 | 8 | 0.5 | 8 |
| Tigecycline | 16 | 0.25 | 16 | 32 | 32 | 33 | 2 | 8 | 1 | 16 |

Mouse Pneumonia Study.

Organism: *K. pneumoniae* UNT023-1 (KPC producing strain)

Animals: Female CD-1 mice (22±2 g) (Harlan laboratories)

Pretreatment: Cytoxan 150 mg/kg IP on day −4 for partial neutropenia (based on previous virulence studies).

Infection procedure: Anesthetized the mice by IP injecting 0.15 mL of a ketamine HCl (40 mg/kg b.w.)+xylazine (6 mg/kg b.w.) mixture. Intranasally (IN) inoculated anesthetized mice with 0.05 mL of the designated inoculum (final infective dose of approximately 6-7 $\log_{10}$ CFU/mouse). For IN inoculation, placed drops onto the external nares and waited for inhalation. After inoculation, placed each mouse back into its cage and monitored for recovery.

Treatment: Dosing was initiated at 2 hours post-infection with a second dose administered at 12 hours post-infection for each dose group.

Endpoint: 24 hour lung CFU counts Animals were euthanized via $CO_2$ inhalation, their lungs aseptically removed, homogenized, diluted and plated for CFU determination.

Results: The results are summarized in Table 9.

What is claimed is:

1. A compound represented by any one of the following structural formulas:

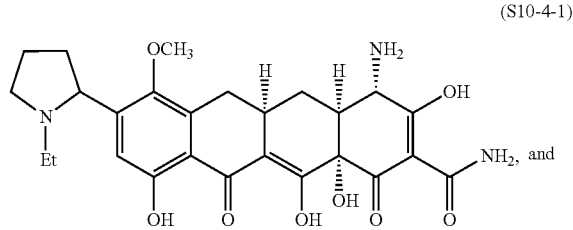

(S10-4-1)

TABLE 9

| Group | Test Article | MIC (µg/mL) | mg/kg/dose | Route/Dose Regimen (hr. post-infection) | Mean $\log_{10}$ CPU/pair Lung | Standard Deviation | $\log_{10}$ change from 24 hr. Control | $\log_{10}$ change from 2 hr. Control |
|---|---|---|---|---|---|---|---|---|
| 1 | S4-14-14-A | 0.0625 | 40 | N. BO @ 2 and 12 hrs. | 8.32 | 0.19 | −3.18 | −1.22 |
| 2 | | | 15 | | 8.71 | 0.81 | −2.79 | −0.83 |
| 3 | | | 5 | | 8.18 | 0.28 | −0.33 | 1.83 |
| 4 | S4-14-5-A | 0.0625 | 40 | | 6.89 | 0.45 | −2.51 | −0.85 |
| 5 | | | 15 | | 7.51 | 0.32 | −1.99 | −0.83 |
| 6 | | | 5 | | 9.11 | 0.14 | −0.38 | 1.58 |
| 7 | S5-10-3-B | 0.125 | 40 | | 8.28 | 0.18 | −3.21 | −1.28 |
| 8 | | | 15 | | 5.92 | 0.20 | −2.58 | −0.82 |
| 9 | | | 5 | | 7.82 | 0.28 | −1.58 | 0.03 |
| 10 | Tigecycline | 1 | 80 | | 5.27 | 0.22 | −1.23 | 0.73 |
| 11 | Vehicle 24 hr. controls | | | | 9.50 | 0.21 | | 1.98 |
| 12 | 2 hr. infection control | | | | 7.54 | 0.19 | −1.96 | |

-continued

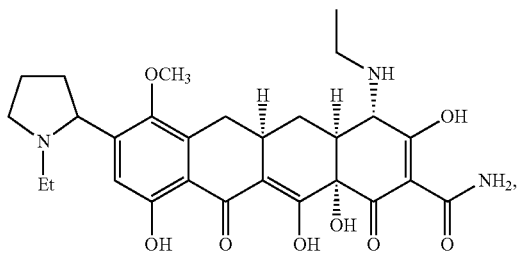
(S10-4-2)

or a pharmaceutically acceptable salt of any of the foregoing.

2. A pharmaceutical composition comprising a pharmaceutically acceptable carrier or diluent and a compound of claim 1 or a pharmaceutically acceptable salt thereof.

3. A compound represented by the following structural formula:

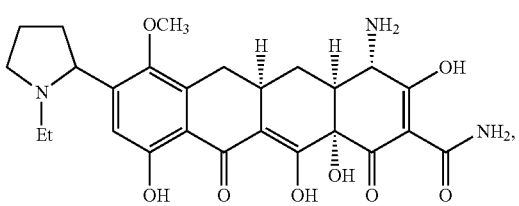
(S10-4-1)

or a pharmaceutically acceptable salt thereof.

4. A pharmaceutical composition comprising a pharmaceutically acceptable carrier or diluent and a compound of claim 3 or a pharmaceutically acceptable salt thereof.

* * * * *